(12) United States Patent
Pauly et al.

(10) Patent No.: US 9,920,327 B2
(45) Date of Patent: Mar. 20, 2018

(54) PLANTS WITH ELEVATED LEVELS OF GLUCAN

(75) Inventors: Markus Pauly, Berkeley, CA (US); Florian J. Kraemer, Berkeley, CA (US); Sarah Hake, Bolinas, CA (US)

(73) Assignee: The Regents of the University of California, Oakland, CA (US)

( * ) Notice: Subject to any disclaimer, the term of this patent is extended or adjusted under 35 U.S.C. 154(b) by 910 days.

(21) Appl. No.: 14/123,482

(22) PCT Filed: Jun. 1, 2012

(86) PCT No.: PCT/US2012/040544
§ 371 (c)(1),
(2), (4) Date: Jul. 23, 2014

(87) PCT Pub. No.: WO2012/170304
PCT Pub. Date: Dec. 13, 2012

(65) Prior Publication Data
US 2014/0366215 A1    Dec. 11, 2014

Related U.S. Application Data

(60) Provisional application No. 61/492,769, filed on Jun. 2, 2011.

(51) Int. Cl.
| C12N 15/82 | (2006.01) |
| C12N 15/01 | (2006.01) |
| C07K 14/415 | (2006.01) |

(52) U.S. Cl.
CPC ........ *C12N 15/8246* (2013.01); *C07K 14/415* (2013.01); *C12N 15/01* (2013.01)

(58) Field of Classification Search
None
See application file for complete search history.

(56) References Cited

U.S. PATENT DOCUMENTS

2005/0009164 A1* 1/2005 Shyur ............ C12Y 302/01073
435/200

OTHER PUBLICATIONS

Ehrenbergerova et al., 2008, Plant Foods Hum. Nutr. 63: 111-117.*
Stewart et al., 2001, Protein Engineering 14: 245-253.*
Licheninase-2 from Zea mays, GenBank Accession No. NP_001148461.1, published Apr. 10, 2009.*
Ahloowalia and Maluszynski, 2001, Euphytica 118: 167-173.*
Stadler, 1946, Genetics 31: 377-394.*
Drake et al., 1998, Genetics 148: 1667-1686.*
Pauly and Keegstra, 2008, The Plant Journal 54: 559-568.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Gaudioso-Pedraza et al., 2014, Frontiers in Plant Science Article 212, vol. 5: 1-14.*
Invitation to pay additional fees received for PCT Patent Application No. PCT/US2012/040544, dated Jan. 30, 2013, 6 pages.
International Search Report and Written Opinion received for PCT Patent Application No. PCT/US2012/040544, dated Apr. 3, 2013, 17 pages.
International Preliminary Report on Patentability received for PCT Patent Application No. PCT/US2012/040544, dated Dec. 12, 2013, 10 pages.
Cheng et al., "Mutagenesis of Trp54 and Trp203 Residues on Fibrobacter Succinogenes 1,3-1,4-β-D-Glucanase Significantly Affects Catalytic Activities of the Enzyme", Biochemistry, vol. 41, No. 27, 2002, pp. 8759-8766.
Guillaumie et al., "Differential Expression of Phenylpropanoid and Related Genes in Brown-Midrib Bm1, Bm2, Bm3, and Bm4 Young Near-Isogenic Maize Plants", Planta, vol. 226, 2007, pp. 235-250.
Hirai et al., "RNAi Vectors for Manipulation of Gene Expression in Higher Plants", The Open Plant Science Journal, vol. 2, 2008, pp. 21-30.
Kraemer et al., "Identifying New Genes Influencing the Cell Wall of Grasses Using a Forward Genetic Approach", In Vitro Cellular & Developmental Biology Animal, vol. 46, No. Supll. S, 2010, pp. S134-S135 (Abstract only).

* cited by examiner

*Primary Examiner* — Amjad Abraham
*Assistant Examiner* — Bratislav Stankovic
(74) *Attorney, Agent, or Firm* — Richard Aron Osman

(57) ABSTRACT

The present disclosure relates to mutations in licheninase genes encoding polypeptides with decreased licheninase activity, which when expressed in plants results in elevated levels of glucan in the plants. In particular, the disclosure relates to licheninase nucleic acids and polypeptides related to glucan accumulation in plants, plants with reduced expression of a licheninase nucleic acid, and methods related to the generation of plants with increased glucan content in the cell walls of leaf tissue.

10 Claims, 61 Drawing Sheets

A  atggcaagcaggcaaggtgtagccgcctccatgttcgccacggcattgctcctcggcgtctttgcatccatcccacaaagt
gctgaggccatcggggtgtgctacggcatgagcgccaacaacctgccggcggcgagcacggtggtgagcatgtacaag
gcgaacggcatctcggcgatgcggctgtacgcgccggaccagggcgcgctgcaggcggtgggcggcacgggcatcagc
gtggccgtgggcgcccccaacgacgtgctgtccaacatcgcggctagccccgcggcggccgcgtcgtgggtgcgcaaca
acatccaggcgtacccgtccgtgtcgttccgctacgtgtgcgtgggcaacgaggtggccggcggcgcggcgcaggacct
ggcgccggccatggagaacgtgcacgcggcgctggcggcggccgggctgggccacatcaaggtgacgacgtcggtgtc
gcaggccatcctgggcgtgtacagcccgccgtccgccgcggagttcaccggcgaggcgcgcggatacatgggccccgtg
ctgcagttcctggcgcgcaccgggtcgccgctcatggccaacatctacccgtacctggcctgggcatacaaccccagcgc
catggacatgagctacgcgctcttcacctcctccggcaccgtcgtgcaggacggcgcctacgggtaccagaacctcttcg
acaccaccgtcgacgccttctacgtcgccatgggcaacaacggcggctccggcgtgccgctcgtggtgtcgaagagcgg
gtggccgtccggcggcggcgtccaggccacgccggccaacgcgagggtgtacaaccagtacctcatcaaccacgtcgg
gcgcgggacgccgcgccacccgggcgccatcgagacctacctcttctccatgttcaacgagaaccagaaggagagcggc
gtggagcagaactgggggctcttctaccccaacatgcagcacgtctaccccatcagcttctga B  masrqgvaasmfatalllgvfasipqsaeaigvcygmsannlpaastvvsmykangisamrlyapdqgalqavg
gtgisvavgapndvlsniaaspaaaaswvrnniqaypsvsfryvcvgnevaggaaqdlapamenvhaalaaagl
ghikvttsvsqailgvysppsaaeftgeargymgpvlqflartgsplmaniypylawaynpsamdmsyalftssgt
vvqdgaygyqnlfdttvdafyvamgnnggsgvplvvsksgwpsgggvqatpanarvynqylinhvgrgtprhp
gaietylfsmfnenqkesgveqnwglfypnmqhvypisf*

C  Atggcaagcaggcaaggtgtagccgcctccatgttcgccacggcattgctcctcggcgtctttgcatccatcccacaaagt
gctgaggccatcggggtgtgctacggcatgagcgccaacaacctgccggcggcgagcacggtggtgagcatgtacaag
gcgaacggcatctcggcgatgcggctgtacgcgccggaccagggcgcgctgcaggcggtgggcggcacgggcatcagc
gtggccgtgggcgcccccaacgacgtgctgtccaacatcgcggctagccccgcggcggccgcgtcgtgggtgcgcaaca
acatccaggcgtacccgtccgtgtcgttccgctacgtgtgcgtgggcaacgaggtggccggcggcgcggcgcaggacct
ggcgccggccatggagaacgtgcacgcggcgctggcggcggccgggctgggccacatcaaggtgacgacgtcggtgtc
gcaggccatcctgggcgtgtacagcccgccgtccgccgcggagttcaccggcgaggcgcgcggatacatgggccccgtg
ctgcagttcctggcgcgcaccgggtcgccgctcatggccaacatctacccgtacctggcctgggcatacaaccccagcgc
catggacatgagctacgcgctcttcacctcctccggcaccgtcgtgcaggacggcgcctacgggtaccagaacctcttcg
acaccaccgtcgacgccttctacgtcgccatgggcaacaacggcggctccggcgtgccgctcgtggtgtcggagagcgg
gtggccgtccggcggcggcgtccaggccacgccggccaacgcgagggtgtacaaccagtacctcatcaaccacgtcgg
gcgcgggacgccgcgccacccgggcgccatcgagacctacctcttctccatgttcaacgagaaccagaaggagagcggc
gtggagcagaactgggggctcttctaccccaacatgcagcacgtctaccccatcagcttctga D  MASRQGVAASMFATALLLGVFASIPQSAEAIGVCYGMSANNLPAASTVVSMYKANGISAM
RLYAPDQGALQAVGGTGISVAVGAPNDVLSNIAASPAAAASWVRNNIQAYPSVSFRYVCV
GNEVAGGAAQDLAPAMENVHAALAAAGLGHIKVTTSVSQAILGVYSPPSAAEFTGEARGY
MGPVLQFLARTGSPLMANIYPYLAWAYNPSAMDMSYALFTSSGTVVQDGAYGYQNLFDTT
VDAFYVAMGKNGGSGVPLVVSESGWPSGGGVQATPANARVYNQYLINHVGRGTPRHPGAI
ETYLFSMFNENQKESGVEQNWGLFYPNMQHVYPISF

FIG. 2

A  atgtgcgtttcgatcgcaggtgctgaggccatcggggtgtgctacggcatgagcgccaacaacctgccggcggcgagca
   cggtggtgagcatgtacaaggcgaacggcatctcggcgatgcggctgtacgcgccggaccagggcgcgctgcaggcgg
   tgggcggcacgggcatcagcgtggccgtgggcgcccccaacgacgtgctgtccaacatcgcggctagccccgcggcggc
   cgcgtcgtgggtgcgcaacaacatccaggcgtacccgtccgtgtcgttccgctacgtgtgcgtgggcaacgaggtggccg
   gcggcgcggcgcaggacctggcgccggccatggagaacgtgcacgcggcgctggcggcggccgggctggggccacatc
   aaggtgacgacgtcggtgtcgcaggccatcctgggcgtgtacagcccgccgtccgccgcggagttcaccggcgaggcgc
   gcggatacatgggcccccgtgctgcagttcctggcgcgcaccgggtcgccgctcatggccaacatctacccgtacctggcct
   gggcatacaaccccagcgccatggacatgagctacgcgctcttcacctcctccggcaccgtcgtgcaggacggcgcctac
   gggtaccagaacctcttcgacaccaccgtcgacgccttctacgtcgccatgggcaacaacggcggctccggcgtgccgct
   cgtggtgtcgaagagcgggtggccgtccggcggcggcgtccaggccacgccggccaacgcgagggtgtacaaccagta
   cctcatcaaccacgtcgggcgcgggacgccgcgccacccgggcgccatcgagacctacctcttctccatgttcaacgaga
   accagaaggagagcggcgtggagcagaactgggggctcttctaccccaacatgcagcacgtctaccccatcagcttctg
   a B  mcvsiagaeaigvcygmsannlpaastvvsmykangisamrlyapdqgalqavggtgisvavgapndvlsniaa
   spaaaaswvrnniqaypsvsfrvcvgnevaggaaqdlapamenvhaalaaaglghikvttsvsqailgvyspps
   aaeftgeargymgpvlqflartgsplmaniypylawaynpsamdmsyalftssgtvvqdgaygyqnlfdttvdaf
   yvamgnnggsgvplvvsksgwpsgggvqatpanarvynqylinhvgrgtprhpgaietylfsmfnenqkesgv
   eqnwglfypnmqhvypisf*

C  Atgtgcgtttcgatcgcaggtgctgaggccatcggggtgtgctacggcatgagcgccaacaacctgccggcggcgagca
   cggtggtgagcatgtacaaggcgaacggcatctcggcgatgcggctgtacgcgccggaccagggcgcgctgcaggcgg
   tgggcggcacgggcatcagcgtggccgtgggcgcccccaacgacgtgctgtccaacatcgcggctagccccgcggcggc
   cgcgtcgtgggtgcgcaacaacatccaggcgtacccgtccgtgtcgttccgctacgtgtgcgtgggcaacgaggtggccg
   gcggcgcggcgcaggacctggcgccggccatggagaacgtgcacgcggcgctggcggcggccgggctggggccacatc
   aaggtgacgacgtcggtgtcgcaggccatcctgggcgtgtacagcccgccgtccgccgcggagttcaccggcgaggcgc
   gcggatacatgggcccccgtgctgcagttcctggcgcgcaccgggtcgccgctcatggccaacatctacccgtacctggcct
   gggcatacaaccccagcgccatggacatgagctacgcgctcttcacctcctccggcaccgtcgtgcaggacggcgcctac
   gggtaccagaacctcttcgacaccaccgtcgacgccttctacgtcgccatgggcaacaacggcggctccggcgtgccgct
   cgtggtgtcggagagcgggtggccgtccggcggcggcgtccaggccacgccggccaacgcgagggtgtacaaccagta
   cctcatcaaccacgtcgggcgcgggacgccgcgccacccgggcgccatcgagacctacctcttctccatgttcaacgaga
   accagaaggagagcggcgtggagcagaactgggggctcttctaccccaacatgcagcacgtctaccccatcagcttctg
   a D  MCVSIAGAEAIGVCYGMSANNLPAASTVVSMYKANGISAMRLYAPDQGALQAVGGTGISV
   AVGAPNDVLSNIAASPAAAASWVRNNIQAYPSVSFRYVCVGNEVAGGAAQDLAPAMENVH
   AALAAAGLGHIKVTTSVSQAILGVYSPPSAAEFTGEARGYMGPVLQFLARTGSPLMANIY
   PYLAWAYNPSAMDMSYALFTSSGTVVQDGAYGYQNLFDTTVDAFYVAMGKNGGSGVPLVV
   SESGWPSGGGVQATPANARVYNQYLINHVGRGTPRHPGAIETYLFSMFNENQKESGVEQN WGLFYPNMQHVYPISF

FIG. 3

```
                                                                    Section 1
                          (1) 1        10        20        30       45
     GRMZM2G137535_P01    (1) MASRQGVAASMFATALLLGVFASIPQSAEAIGVCYGMSANNLPAA
A619 GRMZM2G137535_P01    (1) MASRQGVAASMFATALLLGVFASIPQSAEAIGVCYGMSANNLPAA
ca11 GRMZM2G137535_P01    (1) MASRQGVAASMFATALLLGVFASIPQSAEAIGVCYGMSANNLPAA
GUB2_HORVU Lichenase-2    (1) ----------------------PPSVESIGVCYGMSANNLPAA
             Consensus    (1) MASRQGVAASMFATALLLGVFASIPQSAEAIGVCYGMSANNLPAA
```
```
                                                                    Section 2
                         (46) 46       60        70        80       90
     GRMZM2G137535_P01   (46) STVVSMYKANGISAMRLYAPDQGALQAVGGTGISVAVGAPNDVLS
A619 GRMZM2G137535_P01   (46) STVVSMYKANGISAMRLYAPDQGALQAVGGTGISVAVGAPNDVLS
ca11 GRMZM2G137535_P01   (46) STVVSMYKANGISAMRLYAPDQGALQAVGGTGISVAVGAPNDVLS
GUB2_HORVU Lichenase-2   (22) STVVSMFKFNGIKSMRLYAPNQWALQAVGGTGINVWGAPNDVLS
             Consensus   (46) STVVSMYKANGISAMRLYAPDQGALQAVGGTGISVAVGAPNDVLS
```
```
                                                                    Section 3
                         (91) 91       100       110       120      135
     GRMZM2G137535_P01   (91) NIAASPAAAASWVRNNIQAYPSVSFRYVCVGNEVAGGAAQDLAPA
A619 GRMZM2G137535_P01   (91) NIAASPAAAASWVRNNIQAYPSVSFRYVCVGNEVAGGAAQDLAPA
ca11 GRMZM2G137535_P01   (91) NIAASPAAAASWVRNNIQAYPSVSFRYVCVGNEVAGGAAQDLAPA
GUB2_HORVU Lichenase-2   (67) NIAASPAAAASWVKSNIQAYPKVSFRYVCVGNEVAGGATRNLVPA
             Consensus   (91) NIAASPAAAASWVRNNIQAYPSVSFRYVCVGNEVAGGAAQDLAPA
```
```
                                                                    Section 4
                        (136) 136      150       160       170      180
     GRMZM2G137535_P01  (136) MENVHAALAAAGLGHIKVTTSVSQAILGVYSPPSAAEFTGEARGY
A619 GRMZM2G137535_P01  (136) MENVHAALAAAGLGHIKVTTSVSQAILGVYSPPSAAEFTGEARGY
ca11 GRMZM2G137535_P01  (136) MENVHAALAAAGLGHIKVTTSVSQAILGVYSPPSAAEFTGEARGY
GUB2_HORVU Lichenase-2 (112) MKNVGALVAAGLGHIKVTTSVSQAILGVFSPPSAGSFTGEAAAF
             Consensus (136) MENVHAALAAAGLGHIKVTTSVSQAILGVYSPPSAAEFTGEARGY
```

FIG. 4

```
                                                            Section 5
                        (181)  181      190       200       210      225
        GRMZM2G137535_P01  (181) MGPVLQFLARTGSPLMANIYPYLAWAYNPSAMDMSYALFTSSGTV
   A619_GRMZM2G137535_P01  (181) MGPVLQFLARTGSPLMANIYPYLAWAYNPSAMDMSYALFTSSGTV
    ca11_GRMZM2G137535_P01 (181) MGPVLQFLARTGSPLMANIYPYLAWAYNPSAMDMSYALFTSSGTV
      GUB2_HORVU Lichenase-2 (157) MGPVWQFLARTNPLMANIYPYLAWAYNPSAMDMGYALFNSGTV
                 Consensus (181) MGPVLQFLARTGSPLMANIYPYLAWAYNPSAMDMSYALFTSSGTV
                                                            Section 6
                        (226) 226        240       250       260      270
        GRMZM2G137535_P01  (226) VQDGAYGYQNLFDTTVDAFYVAMGKNGGSGVPLVVSESGWPSGGG
   A619_GRMZM2G137535_P01  (226) VQDGAYGYQNLFDTTVDAFYVAMGNNGGSGVPLVVSESGWPSGGG
    ca11_GRMZM2G137535_P01 (226) VQDGAYGYQNLFDTTVDAFYVAMGNNGGSGVPLVVSKSGWPSGGG
      GUB2_HORVU Lichenase-2 (202) VRDGAYGYQNLFDTTVDAFTTAMGKHGGSSVKLVVSESGWPSGGG
                 Consensus (226) VQDGAYGYQNLFDTTVDAFYVAMGNNGGSGVPLVVSESGWPSGGG
                                                            Section 7
                        (271) 271       280       290       300       315
        GRMZM2G137535_P01  (271) VQATPANARVYNQYLINHVGRGTPRHPGAIETYLFSMFNENQKES
   A619_GRMZM2G137535_P01  (271) VQATPANARVYNQYLINHVGRGTPRHPGAIETYLFSMFNENQKES
    ca11_GRMZM2G137535_P01 (271) VQATPANARVYNQYLINHVGRGTPRHPGAIETYLFSMFNENQKES
      GUB2_HORVU Lichenase-2 (247) TAATPANARFYNQLLINHVGRGTPRHPGAIETYIFAMFNENQKDS
                 Consensus (271) VQATPANARVYNQYLINHVGRGTPRHPGAIETYLFSMFNENQKES (316) 316         337
        GRMZM2G137535_P01  (316) GVEQNWGLFYPNMQHVYPISF-
   A619_GRMZM2G137535_P01  (316) GVEQNWGLFYPNMQHVYPISF-
    ca11_GRMZM2G137535_P01 (316) GVEQNWGLFYPNMQHVYPISF-
      GUB2_HORVU Lichenase-2 (292) GVEQNWGLFYPNMQHVYPINF-
                 Consensus (316) GVEQNWGLFYPNMQHVYPISF
```

FIG. 4 (Cont.)

```
                                                                    Section 1
                    (1)   1        10       20       30         45
  GRMZM2G137535_P02 (1)   MCVSIAGAEAIGVCYGMSANNLPAASTVVSMYKANGISAMRLYAP
A619 GRMZM2G137535_P02 (1) MCVSIAGAEAIGVCYGMSANNLPAASTVVSMYKANGISAMRLYAP
cal1 GRMZM2G137535_P02 (1) MCVSIAGAEAIGVCYGMSANNLPAASTVVSMYKANGISAMRLYAP
 GUB2_HORVU Lichenase-2 (1) ----PPSVESIGVCYGMSANNLPAASTVVSMFKFNGIKSMRLYAP
             Consensus (1) MCVSIAGAEAIGVCYGMSANNLPAASTVVSMYKANGISAMRLYAP Section 2
                   (46)  46       60       70       80         90
  GRMZM2G137535_P02 (46) DQGALQAVGGTGISVAVGAPNDVLSNIAASPAAAASWVRNNIQAY
A619 GRMZM2G137535_P02 (46) DQGALQAVGGTGISVAVGAPNDVLSNIAASPAAAASWVRNNIQAY
cal1 GRMZM2G137535_P02 (46) DQGALQAVGGTGISVAVGAPNDVLSNIAASPAAAASWVRNNIQAY
 GUB2_HORVU Lichenase-2 (42) NQAALQAVGGTGINVMVGAPNDVLSNLAASPAAAASWVKSNIQAY
             Consensus (46) DQGALQAVGGTGISVAVGAPNDVLSNIAASPAAAASWVRNNIQAY Section 3
                   (91)  91       100      110      120        135
  GRMZM2G137535_P02 (91) PSVSFRYVCVGNEVAGGAAQDLAPAMENVHAALAAAGLGHIKVTT
A619 GRMZM2G137535_P02 (91) PSVSFRYVCVGNEVAGGAAQDLAPAMENVHAALAAAGLGHIKVTT
cal1 GRMZM2G137535_P02 (91) PSVSFRYVCVGNEVAGGAAQDLAPAMENVHAALAAAGLGHIKVTT
 GUB2_HORVU Lichenase-2 (87) PKVSFRYVCVGNEVAGGATRNLVPAMKNVHGALVAAGLGHIKVTT
             Consensus (91) PSVSFRYVCVGNEVAGGAAQDLAPAMENVHAALAAAGLGHIKVTT Section 4
                  (136) 136      150      160      170        180
  GRMZM2G137535_P02 (136) SVSQAILGVYSPPSAAEFTGEARGYMGPVLQFLARTGSPLMANIY
A619 GRMZM2G137535_P02 (136) SVSQAILGVYSPPSAAEFTGEARGYMGPVLQFLARTGSPLMANIY
cal1 GRMZM2G137535_P02 (136) SVSQAILGVYSPPSAAEFTGEARGYMGPVLQFLARTGSPLMANIY
 GUB2_HORVU Lichenase-2 (132) SVSQAILGVFSPPSAGSFTGEAAAFMGPVVQFLARTNAPLMANIY
             Consensus (136) SVSQAILGVYSPPSAAEFTGEARGYMGPVLQFLARTGSPLMANIY
```

FIG. 5

```
                                                                            Section 5
                        (181) 181      190      200      210        225
      GRMZM2G137535_P02 (181) PYLAWAYNPSAMDMSYALFTSSGTVVQDGAYGYQNLFDTTVDAFY
 A619_GRMZM2G137535_P02 (181) PYLAWAYNPSAMDMSYALFTSSGTVVQDGAYGYQNLFDTTVDAFY
 ca11_GRMZM2G137535_P02 (181) PYLAWAYNPSAMDMSYALFTSSGTVVQDGAYGYQNLFDTTVDAFY
   GUB2_HORVU Lichenase-2 (177) PYLAWAYNPSAMDMGYALFNASGTVVRDGAYGYQNLFDTTVDAFY
              Consensus (181) PYLAWAYNPSAMDMSYALFTSSGTVVQDGAYGYQNLFDTTVDAFY Section 6
                        (226) 226      240      250       260       270
      GRMZM2G137535_P02 (226) VAMGKNGGSGVPLVVSESGWPSGGGVQATPANARVYNQYLINHVG
 A619_GRMZM2G137535_P02 (226) VAMGNNGGSGVPLVVSESGWPSGGGVQATPANARVYNQYLINHVG
 ca11_GRMZM2G137535_P02 (226) VAMGNNGGSGVPLVVSKSGWPSGGGVQATPANARVYNQYLINHVG
   GUB2_HORVU Lichenase-2 (222) TAMGKHGGSSVKLVVSESGWPSGGGTAATPANARFYNQLLINHVG
              Consensus (226) VAMGNNGGSGVPLVVSESGWPSGGGVQATPANARVYNQYLINHVG Section 7
                        (271) 271      280       290       300      315
      GRMZM2G137535_P02 (271) RGTPRHPGAIETYLFSMFNENQKESGVEQNWGLFYPNMQHVYPIS
 A619_GRMZM2G137535_P02 (271) RGTPRHPGAIETYLFSMFNENQKESGVEQNWGLFYPNMQHVYPIS
 ca11_GRMZM2G137535_P02 (271) RGTPRHPGAIETYLFSMFNENQKESGVEQNWGLFYPNMQHVYPIS
   GUB2_HORVU Lichenase-2 (267) RGTPRHPGAIETYLFAMFNENQKDSGVEQNWGLFYPNMQHVYPIN
              Consensus (271) RGTPRHPGAIETYLFSMFNENQKESGVEQNWGLFYPNMQHVYPIS Section 8
                        (316) 316
      GRMZM2G137535_P02 (316) F-
 A619_GRMZM2G137535_P02 (316) F-
 ca11_GRMZM2G137535_P02 (316) F-
   GUB2_HORVU Lichenase-2 (312) F-
              Consensus (316) F
```

FIG. 5 (Cont.)

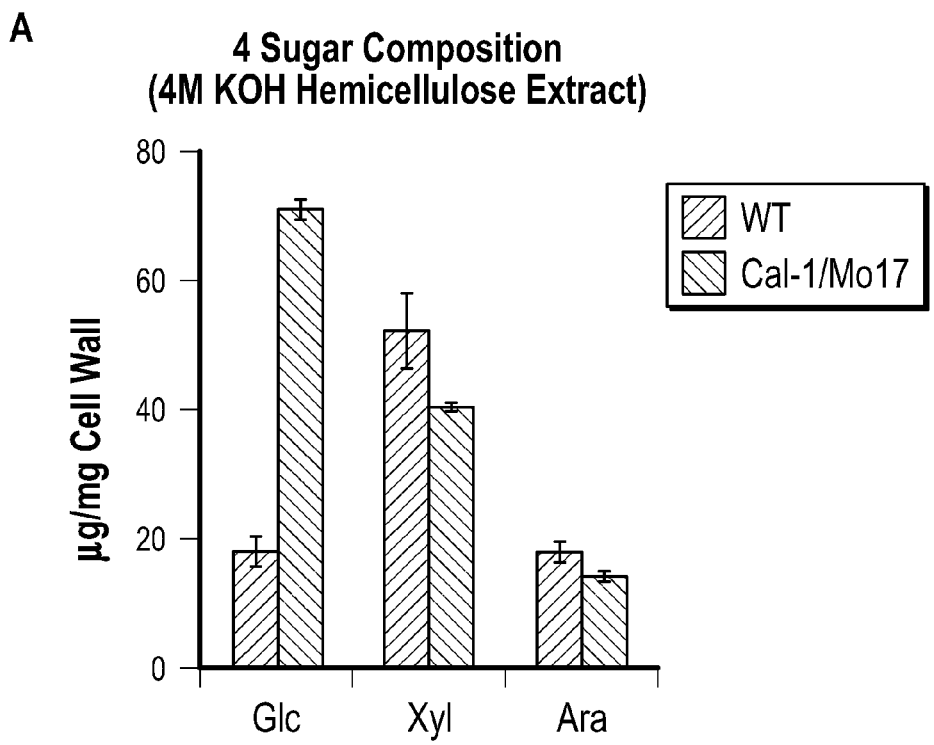
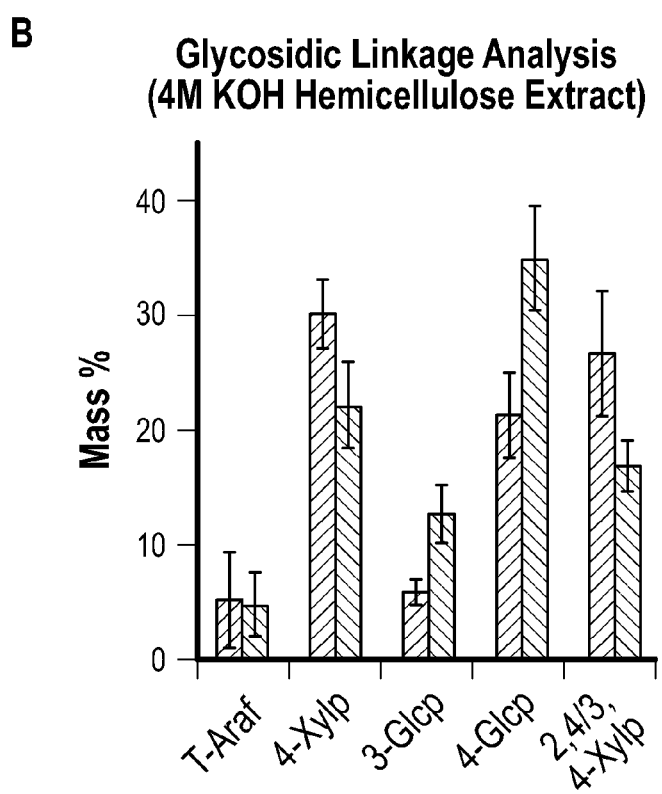
FIG. 8

A
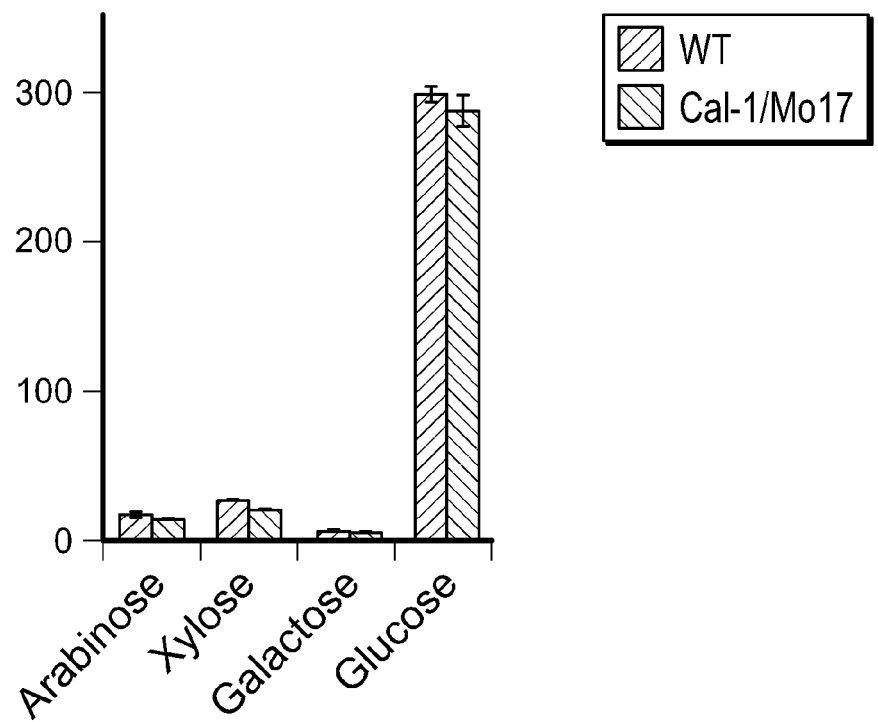
B
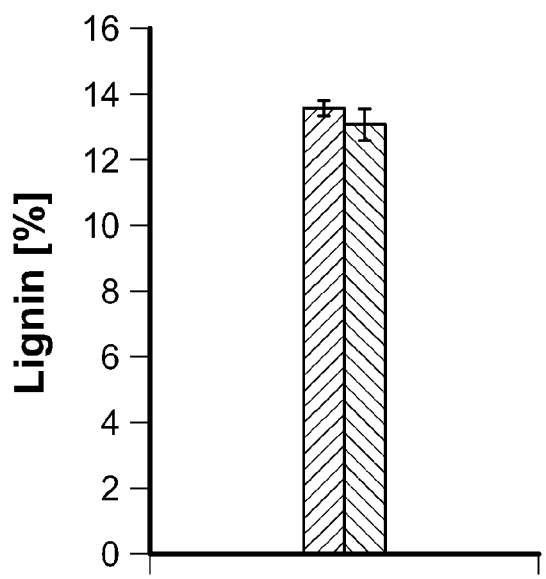
FIG. 9

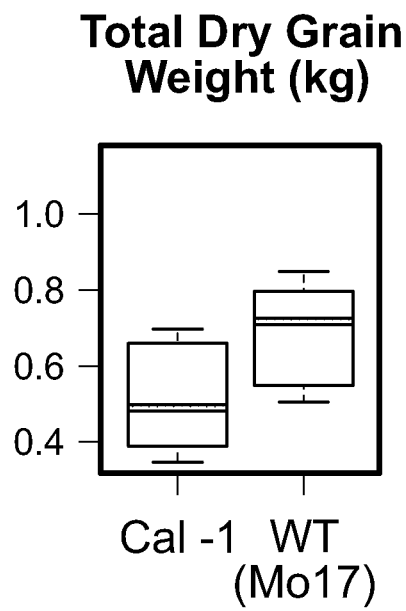
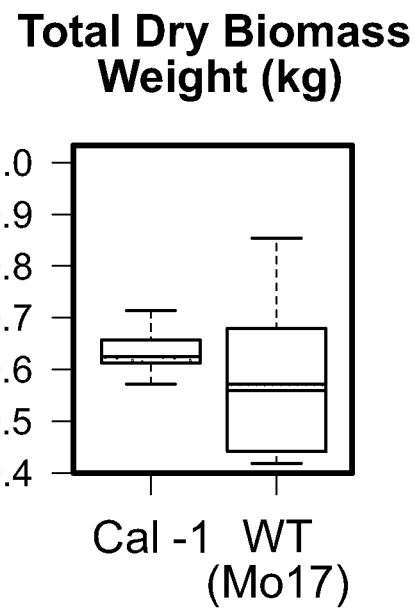
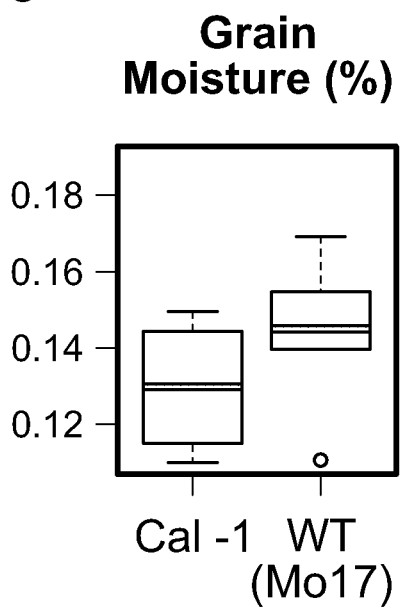
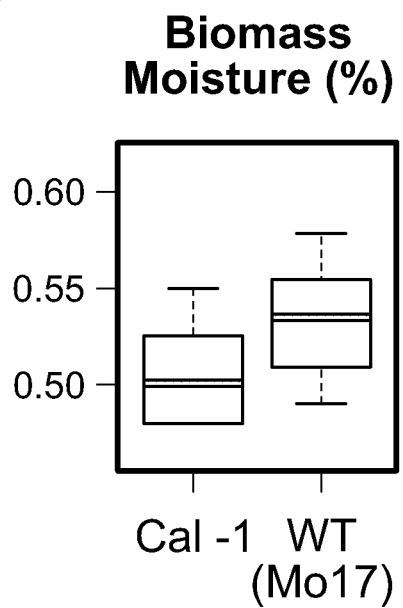
FIG. 11

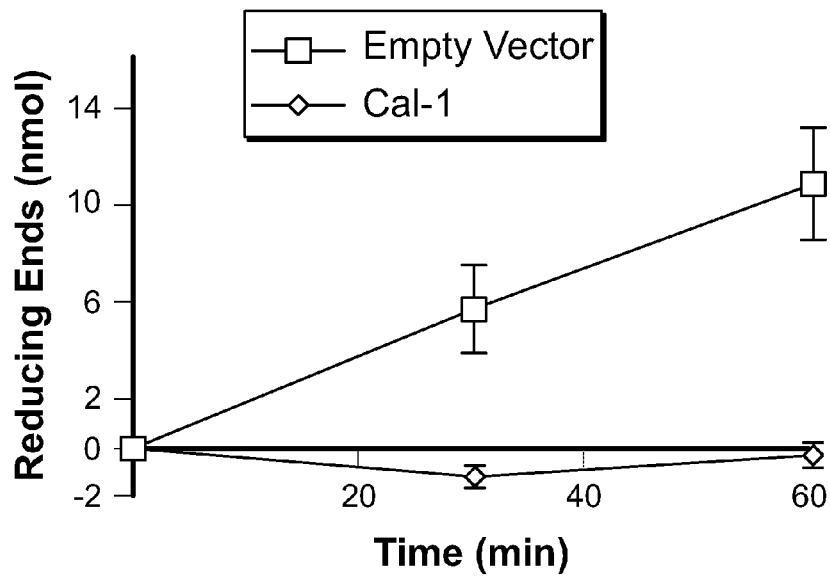
FIG. 12
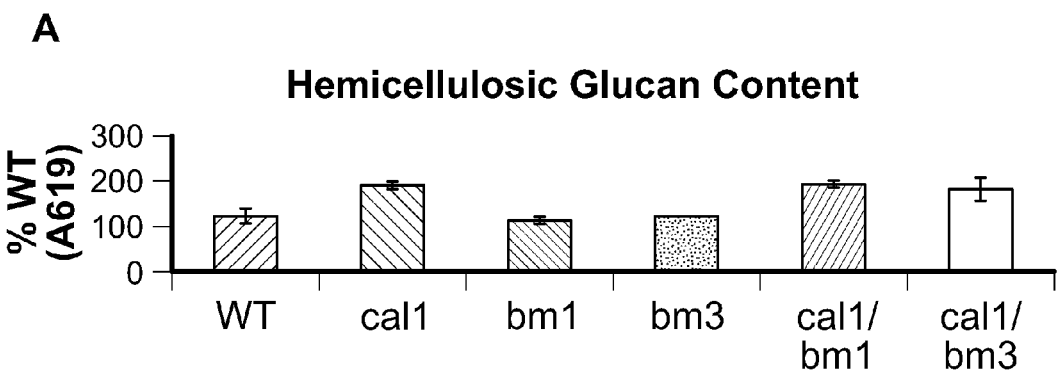
FIG. 13

```
                                             ┌─────────────────────────────────────────────Section 1
                              (1) 1        10        20        30        46
       AC159612.1_FG007       (1) ------------------------------MAQLLRDNGIKKVKLFDA
         GRMZM2G020898        (1) -----------LGVNWGTQATHPL-PPKAVVQVLRDNGIKKVKLFDA
         GRMZM2G078566        (1) -------------NWGTMATHQL-PPATVVRMLEDNGIRKVKLFDA
         GRMZM2G083599        (1) ------------------------KGLAG------TSIET ┐
      GRMZM2G083599(2)        (1) ------------------------KGLAG------TSIET ┤CAL1
         GRMZM2G005798        (1) PAMADDDIVEVGVNWGSQLSHPL-LPGSMVKMLKANRIAPVKMFDA
         GRMZM2G310739        (1) -----------GVNWGTMMSHPI-HPSAVVEMLRANGVDRVKLFDA
       AC217887.3_FG004       (1) ------------------------------VRLLRDNGFDKVKLFEA
         GRMZM2G097207        (1) -----------GANWGTQASHPL-PPETVVRMLKDNGFQKVKLFDA
         GRMZM2G152638        (1) -----------GVNWGTVSNHRA-PPGVVVDLMRANRISKVKLFNA
       GRMZM2G335111@11       (1) -----------GTCHGRVGSNL-PPPSAAAALLK-RNGITKARLFLP
       GRMZM2G014723@16       (1) -----------GVCYGMSANDL-PAASTVVSMYK-ANGISAMRLYAP
     GRMZM2G137535(2)@2       (1) -----------GVCYGMSANNL-PAASTVVSMYK-ANGISAMRLYAP
        GRMZM2G137535@1       (1) -----------GVCYGMSANNL-PAASTVVSMYK-ANGISAMRLYAP
        GRMZM2G041961@4       (1) -----------GVSYGMSGDNL-PPASTVVGMYK-DNGIPLMRIYAP
      GRMZM2G019185(2)@8      (1) -----------VGVCYGTSGDNL-PPASAVVGMLR-DNGFTVVRLYWP
        GRMZM2G019185@7       (1) -----------VGVCYGTSGDNL-PPASAVVGMLR-DNGFTVVRLYWP
        GRMZM2G088951@3       (1) -----------GVNYGMVANNL-PAPEQVVSMYK-AKNISYVRLFHP
        GRMZM2G380561@14      (1) -----------GVNYGMLANNL-PAPEQVVSMYK-AKNISYVRLFHP
        GRMZM2G591605@15      (1) -----------GVNYGTLASNL-PSPDKVIALCK-AKGITDVRLFHP
        GRMZM2G061403@13      (1) -----------GVCYGVLGSGL-PSKSDVVQLYK-SNGIASMRFYFA
        GRMZM2G125032@5       (1) -----------GVCYGTLGNNL-PSSSDVVQLYR-SKGIKGMRIYSP
        GRMZM2G433365@9       (1) -----------HGVCYGMTADDL-PPPSEVVQLYK-SNGIANMRVYSP
        GRMZM2G062600@17      (1) -----------GVCYGMNGDDL-PSASDVVQLYK-DNGIDSMRIYSP
        GRMZM2G065585@6       (1) -----------GVCYGVNGDNL-PPASDVVQLYQ-SNGINLMRIYFP
        GRMZM2G123107@12      (1) ------------------------------------MRIMSP
         GRMZM2G000959        (1) -----------GVNYGTLGDNL-PPHRGMELAR-SAGAVSVRFYDA
         GRMZM2G179354        (1) -----------GINYGTVADDL-PSASRSVQLLR-AAGASAVKIYDA
         GRMZM2G458164        (1) -----------GVNYGRVADDL-PSPWRSVELLR-AAGAGSVKIYDA
         GRMZM2G046459        (1) -----------VGVNYGRVANNL-PNPAAVVQLLK-QQGMAQVKLYDA
        GRMZM2G114140@10      (1) -----------VGVSYGRLGNDL-PGTASVVKLLK-KSGITSVRLYDA
         GRMZM2G454550        (1) -----------VGVNYGRVANDL-PDPASVVQLLK-QSGITMVRLYDA
      GRMZM2G454550(2)        (1) -----------VGVNYGRVANDL-PDPASVVQLLK-QSGITMVRLYDA
         GRMZM2G431039        (1) -----------VGVNYGMVANDL-PNPASVVQLLK-QNGITMVKIYDA
```

FIG. 14

```
    GRMZM2G005082  (1) ---------IGVCYGRNADDLPAPDKVAQLIQ-QQSIKYVRIYDT
 GRMZM2G005082(2)  (1) ---------IGVCYGRNADDLPAPDKVAQLIQ-QQSIKYVRIYDT
    GRMZM2G008627  (1) -------MAGINYGRIADNLPPPEVVMRLLK-LARIRNVKIYDA
    GRMZM2G117872  (1) ---------GINYGRIADNLPPPEVVMRLLK-LARIRNVKIYDA
    GRMZM2G042870  (1) ---------GVNYGRIANNLPSPDKVMELLR-RAKIRNVKIYDS
    GRMZM2G019619  (1) ---------FGINYGQIANNLPQPTQVSGLLQ-SLNVNRVKLYDT
    GRMZM2G127117  (1) ---------FGINYGQIANNLPDPTQVATLLR-SMNVNKVKLYDA
    GRMZM5G805609  (1) ---------FGINYGQIANDLPDPAQVATLLQ-SMGVNKVKLYDA
 GRMZM5G805609(2)  (1) ------------------------------MGVNKVKLYDA
    GRMZM2G076584  (1) ---------MGINYGQIADNLPSPARMSYLVR-SMQVSKVKLYDA
 GRMZM2G076584(2)  (1) ---------MGINYGQIADNLPSPARMSYLVR-SMQVSKVKLYDA
    GRMZM2G030850  (1) ---------LGISYGRVGNNLPAATSVPQIVA-SLGVGRVRLYDA
 GRMZM2G030850(2)  (1) ---------LGISYGRVGNNLPAATSVPQIVA-SLGVGRVRLYDA
    GRMZM2G172537  (1) ---------LGINYGRVGNNLPPPQSVMPLLE-GLGIGRVRMYDA
    GRMZM2G478892  (1) ---------LGINYGQVADNLPPPQAALVLLR-ALNATRVKLYDA
    GRMZM2G148400  (1) ---------LGINYGQVANNLPPPAQVVQLLS-SLRIGKVRIYDV
    GRMZM2G012758  (1) ------------------------------STSIAKIRLYEP

GRMZM2G096591  (1) ---------IGINYGEVADNLP-PPSSTARLVQSTTITKVRLYGT
 GRMZM2G096591(2)  (1) ---------IGINYGEVADNLP-PPSSTARLVQSTTITKVRLYGT
    GRMZM2G046101  (1) ---------IGVNYGEVADNLP-SPDKTARLLKSTSISKVRLYGV
    GRMZM2G064202  (1) ---------IGVNYGTRGTTLPAPADVARFLARDTIFDRVRLLDA
    GRMZM2G111143  (1) ---------IGVNYGANADNLPSPAAVAAFLTKSTTIDRVKLFDA
 GRMZM2G111143(2)  (1) ---------IGVNYGANADNLPSPAAVAAFLTKSTTIDRVKLFDA
 GRMZM2G111143(3)  (1) ---------IGVNYGANADNLPSPAAVAAFLTKSTTIDRVKLFDA
    GRMZM2G111324  (1) ---------IGVNIGTAMSSVPAPTQITTLLR-SQNIRHVRLYDA
 GRMZM2G111324(2)  (1) ------------------------PAPTQITTLLR-SQNIRHVRLYDA
    GRMZM5G824920  (1) ---------IGVNIGTAMSSVPAPTQITTLLR-SQNIRHVRLYDA
    GRMZM2G325008  (1) ---------VGVTIGTQVTNLLSPSDLASFLR-AQRITRVRLYDA
 GRMZM2G325008(2)  (1) ---------VGVTIGTQVTNLLSPSDLASFLR-AQRITRVRLYDA
 GRMZM2G325008(3)  (1) ---------VGVTIGTQVTNLLSPSDLASFLR-AQRITRVRLYDA
 GRMZM2G325008(4)  (1) ---------VGVTIGTQVTNLLSPSDLASFLR-AQRITRVRLYDA
 GRMZM2G325008(5)  (1) ---------VGVTIGTQVTNLLSPSDLASFLR-AQRITRVRLYDA
        Consensus  (1)          IGVNYG VA NLP P  VV LLR S  I KVRLYDA
```

```
GRMZM2G005082      (36)  NIDVIKAFAN--TGVELMVGVPNS-DLLAFAQYQ---SNVDTWLKN
GRMZM2G005082(2)   (36)  NIDVIKAFAN--TGVELMVGVPNS-DLLAFAQYQ---SNVDTWLKN
GRMZM2G008627      (37)  EHKVLDAFRG--TGLNLVVAIPNE-FLKDMAANPAK---AMDWLTE
GRMZM2G117872      (35)  EHKVLDAFRG--TGLNLVVAIPNE-FLKDMAANPAK---AMDWLTE
GRMZM2G042870      (35)  DHSVLDAFKG--SGTNLVIAIPNE-LVKDMAANTSR---SMDWLNQ
GRMZM2G019619      (36)  DPIVLTAFAG--TGVEFLIGN----DDLYNLTDARK---ARAWVAQ
GRMZM2G127117      (36)  DPRVLTAFAN--TGVEFLIAVGNE-NLQTMAGSPAA---ARQWVAA
GRMZM5G805609      (36)  DPRVLTAFAN--TGVGFTIAVGNE-DLQAMAASPDA---ARRWVAA
GRMZM5G805609(2)   (12)  DPRVLTAFAN--TGVGFTIAVGNE-DLQAMAASPDA---ARRWVAA
GRMZM2G076584      (36)  DPYVLSAFVD--TDVEFVVGIGN--ENVSAMVEPAA---ARAWVER
GRMZM2G076584(2)   (36)  DPYVLSAFVD--TDVEFVVGIGN--ENVSAMVEPAA---ARAWVER
GRMZM2G030850      (36)  DSTTIRAFAN--TGVELVVGVPDE-CLATVSTPTG----AASWVRS
GRMZM2G030850(2)   (36)  DSTTIRAFAN--TGVELVVGVPDE-CLATVSTPTG----AASWVRS
GRMZM2G172537      (36)  DPTVLRAFAR--TGVELIVGVPDE-CLAAVADPSG----AAQWLKE
GRMZM2G478892      (36)  DARVLRAFAG--SGVDFTVGVPDR-LVPRLAADRGA---AAAWVRG
GRMZM2G148400      (36)  NPQVLTAFAG--TGIEVWTVPDD-LVPGMASSASQ---ALQWVSA
GRMZM2G012758      (13)  QPDLVAALAG--SNISILLGIPNG-AVPNLASSP----AAAASWAAA

GRMZM2G096591      (36)  DPAITSAFSG--TGVSLLGATNG-DIANLASSP----AAAAAWVAA
GRMZM2G096591(2)   (36)  DPAITSAFSG--TGVSLLGATNG-DIANLASSP----AAAAAWVAA
GRMZM2G046101      (36)  DAGLIRALAG--SGTSVVVGVANG-EIPTLAADP----AAASRWLAA
GRMZM2G064202      (37)  DPVLLRAFAG--TGLAVDVTVPNG-WPHLLN-----LTFARRWVRD
GRMZM2G111143      (37)  NPAFLDAFAANAPSIALAVSIPNS-ALPSFADRSTGLDAARGWVRD
GRMZM2G111143(2)   (37)  NPAFLDAFAANAPSIALAVSIPNS-ALPSFADRSTGLDAARGWVRD
GRMZM2G111143(3)   (37)  NPAFLDAFAANAPSIALAVSIPNS-ALPSFADRSTGLDAARGWVRD
GRMZM2G111324      (36)  DPAMLAALSN--TGLRVTVSVPNE-QLLAIGNSN---ATAANWVAR
GRMZM2G111324(2)   (24)  DPAMLAALSN--TGLRVTVSVPNE-QLLAIGNSN---ATAANWVAR
GRMZM5G824920      (36)  DPAMLAALSN--TGLRVTVSVPNE-QLLAIGNSN---ATAANWVAR
GRMZM2G325008      (36)  DPRLLSALAA--SGVRAIVGVPND-ELLALGSSP---ATAASWVSR
GRMZM2G325008(2)   (36)  DPRLLSALAA--SGVRAIVGVPND-ELLALGSSP---ATAASWVSR
GRMZM2G325008(3)   (36)  DPRLLSALAA--SGVRAIVGVPND-ELLALGSSP---ATAASWVSR
GRMZM2G325008(4)   (36)  DPRLLSALAA--SGVRAIVGVPND-ELLALGSSP---ATAASWVSR
GRMZM2G325008(5)   (36)  DPRLLSALAA--SGVRAIVGVPND-ELLALGSSP---ATAASWVSR
      Consensus    (47)  D  VL ALAG  TGI VVVGVPN   L   AAS       A WV
```

FIG. 14 (Cont.)

```
                                                                    Section 3
                    (93) 93      100       110       120        138
   AC159612.1_FG007  (42) LVPAVALDGATQP--CRYWAVG----------------------
        GRMZM2G020898 (76) NVRRYDFDGGVT---IKYWAVG----------------------
        GRMZM2G078566 (72) NVSRYNFDGGVN---IKYWAVG----------------------
        GRMZM2G083599 (35) NVTKYTFDGGVN---IKQVALGPSARVYIYAVHRHWHGPVRFSAGA ⎫
     GRMZM2G083599(2) (35) NVTKYTFDGGVN---IKFWAVG---------------------- ⎬ CAL1
        GRMZM2G005798 (86) NVTAYG---DKLK--IKYWAVG----------------------
        GRMZM2G310739 (75) NVTANIN--AGVD--VRYWAVG----------------------
   AC217887.3_FG004  (58) NVSTYVSK-YGVD--IRYWAVG----------------------
        GRMZM2G097207 (76) NVSSYLN--DGVS--IRYWAVG----------------------
        GRMZM2G152638 (76) NVSRYVGR-SGVG--IRYIAVG----------------------
      GRMZM2G335111@11 (77) AVLAHAPAER-----VRCLAVGNEVLYNN---------------
      GRMZM2G014723@16 (76) NIQ-AYPSVS-----FRHVCVGNEVAG-----------------
   GRMZM2G137535(2)@2 (76) NIQ-AYPSVS-----FRYVCVGNEVAG-----------------
      GRMZM2G137535@1 (76) NIQ-AYPSVS-----FRYVCVGNEVAG-----------------
      GRMZM2G041961@4 (76) NIQ-AYPKVA-----FRCVCVGNEVEG-----------------
   GRMZM2G019185(2)@8 (76) NVQ-AHPAVA-----FRYVVVGNEVPL-----------------
      GRMZM2G019185@7 (76) NVQ-AHPAVA-----FRYVVVGNEVPL-----------------
      GRMZM2G088951@3 (76) NVQPFAGAVQ-----FRYINAGNEVIPG----------------
      GRMZM2G380561@14 (76) NVQPFAGAVQ-----FRYINAGNEVIPG----------------
      GRMZM2G591605@15 (76) YVRPFAGAVR-----FRYVAAGNEVPG-----------------
      GRMZM2G061403@13 (76) NVQAYYPDVD-----IRYVVGNEVVP------------------
      GRMZM2G125032@5 (78) NVRPYYPAVG-----IKYWAVGNEVQG-----------------
      GRMZM2G433365@9 (76) NVRPYHQDVN-----ILYIAVGNEVDAA----------------
      GRMZM2G062600@17 (76) YVL-AFPAVQ-----FRYIAVGNEVVA-----------------
      GRMZM2G065585@6 (76) NVQ-AFPSVS-----FRYIAVGNEASG-----------------
      GRMZM2G123107@12 (42) NLQPYKDDVS-----FKYIAVGNEVEG-----------------
        GRMZM2G000959 (76) TLLPERGNPR-----LRYLFVGNEFLSN-PT-------------
        GRMZM2G179354 (76) NLAPHIPATR-----VAHLLVGNEVLSNRAI-------------
        GRMZM2G458164 (76) NLVPYYPATR-----VKFLLVGNEILSDLSI-------------
        GRMZM2G046459 (76) NWAAYHPATQ-----IQGIAVGNEVFAS----------------
      GRMZM2G114140@10 (76) NWAAYYPATQ-----IHAVAVGNEVFEE----------------
        GRMZM2G454550 (76) NVAAFYPATH-----IHCVAVGNEVFDS----------------
     GRMZM2G454550(2) (76) NVAAFYPATH-----IHCVAVGNEVFDS----------------
        GRMZM2G431039 (76) NVKKYLPRTQ-----INAVAVGNEVFDD----------------
```

FIG. 14 (Cont.)

```
GRMZM2G005082    (76) SILPYYPDTM-----ITYITVGAEVTES----------------
GRMZM2G005082(2) (76) SILPYYPDTM-----ITYITVGAEVTES----------------
GRMZM2G008627    (77) NVQPYYPSTR-----IVGITVGNEVLGGQD--------------
GRMZM2G117872    (75) NVQPYYPSTR-----IVGITVGNEVLGGQD--------------
GRMZM2G042870    (75) NVQPYLPQTR-----IVGITVGNEVLGGQD--------------
GRMZM2G019619    (73) HVQPFLPSTR-----ITCITVGNEVLSGKD--------------
GRMZM2G127117    (76) NVRPVIPATR-----ITCVTVGNEVFSGND--------------
GRMZM5G805609    (76) NVQPYVPATR-----ITCVTVGNEVLSGND--------------
GRMZM5G805609(2) (52) NVQPYVPATR-----ITCVTVGNEVLSGND--------------
GRMZM2G076584    (75) HVQPYLPGTR-----ITCITVGNEVLKGND--------------
GRMZM2G076584(2) (75) HVQPYLPGTR-----ITCITVGNEVLKGND--------------
GRMZM2G030850    (75) NLSPALPATK-----IAFLTVGNEVLTGVN--------------
GRMZM2G030850(2) (75) NLSPALPATK-----IAFLTVGNEVLTGVN--------------
GRMZM2G172537    (75) NVAPFLPDTK-----ISVLAVGNEVLTGAN--------------
GRMZM2G478892    (76) SLLPHLPATS-----ITAVTVGNEVLSGTD--------------
GRMZM2G148400    (76) SLRPYFPATR-----VTGIAVGNEVFTGDD--------------
GRMZM2G012758    (53) NLPTTLP--------VSSISVGNELLNSG---------------

GRMZM2G096591    (76) HLPASSPA-------VSTVSVGNEVLFA----------------
GRMZM2G096591(2) (76) HLPASSPA-------VSTVSVGNEVLFA----------------
GRMZM2G046101    (76) NVLPFVPA----TTISAVAVGNEVLESG----------------
GRMZM2G064202    (76) NVTPYAGA-T---NISRLLVGDEVT-TEA---------------
GRMZM2G111143    (82) NLSPHVSAGA---NITLLMAGNEVLGPTV---------------
GRMZM2G111143(2) (82) NLSPHVSAGA---NITLLMAGNEVLGPTV---------------
GRMZM2G111143(3) (82) NLSPHVSAGA---NITLLMAGNEVLGPTV---------------
GRMZM2G111324    (76) NVAAHFPAVN-----ITAIAVGSEVLSA----------------
GRMZM2G111324(2) (64) NVAAHFPAVN-----ITAIAVGSEVLSA----------------
GRMZM5G824920    (76) NVAAHFPAVN-----ITAIAVGSEVLSA----------------
GRMZM2G325008    (76) RVVPFAGVNSSTPNVVSAIAVGDEVPTA----------------
GRMZM2G325008(2) (76) RVVPFAGVNSSTPNVVSAIAVGDEVPTA----------------
GRMZM2G325008(3) (76) RVVPFAGVNSSTPNVVSAIAVGDEVPTA----------------
GRMZM2G325008(4) (76) RVVPFAGVNSSTPNVVSAIAVGDEVPTA----------------
GRMZM2G325008(5) (76) RVVPFAGVNSSTPNVVSAIAVGDEVPTA----------------
      Consensus  (93) NV PY PA       I  VAVGNEV
```

FIG. 14 (Cont.)

```
                                                                    Section 4
                        (139) 139      150       160       170        184
       AC159612.1_FG007  (62) ----------------NEPFLAAYNGTFDKVTFPALQNIQNALNE
          GRMZM2G020898  (95) ----------------NEPFLESYNGSFINVTLPALKNMQNALND
          GRMZM2G078566  (91) ----------------NEPFLSSFNGTFLNVTLPALQNIQRALND
          GRMZM2G083599  (78) ETFSIVRVRPSRFVAVGNEPFLRAYNGSFDHVTVPALRNIQRALDE ⎫
       GRMZM2G083599(2)  (54) ----------------N--EPFLRAYNGSFDHVTVPALRNIQRALDE ⎬ CAL1
          GRMZM2G005798 (103) ----------------NEPFLKAYNGSFMKTTFPALKNIQKALDE
          GRMZM2G310739  (93) ----------------NEPFLKSYNGSFINITFPALKNMQRALDE
       AC217887.3_FG004  (77) ----------------NEPFLKSYKGKFEAATLPAMQNMQAALVK
          GRMZM2G097207  (94) ----------------NEPFLETYNGSFLQSTFPALRNIQGALIK
          GRMZM2G152638  (95) ----------------NEPFLTSYQGQFQSYLIPAMTNIQQSLVK
       GRMZM2G335111@11 (101) ------------------------QFYAPHLVPAMRNLHAALAT
       GRMZM2G014723@16  (97) ------------------------GAARNLAPAMENVHAALAA
    GRMZM2G137535(2)@2  (97) ------------------------GAAQDLAPAMENVHAALAA
       GRMZM2G137535@1  (97) ------------------------GAAQDLAPAMENVHAALAA
       GRMZM2G041961@4  (97) ------------------------GAAQSLVPAMENVRAALVA
    GRMZM2G019185(2)@8  (97) ------------------------EQAPLLVPAMENVHAALAA
       GRMZM2G019185@7  (97) ------------------------EQAPLLVPAMENVHAALAA
       GRMZM2G088951@3  (99) ------------------------DAAARVLPAMQNLESALRS
       GRMZM2G380561@14 (99) ------------------------DPAAQVIPAMKNLESALRS
       GRMZM2G591605@15 (99) ------------------------DLASHVLPAMQNLESALRA
       GRMZM2G061403@13 (98) ------------------------GAASVLQAMRNVHAALAS
       GRMZM2G125032@5 (100) ------------------------DDTRSLLPAMRNLDAALAR
       GRMZM2G433365@9  (99) ------------------------AAAQTLLPAMRSIQAALAA
       GRMZM2G062600@17 (97) ------------------------GGR-VLLPAMRNLDRALSA
       GRMZM2G065585@6  (97) ------------------------GDTGSTLPAMKNLNAALAN
       GRMZM2G123107@12 (64) ------------------------GDTQKLLPAMQSLSDALSA
          GRMZM2G000959 (101) ------------------------AKPNWALTVPAMTNAARALRR
          GRMZM2G179354 (102) ------------------------AASTWRGVVPAMANLRRALRA
          GRMZM2G458164 (102) ------------------------ANSTWPHLVPAMENTHRSLRK
          GRMZM2G046459  (99) ------------------------AKNVTAQLVPAMANVHAALAR
       GRMZM2G114140@10 (99) ------------------------AKNLTGQLVPAMSNVHDALVK
          GRMZM2G454550  (99) ------------------------RPDLNSNLVPAMANVHDALAQ
       GRMZM2G454550(2) (99) ------------------------RPDLNSNLVPAMANVHDALAQ
          GRMZM2G431039  (99) ------------------------PNVDKMTLVPAMKNMQKALAD
```

FIG. 14 (Cont.)

```
   GRMZM2G005082  (99) ----------------------PTNVSALVVPAMRNVHTALKK
GRMZM2G005082(2)  (99) ----------------------PTNVSALVVPAMRNVHTALKK
   GRMZM2G008627 (102) ----------------------AGLAQALVGAVLNVHDALKM
   GRMZM2G117872 (100) ----------------------AGLAQALVGAVLNVHDALKM
   GRMZM2G042870 (100) ----------------------QSLYQPLVDAVKNVYDGLKR
   GRMZM2G019619  (98) ----------------------TTAMQSLLPAMQTVYQAVVA
   GRMZM2G127117 (101) ----------------------TATMASLLPAMKAVHAALAD
   GRMZM5G805609 (101) ----------------------TAAMASLLPAMRAVHAALGD
GRMZM5G805609(2)  (77) ----------------------TAAMASLLPAMRAVHAALGD
   GRMZM2G076584 (100) ----------------------SALKASLLPAMQSVYQALTA
GRMZM2G076584(2) (100) ----------------------SALKASLLPAMQSVYQALTA
   GRMZM2G030850 (100) ---------------------SSSLSRYLLPAMRCLHDALAQ
GRMZM2G030850(2) (100) ---------------------SSSLSRYLLPAMRCLHDALAQ
   GRMZM2G172537 (100) ---------------------SSTLSRTLLPAMQSLHGAVAA
   GRMZM2G478892 (101) ----------------------AAMHRALLPAMEALHAAVAA
   GRMZM2G148400 (101) ----------------------EQLKASLVPAMRNLHAALAQ
   GRMZM2G012758  (74) ----------------------DPTLAPQLLPAMQNLAALPA

GRMZM2G096591  (97) ----------------------DASLASQLVPAMQNLHDALPP
GRMZM2G096591(2)  (97) ----------------------DASLASQLVPAMQNLHDALPP
   GRMZM2G046101 (100) ----------------------DAALAAALLPAMQNLRAAAAA
   GRMZM2G064202 (100) ----------------------NRTLLLALVPAMQNLHTALVA
   GRMZM2G111143 (108) ----------------------VPDLVVALLPAMRLYQALQL
GRMZM2G111143(2) (108) ----------------------VPDLVVALLPAMRLYQALQL
GRMZM2G111143(3) (108) ----------------------VPDLVVALLPAMRLYQALQL
   GRMZM2G111324  (99) ----------------------QPSAAPLMPAMRYLQNALVA
GRMZM2G111324(2)  (87) ----------------------QPSAAPLMPAMRYLQNALVA
   GRMZM5G824920  (99) ----------------------QPNAAPLMPAMRYLQNALVA
   GRMZM2G325008 (104) ----------------------LPSALPVLLPATRSLAAALAA
GRMZM2G325008(2) (104) ----------------------LPSALPVLLPATRSLAAALAA
GRMZM2G325008(3) (104) ----------------------LPSALPVLLPATRSLAAALAA
GRMZM2G325008(4) (104) ----------------------LPSALPVLLPATRSLAAALAA
GRMZM2G325008(5) (104) ----------------------LPSALPVLLPATRSLAAALAA
       Consensus (139)                            LLPAMRNLH AL
```

FIG. 14 (Cont.)

———————————————————————————————————————Section 5
```
                          (185)  185    190       200       210       220       230
       AC159612.1_FG007    (91)  AGLGD--TVKATVPLNADMYMSPKDNPVPSAGRMCKFPE-------
          GRMZM2G020898   (124)  AGIGD--RIKATVPLNADMYNSPRSNPVPSAGRFRADIAG-LMADM
          GRMZM2G078566   (120)  AGFGD--TLKATVPLNADMYNSPKDNLVPSAGRFRPDIAG-LMTEL
          GRMZM2G083599   (124)  AGHGA--AVKATVPVNADMYDSPASNPVPSAGRFRSDVAR-VMADM
       GRMZM2G083599(2)    (83)  AGHGA--AVKATVPVNADMYDSPASNPVPSAGRFRSDVAR-VMADM  }CAL1
          GRMZM2G005798   (132)  AGVGN--TVKAVVPLNADMYVSPDDK--PSSGAFRPDING-LMTDM
          GRMZM2G310739   (122)  AGFGQ--HIKVVVPLNADIYSSPENKPVPSAGTFRKDINT-LMVDL
       AC217887.3_FG004   (106)  AGLAR--QMHMIVPLNADMYESGDGR--PSSGDFRPDIAG-LMVSL
          GRMZM2G097207   (123)  AGLGN--QVKVTCPLNADMYSSITSK--PSDGDFRTDIHD-LMLT
          GRMZM2G152638   (124)  ANLAS--YVKLVVPCNADAYQSASVP---SQGVFRTELTQ-LMTQL
        GRMZM2G335111@11  (121)  LGLDG--RVKVSSAHASSMLAAS---YPPSAGAFDAASLP-VIRPM
        GRMZM2G014723@16  (116)  AGLGH---IKVTTSVSQALLGV--YSPPSAMQFTVE--AQGYMGPV
      GRMZM2G137535(2)@2  (116)  AGLGH---IKVTTSVSQALLGV--YSPPSAAEFTGE--ARGYMGPV
         GRMZM2G137535@1  (116)  AGLGH---IKVTTSVSQALLGV--YSPPSAAEFTGE--ARGYMGPV
         GRMZM2G041961@4  (116)  AGLDG---IKVTTSVSQALLGG--YKPPSAAEFTDE--AQGFMGPV
      GRMZM2G019185(2)@8  (116)  AGLGH---VKVTTAVSQGATAV--HLPPSAGEFTEE--ARSFMGYV
         GRMZM2G019185@7  (116)  AGLGH---VKVTTAVSQGATAV--HLPPSAGEFTEE--ARSFMGYV
         GRMZM2G088951@3  (118)  AGVTG---MPMTTAVATSMLGA--SYPPSQGAFSEA--AASVMAPL
         GRMZM2G380561@14 (118)  AGVAG---MPMTTAVATSMLGA--SYPPSQGAFSEA--ATTVMAPL
         GRMZM2G591605@15 (118)  AGLGG---VRMTTAVSTSMLGT--SYPPSQGAFSDA--ALPSMGPL
         GRMZM2G061403@13 (116)  AGLAGS--VKVSTAVKMDAVD---DSSPPSRGVFRI---DPAAMSPL
         GRMZM2G125032@5  (119)  AGFPG---KCSTSVRFDVVA---NSFPPSSGSFIA----QGYMADV
         GRMZM2G433365@9  (118)  AGLAGS--IKVSTCVRLDVMT---DTFPPSSGAFIA----QPYMVDV
         GRMZM2G062600@17 (115)  AGLADD--IKVSTAVAIDVVG---SSFPPSAGTFIAP--SAGYMARV
         GRMZM2G065585@6  (116)  AGLGGS--IKVSTAVQSDVMT----QGFPPSQGTFFS----QGYMAPL
         GRMZM2G123107@12  (83)  AGLGN---IKVSTAVKMSVIAT--PSSPPSTGAFIAD---PSVMGPL
          GRMZM2G000959   (122)  HGLA---HVKVSTTTLSMNDIGN--TVLPPSAGAFRPEIAEAVMGPM
          GRMZM2G179354   (123)  RGLR---GVKLIGTTLAMDALS---ASYPPSAGAFRGDIAEDVVLPL
          GRMZM2G458164   (123)  RSIS---SVKIIGTTLAMDALADGAFPRPPSAAAFRADIAEAVVRPL
          GRMZM2G046459   (120)  LGLDG--AVKVSSPIALTALASS---YPSSAGAFREDLAQAVMKPM
        GRMZM2G114140@10  (120)  LGLDG--AVKVSTPLAFTALQES---WPPSAGRFRDDIARSVMKPM
          GRMZM2G454550   (120)  LGLAD--AVKVSTPVAFSAMQDS---YPPSAGRFRDDIAQSVMKPM
       GRMZM2G454550(2)   (120)  LGLAD--AVKVSTPVAFSAMQDS---YPPSAGRFRDDIAQSVMKPM
          GRMZM2G431039   (120)  LGLAN--AVKVSTPLAFSAMRDS---FPPSGSRFRDDIAQPVMKPM
```
FIG. 14 (Cont.)

FIG. 14 (Cont.)

```
                                                                    Section 6
                    (231) 231      240       250       260      276
      AC159612.1_FG007 (128) ----AKTGAPFTVNHLPRSSPCSETT----TSPVDFAFFDGGRR--
        GRMZM2G020898 (167) VRFLARNGAPFTVNIYPFLS-LYLNE----HFPLDYAFFDGG----
        GRMZM2G078566 (163) VQFLNQSGAPFTVNIYPFLS-LYDND----DFPLDYAFFDGTG---
        GRMZM2G083599 (167) VRFLNRSGAPLTVNIYPFLS-LYGND----DFPLDYAFFDGG----  ⎫
     GRMZM2G083599(2) (126) VRFLNRSGAPLTVNIYPFLS-LYGND----DFPLDYAFFDGG----  ⎬CAL1
        GRMZM2G005798 (173) VKFLHDHGAPFVVNIYPFLS-LYQSD----NFPFLAFFDGG----   ⎭
        GRMZM2G310739 (165) VNYLHANDAPFVVNIYPFLS-LYQNP----NFPLNFSFFDGA----
      AC217887.3_FG004 (147) VRFLLDNGGVLTINIYPFLS-LYADP----NFPVDYAYFPSPGARP
        GRMZM2G097207 (164) VKFLSDNGGAFTVNIYPFIS-LYIDP----NFPVDYAFFEG-----
        GRMZM2G152638 (164) AAFLSSSGAPFVVNIYPFLS-LYQNS----DFPQDYAFFEGS----
     GRMZM2G335111@11 (161) LRFLADTGAPFMVNAYPFISHVNDPAN----MQLAYALFGAG----
     GRMZM2G014723@16 (155) LKFLARTGSPLMANIYPYLAWAYNPS----AMDMSYALFTSSG---
    GRMZM2G137535(2)@2 (155) LQFLARTGSPLMANIYPYLAWAYNPS----AMDMSYALFTSSG---
      GRMZM2G137535@1 (155) LQFLARTGSPLMANIYPYLAWAYNPS----AMDMSYALFTSSG---
      GRMZM2G041961@4 (155) LRFLARTGAPLMASVPYFTYATNPA----AMDLSYALFTAPG---
   GRMZM2G019185(2)@8 (155) VAFLARTRAPLLANLYPYFVYTLGLG----HLGMDFALFTAPG---
      GRMZM2G019185@7 (155) VAFLARTRAPLLANLYPYFVYTLGLG----HLGMDFALFTAPG---
      GRMZM2G088951@3 (157) VSYLSSKGAPLLVNVYPYFAYSSSGG----QVALGYALLS-ADAGA
      GRMZM2G380561@14 (157) VSYLSSRGAPLLVNVYPYFAYSGSGG----QVALGYALLSGAGAGA
      GRMZM2G591605@15 (157) ASFLAPRSTPLLVNVYPYFAYSADPA----SMSLDYALLRSDSGGG
      GRMZM2G061403@13 (154) AQFLAANGAPLLANVYPYFAYQYSDG----GLDLDYALFQPSSTT-
      GRMZM2G125032@5 (155) ARYLAGTGAPLLANVYPYFAYRDNPR----DISLGYATFQPGT-T-
      GRMZM2G433365@9 (155) ARFLAAAGAPLLANVYPYFAYRGSPG----DVGLGYALFQPGA-A-
      GRMZM2G062600@17 (154) ARYQSTGAPLLANLYPYYSYISDPG----AMDLNYALLAMPAGT-
      GRMZM2G065585@6 (152) AQYQSTGAPLLCNVYPYFSYIGNPA----QLDLSYALFTSPG---
      GRMZM2G123107@12 (121) VRFLAGVGSPLLANLYPYFAYRDAAG----TLDLNYALFQPST-T-
        GRMZM2G000959 (163) LAFLQRTGSCFLDATYFTWSANHT----IFPLPYALLEPSPG---
        GRMZM2G179354 (163) LRFLNATRSYYFVDAVPYFAWAGNRD----AISLDYALFQGAAG--
        GRMZM2G458164 (166) LHFLNGTNSYYFVDAVPYFVWADNNL----TMSLDYALFQGGR---
        GRMZM2G046459 (161) LDFLAQTGSYLMVNAYPFFAYSGNAG----DISLDYALFRPN----
     GRMZM2G114140@10 (161) IDFLERTGSYLTVNAYPFFAYAEEPD----KISLDYALGNSN----
        GRMZM2G454550 (161) LGFLDRTGSYLTINIYPYLAYAEHPD----QISLDYALGNPNPGVR
     GRMZM2G454550(2) (161) LGFLDRTGSYLTINIYPYLAYAEHPD----QISLDYALGNPNPGVR
        GRMZM2G431039 (161) LQLLQRTGSFLTVNLYPCLTQMQQPD----DIPLDYALG---N--A-
```

FIG. 14 (Cont.)

```
   GRMZM2G005082 (160) LQFLVENQAPFMVDLYPYMAYQNSRS----NMSLNYALFSPE--S-
GRMZM2G005082(2) (160) LQFLVENQAPFMVDLYPYMAYQNSRS----NMSLNYALFSPE--S-
   GRMZM2G008627 (162) LDFFSKTGAPFYVNAYPFLAYMSDPS----HIDINYALFKPN----
   GRMZM2G117872 (160) LDFFSKTGAPFYVNAYPFLAYMSDPS----HIDINYALFKPN----
   GRMZM2G042870 (160) LDFFAMIGSPFYVNAYPFLAYISDPE----HIDINYALFKPN----
   GRMZM2G019619 (158) LNFHAEVGSPFLVNAYPFFAYKASPG----SVSLPYVLFFPNP---
   GRMZM2G127117 (161) LDFHAQTGSPFLVNAYPFFAYKASPG----SVSLPYVLFFPNP---
   GRMZM5G805609 (161) LDFHAQTGSPFLVNAYPFFSYKASPGPGPGGVSLPYALFQPNP---
GRMZM5G805609(2) (137) LDFHAQTGSPFLVNAYPFFSYKASPGPGPGGVSLPYALFQPNP---
   GRMZM2G076584 (160) LAFLSAARSPFLINCYPYFAYKADPG----NVPLEYVLFQPDA---
GRMZM2G076584(2) (160) LAFLSAARSPFLINCYPYFAYKADPG----NVPLEYVLFQPDA---
   GRMZM2G030850 (161) LDFHARAGSPFLVNAYPYFAYAEEPT----GVELEYALLEPGH---
GRMZM2G030850(2) (161) LDFHARAGSPFLVNAYPYFAYAEEPT----GVELEYALLEPGH---
   GRMZM2G172537 (161) LDYHARTGSPFLVNAYPYFAYSSDPR----GVQLDYALLDPGF---
   GRMZM2G478892 (161) LGFLAPHGRAVPG---------------------------------
   GRMZM2G148400 (161) LRFLAETSSPFWVNAYPYFAYKDDPT----KVSLDYALSNPSH---
   GRMZM2G012758 (132) LDFLHQNGAPFMINPYPYFAYASDTR----PETLAFCLFQPN----

GRMZM2G096591 (155) LAFLSKTGSPFLINPYPYFAYLSDPR----PETLAFCLFQPN----
GRMZM2G096591(2) (155) LAFLSKTGSPFLINPYPYFAYLSDPR----PETLAFCLFQPN----
   GRMZM2G046101 (162) LGFLSKTGAPFMVNPYPWFAYQSDPR----PETLAFCLFQPN----
   GRMZM2G064202 (162) LRFLRATGAPFMVNAYPFYALAN-------DSSLDFALFRVN----
   GRMZM2G111143 (170) LRFHNDTGSPFMVNAYPYFSYN--------AATLDYAVFRPN----
GRMZM2G111143(2) (170) LRFHNDTGSPFMVNAYPYFSYN--------AATLDYAVFRPN----
GRMZM2G111143(3) (170) LRFHNDTGSPFMVNAYPYFSYN--------AATLDYAVFRPN----
   GRMZM2G111324 (160) LRFLQSTGSPLMLNWYPYYDYMRSNG----VTPLDYALFRPLPPN-
GRMZM2G111324(2) (148) LRFLQSTGSPLMLNWYPYYDYMRSNG----VTPLDYALFRPLPPN-
   GRMZM5G824920 (160) LKFLQSTGSPLMLNWYPYYDYMRSNG----VTPLDYALFRPLPAN-
   GRMZM2G325008 (165) LAHLANTSAPLMLNLYPYYSLMQSKG----VTPLDNALFRPLPPS-
GRMZM2G325008(2) (165) LAHLANTSAPLMLNLYPYYSLMQSKG----VTPLDNALFRPLPPS-
GRMZM2G325008(3) (165) LAHLANTSAPLMLNLYPYYSLMQSKG----VTPLDNALFRPLPPS-
GRMZM2G325008(4) (165) LAHLANTSAPLMLNLYPYYSLMQSKG----VTPLDNALFRPLPPS-
GRMZM2G325008(5) (165) LAHLANTSAPLMLNLYPYYSLMQSKG----VTPLDNALFRPLPPS-
       Consensus (231) L FLA TGAPLLVNIYPYFAY         I LDYALF P
```

FIG. 14 (Cont.)

```
                                                                        Section 7
                    (277) 277      290       300       310     322
   AC159612.1_FG007  (164) -------AAGWDPGSGVSYTNVFDANFDTLVAALKSVG--------
      GRMZM2G020898  (204) -------AAPVDDHGVLYTNVFDANFDTLVAALGAVG--------
      GRMZM2G078566  (201) ---------SPVVDNGLQYTNVFDANFDTLVSALAAAG--------
      GRMZM2G083599  (204) -------AGAPVVDGRAVYTNVFDANFDTLVSALKRVG-------- }
   GRMZM2G083599(2)  (163) -------AGAPVVDGRAVYTNVFDANFDTLVSALKRVG-------- } CAL1
      GRMZM2G005798  (210) ---------KNIQDKGGVTYSNVFDANYDTLVHALKKAG--------
      GRMZM2G310739  (202) --------TKPVYDQGMVYTNVFDANFDTLVWSLRKAG--------
   AC217887.3_FG004  (188) --------SQASVQDGNVLYTNVFDANYDTLIAALEKHG--------
      GRMZM2G097207  (200) -------ASSPIVDGSFTYSNVFDANHDTLIWALKKNG--------
      GRMZM2G152638  (201) --------THPVVDGPNVYYDAFDGNFDTLVSALSKIG--------
    GRMZM2G335111@11 (199) --------AAPVQDGALVYTNLFDATVDALVAALEKEGFDG-----
    GRMZM2G014723@16 (194) ----------TVVQDGAYGYQNLFDTTVDAFYLAMASNGGG------
  GRMZM2G137535(2)@2 (194) ----------TVVQDGAYGYQNLFDTTVDAFYVAMGKNGG-------
     GRMZM2G137535@1 (194) ----------TVVQDGAYGYQNLFDTTVDAFYVAMGKNGG-------
     GRMZM2G041961@4 (194) ----------TVLQDGAYEYQNLFDATVDSFYVAMANHGG-------
  GRMZM2G019185(2)@8 (194) ----------TVVQDGEYGYQNLFDATVDALYAAVGRLGVAGG----
     GRMZM2G019185@7 (194) ----------TVVQDGEYGYQNLFDATVDALYAAVGRLGVAGG----
     GRMZM2G088951@3 (198) --------A-SSVTDAGVVYTNVFDAIVDATHAAVEKAGVQ------
     GRMZM2G380561@14 (199) --------A-STVTDGGAVYTNVFDAIVDATHAAVEKAGVQ------
     GRMZM2G591605@15 (199) --------A-VVVADGGASYGNMFDAIVDAVYAALERAGAR------
     GRMZM2G061403@13 (195) ----------VTDPANGLVYTNLFDAMVDAVRAALDKAGA-------
     GRMZM2G125032@5 (195) ----------VRDNGNGLNYNNLFDAMVDAVVAALEKAGA-------
     GRMZM2G433365@9 (195) ----------VRDGGSGLVYTNLFDAMVDSVHAALEKAGA-------
     GRMZM2G062600@17 (195) ----------VVVQDGGYSYDSLFDAMVDCFYSALENAGA-------
     GRMZM2G065585@6 (191) ----------TVVQDGSNAYQNLFDALVDTFVSALQNAGA-------
     GRMZM2G123107@12 (161) ----------VVTDDGGLDYTNLFDAMADAMYSAMEKEGG-------
       GRMZM2G000959 (203) -------FAYHDPGTGLSYANLLDQMLDTAAAAMCRLGYCG------
       GRMZM2G179354 (203) -------SRYVDPGNGLTYTNLLDQMLDAVVAAMGRLGYGN------
       GRMZM2G458164 (205) -------TRYVDPGTGLTYTNLLDEMLDAVVIAMAKLGYGH------
       GRMZM2G046459 (199) -------AGVLDAGNGLKYYSLLDAQLDAVFAAVSRLGEGYNG----
     GRMZM2G114140@10 (199) -------ATGVRDPVTGLVYHSLLDAQLDATYFAMEKLGTSRSSARG
       GRMZM2G454550 (203) VDDDDTGSIALDDDNGVTYHSLLDAQLDATYYAMDAMGFTS------
    GRMZM2G454550(2) (203) VDDDDTGSIALDDDNGVTYHSLLDAQLDATYYAMDAMGFTS------
       GRMZM2G431039 (198) -------QHAVLDGSN--KYYSLLDAQLDATHYAMEALGFGN-----
                                    FIG. 14 (Cont.)
```

```
GRMZM2G005082    (199) -------QDVIDPNTGLVYTNMFDAQVDSIFFALMALNFKT-----
GRMZM2G005082(2) (199) -------QDVIDPNTGLVYTNMFDAQVDSIFFALMALNFKT-----
GRMZM2G008627    (200) -------AGLVDPKTGLHYNNMFDAQVDAAYFALEAAG---YSG--
GRMZM2G117872    (198) -------AGLVDPKTGLHYNNMFDAQVDAAYFALEAAG---YSG--
GRMZM2G042870    (198) -------KGLIDPNSLHYDNMFDAQVDAAYAALHAAG---YDN--
GRMZM2G019619    (197) -------G-VVDPNTNLTYDNMLYAQIDAVYAAMEAMG---HSD--
GRMZM2G127117    (200) -------G-VRDPSTGLSYDNMLYAQIDAVYAAMKAMG---HTD--
GRMZM5G805609    (204) -------G-VRDPGTGLTYDNMLYAQIDAVYAAMQAAGG---RAD--
GRMZM5G805609(2) (180) -------G-VRDPGTGLTYDNMLYAQIDAVYAAMQAAGG---RAD--
GRMZM2G076584    (199) -------AGVTDASTGLRYDNMLYAQVDSVYAALQKLG---HTD--
GRMZM2G076584(2) (199) -------AGVTDASTGLRYDNMLYAQVDSVYAALQKLG---HTD--
GRMZM2G030850    (200) -------AGVADPGTGLHYTNMLAAQVDAVYHALAAANSAAARA--
GRMZM2G030850(2) (200) -------AGVADPGTGLHYTNMLAAQVDAVYHALAAANSAAARA--
GRMZM2G172537    (200) -------AGVQDPNSRLHYPNLLVAQVDAVYHALAAANTAASRV--
GRMZM2G478892    (174) --------GVADAATGLRYDNMLHAQVDAVRAALCAAN--YGRA--
GRMZM2G148400    (200) -------VGAVDPFIKLQYTSMLYAQVDAVTFAAARLG---YGG--
GRMZM2G012758    (170) -------AGRVDAVSGLTYTNMFDAQLDAIRAALDAKGYSD-----

GRMZM2G096591    (193) -------AGRPDAGSSLTYTNMFDAQVDAVRAALDAKGYKD-----
GRMZM2G096591(2) (193) -------AGRPDAGSSLTYTNMFDAQVDAVRAALDAKGYKD-----
GRMZM2G046101    (200) -------AGRVDGGSKVRYANMFDAQLDAVKSALVRAGYGG-----
GRMZM2G064202    (197) -------DGVMDQGTGLVYGNMLDAQLDAVHSAVRRMGFGD-----
GRMZM2G111143    (204) -------AGVYDPATRLNYTSMFDAQMDAIHTAMKKLGYGG-----
GRMZM2G111143(2) (204) -------AGVYDPATRLNYTSMFDAQMDAIHTAMKKLGYGG-----
GRMZM2G111143(3) (204) -------AGVYDPATRLNPTSMFDAQMDAIHTAMKKLGYGG-----
GRMZM2G111324    (201) -------KEAVDANTLLHYTNVFDAVVDAAYFAMAYLNVTN-----
GRMZM2G111324(2) (189) -------KEAVDANTLLHYTNVFDAVVDAAYFAMAYLNVTN-----
GRMZM5G824920    (201) -------KEAVDANTLLHYTNVFDAVVDAAYFAMAYLNVTN-----
GRMZM2G325008    (206) -------MEMVDPNTLLRYTNVFDAMLDAVRVAVRNLNATGGAG--
GRMZM2G325008(2) (206) -------MEMVDPNTLLRYTNVFDAMLDAVRVAVRNLNATGGAG--
GRMZM2G325008(3) (206) -------MEMVDPNTLLRYTNVFDAMLDAVRVAVRNLNATGGAG--
GRMZM2G325008(4) (206) -------MEMVDPNTLLRYTNVFDAMLDAVRVAVRNLNATGGAG--
GRMZM2G325008(5) (206) -------MEMVDPNTLLRYTNVFDAMLDAVRVAVRNLNATGGAG--
       Consensus  (277)         VVD TGL YTNMFDAQVDAVYAAL LG
```

FIG. 14 (Cont.)

```
                                                                    Section 8
                         (323) 323    330        340       350        368
        AC159612.1_FG007 (195) --HGDMPVWVGEVGWPTDG----------------------D
           GRMZM2G020898 (234) --HGDMPVWVGEVGWPTDG----------------------D
           GRMZM2G078566 (230) --VGGLPVWVGEVGWPTDG----------------------D
           GRMZM2G083599 (235) --LGHLPVMTGEVGWPTDG----------------------D ⎫
        GRMZM2G083599(2) (194) --LGHLPVMTGEVGWPTDG----------------------D ⎬CAL1
           GRMZM2G005798 (240) --VPDLKVTVGLAGWPTDG----------------------N ⎭
           GRMZM2G310739 (232) --VPDMRTIVGEVGWPSDG----------------------D
        AC217887.3_FG004 (219) --LGALPVIVGEIGWPTDG----------------------D
           GRMZM2G097207 (231) --FGNLPVTVGEIGWPTDG----------------------D
           GRMZM2G152638 (231) --YGNLPTATGEIGWPTEG----------------------A
        GRMZM2G335111@11 (232) -----VPVAVTETGWPTAG----------------------H
        GRMZM2G014723@16 (225) ---SGVPLVVSETGWPSGGG----------------------
     GRMZM2G137535(2)@2 (224) ---SGVPLVVSESGWPSGGG----------------------
        GRMZM2G137535@1 (224) ---SGVPLVVSESGWPSGGG----------------------
        GRMZM2G041961@4 (224) ---SGVTLVVSESGWPSAGG----------------------
     GRMZM2G019185(2)@8 (227) ---DGVRVWVSETGWPTAGG----------------------
        GRMZM2G019185@7 (227) ---DGVRVWVSETGWPTAGG----------------------
        GRMZM2G088951@3 (230) ----GLELVVSETGWPSAGG----------------------
        GRMZM2G380561@14 (231) ----GLELVVSETGWPSAGG----------------------
        GRMZM2G591605@15 (231) ----GLELVVSETGWPSGGGG---------------------
        GRMZM2G061403@13 (225) ---GGVDVWVSETGWPSADG----------------------
        GRMZM2G125032@5 (225) ---PNVRVWVSESGWPSAGG----------------------
        GRMZM2G433365@9 (225) ---PDVRVWVSESGWPSAGG----------------------
        GRMZM2G062600@17 (225) ---GNVTVWVSESGWPSAGS----------------------
        GRMZM2G065585@6 (221) ---GNVPVWVSESGWPSAGG----------------------
        GRMZM2G123107@12 (191) ---SGVPLVVSESGWPSGGGGT--------------------
           GRMZM2G000959 (237) -----VGLALAETGWPTAG---------------DLD--Q
           GRMZM2G179354 (237) -----VRLAVSETGWPSGG---------------DAG--E
           GRMZM2G458164 (239) -----VKLATAETGWPNGC---------------DYN--Q
           GRMZM2G046459 (235) -----VRVWVSETGWPSKG---------------DAN--E
        GRMZM2G114140@10 (239) PKSVAPAHVSESGWPSGGKPKRGGRPRPRPRGGGRRLELEQAGG-
           GRMZM2G454550 (244) -----LKAHVGETGHPSGGRP-RPGRRPPR--GGRRHLVAGDDDGY
        GRMZM2G454550(2) (244) -----LKAHVGETGHPSGGRP-RPGRRPPR--GGRRHLVAGDDDGY
           GRMZM2G431039 (231) -----VEAVLGETGCPNKGKI-GKHRPPRRGVGSSRRRLLDDGGSE
```

FIG. 14 (Cont.)

```
       GRMZM2G005082 (233)  ----LKIMITESGWPNKGAVK-------------E
    GRMZM2G005082(2) (233)  ----LKIMITESGWPNKGAVK-------------E
       GRMZM2G008627 (234)  ----MEVRVAETGWASAGDAT-------------E
       GRMZM2G117872 (232)  ----MEVRVAETGWASAGDAT-------------E
       GRMZM2G042870 (232)  ----MEVRVAETGWASSGDQN-------------E
       GRMZM2G019619 (230)  ----LTVRISETGWPSRGDED-------------E
       GRMZM2G127117 (233)  ----VGVRISETGWPSRGDED-------------E
       GRMZM5G805609 (238)  ----VGVTVSETGWPSRGDDD-------------E
    GRMZM5G805609(2) (214)  ----VGVTVSETGWPSRGDDD-------------E
       GRMZM2G076584 (233)  ----VDVKVSETGWPSRGDPD-------------E
    GRMZM2G076584(2) (233)  ----VDVKVSETGWPSRGDPD-------------E
       GRMZM2G030850 (237)  ----VEVRVSETGWPSAGDAN-------------E
    GRMZM2G030850(2) (237)  ----VEVRVSETGWPSAGDAN-------------E
       GRMZM2G172537 (237)  ----VEVRVSETGWPSAGAAN-------------E
       GRMZM2G478892 (208)  ----LEIRVSETGWPSQGDDD-------------E
       GRMZM2G148400 (234)  ----VPVHVSETGWPSKGDAN-------------E
       GRMZM2G012758 (204)  ----VELVIAETGWPYKGDAD-------------E

GRMZM2G096591 (227)  ----VDIVVAETGWPHKGDPD-------------E
    GRMZM2G096591(2) (227)  ----VDIVVAETGWPHKGDPD-------------E
       GRMZM2G046101 (234)  ----VDIVVAETGWPTRGDAG-------------E
       GRMZM2G064202 (231)  ----VDIAVSETGWPSAGEDW-------------E
       GRMZM2G111143 (238)  ----VQIAVGLAGWPTKAEAG-------------Q
    GRMZM2G111143(2) (238)  ----VQIAVGLAGWPTKAEAG-------------Q
    GRMZM2G111143(3) (238)  ----VQIAVGLAGWPTKAEAG-------------Q
       GRMZM2G111324 (235)  ----VPVMVTETGWPHKGDSSS------------E
    GRMZM2G111324(2) (223)  ----VPVMVTETGWPHKGDSSS------------E
       GRMZM5G824920 (235)  ----VPVMVTETGWPHKGDPSS------------E
       GRMZM2G325008 (243)  ----VPILLVTETGWPSYGDRRA-----------E
    GRMZM2G325008(2) (243)  ----VPILLVTETGWPSYGDRRA-----------E
    GRMZM2G325008(3) (243)  ----VPILLVTETGWPSYGDRRA-----------E
    GRMZM2G325008(4) (243)  ----VPILLVTETGWPSYGDRRA-----------E
    GRMZM2G325008(5) (243)  ----VPILLVTETGWPSYGDRRA-----------E
           Consensus (323)       V  VVVSETGWPS G              E
```

FIG. 14 (Cont.)

```
                                                                            Section 9
                        (369) 369       380       390        400        414
       AC159612.1_FG007  (213) KHATNAYAQRFYNGLRRLAAN--AGTPARPNQ--YIEVYLFGLLD
         GRMZM2G020898   (252) RHAKASYAQRFYAGLRRLAAN--TGTPARPGQR-PAEVYLFGLVD
         GRMZM2G078566   (248) KHATAAFAQKFYAGLRKLAAS--AGTPLRPGQ--YIEVYLFSLID
         GRMZM2G083599   (253) RHATAALAERFYAGLQRLAAR--RGTPLRPGA--RIEAYLFGLVD ⎫
       GRMZM2G083599(2)  (212) RHATAALAERFYAGLQRLAAR--RGTPLRPGA--RIEAYLFGLVD ⎬CAL1
         GRMZM2G005798   (258) KYANFKLARRFYDGLRKLAKN--EGTPVRKGK----MEVYLFGLFD
         GRMZM2G310739   (250) KNANTKYAQRFYNGFLKKMTKN--VGTPLRPGR----MEVYLFALID
       AC217887.3_FG004  (237) KNANAANAQRFNQGLFDRLIAG--KGTPRRPQM---PDVYWFALLD
         GRMZM2G097207   (249) RNANAQMAQRFNQGFYTHLASG--RGTPMRPGP---VDAYLFSLID
         GRMZM2G152638   (249) PSANLTAARAFNQGLINRLTSN--KGTPLRPGVP-PADVYLFSLLD
       GRMZM2G335111@11  (247) PAATPQNAAAYNAKIVERAARG--VGTPKRPG--VPVEVFFDLYD
       GRMZM2G014723@16  (242) VQATPANARVYNQYLINHVGRG----TPRHPG---GIETYLFSMFN
      GRMZM2G137535(2)@2 (241) VQATPANARVYNQYLINHVGRG----TPRHPG---AIETYLFSMFN
        GRMZM2G137535@1  (241) VQATPANARVYNQYLINHVGRG----TPRHPG---AIETYLFSMFN
        GRMZM2G041961@4  (241) VAASPENAAIYNQNLINHVGRG----TPRHPG---AIETILFSMFN
      GRMZM2G019185(2)@8 (244) AAASLENARTYNQNLVRHVWKG----TPRRPR---RVEAYYFAMFN
         GRMZM2G019185@7 (244) AAASLENARTYNQNLVRHVWKG----TPRRPR---RVEAYYFAMFN
         GRMZM2G088951@3 (246) EGATVENAAAYNNNVVRHVGGG----TPRRPGK--AVETYLFAMFN
        GRMZM2G380561@14 (247) EGASVENAAAYNNNVVRHVDGG----TPRRPGK--ALETYLFAMFN
        GRMZM2G591605@15 (248) AGASVGNASAYVNNVVRHVGSGR--GTPRRPGK--PVEALIFAMFN
        GRMZM2G061403@13 (242) NGATLDNARTYNQNLIDHASKG----TPRKPG---PMEVYYFAMFN
         GRMZM2G125032@5 (242) FGASVDNARKYNQGLIDHVGRG----TPKRTG---PLETFVFAMFN
         GRMZM2G433365@9 (242) AAASVQNAQAYVQNLVDHVAQG----TPKRPG---PLETYYFAMFN
        GRMZM2G062600@17 (242) DAANTTNCQAYSQNLINHVGQG----TPKRPG---PIEAYLFAIFN
         GRMZM2G065585@6 (238) DAATAANAQTYNQNLINHVGQG----TPKRPG---PIETYLFAMFN
        GRMZM2G123107@12 (210) GAETVDNARTYNQNLINHVGNG----TPKRSG---PLETYLFAMFN
         GRMZM2G000959   (255) FGANVRNAATYNRNLARRLAS--GAGTPRRPGVPVP--AMYFALFN
         GRMZM2G179354   (255) AGANVRNAATYNRNLALRMSN--SPGTPARPGAEVP---VLFSLYN
         GRMZM2G458164   (257) IGGNVHNAAIYNRNLAARMAK--NPGTPVRPGAKMP--VLYFSLYN
         GRMZM2G046459   (253) AGASAANAAAYNGNLARRVLSG-NAGTPRRPDADID--VYLFALFN
        GRMZM2G114140@10 (284) EAASVANAQAYNNYLIKRVLSG-DTGTPYHPDADMD--VYIFSLFN
         GRMZM2G454550   (282) PVASIANAHAYVNNVINRVLSG-NTGTPHRPDADMD--VYIFALFN
        GRMZM2G454550(2) (282) PVASIANAHAYVNNVINRVLSG-NTGTPHRPDADMD--VYIFALFN
         GRMZM2G431039   (271) PEASVANARAYNNYVINRVLSG-NTGTPHRPRADMH--VYIFALFN
```

FIG. 14 (Cont.)

```
      GRMZM2G005082 (251) TGATPDNAQTYNTNLIRHVVND--SGTPAKPGEEID--VYIFSLFN
   GRMZM2G005082(2) (251) TGATPDNAQTYNTNLIRHVVND--SGTPAKPGEEID--VYIFSLFN
      GRMZM2G008627 (252) AGANMENAITYDRNLRKRLFLR--KGTPYRPDRVAK--AYIFALFN
      GRMZM2G117872 (250) AGANMENAITYDRNLRKRLFLR--KGTPYRPDRVAK--AYIFALFN
      GRMZM2G042870 (250) AGASSENARTYNFNLRKRLFLR--TGTPLKPKRPVK--AYIFALFN
      GRMZM2G019619 (248) VGATVANAAAYNGNLMKRIAMG--QGTPLKPHVPVD--VFVFALFN
      GRMZM2G127117 (251) TGATVQNAAAYNGNLMQRVAMS--QGTPLKPNVPVD--VYVFALFN
      GRMZM5G805609 (256) PGATAQNAAAYNGNLMRRVAAG--QGTPLRPAVPVD--VYWFALFN
   GRMZM5G805609(2) (232) PGATAQNAAAYNGNLMRRVAAG--QGTPLRPAVPVD--VYWFALFN
      GRMZM2G076584 (251) AGATPEYARTYIGNLLQRIEMG--QGTPMRPSAPVD--VYWFALFN
   GRMZM2G076584(2) (251) AGATPEYARTYIGNLLQRIEMG--QGTPMRPSAPVD--VYWFALFN
      GRMZM2G030850 (255) TGATPQNAARYNGNVMRLVAQG--KGTPLRPAAPLR--VYMFALFN
   GRMZM2G030850(2) (255) TGATPQNAARYNGNVMRLVAQG--KGTPLRPAAPLR--VYMFALFN
      GRMZM2G172537 (255) TAATPQNAARYNSNAMRLVAEG--KGTPLKPGAPLR--AYWFALFN
      GRMZM2G478892 (226) AGATPENAARYNGNLMRLVAQG--KGTPAAPDEPLQ--VYWFALFN
      GRMZM2G148400 (252) AGATVENARQYNRNLLMRQVSG--EGTPLRPRLRLE--VYLFALFN
      GRMZM2G012758 (222) AGATVDNAKAYNSNLWAHLKSQ--VGTPRTPGKSVD--TYIFALYD

GRMZM2G096591 (245) AGATVENARAFVSGLVSHLRSL--SGTPRAPGKSVE--TYIFAMYD
   GRMZM2G096591(2) (245) AGATVENARAFVSGLVSHLRSL--SGTPRAPGKSVE--TYIFAMYD
      GRMZM2G046101 (252) PGATVENARAYVSNLVAHLRSG--AGTPLMPGRSVD--TYLFALYD
      GRMZM2G064202 (249) VGVGADLARDYNSNAIRHLGSG--VGTPLMPNRTFE--VSIFSLFD
      GRMZM2G111143 (256) VGVGPEEARDFNAGMIRVCSGG--KGTPLMPGRTFE--TYWFSLFD
   GRMZM2G111143(2) (256) VGVGPEEARDFNAGMIRVCSGG--KGTPLMPGRTFE--TYWFSLFD
   GRMZM2G111143(3) (256) VGVGPEEARDFNAGMIRVCSGG--KGTPLMPGRTFE--TYWFSLFD
      GRMZM2G111324 (254) PDATSDNADTYNSNLIRHVMNS---TGTPKHPGVAVP--TYYYELYD
   GRMZM2G111324(2) (242) PDATSDNADTYNSNLIRHVMNS---TGTPKHPGVAVP--TYYYELYD
      GRMZM5G824920 (254) PDATSDNADTYNSNLIRHVMNS---TGTPKHPRVAVP--TYIYELYD
      GRMZM2G325008 (262) PYAGRDNADAYNSNLTKHVLEE-KAGTPMAPGAGAQSSAYIYELFN
   GRMZM2G325008(2) (262) PYAGRDNADAYNSNLTKHVLEE-KAGTPMAPGAGAQSSAYIYELFN
   GRMZM2G325008(3) (262) PYAGRDNADAYNSNLTKHVLEE-KAGTPMAPGAGAQSSAYIYELFN
   GRMZM2G325008(4) (262) PYAGRDNADAYNSNLTKHVLEE-KAGTPMAPGAGAQSSAYIYELFN
   GRMZM2G325008(5) (262) PYAGRDNADAYNSNLTKHVLEE-KAGTPMAPGAGAQSSAYIYELFN
          Consensus (369) GAT ENA  YN NLIR V G   GTP RPG          YIFALFN
```

FIG. 14 (Cont.)

Section 10

```
                       (415) 415    420       430        445
   AC159612.1_FG007   (255) EDVKSVAPGNFERHWGILRY-DGQPKYPMD-
      GRMZM2G020898   (295) EDAKSVAPGNFERHWGVLRY-DGQPKFAMD-
      GRMZM2G078566   (290) EDAKSVAPGNFERHWGIMRY-DGQPKYAMD-
      GRMZM2G083599   (295) EDAKSVAPGNFERHWGIFTF-DGRPKFPL--  ⎫
   GRMZM2G083599(2)   (254) EDAKSVAPGNFERHWGIFTF-DGRPKFPLD-  ⎬CAL1
      GRMZM2G005798   (299) EDMKSIAPGNFERHWGIFTY-DGKPKFPLD-  ⎭
      GRMZM2G310739   (291) ENQKSVLPGRFERHWGLFTY-DGKPKFSMD-
   AC217887.3_FG004   (278) EDNKSIDPGSFERHWGVFNY-DGSPKYP---
      GRMZM2G097207   (290) EDDKSIQPGNFERHWGIFTY-DGLPKYQLN-
      GRMZM2G152638   (292) EEGKSILPGNFERHWGIFSF-DGQAKYPLN-
    GRMZM2G335111@11  (289) EDGK--PGPEFERHFGIFRA-DGSKAYDLNF
    GRMZM2G014723@16  (281) ENQK-ESGVEQN--WGLFYP-NMHHVYPLSF
  GRMZM2G137535(2)@2  (280) ENQK-ESGVEQN--WGLFYP-NMQHVYPLSF
    GRMZM2G137535@1   (280) ENQK-ESGVEQN--WGLFYP-NMQHVYPLSF
    GRMZM2G041961@4   (280) ENLK-QSGVEQN--WGLFYP-NMQRVYPIKF
  GRMZM2G019185(2)@8  (283) EDKK-DAGVEQN--WGLFYP-NMERVYPITF
    GRMZM2G019185@7   (283) EDKK-DAGVEQN--WGLFYP-NMERVYPITF
    GRMZM2G088951@3   (286) ENGK-AEGVEQH--FGLFQP-DMSEVYHVDF
    GRMZM2G380561@14  (287) ENGK-AEGVEQH--FGLFQP-DMSEVYHVDF
    GRMZM2G591605@15  (290) ENQK-PEGVEQH--FGMFQP-DMTEVYHVDF
    GRMZM2G061403@13  (281) EDQK-DGDPTEK-KFGLFNP-DKTPVYPINF
    GRMZM2G125032@5   (281) ENQK-GGDPTEK-NFGLFYG-NKQPVYPIRF
    GRMZM2G433365@9   (281) ENQK-PGEPTEK-NFGLFYP-SKAPVYPIVF
    GRMZM2G062600@17  (281) EDQK-LGDDETRRHFGLFNK-DRSLAVPIDF
    GRMZM2G065585@6   (277) EDQK-TGAESER-HFGLFNP-DKSPAVPINF
    GRMZM2G123107@12  (249) EDKK-QGDETEK-HFGLFNGPDQSPVYQLSF
      GRMZM2G000959   (297) EDLK--WGPDTERHWGLFYP-NGSAVYELD-
      GRMZM2G179354   (297) EDRK--PGPGSERHWGLYYP-NGSMVYELD-
      GRMZM2G458164   (299) EDLK--PGPGTERHWGLYYA-NGTAVYELD-
      GRMZM2G046459   (296) ENQK--PGPTSERNGVFYP-NQQKVYDVEF
    GRMZM2G114140@10  (327) ENQKGDGADDVEQHFGLFYP-NRTKVYEFDF
      GRMZM2G454550   (325) ENQKGDGPDDIEQNFGLFYP-SEQKVYEFDF
   GRMZM2G454550(2)   (325) ENQKGDGPDDIEQNFGLFYP-SEQKVYEFDF
      GRMZM2G431039   (314) ENNKSADPDDVENNFGLFYP-NMQKLYDFNF
```

FIG. 14 (Cont.)

```
GRMZM2G005082    (293)  ENRK---PGIESERNWGLFFP-DKSSIYSLD-
GRMZM2G005082(2) (293)  ENRK---PGIESERNWGLFFP-DKSSIYSLD-
GRMZM2G008627    (294)  EDLK---PGPTSERHYGLFKP-DGS------
GRMZM2G117872    (292)  EDLK---PGPTSERHYGLFKP-DGS------
GRMZM2G042870    (292)  ENQK---PGAGSERHYGLFLP-DGRISYDI--
GRMZM2G019619    (290)  EDMK---PGATSERNYGLFYP-NGTPVYSLGF
GRMZM2G127117    (293)  ENMK---PGPTSERNYGLFYP-NGSPVYAL--
GRMZM5G805609    (298)  EDLK---PGPTSERNYGLLYP-DGSPVYALD-
GRMZM5G805609(2) (274)  EDLK---PGPTSERNYGLLYP-DGSPVYALD-
GRMZM2G076584    (293)  ENLK---PGPASERNYGLLYP-DGTPVYDV--
GRMZM2G076584(2) (293)  ENLK---PGPASERNYGLLYP-DGTPVYDV--
GRMZM2G030850    (297)  ENMK---PGPTSERNYGLFKP-DGTPAYELSY
GRMZM2G030850(2) (297)  ENMK---PGPTSERNYGLFKP-DGTPAYELSY
GRMZM2G172537    (297)  ENLK---PGLASERYYGLFKP-DGTPAYELSF
GRMZM2G478892    (268)  EDQK---PGPASERHYGLFKP-DGTPAYNV--
GRMZM2G148400    (294)  EDMK---PGPASERNYGLYQP-DMSMVYNV--
GRMZM2G012758    (264)  EDLK--GGPESERSFGLYKT-DLTANYDV--

GRMZM2G096591    (287)  EDLK---PGKASERYFGLFQT-SLAETYP---
GRMZM2G096591(2) (287)  EDLK---PGKASERYFGLFQT-SLAETYP---
GRMZM2G046101    (294)  EDLK---PGPTSERSFGLYHT-DLTMAYD---
GRMZM2G064202    (291)  ENLK---PGVSERNFGLFRG-DMTPVYDV---
GRMZM2G111143    (298)  ENQK---PGPVAERNFGIFNT-DLTPKYDL--
GRMZM2G111143(2) (298)  ENQK---PGPVAERNFGIFNT-DLTPKYDL--
GRMZM2G111143(3) (298)  ENQK---PGPVAERNFGIFNT-DLTPKYDL--
GRMZM2G111324    (296)  EDTR---PGSTSEKYWGLFDM-NGVPAYTL--
GRMZM2G111324(2) (284)  EDTR---PGSTSEKYWGLFDM-NGVPAYTL--
GRMZM5G824920    (296)  EDTR---PGSTSEKYWGLFDM-NGVPAYTL--
GRMZM2G325008    (307)  EDLR---AGPVSEANWGLFYG-NGTPVY----
GRMZM2G325008(2) (307)  EDLR---AGPVSEANWGLFYG-NGTPVY----
GRMZM2G325008(3) (307)  EDLR---AGPVSEANWGLFYG-NGTPVY----
GRMZM2G325008(4) (307)  EDLR---AGPVSEANWGLFYG-NGTPVY----
GRMZM2G325008(5) (307)  EDLR---AGPVSEANWGLFYG-NGTPVY----
       Consensus (415)  ED K   G   SER WGLF P DGTPVY L
```

|                      |      | Section 2 |
|----------------------|------|-----------|
|                      |      | (53) 53        60        70        80        90      104 |
| Bradi2g27140.1       | (53) | GAPN--DVLSNIASS-PAAAASWVRNNLQAY-PSVSFRYMWGNEVAGGA-- |
| Bradi2g27140.2       | (53) | GAPN--DVLSNIASS-PAAAASWVRNNLQAY-PSVSFRYMWGNEVAGGA-- |
| GRMZM2G014723        | (53) | GTPN--DALSNIAAS-PAAAASWVRNNLQAY-PSVSFRFVCVGNEVAGGA-- |
| GRMZM2G137535        | (53) | GAPN--DVLSNIAAS-PAAAASWVRNNLQAY-PSVSFRYVCVGNEVAGGA-- ⎫ |
| GRMZM2G137535(2)     | (53) | GAPN--DVLSNIAAS-PAAAASWVRNNLQAY-PSVSFRYVCVGNEVAGGA-- ⎬ CAL1 |
| Sb09g018730.1        | (53) | GAPN--DVLSSIAGS-PAAAASWVRNNLQAY-PSVSFRYMCVGNEVAGGA-- |
| Sb09g018730.3        | (47) | GAPN--DVLSSIAGS-PAAAASWVRNNLQAY-PSVSFRYMCVGNEVAGGA-- |
| Sb09g018730.4        | (47) | GAPN--DVLSSIAGS-PAAAASWVRNNLQAY-PSVSFRYMCVGNEVAGGA-- |
| Sb09g018730.2        | (53) | GAPN--DVLSSIAGS-PAAAASWVRNNLQAY-PSVSFRYMCVGNEVAGGA-- |
| Si022614m            | (53) | GAPN--DVLSNIAAS-PAAAASWVRNNLQAY-PSVSFRYICVGNEVAGGA-- |
| Si022791m            | (47) | GAPN--DVLSNIAAS-PAAAASWVRNNLQAY-PSVSFRYICVGNEVAGGA-- |
| Si022794m            | (47) | GAPN--DVLSNIAAS-PAAAASWVRNNLQAY-PSVSFRYICVGNEVAGGA-- |
| Si022731m            | (53) | GAPN--DVLSNIAAS-PAAAASWVRNNLQAY-PSVSFRYICVGNEVAGGA-- |
| LOC_Os05g31140.1     | (53) | GAPN--DVLSNLAAS-PAAAASWVRNNLQAY-PSVSFRYMAVGNEVAGGA-- |
| LOC_Os05g31140.2     | (47) | GAPN--DVLSNLAAS-PAAAASWVRNNLQAY-PSVSFRYMAVGNEVAGGA-- |
| LOC_Os05g31140.3     | (47) | GAPN--DVLSNLAAS-PAAAASWVRNNLQAY-PSVSFRYMAVGNEVAGGA-- |
| GRMZM2G041961        | (53) | GAPN--DVLSSLAAS-PAAAASWVRNNLQAY-PKVAFRCVCVGNEVEGGA-- |
| Sb09g018750.1        | (53) | GAPN--DVLSSLAAS-PAAAASWVRNNLQAY-PKVSFRCVCVGNEVAGGA-- |
| Si022606m            | (53) | GAPN--DVLSSLAAS-PAAAAWVRNNLAAY-PDVTFRCVCVGNEVEGGA-- |
| Si028122m            | (53) | GAPN--DVLSNLTDA-KAAAAL WVRDNLEAY-PSVSFGYIAVGNEVAGKA-- |
| Bradi2g60500.1       | (53) | GAPN--DWPSLSTN-PSFAASWVRDNLAAH-PMVSFKYLSVGNETSGEN-- |
| GRMZM2G019185        | (53) | GAPN--EALPALASG-AAAAWVRDNVQAH-PAVAFRYMWGNEVPLEQ-- |
| GRMZM2G019185(2)     | (53) | GAPN--EALPALASG-AAAAWVRDNVQAH-PAVAFRYMWGNEVPLEQ-- |
| Sb03g045480.1        | (53) | GAPN--EVLTTLASS-ASAAAWVRDNLQAH-PTVSFRYMWGNEVPVGQ-- |
| Si002273m            | (53) | GAPN--DVLPSLASS-ESAAAWVRQNLQAH-PLVTFRYMWGNEVPAGE-- |
| LOC_Os01g71474.1     | (53) | GAPN--YDLPALAHGGTAAAAWIRENLQAY-PTVLFRFVWGNEVAGAD-- |
| Bradi3g57610.1       | (53) | ALPN--EQVAAARR-PSYALAWRRNVAAYYPATQIQGVAVGNEVFATAGN |
| LOC_Os02g53200.1     | (53) | ALPN--EQLLAAASR-PSYALAWVRRNVAAYYPATQIQGIAVGNEVFASAKN |
| LOC_Os02g53200.2     | (53) | ALPN--EQLLAAASR-PSYALAWVRRNVAAYYPATQIQGIAVGNEVFASAKN |
| Si017035m            | (53) | ALPN--EQVAAAASR-ASYALLWVRRNVAAYYPATQIQGIAVGNEVFAVAKN |

FIG. 16 (Cont.)

```
GRMZM2G114140    (53) MLPN--DKLAAAAD-PSSARRWVRRNVAAYYPATQIHAVAVGNEVFEEAKN
GRMZM2G335111    (53) GVPN--ENLTFLAAAGPEGAAQWLRSAVLAHAPAERVRCLAVGNEVLYNNQF
Sb02g030930.1    (53) GVPN--ENLTFLAASGPEGAAQWLRSAVLAHAPADRVRYLAVGNEVLYNNQF
LOC_Os09g36280.1 (53) GVPN--ENLTFLSAAGPDGALRWLQSAVLAHAPADRVRYLAVGNEVLYNNQF
GRMZM2G088951    (53) GTLN--EDLPRLASD-PSFAASWVATNVQPFAGAVQFRYINAGNEVIPGD--
Sb09g024320.1    (53) GTLN--EDLQRLASD-PSYAASWVATNVQPFAGAVQFRYINAGNEVIPGD--
Si022492m        (53) GTLN--EDLQRLASD-QSFAASWVATNVQPFAGAVQFRYINAGNEVIPGE--
GRMZM2G380561    (53) GTLN--EDLPRLASD-PSFAASWVATNVQPFAGAVQFRYINAGNEVIPGD--
LOC_Os05g41610.1 (53) GTYN--EDLARLASD-PSFAASWVSSYVQPFAGAVSFRYINAGNEVIPGD--
GRMZM2G591605    (53) GTLN--EDLARLASD-PSFAASWVQAYVRPFAGAVRFRYVAAGNEVVPGD--
Sb03g037270.1    (53) GTLN--EDLARLASD-PSFAASWVQTYVQPFAGAVRFRYVAAGNEVIPGD--
Si002065m        (53) GTLN--EDLARLASD-ASFAASWVQSYVQPFAGAVRFRYVAAGNEVIPGD--
LOC_Os01g58730.1 (53) GTLN--EDLARLATD-ASFAASWVQSYVQPFAGAVRFRYINAGNEVIPGD--
GRMZM2G062600    (53) GVPN--ADVGGLASR-PSAAAAWVQSYVLAF-PAVQFRYIAVGNEVWAG---
GRMZM2G065585    (53) DVPN--TDLASLASD-PSAAAAWVQSNVQAF-PSVSFRYIAVGNEASGGD--
Sb03g045450.1    (53) DVPN--SDLSSLASD-PSAAATWVQRNLQAF-PGVNFKYIAVGNEVSGGD--
Sb03g045460.1    (53) DVPN--TDLSSLASD-PSAAATWVKSNVQAF-PGVNFKYIAVGNEVSGGD--
Si002182m        (53) DVPN--DKLGSIASD-PNAAAGWVRDNVQAF-SGVSFRYIAVGNEVAGGD--
LOC_Os01g71340.1 (53) DVGN--DQLGSLASD-PSAAAATVQNNIQAF-PGVNFRYITVGNEVSGGD--
LOC_Os01g71400.1 (53) GVAN--ENLSAFASD-PSAVANWVKQNVQVY-PGVNFRYIAVGNEVESGN--
LOC_Os01g71650.1  (2) GVAN--ENLSAFASD-PSAVANWVKQNVQVM-PGVNFRYIAVGNEVESGN--
LOC_Os01g71930.1 (53) DVEG--QFLPSFASE-PSVAAAWVKTNVQAFYPAVSFKFITVGNQVALRE--
GRMZM2G123107    (24) DETNLD-----SLIS-D--APGWVQANLQPYKDDVSFKYIAVGNEVEGG---
Sb08g019670.1    (53) DETNLD-----ALIS-D--AGSWVQANVQPYIGDVKFKYIAVGNEVEGS---
Si022625m        (53) DETDLN-----ALLS-D--ASVWVQANVLPYKDDVKEKYIAVGNEVEGS---
LOC_Os01g71410.1 (53) DEPAIDQ---FLTLS-A--ASDWVQSNIKPYQG-VNIRYIAVGNEVSGD---
LOC_Os01g51570.1 (53) DVGN--GNLSSLASS-PSAAAGWVRDNIQ-AYPGVSFRYIAVGNEVQGS---
LOC_Os01g71350.1 (53) DVAN--ENLAAFAAD-ATAAAAWVKQNVQ-AYPGVSFRYIAVGNEVTGD---
Bradi2g60490.1   (53) DIGN--DNLAGIASS-ASNAATWVNNVKPYYPAVNIKYIAAGNEILGG---
GRMZM2G125032    (53) DTGNGGGVLGQLARS-ASFADSWVQSNVRPYYPAVGIKYVAVGNEVQGD---
```

FIG. 16 (Cont.)

```
Sb03g045490.1  (53) DTGNGN-ELSQLARS-ASYAASWQSNVKPYYPAVNIKYIAVGNEVQGG---
   Si004560m   (53) DTGNDV--LGQLASS-PSSAASWQSNVRPYYPAVNIKYIAVGNEVAGS---
LOC_Os01g71380.1 (53) DVGG-FDTVSYLAAS-SSNAAAWVRDNVRPYYPAVNIRYIAVGNEVEGG---
LOC_Os01g71670.1 (53) DVG---DQLSNLAAS-SSNAAAWVRDNVRPYYPAVNIKYIAVGNEVEGG---
  GRMZM2G433365  (53) GVAN---EDVASLATC-APCAASWVEANVRPYHQDVNILYIAVGNEVDAAA--
Sb03g045510.1  (52) GVAN---EDIANLAAC-APCAASWVQTNVRTYHPDVSVLYIAVGNEVDAPA--
   Si003802m   (52) GVVN---QDIVGLAGC-QSCAASWVQTNVRTYYPAVNILYIAVGNEVSDG---
   Si005124m   (39) GVAN---EDLAGLAAS-EPTAASWVQANVKPYYPAVNIRYIAIGNKVGGE---
LOC_Os01g71680.1 (53) GVAN---DILIDLAAN-PASAASWDANVKPFVPAVNIKYIAVGNEISGE---
 Bradi2g60560.1 (53) GTAN---ADVPLLASK-PGYAASWVATNVQPYYPSVNISYITVGNEITGDPA-
  GRMZM2G061403  (53) DVGNGK--VGELAAD-PASAASWVRDNVQAYYPDVDIRYWVGNEVWP----
Sb03g045520.1  (53) DVGNDK--VGELASD-SAAAASWVRDNVQAYYPDVDIRYWVGNEVP-----
   Si000491m   (53) DVGNDK--VGDLAND-PAAAASWVKDNVQAYYPDVSIRYWVGNEVD-----
LOC_Os01g71690.2 (53) DVGER----NDVGQL-AANADSWVQDNVKAYYPDVKIKYIMVGNELTGTG--
LOC_Os01g71690.3 (53) DVGER----NDVGQL-AANADSWVQDNVKAYYPDVKIKYIMVGNELTGTG--
LOC_Os01g71810.1 (53) DVGG-SSAVANLANN-PSAAADWVRDNVQAYWPNVIIRYIAVGNELGPGD--
LOC_Os01g71820.1 (53) DVGG-IGAVANLANN-PSAAADWVRDNVQAYWPNVIIRYIAVGNELGPGD--
LOC_Os01g71830.1 (53) DVGD-KGAVANLANN-PSAAADWVRNNVQAYWPSVFIRYIAVGNELGPGD--
LOC_Os01g71860.1 (52) DVGD-SGAVANLASN-PSAAGDWVRDNEAYWPSVIIRYITVGNELPAGD--
Sb03g045630.1  (44) DVGG-VDAVRALAGS-ASVAADWVQANVQAYQRDVLIRYIAVGNEVGPGDG-
   Si002306m   (53) DVGG-IGDVRRLAGS-ASEAAAWVQAHVQPYSRDVIIRYIAVGNEVPPGD--
Sb09g025890.1  (53) DVGG-VDDVRGLASS-ASAAAAWVHANVAHYPDVLIRYIAVGNEVPAG-D-
   Si024558m   (46) DVGG-VDATRALAGS-AAAAAWVEANVQAYYPDVLIRYIAVGNEVPAGDD-
   Consensus   (53)  G  N    D LS LAS  PSAAASWVR NVQAY PAV FRYIAVGNEV GG
```

FIG. 16 (Cont.)

Section 3

|  | | 105 | 110 | 120 | 130 | 140 | 156 |
|---|---|---|---|---|---|---|---|

```
Bradi2g27140.1    (99)  -TQNLVPAMKNVHSALASAGLGH----IKVTTSVSQAILGVYS-PPSAGSFT
Bradi2g27140.2    (99)  -TQNLVPAMKNVHSALASAGLGH----IKVTTSVSQAILGVYS-PPSAGSFT
GRMZM2G014723     (99)  -ARNLAPAMENVHAALAAAGLGH----IKVTTSVSQAILGVYS-PPSAAQFT
GRMZM2G137535     (99)  -AQDLAPAMENVHAALAAAGLGH----IKVTTSVSQAILGVYS-PPSAAEFT  ⎫
GRMZM2G137535(2)  (99)  -AQDLAPAMENVHAALAAAGLGH----IKVTTSVSQAILGVYS-PPSAAEFT  ⎬CAL1
Sb09g018730.1     (99)  -AQNLAPAMENVHAALAAAGLGH----IKVTTSVSQAILGVYS-PPSAAQFT  ⎭
Sb09g018730.3     (93)  -AQNLAPAMENVHAALAAAGLGH----IKVTTSVSQAILGVYS-PPSAAQFT
Sb09g018730.4     (93)  -AQNLAPAMENVHAALAAAGLGH----IKVTTSVSQAILGVYS-PPSAAQFT
Sb09g018730.2     (99)  -AQNLAPAMENVHAALAAAGLGH----IKVTTSVSQAILGVYS-PPSAAQFT
Si022614m         (99)  -AQNLAPAMENVHAALAAAGLGH----IKVTTSVSQAILGVYS-PPSAAEFT
Si022791m         (93)  -AQNLAPAMENVHAALAAAGLGH----IKVTTSVSQAILGVYS-PPSAAEFT
Si022794m         (93)  -AQNLAPAMENVHAALAAAGLGH----IKVTTSVSQAILGVYS-PPSAAEFT
Si022731m         (99)  -AQNLAPAMENVHAALAAAGLGH----IKVTTSVSQAILGVYS-PPSAAEFT
LOC_Os05g31140.1  (99)  -TSSLVPAMENVRGALVSAGLGH----IKVTTSVSQALLAVYS-PPSAAEFT
LOC_Os05g31140.2  (93)  -TSSLVPAMENVRGALVSAGLGH----IKVTTSVSQALLAVYS-PPSAAEFT
LOC_Os05g31140.3  (93)  -TSSLVPAMENVRGALVSAGLGH----IKVTTSVSQALLAVYS-PPSAAEFT
GRMZM2G041961     (99)  -AQSLVPAMENVRAALVAAGLDG----IKVTTSVSQAILGGYK-PPSAAEFT
Sb09g018750.1     (99)  -AQNLVPAMENVRAALAAAGLDG----IKVTTSVSQAILGGYK-PPSAAEFT
Si022606m         (99)  -AQNLVPAMENTRAALAAAGLDG----IKVTTSVSQAILGGYK-PPSAAEFT
Si028122m         (98)  -ADLLAPAMENVHSALDAAGLGH----IKVTTSVSQALVFNK-PLSGGNFT
Bradi2g60500.1    (99)  -TQHLVPAMENVLAALNAAGLGMG---VQVTTALSQATIAVHT-PPSAGAFA
GRMZM2G019185     (99)  -APLLVPAMENVHAALAAAGLGH----VKVTTAVSQGAIAVHL-PPSAGEFT
GRMZM2G019185(2)  (99)  -APLLVPAMENVHAALAAAGLGH----VKVTTAVSQGAIAVHL-PPSAGEFT
Sb03g045480.1     (99)  -TQFLVPAMENVHAALAAAGLGH----VKVTTAISQGTIAVHL-PPSAGVFT
Si002273m         (99)  -TEHLVPAMENVHAALAAVGLGH----VKVTTAISQGTIAVHL-PPSAGAFT
LOC_Os01g71474.1  (100) -TQLLVPAMENVHAALAAAGLGH----IKVTTSISQATIGVHI-PPSAGEFT
Bradi3g57610.1    (102) VTAQLVPAMANTHAALQRLNLDK---AWKVSSPIALTALASSYPPSAGVFRE
LOC_Os02g53200.1  (102) LTAQLVPAMTNVHAALARLSLDK---PWKVSSPIALTALAGSYPPSAGVFRE
LOC_Os02g53200.2  (102) LTAQLVPAMTNVHAALARLSLDK---PWKVSSPIALTALAGSYPPSAGVFRE
Si017035m         (102) VTAQLVPAMMNVHAALARLGLDK---AWKVSSPVALTALANSYPSSAGVFRE
```

FIG. 16 (Cont.)

```
GRMZM2G114140   (102) LTGQLVPAMSNVHDALVKLGLDG---AVKVSTPIAFTALQESWPPSAGRFRD
GRMZM2G335111   (103) YAPHLVPAMRNLHAALATLGLDG---RVKVSSAHASSVLAASYPPSAGAF-D
Sb02g030930.1   (103) YAPHLVPAMRNLHAALAALGLGG---RVKVSSAHASSVLAASYPPSAGAF-D
LOC_Os09g36280.1 (103) YAPHLVPAMHNLHAALVSLGLGD---KVKVSSAHASSVLASSYPPSAGAF-D
GRMZM2G088951   (100) AAARVLPAMQNLESALRSAGVT----GVPVTTAVATSVLGASY-PPSQGAFS
Sb09g024320.1   (100) AAAQVLPAMQNLESALRSAGVT----GVPVTTAVATSVLGTSY-PPSQGAFS
Si022492m       (100) SAAHVLPAMQNLESALRSAGVS----GVAVTTAVATAVLGASY-PPSQGAFS
GRMZM2G380561   (100) PAAQVLPAMKNLESALRSAGVA----GVPVTTAVATSVLGASY-PPSQGAFS
LOC_Os05g41610.1 (100) PAANVLPAMRNLDAALKAAGTS----GIPVTTAVATSVLGVSY-PPSQGAFS
GRMZM2G591605   (100) LASHVLPAMQNLESALRAAGLG----GVRVTTAVSTSVLGTSY-PPSQGAFS
Sb03g037270.1   (100) LASHVLPAMQNLESALRAAGLGDGD-GVRVTTAVSTSVLGSSY-PPSQGAFS
Si002065m       (100) LAAYVLPAMRNLESALHAAGTA----GVPVTTAVSTSVLGSSY-PPSQGAFS
LOC_Os01g58730.1 (100) EAASVLPAMRNLQSALRAAGLG-----VPVTTVVATSVLGSSY-PPSQGAFS
GRMZM2G062600   (98)  -GRVLLPAMRNLDRALSAAGLAD---DIKVSTAVAIDVVGSSF-PPSAGTFA
GRMZM2G065585   (99)  -TGSLLPAMKNLNAALANAGLGG---SIKVSTAVQ-SDVTQGF-PPSQGTFS
Sb03g045450.1   (99)  -TNSLLPAMQNVNSALANAGLG----GIKVSTAVE-SGVTQGF-PPSQGSFS
Sb03g045460.1   (99)  -TNNLLPAMKNVNSALSNAGLG----KIKVSTAVQ-SGVTQGY-PPSQGSFS
Si002182m       (99)  -TANLLPAMRNINDALNNAGLG----SIKVSTAVQ-SGVTQGF-PPSQGSFS
LOC_Os01g71340.1 (99)  -TQNILPAMQNVNSALSAAGLG----NIKVSTSVS-QGVTAGF-PPSAGTFS
LOC_Os01g71400.1 (99)  -TQNVLPAMQNVNSALSAAGLS----NIKVSVSVSQKGVLAGY-PPSNGMFS
LOC_Os01g71650.1 (48)  -TQNVLPAMQNVNSALSAAGLS----NIKVSVSVSQKGVLAGY-PPSNGMFS
LOC_Os01g71930.1 (100) -MRYILPAMQNIYAALSAVGLD----HIKVSTSVRRDVLGLSY-PPSAGAFS
GRMZM2G123107   (65)  DTQKILPAMQSLSDALSAAGLG----NIKVSTAVKMSVLATPSSPPSTGAFA

Sb08g019670.1   (94)  DTQKILPAMQSLAGALSAAGFG----DIKVSTAVKMSVLATSS-PPSSGAFK
Si022625m       (94)  DTQKILPAMQKLNAALSAAGLS----NIKVSTAVKMSVLDTPSSPPSNGVFA
LOC_Os01g71410.1 (95)  ATRSLLPAMENLTKALSAAGFG----KIKVSTAVKMDVLGTSS-PPSQGEFS
LOC_Os01g51570.1 (98)  DTANLLPAMRNVNSALVAAGLG----NIKVSTSVRFDAFADTF-PPSSGRFR
LOC_Os01g71350.1 (98)  DTGNILPAMKNINAALAAAGLG----GVGVSTSVSQGVIANSY-PPSNGVFN
Bradi2g60490.1  (99)  ATGSLVPAMRNLNAALASAGLGD---RIKVSTSIRFDAVADSF-PPSKGVFK
GRMZM2G125032   (101) DTRSLLPAMRNLDAALAPAGFP----GIKCSTSVRFDVVANSF-PPSSGSFA
```

FIG. 16 (Cont.)

```
Sb03g045490.1  (100) ATQSILPAIRNLDAALARAGLS----AIKCSTSMRFDVIANSY-PPSSGSFA
    Si004560m   (99) ATQSILPAMRNLNAALAAAGLG----SIKVSTSMQSNVIANSF-PPSSGVFA
LOC_Os01g71380.1 (100) ATNSILPAIRNVNSALASSGLG----AIKASTAVKFDVISNSY-PPSAGVFR
LOC_Os01g71670.1  (98) ATSSILPAIRNVNSALASSGLG----AIKASTAVKFDVISNSY-PPSAGVFR
   GRMZM2G433365 (100) AAQTILPAMRSLQAALAAAGLAG---SIKVSTCMRLDVVTDTF-PPSSGAFA
Sb03g045510.1   (99) AAQSILPAMRNLQAALAAAGLDG---DIKVSTCMKLDVVTNTF-PPSSGVFA
    Si003802m   (98) AAQSILPAMRNLQAALAAAGLA----AIKVSTCMRLDVVTNTF-PPSAGVFA
    Si005124m   (85) AAHSILPAMRNLERALAAAGLA----AVKVSTCMRLDVITNSF-PPSAGVFA
LOC_Os01g71680.1  (99) PTQNILPVMQNTNAALAAASIT----GVKASTAVKLDVVTNTF-PPSAGVFA
 Bradi2g60560.1 (101) FKSSILPAMKSLHFALAGALGARAAGGIKVSTALRFDALVDTF-PPSKGAFK
   GRMZM2G061403  (98) GAASVLQAMRNVHAALASAGLAG---SVKVSTAVKMDAVDDSS-PPSRGVFR
Sb03g045520.1   (97) GAASVLQAMQNVHAALASAGLAG---NVRVSTAVKMDALENSS-PPSSGVFK
    Si000491m   (97) GAASVLQAMKNVHDALTSANLAG---SIKVSTAVKMDAIINSS-PPSNGAFK
LOC_Os01g71690.2  (98) DAASILPAMQNVQAALASAGLAD---SIKVITTALKMDTLAASS-PPSAGVFT
LOC_Os01g71690.3  (98) DAASILPAMQNVQAALASAGLAD---SIKVITTALKMDTLAASS-PPSAGVFT
LOC_Os01g71810.1 (101) -MGTILPAMQNVYDALVSAGLSN---SIKVSTAVRMDVITASS-PPSHGVFR
LOC_Os01g71820.1 (101) -MGTILPAMQNVYDALVSAGLSN---SIKVSTAVRMDALTDSF-PPSHGVFR
LOC_Os01g71830.1 (101) -MGTILPAMQNLYNALVSAGLSN---SIKVSTAVKMDVITNSF-PPSHGVFR
LOC_Os01g71860.1 (100) -MGLILPAMQNVHKALVSAGLSS---SIKVSTALKMDVVANTF-PPSHGVFR
Sb03g045630.1   (93) AAALLLPAMRNVHAALVSAGLDG---SIKVSTAVKMDAFADTF-PPSRGAFA
    Si002306m  (101) AAGILLPAMRNVRGALVSAGLDG----IKVSTAVKMDVFTDTF-PPSRGVFR
Sb09g025890.1  (101) AGLILLPAMRNVRAAVASAGLAG---AIKVSTAVRMDVVTDSF-PPSRGVFS
    Si024558m   (95) AAGLILPAMRNVRAALAAAGLAG---AVRVSTAVRMDVITDSF-PPSRGVFS
     Consensus (105)      A LLPAM NV AALAAAGLG    IKVSTAVS VLG SY PPSAG FT
```

FIG. 16 (Cont.)

```
                                                                    Section 4
                      (157) 157         170       180       180         208
    Bradi2g27140.1    (145) GEADAFMGPWVQFLASAGSPLMANIYPYLAWAYNPS----AMDMSYALFTAS
    Bradi2g27140.2    (145) GEADAFMGPWVQFLASAGSPLMANIYPYLAWAYNPS----AMDMSYALFTAS
    GRMZM2G014723     (145) VEAQGYMGPVLKFLARTGSPLMANIYPYLAWAYNPS----AMDMSYALFTSS
    GRMZM2G137535     (145) GEARGYMGPVLQFLARTGSPLMANIYPYLAWAYNPS----AMDMSYALFTSS  ⎤
    GRMZM2G137535(2)  (145) GEARGYMGPVLQFLARTGSPLMANIYPYLAWAYNPS----AMDMSYALFTSS  ⎦ CAL1
    Sb09g018730.1     (145) AEAQGFMGPVLQFLSRTGSPLMANIYPYLAWAYNPS----AMDMSYALFTAS
    Sb09g018730.3     (139) AEAQGFMGPVLQFLSRTGSPLMANIYPYLAWAYNPS----AMDMSYALFTAS
    Sb09g018730.4     (139) AEAQGFMGPVLQFLSRTGSPLMANIYPYLAWAYNPS----AMDMSYALFTAS
    Sb09g018730.2     (145) AEAQGFMGPVLQFLSRTGSPLMANIYPYLAWAYNPS----AMDMSYALFTAS
    Si022614m         (145) GEAKGYMGPVLSFLARTGSPLMANIYPYLAWAYNPS----AMDMSYALFTSK
    Si022791m         (139) GEAKGYMGPVLSFLARTGSPLMANIYPYLAWAYNPS----AMDMSYALFTSK
    Si022794m         (139) GEAKGYMGPVLSFLARTGSPLMANIYPYLAWAYNPS----AMDMSYALFTSK
    Si022731m         (145) GEAKGYMGPVLSFLARTGSPLMANIYPYLAWAYNPS----AMDMSYALFTSK
    LOC_Os05g31140.1  (145) GESQAFMAPVLSFLARTGAPLLANIYPYFSYTYSQG----SVDVSYALFTAA
    LOC_Os05g31140.2  (139) GESQAFMAPVLSFLARTGAPLLANIYPYFSYTYSQG----SVDVSYALFTAA
    LOC_Os05g31140.3  (139) GESQAFMAPVLSFLARTGAPLLANIYPYFSYTYSQG----SVDVSYALFTAA
    GRMZM2G041961     (145) DEAQGFMGPVLRFLARTGAPLMASVYPYFTYATNPA----AMDLSYALFTAP
    Sb09g018750.1     (145) DEAQGFMGPVLDFLARTGAPLMASVYPYFTYATNPS----AMDVSYALFTAP
    Si022606m         (145) DEAQGFMGPVLEFLARTGAPLMASTYPYFTYATNPS----AMDLSYALFTAP
    Si028122m         (143) KEAQGFMGPVLKFLARTGAPLMANIYPYFTYAYNTA----GMDVDYALFTAP
    Bradi2g60500.1    (146) EDCKPFLLPVLQFLARTGAPLLANIYPYFAYTYRAAG---DIDVSFALFTAE
    GRMZM2G019185     (145) EEARSFMGYVVAFLARTRAPLLANIYPYFVYTLGLG----HLGMDFALFTAP
    GRMZM2G019185(2)  (145) EEARSFMGYVVAFLARTRAPLLANIYPYFVYTLGLG----HLGMDFALFTAP
    Sb03g045480.1     (145) EEALSFMSYVAFLARTRAPLLANIYPYFVYTLALG-----HNSMDFPLFTAP
    Si002273m         (145) EEALSFMGYWAFLERTRAPLLANIYPYFVYTLGLG-----HMDMSFALFTSP
    LOC_Os01g71474.1  (146) DEAKPFYSYVIPFLERTHAPLLANIYPYFIYSYNPG----GMDLSYALFTAS
    Bradi3g57610.1    (151) ELAQAVMKPMDFLSQTGSYLMVIAYPFFAYAENAG-----VISLDYALFRPN
    LOC_Os02g53200.1  (151) DLAQAVMKPMDFLAQTGSYLMVIAYPFFAYSGNAD-----VISLDYALFRPN
    LOC_Os02g53200.2  (151) DLAQAVMKPMDFLAQTGSYLMVIAYPFFAYSGNAD-----VISLDYALFRPN
    Si017035m         (151) DLAQAVMKPMDFLAQTGSYLMVIAYPFFAYSANAG-----DISLDYALFRPN
```

FIG. 16 (Cont.)

```
GRMZM2G114140    (151) DIARSVMKPMTDFLERTGSYLTVNAYPFFAYAEEPD----KISLDYALGNSN
GRMZM2G335111    (151) AASLPVLRPMLRFLADTGAPFMVNAYPFISHVNDPA----NVQLAYALFGAG
Sb02g030930.1    (151) AASLPVLRPMLQFLADTGAPFMVNTYPFISYVNDPA----NVQLAYALFGAG
LOC_Os09g36280.1 (151) AASLDVLRPMLRFLADTGAPFMVNTYPFISYVNDPV----NVQLAYALFGAG
GRMZM2G088951    (147) EAAASVMAPLVSYLSSKGAPLLVNVYPYFAYSSSGG----QVALGYALLSAD
Sb09g024320.1    (147) EAAAPVMAPLVSYLSSKGAPLLVNVYPYFAYSGSGG----QVALGYALLSSD
Si022492m        (147) EAAAPVMAPLVSYLSSKNAPLLVNVYPYFAYSNSGG----QVALGYALLSAA
GRMZM2G380561    (147) EAATTVMAPLVSYLSSRGAPLLVNVYPYFAYSGSGG----QVALGYALLSGA
LOC_Os05g41610.1 (147) EAASPMMAPLVAYLASRGAPLLVNVYPYFAYAADAE----RVQLGYALLSAS
GRMZM2G591605    (147) DAALPSMGPIASFLAPRSTPLLVNVYPYFAYSADPA----SVSLDYALLRSD
Sb03g037270.1    (150) EAALPSMAPIASFLASRSTPLLANVYPYFAYSADPS----SVPLDYALLQSA
Si002065m        (147) EAALPTVGPIASFLASRSTPLLVNVYPYFAYAADPS----SVQLDYALLEPA
LOC_Os01g58730.1 (146) EAALPTVAPIVSFLASSGTPLLVNVYPYFAYSADPS----SVRLDYALLSPS
GRMZM2G062600    (145) P-SAGMMARVARYLQSTGAPLLANLYPMYSYISD----PGAVDINYALLAMP
GRMZM2G065585    (145) ---QGMMAPIAQYLQSTGAPLLCNVYPYFSYIGN----PAQIDLSYALFTSP
Sb03g045450.1    (144) ---QGMMGPIAQYLQSTGAPLLCNVYPYFSYTGN----EAQIALSYALFTSP
Sb03g045460.1    (144) ---QSMMAPIAQYLQSTGAPLLCNVYPYFSYTGN----EAQIALSYALFTSP
Si002182m        (144) ---AGHMGPIAQFLQSTGAPLLANVYPYFSYVGN----QAQIDINYALFTSP
LOC_Os01g71340.1 (144) ---ASHMGPIAQYLASTGAPLLANVYPYFAYVG--N--QAQIDINYALFTSP
LOC_Os01g71400.1 (145) PEATSMMTPIAKYLASTGAPLMANVYPYFAYVGNLR--AQIDDINYALFTSP
LOC_Os01g71650.1  (94) PEATSMMTPIAKYLASTGAPLMANVYPYFAYVGNLR--AQIDDINYALFTSP
LOC_Os01g71930.1 (146) SAMEQMMAPLVQFLAKIGAPLLASVPPYFTVHN----QEGIDLDYALFTSP
GRMZM2G123107    (113) DP--SVMGPIVRFLAGVGSPLLANIYPYFAYRDA----AGTIDLNYALFQPS
Sb08g019670.1    (141) DS--SVMGPVVRFLAGSGAPLLANVYPYFAYRDA----GGSIDLGFSLFEQS
Si022625m        (142) DP--SIMGPLVQFLASTGSPLLANIYPYFAYKGA----DGNIDLNYALFKPS
LOC_Os01g71410.1 (142) DA--AVMAPIAKFLASNGSPLLANVYPYFAYKG------GDVDLNFALFQPT
LOC_Os01g51570.1 (145) DD---YMTPIARFLATTGAPLLANYYPYFAYKDDQESGQKNIMLNYATFQPG
LOC_Os01g71350.1 (145) DD---MMFDLVEYLASTGAPLLVNVYPYFAYVGDT----KDISLNYATFQPG
Bradi2g60490.1   (147) DA---MMSDVARLLASTGAPLLANVYPYFAYRDS----PSAIQLNYATFQPG
GRMZM2G125032    (148) QG---MMADVARYLAGTGAPLLANVYPYFAYRDN----PRDISLGYATFQPG
```

FIG. 16 (Cont.)

```
Sb03g045490.1  (147) QG---YMADWARYLAGTGAPLLVNVYPYFSYRDN----PRDISLGYATFQPG
    Si004560m  (146) QG---YMVELARYLASTGAPLLANVYPYFAYRGN----PRDISLGYATFQPG
LOC_Os01g71380.1 (147) DA---YMKDIARYLASTGAPLLANVYPYFAYRGN----PRDISLNYATFRPG
LOC_OS01g71670.1 (145) DA---YMKDIARYLASTGAPLLANVYPYFAYRGN----PRDISLNYATFRPG
  GRMZM2G433365 (148) QP---YMVDWARFLAAAGAPLLANVYPYFAYRGS----PGDVGLGYALFQPG
 Sb03g045510.1  (147) QA---YMTDIARFLAATGAPLLANVYPYFAYRGSN---PGDISLSYALFQPG
    Si003802m  (145) QP---YMVDIAQFLAGAGASLLANVYPYFAYRGS----PGDISLNYALFLPG
    Si005124m  (132) QP---YMADIARFLATTGAPLLANVFPYFAYKDD----PRAISLEYATFRPG
LOC_Os01g71680.1 (146) AP---YMTAWAKLLASTGAPLLANIYPYFAYIGN----KKDISLNYATFQAG
  Bradi2g60560.1 (152) DAET--MVPLAGFLASTGAPLLADVYPYFAYRDN----PKDIALSYATFQPG
  GRMZM2G061403 (146) DP--AAMSPIAQFLAANGAPLLANVYPYFAYQYSDGG----IDLDYALFQPS
 Sb03g045520.1  (145) DP--AAMSPIVQFLAGNGAPLLANVYPYFAYEYSDG-----IDLNYALFQPS
    Si000491m  (145) DP--SVMSPIVQFLAGNGAPLLANVYPYFAYKDNQN----IDLNYALFEPS
LOC_Os01g71690.2 (146) NP--SVMEPIVRFLTGNGAPLLANVYPYFAYRDSQD-----IDLSYALFQPS
LOC_Os01g71690.3 (146) NP--SVMEPIVRFLTGNGAPLLANVYPYFAYRDSQD-----IDLSYALFQPS
LOC_Os01g71810.1 (148) PDLQQFMVPIAQFLANTMSPLLANVYPYFAYRDN----PRDIPLNYATFQPG
LOC_Os01g71820.1 (148) PDLQQFMVPIAQFLANTMSPLLANVYPYFAYRDN----PRDIPLNYATFQPG
LOC_Os01g71830.1 (148) PDLQRFIVPIAQFLANTMSPLLVNVYPYFAYRDN----PRDIPLNYATFQPG
LOC_Os01g71860.1 (147) PDVQQFMAPIARFLANTVSPLLVNVPYMSYREN----PRDISLNYATFQPG
 Sb03g045630.1  (141) QG---YMADWARFLADTGAPLLANVYPYFAYRDD----PRNISLEFASFRPG
    Si002306m  (148) DPS--VMSPIVQFLAGTGAPLLANVYPYFAYKDN----PRDINLNFATFRPG
 Sb09g025890.1  (149) PSVQRHMVPWARFLADAGSPLLANVYPYFAYRDN----PRDITLGYATFQPG
    Si024558m  (143) ASAGRHMPPWARFLADTGAPLLANVYPYFAYRDN----PRDIALAYATFQPG
    Consensus  (157)     A YMGPIL FLA TGAPLLANVYPYFAY N       I L YALF A
```

```
GRMZM2G114140  (199) ATG---VRDPV-TGLVYHSLLDAQLDATYFAMEKLGTSRSSARGPKSVAPAA
GRMZM2G335111  (199) AAP---VQDG---ALVYTNLFDATVDALVAALEKEGFD----------GVPV
Sb02g030930.1  (199) AAP---VQDG---ALVYTNLFDATVDALVAALEKEGFG----------AVPV
LOC_Os09g36280.1 (199) APA---VSDG---ALVYTNMFDATVDALAAALDREGFG----------AVPI
GRMZM2G088951  (195) AGAASS---VTDAGVVYTNMFDATVDATHAAVEKAG-VQG--------LEL
Sb09g024320.1  (195) ASAASSS-SVTDGGVVYTNMFDATVDATHAAVEKAG-VQG--------LEL
Si022492m      (195) GSGAASSSSVADGGVVYTNMFDATVDATHAAVEKAG-VQG--------LEL
GRMZM2G380561  (195) GAGAAS--TVTDGGAVYTNMFDATVDATHAAVEKAG-VQG--------LEL
LOC_Os05g41610.1 (195) QSASVT-----DGGVTYTNMFDATVDAAHAAVEKATGGQA---------VEL
GRMZM2G591605  (195) SGGGAVVWA--DGGASYGNMFDATVDAVYAALERAGAR----------GLEL
Sb03g037270.1  (198) S---AAVT---DGGASYGNMFDATVDAVYAALERAGAPP---------GLEV
Si002065m      (195) S---AAAVT--DGGVAYTNMFDATVDAVHAALDRVAGAQGQ-----EGVEV
LOC_Os01g58730.1 (194) T---SAAVT--DGGVTYTNMFDATLDAVYAALEKAGGQ----------GLEV
GRMZM2G062600  (192) AGT-VVVQDGG---YSYDSLFDAMVDCFYSALENAGAGN---------VTV
GRMZM2G065585  (190) G---TVVQDGS---NAYQNLFDALVDTFVSALQNAGAGN---------VPV
Sb03g045450.1  (189) G---TVVQDDDG--NAYQNLFDALVDTFVSALENAGAGN---------VGV
Sb03g045460.1  (189) G---TVVQDGS---NAYQNLFDALVDTFVSALENAGAGN---------VGV
Si002182m      (189) G---TVVQDGG---NAYQNLFDALVDTFYSALENAGAGS---------VGI
LOC_Os01g71340.1 (189) G---TVVQDGG---NAYQNLFDATMDTFYSALESAGAGS---------VPI
LOC_Os01g71400.1 (195) G---TVVPDGS---KAYQNQFDATMDTFYSALESAGAGS---------VPI
LOC_Os01g71650.1 (144) G---TVVPDGS---KAYQNQFDATMDTFYSALESAGAGS---------VPI
LOC_Os01g71930.1 (194) G---TVVQDGE---HSYQNLFDATVDALYSAMEKVGGST---------VRI
GRMZM2G123107  (159) T---TVVTDDGG--LDYTNLFDAMADAMYSAMEKEGGSG---------VPI
Sb08g019670.1  (187) S---TTVNDDG---HVYTNLFDAMADATYSAMEKEGESG---------VPI
Si022625m      (188) P---PTSNGPE----VYTNLFDAVTDAMYTAMEKVGGSN---------VPI
LOC_Os01g71410.1 (186) T---ATVADDG---RTYSNMFAAMVDAMYSALEKAGAPG---------VAV
LOC_Os01g51570.1 (194) ----TTVWDNG-NRTYTCLFDAMVDSTYAALEKAGTPS---------VSV
LOC_Os01g71350.1 (190) ----TTVTDDG-SGLIYTSLFDAMVDSVYAALEDAGAPD---------VGV
Bradi2g60490.1 (192) ----TQVRDDG-NGLVYTNLFDAMVDAVHAAMEKAGAGG---------VKV
```

FIG. 16 (Cont.)

```
GRMZM2G125032   (193) ----TTVRDNG-NGLYYNNLFDAMVDAVMAALEKAGAPN---------VRV
Sb03g045490.1   (192) ----TTVRDNG-NGLTYTNLFDAMVDAVMAALEKAGAGG---------VRT
Si004560m       (191) ----TTVRDGG-NGLTYTNLFDAMVDATVAALEKAGAPN---------VRT
LOC_Os01g71380.1(192) ----TTVRDPN-NGLTYTNLFDAMVDAVYAALEKAGAGN---------VKV
LOC_Os01g71670.1(190) ----TTVRDPN-NGLTYTNLFDAMVDAVYAALEKAGAGN---------VRV
GRMZM2G433365   (193) ----AAVRDGG-SGLVYTNLFDAMVDSVHAALEKAGAPD---------VRV
Sb03g045510.1   (193) ----TTVRDGG-SGLVYTNLLDAMVDSVHAALEKAGAPT---------VRV
Si003802m       (190) ----TTVRDGG-NGLVYTNLFDAMVDAVMAALEKAGAAS---------VRV
Si005124m       (177) ----TTVSDRG-NGLSYTNLFDAMVDAVYAALEKAGAAG---------VRV
LOC_Os01g71680.1(191) ----TTVPDPN-TGLVYTNLFDAMVDSVYAALDKAGAAG---------VSI
Bradi2g60560.1  (198) S---TPVRDDG-SGLVYTTLFDAMVDALYSALEKAGEPA---------VRV
GRMZM2G061403   (192) S---TTVTDPAN-GLVYTNLFDAMVDAVRAALDKAGAGG---------VDV
Sb03g045520.1   (190) S---TTVTDPAN-GLVYTNLFDAMVDAVRAALDKAGGGGG--------VDV
Si000491m       (190) S---TTVGDPN--GLTYTNLFDAMVDAVHAALDKVGGGG---------VDV
LOC_Os01g71690.2(191) S---TTVSDPNGGGLSYTNLFDAMVDAVRAAVEKVSGGGS------SWDV
LOC_Os01g71690.3(191) S---TTVSDPNGGGLSYTNLFDAMVDAVRAAVEKVSGGGS------SWDV
LOC_Os01g71810.1(196) ----TTVRDND-SGLTYTNLFNAMVDAVAALEKAGAPG----------VRV
LOC_Os01g71820.1(196) ----TTVRDND-SGLTYTNLFSAMVDAVYAALEKAGEPG---------VRV
LOC_Os01g71830.1(196) ----TTVRDND-SGLTYTNLFSAMVDAVYAALEKAGAPG---------VRV
LOC_Os01g71860.1(195) ----TTVRDSD-SGLTYTNLFNAMVDAVYAALEKAGTPN---------VRT
Sb03g045630.1   (186) A---ATVTDGG-NGLAYTNLLDAMVDATYAALEKAGAPG---------VQV
Si002306m       (194) ----TTVRDDG-NGLVYTNLFDAMVDATYAALEKAGAPG---------VGV
Sb09g025890.1   (197) T---AVTDDG--SGLTYTNLFAAMVDATHAALEKAGAPG---------VRT
Si024558m       (191) A---AAVRDGG-SGLAYTNLFAAMVDATHAALEKAGAPG---------VGV
Consensus       (209)     T V DGG  GL Y NLFDAMVDAVYAALEK GG            V V
```

FIG. 16 (Cont.)

|  | (261) | 261 | 270 | 280 | 290 | 300 | 312 | Section 6 |
|---|---|---|---|---|---|---|---|---|
| Bradi2g27140.1 | (229) | VVSESGWPSAGG | ---TAAT | | | ---PANARVYNQYL | | |
| Bradi2g27140.2 | (229) | VVSESGWPSAGG | ---TAAT | | | ---PANARVYNQYL | | |
| GRMZM2G014723 | (230) | VVSETGWPSGGG | ---VQAT | | | ---PANARVYNQYL | | |
| GRMZM2G137535 | (229) | VVSESGWPSGGG | ---VQAT | | | ---PANARVYNQYL | | } CAL1 |
| GRMZM2G137535(2) | (229) | VVSESGWPSGGG | ---VQAT | | | ---PANARVYNQYL | | |
| Sb09g018730.1 | (229) | VVSESGWPSGGG | ---VQAT | | | ---PANARVYNQYL | | |
| Sb09g018730.3 | (223) | VVSESGWPSGGG | ---VQAT | | | ---PANARVYNQYL | | |
| Sb09g018730.4 | (223) | VVSESGWPSGGG | ---VQAT | | | ---PANARVYNQYL | | |
| Sb09g018730.2 | (229) | VVSESGWPSGGG | ---VQAT | | | ---PANARVYNQYL | | |
| Si022614m | (229) | VVSESGWPSGGG | ---EQAN | | | ---AANARIYNQYL | | |
| Si022791m | (223) | VVSESGWPSGGG | ---EQAN | | | ---AANARIYNQYL | | |
| Si022794m | (223) | VVSESGWPSGGG | ---EQAN | | | ---AANARIYNQYL | | |
| Si022731m | (229) | VVSESGWPSGGG | ---EQAN | | | ---AANARIYNQYL | | |
| LOC_Os05g31140.1 | (229) | VVSETGWPSAGG | ---MSAS | | | ---PANARIYNQNL | | |
| LOC_Os05g31140.2 | (223) | VVSETGWPSAGG | ---MSAS | | | ---PANARIYNQNL | | |
| LOC_Os05g31140.3 | (223) | VVSETGWPSAGG | ---MSAS | | | ---PANARIYNQNL | | |
| GRMZM2G041961 | (229) | VVSESGWPSAGG | ---WAAS | | | ---PENAAIYNQNL | | |
| Sb090g18750.1 | (229) | VVSESGWPSAGG | ---WAAS | | | ---PENAAIYNQNL | | |
| Si022606m | (229) | VVSESGWPSAGG | ---WAAS | | | ---PENAALYNQNL | | |
| Si028122m | (227) | LVSETGWPSGGG | ---KAAT | | | ---PENAKIYNQNL | | |
| Bradi2g60500.1 | (237) | VVSETGWPSAGG | ---EAAS | | | ---VENARTYNQNL | | |
| GRMZM2G019185 | (232) | VVSETGWPTAGG | ---AAAS | | | ---LENARTYNQNL | | |
| GRMZM2G019185(2) | (232) | VVSETGWPTAGG | ---AAAS | | | ---LENARTYNQNL | | |
| Sb03g045480.1 | (232) | VVSETGWPTAGG | ---AAAS | | | ---VENARTYNQNL | | |
| Si002273m | (229) | VVSETGWPTAGG | ---AAAS | | | ---VENAMTYNQNL | | |
| LOC_Os01g71474.1 | (230) | VVSETGWPTAGG | ---VGAS | | | ---VENAMTYNQNL | | |
| Bradi3g57610.1 | (239) | VVSETGWPSKGDAKETG | | | | ---AAASNAEYNGNL | | |
| LOC_Os02g53200.1 | (237) | VVSETGWPSKGDAKETG | | | | ---AAANAAAYNGNL | | |
| LOC_Os02g53200.2 | (237) | VVSETGWPSKGDAKETG | | | | ---AAANAAAYNGNL | | |
| Si017035m | (237) | VVSETGWPSKGDASEVG | | | | ---ASPANAAAYNGNL | | |

FIG. 16 (Cont.)

| | | |
|---|---|---|
| GRMZM2G114140 | (247) | HVSESGWPSGGKPKRGGRPRPRPRGGGRRLELEQAGGEAASVANAQAYNNYL |
| GRMZM2G335111 | (235) | AVTETGWPTAGHPAATP----------------------QNAAAYNAKI |
| Sb02g030930.1 | (235) | AVTETGWPTAGHPAATP----------------------QNAAAYNAKI |
| LOC_Os09g36280.1 | (235) | AVTETGWPTAGHPAATP----------------------QNAAAYNAKI |
| GRMZM2G088951 | (234) | VVSETGWPSAGG---EGAT------------------VENAAAYNNNV |
| Sb09g024320.1 | (236) | VVSETGWPSGGG---DGAT------------------VENAAAYNNNV |
| Si022492m | (237) | VVSETGWPSGG----EGAS------------------VENAAAYNNNV |
| GRMZM2G380561 | (235) | VVSETGWPSAGG---EGAS------------------VENAAAYNNNV |
| LOC_Os05g41610.1 | (233) | VVSETGWPSGGG---VGAT------------------VENAAAYNNN |
| GRMZM2G591605 | (235) | VVSETGWPSGGG---AGAS------------------VGNASAYMNNV |
| Sb03g037270.1 | (235) | VVSETGWPSGGG---AGAS------------------VGNAAAYMNNV |
| Si002065m | (236) | VVSETGWPSGGG---AGAS------------------VGNAAAYMNNV |
| LOC_Os01g58730.1 | (231) | VVSETGWPSGGG---AGAS------------------VENAAAYSNN |
| GRMZM2G062600 | (230) | VVSESGWPSAGS---DAAN------------------TTNSQAYSQN |
| GRMZM2G065585 | (226) | VVSESGWPSAGG---DAAT------------------AANAQTYNQN |
| Sb03g045450.1 | (226) | VVSESGWPSDGG---DAAT------------------PGNAQTYNQN |
| Sb03g045460.1 | (225) | VVSESGWPSAGG---DAAT------------------PGNAQTYNQN |
| Si002182m | (225) | VVSESGWPSAGG---DAAS------------------TDNARTYNQN |
| LOC_Os01g71340.1 | (225) | VVSESGWPSAGG---TAAS------------------AGNAQTYNQN |
| LOC_Os01g71400.1 | (231) | VVSESGWPSAGG---TAAS------------------ASNAQTYNQN |
| LOC_Os01g71650.1 | (180) | VVSESGWPSAGG---TAAS------------------ASNAQTYNQN |
| LOC_Os01g71930.1 | (230) | VVSDSGWPSAGA---PAAT------------------KDNARAYMQN |
| GRMZM2G123107 | (196) | VVSESGWPSGGGT-GNFT------------------VDNARTYNQN |
| Sb08g019670.1 | (223) | VVSESGWPSDGGL-GAS-------------------VDNAQTYNQN |
| Si022625m | (222) | VVSESGWPSDGG-F-GAS-------------------VQNAQTYNQN |
| LOC_Os01g71410.1 | (222) | VVSESGWPSAGG-S-GAS-------------------ADNARRYNQG |
| LOC_Os01g51570.1 | (231) | VVSESGWPSAGG--KVGAS------------------VNNAQTYNQG |
| LOC_Os01g71350.1 | (227) | VVSETGWPSAGG---FGAS------------------VSNAQTYNQK |
| Bradi2g60490.1 | (229) | VVSESGWPSDGG---FAAN------------------ADNARAYNQG |

FIG. 16 (Cont.)

| | | | |
|---|---|---|---|
| GRMZM2G125032 (230) | VVSESGWPSAGG | -FGAS | VDNARKYNQGL |
| Sb03g045490.1 (229) | VVSESGWPSAGG | -SGAS | VDNARKYNQGL |
| Si004560m (228) | VISESGWPSAGG | -FGAS | VENARNYNQGL |
| LOC_Os01g71380.1 (229) | VVSESGWPSAGG | -FGAS | VDNARAYNQGL |
| LOC_Os01g71670.1 (227) | VVSESGWPSAGG | -FGAS | VDNARAYNQGL |
| GRMZM2G433365 (230) | VVSESGWPSAGG | -AAAS | VQNAQAYMQNL |
| Sb03g045510.1 (230) | VVSETGWPSAGG | -AAAT | VQNAQTYMQNM |
| Si003802m (227) | VVSESGWPSAGG | -TAAS | VENARTYMQNL |
| Si005124m (214) | VVAETGWPSAAG | -FAAS | VDNARAYNQGV |
| LOC_Os01g71680.1 (228) | VVSESGWPSAGG | -DSAT | IDIARTYMQNL |
| Bradi2g60560.1 (236) | VVSESGWPSAGG | -FGAT | VENARAYNQGL |
| GRMZM2G061403 (230) | VVSETGWPSADG | -NGAT | LDNARTYNQNL |
| Sb03g045520.1 (229) | VVSESGWPSADG | -KGAT | VDNARTYNQNL |
| Si000491m (227) | VVSESGWPSADG | -RGAT | VDNARTYNQNL |
| LOC_Os01g71690.2 (233) | VVSESGWPSDGG | -KGAT | VENARAYNQNL |
| LOC_Os01g71690.3 (233) | VVSESGWPSDGG | -KGAT | VENARAYNQNL |
| LOC_Os01g71810.1 (233) | VVSESGWPSAGG | -FAAN | VENARNHNQGV |
| LOC_Os01g71820.1 (233) | VVSESGWPSAGG | -FAAN | VENARNHNQGV |
| LOC_Os01g71830.1 (233) | VVSESGWPSAGG | -FAAN | VENARNHNQGV |
| LOC_Os01g71860.1 (232) | AVSETGWPSAGG | -FAAT | AENAMNHNQGV |
| Sb03g045630.1 (224) | VVSESGWPSAGG | -FAAS | VDNARQYNQGV |
| Si002306m (231) | VVSESGWPSAGG | -FAAS | VENARAHNQGV |
| Sb09g025890.1 (234) | VVSESGWPSAGG | -FAAT | VENARRYNQGL |
| Si024558m (229) | VVSESGWPSAGG | -FAAT | VENARRYNQGL |
| Consensus (261) | VVSESGWPSAGG | AAS | VENAR YNQNL |

FIG. 16 (Cont.)

```
                                                                           Section 7
                       (313) 313    320       330       340       350       364
     Bradi2g27140.1  (256)  INHVG---RGTPRHPGA-IETYWFSMFNENQK-DS--GVEQNWGLFY-PNMQ
     Bradi2g27140.2  (256)  INHVG---RGTPRHPGA-IETYWFSMFNENQK-DS--GVEQNWGLFY-PNMQ
       GRMZM2G014723 (257)  INHVG---RGTPRHPGG-IETYLFSMFNENQK-ES--GVEQNWGLFY-PNMH
      GRMZM2G137535  (256)  INHVG---RGTPRHPGA-IETYLFSMFNENQK-ES--GVEQNWGLFY-PNMQ ⎫
   GRMZM2G137535(2)  (256)  INHVG---RGTPRHPGA-IETYLFSMFNENQK-ES--GVEQNWGLFY-PNMQ ⎬CAL1
       Sb09g018730.1 (256)  VNHVR---RGTPRHPGA-IETYLFSMFNENQK-ES--GVEQNWGLFY-PNMQ
       Sb09g018730.3 (250)  VNHVR---RGTPRHPGA-IETYLFSMFNENQK-ES--GVEQNWGLFY-PNMQ
       Sb09g018730.4 (250)  VNHVR---RGTPRHPGA-IETYLFSMFNENQK-ES--GVEQNWGLFY-PNMQ
       Sb09g018730.2 (256)  VNHVR---RGTPRHPGA-IETYLFSMFNENQK-ES--GVEQNWGLFY-PNMQ
           Si022614m (256)  INHVG---RGTPRHPGG-IETYLFSMFNENQK-DS--GVEQNWGLFY-PNMQ
           Si022791m (250)  INHVG---RGTPRHPGG-IETYLFSMFNENQK-DS--GVEQNWGLFY-PNMQ
           Si022794m (250)  INHVG---RGTPRHPGG-IETYLFSMFNENQK-DS--GVEQNWGLFY-PNMQ
           Si022731m (256)  INHVG---RGTPRHPGG-IETYLFSMFNENQK-DS--GVEQNWGLFY-PNMQ
    LOC_Os05g31140.1 (256)  INHVG---RGTPRHPGA-IETYWFSMFNENQK-DA--GVEQNWGLFY-PNMQ
    LOC_Os05g31140.2 (250)  INHVG---RGTPRHPGA-IETYWFSMFNENQK-DA--GVEQNWGLFY-PNMQ
    LOC_Os05g31140.3 (250)  INHVG---RGTPRHPGA-IETYWFSMFNENQK-DA--GVEQNWGLFY-PNMQ
       GRMZM2G041961 (256)  INHVG---RGTPRHPGA-IETILFSMFNENLK-QS--GVEQNWGLFY-PNMQ
       Sb09g018750.1 (256)  INHVG---RGTPRHPGA-IETILFSMFNENLK-EN--GVEQNWGLFY-PNMQ
           Si022606m (256)  INHVG---RGTPRHPGA-IETILFSMFNENLK-ES--GVEQNWGLFY-PNKQ
           Si028122m (254)  IEHIR---KGTPRHPEP-KTYWFSMFNENQK-DK--GVEQNWGLFY-PNMK
      Bradi2g60500.1 (264)  VDHVR---KGTPRRPWK-VETYLFAMFNENLK-EG--GVEQNWGLFY-PSTD
       GRMZM2G019185 (259)  VRHVW---KGTPRRPRR-VEAYWFAMFNEDKK-DA--GVEQNWGLFY-PNME
    GRMZM2G019185(2) (259)  VRHVW---KGTPRRPRR-VEAYWFAMFNEDKK-DA--GVEQNWGLFY-PNME
       Sb03g045480.1 (259)  VTHVW---KGTPRRPRR-VEAYWFAMFNEDQK-EA--GVEQNWGLFY-PNME
           Si002273m (256)  VRHVW---KGTPRRPRRVEAYWFALFNENLK-EE--GVEQNWGLFY-PNME
    LOC_Os01g71474.1 (257)  VRHVR---NGTPRHPGKKTETYWFAMFNENLK-EA--GVEQNWGLFY-PSTD
      Bradi3g57610.1 (269)  VRRVLSGNAGTPRRGDADEDVYLFALFNENQK--PGPTSERNYGVFY-PNQQ
    LOC_Os02g53200.1 (267)  VRRVLSGNAGTPRRPDADMDVYLFALFNENQK--PGPTSERNYGVFY-PNQQ
    LOC_Os02g53200.2 (267)  VRRVLSGNAGTPRRPDADMDVYLFALFNENQK--PGPTSERNYGVFY-PNQQ
           Si017035m (267)  ARRVLSGNAGTPLRPNADMDVYLFALFNENQK--PGPTSERNYGVFY-PNQQ
```

FIG. 16 (Cont.)

```
GRMZM2G114140  (299) IKRMLSGDTGTPYHPDADMDVYIFSLFNENQKGDGADDVEQHFGLFYIPNRT
GRMZM2G335111  (262) VERAARG-VGTPKRPGVPVEVFLFDLYDEDGK--PGPEFERHFGIIFR-ADGS
Sb02g030930.1  (262) VERAVRG-VGTPKRPGVPVEVFLFDLYDEDGK--PGPEFERHFGIIFR-ADGG
LOC_Os09g36280.1 (262) VERMARG-AGTPRRPGVPVEVFLFDLYDEDGK--PGAEFERHFGIIFR-ADGS
GRMZM2G088951  (261) VRHVGG---GTPRRPGKAVETYLFAMFNENGK-AE--GVEQHFGLFQ-PDMS
Sb09g024320.1  (264) VRHVGG---GTPRRPGKAVETYLFAMFNENGK-AE--GVEQHFGLFQ-PDMS
Si022492m      (264) VRHVGG---GTPRRPGKPVETYLFAMFNENQK-TE--GVEQHFGLFQ-PDMS
GRMZM2G380561  (262) VRHVDG---GTPRRPGKALETYLFAMFNENGK-AE--GVEQHFGLFQ-PDMS
LOC_Os05g41610.1 (261) IRHVSGG-AGTPRRPGKPVETYLFAMFNENQK-PE--GVEQHFGLFQ-PDMT
GRMZM2G591605  (263) VRHVSG-RGTPRRPGKPVEAFIFAMFNENQK-PE--GVEQHFGMFQ-PDMT
Sb03g037270.1  (263) VRHWASG-RGTPRRPGKAVEAFVFAMFNENQK-PE--GVEQHFGLFQ-PDMT
Si002065m      (264) VRHVGSG-RGTPRRPGKALEAFLFAMFNENEK-PE--GVEQHFGLFQ-PDMT
LOC_Os01g58730.1 (259) VRHVG---RGTPRRPGKAVETYLFAMFNENQK-PE--GVEQNFGLFH-PDMS
GRMZM2G062600  (257) INHVG---QGTPKRP-GPIEAYIFATFNEDQK-LGDDETRRHFGLFN-KDRS
GRMZM2G065585  (253) INHVG---QGTPKRP-GPIETYIFAMFNEDQK-TG-AESERHFGLFN-PDKS
Sb03g045450.1  (253) INHVG---QGTPKRP-GAIETYIFAMFNEDKK-TG-AETERHFGLFN-PDKS
Sb03g045460.1  (252) INHVG---KGTPKRP-GAIETYIFAMFNEDKK-TG-AETERHFGLFN-PDKS
Si002182m      (252) INHVG---QGTPKRP-GAIETYIFAMFNEDQK-PG-AETEKHFGLFN-PDKS
LOC_Os01g71340.1 (252) INHVG---QGTPKRP-GSIETYIFAMFNENQK-GG-DETERHFGLFN-PDQS
LOC_Os01g71400.1 (258) IKHVG---QGTPKRA-GRIETYIFAMFNENDK-RG-DETERHFGLFN-PDQS
LOC_Os01g71650.1 (207) IKHVG---QGTPKRA-GRIETYIF----------------------------
LOC_Os01g71930.1 (257) INHVS---KGTPKRP-VPIETYIFAMFNENEK-TG-DEIERNFGLFE-PDKS
GRMZM2G123107  (225) INHVG---NGTPKRS-GPLETYIFAMFNEDKK-QG-DETEKHFGLFNGPDQS

**********  ****  **************************************

GRMZM2G125032  (257) IDHVG---RGTPKRT-GPLETFVFAMFNENQK-GG-DPTEKNFGLFY-GNKQ
Sb03g045490.1  (256) INHVG---RGTPKRR-GTLETFLFAMFNENQK-TG-DPTEKNFGLFY-GNKQ
Si004560m      (255) IDHVG---RGTPKRS-GALDTFIFAMFNENQK-SG-DPTERNFGLFY-PNKQ
LOC_Os01g71380.1 (256) IDHVG---RGTPKRP-GPLEAYIFAMFNENQK-NG-DPTEKNFGLSY-PNKS
LOC_Os01g71670.1 (254) IDHVG---RGTPKRP-GALEAYIFAMFNENQK-NG-DPTERNFGLFY-PNKS
```

FIG. 16 (Cont.)

```
GRMZM2G433365 (257) IDHVA---QGTPKRP-GPIETYVFAMFNENQK-PG-EPTEKNFGLFY-PSKA
Sb03g045510.1 (257) IDHAG---QGTPKKP-GPIETYVFAMFNEDQK-PG-ELTERNFGLFY-PNKA
Si003802m     (254) IDHAA---QGTPKRP-GALETYVFAMFNENQK-PG-ELTEQNFGLFY-PNKS
Si005124m     (241) IDHVG---NGTPRKPGAALETLVFAMFNENQK-PG-EPTEKNFGLFY-PKKS
LOC_Os01g71680.1 (255) IKHAK---RGTPKRP-GVIETYVFAMFNENQK-PG-EATEQNFGAFY-PNKT
Bradi2g60560.1 (263) IDHVG---KGTPKRPGAPVCAMISMFNENLK-PG-DETERHFGLFY-PSKA
GRMZM2G061403 (257) IDHAS---KGTPRKP-GPMEVVVFAMFNEDQK-DG-DPTEKKFGLFN-PDKT
Sb03g045520.1 (256) INHAG---KGTPRKP-GSMEVVVFAMFNEDQK-DG-DPTEKKFGLFN-PDKT
Si000491m     (254) INHAG---KGTPRKP-GPMEVVVFAMFNEDNK-DG-DPTEKKFGLFN-PDKT
LOC_Os01g71690.2 (260) IDHVA---QGTPKKP-GDMEVVVFALFNENRK-EG-DATEKKFGLFN-P---
LOC_Os01g71690.3 (260) IDHVA---QGTPKKP-GDMEVVVFALFNENRK-EG-DATEKKFGLFN-P---
LOC_Os01g71810.1 (260) IDNVK---NGTPKRP-GCLETYVFAMFNENQK-PG-DETERHFGLFY-PDKT
LOC_Os01g71820.1 (260) IDNVK---NGTPKRP-GCLETYVFAMFNENQK-PG-DETERHFGLFY-PDKT
LOC_Os01g71830.1 (260) IDNVK---NGTPKRP-GCLETYVFAMFNENQK-PG-DETERHFGLFN-PDKT
LOC_Os01g71860.1 (259) IDNVK---NGTPKRP-GPLETYVFAMFNENQ-TG-DETRRHFGLFN-PDKT
Sb03g045630.1 (251) IDHVR---QGTPRRP-GLLETYVFAMFNENQK-TG-DETERHFGLFN-PDKT
Si002306m     (258) IDHVR---RGTPKRP-GVLETYVFAMFNENQK-PG-EEIERHFGLFN-PDKS
Sb09g025890.1 (261) IDHAY---RGTPKRP-GALETYVFAMFNENQK-PG-DPTERNFGLFY-PNKE
Si024558m     (256) IDQAY---RGTPKRP-GVLETYVFAMFNENQK-PG-DPTERNFGLFY-PNKQ
Consensus     (313) I HVG    RGTPRRP G IETYVFAMFNENQK  G   ERNFGLFY PN
```

FIG. 16 (Cont.)

_____ Section 8

```
                        (365) 365  371
       Bradi2g27140.1 (300) HVYPISF
       Bradi2g27140.2 (300) HVYPISF
        GRMZM2G014723 (301) HVYPISF
        GRMZM2G137535 (300) HVYPISF  } CAL1
     GRMZM2G137535(2) (300) HVYPISF
        Sb09g018730.1 (300) RVYPISF
        Sb09g018730.3 (294) RVYPISF
        Sb09g018730.4 (294) RVYPISF
        Sb09q018730.2 (300) RVYPISF
            Si022614m (300) HVYPISF
            Si022791m (294) HVYPISF
            Si022794m (294) HVYPISF
            Si022731m (300) HVYPISF
     LOC_Os05g31140.1 (300) HVYPISF
     LOC_Os05g31140.2 (294) HVYPISF
     LOC_Os05q31140.3 (294) HVYPISF
        GRMZM2G041961 (300) RVYPIKF
        Sb09g018750.1 (300) RVYPISF
            Si022606m (300) RVYPISF
            Si028122m (298) PVY----
       Bradi2g60500.1 (308) RVYPIDF
        GRMZM2G019185 (303) RVYPITF
     GRMZM2G019185(2) (303) RVYPITF
        Sb03q045480.1 (303) RVYPITF
            Si002273m (301) RVYPITF
     LOC_Os01g71474.1 (302) RVYPISF
       Bradi3g57610.1 (318) KVYDMEF
     LOC_Os02g53200.1 (316) KVYDMEF
     LOC_Os02g53200.2 (316) KVYDMEF
            Si017035m (316) KVYDMEF
        GRMZM2G114140 (350) KVYEFDF
        GRMZM2G335111 (310) KAYDINF
        Sb02g030930.1 (310) KAYDINF
     LOC_Os09g36280.1 (310) KAMNINF
```

FIG. 16 (Cont.)

```
GRMZM2G088951  (306) EVYHMDF
Sb09g024320.1  (309) EVYHMDF
    Si022492m  (309) EVYHMDF
GRMZM2G380561  (307) EVYHMDF
LOC_Os05g41610.1 (308) EVYHMDF
GRMZM2G591605  (310) EVYHMDF
Sb03g037270.1  (310) EVYHMDF
    Si002065m  (311) EVYHMDF
LOC_Os01g58730.1 (304) AVYHMDF
GRMZM2G062600  (303) LAYPIDF
GRMZM2G065585  (298) PAYPINF
Sb03g045450.1  (298) PAYPINF
Sb03g045460.1  (297) PAYSINF
    Si002182m  (297) PVYDINF
LOC_Os01g71340.1 (297) PAYSINF
LOC_Os01g71400.1 (303) PAYTINF
LOC_Os01g71650.1 (227) -------
LOC_Os01g71930.1 (302) PVYPITF
GRMZM2G123107  (271) PVYQISF

Sb08g019670.1  (297) PVYPISF
    Si022625m  (295) PVYTIRF
LOC_Os01g71410.1 (294) PAYPIKF
LOC_Os01g51570.1 (304) PSYSISF
LOC_Os01g71350.1 (300) PSMKIRF
Bradi2g60490.1 (301) PAMDIRF
GRMZM2G125032  (302) PVYPIRF
Sb03g045490.1  (301) PVYPISF
    Si004560m  (300) PVYSIRF
LOC_Os01g71380.1 (301) PVYPIRF
LOC_Os01g71670.1 (299) PVYPIRF
GRMZM2G433365  (302) PVYPIVF
Sb03g045510.1  (302) PVYPMVF
```

FIG. 16 (Cont.)

```
       Si003802m (299) PVYPIIF
       Si005124m (287) PVYPIAF
  LOC_Os01g71680.1 (300) AVYPINF
     Bradi2g60560.1 (309) PVCPISF
     GRMZM2G061403 (302) PVYPINF
     Sb03g045520.1 (301) PVYPINF
       Si000491m (299) PVYPINF
  LOC_Os01g71690.2 (302) -------
  LOC_Os01g71690.3 (302) -------
  LOC_Os01g71810.1 (305) PVYPITF
  LOC_Os01g71820.1 (305) PVYPITF
  LOC_Os01g71830.1 (305) PVYPITF
  LOC_Os01g71860.1 (304) PAYPIT-
     Sb03g045630.1 (296) PVYPINF
       Si002306m (303) PVYPITF
     Sb09g025890.1 (306) PVYSISF
       Si024558m (301) PVYPIIF
        Consensus (365)  VYPI F
```

FIG. 16 (Cont.)

SEQUENCE LISTING

```
<160> NUMBER OF SEQ ID NOS: 164

<210> SEQ ID NO 1
<211> LENGTH: 1011
<212> TYPE: DNA
<213> ORGANISM: Zea mays

<400> SEQUENCE: 1
atggcaagca ggcaaggtgt agccgcctcc atgttcgcca cggcattgct cctcggcgtc      60
tttgcatcca tcccacaaag tgctgaggcc atcggggtgt gctacggcat gagcgccaac     120
aacctgccgg cggcgagcac ggtggtgagc atgtacaagg cgaacggcat ctcggcgatg     180
cggctgtacg cgccggacca gggcgcgctg caggcggtgg gcggcacggg catcagcgtg     240
gccgtgggcg cccccaacga cgtgctgtcc aacatcgcgg ctagccccgc ggcggccgcg     300
tcgtgggtgc gcaacaacat ccaggcgtac ccgtccgtgt cgttccgcta cgtgtgcgtg     360
```

-continued

```
ggcaacgagg tggccggcgg cgcggcgcag gacctggcgc cggccatgga gaacgtgcac      420
gcggcgctgg cggcggccgg gctgggccac atcaaggtga cgacgtcggt gtcgcaggcc      480
atcctgggcg tgtacagccc gccgtccgcc gcggagttca ccggcgaggc gcgcggatac      540
atgggccccg tgctgcagtt cctggcgcgc accgggtcgc cgctcatggc caacatctac      600
ccgtacctgg cctgggcata accccagc gccatggaca tgagctacgc gctcttcacc       660
tcctccggca ccgtcgtgca ggacggcgcc tacgggtacc agaacctctt cgacaccacc      720
gtcgacgcct tctacgtcgc catgggcaac aacggcggct ccggcgtgcc gctcgtggtg      780
tcgaagagcg ggtggccgtc cggcggcggc gtccaggcca cgccggccaa cgcgagggtg      840
tacaaccagt acctcatcaa ccacgtcggg cgcgggacgc cgcgccaccc gggcgccatc      900
gagacctacc tcttctccat gttcaacgag aaccagaagg agagcggcgt ggagcagaac      960
tgggggctct tctaccccaa catgcagcac gtctaccccca tcagcttctg a             1011
```

<210> SEQ ID NO 2
<211> LENGTH: 336
<212> TYPE: PRT
<213> ORGANISM: Zea mays

<400> SEQUENCE: 2

```
Met Ala Ser Arg Gln Gly Val Ala Ala Ser Met Phe Ala Thr Ala Leu
 1               5                  10                  15

Leu Leu Gly Val Phe Ala Ser Ile Pro Gln Ser Ala Glu Ala Ile Gly
                20                  25                  30

Val Cys Tyr Gly Met Ser Ala Asn Asn Leu Pro Ala Ala Ser Thr Val
            35                  40                  45

Val Ser Met Tyr Lys Ala Asn Gly Ile Ser Ala Met Arg Leu Tyr Ala
        50                  55                  60

Pro Asp Gln Gly Ala Leu Gln Ala Val Gly Gly Thr Gly Ile Ser Val
 65                  70                  75                  80

Ala Val Gly Ala Pro Asn Asp Val Leu Ser Asn Ile Ala Ala Ser Pro
                85                  90                  95

Ala Ala Ala Ala Ser Trp Val Arg Asn Asn Ile Gln Ala Tyr Pro Ser
            100                 105                 110

Val Ser Phe Arg Tyr Val Cys Val Gly Asn Glu Val Ala Gly Gly Ala
        115                 120                 125

Ala Gln Asp Leu Ala Pro Ala Met Glu Asn Val His Ala Ala Leu Ala
    130                 135                 140

Ala Ala Gly Leu Gly His Ile Lys Val Thr Thr Ser Val Ser Gln Ala
145                 150                 155                 160

Ile Leu Gly Val Tyr Ser Pro Pro Ser Ala Ala Glu Phe Thr Gly Glu
                165                 170                 175

Ala Arg Gly Tyr Met Gly Pro Val Leu Gln Phe Leu Ala Arg Thr Gly
            180                 185                 190

Ser Pro Leu Met Ala Asn Ile Tyr Pro Tyr Leu Ala Trp Ala Tyr Asn
        195                 200                 205

Pro Ser Ala Met Asp Met Ser Tyr Ala Leu Phe Thr Ser Ser Gly Thr
    210                 215                 220

Val Val Gln Asp Gly Ala Tyr Gly Tyr Gln Asn Leu Phe Asp Thr Thr
225                 230                 235                 240

Val Asp Ala Phe Tyr Val Ala Met Gly Asn Asn Gly Gly Ser Gly Val
                245                 250                 255
```

```
Pro Leu Val Val Ser Lys Ser Gly Trp Ser Gly Gly Gly Val Gln
                260                 265                 270

Ala Thr Pro Ala Asn Ala Arg Val Tyr Asn Gln Tyr Leu Ile Asn His
            275                 280                 285

Val Gly Arg Gly Thr Pro Arg His Pro Gly Ala Ile Glu Thr Tyr Leu
        290                 295                 300

Phe Ser Met Phe Asn Glu Asn Gln Lys Glu Ser Gly Val Glu Gln Asn
305                 310                 315                 320

Trp Gly Leu Phe Tyr Pro Asn Met Gln His Val Tyr Pro Ile Ser Phe
                325                 330                 335

<210> SEQ ID NO 3
<211> LENGTH: 1011
<212> TYPE: DNA
<213> ORGANISM: Zea mays

<400> SEQUENCE: 3
atggcaagca ggcaaggtgt agccgcctcc atgttcgcca cggcattgct cctcggcgtc      60
tttgcatcca tcccacaaag tgctgaggcc atcggggtgt gctacggcat gagcgccaac     120
aacctgccgg cggcgagcac ggtggtgagc atgtacaagg cgaacggcat ctcggcgatg     180
cggctgtacg cgccggacca gggcgcgctg caggcggtgg gcggcacggg catcagcgtg     240
gccgtgggcg cccccaacga cgtgctgtcc aacatcgcgg ctagccccgc ggcggccgcg     300
tcgtgggtgc gcaacaacat ccaggcgtac ccgtccgtgt cgttccgcta cgtgtgcgtg     360
ggcaacgagg tggccggcgg cgcggcgcag gacctggcgc cggccatgga gaacgtgcac     420
gcggcgctgg cggcggccgg gctgggccac atcaaggtga cgacgtcggt gtcgcaggcc     480
atcctgggcg tgtacagccc gccgtccgcc gcggagttca ccggcgaggc gcgcggatac     540
atgggccccg tgctgcagtt cctggcgcgc accgggtcgc cgctcatggc caacatctac     600
ccgtacctgg cctgggcata aaccccagc gccatggaca tgagctacgc gctcttcacc     660
tcctccggca ccgtcgtgca ggacggcgcc tacgggtacc agaacctctt cgacaccacc     720
gtcgacgcct tctacgtcgc catgggcaac acggcggct ccggcgtgcc gctcgtggtg     780
tcggagagcg ggtggccgtc cggcggcggc gtccaggcca cgccggccaa cgcgagggtg     840
tacaaccagt acctcatcaa ccacgtcggg cgcgggacgc cgcgccaccc gggcgccatc     900
gagacctacc tcttctccat gttcaacgag aaccagaagg agagcggcgt ggagcagaac     960
tgggggctct ctaccccaa catgcagcac gtctacccca tcagcttctg a              1011

<210> SEQ ID NO 4
<211> LENGTH: 336
<212> TYPE: PRT
<213> ORGANISM: Zea mays

<400> SEQUENCE: 4

Met Ala Ser Arg Gln Gly Val Ala Ala Ser Met Phe Ala Thr Ala Leu
  1               5                  10                  15

Leu Leu Gly Val Phe Ala Ser Ile Pro Gln Ser Ala Glu Ala Ile Gly
             20                  25                  30

Val Cys Tyr Gly Met Ser Ala Asn Asn Leu Pro Ala Ala Ser Thr Val
         35                  40                  45

Val Ser Met Tyr Lys Ala Asn Gly Ile Ser Ala Met Arg Leu Tyr Ala
     50                  55                  60

Pro Asp Gln Gly Ala Leu Gln Ala Val Gly Gly Thr Gly Ile Ser Val
 65                  70                  75                  80
```

Ala Val Gly Ala Pro Asn Asp Val Leu Ser Asn Ile Ala Ala Ser Pro
                85                  90                  95

Ala Ala Ala Ala Ser Trp Val Arg Asn Asn Ile Gln Ala Tyr Pro Ser
            100                 105                 110

Val Ser Phe Arg Tyr Val Cys Val Gly Asn Glu Val Ala Gly Gly Ala
        115                 120                 125

Ala Gln Asp Leu Ala Pro Ala Met Glu Asn Val His Ala Ala Leu Ala
    130                 135                 140

Ala Ala Gly Leu Gly His Ile Lys Val Thr Thr Ser Val Ser Gln Ala
145                 150                 155                 160

Ile Leu Gly Val Tyr Ser Pro Pro Ser Ala Ala Glu Phe Thr Gly Glu
                165                 170                 175

Ala Arg Gly Tyr Met Gly Pro Val Leu Gln Phe Leu Ala Arg Thr Gly
            180                 185                 190

Ser Pro Leu Met Ala Asn Ile Tyr Pro Tyr Leu Ala Trp Ala Tyr Asn
        195                 200                 205

Pro Ser Ala Met Asp Met Ser Tyr Ala Leu Phe Thr Ser Ser Gly Thr
    210                 215                 220

Val Val Gln Asp Gly Ala Tyr Gly Tyr Gln Asn Leu Phe Asp Thr Thr
225                 230                 235                 240

Val Asp Ala Phe Tyr Val Ala Met Gly Asn Asn Gly Gly Ser Gly Val
                245                 250                 255

Pro Leu Val Val Ser Glu Ser Gly Trp Pro Ser Gly Gly Gly Val Gln
            260                 265                 270

Ala Thr Pro Ala Asn Ala Arg Val Tyr Asn Gln Tyr Leu Ile Asn His
        275                 280                 285

Val Gly Arg Gly Thr Pro Arg His Pro Gly Ala Ile Glu Thr Tyr Leu
    290                 295                 300

Phe Ser Met Phe Asn Glu Asn Gln Lys Glu Ser Gly Val Glu Gln Asn
305                 310                 315                 320

Trp Gly Leu Phe Tyr Pro Asn Met Gln His Val Tyr Pro Ile Ser Phe
                325                 330                 335

<210> SEQ ID NO 5
<211> LENGTH: 951
<212> TYPE: DNA
<213> ORGANISM: Zea mays

<400> SEQUENCE: 5
atgtgcgttt cgatcgcagg tgctgaggcc atcggggtgt gctacggcat gagcgccaac      60
aacctgccgg cggcgagcac ggtggtgagc atgtacaagg cgaacggcat ctcggcgatg     120
cggctgtacg cgccggacca gggcgcgctg caggcggtgg cggcacgggc atcagcgtg     180 gccgtgggcg ccccaacga cgtgctgtcc aacatcgcgg ctagccccgc ggcggccgcg     240
tcgtgggtgc gcaacaacat ccaggcgtac cgtccgtgt cgttccgcta cgtgtgcgtg     300
ggcaacgagg tggccggcgg cgcggcgcag gacctggcgc cggccatgga gaacgtgcac     360
gcggcgctgg cggcggccgg gctgggccac atcaaggtga cgacgtcggt gtcgcaggcc     420
atcctgggcg tgtacagccc gccgtccgcc gcggagttca ccggcgaggc gcgcggatac     480 atgggcccg tgctgcagtt cctggcgcgc accgggtcgc cgctcatggc caacatctac     540
ccgtacctgg cctgggcata aaccccagc gccatggaca tgagctacgc gctcttcacc     600
tcctccggca ccgtcgtgca ggacggcgcc tacgggtacc agaacctctt cgacaccacc     660

```
gtcgacgcct tctacgtcgc catgggcaac aacggcggct ccggcgtgcc gctcgtggtg      720
tcgaagagcg ggtggccgtc cggcggcggc gtccaggcca cgccggccaa cgcgagggtg      780
tacaaccagt acctcatcaa ccacgtcggg cgcgggacgc cgcgccaccc gggcgccatc      840
gagacctacc tcttctccat gttcaacgag aaccagaagg agagcggcgt ggagcagaac      900
tgggggctct tctaccccaa catgcagcac gtctacccca tcagcttctg a               951
```

<210> SEQ ID NO 6
<211> LENGTH: 316
<212> TYPE: PRT
<213> ORGANISM: Zea mays

<400> SEQUENCE: 6

```
Met Cys Val Ser Ile Ala Gly Ala Glu Ala Ile Gly Val Cys Tyr Gly
  1               5                  10                  15

Met Ser Ala Asn Asn Leu Pro Ala Ala Ser Thr Val Val Ser Met Tyr
             20                  25                  30

Lys Ala Asn Gly Ile Ser Ala Met Arg Leu Tyr Ala Pro Asp Gln Gly
         35                  40                  45

Ala Leu Gln Ala Val Gly Gly Thr Gly Ile Ser Val Ala Val Gly Ala
     50                  55                  60

Pro Asn Asp Val Leu Ser Asn Ile Ala Ala Ser Pro Ala Ala Ala
 65                  70                  75                  80

Ser Trp Val Arg Asn Asn Ile Gln Ala Tyr Pro Ser Val Ser Phe Arg
                 85                  90                  95

Tyr Val Cys Val Gly Asn Glu Val Ala Gly Gly Ala Ala Gln Asp Leu
            100                 105                 110

Ala Pro Ala Met Glu Asn Val His Ala Ala Leu Ala Ala Ala Gly Leu
        115                 120                 125

Gly His Ile Lys Val Thr Thr Ser Val Ser Gln Ala Ile Leu Gly Val
130                 135                 140

Tyr Ser Pro Pro Ser Ala Ala Glu Phe Thr Gly Glu Ala Arg Gly Tyr
145                 150                 155                 160

Met Gly Pro Val Leu Gln Phe Leu Ala Arg Thr Gly Ser Pro Leu Met
                165                 170                 175

Ala Asn Ile Tyr Pro Tyr Leu Ala Trp Ala Tyr Asn Pro Ser Ala Met
            180                 185                 190

Asp Met Ser Tyr Ala Leu Phe Thr Ser Ser Gly Thr Val Val Gln Asp
        195                 200                 205

Gly Ala Tyr Gly Tyr Gln Asn Leu Phe Asp Thr Thr Val Asp Ala Phe
    210                 215                 220

Tyr Val Ala Met Gly Asn Asn Gly Gly Ser Gly Val Pro Leu Val Val
225                 230                 235                 240

Ser Lys Ser Gly Trp Pro Ser Gly Gly Val Gln Ala Thr Pro Ala
                245                 250                 255

Asn Ala Arg Val Tyr Asn Gln Tyr Leu Ile Asn His Val Gly Arg Gly
            260                 265                 270

Thr Pro Arg His Pro Gly Ala Ile Glu Thr Tyr Leu Phe Ser Met Phe
        275                 280                 285

Asn Glu Asn Gln Lys Glu Ser Gly Val Glu Gln Asn Trp Gly Leu Phe
    290                 295                 300

Tyr Pro Asn Met Gln His Val Tyr Pro Ile Ser Phe
305                 310                 315
```

<210> SEQ ID NO 7
<211> LENGTH: 951
<212> TYPE: DNA
<213> ORGANISM: Zea mays

<400> SEQUENCE: 7

| | | | | | |
|---|---|---|---|---|---|
| atgtgcgttt | cgatcgcagg | tgctgaggcc | atcggggtgt | gctacggcat | gagcgccaac | 60 |
| aacctgccgg | cggcgagcac | ggtggtgagc | atgtacaagg | cgaacggcat | ctcggcgatg | 120 |
| cggctgtacg | cgccggacca | gggcgcgctg | caggcggtgg | gcggcacggg | catcagcgtg | 180 |
| gccgtgggcg | ccccccaacga | cgtgctgtcc | aacatcgcgg | ctagccccgc | ggcggccgcg | 240 |
| tcgtgggtgc | gcaacaacat | ccaggcgtac | ccgtccgtgt | cgttccgcta | cgtgtgcgtg | 300 |
| ggcaacgagg | tggccggcgg | cgcggcgcag | gacctggcgc | cggccatgga | gaacgtgcac | 360 |
| gcggcgctgg | cggcggccgg | gctgggccac | atcaaggtga | cgacgtcggt | gtcgcaggcc | 420 |
| atcctgggcg | tgtacagccc | gccgtccgcc | gcggagttca | ccggcgaggc | gcgcggatac | 480 |
| atgggccccg | tgctgcagtt | cctggcgcgc | accgggtcgc | cgctcatggc | caacatctac | 540 |
| ccgtacctgg | cctgggcata | caaccccagc | gccatggaca | tgagctacgc | gctcttcacc | 600 |
| tcctccggca | ccgtcgtgca | ggacggcgcc | tacgggtacc | agaacctctt | cgacaccacc | 660 |
| gtcgacgcct | tctacgtcgc | catgggcaac | aacggcggct | ccggcgtgcc | gctcgtggtg | 720 |
| tcggagagcg | gtggccgtc | cggcggcggc | gtccaggcca | cgccggccaa | cgcgagggtg | 780 |
| tacaaccagt | acctcatcaa | ccacgtcggg | cgcgggacgc | cgcgccaccc | gggcgccatc | 840 |
| gagacctacc | tcttctccat | gttcaacgag | aaccagaagg | agagcggcgt | ggagcagaac | 900 |
| tgggggctct | ctaccccaa | catgcagcac | gtctacccca | tcagcttctg | a | 951 |

<210> SEQ ID NO 8
<211> LENGTH: 316
<212> TYPE: PRT
<213> ORGANISM: Zea mays

<400> SEQUENCE: 8

Met Cys Val Ser Ile Ala Gly Ala Glu Ala Ile Gly Val Cys Tyr Gly
1               5                   10                  15

Met Ser Ala Asn Asn Leu Pro Ala Ala Ser Thr Val Val Ser Met Tyr
            20                  25                  30

Lys Ala Asn Gly Ile Ser Ala Met Arg Leu Tyr Ala Pro Asp Gln Gly
        35                  40                  45

Ala Leu Gln Ala Val Gly Gly Thr Gly Ile Ser Val Ala Val Gly Ala
    50                  55                  60

Pro Asn Asp Val Leu Ser Asn Ile Ala Ala Ser Pro Ala Ala Ala
65                  70                  75                  80

Ser Trp Val Arg Asn Asn Ile Gln Ala Tyr Pro Ser Val Ser Phe Arg
                85                  90                  95

Tyr Val Cys Val Gly Asn Glu Val Ala Gly Gly Ala Ala Gln Asp Leu
            100                 105                 110

Ala Pro Ala Met Glu Asn Val His Ala Ala Leu Ala Ala Ala Gly Leu
        115                 120                 125

Gly His Ile Lys Val Thr Thr Ser Val Ser Gln Ala Ile Leu Gly Val
    130                 135                 140

Tyr Ser Pro Pro Ser Ala Ala Glu Phe Thr Gly Glu Ala Arg Gly Tyr
145                 150                 155                 160

Met Gly Pro Val Leu Gln Phe Leu Ala Arg Thr Gly Ser Pro Leu Met
                165                 170                 175

```
Ala Asn Ile Tyr Pro Tyr Leu Ala Trp Ala Tyr Asn Pro Ser Ala Met
            180                 185                 190

Asp Met Ser Tyr Ala Leu Phe Thr Ser Ser Gly Thr Val Val Gln Asp
        195                 200                 205

Gly Ala Tyr Gly Tyr Gln Asn Leu Phe Asp Thr Thr Val Asp Ala Phe
    210                 215                 220

Tyr Val Ala Met Gly Asn Asn Gly Gly Ser Gly Val Pro Leu Val Val
225                 230                 235                 240

Ser Glu Ser Gly Trp Pro Ser Gly Gly Val Gln Ala Thr Pro Ala
                245                 250                 255

Asn Ala Arg Val Tyr Asn Gln Tyr Leu Ile Asn His Val Gly Arg Gly
            260                 265                 270

Thr Pro Arg His Pro Gly Ala Ile Glu Thr Tyr Leu Phe Ser Met Phe
        275                 280                 285

Asn Glu Asn Gln Lys Glu Ser Gly Val Glu Gln Asn Trp Gly Leu Phe
    290                 295                 300

Tyr Pro Asn Met Gln His Val Tyr Pro Ile Ser Phe
305                 310                 315
```

```
<210> SEQ ID NO 9
<211> LENGTH: 445
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 10
<223> OTHER INFORMATION: Xaa = Any Amino Acid
<220> FEATURE:
<221> NAME/KEY: VARIANT
<222> LOCATION: 11
<223> OTHER INFORMATION: Xaa = Ile or Leu or Val or His or Ala or Phe
```

```
<220> FEATURE:
<221> NAME/KEY: VARIANT
<222> LOCATION: 13
<223> OTHER INFORMATION: Xaa = Val or Ile or Ala
<220> FEATURE:
<221> NAME/KEY: VARIANT
<222> LOCATION: 14
<223> OTHER INFORMATION: Xaa = Asn or Thr or Ser or Cys
<220> FEATURE:
<221> NAME/KEY: VARIANT
<222> LOCATION: 15
<223> OTHER INFORMATION: Xaa = Tyr or Asn or Ile or Trp or His
<220> FEATURE:
<221> NAME/KEY: VARIANT
<222> LOCATION: 17
<223> OTHER INFORMATION: Xaa = Any Amino Acid
<220> FEATURE:
<221> NAME/KEY: VARIANT
<222> LOCATION: 18
<223> OTHER INFORMATION: Xaa = Val or Gln or Met or Ser or Ile or Leu
     or Thr or Asn or Arg or Ala
<220> FEATURE:
<221> NAME/KEY: VARIANT
<222> LOCATION: 19
<223> OTHER INFORMATION: Xaa = Ala or Ser or Gly or Met or Val
<220> FEATURE:
<221> NAME/KEY: VARIANT
<222> LOCATION: 20
<223> OTHER INFORMATION: Xaa = Any Amino Acid
<220> FEATURE:
<221> NAME/KEY: VARIANT
<222> LOCATION: 21
<223> OTHER INFORMATION: Xaa = Asn or His or Asp or Thr or Ser
<220> FEATURE:
<221> NAME/KEY: VARIANT
<222> LOCATION: 22
<223> OTHER INFORMATION: Xaa = Leu or Pro or Gln or Arg or Ile
<220> FEATURE:
<221> NAME/KEY: VARIANT
<222> LOCATION: 23
<223> OTHER INFORMATION: Xaa = Pro or Leu or Ile or Ala
<220> FEATURE:
<221> NAME/KEY: VARIANT
<222> LOCATION: 24
<223> OTHER INFORMATION: Xaa = Any Amino Acid
<220> FEATURE:
<221> NAME/KEY: VARIANT
<222> LOCATION: 25
<223> OTHER INFORMATION: Xaa = Pro or Leu or  or His or Ala or Lys
     or Ser or Thr
<220> FEATURE:
<221> NAME/KEY: VARIANT
<222> LOCATION: 26
<223> OTHER INFORMATION: Xaa = Any Amino Acid
<220> FEATURE:
<221> NAME/KEY: VARIANT
<222> LOCATION: 27
<223> OTHER INFORMATION: Xaa = Any Amino Acid
<220> FEATURE:
<221> NAME/KEY: VARIANT
<222> LOCATION: 28
<223> OTHER INFORMATION: Xaa = Val or Ala or Met or Ser or Pro or Leu
     or Lys or Ile
<220> FEATURE:
<221> NAME/KEY: VARIANT
<222> LOCATION: 29
<223> OTHER INFORMATION: Xaa = Val or Ala or Ile or Met or Ser or Pro
     or Leu or Thr
<220> FEATURE:
<221> NAME/KEY: VARIANT
<222> LOCATION: 30
<223> OTHER INFORMATION: Xaa = Any Amino Acid
<220> FEATURE:
<221> NAME/KEY: VARIANT
<222> LOCATION: 31
<223> OTHER INFORMATION: Xaa = Leu or Gln or Arg or Lys or Glu or Asp
     or Met or Ile or Phe
<220> FEATURE:
<221> NAME/KEY: VARIANT
```

```
<222> LOCATION: 32
<223> OTHER INFORMATION: Xaa = Leu or Val or Met or Gly or Tyr or Cys
      or Ala or Ile
<220> FEATURE:
<221> NAME/KEY: VARIANT
<222> LOCATION: 33
<223> OTHER INFORMATION: Xaa = Arg or Leu or Lys or Gln or Ala or Glu
      or Ser or Val or Leu or Thr
<220> FEATURE:
<221> NAME/KEY: VARIANT
<222> LOCATION: 34
<223> OTHER INFORMATION: Xaa = Any Amino Acid
<220> FEATURE:
<221> NAME/KEY: VARIANT
<222> LOCATION: 35
<223> OTHER INFORMATION: Xaa = Ser or Asp or Gly or Ala or Arg or Lys
      or Leu or Gln
<220> FEATURE:
<221> NAME/KEY: VARIANT
<222> LOCATION: 36
<223> OTHER INFORMATION: Xaa = Any Amino Acid
<220> FEATURE:
<221> NAME/KEY: VARIANT
<222> LOCATION: 37
<223> OTHER INFORMATION: Xaa = Any Amino Acid
<220> FEATURE:
<221> NAME/KEY: VARIANT
<222> LOCATION: 38
<223> OTHER INFORMATION: Xaa = Ile or Val or Phe or Ala
<220> FEATURE:
<221> NAME/KEY: VARIANT
<222> LOCATION: 39
<223> OTHER INFORMATION: Xaa = Any Amino Acid
<220> FEATURE:
<221> NAME/KEY: VARIANT
<222> LOCATION: 40
<223> OTHER INFORMATION: Xaa = Lys or Arg or Ala or Leu or Val or Tyr or
      Asp or Ser or Gly or Asn or Met or His
<220> FEATURE:
<221> NAME/KEY: VARIANT
<222> LOCATION: 41
<223> OTHER INFORMATION: Xaa = Val or Ala or Met or Leu
<220> FEATURE:
<221> NAME/KEY: VARIANT
<222> LOCATION: 42
<223> OTHER INFORMATION: Xaa = Arg or Lys or Thr
<220> FEATURE:
<221> NAME/KEY: VARIANT
<222> LOCATION: 43
<223> OTHER INFORMATION: Xaa = Leu or Ser or Met or Ile or Thr
<220> FEATURE:
<221> NAME/KEY: VARIANT
<222> LOCATION: 44
<223> OTHER INFORMATION: Xaa = Tyr or Phe or Ile or Leu
<220> FEATURE:
<221> NAME/KEY: VARIANT
<222> LOCATION: 45
<223> OTHER INFORMATION: Xaa = Asp or Glu or Asn or Leu or Ala or Trp or
      His or Phe or Ser or Gly
<220> FEATURE:
<221> NAME/KEY: VARIANT
<222> LOCATION: 46
<223> OTHER INFORMATION: Xaa = Ala or Thr or Pro or Ser or Val
<220> FEATURE:
<221> NAME/KEY: VARIANT
<222> LOCATION: 47
<223> OTHER INFORMATION: Xaa = Asp or Met or Glu or Val or Asn or Gln
<220> FEATURE:
<221> NAME/KEY: VARIANT
<222> LOCATION: 48
<223> OTHER INFORMATION: Xaa = Any Amino Acid
<220> FEATURE:
<221> NAME/KEY: VARIANT
<222> LOCATION: 49
<223> OTHER INFORMATION: Xaa = Any Amino Acid
<220> FEATURE:
<221> NAME/KEY: VARIANT
<222> LOCATION: 50
<223> OTHER INFORMATION: Xaa = Val or Ala or Pro or Thr or Ile
```

-continued

```
      or Leu or Phe or Met
<220> FEATURE:
<221> NAME/KEY: VARIANT
<222> LOCATION: 51
<223> OTHER INFORMATION: Xaa = Leu or Met or Pro or Val or Ile
<220> FEATURE:
<221> NAME/KEY: VARIANT
<222> LOCATION: 52
<223> OTHER INFORMATION: Xaa = Any Amino Acid
<220> FEATURE:
<221> NAME/KEY: VARIANT
<222> LOCATION: 53
<223> OTHER INFORMATION: Xaa = Ala or Ser
<220> FEATURE:
<221> NAME/KEY: VARIANT
<222> LOCATION: 54
<223> OTHER INFORMATION: Xaa = Leu or Phe or Val or Ala
<220> FEATURE:
<221> NAME/KEY: VARIANT
<222> LOCATION: 55
<223> OTHER INFORMATION: Xaa = Ala or Val or Gly or Arg or Ser
<220> FEATURE:
<221> NAME/KEY: VARIANT
<222> LOCATION: 56
<223> OTHER INFORMATION: Xaa = Gly or Asp or His or Lys or Asn
      or Arg or Ala
<220> FEATURE:
<221> NAME/KEY: VARIANT
<222> LOCATION: 57
<223> OTHER INFORMATION: Xaa = Any Amino Acid
<220> FEATURE:
<221> NAME/KEY: VARIANT
<222> LOCATION: 58
<223> OTHER INFORMATION: Xaa = Any Amino Acid
<220> FEATURE:
<221> NAME/KEY: VARIANT
<222> LOCATION: 59
<223> OTHER INFORMATION: Xaa = Thr or Ser or Ala or Pro
<220> FEATURE:
<221> NAME/KEY: VARIANT
<222> LOCATION: 60
<223> OTHER INFORMATION: Xaa = Gly or Ser or Asp or Arg or Asn
<220> FEATURE:
<221> NAME/KEY: VARIANT
<222> LOCATION: 61
<223> OTHER INFORMATION: Xaa = Ile or Val or Leu or Trp
<220> FEATURE:
<221> NAME/KEY: VARIANT
<222> LOCATION: 62
<223> OTHER INFORMATION: Xaa = Any Amino Acid
<220> FEATURE:
<221> NAME/KEY: VARIANT
<222> LOCATION: 63
<223> OTHER INFORMATION: Xaa = Val or Ala or Leu or Phe
<220> FEATURE:
<221> NAME/KEY: VARIANT
<222> LOCATION: 64
<223> OTHER INFORMATION: Xaa = Val or Met or Thr or Ala or Ile or Asp
<220> FEATURE:
<221> NAME/KEY: VARIANT
<222> LOCATION: 65
<223> OTHER INFORMATION: Xaa = Val or Leu or Ala or Pro or Ile
<220> FEATURE:
<221> NAME/KEY: VARIANT
<222> LOCATION: 66
<223> OTHER INFORMATION: Xaa = Gly or Ala or Asp or Ser or Met or Thr
<220> FEATURE:
<221> NAME/KEY: VARIANT
<222> LOCATION: 67
<223> OTHER INFORMATION: Xaa = Val or Ile or Ala or Leu or Thr
      or Glu or Phe
<220> FEATURE:
<221> NAME/KEY: VARIANT
<222> LOCATION: 68
<223> OTHER INFORMATION: Xaa = Pro or Thr or Leu or Gly or Ala
<220> FEATURE:
<221> NAME/KEY: VARIANT
<222> LOCATION: 69
<223> OTHER INFORMATION: Xaa = Asn or Asp
```

```
<220> FEATURE:
<221> NAME/KEY: VARIANT
<222> LOCATION: 70
<223> OTHER INFORMATION: Xaa = Any Amino Acid
<220> FEATURE:
<221> NAME/KEY: VARIANT
<222> LOCATION: 71
<223> OTHER INFORMATION: Xaa = Any Amino Acid
<220> FEATURE:
<221> NAME/KEY: VARIANT
<222> LOCATION: 72
<223> OTHER INFORMATION: Xaa = Any Amino Acid
<220> FEATURE:
<221> NAME/KEY: VARIANT
<222> LOCATION: 73
<223> OTHER INFORMATION: Xaa = Leu or Arg or Ala or Asp or Glu or Gly
      or Ser or Lys or Ile
<220> FEATURE:
<221> NAME/KEY: VARIANT
<222> LOCATION: 74
<223> OTHER INFORMATION: Xaa = Any Amino Acid
<220> FEATURE:
<221> NAME/KEY: VARIANT
<222> LOCATION: 75
<223> OTHER INFORMATION: Xaa = Any Amino Acid
<220> FEATURE:
<221> NAME/KEY: VARIANT
<222> LOCATION: 76
<223> OTHER INFORMATION: Xaa = Any Amino Acid
<220> FEATURE:
<221> NAME/KEY: VARIANT
<222> LOCATION: 77
<223> OTHER INFORMATION: Xaa = Ala or Pro or DS or Arg or Thr or Gly
      or Ile or Leu or Met
<220> FEATURE:
<221> NAME/KEY: VARIANT
<222> LOCATION: 78
<223> OTHER INFORMATION: Xaa = Ala or Asp or Tyr or Ser or Gly or Arg
      or Gln or Thr or Val or Asn
<220> FEATURE:
<221> NAME/KEY: VARIANT
<222> LOCATION: 79
<223> OTHER INFORMATION: Xaa = Ser or Ala or Gly or Asp or Tyr or Pro or
      Val or Met or Gln or Arg or Thr or Asn
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 81
<223> OTHER INFORMATION: Xaa = Any Amino Acid
<220> FEATURE:
<221> NAME/KEY: VARIANT
<222> LOCATION: 82
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 84
<223> OTHER INFORMATION: Xaa = Any Amino Acid
<220> FEATURE:
<221> NAME/KEY: VARIANT
<222> LOCATION: 85
<223> OTHER INFORMATION: Xaa = Any Amino Acid
<220> FEATURE:
<221> NAME/KEY: VARIANT
<222> LOCATION: 86
<223> OTHER INFORMATION: Xaa = Ala or Val or Ser
<220> FEATURE:
<221> NAME/KEY: VARIANT
<222> LOCATION: 87
<223> OTHER INFORMATION: Xaa = Any Amino Acid
<220> FEATURE:
<221> NAME/KEY: VARIANT
<222> LOCATION: 88
```

```
<223> OTHER INFORMATION: Xaa = Any Amino Acid
<220> FEATURE:
<221> NAME/KEY: VARIANT
<222> LOCATION: 89
<223> OTHER INFORMATION: Xaa = Trp or Cys or Leu
<220> FEATURE:
<221> NAME/KEY: VARIANT
<222> LOCATION: 90
<223> OTHER INFORMATION: Xaa = Val or Ala or Leu
<220> FEATURE:
<221> NAME/KEY: VARIANT
<222> LOCATION: 91
<223> OTHER INFORMATION: Xaa = Any Amino Acid
<220> FEATURE:
<221> NAME/KEY: VARIANT
<222> LOCATION: 92
<223> OTHER INFORMATION: Xaa = Any Amino Acid
<220> FEATURE:
<221> NAME/KEY: VARIANT
<222> LOCATION: 93
<223> OTHER INFORMATION: Xaa = Asn or Leu or Ala or Tyr or Thr or Ser
      or His or Arg
<220> FEATURE:
<221> NAME/KEY: VARIANT
<222> LOCATION: 94
<223> OTHER INFORMATION: Xaa = Val or Ile or Leu
<220> FEATURE:
<221> NAME/KEY: VARIANT
<222> LOCATION: 95
<223> OTHER INFORMATION: Xaa = Any Amino Acid
<220> FEATURE:
<221> NAME/KEY: VARIANT
<222> LOCATION: 96
<223> OTHER INFORMATION: Xaa = Pro or Ala or Arg or Lys or Thr or Ser
<220> FEATURE:
<221> NAME/KEY: VARIANT
<222> LOCATION: 97
<223> OTHER INFORMATION: Xaa = Tyr or Val or Asn or His or Ala or Phe
      or Thr or Ser
<220> FEATURE:
<221> NAME/KEY: VARIANT
<222> LOCATION: 98
<223> OTHER INFORMATION: Xaa = Any Amino Acid
<220> FEATURE:
<221> NAME/KEY: VARIANT
<222> LOCATION: 99
<223> OTHER INFORMATION: Xaa = Pro or Leu or Phe or Asn or Ser or Gly
      or Gln or Asp
<220> FEATURE:
<221> NAME/KEY: VARIANT
<222> LOCATION: 100
<223> OTHER INFORMATION: Xaa = Ala or Asp or Lys or Arg or Ser
      or Gln or Val
<220> FEATURE:
<221> NAME/KEY: VARIANT
<222> LOCATION: 101
<223> OTHER INFORMATION: Xaa = Any Amino Acid
<220> FEATURE:
<221> NAME/KEY: VARIANT
<222> LOCATION: 102
<223> OTHER INFORMATION: Xaa = Any Amino Acid
<220> FEATURE:
<221> NAME/KEY: VARIANT
<222> LOCATION: 103
<223> OTHER INFORMATION: Xaa = Any Amino Acid
<220> FEATURE:
<221> NAME/KEY: VARIANT
<222> LOCATION: 104
<223> OTHER INFORMATION: Xaa = Any Amino Acid
<220> FEATURE:
<221> NAME/KEY: VARIANT
<222> LOCATION: 105
<223> OTHER INFORMATION: Xaa = Any Amino Acid
<220> FEATURE:
<221> NAME/KEY: VARIANT
<222> LOCATION: 106
<223> OTHER INFORMATION: Xaa = Any Amino Acid
<220> FEATURE:
<221> NAME/KEY: VARIANT
```

```
<222> LOCATION: 107
<223> OTHER INFORMATION: Xaa = Any Amino Acid
<220> FEATURE:
<221> NAME/KEY: VARIANT
<222> LOCATION: 108
<223> OTHER INFORMATION: Xaa = Ile or Cys or Leu or Phe or Val
      or Ser or Thr
<220> FEATURE:
<221> NAME/KEY: VARIANT
<222> LOCATION: 109
<223> OTHER INFORMATION: Xaa = Any Amino Acid
<220> FEATURE:
<221> NAME/KEY: VARIANT
<222> LOCATION: 110
<223> OTHER INFORMATION: Xaa = Any Amino Acid
<220> FEATURE:
<221> NAME/KEY: VARIANT
<222> LOCATION: 111
<223> OTHER INFORMATION: Xaa = Val or Ile or Leu or Met
<220> FEATURE:
<221> NAME/KEY: VARIANT
<222> LOCATION: 112
<223> OTHER INFORMATION: Xaa = Ala or Cys or Asn or Val or Thr or Ser
<220> FEATURE:
<221> NAME/KEY: VARIANT
<222> LOCATION: 113
<223> OTHER INFORMATION: Xaa = Val or Leu or Ala or Gly
<220> FEATURE:
<221> NAME/KEY: VARIANT
<222> LOCATION: 114
<223> OTHER INFORMATION: Xaa = Gly or Asp or Asn
<220> FEATURE:
<221> NAME/KEY: VARIANT
<222> LOCATION: 115
<223> OTHER INFORMATION: Xaa = Asn or Pro or Ala or Glu or Ser or Asp
<220> FEATURE:
<221> NAME/KEY: VARIANT
<222> LOCATION: 116
<223> OTHER INFORMATION: Xaa = Glu or Ser or Val
<220> FEATURE:
<221> NAME/KEY: VARIANT
<222> LOCATION: 117
<223> OTHER INFORMATION: Xaa = Val or Ala or Phe or Ile or Leu or Thr
<220> FEATURE:
<221> NAME/KEY: VARIANT
<222> LOCATION: 118
<223> OTHER INFORMATION: Xaa = Any Amino Acid
<220> FEATURE:
<221> NAME/KEY: VARIANT
<222> LOCATION: 119
<223> OTHER INFORMATION: Xaa = Any Amino Acid
<220> FEATURE:
<221> NAME/KEY: VARIANT
<222> LOCATION: 120
<223> OTHER INFORMATION: Xaa = Any Amino Acid
<220> FEATURE:
<221> NAME/KEY: VARIANT
<222> LOCATION: 121
<223> OTHER INFORMATION: Xaa = Any Amino Acid
<220> FEATURE:
<221> NAME/KEY: VARIANT
<222> LOCATION: 122
<223> OTHER INFORMATION: Xaa = Any Amino Acid
<220> FEATURE:
<221> NAME/KEY: VARIANT
<222> LOCATION: 123
<223> OTHER INFORMATION: Xaa = Any Amino Acid
<220> FEATURE:
<221> NAME/KEY: VARIANT
<222> LOCATION: 124
<223> OTHER INFORMATION: Xaa = Any Amino Acid
<220> FEATURE:
<221> NAME/KEY: VARIANT
<222> LOCATION: 125
<223> OTHER INFORMATION: Xaa = Any Amino Acid
<220> FEATURE:
<221> NAME/KEY: VARIANT
<222> LOCATION: 126
<223> OTHER INFORMATION: Xaa = Any Amino Acid
```

```
<220> FEATURE:
<221> NAME/KEY: VARIANT
<222> LOCATION: 127
<223> OTHER INFORMATION: Xaa = Any Amino Acid
<220> FEATURE:
<221> NAME/KEY: VARIANT
<222> LOCATION: 128
<223> OTHER INFORMATION: Xaa = Any Amino Acid
<220> FEATURE:
<221> NAME/KEY: VARIANT
<222> LOCATION: 129
<223> OTHER INFORMATION: Xaa = Any Amino Acid
<220> FEATURE:
<221> NAME/KEY: VARIANT
<222> LOCATION: 130
<223> OTHER INFORMATION: Xaa = Any Amino Acid
<220> FEATURE:
<221> NAME/KEY: VARIANT
<222> LOCATION: 131
<223> OTHER INFORMATION: Xaa = Any Amino Acid
<220> FEATURE:
<221> NAME/KEY: VARIANT
<222> LOCATION: 132
<223> OTHER INFORMATION: Xaa = Any Amino Acid
<220> FEATURE:
<221> NAME/KEY: VARIANT
<222> LOCATION: 133
<223> OTHER INFORMATION: Xaa = Any Amino Acid
<220> FEATURE:
<221> NAME/KEY: VARIANT
<222> LOCATION: 134
<223> OTHER INFORMATION: Xaa = Any Amino Acid
<220> FEATURE:
<221> NAME/KEY: VARIANT
<222> LOCATION: 135
<223> OTHER INFORMATION: Xaa = Any Amino Acid
<220> FEATURE:
<221> NAME/KEY: VARIANT
<222> LOCATION: 136
<223> OTHER INFORMATION: Xaa = Any Amino Acid
<220> FEATURE:
<221> NAME/KEY: VARIANT
<222> LOCATION: 137
<223> OTHER INFORMATION: Xaa = Any Amino Acid
<220> FEATURE:
<221> NAME/KEY: VARIANT
<222> LOCATION: 138
<223> OTHER INFORMATION: Xaa = Any Amino Acid
<220> FEATURE:
<221> NAME/KEY: VARIANT
<222> LOCATION: 139
<223> OTHER INFORMATION: Xaa = Any Amino Acid
<220> FEATURE:
<221> NAME/KEY: VARIANT
<222> LOCATION: 140
<223> OTHER INFORMATION: Xaa = Any Amino Acid
<220> FEATURE:
<221> NAME/KEY: VARIANT
<222> LOCATION: 141
<223> OTHER INFORMATION: Xaa = Any Amino Acid
<220> FEATURE:
<221> NAME/KEY: VARIANT
<222> LOCATION: 142
<223> OTHER INFORMATION: Xaa = Any Amino Acid
<220> FEATURE:
<221> NAME/KEY: VARIANT
<222> LOCATION: 143
<223> OTHER INFORMATION: Xaa = Any Amino Acid
<220> FEATURE:
<221> NAME/KEY: VARIANT
<222> LOCATION: 144
<223> OTHER INFORMATION: Xaa = Any Amino Acid
<220> FEATURE:
<221> NAME/KEY: VARIANT
<222> LOCATION: 145
<223> OTHER INFORMATION: Xaa = Any Amino Acid
<220> FEATURE:
<221> NAME/KEY: VARIANT
<222> LOCATION: 146
```

```
<223> OTHER INFORMATION: Xaa = Any Amino Acid
<220> FEATURE:
<221> NAME/KEY: VARIANT
<222> LOCATION: 147
<223> OTHER INFORMATION: Xaa = Any Amino Acid
<220> FEATURE:
<221> NAME/KEY: VARIANT
<222> LOCATION: 148
<223> OTHER INFORMATION: Xaa = Any Amino Acid
<220> FEATURE:
<221> NAME/KEY: VARIANT
<222> LOCATION: 149
<223> OTHER INFORMATION: Xaa = Any Amino Acid
<220> FEATURE:
<221> NAME/KEY: VARIANT
<222> LOCATION: 150
<223> OTHER INFORMATION: Xaa = Any Amino Acid
<220> FEATURE:
<221> NAME/KEY: VARIANT
<222> LOCATION: 151
<223> OTHER INFORMATION: Xaa = Any Amino Acid
<220> FEATURE:
<221> NAME/KEY: VARIANT
<222> LOCATION: 152
<223> OTHER INFORMATION: Xaa = Any Amino Acid
<220> FEATURE:
<221> NAME/KEY: VARIANT
<222> LOCATION: 153
<223> OTHER INFORMATION: Xaa = Any Amino Acid
<220> FEATURE:
<221> NAME/KEY: VARIANT
<222> LOCATION: 154
<223> OTHER INFORMATION: Xaa = Any Amino Acid
<220> FEATURE:
<221> NAME/KEY: VARIANT
<222> LOCATION: 155
<223> OTHER INFORMATION: Xaa = Any Amino Acid
<220> FEATURE:
<221> NAME/KEY: VARIANT
<222> LOCATION: 156
<223> OTHER INFORMATION: Xaa = Any Amino Acid
<220> FEATURE:
<221> NAME/KEY: VARIANT
<222> LOCATION: 157
<223> OTHER INFORMATION: Xaa = Any Amino Acid
<220> FEATURE:
<221> NAME/KEY: VARIANT
<222> LOCATION: 158
<223> OTHER INFORMATION: Xaa = Any Amino Acid
<220> FEATURE:
<221> NAME/KEY: VARIANT
<222> LOCATION: 159
<223> OTHER INFORMATION: Xaa = Any Amino Acid
<220> FEATURE:
<221> NAME/KEY: VARIANT
<222> LOCATION: 160
<223> OTHER INFORMATION: Xaa = Any Amino Acid
<220> FEATURE:
<221> NAME/KEY: VARIANT
<222> LOCATION: 161
<223> OTHER INFORMATION: Xaa = Any Amino Acid
<220> FEATURE:
<221> NAME/KEY: VARIANT
<222> LOCATION: 162
<223> OTHER INFORMATION: Xaa = Any Amino Acid
<220> FEATURE:
<221> NAME/KEY: VARIANT
<222> LOCATION: 163
<223> OTHER INFORMATION: Xaa = Any Amino Acid
<220> FEATURE:
<221> NAME/KEY: VARIANT
<222> LOCATION: 164
<223> OTHER INFORMATION: Xaa = Any Amino Acid
<220> FEATURE:
<221> NAME/KEY: VARIANT
<222> LOCATION: 165
<223> OTHER INFORMATION: Xaa = Any Amino Acid
<220> FEATURE:
<221> NAME/KEY: VARIANT
```

```
<222> LOCATION: 166
<223> OTHER INFORMATION: Xaa = Any Amino Acid
<220> FEATURE:
<221> NAME/KEY: VARIANT
<222> LOCATION: 167
<223> OTHER INFORMATION: Xaa = Any Amino Acid
<220> FEATURE:
<221> NAME/KEY: VARIANT
<222> LOCATION: 168
<223> OTHER INFORMATION: Xaa = Any Amino Acid
<220> FEATURE:
<221> NAME/KEY: VARIANT
<222> LOCATION: 169
<223> OTHER INFORMATION: Xaa = Any Amino Acid
<220> FEATURE:
<221> NAME/KEY: VARIANT
<222> LOCATION: 170
<223> OTHER INFORMATION: Xaa = Any Amino Acid
<220> FEATURE:
<221> NAME/KEY: VARIANT
<222> LOCATION: 171
<223> OTHER INFORMATION: Xaa = Leu or Thr or Ile or Val
<220> FEATURE:
<221> NAME/KEY: VARIANT
<222> LOCATION: 172
<223> OTHER INFORMATION: Xaa = Leu or Phe or Val or Ile or Ala or Met
<220> FEATURE:
<221> NAME/KEY: VARIANT
<222> LOCATION: 173
<223> OTHER INFORMATION: Xaa = Pro or Gln or Gly or Asp
<220> FEATURE:
<221> NAME/KEY: VARIANT
<222> LOCATION: 175
<223> OTHER INFORMATION: Xaa = Met or Leu or Val or Ile
<220> FEATURE:
<221> NAME/KEY: VARIANT
<222> LOCATION: 176
<223> OTHER INFORMATION: Xaa = Arg or Gln or Lys or Thr or Glu or Ala
      or Ser or Leu
<220> FEATURE:
<221> NAME/KEY: VARIANT
<222> LOCATION: 177
<223> OTHER INFORMATION: Xaa = Asn or Ser or Thr or Ala or Cys
      or Arg or Tyr
<220> FEATURE:
<221> NAME/KEY: VARIANT
<222> LOCATION: 178
<223> OTHER INFORMATION: Xaa = Leu or Ile or Val or Met or Ala
<220> FEATURE:
<221> NAME/KEY: VARIANT
<222> LOCATION: 179
<223> OTHER INFORMATION: Xaa = His or Gln or Arg or Glu or Asp
      or Asn or Ser or Ala or Tyr or Leu
<220> FEATURE:
<221> NAME/KEY: VARIANT
<222> LOCATION: 180
<223> OTHER INFORMATION: Xaa = Any Amino Acid
<220> FEATURE:
<221> NAME/KEY: VARIANT
<222> LOCATION: 181
<223> OTHER INFORMATION: Xaa = Ala or Ser or Gly
<220> FEATURE:
<221> NAME/KEY: VARIANT
<222> LOCATION: 182
<223> OTHER INFORMATION: Xaa = Leu or Ile or Val or Ala
<220> FEATURE:
<221> NAME/KEY: VARIANT
<222> LOCATION: 183
<223> OTHER INFORMATION: Xaa = Any Amino Acid
<220> FEATURE:
<221> NAME/KEY: VARIANT
<222> LOCATION: 184
<223> OTHER INFORMATION: Xaa = Any Amino Acid
<220> FEATURE:
<221> NAME/KEY: VARIANT
<222> LOCATION: 185
<223> OTHER INFORMATION: Xaa = Ala or Leu or His or Arg or Val or Ser
      or Gly or Asn or Glu
<220> FEATURE:
```

```
<221> NAME/KEY: VARIANT
<222> LOCATION: 186
<223> OTHER INFORMATION: Xaa = Gly or Asn or Ser or Arg or His or Ala
<220> FEATURE:
<221> NAME/KEY: VARIANT
<222> LOCATION: 187
<223> OTHER INFORMATION: Xaa = Leu or Ile or Phe or His or Val or Phe
      or Met or Asp
<220> FEATURE:
<221> NAME/KEY: VARIANT
<222> LOCATION: 188
<223> OTHER INFORMATION: Xaa = Any Amino Acid
<220> FEATURE:
<221> NAME/KEY: VARIANT
<222> LOCATION: 189
<223> OTHER INFORMATION: Xaa = Any Amino Acid
<220> FEATURE:
<221> NAME/KEY: VARIANT
<222> LOCATION: 190
<223> OTHER INFORMATION: Xaa = Any Amino Acid
<220> FEATURE:
<221> NAME/KEY: VARIANT
<222> LOCATION: 191
<223> OTHER INFORMATION: Xaa = Any Amino Acid
<220> FEATURE:
<221> NAME/KEY: VARIANT
<222> LOCATION: 192
<223> OTHER INFORMATION: Xaa = Any Amino Acid
<220> FEATURE:
<221> NAME/KEY: VARIANT
<222> LOCATION: 193
<223> OTHER INFORMATION: Xaa = Val or Ile or Ala or Thr
<220> FEATURE:
<221> NAME/KEY: VARIANT
<222> LOCATION: 194
<223> OTHER INFORMATION: Xaa = Lys or His or Pro or Arg or Thr or Glu
      or Asn or Ala
<220> FEATURE:
<221> NAME/KEY: VARIANT
<222> LOCATION: 195
<223> OTHER INFORMATION: Xaa = Val or Ala or Leu or Cys or Ile or Phe
<220> FEATURE:
<221> NAME/KEY: VARIANT
<222> LOCATION: 196
<223> OTHER INFORMATION: Xaa = Ser or Thr or Val or Gly or Phe
<220> FEATURE:
<221> NAME/KEY: VARIANT
<222> LOCATION: 197
<223> OTHER INFORMATION: Xaa = Thr or Val or Cys or Ser
<220> FEATURE:
<221> NAME/KEY: VARIANT
<222> LOCATION: 198
<223> OTHER INFORMATION: Xaa = Any Amino Acid
<220> FEATURE:
<221> NAME/KEY: VARIANT
<222> LOCATION: 199
<223> OTHER INFORMATION: Xaa = Val or Leu or Cys or His or Ile or Asn
<220> FEATURE:
<221> NAME/KEY: VARIANT
<222> LOCATION: 200
<223> OTHER INFORMATION: Xaa = Ser or Asn or Ala or Lys or Arg or Gln
      or Thr or Tyr or Pro
<220> FEATURE:
<221> NAME/KEY: VARIANT
<222> LOCATION: 201
<223> OTHER INFORMATION: Xaa = Any Amino Acid
<220> FEATURE:
<221> NAME/KEY: VARIANT
<222> LOCATION: 202
<223> OTHER INFORMATION: Xaa = Any Amino Acid
<220> FEATURE:
<221> NAME/KEY: VARIANT
<222> LOCATION: 203
<223> OTHER INFORMATION: Xaa = Val or Ile or Ala or Asp
<220> FEATURE:
<221> NAME/KEY: VARIANT
<222> LOCATION: 204
<223> OTHER INFORMATION: Xaa = Leu or Tyr or Ile or Val or Thr or Phe or
      Met
```

-continued

```
<220> FEATURE:
<221> NAME/KEY: VARIANT
<222> LOCATION: 205
<223> OTHER INFORMATION: Xaa = Ala or Met or Asn or Asp or Ser or Glu
      or Gln or Gly or Thr or Arg or Leu or Val
<220> FEATURE:
<221> NAME/KEY: VARIANT
<222> LOCATION: 206
<223> OTHER INFORMATION: Xaa = Any Amino Acid
<220> FEATURE:
<221> NAME/KEY: VARIANT
<222> LOCATION: 207
<223> OTHER INFORMATION: Xaa = Ser or Pro or Gln or Thr or Ala
<220> FEATURE:
<221> NAME/KEY: VARIANT
<222> LOCATION: 208
<223> OTHER INFORMATION: Xaa = Any Amino Acid
<220> FEATURE:
<221> NAME/KEY: VARIANT
<222> LOCATION: 209
<223> OTHER INFORMATION: Xaa = Any Amino Acid
<220> FEATURE:
<221> NAME/KEY: VARIANT
<222> LOCATION: 210
<223> OTHER INFORMATION: Xaa = Any Amino Acid
<220> FEATURE:
<221> NAME/KEY: VARIANT
<222> LOCATION: 211
<223> OTHER INFORMATION: Xaa = Any Amino Acid
<220> FEATURE:
<221> NAME/KEY: VARIANT
<222> LOCATION: 212
<223> OTHER INFORMATION: Xaa = Pro or Val or Gln or Ile
<220> FEATURE:
<221> NAME/KEY: VARIANT
<222> LOCATION: 213
<223> OTHER INFORMATION: Xaa = Pro or Ser
<220> FEATURE:
<221> NAME/KEY: VARIANT
<222> LOCATION: 214
<223> OTHER INFORMATION: Xaa = Ser or Ala or Gln
<220> FEATURE:
<221> NAME/KEY: VARIANT
<222> LOCATION: 215
<223> OTHER INFORMATION: Xaa = Ala or Gln or Gly or Arg or Asp or Ser
      or Thr or Asn
<220> FEATURE:
<221> NAME/KEY: VARIANT
<222> LOCATION: 216
<223> OTHER INFORMATION: Xaa = Gly or Gln or Glu or Ala or Ser or Cys
<220> FEATURE:
<221> NAME/KEY: VARIANT
<222> LOCATION: 217
<223> OTHER INFORMATION: Xaa = Any Amino Acid
<220> FEATURE:
<221> NAME/KEY: VARIANT
<222> LOCATION: 218
<223> OTHER INFORMATION: Xaa = Phe or Trp or Thr or Ser
<220> FEATURE:
<221> NAME/KEY: VARIANT
<222> LOCATION: 219
<223> OTHER INFORMATION: Xaa =Arg or Cys or Asp or Val or Gly or Glu
      or Ala or Ser or Asn or Thr or His
<220> FEATURE:
<221> NAME/KEY: VARIANT
<222> LOCATION: 220
<223> OTHER INFORMATION: Xaa = Any Amino Acid
<220> FEATURE:
<221> NAME/KEY: VARIANT
<222> LOCATION: 221
<223> OTHER INFORMATION: Xaa = Any Amino Acid
<220> FEATURE:
<221> NAME/KEY: VARIANT
<222> LOCATION: 222
<223> OTHER INFORMATION: Xaa = Leu or Pro or Ile or Val or Leu or Ser
      or Tyr or Ala or Asp or Glu
<220> FEATURE:
<221> NAME/KEY: VARIANT
<222> LOCATION: 223
```

-continued

```
<223> OTHER INFORMATION: Xaa = Any Amino Acid
<220> FEATURE:
<221> NAME/KEY: VARIANT
<222> LOCATION: 224
<223> OTHER INFORMATION: Xaa = Any Amino Acid
<220> FEATURE:
<221> NAME/KEY: VARIANT
<222> LOCATION: 225
<223> OTHER INFORMATION: Xaa = Any Amino Acid
<220> FEATURE:
<221> NAME/KEY: VARIANT
<222> LOCATION: 226
<223> OTHER INFORMATION: Xaa = Any Amino Acid
<220> FEATURE:
<221> NAME/KEY: VARIANT
<222> LOCATION: 227
<223> OTHER INFORMATION: Xaa = Met or Leu or Val or Ile
<220> FEATURE:
<221> NAME/KEY: VARIANT
<222> LOCATION: 228
<223> OTHER INFORMATION: Xaa = Any Amino Acid
<220> FEATURE:
<221> NAME/KEY: VARIANT
<222> LOCATION: 229
<223> OTHER INFORMATION: Xaa = Pro or Asp or Glu or Ser or Thr or Gln
      or Tyr or Arg
<220> FEATURE:
<221> NAME/KEY: VARIANT
<222> LOCATION: 230
<223> OTHER INFORMATION: Xaa = Leu or Met or Ile or Val
<220> FEATURE:
<221> NAME/KEY: VARIANT
<222> LOCATION: 231
<223> OTHER INFORMATION: Xaa = Leu or Val or Ala or Ile
<220> FEATURE:
<221> NAME/KEY: VARIANT
<222> LOCATION: 232
<223> OTHER INFORMATION: Xaa = Any Amino Acid
<220> FEATURE:
<221> NAME/KEY: VARIANT
<222> LOCATION: 233
<223> OTHER INFORMATION: Xaa = Phe or Tyr or Leu or His
<220> FEATURE:
<221> NAME/KEY: VARIANT
<222> LOCATION: 234
<223> OTHER INFORMATION: Xaa = Leu or Phe or His
<220> FEATURE:
<221> NAME/KEY: VARIANT
<222> LOCATION: 235
<223> OTHER INFORMATION: Xaa = Ala or Asn or His or Leu or Ser
      or Gln or Glu or Asp or Val or Arg
<220> FEATURE:
<221> NAME/KEY: VARIANT
<222> LOCATION: 236
<223> OTHER INFORMATION: Xaa = Any Amino Acid
<220> FEATURE:
<221> NAME/KEY: VARIANT
<222> LOCATION: 237
<223> OTHER INFORMATION: Xaa = Thr or Asn or Ser or His or Lys or Arg
      or Ile or Val or Ala
<220> FEATURE:
<221> NAME/KEY: VARIANT
<222> LOCATION: 238
<223> OTHER INFORMATION: Xaa = Gly or Asp or Arg or Asn or Gln or Ser
<220> FEATURE:
<221> NAME/KEY: VARIANT
<222> LOCATION: 239
<223> OTHER INFORMATION: Xaa = Ala or Gly or Ser or Thr or Arg
<220> FEATURE:
<221> NAME/KEY: VARIANT
<222> LOCATION: 240
<223> OTHER INFORMATION: Xaa = Pro or Val or Ala or Cys or Tyr or Phe
<220> FEATURE:
<221> NAME/KEY: VARIANT
<222> LOCATION: 241
<223> OTHER INFORMATION: Xaa = Leu or Phe or Tyr or Val
<220> FEATURE:
<221> NAME/KEY: VARIANT
<222> LOCATION: 242
```

```
<223> OTHER INFORMATION: Xaa = Leu or Thr or Val or Met or Phe or Tyr
      or Pro or Trp or Leu
<220> FEATURE:
<221> NAME/KEY: VARIANT
<222> LOCATION: 243
<223> OTHER INFORMATION: Xaa = Val or Ile or Ala or Cys or Leu or Ile
<220> FEATURE:
<221> NAME/KEY: VARIANT
<222> LOCATION: 244
<223> OTHER INFORMATION: Xaa = Asn or Ser or Asp
<220> FEATURE:
<221> NAME/KEY: VARIANT
<222> LOCATION: 245
<223> OTHER INFORMATION: Xaa = Ile or His or Ala or Val or Leu or Cys
      or Pro
<220> FEATURE:
<221> NAME/KEY: VARIANT
<222> LOCATION: 246
<223> OTHER INFORMATION: Xaa = Tyr or Leu
<220> FEATURE:
<221> NAME/KEY: VARIANT
<222> LOCATION: 247
<223> OTHER INFORMATION: Xaa = Pro or Thr
<220> FEATURE:
<221> NAME/KEY: VARIANT
<222> LOCATION: 248
<223> OTHER INFORMATION: Xaa = Tyr or Arg or Phe or Cys or Trp
<220> FEATURE:
<221> NAME/KEY: VARIANT
<222> LOCATION: 249
<223> OTHER INFORMATION: Xaa = Phe or Ser or Leu or Tyr
<220> FEATURE:
<221> NAME/KEY: VARIANT
<222> LOCATION: 250
<223> OTHER INFORMATION: Xaa = Ala or Ser or Thr or Val or Asp
<220> FEATURE:
<221> NAME/KEY: VARIANT
<222> LOCATION: 251
<223> OTHER INFORMATION: Xaa = Tyr or Pro or His or Trp or Gln or Leu
<220> FEATURE:
<221> NAME/KEY: VARIANT
<222> LOCATION: 252
<223> OTHER INFORMATION: Xaa = Any Amino Acid
<220> FEATURE:
<221> NAME/KEY: VARIANT
<222> LOCATION: 253
<223> OTHER INFORMATION: Xaa = Any Amino Acid
<220> FEATURE:
<221> NAME/KEY: VARIANT
<222> LOCATION: 254
<223> OTHER INFORMATION: Xaa = Any Amino Acid
<220> FEATURE:
<221> NAME/KEY: VARIANT
<222> LOCATION: 255
<223> OTHER INFORMATION: Xaa = Any Amino Acid
<220> FEATURE:
<221> NAME/KEY: VARIANT
<222> LOCATION: 256
<223> OTHER INFORMATION: Xaa = Any Amino Acid
<220> FEATURE:
<221> NAME/KEY: VARIANT
<222> LOCATION: 257
<223> OTHER INFORMATION: Xaa = Any Amino Acid
<220> FEATURE:
<221> NAME/KEY: VARIANT
<222> LOCATION: 258
<223> OTHER INFORMATION: Xaa = Any Amino Acid
<220> FEATURE:
<221> NAME/KEY: VARIANT
<222> LOCATION: 259
<223> OTHER INFORMATION: Xaa = Any Amino Acid
<220> FEATURE:
<221> NAME/KEY: VARIANT
<222> LOCATION: 260
<223> OTHER INFORMATION: Xaa = Any Amino Acid
<220> FEATURE:
<221> NAME/KEY: VARIANT
<222> LOCATION: 261
<223> OTHER INFORMATION: Xaa = Any Amino Acid
```

```
<220> FEATURE:
<221> NAME/KEY: VARIANT
<222> LOCATION: 262
<223> OTHER INFORMATION: Xaa = Ile or Ser or Phe or Val or Met or Leu
      or Glu or Ser or Ala
<220> FEATURE:
<221> NAME/KEY: VARIANT
<222> LOCATION: 263
<223> OTHER INFORMATION: Xaa = Any Amino Acid
<220> FEATURE:
<221> NAME/KEY: VARIANT
<222> LOCATION: 264
<223> OTHER INFORMATION: Xaa = Leu or Val or Phe or Gln or Met or Ile
<220> FEATURE:
<221> NAME/KEY: VARIANT
<222> LOCATION: 265
<223> OTHER INFORMATION: Xaa = Asp or Glu or Asn or Ala or Ser
      or Gly or Pro
<220> FEATURE:
<221> NAME/KEY: VARIANT
<222> LOCATION: 266
<223> OTHER INFORMATION: Xaa = Tyr or Phe or Asn
<220> FEATURE:
<221> NAME/KEY: VARIANT
<222> LOCATION: 267
<223> OTHER INFORMATION: Xaa = Ala or Ser or Val or Cys
<220> FEATURE:
<221> NAME/KEY: VARIANT
<222> LOCATION: 268
<223> OTHER INFORMATION: Xaa = Leu or Phe or Tyr or Ile or Thr or Val
<220> FEATURE:
<221> NAME/KEY: VARIANT
<222> LOCATION: 269
<223> OTHER INFORMATION: Xaa = Phe or Leu or Gly or Ser
<220> FEATURE:
<221> NAME/KEY: VARIANT
<222> LOCATION: 270
<223> OTHER INFORMATION: Xaa = Any Amino Acid
<220> FEATURE:
<221> NAME/KEY: VARIANT
<222> LOCATION: 271
<223> OTHER INFORMATION: Xaa = Pro or Gly or Ser or Ala or Met or Val
<220> FEATURE:
<221> NAME/KEY: VARIANT
<222> LOCATION: 272
<223> OTHER INFORMATION: Xaa = Any Amino Acid
<220> FEATURE:
<221> NAME/KEY: VARIANT
<222> LOCATION: 273
<223> OTHER INFORMATION: Xaa = Any Amino Acid
<220> FEATURE:
<221> NAME/KEY: VARIANT
<222> LOCATION: 274
<223> OTHER INFORMATION: Xaa = Any Amino Acid
<220> FEATURE:
<221> NAME/KEY: VARIANT
<222> LOCATION: 275
<223> OTHER INFORMATION: Xaa = Any Amino Acid
<220> FEATURE:
<221> NAME/KEY: VARIANT
<222> LOCATION: 276
<223> OTHER INFORMATION: Xaa = Any Amino Acid
<220> FEATURE:
<221> NAME/KEY: VARIANT
<222> LOCATION: 277
<223> OTHER INFORMATION: Xaa = Any Amino Acid
<220> FEATURE:
<221> NAME/KEY: VARIANT
<222> LOCATION: 278
<223> OTHER INFORMATION: Xaa = Any Amino Acid
<220> FEATURE:
<221> NAME/KEY: VARIANT
<222> LOCATION: 279
<223> OTHER INFORMATION: Xaa = Any Amino Acid
<220> FEATURE:
<221> NAME/KEY: VARIANT
<222> LOCATION: 280
<223> OTHER INFORMATION: Xaa = Any Amino Acid
<220> FEATURE:
```

```
<221> NAME/KEY: VARIANT
<222> LOCATION: 281
<223> OTHER INFORMATION: Xaa = Any Amino Acid
<220> FEATURE:
<221> NAME/KEY: VARIANT
<222> LOCATION: 282
<223> OTHER INFORMATION: Xaa = Any Amino Acid
<220> FEATURE:
<221> NAME/KEY: VARIANT
<222> LOCATION: 283
<223> OTHER INFORMATION: Xaa = Any Amino Acid
<220> FEATURE:
<221> NAME/KEY: VARIANT
<222> LOCATION: 284
<223> OTHER INFORMATION: Xaa = Any Amino Acid
<220> FEATURE:
<221> NAME/KEY: VARIANT
<222> LOCATION: 285
<223> OTHER INFORMATION: Xaa = Any Amino Acid
<220> FEATURE:
<221> NAME/KEY: VARIANT
<222> LOCATION: 286
<223> OTHER INFORMATION: Xaa = Val or Gly or Ala or Ser or Asn or Lys or
      His or Thr or Tyr or Arg or Met
<220> FEATURE:
<221> NAME/KEY: VARIANT
<222> LOCATION: 287
<223> OTHER INFORMATION: Xaa = Val or Trp or Pro or Ile or Ser or Thr or
      Arg or Leu or Ala or Gln or Met or Tyr
<220> FEATURE:
<221> NAME/KEY: VARIANT
<222> LOCATION: 288
<223> OTHER INFORMATION: Xaa = Asp or Val or Gln or Ile or Leu or Thr
<220> FEATURE:
<221> NAME/KEY: VARIANT
<222> LOCATION: 289
<223> OTHER INFORMATION: Xaa = Any Amino Acid
<220> FEATURE:
<221> NAME/KEY: VARIANT
<222> LOCATION: 290
<223> OTHER INFORMATION: Xaa = Any Amino Acid
<220> FEATURE:
<221> NAME/KEY: VARIANT
<222> LOCATION: 291
<223> OTHER INFORMATION: Xaa = Thr or Ser or His or Asn or Gly or Ala
<220> FEATURE:
<221> NAME/KEY: VARIANT
<222> LOCATION: 292
<223> OTHER INFORMATION: Xaa = Gly or Arg or Asn or Ser or Pro
      or Ala or Glu or Lys
<220> FEATURE:
<221> NAME/KEY: VARIANT
<222> LOCATION: 293
<223> OTHER INFORMATION: Xaa = Leu or Val or Ile or Ala or Met
      or Phe or Asn or Tyr
<220> FEATURE:
<221> NAME/KEY: VARIANT
<222> LOCATION: 294
<223> OTHER INFORMATION: Xaa = Any Amino Acid
<220> FEATURE:
<221> NAME/KEY: VARIANT
<222> LOCATION: 296
<223> OTHER INFORMATION: Xaa = Thr or Ser or Tyr or Gln or Asn or Gly
      or Asp or His or Ala or Pro
<220> FEATURE:
<221> NAME/KEY: VARIANT
<222> LOCATION: 297
<223> OTHER INFORMATION: Xaa = Asn or Asp or Ser
<220> FEATURE:
<221> NAME/KEY: VARIANT
<222> LOCATION: 298
<223> OTHER INFORMATION: Xaa = Met or Val or Ala or Leu
<220> FEATURE:
<221> NAME/KEY: VARIANT
<222> LOCATION: 299
<223> OTHER INFORMATION: Xaa = Phe or Leu
<220> FEATURE:
<221> NAME/KEY: VARIANT
<222> LOCATION: 300
```

```
<223> OTHER INFORMATION: Xaa = Asp or Tyr or His or Ala or Val
<220> FEATURE:
<221> NAME/KEY: VARIANT
<222> LOCATION: 301
<223> OTHER INFORMATION: Xaa = Ala or Gly or Thr or Gln or Glu
<220> FEATURE:
<221> NAME/KEY: VARIANT
<222> LOCATION: 302
<223> OTHER INFORMATION: Xaa = Gln or Asn or Thr or Ile or Met
      or Leu or Val
<220> FEATURE:
<221> NAME/KEY: VARIANT
<222> LOCATION: 303
<223> OTHER INFORMATION: Xaa = Val or Phe or Tyr or His or Ala
      or Met or Leu
<220> FEATURE:
<221> NAME/KEY: VARIANT
<222> LOCATION: 305
<223> OTHER INFORMATION: Xaa = Ala or Thr or Ser or Cys
<220> FEATURE:
<221> NAME/KEY: VARIANT
<222> LOCATION: 306
<223> OTHER INFORMATION: Xaa = Val or Leu or Phe or Thr or Ile or Ala
<220> FEATURE:
<221> NAME/KEY: VARIANT
<222> LOCATION: 307
<223> OTHER INFORMATION: Xaa = Tyr or Val or Ile or His or Arg or Phe
      or Thr or Lys
<220> FEATURE:
<221> NAME/KEY: VARIANT
<222> LOCATION: 308
<223> OTHER INFORMATION: Xaa = Ala or Ser or His or Trp or Leu or Val
      or Ile or Phe or Tyr or Thr
<220> FEATURE:
<221> NAME/KEY: VARIANT
<222> LOCATION: 309
<223> OTHER INFORMATION: Xaa = Ala or Ser
<220> FEATURE:
<221> NAME/KEY: VARIANT
<222> LOCATION: 310
<223> OTHER INFORMATION: Xaa = Leu or Met or Val or Ile or Ala
<220> FEATURE:
<221> NAME/KEY: VARIANT
<222> LOCATION: 311
<223> OTHER INFORMATION: Xaa = Any Amino Acid
<220> FEATURE:
<221> NAME/KEY: VARIANT
<222> LOCATION: 312
<223> OTHER INFORMATION: Xaa = Any Amino Acid
<220> FEATURE:
<221> NAME/KEY: VARIANT
<222> LOCATION: 313
<223> OTHER INFORMATION: Xaa = Leu or Val or Ala or His or Asn or Ile
      or Glu or Met or Lys
<220> FEATURE:
<221> NAME/KEY: VARIANT
<222> LOCATION: 314
<223> OTHER INFORMATION: Xaa = Gly or Asn
<220> FEATURE:
<221> NAME/KEY: VARIANT
<222> LOCATION: 315
<223> OTHER INFORMATION: Xaa = Any Amino Acid
<220> FEATURE:
<221> NAME/KEY: VARIANT
<222> LOCATION: 316
<223> OTHER INFORMATION: Xaa = Any Amino Acid
<220> FEATURE:
<221> NAME/KEY: VARIANT
<222> LOCATION: 317
<223> OTHER INFORMATION: Xaa = Any Amino Acid
<220> FEATURE:
<221> NAME/KEY: VARIANT
<222> LOCATION: 318
<223> OTHER INFORMATION: Xaa = Any Amino Acid
<220> FEATURE:
<221> NAME/KEY: VARIANT
<222> LOCATION: 319
<223> OTHER INFORMATION: Xaa = Any Amino Acid
<220> FEATURE:
```

```
<221> NAME/KEY: VARIANT
<222> LOCATION: 320
<223> OTHER INFORMATION: Xaa = Any Amino Acid
<220> FEATURE:
<221> NAME/KEY: VARIANT
<222> LOCATION: 321
<223> OTHER INFORMATION: Xaa = Any Amino Acid
<220> FEATURE:
<221> NAME/KEY: VARIANT
<222> LOCATION: 322
<223> OTHER INFORMATION: Xaa = Any Amino Acid
<220> FEATURE:
<221> NAME/KEY: VARIANT
<222> LOCATION: 323
<223> OTHER INFORMATION: Xaa = Any Amino Acid
<220> FEATURE:
<221> NAME/KEY: VARIANT
<222> LOCATION: 324
<223> OTHER INFORMATION: Xaa = Any Amino Acid
<220> FEATURE:
<221> NAME/KEY: VARIANT
<222> LOCATION: 325
<223> OTHER INFORMATION: Xaa = Any Amino Acid
<220> FEATURE:
<221> NAME/KEY: VARIANT
<222> LOCATION: 326
<223> OTHER INFORMATION: Xaa = Any Amino Acid
<220> FEATURE:
<221> NAME/KEY: VARIANT
<222> LOCATION: 327
<223> OTHER INFORMATION: Xaa = Any Amino Acid
<220> FEATURE:
<221> NAME/KEY: VARIANT
<222> LOCATION: 328
<223> OTHER INFORMATION: Xaa = Val or Met or Leu or Ile or Pro
<220> FEATURE:
<221> NAME/KEY: VARIANT
<222> LOCATION: 329
<223> OTHER INFORMATION: Xaa = Any Amino Acid
<220> FEATURE:
<221> NAME/KEY: VARIANT
<222> LOCATION: 330
<223> OTHER INFORMATION: Xaa = Val or Ile or Leu or Ala
<220> FEATURE:
<221> NAME/KEY: VARIANT
<222> LOCATION: 331
<223> OTHER INFORMATION: Xaa = Val or Met or Ile or Ala or His or Arg
      or Thr or Lys or Leu
<220> FEATURE:
<221> NAME/KEY: VARIANT
<222> LOCATION: 332
<223> OTHER INFORMATION: Xaa = Val or Ile or Leu
<220> FEATURE:
<221> NAME/KEY: VARIANT
<222> LOCATION: 333
<223> OTHER INFORMATION: Xaa = Ser or Gly or Thr or Ala
<220> FEATURE:
<221> NAME/KEY: VARIANT
<222> LOCATION: 335
<223> OTHER INFORMATION: Xaa = Thr or Val or Ala or Ile or Ser
<220> FEATURE:
<221> NAME/KEY: VARIANT
<222> LOCATION: 337
<223> OTHER INFORMATION: Xaa = Trp or His or Cys
<220> FEATURE:
<221> NAME/KEY: VARIANT
<222> LOCATION: 338
<223> OTHER INFORMATION: Xaa = Pro or Ala
<220> FEATURE:
<221> NAME/KEY: VARIANT
<222> LOCATION: 339
<223> OTHER INFORMATION: Xaa = Ser or Thr or Asn or Tyr or His
<220> FEATURE:
<221> NAME/KEY: VARIANT
<222> LOCATION: 340
<223> OTHER INFORMATION: Xaa = Any Amino Acid
<220> FEATURE:
<221> NAME/KEY: VARIANT
<222> LOCATION: 341
```

```
<223> OTHER INFORMATION: Xaa = Gly or Asp or Cys or Ala
<220> FEATURE:
<221> NAME/KEY: VARIANT
<222> LOCATION: 342
<223> OTHER INFORMATION: Xaa = Any Amino Acid
<220> FEATURE:
<221> NAME/KEY: VARIANT
<222> LOCATION: 343
<223> OTHER INFORMATION: Xaa = Any Amino Acid
<220> FEATURE:
<221> NAME/KEY: VARIANT
<222> LOCATION: 344
<223> OTHER INFORMATION: Xaa = Any Amino Acid
<220> FEATURE:
<221> NAME/KEY: VARIANT
<222> LOCATION: 345
<223> OTHER INFORMATION: Xaa = Any Amino Acid
<220> FEATURE:
<221> NAME/KEY: VARIANT
<222> LOCATION: 346
<223> OTHER INFORMATION: Xaa = Any Amino Acid
<220> FEATURE:
<221> NAME/KEY: VARIANT
<222> LOCATION: 347
<223> OTHER INFORMATION: Xaa = Any Amino Acid
<220> FEATURE:
<221> NAME/KEY: VARIANT
<222> LOCATION: 348
<223> OTHER INFORMATION: Xaa = Any Amino Acid
<220> FEATURE:
<221> NAME/KEY: VARIANT
<222> LOCATION: 349
<223> OTHER INFORMATION: Xaa = Any Amino Acid
<220> FEATURE:
<221> NAME/KEY: VARIANT
<222> LOCATION: 350
<223> OTHER INFORMATION: Xaa = Any Amino Acid
<220> FEATURE:
<221> NAME/KEY: VARIANT
<222> LOCATION: 351
<223> OTHER INFORMATION: Xaa = Any Amino Acid
<220> FEATURE:
<221> NAME/KEY: VARIANT
<222> LOCATION: 352
<223> OTHER INFORMATION: Xaa = Any Amino Acid
<220> FEATURE:
<221> NAME/KEY: VARIANT
<222> LOCATION: 353
<223> OTHER INFORMATION: Xaa = Any Amino Acid
<220> FEATURE:
<221> NAME/KEY: VARIANT
<222> LOCATION: 354
<223> OTHER INFORMATION: Xaa = Any Amino Acid
<220> FEATURE:
<221> NAME/KEY: VARIANT
<222> LOCATION: 355
<223> OTHER INFORMATION: Xaa = Any Amino Acid
<220> FEATURE:
<221> NAME/KEY: VARIANT
<222> LOCATION: 356
<223> OTHER INFORMATION: Xaa = Any Amino Acid
<220> FEATURE:
<221> NAME/KEY: VARIANT
<222> LOCATION: 357
<223> OTHER INFORMATION: Xaa = Any Amino Acid
<220> FEATURE:
<221> NAME/KEY: VARIANT
<222> LOCATION: 358
<223> OTHER INFORMATION: Xaa = Any Amino Acid
<220> FEATURE:
<221> NAME/KEY: VARIANT
<222> LOCATION: 359
<223> OTHER INFORMATION: Xaa = Any Amino Acid
<220> FEATURE:
<221> NAME/KEY: VARIANT
<222> LOCATION: 360
<223> OTHER INFORMATION: Xaa = Any Amino Acid
<220> FEATURE:
<221> NAME/KEY: VARIANT
```

```
<222> LOCATION: 361
<223> OTHER INFORMATION: Xaa = Any Amino Acid
<220> FEATURE:
<221> NAME/KEY: VARIANT
<222> LOCATION: 362
<223> OTHER INFORMATION: Xaa = Any Amino Acid
<220> FEATURE:
<221> NAME/KEY: VARIANT
<222> LOCATION: 363
<223> OTHER INFORMATION: Xaa = Any Amino Acid
<220> FEATURE:
<221> NAME/KEY: VARIANT
<222> LOCATION: 364
<223> OTHER INFORMATION: Xaa = Any Amino Acid
<220> FEATURE:
<221> NAME/KEY: VARIANT
<222> LOCATION: 365
<223> OTHER INFORMATION: Xaa = Any Amino Acid
<220> FEATURE:
<221> NAME/KEY: VARIANT
<222> LOCATION: 366
<223> OTHER INFORMATION: Xaa = Any Amino Acid
<220> FEATURE:
<221> NAME/KEY: VARIANT
<222> LOCATION: 367
<223> OTHER INFORMATION: Xaa = Any Amino Acid
<220> FEATURE:
<221> NAME/KEY: VARIANT
<222> LOCATION: 368
<223> OTHER INFORMATION: Xaa = Glu or Asp or Asn or Ala or His
     or Gln or Tyr
<220> FEATURE:
<221> NAME/KEY: VARIANT
<222> LOCATION: 369
<223> OTHER INFORMATION: Xaa = Any Amino Acid
<220> FEATURE:
<221> NAME/KEY: VARIANT
<222> LOCATION: 370
<223> OTHER INFORMATION: Xaa = Gly or His or Tyr or Asn or Ser or Ala
     or Gln or Val or Glu or Asp
<220> FEATURE:
<221> NAME/KEY: VARIANT
<222> LOCATION: 371
<223> OTHER INFORMATION: Xaa = Ala or Glu or Gly or Val
<220> FEATURE:
<221> NAME/KEY: VARIANT
<222> LOCATION: 372
<223> OTHER INFORMATION: Xaa = Thr or Lys or Asn or Ser or Gly
<220> FEATURE:
<221> NAME/KEY: VARIANT
<222> LOCATION: 373
<223> OTHER INFORMATION: Xaa = Any Amino Acid
<220> FEATURE:
<221> NAME/KEY: VARIANT
<222> LOCATION: 374
<223> OTHER INFORMATION: Xaa = Glu or Ala or Ser or Lys or Gln or Thr
     or Gly or Asp or Arg or His
<220> FEATURE:
<221> NAME/KEY: VARIANT
<222> LOCATION: 375
<223> OTHER INFORMATION: Xaa = Asn or Tyr or Phe or Leu or Met
     or Ala or Glu
<220> FEATURE:
<221> NAME/KEY: VARIANT
<222> LOCATION: 376
<223> OTHER INFORMATION: Xaa = Ala or Ser
<220> FEATURE:
<221> NAME/KEY: VARIANT
<222> LOCATION: 377
<223> OTHER INFORMATION: Xaa = Any Amino Acid
<220> FEATURE:
<221> NAME/KEY: VARIANT
<222> LOCATION: 378
<223> OTHER INFORMATION: Xaa = Any Amino Acid
<220> FEATURE:
<221> NAME/KEY: VARIANT
<222> LOCATION: 379
<223> OTHER INFORMATION: Xaa = Tyr or Phe
<220> FEATURE:
```

```
<221> NAME/KEY: VARIANT
<222> LOCATION: 380
<223> OTHER INFORMATION: Xaa = Asn or Tyr or Val or Ser or Asp
      or Ile
<220> FEATURE:
<221> NAME/KEY: VARIANT
<222> LOCATION: 381
<223> OTHER INFORMATION: Xaa = Any Amino Acid
<220> FEATURE:
<221> NAME/KEY: VARIANT
<222> LOCATION: 382
<223> OTHER INFORMATION: Xaa = Asn or Gly or Lys or Tyr
<220> FEATURE:
<221> NAME/KEY: VARIANT
<222> LOCATION: 383
<223> OTHER INFORMATION: Xaa = Leu or Phe or Ile or Val or Ala
      or Met
<220> FEATURE:
<221> NAME/KEY: VARIANT
<222> LOCATION: 384
<223> OTHER INFORMATION: Xaa = Ile or Leu or Phe or Met or Val
      or Ala or Arg
<220> FEATURE:
<221> NAME/KEY: VARIANT
<222> LOCATION: 385
<223> OTHER INFORMATION: Xaa = Arg or Gln or Asp or Thr or Asn
      or Glu or Leu or Ala or Lys or Met or Ser
<220> FEATURE:
<221> NAME/KEY: VARIANT
<222> LOCATION: 386
<223> OTHER INFORMATION: Xaa = Any Amino Acid
<220> FEATURE:
<221> NAME/KEY: VARIANT
<222> LOCATION: 387
<223> OTHER INFORMATION: Xaa = Val or Leu or Met or Ile or Ala
      or Gln or Cys
<220> FEATURE:
<221> NAME/KEY: VARIANT
<222> LOCATION: 388
<223> OTHER INFORMATION: Xaa = Any Amino Acid
<220> FEATURE:
<221> NAME/KEY: VARIANT
<222> LOCATION: 389
<223> OTHER INFORMATION: Xaa = Any Amino Acid
<220> FEATURE:
<221> NAME/KEY: VARIANT
<222> LOCATION: 390
<223> OTHER INFORMATION: Xaa = Gly or Asn or Ser or Arg or Asp
      or Gln or Leu or Glu
<220> FEATURE:
<221> NAME/KEY: VARIANT
<222> LOCATION: 391
<223> OTHER INFORMATION: Xaa = Any Amino Acid
<220> FEATURE:
<221> NAME/KEY: VARIANT
<222> LOCATION: 392
<223> OTHER INFORMATION: Xaa = Any Amino Acid
<220> FEATURE:
<221> NAME/KEY: VARIANT
<222> LOCATION: 393
<223> OTHER INFORMATION: Xaa = Any Amino Acid
<220> FEATURE:
<221> NAME/KEY: VARIANT
<222> LOCATION: 397
<223> OTHER INFORMATION: Xaa = Any Amino Acid
<220> FEATURE:
<221> NAME/KEY: VARIANT
<222> LOCATION: 398
<223> OTHER INFORMATION: Xaa = Arg or His or Lys or Ala or Thr or Met
<220> FEATURE:
<221> NAME/KEY: VARIANT
<222> LOCATION: 399
<223> OTHER INFORMATION: Xaa = Pro or Lys or Thr or Ser
<220> FEATURE:
<221> NAME/KEY: VARIANT
<222> LOCATION: 400
<223> OTHER INFORMATION: Xaa = Gly or Asn or Gln or Arg or Asp or Lys
      or His or Ala or Ser
<220> FEATURE:
```

-continued

```
<221> NAME/KEY: VARIANT
<222> LOCATION: 401
<223> OTHER INFORMATION: Xaa = Any Amino Acid
<220> FEATURE:
<221> NAME/KEY: VARIANT
<222> LOCATION: 402
<223> OTHER INFORMATION: Xaa = Any Amino Acid
<220> FEATURE:
<221> NAME/KEY: VARIANT
<222> LOCATION: 403
<223> OTHER INFORMATION: Xaa = Any Amino Acid
<220> FEATURE:
<221> NAME/KEY: VARIANT
<222> LOCATION: 404
<223> OTHER INFORMATION: Xaa = Any Amino Acid
<220> FEATURE:
<221> NAME/KEY: VARIANT
<222> LOCATION: 405
<223> OTHER INFORMATION: Xaa = Any Amino Acid
<220> FEATURE:
<221> NAME/KEY: VARIANT
<222> LOCATION: 406
<223> OTHER INFORMATION: Xaa = Any Amino Acid
<220> FEATURE:
<221> NAME/KEY: VARIANT
<222> LOCATION: 407
<223> OTHER INFORMATION: Xaa = Any Amino Acid
<220> FEATURE:
<221> NAME/KEY: VARIANT
<222> LOCATION: 408
<223> OTHER INFORMATION: Xaa = Tyr or Phe or Ile or Met or Ser
<220> FEATURE:
<221> NAME/KEY: VARIANT
<222> LOCATION: 409
<223> OTHER INFORMATION: Xaa = Ile or Leu or Val or Met
<220> FEATURE:
<221> NAME/KEY: VARIANT
<222> LOCATION: 410
<223> OTHER INFORMATION: Xaa = Phe or Tyr
<220> FEATURE:
<221> NAME/KEY: VARIANT
<222> LOCATION: 411
<223> OTHER INFORMATION: Xaa = Ala or Gly or Ser or Asp or Glu
<220> FEATURE:
<221> NAME/KEY: VARIANT
<222> LOCATION: 412
<223> OTHER INFORMATION: Xaa = Leu or Met or Thr
<220> FEATURE:
<221> NAME/KEY: VARIANT
<222> LOCATION: 413
<223> OTHER INFORMATION: Xaa = Phe or Leu or Val or Ile or Tyr
<220> FEATURE:
<221> NAME/KEY: VARIANT
<222> LOCATION: 414
<223> OTHER INFORMATION: Xaa = Asn or Asp
<220> FEATURE:
<221> NAME/KEY: VARIANT
<222> LOCATION: 416
<223> OTHER INFORMATION: Xaa = Asp or Glu or Asn
<220> FEATURE:
<221> NAME/KEY: VARIANT
<222> LOCATION: 417
<223> OTHER INFORMATION: Xaa = Any Amino Acid
<220> FEATURE:
<221> NAME/KEY: VARIANT
<222> LOCATION: 418
<223> OTHER INFORMATION: Xaa = Lys or Arg
<220> FEATURE:
<221> NAME/KEY: VARIANT
<222> LOCATION: 419
<223> OTHER INFORMATION: Xaa = Any Amino Acid
<220> FEATURE:
<221> NAME/KEY: VARIANT
<222> LOCATION: 420
<223> OTHER INFORMATION: Xaa = Any Amino Acid
<220> FEATURE:
<221> NAME/KEY: VARIANT
<222> LOCATION: 421
<223> OTHER INFORMATION: Xaa = Any Amino Acid
```

```
<220> FEATURE:
<221> NAME/KEY: VARIANT
<222> LOCATION: 422
<223> OTHER INFORMATION: Xaa = Gly or Pro or Asp or Glu or Ala
<220> FEATURE:
<221> NAME/KEY: VARIANT
<222> LOCATION: 423
<223> OTHER INFORMATION: Xaa = Any Amino Acid
<220> FEATURE:
<221> NAME/KEY: VARIANT
<222> LOCATION: 424
<223> OTHER INFORMATION: Xaa = Any Amino Acid
<220> FEATURE:
<221> NAME/KEY: VARIANT
<222> LOCATION: 425
<223> OTHER INFORMATION: Xaa = Ser or Phe or Gln or Glu or Thr
      or Val or Ile or Ala
<220> FEATURE:
<221> NAME/KEY: VARIANT
<222> LOCATION: 426
<223> OTHER INFORMATION: Xaa = Glu or Asn or His or Lys or Arg
<220> FEATURE:
<221> NAME/KEY: VARIANT
<222> LOCATION: 427
<223> OTHER INFORMATION: Xaa = Arg or Gln or Asn or Lys or Ala
<220> FEATURE:
<221> NAME/KEY: VARIANT
<222> LOCATION: 428
<223> OTHER INFORMATION: Xaa = Any Amino Acid
<220> FEATURE:
<221> NAME/KEY: VARIANT
<222> LOCATION: 429
<223> OTHER INFORMATION: Xaa = Trp or Phe or Tyr
<220> FEATURE:
<221> NAME/KEY: VARIANT
<222> LOCATION: 431
<223> OTHER INFORMATION: Xaa = Leu or Ile or Val or Met
<220> FEATURE:
<221> NAME/KEY: VARIANT
<222> LOCATION: 432
<223> OTHER INFORMATION: Xaa = Phe or Leu or Met or Tyr
<220> FEATURE:
<221> NAME/KEY: VARIANT
<222> LOCATION: 433
<223> OTHER INFORMATION: Xaa = Any Amino Acid
<220> FEATURE:
<221> NAME/KEY: VARIANT
<222> LOCATION: 434
<223> OTHER INFORMATION: Xaa = Pro or Tyr or Phe or Ala or Gly
      or Lys or Thr or Met
<220> FEATURE:
<221> NAME/KEY: VARIANT
<222> LOCATION: 435
<223> OTHER INFORMATION: Xaa = Any Amino Acid
<220> FEATURE:
<221> NAME/KEY: VARIANT
<222> LOCATION: 436
<223> OTHER INFORMATION: Xaa = Asp or Asn or Ser
<220> FEATURE:
<221> NAME/KEY: VARIANT
<222> LOCATION: 437
<223> OTHER INFORMATION: Xaa = Gly or Met or Lys or Arg or Gln
      or Glu or Leu
<220> FEATURE:
<221> NAME/KEY: VARIANT
<222> LOCATION: 438
<223> OTHER INFORMATION: Xaa = Thr or Gln or Arg or Lys or Ser
      or Leu or His or Glu or Ala or Val
<220> FEATURE:
<221> NAME/KEY: VARIANT
<222> LOCATION: 439
<223> OTHER INFORMATION: Xaa = Pro or Ala or Lys or His or Arg
      or Glu or Leu or Met or Ser or Ile
<220> FEATURE:
<221> NAME/KEY: VARIANT
<222> LOCATION: 440
<223> OTHER INFORMATION: Xaa = Val or Lys or Ala or Ile or Ser
      or Asn or Thr
<220> FEATURE:
```

```
<221> NAME/KEY: VARIANT
<222> LOCATION: 441
<223> OTHER INFORMATION: Xaa = Tyr or Phe
<220> FEATURE:
<221> NAME/KEY: VARIANT
<222> LOCATION: 442
<223> OTHER INFORMATION: Xaa = Any Amino Acid
<220> FEATURE:
<221> NAME/KEY: VARIANT
<222> LOCATION: 443
<223> OTHER INFORMATION: Xaa = Leu or Met or Ile or Val or Phe
<220> FEATURE:
<221> NAME/KEY: VARIANT
<222> LOCATION: 444
<223> OTHER INFORMATION: Xaa = Any Amino Acid
<220> FEATURE:
<221> NAME/KEY: VARIANT
<222> LOCATION: 445
<223> OTHER INFORMATION: Xaa = Any Amino Acid

<400> SEQUENCE: 9

Xaa Xaa Xaa Xaa Xaa Xaa Xaa Xaa Xaa Xaa Xaa Gly Xaa Xaa Xaa Gly
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Ala Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Tyr Xaa Xaa Xaa Xaa Xaa Xaa Xaa Xaa Asp
    290                 295                 300
```

```
Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Glu Xaa Gly
            325                 330                 335

Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa
    355                 360                 365

Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Gly Thr Pro Xaa Xaa Xaa
385                 390                 395                 400

Xaa Xaa Xaa Xaa Xaa Xaa Xaa Xaa Xaa Xaa Xaa Xaa Glu Xaa
            405                 410                 415

Xaa Xaa Xaa Xaa Xaa Xaa Xaa Xaa Xaa Xaa Xaa Gly Xaa Xaa
        420                 425                 430

Xaa Xaa Xaa Xaa Xaa Xaa Xaa Xaa Xaa Xaa Xaa Xaa
    435                 440                 445

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
acgtgctgtc caacatcg                                                 18

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
aggtgatgag tcagccctag c                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
accagaacct cttcgacacc a                                             21

<210> SEQ ID NO 13
<211> LENGTH: 336
<212> TYPE: PRT
<213> ORGANISM: Zea mays

<400> SEQUENCE: 13

Met Ala Ser Arg Gln Gly Val Ala Ala Ser Met Phe Ala Thr Ala Leu
1               5                   10                  15

Leu Leu Gly Val Phe Ala Ser Ile Pro Gln Ser Ala Glu Ala Ile Gly
            20                  25                  30

Val Cys Tyr Gly Met Ser Ala Asn Asn Leu Pro Ala Ala Ser Thr Val
        35                  40                  45
```

```
Val Ser Met Tyr Lys Ala Asn Gly Ile Ser Ala Met Arg Leu Tyr Ala
     50                  55                  60

Pro Asp Gln Gly Ala Leu Gln Ala Val Gly Gly Thr Gly Ile Ser Val
 65                  70                  75                  80

Ala Val Gly Ala Pro Asn Asp Val Leu Ser Asn Ile Ala Ala Ser Pro
                 85                  90                  95

Ala Ala Ala Ala Ser Trp Val Arg Asn Asn Ile Gln Ala Tyr Pro Ser
             100                 105                 110

Val Ser Phe Arg Tyr Val Cys Val Gly Asn Glu Val Ala Gly Gly Ala
         115                 120                 125

Ala Gln Asp Leu Ala Pro Ala Met Glu Asn Val His Ala Ala Leu Ala
     130                 135                 140

Ala Ala Gly Leu Gly His Ile Lys Val Thr Thr Ser Val Ser Gln Ala
145                 150                 155                 160

Ile Leu Gly Val Tyr Ser Pro Pro Ser Ala Ala Glu Phe Thr Gly Glu
                165                 170                 175

Ala Arg Gly Tyr Met Gly Pro Val Leu Gln Phe Leu Ala Arg Thr Gly
             180                 185                 190

Ser Pro Leu Met Ala Asn Ile Tyr Pro Tyr Leu Ala Trp Ala Tyr Asn
         195                 200                 205

Pro Ser Ala Met Asp Met Ser Tyr Ala Leu Phe Thr Ser Ser Gly Thr
     210                 215                 220

Val Val Gln Asp Gly Ala Tyr Gly Tyr Gln Asn Leu Phe Asp Thr Thr
225                 230                 235                 240

Val Asp Ala Phe Tyr Val Ala Met Gly Lys Asn Gly Gly Ser Gly Val
                245                 250                 255

Pro Leu Val Val Ser Glu Ser Gly Trp Pro Ser Gly Gly Gly Val Gln
             260                 265                 270

Ala Thr Pro Ala Asn Ala Arg Val Tyr Asn Gln Tyr Leu Ile Asn His
         275                 280                 285

Val Gly Arg Gly Thr Pro Arg His Pro Gly Ala Ile Glu Thr Tyr Leu
     290                 295                 300

Phe Ser Met Phe Asn Glu Asn Gln Lys Glu Ser Gly Val Glu Gln Asn
305                 310                 315                 320

Trp Gly Leu Phe Tyr Pro Asn Met Gln His Val Tyr Pro Ile Ser Phe
                325                 330                 335

<210> SEQ ID NO 14
<211> LENGTH: 316
<212> TYPE: PRT
<213> ORGANISM: Zea mays

<400> SEQUENCE: 14

Met Cys Val Ser Ile Ala Gly Ala Glu Ala Ile Gly Val Cys Tyr Gly
 1               5                  10                  15

Met Ser Ala Asn Asn Leu Pro Ala Ala Ser Thr Val Val Ser Met Tyr
                 20                  25                  30

Lys Ala Asn Gly Ile Ser Ala Met Arg Leu Tyr Ala Pro Asp Gln Gly
             35                  40                  45

Ala Leu Gln Ala Val Gly Gly Thr Gly Ile Ser Val Ala Val Gly Ala
     50                  55                  60

Pro Asn Asp Val Leu Ser Asn Ile Ala Ala Ser Pro Ala Ala Ala Ala
 65                  70                  75                  80

Ser Trp Val Arg Asn Asn Ile Gln Ala Tyr Pro Ser Val Ser Phe Arg
```

```
                    85                  90                  95
Tyr Val Cys Val Gly Asn Glu Val Ala Gly Ala Ala Gln Asp Leu
                100                 105                 110
Ala Pro Ala Met Glu Asn Val His Ala Ala Leu Ala Ala Gly Leu
                115                 120                 125
Gly His Ile Lys Val Thr Thr Ser Val Ser Gln Ala Ile Leu Gly Val
130                 135                 140
Tyr Ser Pro Pro Ser Ala Ala Glu Phe Thr Gly Glu Ala Arg Gly Tyr
145                 150                 155                 160
Met Gly Pro Val Leu Gln Phe Leu Ala Arg Thr Gly Ser Pro Leu Met
                165                 170                 175
Ala Asn Ile Tyr Pro Tyr Leu Ala Trp Ala Tyr Asn Pro Ser Ala Met
                180                 185                 190
Asp Met Ser Tyr Ala Leu Phe Thr Ser Ser Gly Thr Val Val Gln Asp
                195                 200                 205
Gly Ala Tyr Gly Tyr Gln Asn Leu Phe Asp Thr Thr Val Asp Ala Phe
                210                 215                 220
Tyr Val Ala Met Gly Lys Asn Gly Gly Ser Gly Val Pro Leu Val Val
225                 230                 235                 240
Ser Glu Ser Gly Trp Pro Ser Gly Gly Val Gln Ala Thr Pro Ala
                245                 250                 255
Asn Ala Arg Val Tyr Asn Gln Tyr Leu Ile Asn His Val Gly Arg Gly
                260                 265                 270
Thr Pro Arg His Pro Gly Ala Ile Glu Thr Tyr Leu Phe Ser Met Phe
                275                 280                 285
Asn Glu Asn Gln Lys Glu Ser Gly Val Glu Gln Asn Trp Gly Leu Phe
                290                 295                 300
Tyr Pro Asn Met Gln His Val Tyr Pro Ile Ser Phe
305                 310                 315

<210> SEQ ID NO 15
<211> LENGTH: 312
<212> TYPE: PRT
<213> ORGANISM: Hordeum vulgare

<400> SEQUENCE: 15

Pro Pro Ser Val Glu Ser Ile Gly Val Cys Tyr Gly Met Ser Ala Asn
1               5                   10                  15
Asn Leu Pro Ala Ala Ser Thr Val Ser Met Phe Lys Phe Asn Gly
                20                  25                  30
Ile Lys Ser Met Arg Leu Tyr Ala Pro Asn Gln Ala Ala Leu Gln Ala
                35                  40                  45
Val Gly Gly Thr Gly Ile Asn Val Val Val Gly Ala Pro Asn Asp Val
                50                  55                  60
Leu Ser Asn Leu Ala Ala Ser Pro Ala Ala Ala Ser Trp Val Lys
65                  70                  75                  80
Ser Asn Ile Gln Ala Tyr Pro Lys Val Ser Phe Arg Tyr Val Cys Val
                85                  90                  95
Gly Asn Glu Val Ala Gly Gly Ala Thr Arg Asn Leu Val Pro Ala Met
                100                 105                 110
Lys Asn Val His Gly Ala Leu Val Ala Ala Gly Leu Gly His Ile Lys
                115                 120                 125
Val Thr Thr Ser Val Ser Gln Ala Ile Leu Gly Val Phe Ser Pro Pro
130                 135                 140
```

```
Ser Ala Gly Ser Phe Thr Gly Glu Ala Ala Ala Phe Met Gly Pro Val
145                 150                 155                 160

Val Gln Phe Leu Ala Arg Thr Asn Ala Pro Leu Met Ala Asn Ile Tyr
                165                 170                 175

Pro Tyr Leu Ala Trp Ala Tyr Asn Pro Ser Ala Met Asp Met Gly Tyr
            180                 185                 190

Ala Leu Phe Asn Ala Ser Gly Thr Val Val Arg Asp Gly Ala Tyr Gly
        195                 200                 205

Tyr Gln Asn Leu Phe Asp Thr Thr Val Asp Ala Phe Tyr Thr Ala Met
    210                 215                 220

Gly Lys His Gly Gly Ser Ser Val Lys Leu Val Val Ser Glu Ser Gly
225                 230                 235                 240

Trp Pro Ser Gly Gly Gly Thr Ala Ala Thr Pro Ala Asn Ala Arg Phe
                245                 250                 255

Tyr Asn Gln His Leu Ile Asn His Val Gly Arg Gly Thr Pro Arg His
                260                 265                 270

Pro Gly Ala Ile Glu Thr Tyr Ile Phe Ala Met Phe Asn Glu Asn Gln
            275                 280                 285

Lys Asp Ser Gly Val Glu Gln Asn Trp Gly Leu Phe Tyr Pro Asn Met
290                 295                 300

Gln His Val Tyr Pro Ile Asn Phe
305                 310

<210> SEQ ID NO 16
<211> LENGTH: 336
<212> TYPE: PRT
<213> ORGANISM: Artificial Sequence
<220> FEATURE:
<223> OTHER INFORMATION: Consensus Sequence

<400> SEQUENCE: 16

Met Ala Ser Arg Gln Gly Val Ala Ala Ser Met Phe Ala Thr Ala Leu
1               5                   10                  15

Leu Leu Gly Val Phe Ala Ser Ile Pro Gln Ser Ala Glu Ala Ile Gly
            20                  25                  30

Val Cys Tyr Gly Met Ser Ala Asn Asn Leu Pro Ala Ala Ser Thr Val
        35                  40                  45

Val Ser Met Tyr Lys Ala Asn Gly Ile Ser Ala Met Arg Leu Tyr Ala
    50                  55                  60

Pro Asp Gln Gly Ala Leu Gln Ala Val Gly Gly Thr Gly Ile Ser Val
65                  70                  75                  80

Ala Val Gly Ala Pro Asn Asp Val Leu Ser Asn Ile Ala Ala Ser Pro
                85                  90                  95

Ala Ala Ala Ala Ser Trp Val Arg Asn Asn Ile Gln Ala Tyr Pro Ser
            100                 105                 110

Val Ser Phe Arg Tyr Val Cys Val Gly Asn Glu Val Ala Gly Gly Ala
        115                 120                 125

Ala Gln Asp Leu Ala Pro Ala Met Glu Asn Val His Ala Ala Leu Ala
    130                 135                 140

Ala Ala Gly Leu Gly His Ile Lys Val Thr Thr Ser Val Ser Gln Ala
145                 150                 155                 160

Ile Leu Gly Val Tyr Ser Pro Pro Ser Ala Ala Glu Phe Thr Gly Glu
                165                 170                 175

Ala Arg Gly Tyr Met Gly Pro Val Leu Gln Phe Leu Ala Arg Thr Gly
            180                 185                 190
```

```
Ser Pro Leu Met Ala Asn Ile Tyr Pro Tyr Leu Ala Trp Ala Tyr Asn
            195                 200                 205

Pro Ser Ala Met Asp Met Ser Tyr Ala Leu Phe Thr Ser Ser Gly Thr
    210                 215                 220

Val Val Gln Asp Gly Ala Tyr Gly Tyr Gln Asn Leu Phe Asp Thr Thr
225                 230                 235                 240

Val Asp Ala Phe Tyr Val Ala Met Gly Asn Asn Gly Gly Ser Gly Val
                245                 250                 255

Pro Leu Val Val Ser Glu Ser Gly Trp Pro Ser Gly Gly Val Gln
            260                 265                 270

Ala Thr Pro Ala Asn Ala Arg Val Tyr Asn Gln Tyr Leu Ile Asn His
            275                 280                 285

Val Gly Arg Gly Thr Pro Arg His Pro Gly Ala Ile Glu Thr Tyr Leu
    290                 295                 300

Phe Ser Met Phe Asn Glu Asn Gln Lys Glu Ser Gly Val Glu Gln Asn
305                 310                 315                 320

Trp Gly Leu Phe Tyr Pro Asn Met Gln His Val Tyr Pro Ile Ser Phe
                325                 330                 335

<210> SEQ ID NO 17
<211> LENGTH: 316
<212> TYPE: PRT
<213> ORGANISM: Artificial Sequence
<220> FEATURE:
<223> OTHER INFORMATION: Consensus Sequence

<400> SEQUENCE: 17

Met Cys Val Ser Ile Ala Gly Ala Glu Ala Ile Gly Val Cys Tyr Gly
1               5                   10                  15

Met Ser Ala Asn Asn Leu Pro Ala Ala Ser Thr Val Val Ser Met Tyr
            20                  25                  30

Lys Ala Asn Gly Ile Ser Ala Met Arg Leu Tyr Ala Pro Asp Gln Gly
        35                  40                  45

Ala Leu Gln Ala Val Gly Gly Thr Gly Ile Ser Val Ala Val Gly Ala
    50                  55                  60

Pro Asn Asp Val Leu Ser Asn Ile Ala Ala Ser Pro Ala Ala Ala Ala
65                  70                  75                  80

Ser Trp Val Arg Asn Asn Ile Gln Ala Tyr Pro Ser Val Ser Phe Arg
                85                  90                  95

Tyr Val Cys Val Gly Asn Glu Val Ala Gly Ala Ala Gln Asp Leu
            100                 105                 110

Ala Pro Ala Met Glu Asn Val His Ala Ala Leu Ala Ala Ala Gly Leu
        115                 120                 125

Gly His Ile Lys Val Thr Thr Ser Val Ser Gln Ala Ile Leu Gly Val
    130                 135                 140

Tyr Ser Pro Pro Ser Ala Ala Glu Phe Thr Gly Glu Ala Arg Gly Tyr
145                 150                 155                 160

Met Gly Pro Val Leu Gln Phe Leu Ala Arg Thr Gly Ser Pro Leu Met
                165                 170                 175

Ala Asn Ile Tyr Pro Tyr Leu Ala Trp Ala Tyr Asn Pro Ser Ala Met
            180                 185                 190

Asp Met Ser Tyr Ala Leu Phe Thr Ser Ser Gly Thr Val Val Gln Asp
        195                 200                 205

Gly Ala Tyr Gly Tyr Gln Asn Leu Phe Asp Thr Thr Val Asp Ala Phe
    210                 215                 220
```

```
Tyr Val Ala Met Gly Asn Asn Gly Gly Ser Gly Val Pro Leu Val Val
225                 230                 235                 240

Ser Glu Ser Gly Trp Pro Ser Gly Gly Gly Val Gln Ala Thr Pro Ala
            245                 250                 255

Asn Ala Arg Val Tyr Asn Gln Tyr Leu Ile Asn His Val Gly Arg Gly
        260                 265                 270

Thr Pro Arg His Pro Gly Ala Ile Glu Thr Tyr Leu Phe Ser Met Phe
    275                 280                 285

Asn Glu Asn Gln Lys Glu Ser Gly Val Glu Gln Asn Trp Gly Leu Phe
290                 295                 300

Tyr Pro Asn Met Gln His Val Tyr Pro Ile Ser Phe
305                 310                 315

<210> SEQ ID NO 18
<211> LENGTH: 283
<212> TYPE: PRT
<213> ORGANISM: Zea mays

<400> SEQUENCE: 18

Val Ala Gln Leu Leu Arg Asp Asn Gly Ile Lys Lys Val Lys Leu Phe
1               5                   10                  15

Asp Ala Asp Gln Gly Asn Ala Ser Ala Arg Ser Pro Ala Pro Ala Ser
            20                  25                  30

Ser Phe Ala Tyr Arg Cys Ala Arg Gly Leu Val Pro Ala Val Ala Leu
        35                  40                  45

Asp Gly Ala Thr Gln Pro Cys Arg Tyr Val Ala Val Gly Asn Glu Pro
    50                  55                  60

Phe Leu Ala Ala Tyr Asn Gly Thr Phe Asp Lys Val Thr Phe Pro Ala
65                  70                  75                  80

Leu Gln Asn Ile Gln Asn Ala Leu Asn Glu Ala Gly Leu Gly Asp Thr
                85                  90                  95

Val Lys Ala Thr Val Pro Leu Asn Ala Asp Val Tyr Met Ser Pro Lys
            100                 105                 110

Asp Asn Pro Val Pro Ser Ala Gly Arg Trp Cys Lys Phe Pro Glu Ala
        115                 120                 125

Lys Thr Gly Ala Pro Phe Thr Val Asn His Leu Pro Arg Ser Ser Pro
    130                 135                 140

Cys Ser Glu Thr Thr Thr Ser Pro Val Asp Phe Ala Phe Phe Asp Gly
145                 150                 155                 160

Gly Arg Arg Ala Ala Gly Trp Asp Pro Gly Ser Gly Val Ser Tyr Thr
                165                 170                 175

Asn Val Phe Asp Ala Asn Phe Asp Thr Leu Val Ala Ala Leu Lys Ser
            180                 185                 190

Val Gly His Gly Asp Met Pro Val Val Gly Glu Val Gly Trp Pro
        195                 200                 205

Thr Asp Gly Asp Lys His Ala Thr Asn Ala Tyr Ala Gln Arg Phe Tyr
    210                 215                 220

Asn Gly Leu Leu Arg Arg Leu Ala Ala Asn Ala Gly Thr Pro Ala Arg
225                 230                 235                 240

Pro Asn Gln Tyr Ile Glu Val Tyr Leu Phe Gly Leu Leu Asp Glu Asp
                245                 250                 255

Val Lys Ser Val Ala Pro Gly Asn Phe Glu Arg His Trp Gly Ile Leu
            260                 265                 270

Arg Tyr Asp Gly Gln Pro Lys Tyr Pro Met Asp
        275                 280
```

<210> SEQ ID NO 19
<211> LENGTH: 323
<212> TYPE: PRT
<213> ORGANISM: Zea mays

<400> SEQUENCE: 19

```
Leu Gly Val Asn Trp Gly Thr Gln Ala Thr His Pro Leu Pro Pro Lys
  1               5                  10                  15

Ala Val Val Gln Val Leu Arg Asp Asn Gly Ile Lys Lys Val Lys Leu
             20                  25                  30

Phe Asp Ala Asp Pro Ala Ala Met Arg Ala Leu Ala Gly Thr Gly Ile
         35                  40                  45

Glu Val Met Val Ala Ile Pro Asn Ala Met Leu Ala Gly Leu Ala Ala
 50                  55                  60

Asp Ala Gly Gln Ala Arg Asn Trp Val Lys His Asn Val Arg Arg Tyr
 65                  70                  75                  80

Asp Phe Asp Gly Gly Val Thr Ile Lys Tyr Val Ala Val Gly Asn Glu
                 85                  90                  95

Pro Phe Leu Glu Ser Tyr Asn Gly Ser Phe Ile Asn Val Thr Leu Pro
            100                 105                 110

Ala Leu Lys Asn Val Gln Asn Ala Leu Asn Asp Ala Gly Ile Gly Asp
        115                 120                 125

Arg Ile Lys Ala Thr Val Pro Leu Asn Ala Asp Val Tyr Asn Ser Pro
130                 135                 140

Arg Ser Asn Pro Val Pro Ser Ala Gly Arg Phe Arg Ala Asp Ile Ala
145                 150                 155                 160

Gly Leu Met Ala Asp Met Val Arg Phe Leu Ala Arg Asn Gly Ala Pro
                165                 170                 175

Phe Thr Val Asn Ile Tyr Pro Phe Leu Ser Leu Tyr Leu Asn Glu His
            180                 185                 190

Phe Pro Leu Asp Tyr Ala Phe Phe Asp Gly Gly Ala Ala Pro Val Asp
        195                 200                 205

Asp His Gly Val Leu Tyr Thr Asn Val Phe Asp Ala Asn Phe Asp Thr
    210                 215                 220

Leu Val Ala Ala Leu Gly Ala Val Gly His Gly Asp Met Pro Val Val
225                 230                 235                 240

Val Gly Glu Val Gly Trp Pro Thr Asp Gly Asp Arg His Ala Lys Ala
                245                 250                 255

Ser Tyr Ala Gln Arg Phe Tyr Ala Gly Leu Leu Arg Arg Leu Ala Ala
            260                 265                 270

Asn Thr Gly Thr Pro Ala Arg Pro Gly Gln Arg Pro Ala Glu Val Tyr
        275                 280                 285

Leu Phe Gly Leu Val Asp Glu Asp Ala Lys Ser Val Ala Pro Gly Asn
    290                 295                 300

Phe Glu Arg His Trp Gly Val Leu Arg Tyr Asp Gly Gln Pro Lys Phe
305                 310                 315                 320

Ala Met Asp
```

<210> SEQ ID NO 20
<211> LENGTH: 318
<212> TYPE: PRT
<213> ORGANISM: Zea mays

<400> SEQUENCE: 20

```
Asn Trp Gly Thr Met Ala Thr His Gln Leu Pro Ala Thr Val Val
1               5                   10                  15

Arg Met Leu Glu Asp Asn Gly Ile Arg Lys Val Lys Leu Phe Asp Ala
            20                  25                  30

Asp Ala Gly Pro Met Asp Ala Leu Ala Gly Thr Ser Val Glu Val Met
        35                  40                  45

Val Ala Ile Pro Asn Asn Met Leu Asp Met Met Thr Asp Tyr Gly Thr
50                  55                  60

Ala Arg Asp Trp Val Arg Gln Asn Val Ser Arg Tyr Asn Phe Asp Gly
65                  70                  75                  80

Gly Val Asn Ile Lys Tyr Val Ala Val Gly Asn Glu Pro Phe Leu Ser
                85                  90                  95

Ser Phe Asn Gly Thr Phe Leu Asn Val Thr Leu Pro Ala Leu Gln Asn
            100                 105                 110

Ile Gln Arg Ala Leu Asn Asp Ala Gly Phe Gly Asp Thr Ile Lys Ala
        115                 120                 125

Thr Val Pro Leu Asn Ala Asp Val Tyr Asn Ser Pro Lys Asp Asn Leu
130                 135                 140

Val Pro Ser Ala Gly Arg Phe Arg Pro Asp Ile Ala Gly Leu Met Thr
145                 150                 155                 160

Glu Ile Val Gln Phe Leu Asn Gln Ser Gly Ala Pro Phe Thr Val Asn
                165                 170                 175

Ile Tyr Pro Phe Leu Ser Leu Tyr Asp Asn Asp Phe Pro Leu Asp
            180                 185                 190

Tyr Ala Phe Phe Asp Gly Thr Gly Ser Pro Val Val Asp Asn Gly Ile
        195                 200                 205

Gln Tyr Thr Asn Val Phe Asp Ala Asn Phe Asp Thr Leu Val Ser Ala
210                 215                 220

Leu Ala Ala Ala Gly Val Gly Gly Leu Pro Val Val Gly Glu Val
225                 230                 235                 240

Gly Trp Pro Thr Asp Gly Asp Lys His Ala Thr Ala Ala Phe Ala Gln
                245                 250                 255

Lys Phe Tyr Ala Gly Leu Leu Arg Lys Leu Ala Ala Ser Ala Gly Thr
            260                 265                 270

Pro Leu Arg Pro Gly Gln Tyr Ile Glu Val Tyr Leu Phe Ser Leu Ile
        275                 280                 285

Asp Glu Asp Ala Lys Ser Val Ala Pro Gly Asn Phe Glu Arg His Trp
290                 295                 300

Gly Ile Met Arg Tyr Asp Gly Gln Pro Lys Tyr Ala Met Asp
305                 310                 315

<210> SEQ ID NO 21
<211> LENGTH: 281
<212> TYPE: PRT
<213> ORGANISM: Zea mays

<400> SEQUENCE: 21

Lys Gly Leu Ala Gly Thr Ser Ile Glu Thr Met Ile Ala Val Pro Asn
1               5                   10                  15

Asp Met Leu Ala Ala Val Ala Asp Tyr Asp Arg Ala Arg Arg Trp Val
            20                  25                  30

Arg Asp Asn Val Thr Lys Tyr Thr Phe Asp Gly Gly Val Asn Ile Lys
        35                  40                  45

Phe Val Ala Val Gly Asn Glu Pro Phe Leu Arg Ala Tyr Asn Gly Ser
50                  55                  60
```

Phe Asp His Val Thr Val Pro Ala Leu Arg Asn Ile Gln Arg Ala Leu
65                  70                  75                  80

Asp Glu Ala Gly His Gly Ala Ala Val Lys Ala Thr Val Pro Val Asn
            85                  90                  95

Ala Asp Val Tyr Asp Ser Pro Ala Ser Asn Pro Val Pro Ser Ala Gly
            100                 105                 110

Arg Phe Arg Ser Asp Val Ala Arg Val Met Ala Asp Met Val Arg Phe
            115                 120                 125

Leu Asn Arg Ser Gly Ala Pro Leu Thr Val Asn Ile Tyr Pro Phe Leu
130                 135                 140

Ser Leu Tyr Gly Asn Asp Asp Phe Pro Leu Asp Tyr Ala Phe Phe Asp
145                 150                 155                 160

Gly Gly Ala Gly Ala Pro Val Val Asp Gly Arg Ala Val Tyr Thr Asn
            165                 170                 175

Val Phe Asp Ala Asn Phe Asp Thr Leu Val Ser Ala Leu Lys Arg Val
            180                 185                 190

Gly Leu Gly His Leu Pro Val Met Ile Gly Glu Val Gly Trp Pro Thr
            195                 200                 205

Asp Gly Asp Arg His Ala Thr Ala Ala Leu Ala Glu Arg Phe Tyr Ala
210                 215                 220

Gly Leu Leu Gln Arg Leu Ala Ala Arg Gly Thr Pro Leu Arg Pro
225                 230                 235                 240

Gly Ala Arg Ile Glu Ala Tyr Leu Phe Gly Leu Val Asp Glu Asp Ala
            245                 250                 255

Lys Ser Val Ala Pro Gly Asn Phe Glu Arg His Trp Gly Ile Phe Thr
            260                 265                 270

Phe Asp Gly Arg Pro Lys Phe Pro Leu
            275                 280

<210> SEQ ID NO 22
<211> LENGTH: 323
<212> TYPE: PRT
<213> ORGANISM: Zea mays

<400> SEQUENCE: 22

Lys Gly Leu Ala Gly Thr Ser Ile Glu Thr Met Ile Ala Val Pro Asn
1               5                   10                  15

Asp Met Leu Ala Ala Val Ala Asp Tyr Asp Arg Ala Arg Arg Trp Val
            20                  25                  30

Arg Asp Asn Val Thr Lys Tyr Thr Phe Asp Gly Gly Val Asn Ile Lys
            35                  40                  45

Cys Val Ala Leu Gly Pro Ser Ala Arg Val Tyr Ile Tyr Ala Val His
            50                  55                  60

Arg His Trp His Gly Pro Val Arg Phe Ser Ala Gly Ala Glu Thr Phe
65                  70                  75                  80

Ser Ile Val Arg Val Arg Pro Ser Arg Phe Val Ala Val Gly Asn Glu
            85                  90                  95

Pro Phe Leu Arg Ala Tyr Asn Gly Ser Phe Asp His Val Thr Val Pro
            100                 105                 110

Ala Leu Arg Asn Ile Gln Arg Ala Leu Asp Glu Ala Gly His Gly Ala
            115                 120                 125

Ala Val Lys Ala Thr Val Pro Val Asn Ala Asp Val Tyr Asp Ser Pro
130                 135                 140

Ala Ser Asn Pro Val Pro Ser Ala Gly Arg Phe Arg Ser Asp Val Ala

-continued

```
            145                 150                 155                 160
Arg Val Met Ala Asp Met Val Arg Phe Leu Asn Arg Ser Gly Ala Pro
                    165                 170                 175
Leu Thr Val Asn Ile Tyr Pro Phe Leu Ser Leu Tyr Gly Asn Asp Asp
                180                 185                 190
Phe Pro Leu Asp Tyr Ala Phe Phe Asp Gly Gly Ala Gly Ala Pro Val
            195                 200                 205
Val Asp Gly Arg Ala Val Tyr Thr Asn Val Phe Asp Ala Asn Phe Asp
        210                 215                 220
Thr Leu Val Ser Ala Leu Lys Arg Val Gly Leu Gly His Leu Pro Val
225                 230                 235                 240
Met Ile Gly Glu Val Gly Trp Pro Thr Asp Gly Asp Arg His Ala Thr
                245                 250                 255
Ala Ala Leu Ala Glu Arg Phe Tyr Ala Gly Leu Leu Gln Arg Leu Ala
            260                 265                 270
Ala Arg Arg Gly Thr Pro Leu Arg Pro Gly Ala Arg Ile Glu Ala Tyr
        275                 280                 285
Leu Phe Gly Leu Val Asp Glu Asp Ala Lys Ser Val Ala Pro Gly Asn
    290                 295                 300
Phe Glu Arg His Trp Gly Ile Phe Thr Phe Asp Gly Arg Pro Lys Phe
305                 310                 315                 320
Pro Leu Asp
```

<210> SEQ ID NO 23
<211> LENGTH: 327
<212> TYPE: PRT
<213> ORGANISM: Zea mays

<400> SEQUENCE: 23

```
Pro Ala Met Ala Asp Asp Ile Val Glu Val Gly Val Asn Trp Gly
1               5                  10                  15
Ser Gln Leu Ser His Pro Leu Leu Pro Gly Ser Val Val Lys Met Leu
                20                  25                  30
Lys Ala Asn Arg Ile Ala Arg Val Lys Met Phe Asp Ala Asp Ser Trp
            35                  40                  45
Pro Val Gly Ala Leu Val Asp Ser Gly Ile Glu Val Met Leu Gly Ile
        50                  55                  60
Pro Asn Asp Met Leu Glu Thr Met Ser Ser Ser Tyr Gly Asn Ala Gln
65                  70                  75                  80
Asp Trp Val Lys Glu Asn Val Thr Ala Tyr Gly Asp Lys Leu Lys Leu
                85                  90                  95
Lys Tyr Val Ala Val Gly Asn Glu Pro Phe Leu Lys Ala Tyr Asn Gly
            100                 105                 110
Ser Phe Met Lys Thr Thr Phe Pro Ala Leu Lys Asn Ile Gln Lys Ala
        115                 120                 125
Leu Asp Glu Ala Gly Val Gly Asn Thr Val Lys Ala Val Val Pro Leu
    130                 135                 140
Asn Ala Asp Val Tyr Val Ser Pro Asp Lys Pro Ser Ser Gly Ala
145                 150                 155                 160
Phe Arg Pro Asp Ile Asn Gly Leu Met Thr Asp Met Val Lys Phe Leu
                165                 170                 175
His Asp His Gly Ala Pro Phe Val Val Asn Ile Tyr Pro Phe Leu Ser
            180                 185                 190
Leu Tyr Gln Ser Asp Asn Phe Pro Phe Glu Phe Ala Phe Phe Asp Gly
```

```
            195                 200                 205
Gly Lys Asn Ile Gln Asp Lys Gly Val Thr Tyr Ser Asn Val Phe
210                 215                 220

Asp Ala Asn Tyr Asp Thr Leu Val His Ala Leu Lys Lys Ala Gly Val
225                 230                 235                 240

Pro Asp Leu Lys Val Ile Val Gly Glu Ala Gly Trp Pro Thr Asp Gly
                245                 250                 255

Asn Lys Tyr Ala Asn Phe Lys Leu Ala Arg Arg Phe Tyr Asp Gly Leu
            260                 265                 270

Leu Arg Lys Leu Ala Lys Asn Glu Gly Thr Pro Val Arg Lys Gly Lys
        275                 280                 285

Met Glu Val Tyr Leu Phe Gly Leu Phe Asp Glu Asp Met Lys Ser Ile
    290                 295                 300

Ala Pro Gly Asn Phe Glu Arg His Trp Gly Ile Phe Thr Tyr Asp Gly
305                 310                 315                 320

Lys Pro Lys Phe Pro Ile Asp
                325

<210> SEQ ID NO 24
<211> LENGTH: 319
<212> TYPE: PRT
<213> ORGANISM: Zea mays

<400> SEQUENCE: 24

Gly Val Asn Trp Gly Thr Met Met Ser His Pro Ile His Pro Ser Ala
1               5                   10                  15

Val Val Glu Met Leu Arg Ala Asn Gly Val Asp Arg Val Lys Leu Phe
                20                  25                  30

Asp Ala Asp Pro Trp Thr Val Ser Ala Leu Ala Gly Ser Gly Val Gln
            35                  40                  45

Ala Met Leu Ala Ala Pro Asn Asp Gln Leu Ala Ser Leu Ala Arg Asp
        50                  55                  60

Pro Arg Arg Ala Arg Asp Trp Val Arg Gln Asn Val Thr Ala Asn Ile
65                  70                  75                  80

Asn Ala Gly Val Asp Val Arg Tyr Val Ala Val Gly Asn Glu Pro Phe
                85                  90                  95

Leu Lys Ser Tyr Asn Gly Ser Phe Ile Asn Ile Thr Phe Pro Ala Leu
            100                 105                 110

Lys Asn Met Gln Arg Ala Ile Asp Glu Ala Gly Phe Gly Gln His Ile
        115                 120                 125

Lys Val Val Val Pro Leu Asn Ala Asp Ile Tyr Ser Ser Pro Glu Asn
    130                 135                 140

Lys Pro Val Pro Ser Ala Gly Thr Phe Arg Lys Asp Ile Asn Thr Leu
145                 150                 155                 160

Met Val Asp Ile Val Asn Tyr Leu His Ala Asn Asp Ala Pro Phe Val
                165                 170                 175

Val Asn Ile Tyr Pro Phe Leu Ser Leu Tyr Gln Asn Pro Asn Phe Pro
            180                 185                 190

Leu Asn Phe Ser Phe Phe Asp Gly Ala Thr Lys Pro Val Tyr Asp Gln
        195                 200                 205

Gly Met Val Tyr Thr Asn Val Phe Asp Ala Asn Phe Asp Thr Leu Val
    210                 215                 220

Trp Ser Leu Arg Lys Ala Gly Val Pro Asp Met Arg Ile Ile Val Gly
225                 230                 235                 240
```

-continued

Glu Val Gly Trp Pro Ser Asp Gly Asp Lys Asn Ala Asn Thr Lys Tyr
                245                 250                 255

Ala Gln Arg Phe Tyr Asn Gly Phe Leu Lys Met Thr Lys Asn Val
        260                 265                 270

Gly Thr Pro Leu Arg Pro Gly Arg Met Glu Val Tyr Leu Phe Ala Leu
            275                 280                 285

Ile Asp Glu Asn Gln Lys Ser Val Leu Pro Gly Arg Phe Glu Arg His
    290                 295                 300

Trp Gly Leu Phe Thr Tyr Asp Gly Lys Pro Lys Phe Ser Met Asp
305                 310                 315

<210> SEQ ID NO 25
<211> LENGTH: 305
<212> TYPE: PRT
<213> ORGANISM: Zea mays

<400> SEQUENCE: 25

Val Arg Leu Leu Arg Asp Asn Gly Phe Asp Lys Val Lys Leu Phe Glu
  1               5                  10                  15

Ala Asp Pro Pro Ala Leu Arg Ala Leu Gly His Ser Gly Ile Gln Val
             20                  25                  30

Met Leu Gly Leu Pro Asn Glu Leu Leu Gly Ser Val Ala Ala Ser Val
         35                  40                  45

Thr Ala Ala Glu Gln Trp Val Ile Gln Asn Val Ser Thr Tyr Val Ser
 50                  55                  60

Lys Tyr Gly Val Asp Ile Arg Tyr Val Ala Val Gly Asn Glu Pro Phe
 65                  70                  75                  80

Leu Lys Ser Tyr Lys Gly Lys Phe Glu Ala Ala Thr Leu Pro Ala Val
                 85                  90                  95

Gln Asn Val Gln Ala Ala Leu Val Lys Ala Gly Leu Ala Arg Gln Val
            100                 105                 110

His Val Thr Val Pro Leu Asn Ala Asp Val Tyr Glu Ser Gly Asp Gly
        115                 120                 125

Arg Pro Ser Ser Gly Asp Phe Arg Pro Asp Ile Ala Gly Leu Met Val
    130                 135                 140

Ser Leu Val Arg Phe Leu Leu Asp Asn Gly Gly Val Leu Thr Ile Asn
145                 150                 155                 160

Ile Tyr Pro Phe Leu Ser Leu Tyr Ala Asp Pro Asn Phe Pro Val Asp
                165                 170                 175

Tyr Ala Tyr Phe Pro Ser Pro Gly Ala Arg Pro Ser Gln Ala Ser Val
            180                 185                 190

Gln Asp Gly Asn Val Leu Tyr Thr Asn Val Phe Asp Ala Asn Tyr Asp
        195                 200                 205

Thr Leu Ile Ala Ala Leu Glu Lys His Gly Leu Gly Ala Ile Pro Val
    210                 215                 220

Ile Val Gly Glu Ile Gly Trp Pro Thr Asp Gly Asp Lys Asn Ala Asn
225                 230                 235                 240

Ala Ala Asn Ala Gln Arg Phe Asn Gln Gly Leu Phe Asp Arg Ile Ile
                245                 250                 255

Ala Gly Lys Gly Thr Pro Arg Arg Pro Gln Met Pro Asp Val Tyr Val
            260                 265                 270

Phe Ala Leu Leu Asp Glu Asp Asn Lys Ser Ile Asp Pro Gly Ser Phe
        275                 280                 285

Glu Arg His Trp Gly Val Phe Asn Tyr Asp Gly Ser Pro Lys Tyr Pro
    290                 295                 300

Leu
305

<210> SEQ ID NO 26
<211> LENGTH: 318
<212> TYPE: PRT
<213> ORGANISM: Zea mays

<400> SEQUENCE: 26

```
Ile Gly Ala Asn Trp Gly Thr Gln Ala Ser His Pro Leu Pro Pro Glu
  1               5                  10                  15

Thr Val Val Arg Met Leu Lys Asp Asn Gly Phe Gln Lys Val Lys Leu
             20                  25                  30

Phe Asp Ala Glu Glu Gly Thr Met Ser Ala Leu Arg Lys Ser Gly Leu
         35                  40                  45

Glu Val Met Val Gly Ile Pro Asn Asp Leu Leu Ser Thr Met Ala Thr
     50                  55                  60

Ser Met Lys Ala Ala Glu Lys Trp Val Asp Thr Asn Val Ser Ser Tyr
 65                  70                  75                  80

Leu Asn Asp Gly Val Ser Ile Arg Tyr Val Ala Val Gly Asn Glu Pro
                 85                  90                  95

Phe Leu Glu Thr Tyr Asn Gly Ser Phe Leu Gln Ser Thr Phe Pro Ala
            100                 105                 110

Ile Arg Asn Ile Gln Gly Ala Leu Ile Lys Ala Gly Leu Gly Asn Gln
        115                 120                 125

Val Lys Val Thr Cys Pro Leu Asn Ala Asp Val Tyr Ser Ser Thr Thr
    130                 135                 140

Ser Lys Pro Ser Asp Gly Asp Phe Arg Thr Asp Ile His Asp Leu Met
145                 150                 155                 160

Leu Thr Ile Val Lys Phe Leu Ser Asp Asn Gly Gly Ala Phe Thr Val
                165                 170                 175

Asn Ile Tyr Pro Phe Ile Ser Leu Tyr Ile Asp Pro Asn Phe Pro Val
            180                 185                 190

Asp Tyr Ala Phe Phe Glu Gly Ala Ser Ser Pro Ile Val Asp Gly Ser
        195                 200                 205

Phe Thr Tyr Ser Asn Met Phe Asp Ala Asn His Asp Thr Leu Ile Trp
    210                 215                 220

Ala Leu Lys Lys Asn Gly Phe Gly Asn Leu Pro Val Ile Val Gly Glu
225                 230                 235                 240

Ile Gly Trp Pro Thr Asp Gly Asp Arg Asn Ala Asn Ala Gln Met Ala
                245                 250                 255

Gln Arg Phe Asn Gln Gly Phe Met Thr His Ile Ala Ser Gly Arg Gly
            260                 265                 270

Thr Pro Met Arg Pro Gly Pro Val Asp Ala Tyr Leu Phe Ser Leu Ile
        275                 280                 285

Asp Glu Asp Asp Lys Ser Ile Gln Pro Gly Asn Phe Glu Arg His Trp
    290                 295                 300

Gly Ile Phe Thr Tyr Asp Gly Leu Pro Lys Tyr Gln Leu Asn
305                 310                 315
```

<210> SEQ ID NO 27
<211> LENGTH: 320
<212> TYPE: PRT
<213> ORGANISM: Zea mays

<400> SEQUENCE: 27

Ile Gly Val Asn Trp Gly Thr Val Ser Asn His Arg Ala Pro Pro Gly
1               5                   10                  15

Val Val Val Asp Leu Met Arg Ala Asn Arg Ile Ser Lys Val Lys Leu
            20                  25                  30

Phe Asn Ala Asp Pro Gly Val Leu Arg Ala Leu Ala Gly Ser Gly Ile
        35                  40                  45

Gln Val Met Val Gly Val Thr Asn Asp Glu Leu Ala Ser Ile Ala Gly
    50                  55                  60

Ser Gln Ala Ala Ala Asp Asp Trp Val Ala Gln Asn Val Ser Arg Tyr
65                  70                  75                  80

Val Gly Arg Ser Gly Val Gly Ile Arg Tyr Ile Ala Val Gly Asn Glu
                85                  90                  95

Pro Phe Leu Thr Ser Tyr Gln Gly Gln Phe Gln Ser Tyr Ile Ile Pro
            100                 105                 110

Ala Met Thr Asn Ile Gln Gln Ser Leu Val Lys Ala Asn Leu Ala Ser
        115                 120                 125

Tyr Val Lys Leu Val Val Pro Cys Asn Ala Asp Ala Tyr Gln Ser Ala
    130                 135                 140

Ser Val Pro Ser Gln Gly Val Phe Arg Thr Glu Leu Thr Gln Leu Met
145                 150                 155                 160

Thr Gln Leu Ala Ala Phe Leu Ser Ser Ser Gly Ala Pro Phe Val Val
                165                 170                 175

Asn Ile Tyr Pro Phe Leu Ser Leu Tyr Gln Asn Ser Asp Phe Pro Gln
            180                 185                 190

Asp Tyr Ala Phe Phe Glu Gly Ser Thr His Pro Val Val Asp Gly Pro
        195                 200                 205

Asn Val Tyr Tyr Asp Ala Phe Asp Gly Asn Phe Asp Thr Leu Val Ser
    210                 215                 220

Ala Leu Ser Lys Ile Gly Tyr Gly Asn Leu Pro Ile Ala Ile Gly Glu
225                 230                 235                 240

Ile Gly Trp Pro Thr Glu Gly Ala Pro Ser Ala Asn Leu Thr Ala Ala
                245                 250                 255

Arg Ala Phe Asn Gln Gly Leu Ile Asn Arg Ile Thr Ser Asn Lys Gly
            260                 265                 270

Thr Pro Leu Arg Pro Gly Val Pro Pro Ala Asp Val Tyr Leu Phe Ser
        275                 280                 285

Leu Leu Asp Glu Glu Gly Lys Ser Ile Leu Pro Gly Asn Phe Glu Arg
    290                 295                 300

His Trp Gly Ile Phe Ser Phe Asp Gly Gln Ala Lys Tyr Pro Leu Asn
305                 310                 315                 320

<210> SEQ ID NO 28
<211> LENGTH: 316
<212> TYPE: PRT
<213> ORGANISM: Zea mays

<400> SEQUENCE: 28

Ile Gly Ile Cys His Gly Arg Val Gly Ser Asn Leu Pro Pro Ser
1               5                   10                  15

Ala Ala Ala Ala Leu Leu Lys Arg Asn Gly Ile Thr Lys Ala Arg Leu
            20                  25                  30

Phe Leu Pro Asp Pro Ala Val Leu Pro Ala Phe Ala Ala Ala Gly Ile
        35                  40                  45

Asp Leu Met Val Gly Val Pro Asn Glu Asn Leu Thr Phe Leu Ala Ala

```
            50                  55                  60
Ala Gly Pro Glu Gly Ala Ala Gln Trp Leu Arg Ser Ala Val Leu Ala
 65                  70                  75                  80

His Ala Pro Ala Glu Arg Val Arg Cys Leu Ala Val Gly Asn Glu Val
                 85                  90                  95

Leu Tyr Asn Asn Gln Phe Tyr Ala Pro His Leu Val Pro Ala Met Arg
                100                 105                 110

Asn Leu His Ala Ala Leu Ala Thr Leu Gly Leu Asp Gly Arg Val Lys
                115                 120                 125

Val Ser Ser Ala His Ala Ser Ser Val Leu Ala Ala Ser Tyr Pro Pro
                130                 135                 140

Ser Ala Gly Ala Phe Asp Ala Ala Ser Leu Pro Val Leu Arg Pro Met
145                 150                 155                 160

Leu Arg Phe Leu Ala Asp Thr Gly Ala Pro Phe Met Val Asn Ala Tyr
                165                 170                 175

Pro Phe Ile Ser His Val Asn Asp Pro Ala Asn Val Gln Leu Ala Tyr
                180                 185                 190

Ala Leu Phe Gly Ala Gly Ala Ala Pro Val Gln Asp Gly Ala Leu Val
                195                 200                 205

Tyr Thr Asn Leu Phe Asp Ala Thr Val Asp Ala Leu Val Ala Ala Leu
                210                 215                 220

Glu Lys Glu Gly Phe Asp Gly Val Pro Val Ala Val Thr Glu Thr Gly
225                 230                 235                 240

Trp Pro Thr Ala Gly His Pro Ala Ala Thr Pro Gln Asn Ala Ala Ala
                245                 250                 255

Tyr Asn Ala Lys Ile Val Glu Arg Ala Ala Arg Gly Val Gly Thr Pro
                260                 265                 270

Lys Arg Pro Gly Val Pro Val Glu Val Phe Leu Phe Asp Leu Tyr Asp
                275                 280                 285

Glu Asp Gly Lys Pro Gly Pro Glu Phe Glu Arg His Phe Gly Ile Phe
                290                 295                 300

Arg Ala Asp Gly Ser Lys Ala Tyr Asp Ile Asn Phe
305                 310                 315

<210> SEQ ID NO 29
<211> LENGTH: 307
<212> TYPE: PRT
<213> ORGANISM: Zea mays

<400> SEQUENCE: 29

Ile Gly Val Cys Tyr Gly Met Ser Ala Asn Asp Leu Pro Ala Ala Ser
  1               5                  10                  15

Thr Val Val Ser Met Tyr Lys Ala Asn Gly Ile Ser Ala Met Arg Leu
                 20                  25                  30

Tyr Ala Pro Asp Gln Gly Val Leu Gln Ala Val Gly Gly Thr Asp Ile
                 35                  40                  45

Ser Val Thr Val Gly Thr Pro Asn Asp Ala Leu Ser Asn Ile Ala Ala
                 50                  55                  60

Ser Pro Ala Ala Ala Ser Trp Val Arg Asn Asn Ile Gln Ala Tyr
 65                  70                  75                  80

Pro Ser Val Ser Phe Arg His Val Cys Val Gly Asn Glu Val Ala Gly
                 85                  90                  95

Gly Ala Ala Arg Asn Leu Ala Pro Ala Met Glu Asn Val His Ala Ala
                100                 105                 110
```

```
Leu Ala Ala Ala Gly Leu Gly His Ile Lys Val Thr Thr Ser Val Ser
            115                 120                 125

Gln Ala Ile Leu Gly Val Tyr Ser Pro Ser Ala Ala Gln Phe Thr
        130                 135                 140

Val Glu Ala Gln Gly Tyr Met Gly Pro Val Leu Lys Phe Leu Ala Arg
145                 150                 155                 160

Thr Gly Ser Pro Leu Met Ala Asn Ile Tyr Pro Tyr Leu Ala Trp Ala
                165                 170                 175

Tyr Asn Pro Ser Ala Met Asp Met Ser Tyr Ala Ile Phe Thr Ser Ser
            180                 185                 190

Gly Thr Val Val Gln Asp Gly Ala Tyr Gly Tyr Gln Asn Leu Phe Asp
        195                 200                 205

Thr Thr Val Asp Ala Phe Tyr Leu Ala Met Ala Ser Asn Gly Gly Gly
210                 215                 220

Ser Gly Val Pro Leu Val Val Ser Glu Thr Gly Trp Pro Ser Gly Gly
225                 230                 235                 240

Gly Val Gln Ala Thr Pro Ala Asn Ala Arg Val Tyr Asn Gln Tyr Leu
                245                 250                 255

Ile Asn His Val Gly Arg Gly Thr Pro Arg His Pro Gly Gly Ile Glu
            260                 265                 270

Thr Tyr Leu Phe Ser Met Phe Asn Glu Asn Gln Lys Glu Ser Gly Val
        275                 280                 285

Glu Gln Asn Trp Gly Leu Phe Tyr Pro Asn Met His His Val Tyr Pro
290                 295                 300

Ile Ser Phe
305

<210> SEQ ID NO 30
<211> LENGTH: 306
<212> TYPE: PRT
<213> ORGANISM: Zea mays

<400> SEQUENCE: 30

Ile Gly Val Ser Tyr Gly Met Ser Gly Asp Asn Leu Pro Pro Ala Ser
1               5                   10                  15

Thr Val Ile Gly Met Tyr Lys Asp Asn Gly Ile Pro Leu Met Arg Ile
            20                  25                  30

Tyr Ala Pro Asp Gln Ala Ala Leu Gln Ala Val Gly Gly Thr Gly Ile
        35                  40                  45

Arg Val Val Ala Gly Ala Pro Asn Asp Val Leu Ser Ser Leu Ala Ala
50                  55                  60

Ser Pro Ala Ala Ala Ser Trp Val Arg Asn Asn Ile Gln Ala Tyr
65                  70                  75                  80

Pro Lys Val Ala Phe Arg Cys Val Cys Val Gly Asn Glu Val Glu Gly
                85                  90                  95

Gly Ala Ala Gln Ser Leu Val Pro Ala Met Glu Asn Val Arg Ala Ala
            100                 105                 110

Leu Val Ala Ala Gly Leu Asp Gly Ile Lys Val Thr Thr Ser Val Ser
        115                 120                 125

Gln Ala Ile Leu Gly Gly Tyr Lys Pro Pro Ser Ala Ala Glu Phe Thr
    130                 135                 140

Asp Glu Ala Gln Gly Phe Met Gly Pro Val Leu Arg Phe Leu Ala Arg
145                 150                 155                 160

Thr Gly Ala Pro Leu Met Ala Ser Val Tyr Pro Tyr Phe Thr Tyr Ala
                165                 170                 175
```

```
Thr Asn Pro Ala Ala Met Asp Leu Ser Tyr Ala Leu Phe Thr Ala Pro
            180                 185                 190

Gly Thr Val Leu Gln Asp Gly Ala Tyr Glu Tyr Gln Asn Leu Phe Asp
        195                 200                 205

Ala Thr Val Asp Ser Phe Tyr Val Ala Met Ala Asn His Gly Gly Ser
    210                 215                 220

Gly Val Thr Leu Val Val Ser Glu Ser Gly Trp Pro Ser Ala Gly Gly
225                 230                 235                 240

Val Ala Ala Ser Pro Glu Asn Ala Ala Ile Tyr Asn Gln Asn Leu Ile
                245                 250                 255

Asn His Val Gly Arg Gly Thr Pro Arg His Pro Gly Ala Ile Glu Thr
            260                 265                 270

Ile Leu Phe Ser Met Phe Asn Glu Asn Leu Lys Gln Ser Gly Val Glu
        275                 280                 285

Gln Asn Trp Gly Leu Phe Tyr Pro Asn Met Gln Arg Val Tyr Pro Ile
    290                 295                 300

Lys Phe
305

<210> SEQ ID NO 31
<211> LENGTH: 309
<212> TYPE: PRT
<213> ORGANISM: Zea mays

<400> SEQUENCE: 31

Val Gly Val Cys Tyr Gly Thr Ser Gly Asp Asn Leu Pro Pro Ala Ser
1               5                   10                  15

Ala Val Val Gly Met Leu Arg Asp Asn Gly Phe Thr Val Val Arg Leu
                20                  25                  30

Tyr Trp Pro Asp Gly Asp Ala Leu Ala Ala Leu Gly Gly Ser Gly Ile
            35                  40                  45

Arg Val Val Val Gly Ala Pro Asn Glu Ala Leu Pro Ala Leu Ala Ser
    50                  55                  60

Gly Ala Ala Ala Ala Ala Trp Val Arg Asp Asn Val Gln Ala His
65                  70                  75                  80

Pro Ala Val Ala Phe Arg Tyr Val Val Gly Asn Glu Val Pro Leu
                85                  90                  95

Glu Gln Ala Pro Leu Leu Val Pro Ala Met Glu Asn Val His Ala Ala
            100                 105                 110

Leu Ala Ala Ala Gly Leu Gly His Val Lys Val Thr Thr Ala Val Ser
        115                 120                 125

Gln Gly Ala Ile Ala Val His Leu Pro Pro Ser Ala Gly Glu Phe Thr
    130                 135                 140

Glu Glu Ala Arg Ser Phe Met Gly Tyr Val Val Ala Phe Leu Ala Arg
145                 150                 155                 160

Thr Arg Ala Pro Leu Leu Ala Asn Leu Tyr Pro Tyr Phe Val Tyr Thr
                165                 170                 175

Leu Gly Leu Gly His Leu Gly Met Asp Phe Ala Leu Phe Thr Ala Pro
            180                 185                 190

Gly Thr Val Val Gln Asp Gly Glu Tyr Gly Tyr Gln Asn Leu Phe Asp
        195                 200                 205

Ala Thr Val Asp Ala Leu Tyr Ala Ala Val Gly Arg Leu Gly Val Ala
    210                 215                 220

Gly Gly Asp Gly Val Arg Val Val Val Ser Glu Thr Gly Trp Pro Thr
```

Ala Gly Gly Ala Ala Ala Ser Leu Glu Asn Ala Arg Thr Tyr Asn Gln
            245                 250                 255

Asn Leu Val Arg His Val Trp Lys Gly Thr Pro Arg Pro Arg Arg
            260                 265                 270

Val Glu Ala Tyr Val Phe Ala Met Phe Asn Glu Asp Lys Lys Asp Ala
            275                 280                 285

Gly Val Glu Gln Asn Trp Gly Leu Phe Tyr Pro Asn Met Glu Arg Val
            290                 295                 300

Tyr Pro Ile Thr Phe
305

<210> SEQ ID NO 32
<211> LENGTH: 309
<212> TYPE: PRT
<213> ORGANISM: Zea mays

<400> SEQUENCE: 32

Val Gly Val Cys Tyr Gly Thr Ser Gly Asp Asn Leu Pro Pro Ala Ser
1               5                   10                  15

Ala Val Val Gly Met Leu Arg Asp Asn Gly Phe Thr Val Val Arg Leu
            20                  25                  30

Tyr Trp Pro Asp Gly Asp Ala Leu Ala Ala Leu Gly Gly Ser Gly Ile
            35                  40                  45

Arg Val Val Gly Ala Pro Asn Glu Ala Leu Pro Ala Leu Ala Ser
        50                  55                  60

Gly Ala Ala Ala Ala Ala Trp Val Arg Asp Asn Val Gln Ala His
65                  70                  75                  80

Pro Ala Val Ala Phe Arg Tyr Val Val Gly Asn Glu Val Pro Leu
                85                  90                  95

Glu Gln Ala Pro Leu Leu Val Pro Ala Met Glu Asn Val His Ala Ala
            100                 105                 110

Leu Ala Ala Ala Gly Leu Gly His Val Lys Val Thr Thr Ala Val Ser
            115                 120                 125

Gln Gly Ala Ile Ala Val His Leu Pro Pro Ser Ala Gly Glu Phe Thr
        130                 135                 140

Glu Glu Ala Arg Ser Phe Met Gly Tyr Val Val Ala Phe Leu Ala Arg
145                 150                 155                 160

Thr Arg Ala Pro Leu Leu Ala Asn Leu Tyr Pro Tyr Phe Val Tyr Thr
                165                 170                 175

Leu Gly Leu Gly His Leu Gly Met Asp Phe Ala Leu Phe Thr Ala Pro
            180                 185                 190

Gly Thr Val Val Gln Asp Gly Glu Tyr Gly Tyr Gln Asn Leu Phe Asp
            195                 200                 205

Ala Thr Val Asp Ala Leu Tyr Ala Ala Val Gly Arg Leu Gly Val Ala
        210                 215                 220

Gly Gly Asp Gly Val Arg Val Val Ser Glu Thr Gly Trp Pro Thr
225                 230                 235                 240

Ala Gly Gly Ala Ala Ala Ser Leu Glu Asn Ala Arg Thr Tyr Asn Gln
                245                 250                 255

Asn Leu Val Arg His Val Trp Lys Gly Thr Pro Arg Pro Arg Arg
            260                 265                 270

Val Glu Ala Tyr Val Phe Ala Met Phe Asn Glu Asp Lys Lys Asp Ala
            275                 280                 285

```
Gly Val Glu Gln Asn Trp Gly Leu Phe Tyr Pro Asn Met Glu Arg Val
        290                 295                 300

Tyr Pro Ile Thr Phe
305

<210> SEQ ID NO 33
<211> LENGTH: 312
<212> TYPE: PRT
<213> ORGANISM: Zea mays

<400> SEQUENCE: 33

Ile Gly Val Asn Tyr Gly Met Val Ala Asn Asn Leu Pro Ala Pro Glu
  1               5                  10                  15

Gln Val Val Ser Met Tyr Lys Ala Lys Asn Ile Ser Tyr Val Arg Leu
             20                  25                  30

Phe His Pro Asp Thr Asp Ala Leu Asn Ala Leu Arg Gly Ser Gly Val
         35                  40                  45

Gly Val Val Leu Gly Thr Leu Asn Glu Asp Leu Pro Arg Leu Ala Ser
     50                  55                  60

Asp Pro Ser Phe Ala Ala Ser Trp Val Ala Thr Asn Val Gln Pro Phe
 65                  70                  75                  80

Ala Gly Ala Val Gln Phe Arg Tyr Ile Asn Ala Gly Asn Glu Val Ile
                 85                  90                  95

Pro Gly Asp Ala Ala Arg Val Leu Pro Ala Met Gln Asn Leu Glu
            100                 105                 110

Ser Ala Leu Arg Ser Ala Gly Val Thr Gly Val Pro Val Thr Thr Ala
        115                 120                 125

Val Ala Thr Ser Val Leu Gly Ala Ser Tyr Pro Pro Ser Gln Gly Ala
    130                 135                 140

Phe Ser Glu Ala Ala Ala Ser Val Met Ala Pro Ile Val Ser Tyr Leu
145                 150                 155                 160

Ser Ser Lys Gly Ala Pro Leu Leu Val Asn Val Tyr Pro Tyr Phe Ala
                165                 170                 175

Tyr Ser Ser Ser Gly Gly Gln Val Ala Leu Gly Tyr Ala Leu Leu Ser
            180                 185                 190

Ala Asp Ala Gly Ala Ala Ser Ser Val Thr Asp Ala Gly Val Val Tyr
        195                 200                 205

Thr Asn Met Phe Asp Ala Ile Val Asp Ala Thr His Ala Ala Val Glu
    210                 215                 220

Lys Ala Gly Val Gln Gly Leu Glu Leu Val Val Ser Glu Thr Gly Trp
225                 230                 235                 240

Pro Ser Ala Gly Gly Glu Gly Ala Thr Val Glu Asn Ala Ala Ala Tyr
                245                 250                 255

Asn Asn Asn Val Val Arg His Val Gly Gly Thr Pro Arg Arg Pro
            260                 265                 270

Gly Lys Ala Val Glu Thr Tyr Leu Phe Ala Met Phe Asn Glu Asn Gly
        275                 280                 285

Lys Ala Glu Gly Val Glu Gln His Phe Gly Leu Phe Gln Pro Asp Met
    290                 295                 300

Ser Glu Val Tyr His Val Asp Phe
305                 310

<210> SEQ ID NO 34
<211> LENGTH: 313
<212> TYPE: PRT
<213> ORGANISM: Zea mays
```

<400> SEQUENCE: 34

```
Ile Gly Val Asn Tyr Gly Met Ile Ala Asn Asn Leu Pro Ala Pro Glu
  1               5                  10                  15

Gln Val Val Ser Met Tyr Lys Ala Lys Asn Ile Ser Tyr Val Arg Leu
             20                  25                  30

Phe His Pro Asp Thr Thr Val Leu Asn Ala Leu Arg Gly Ser Gly Ile
         35                  40                  45

Gly Val Ile Leu Gly Thr Leu Asn Glu Asp Leu Pro Arg Leu Ala Ser
 50                  55                  60

Asp Pro Ser Phe Ala Ala Ser Trp Val Ala Thr Asn Val Gln Pro Phe
 65                  70                  75                  80

Ala Gly Ala Val Gln Phe Arg Tyr Ile Asn Ala Gly Asn Glu Val Ile
                 85                  90                  95

Pro Gly Asp Pro Ala Ala Gln Val Leu Pro Ala Met Lys Asn Leu Glu
            100                 105                 110

Ser Ala Leu Arg Ser Ala Gly Val Ala Gly Val Pro Val Thr Thr Ala
            115                 120                 125

Val Ala Thr Ser Val Leu Gly Ala Ser Tyr Pro Pro Ser Gln Gly Ala
130                 135                 140

Phe Ser Glu Ala Ala Thr Thr Val Met Ala Pro Leu Val Ser Tyr Leu
145                 150                 155                 160

Ser Ser Arg Gly Ala Pro Leu Leu Val Asn Val Tyr Pro Tyr Phe Ala
                165                 170                 175

Tyr Ser Gly Ser Gly Gly Gln Val Ala Leu Gly Tyr Ala Leu Leu Ser
            180                 185                 190

Gly Ala Gly Ala Gly Ala Ala Ser Thr Val Thr Asp Gly Gly Ala Val
            195                 200                 205

Tyr Thr Asn Met Phe Asp Ala Ile Val Asp Ala Thr His Ala Ala Val
210                 215                 220

Glu Lys Ala Gly Val Gln Gly Leu Glu Leu Val Val Ser Glu Thr Gly
225                 230                 235                 240

Trp Pro Ser Ala Gly Gly Glu Gly Ala Ser Val Glu Asn Ala Ala Ala
                245                 250                 255

Tyr Asn Asn Asn Val Val Arg His Val Asp Gly Gly Thr Pro Arg Arg
            260                 265                 270

Pro Gly Lys Ala Leu Glu Thr Tyr Leu Phe Ala Met Phe Asn Glu Asn
            275                 280                 285

Gly Lys Ala Glu Gly Val Glu Gln His Phe Gly Leu Phe Gln Pro Asp
            290                 295                 300

Met Ser Glu Val Tyr His Val Asp Phe
305                 310
```

<210> SEQ ID NO 35
<211> LENGTH: 316
<212> TYPE: PRT
<213> ORGANISM: Zea mays

<400> SEQUENCE: 35

```
Ile Gly Val Asn Tyr Gly Thr Ile Ala Ser Asn Leu Pro Ser Pro Asp
  1               5                  10                  15

Lys Val Ile Ala Leu Cys Lys Ala Lys Gly Ile Thr Asp Val Arg Leu
             20                  25                  30

Phe His Pro Asp Thr Ala Val Leu Ala Ala Leu Arg Gly Ser Gly Leu
         35                  40                  45
```

Gly Val Val Leu Gly Thr Leu Asn Glu Asp Leu Ala Arg Leu Ala Ser
 50                  55                  60

Asp Pro Ser Phe Ala Ala Ser Trp Val Gln Ala Tyr Val Arg Pro Phe
 65                  70                  75                  80

Ala Gly Ala Val Arg Phe Arg Tyr Val Ala Ala Gly Asn Glu Val Val
                 85                  90                  95

Pro Gly Asp Leu Ala Ser His Val Leu Pro Ala Met Gln Asn Leu Glu
            100                 105                 110

Ser Ala Leu Arg Ala Ala Gly Leu Gly Gly Val Arg Val Thr Thr Ala
        115                 120                 125

Val Ser Thr Ser Val Leu Gly Thr Ser Tyr Pro Pro Ser Gln Gly Ala
    130                 135                 140

Phe Ser Asp Ala Ala Leu Pro Ser Met Gly Pro Ile Ala Ser Phe Leu
145                 150                 155                 160

Ala Pro Arg Ser Thr Pro Leu Leu Val Asn Val Tyr Pro Tyr Phe Ala
                165                 170                 175

Tyr Ser Ala Asp Pro Ala Ser Val Ser Leu Asp Tyr Ala Leu Leu Arg
            180                 185                 190

Ser Asp Ser Gly Gly Gly Ala Val Val Ala Asp Gly Gly Ala Ser
        195                 200                 205

Tyr Gly Asn Met Phe Asp Ala Ile Val Asp Ala Val Tyr Ala Ala Leu
    210                 215                 220

Glu Arg Ala Gly Ala Arg Gly Leu Glu Leu Val Val Ser Glu Thr Gly
225                 230                 235                 240

Trp Pro Ser Gly Gly Gly Gly Ala Gly Ala Ser Val Gly Asn Ala Ser
                245                 250                 255

Ala Tyr Val Asn Asn Val Val Arg His Val Gly Ser Gly Arg Gly Thr
            260                 265                 270

Pro Arg Arg Pro Gly Lys Pro Val Glu Ala Phe Ile Phe Ala Met Phe
        275                 280                 285

Asn Glu Asn Gln Lys Pro Glu Gly Val Glu Gln His Phe Gly Met Phe
    290                 295                 300

Gln Pro Asp Met Thr Glu Val Tyr His Val Asp Phe
305                 310                 315

<210> SEQ ID NO 36
<211> LENGTH: 308
<212> TYPE: PRT
<213> ORGANISM: Zea mays

<400> SEQUENCE: 36

Ile Gly Val Cys Tyr Gly Val Leu Gly Ser Gly Leu Pro Ser Lys Ser
 1                   5                  10                  15

Asp Val Val Gln Leu Tyr Lys Ser Asn Gly Ile Ala Ser Met Arg Phe
                 20                  25                  30

Tyr Phe Ala Asp Gln Asp Leu Leu Thr Ala Leu Arg Gly Ser Gly Val
            35                  40                  45

Ala Leu Ala Leu Asp Val Gly Asn Gly Lys Val Gly Glu Leu Ala Ala
        50                  55                  60

Asp Pro Ala Ser Ala Ala Ser Trp Val Arg Asp Asn Val Gln Ala Tyr
 65                  70                  75                  80

Tyr Pro Asp Val Asp Ile Arg Tyr Val Val Gly Asn Glu Val Val
                 85                  90                  95

Pro Gly Ala Ala Ser Val Leu Gln Ala Met Arg Asn Val His Ala Ala

```
                 100                 105                 110
Leu Ala Ser Ala Gly Leu Ala Gly Ser Val Lys Val Ser Thr Ala Val
            115                 120                 125
Lys Met Asp Ala Val Asp Asp Ser Ser Pro Ser Arg Gly Val Phe
        130                 135                 140
Arg Asp Pro Ala Ala Met Ser Pro Ile Ala Gln Phe Leu Ala Ala Asn
145                 150                 155                 160
Gly Ala Pro Leu Leu Ala Asn Val Tyr Pro Tyr Phe Ala Tyr Gln Tyr
                165                 170                 175
Ser Asp Gly Gly Ile Asp Leu Asp Tyr Ala Leu Phe Gln Pro Ser Ser
            180                 185                 190
Thr Thr Val Thr Asp Pro Ala Asn Gly Leu Val Tyr Thr Asn Leu Phe
        195                 200                 205
Asp Ala Met Val Asp Ala Val Arg Ala Ala Leu Asp Lys Ala Gly Ala
    210                 215                 220
Gly Gly Val Asp Val Val Ser Glu Thr Gly Trp Pro Ser Ala Asp
225                 230                 235                 240
Gly Asn Gly Ala Thr Leu Asp Asn Ala Arg Thr Tyr Asn Gln Asn Leu
                245                 250                 255
Ile Asp His Ala Ser Lys Gly Thr Pro Arg Lys Pro Gly Pro Met Glu
            260                 265                 270
Val Tyr Val Phe Ala Met Phe Asn Glu Asp Gln Lys Asp Gly Asp Pro
        275                 280                 285
Thr Glu Lys Lys Phe Gly Leu Phe Asn Pro Asp Lys Thr Pro Val Tyr
    290                 295                 300
Pro Ile Asn Phe
305

<210> SEQ ID NO 37
<211> LENGTH: 308
<212> TYPE: PRT
<213> ORGANISM: Zea mays

<400> SEQUENCE: 37

Ile Gly Val Cys Tyr Gly Thr Leu Gly Asn Asn Leu Pro Ser Ser Ser
1               5                   10                  15
Asp Val Val Gln Leu Tyr Arg Ser Lys Gly Ile Lys Gly Met Arg Ile
            20                  25                  30
Tyr Ser Pro Asp Ala Lys Ala Leu Ala Ala Leu Arg Asn Ser Gly Ile
        35                  40                  45
Ala Leu Ile Leu Asp Thr Gly Asn Gly Gly Val Leu Gly Gln Leu
    50                  55                  60
Ala Arg Ser Ala Ser Phe Ala Asp Ser Trp Val Gln Ser Asn Val Arg
65                  70                  75                  80
Pro Tyr Tyr Pro Ala Val Gly Ile Lys Tyr Val Ala Val Gly Asn Glu
                85                  90                  95
Val Gln Gly Asp Asp Thr Arg Ser Leu Leu Pro Ala Met Arg Asn Leu
            100                 105                 110
Asp Ala Ala Leu Ala Arg Ala Gly Phe Pro Gly Ile Lys Cys Ser Thr
        115                 120                 125
Ser Val Arg Phe Asp Val Val Ala Asn Ser Phe Pro Pro Ser Ser Gly
    130                 135                 140
Ser Phe Ala Gln Gly Tyr Met Ala Asp Val Ala Arg Tyr Leu Ala Gly
145                 150                 155                 160
```

```
Thr Gly Ala Pro Leu Leu Ala Asn Val Tyr Pro Tyr Phe Ala Tyr Arg
            165                 170                 175

Asp Asn Pro Arg Asp Ile Ser Leu Gly Tyr Ala Thr Phe Gln Pro Gly
        180                 185                 190

Thr Thr Val Arg Asp Asn Gly Asn Gly Leu Asn Tyr Asn Asn Leu Phe
        195                 200                 205

Asp Ala Met Val Asp Ala Val Ala Ala Leu Glu Lys Ala Gly Ala
    210                 215                 220

Pro Asn Val Arg Val Val Ser Glu Ser Gly Trp Pro Ser Ala Gly
225                 230                 235                 240

Gly Phe Gly Ala Ser Val Asp Asn Ala Arg Lys Tyr Asn Gln Gly Leu
                245                 250                 255

Ile Asp His Val Gly Arg Gly Thr Pro Lys Arg Thr Gly Pro Leu Glu
            260                 265                 270

Thr Phe Val Phe Ala Met Phe Asn Glu Asn Gln Lys Gly Gly Asp Pro
        275                 280                 285

Thr Glu Lys Asn Phe Gly Leu Phe Tyr Gly Asn Lys Gln Pro Val Tyr
    290                 295                 300

Pro Ile Arg Phe
305

<210> SEQ ID NO 38
<211> LENGTH: 308
<212> TYPE: PRT
<213> ORGANISM: Zea mays

<400> SEQUENCE: 38

His Gly Val Cys Tyr Gly Met Thr Ala Asp Asp Leu Pro Pro Pro Ser
1               5                   10                  15

Glu Val Val Gln Leu Tyr Lys Ser Asn Gly Ile Ala Asn Met Arg Val
            20                  25                  30

Tyr Ser Pro Val Gly Glu Val Met Glu Ala Leu Arg Gly Ser Gly Ile
        35                  40                  45

Gly Leu Val Leu Gly Val Ala Asn Glu Asp Val Ala Ser Leu Ala Thr
    50                  55                  60

Cys Ala Pro Cys Ala Ala Ser Trp Val Glu Ala Asn Val Arg Pro Tyr
65              70                  75                  80

His Gln Asp Val Asn Ile Leu Tyr Ile Ala Val Gly Asn Glu Val Asp
                85                  90                  95

Ala Ala Ala Ala Ala Gln Thr Ile Leu Pro Ala Met Arg Ser Leu Gln
            100                 105                 110

Ala Ala Leu Ala Ala Ala Gly Leu Ala Gly Ser Ile Lys Val Ser Thr
        115                 120                 125

Cys Val Arg Leu Asp Val Val Thr Asp Thr Phe Pro Pro Ser Ser Gly
    130                 135                 140

Ala Phe Ala Gln Pro Tyr Met Val Asp Val Ala Arg Phe Leu Ala Ala
145                 150                 155                 160

Ala Gly Ala Pro Leu Leu Ala Asn Val Tyr Pro Tyr Phe Ala Tyr Arg
                165                 170                 175

Gly Ser Pro Gly Asp Val Gly Leu Gly Tyr Ala Leu Phe Gln Pro Gly
            180                 185                 190

Ala Ala Val Arg Asp Gly Gly Ser Gly Leu Val Tyr Thr Asn Leu Phe
        195                 200                 205

Asp Ala Met Val Asp Ser Val His Ala Ala Leu Glu Lys Ala Gly Ala
    210                 215                 220
```

```
Pro Asp Val Arg Val Val Ser Glu Ser Gly Trp Pro Ser Ala Gly
225                 230                 235                 240

Gly Ala Ala Ala Ser Val Gln Asn Ala Gln Ala Tyr Val Gln Asn Leu
                245                 250                 255

Val Asp His Val Ala Gln Gly Thr Pro Lys Arg Pro Gly Pro Leu Glu
            260                 265                 270

Thr Tyr Val Phe Ala Met Phe Asn Glu Asn Gln Lys Pro Gly Glu Pro
        275                 280                 285

Thr Glu Lys Asn Phe Gly Leu Phe Tyr Pro Ser Lys Ala Pro Val Tyr
    290                 295                 300

Pro Ile Val Phe
305

<210> SEQ ID NO 39
<211> LENGTH: 309
<212> TYPE: PRT
<213> ORGANISM: Zea mays

<400> SEQUENCE: 39

Ile Gly Val Cys Tyr Gly Met Asn Gly Asp Asp Leu Pro Ser Ala Ser
1               5                   10                  15

Asp Val Val Gln Leu Tyr Lys Asp Asn Gly Ile Asp Ser Met Arg Ile
            20                  25                  30

Tyr Ser Pro Asp Thr Asp Val Leu Gln Ala Leu Ser Gly Ser Gly Ile
        35                  40                  45

Ala Val Thr Val Gly Val Pro Asn Ala Asp Val Gly Gly Leu Ala Ser
    50                  55                  60

Arg Pro Ser Ala Ala Ala Trp Val Gln Ser Tyr Val Leu Ala Phe
65                  70                  75                  80

Pro Ala Val Gln Phe Arg Tyr Ile Ala Val Gly Asn Glu Val Val Ala
                85                  90                  95

Gly Gly Arg Val Leu Leu Pro Ala Met Arg Asn Leu Asp Arg Ala Leu
            100                 105                 110

Ser Ala Ala Gly Leu Ala Asp Asp Ile Lys Val Ser Thr Ala Val Ala
        115                 120                 125

Ile Asp Val Val Gly Ser Ser Phe Pro Pro Ser Ala Gly Thr Phe Ala
    130                 135                 140

Pro Ser Ala Gly Tyr Met Ala Arg Val Ala Arg Tyr Leu Gln Ser Thr
145                 150                 155                 160

Gly Ala Pro Leu Leu Ala Asn Leu Tyr Pro Tyr Tyr Ser Tyr Ile Ser
                165                 170                 175

Asp Pro Gly Ala Val Asp Ile Asn Tyr Ala Leu Leu Ala Met Pro Ala
            180                 185                 190

Gly Thr Val Val Gln Asp Gly Gly Tyr Ser Tyr Asp Ser Leu Phe
        195                 200                 205

Asp Ala Met Val Asp Cys Phe Tyr Ser Ala Leu Glu Asn Ala Gly Ala
    210                 215                 220

Gly Asn Val Thr Val Val Ser Glu Ser Gly Trp Pro Ser Ala Gly
225                 230                 235                 240

Ser Asp Ala Ala Asn Thr Thr Asn Ser Gln Ala Tyr Ser Gln Asn Leu
                245                 250                 255

Ile Asn His Val Gly Gln Gly Thr Pro Lys Arg Pro Gly Pro Ile Glu
            260                 265                 270

Ala Tyr Ile Phe Ala Thr Phe Asn Glu Asp Gln Lys Leu Gly Asp Asp
```

```
                       275                 280                 285
Glu Thr Arg Arg His Phe Gly Leu Phe Asn Lys Asp Arg Ser Leu Ala
    290                 295                 300
Tyr Pro Ile Asp Phe
305

<210> SEQ ID NO 40
<211> LENGTH: 304
<212> TYPE: PRT
<213> ORGANISM: Zea mays

<400> SEQUENCE: 40

Ile Gly Val Cys Tyr Gly Val Asn Gly Asp Asn Leu Pro Pro Ala Ser
  1               5                  10                  15

Asp Val Val Gln Leu Tyr Gln Ser Asn Gly Ile Asn Leu Met Arg Ile
                 20                  25                  30

Tyr Phe Pro Asp Ala Asn Ala Leu Asn Ala Leu Ser Gly Thr Ser Ile
             35                  40                  45

Gly Leu Ile Met Asp Val Pro Asn Thr Asp Leu Ala Ser Leu Ala Ser
         50                  55                  60

Asp Pro Ser Ala Ala Ala Trp Val Gln Ser Asn Val Gln Ala Phe
 65                  70                  75                  80

Pro Ser Val Ser Phe Arg Tyr Ile Ala Val Gly Asn Glu Ala Ser Gly
                 85                  90                  95

Gly Asp Thr Gly Ser Ile Leu Pro Ala Met Lys Asn Leu Asn Ala Ala
                100                 105                 110

Leu Ala Asn Ala Gly Leu Gly Gly Ser Ile Lys Val Ser Thr Ala Val
                115                 120                 125

Gln Ser Asp Val Thr Gln Gly Phe Pro Pro Ser Gln Gly Thr Phe Ser
            130                 135                 140

Gln Gly Tyr Met Ala Pro Ile Ala Gln Tyr Leu Gln Ser Thr Gly Ala
145                 150                 155                 160

Pro Leu Leu Cys Asn Val Tyr Pro Tyr Phe Ser Tyr Ile Gly Asn Pro
                165                 170                 175

Ala Gln Ile Asp Leu Ser Tyr Ala Leu Phe Thr Ser Pro Gly Thr Val
                180                 185                 190

Val Gln Asp Gly Ser Asn Ala Tyr Gln Asn Leu Phe Asp Ala Leu Val
            195                 200                 205

Asp Thr Phe Val Ser Ala Leu Gln Asn Ala Gly Ala Gly Asn Val Pro
        210                 215                 220

Val Val Val Ser Glu Ser Gly Trp Pro Ser Ala Gly Gly Asp Ala Ala
225                 230                 235                 240

Thr Ala Ala Asn Ala Gln Thr Tyr Asn Gln Asn Leu Ile Asn His Val
                245                 250                 255

Gly Gln Gly Thr Pro Lys Arg Pro Gly Pro Ile Glu Thr Tyr Ile Phe
            260                 265                 270

Ala Met Phe Asn Glu Asp Gln Lys Thr Gly Ala Glu Ser Glu Arg His
        275                 280                 285

Phe Gly Leu Phe Asn Pro Asp Lys Ser Pro Ala Tyr Pro Ile Asn Phe
    290                 295                 300

<210> SEQ ID NO 41
<211> LENGTH: 277
<212> TYPE: PRT
<213> ORGANISM: Zea mays
```

```
<400> SEQUENCE: 41

Met Arg Ile Tyr Ser Pro Asp Ala Thr Ile Leu Gln Ala Leu Arg Gly
1               5                   10                  15

Ser Gly Ile Asp Leu Ile Val Asp Glu Thr Asn Leu Asp Ser Leu Ile
            20                  25                  30

Ser Asp Ala Pro Gly Trp Val Gln Ala Asn Leu Gln Pro Tyr Lys Asp
        35                  40                  45

Asp Val Ser Phe Lys Tyr Ile Ala Val Gly Asn Glu Val Glu Gly Gly
    50                  55                  60

Asp Thr Gln Lys Ile Leu Pro Ala Met Gln Ser Leu Ser Asp Ala Leu
65                  70                  75                  80

Ser Ala Ala Gly Leu Gly Asn Ile Lys Val Ser Thr Ala Val Lys Met
                85                  90                  95

Ser Val Leu Ala Thr Pro Ser Pro Pro Ser Thr Gly Ala Phe Ala
                100                 105                 110

Asp Pro Ser Val Met Gly Pro Ile Val Arg Phe Leu Ala Gly Val Gly
            115                 120                 125

Ser Pro Leu Leu Ala Asn Ile Tyr Pro Tyr Phe Ala Tyr Arg Asp Ala
    130                 135                 140

Ala Gly Thr Ile Asp Leu Asn Tyr Ala Leu Phe Gln Pro Ser Thr Thr
145                 150                 155                 160

Val Val Thr Asp Gly Gly Leu Asp Tyr Thr Asn Leu Phe Asp Ala
                165                 170                 175

Met Ala Asp Ala Met Tyr Ser Ala Met Glu Lys Glu Gly Gly Ser Gly
            180                 185                 190

Val Pro Ile Val Val Ser Glu Ser Gly Trp Pro Ser Gly Gly Gly Gly
        195                 200                 205

Thr Gly Ala Glu Thr Val Asp Asn Ala Arg Thr Tyr Asn Gln Asn Leu
    210                 215                 220

Ile Asn His Val Gly Asn Gly Thr Pro Lys Arg Ser Gly Pro Leu Glu
225                 230                 235                 240

Thr Tyr Ile Phe Ala Met Phe Asn Glu Asp Lys Lys Gln Gly Asp Glu
                245                 250                 255

Thr Glu Lys His Phe Gly Leu Phe Asn Gly Pro Asp Gln Ser Pro Val
            260                 265                 270

Tyr Gln Ile Ser Phe
            275

<210> SEQ ID NO 42
<211> LENGTH: 323
<212> TYPE: PRT
<213> ORGANISM: Zea mays

<400> SEQUENCE: 42

Leu Gly Val Asn Tyr Gly Thr Leu Gly Asp Asn Leu Pro Pro Pro His
1               5                   10                  15

Arg Gly Met Glu Leu Ala Arg Ser Ala Gly Ala Val Ser Val Arg Phe
            20                  25                  30

Tyr Asp Ala Asn Ala Thr Leu Leu Ala Ala Ala Ala Ser Gly Leu
        35                  40                  45

Asp Phe Val Pro Ser Phe Pro Asn Glu Leu Ile Pro Ser Leu Ala Gly
    50                  55                  60

Ser Gln Arg Ala Ala Asp Ala Leu Val Ala Ala Thr Leu Leu Pro Phe
65                  70                  75                  80
```

```
Arg Gly Asn Pro Arg Leu Arg Tyr Leu Phe Val Gly Asn Glu Phe Leu
                85                  90                  95

Ser Asn Pro Thr Ala Lys Pro Asn Trp Ala Leu Ile Val Pro Ala Met
            100                 105                 110

Thr Asn Ala Ala Arg Ala Leu Arg Arg His Gly Leu Ala His Val Lys
        115                 120                 125

Val Ser Thr Thr Leu Ser Met Asn Asp Leu Gly Asn Thr Val Leu Pro
    130                 135                 140

Pro Ser Ala Gly Ala Phe Arg Pro Glu Ile Ala Glu Ala Val Met Gly
145                 150                 155                 160

Pro Met Leu Ala Phe Leu Gln Arg Thr Gly Ser Cys Leu Phe Leu Asp
                165                 170                 175

Ala Tyr Thr Tyr Phe Thr Trp Ser Ala Asn His Thr Ile Phe Pro Leu
            180                 185                 190

Pro Tyr Ala Leu Leu Glu Pro Ser Pro Gly Phe Ala Tyr His Asp Pro
        195                 200                 205

Gly Thr Gly Leu Ser Tyr Ala Asn Leu Leu Asp Gln Met Leu Asp Thr
    210                 215                 220

Ala Ala Ala Ala Met Cys Arg Leu Gly Tyr Cys Gly Val Gly Leu Ala
225                 230                 235                 240

Leu Ala Glu Thr Gly Trp Pro Thr Ala Gly Asp Leu Asp Gln Phe Gly
                245                 250                 255

Ala Asn Val Arg Asn Ala Ala Thr Tyr Asn Arg Asn Leu Ala Arg Arg
            260                 265                 270

Leu Ala Ser Gly Ala Gly Thr Pro Arg Arg Pro Gly Val Pro Val Pro
        275                 280                 285

Ala Met Val Phe Ala Leu Phe Asn Glu Asp Leu Lys Trp Gly Pro Asp
    290                 295                 300

Thr Glu Arg His Trp Gly Leu Phe Tyr Pro Asn Gly Ser Ala Val Tyr
305                 310                 315                 320

Glu Val Asp

<210> SEQ ID NO 43
<211> LENGTH: 323
<212> TYPE: PRT
<213> ORGANISM: Zea mays

<400> SEQUENCE: 43

Leu Gly Ile Asn Tyr Gly Thr Val Ala Asp Asp Leu Pro Ser Ala Ser
 1               5                  10                  15

Arg Ser Val Gln Leu Leu Arg Ala Ala Gly Ala Ser Ala Val Lys Ile
             20                  25                  30

Tyr Asp Ala Asn Ala Asp Ile Leu Arg Ala Leu Ala Gly Thr Gly Val
         35                  40                  45

Pro Val Ser Ile Met Val Pro Asn Ser Ala Ile Pro Ser Leu Ala Ser
     50                  55                  60

Ser Arg Ala Ala Ala Glu Ala Trp Val Ala Ala Asn Leu Ala Pro His
 65                  70                  75                  80

Ile Pro Ala Thr Arg Val Ala His Leu Leu Val Gly Asn Glu Val Leu
                 85                  90                  95

Ser Asn Arg Ala Ile Ala Ala Ser Thr Trp Arg Gly Val Val Pro Ala
            100                 105                 110

Met Ala Asn Leu Arg Arg Ala Leu Arg Ala Arg Gly Leu Arg Gly Val
        115                 120                 125
```

```
Lys Leu Gly Thr Thr Leu Ala Met Asp Ala Leu Ser Ala Ser Tyr Pro
130                 135                 140

Pro Ser Ala Gly Ala Phe Arg Gly Asp Ile Ala Glu Asp Val Val Leu
145                 150                 155                 160

Pro Leu Leu Arg Phe Leu Asn Ala Thr Arg Ser Tyr Tyr Phe Val Asp
                165                 170                 175

Ala Tyr Pro Tyr Phe Ala Trp Ala Gly Asn Arg Asp Ala Ile Ser Leu
            180                 185                 190

Asp Tyr Ala Leu Phe Gln Gly Ala Ala Gly Ser Arg Tyr Val Asp Pro
        195                 200                 205

Gly Asn Gly Leu Thr Tyr Thr Asn Leu Leu Asp Gln Met Leu Asp Ala
    210                 215                 220

Val Val Ala Ala Met Gly Arg Leu Gly Tyr Gly Asn Val Arg Leu Ala
225                 230                 235                 240

Val Ser Glu Thr Gly Trp Pro Ser Gly Gly Asp Ala Gly Glu Ala Gly
                245                 250                 255

Ala Asn Val Arg Asn Ala Ala Thr Tyr Asn Arg Asn Leu Ala Leu Arg
            260                 265                 270

Met Ser Asn Ser Pro Gly Thr Pro Ala Arg Pro Gly Ala Glu Val Pro
        275                 280                 285

Val Phe Leu Phe Ser Leu Tyr Asn Glu Asp Arg Lys Pro Gly Pro Gly
    290                 295                 300

Ser Glu Arg His Trp Gly Leu Tyr Tyr Pro Asn Gly Ser Met Val Tyr
305                 310                 315                 320

Glu Leu Asp

<210> SEQ ID NO 44
<211> LENGTH: 325
<212> TYPE: PRT
<213> ORGANISM: Zea mays

<400> SEQUENCE: 44

Leu Gly Val Asn Tyr Gly Arg Val Ala Asp Asp Ile Pro Ser Pro Trp
1               5                   10                  15

Arg Ser Val Glu Leu Leu Arg Ala Ala Gly Ala Gly Ser Val Lys Ile
                20                  25                  30

Tyr Asp Ala Asn Pro Gly Val Leu Arg Ala Leu Ala Gly Thr Arg Trp
            35                  40                  45

Pro Val Ser Ile Met Val Pro Asn Gln Ile Ile Pro Asp Leu Ala Ala
50                  55                  60

Ser Ala Ala Ala Asp Arg Trp Val Ala Glu Asn Leu Val Pro Tyr
65                  70                  75              80

Tyr Pro Ala Thr Arg Val Lys Phe Leu Leu Val Gly Asn Glu Ile Leu
            85                  90                  95

Ser Asp Leu Ser Ile Ala Asn Ser Thr Trp Pro His Leu Val Pro Ala
        100                 105                 110

Met Glu Asn Ile His Arg Ser Leu Arg Lys Arg Ser Ile Ser Ser Val
    115                 120                 125

Lys Ile Gly Thr Thr Leu Ala Met Asp Ala Leu Ala Asp Gly Ala Phe
130                 135                 140

Pro Arg Pro Pro Ser Ala Ala Ala Phe Arg Ala Asp Ile Ala Glu Ala
145                 150                 155                 160

Val Val Arg Pro Leu Leu His Phe Leu Asn Gly Thr Asn Ser Tyr Tyr
                165                 170                 175
```

```
Phe Val Asp Ala Tyr Pro Tyr Phe Val Trp Ala Asp Asn Asn Leu Thr
            180                 185                 190

Val Ser Leu Asp Tyr Ala Leu Phe Gln Gly Gly Arg Thr Arg Tyr Val
        195                 200                 205

Asp Pro Gly Thr Gly Leu Thr Tyr Thr Asn Leu Leu Asp Glu Met Leu
    210                 215                 220

Asp Ala Val Val Ile Ala Met Ala Lys Leu Gly Tyr Gly His Val Lys
225                 230                 235                 240

Leu Ala Ile Ala Glu Thr Gly Trp Pro Asn Gly Cys Asp Tyr Asn Gln
                245                 250                 255

Ile Gly Gly Asn Val His Asn Ala Ala Ile Tyr Asn Arg Asn Leu Ala
            260                 265                 270

Ala Arg Met Ala Lys Asn Pro Gly Thr Pro Val Arg Pro Gly Ala Lys
        275                 280                 285

Met Pro Val Phe Val Phe Ser Leu Tyr Asn Glu Asp Leu Lys Pro Gly
    290                 295                 300

Pro Gly Thr Glu Arg His Trp Gly Leu Tyr Tyr Ala Asn Gly Thr Ala
305                 310                 315                 320

Val Tyr Glu Ile Asp
                325

<210> SEQ ID NO 45
<211> LENGTH: 323
<212> TYPE: PRT
<213> ORGANISM: Zea mays

<400> SEQUENCE: 45

Val Gly Val Asn Tyr Gly Arg Val Ala Asn Asn Leu Pro Asn Pro Ala
1               5                   10                  15

Ala Val Val Gln Leu Leu Lys Gln Gln Gly Val Ala Gln Val Lys Leu
            20                  25                  30

Tyr Asp Ala Asp Pro Thr Val Leu Arg Ala Leu Ala Asn Thr Gly Ile
        35                  40                  45

Lys Val Val Ala Leu Pro Asn Glu Gln Val Ala Ala Ala Ala Ala Ser
    50                  55                  60

Arg Ala Ser Tyr Ala Leu Leu Trp Val Arg Arg Asn Val Ala Ala Tyr
65                  70                  75                  80

His Pro Ala Thr Gln Ile Gln Gly Ile Ala Val Gly Asn Glu Val Phe
                85                  90                  95

Ala Ser Ala Lys Asn Val Thr Ala Gln Leu Val Pro Ala Met Ala Asn
            100                 105                 110

Val His Ala Ala Leu Ala Arg Leu Gly Leu Asp Gly Ala Val Lys Val
        115                 120                 125

Ser Ser Pro Ile Ala Leu Thr Ala Leu Ala Ser Ser Tyr Pro Ser Ser
    130                 135                 140

Ala Gly Ala Phe Arg Glu Asp Leu Ala Gln Ala Val Met Lys Pro Met
145                 150                 155                 160

Leu Asp Phe Leu Ala Gln Thr Gly Ser Tyr Leu Met Val Asn Ala Tyr
                165                 170                 175

Pro Phe Phe Ala Tyr Ser Gly Asn Ala Gly Asp Ile Ser Leu Asp Tyr
            180                 185                 190

Ala Leu Phe Arg Pro Asn Ala Gly Val Leu Asp Ala Gly Asn Gly Leu
        195                 200                 205

Lys Tyr Tyr Ser Leu Leu Asp Ala Gln Leu Asp Ala Val Phe Ala Ala
    210                 215                 220
```

```
Val Ser Arg Leu Gly Glu Gly Tyr Asn Gly Val Arg Val Val Ser
225                 230                 235                 240

Glu Thr Gly Trp Pro Ser Lys Gly Asp Ala Asn Glu Ala Gly Ala Ser
                245                 250                 255

Ala Ala Asn Ala Ala Ala Tyr Asn Gly Asn Leu Ala Arg Arg Val Leu
                260                 265                 270

Ser Gly Asn Ala Gly Thr Pro Arg Arg Pro Asp Ala Asp Ile Asp Val
                275                 280                 285

Tyr Leu Phe Ala Leu Phe Asn Glu Asn Gln Lys Pro Gly Pro Thr Ser
290                 295                 300

Glu Arg Asn Tyr Gly Val Phe Tyr Pro Asn Gln Gln Lys Val Tyr Asp
305                 310                 315                 320

Val Glu Phe

<210> SEQ ID NO 46
<211> LENGTH: 356
<212> TYPE: PRT
<213> ORGANISM: Zea mays

<400> SEQUENCE: 46

Val Gly Val Ser Tyr Gly Arg Leu Gly Asn Asp Leu Pro Gly Thr Ala
1               5                   10                  15

Ser Val Val Lys Leu Leu Lys Lys Ser Gly Ile Thr Ser Val Arg Leu
                20                  25                  30

Tyr Asp Ala Asn Ser Lys Val Leu Lys Ala Leu Ala Asn Thr Gly Ile
                35                  40                  45

Thr Val Met Val Met Leu Pro Asn Asp Lys Leu Ala Ala Ala Ala Ala
        50                  55                  60

Asp Pro Ser Ser Ala Arg Arg Trp Val Arg Arg Asn Val Ala Ala Tyr
65                  70                  75                  80

Tyr Pro Ala Thr Gln Ile His Ala Val Ala Val Gly Asn Glu Val Phe
                85                  90                  95

Glu Glu Ala Lys Asn Leu Thr Gly Gln Leu Val Pro Ala Met Ser Asn
                100                 105                 110

Val His Asp Ala Leu Val Lys Leu Gly Leu Asp Gly Ala Val Lys Val
            115                 120                 125

Ser Thr Pro Ile Ala Phe Thr Ala Leu Gln Glu Ser Trp Pro Pro Ser
        130                 135                 140

Ala Gly Arg Phe Arg Asp Asp Ile Ala Arg Ser Val Met Lys Pro Met
145                 150                 155                 160

Ile Asp Phe Leu Glu Arg Thr Gly Ser Tyr Leu Thr Val Asn Ala Tyr
                165                 170                 175

Pro Phe Phe Ala Tyr Ala Glu Glu Pro Asp Lys Ile Ser Leu Asp Tyr
                180                 185                 190

Ala Leu Gly Asn Ser Asn Ala Thr Gly Val Arg Asp Pro Val Thr Gly
            195                 200                 205

Leu Val Tyr His Ser Leu Leu Asp Ala Gln Leu Asp Ala Thr Tyr Phe
        210                 215                 220

Ala Met Glu Lys Leu Gly Thr Ser Arg Ser Ser Ala Arg Gly Pro Lys
225                 230                 235                 240

Ser Val Ala Pro Ala Ala His Val Ser Glu Ser Gly Trp Pro Ser Gly
                245                 250                 255

Gly Lys Pro Lys Arg Gly Gly Arg Pro Arg Pro Arg Gly Gly
                260                 265                 270
```

```
Gly Arg Arg Leu Glu Leu Glu Gln Ala Gly Glu Ala Ala Ser Val
        275                 280                 285

Ala Asn Ala Gln Ala Tyr Asn Asn Tyr Leu Ile Lys Arg Val Leu Ser
290                 295                 300

Gly Asp Thr Gly Thr Pro Tyr His Pro Asp Ala Asp Met Asp Val Tyr
305                 310                 315                 320

Ile Phe Ser Leu Phe Asn Glu Asn Gln Lys Gly Asp Gly Ala Asp Asp
                325                 330                 335

Val Glu Gln His Phe Gly Leu Phe Tyr Pro Asn Arg Thr Lys Val Tyr
                340                 345                 350

Glu Phe Asp Phe
                355

<210> SEQ ID NO 47
<211> LENGTH: 354
<212> TYPE: PRT
<213> ORGANISM: Zea mays

<400> SEQUENCE: 47

Val Gly Val Asn Tyr Gly Arg Val Ala Asn Asp Leu Pro Asp Pro Ala
1               5                   10                  15

Ser Val Val Gln Leu Leu Lys Gln Ser Gly Ile Thr Met Val Arg Leu
            20                  25                  30

Tyr Asp Ala Asn Pro Lys Val Leu Thr Ser Leu Ala Asn Thr Gly Ile
        35                  40                  45

Lys Val Met Val Met Leu Pro Asn Glu Glu Leu Ala Ala Ala Ala Ser
    50                  55                  60

Asp Pro Ser Tyr Ala Leu Gln Trp Ala Arg Ala Asn Val Ala Ala Phe
65                  70                  75                  80

Tyr Pro Ala Thr His Ile His Cys Val Ala Val Gly Asn Glu Val Phe
                85                  90                  95

Asp Ser Arg Pro Asp Leu Asn Ser Asn Leu Val Pro Ala Met Ala Asn
            100                 105                 110

Val His Asp Ala Leu Ala Gln Leu Gly Leu Ala Asp Ala Val Lys Val
        115                 120                 125

Ser Thr Pro Val Ala Phe Ser Ala Val Gln Asp Ser Tyr Pro Pro Ser
    130                 135                 140

Ala Gly Arg Phe Arg Asp Asp Ile Ala Gln Ser Val Met Lys Pro Met
145                 150                 155                 160

Leu Gly Phe Leu Asp Arg Thr Gly Ser Tyr Leu Thr Ile Asn Ile Tyr
                165                 170                 175

Pro Tyr Leu Ala Tyr Ala Glu His Pro Asp Gln Ile Ser Leu Asp Tyr
            180                 185                 190

Ala Leu Gly Asn Pro Asn Pro Gly Val Arg Val Asp Asp Asp Asp Thr
        195                 200                 205

Gly Ser Ile Ala Leu Asp Asp Asn Gly Val Thr Tyr His Ser Leu
    210                 215                 220

Leu Asp Ala Gln Leu Asp Ala Thr Tyr Tyr Ala Met Asp Ala Met Gly
225                 230                 235                 240

Phe Thr Ser Leu Lys Ala His Val Gly Glu Thr Gly His Pro Ser Gly
                245                 250                 255

Gly Arg Pro Arg Pro Gly Arg Pro Pro Arg Gly Arg Arg His
            260                 265                 270

Leu Val Ala Gly Asp Asp Asp Gly Tyr Pro Val Ala Ser Ile Ala Asn
```

```
            275                 280                 285
Ala His Ala Tyr Val Asn Asn Val Ile Asn Arg Val Leu Ser Gly Asn
    290                 295                 300

Thr Gly Thr Pro His Arg Pro Asp Ala Asp Met Asp Val Tyr Ile Phe
305                 310                 315                 320

Ala Leu Phe Asn Glu Asn Gln Lys Gly Asp Gly Pro Asp Asp Ile Glu
                325                 330                 335

Gln Asn Phe Gly Leu Phe Tyr Pro Ser Glu Gln Lys Val Tyr Glu Phe
                340                 345                 350

Asp Phe

<210> SEQ ID NO 48
<211> LENGTH: 354
<212> TYPE: PRT
<213> ORGANISM: Zea mays

<400> SEQUENCE: 48

Val Gly Val Asn Tyr Gly Arg Val Ala Asn Asp Leu Pro Asp Pro Ala
1               5                   10                  15

Ser Val Val Gln Leu Leu Lys Gln Ser Gly Ile Thr Met Val Arg Leu
                20                  25                  30

Tyr Asp Ala Asn Pro Lys Val Leu Thr Ser Leu Ala Asn Thr Gly Ile
            35                  40                  45

Lys Val Met Val Met Leu Pro Asn Glu Glu Leu Ala Ala Ala Ala Ser
        50                  55                  60

Asp Pro Ser Tyr Ala Leu Gln Trp Ala Arg Ala Asn Val Ala Ala Phe
65                  70                  75                  80

Tyr Pro Ala Thr His Ile His Cys Val Ala Val Gly Asn Glu Val Phe
                85                  90                  95

Asp Ser Arg Pro Asp Leu Asn Ser Asn Leu Val Pro Ala Met Ala Asn
                100                 105                 110

Val His Asp Ala Leu Ala Gln Leu Gly Leu Ala Asp Ala Val Lys Val
            115                 120                 125

Ser Thr Pro Val Ala Phe Ser Ala Val Gln Asp Ser Tyr Pro Pro Ser
        130                 135                 140

Ala Gly Arg Phe Arg Asp Asp Ile Ala Gln Ser Val Met Lys Pro Met
145                 150                 155                 160

Leu Gly Phe Leu Asp Arg Thr Gly Ser Tyr Leu Thr Ile Asn Ile Tyr
                165                 170                 175

Pro Tyr Leu Ala Tyr Ala Glu His Pro Asp Gln Ile Ser Leu Asp Tyr
            180                 185                 190

Ala Leu Gly Asn Pro Asn Pro Gly Val Arg Val Asp Asp Asp Thr
        195                 200                 205

Gly Ser Ile Ala Leu Asp Asp Asn Gly Val Thr Tyr His Ser Leu
    210                 215                 220

Leu Asp Ala Gln Leu Asp Ala Thr Tyr Tyr Ala Met Asp Ala Met Gly
225                 230                 235                 240

Phe Thr Ser Leu Lys Ala His Val Gly Glu Thr Gly His Pro Ser Gly
                245                 250                 255

Gly Arg Pro Arg Pro Gly Arg Arg Pro Arg Gly Gly Arg Arg His
            260                 265                 270

Leu Val Ala Gly Asp Asp Asp Gly Tyr Pro Val Ala Ser Ile Ala Asn
        275                 280                 285

Ala His Ala Tyr Val Asn Asn Val Ile Asn Arg Val Leu Ser Gly Asn
```

```
            290                 295                 300
Thr Gly Thr Pro His Arg Pro Asp Ala Asp Met Asp Val Tyr Ile Phe
305                 310                 315                 320

Ala Leu Phe Asn Glu Asn Gln Lys Gly Asp Gly Pro Asp Asp Ile Glu
                325                 330                 335

Gln Asn Phe Gly Leu Phe Tyr Pro Ser Glu Gln Lys Val Tyr Glu Phe
                340                 345                 350

Asp Phe

<210> SEQ ID NO 49
<211> LENGTH: 343
<212> TYPE: PRT
<213> ORGANISM: Zea mays

<400> SEQUENCE: 49

Val Gly Val Asn Tyr Gly Met Val Ala Asn Asp Leu Pro Asn Pro Ala
1               5                   10                  15

Ser Val Val Gln Leu Leu Lys Gln Asn Gly Ile Thr Met Val Lys Ile
                20                  25                  30

Tyr Asp Ala Asn Ala Thr Val Leu Thr Ser Leu Ala Asn Thr Gly Ile
            35                  40                  45

Lys Ala Met Val Met Met Pro Asn Gln Asn Leu Ala His Ala Ala Arg
50                  55                  60

Asp Pro Val Tyr Ala Ala Gln Trp Val Gln Asp Asn Val Lys Lys Tyr
65                  70                  75                  80

Leu Pro Arg Thr Gln Ile Asn Ala Val Ala Val Gly Asn Glu Val Phe
                85                  90                  95

Asp Asp Pro Asn Val Asp Lys Met Thr Leu Val Pro Ala Met Lys Asn
            100                 105                 110

Val Gln Lys Ala Leu Ala Asp Leu Gly Leu Ala Asn Ala Val Lys Val
        115                 120                 125

Ser Thr Pro Ile Ala Phe Ser Ala Val Arg Asp Ser Phe Pro Pro Ser
130                 135                 140

Gly Ser Arg Phe Arg Asp Asp Ile Ala Gln Pro Val Met Lys Pro Met
145                 150                 155                 160

Leu Gln Leu Leu Gln Arg Thr Gly Ser Phe Leu Thr Val Asn Ile Tyr
                165                 170                 175

Pro Cys Leu Thr Gln Met Gln Gln Pro Asp Asp Ile Pro Leu Asp Tyr
            180                 185                 190

Ala Leu Gly Asn Ala Gln His Ala Val Leu Asp Gly Ser Asn Lys Tyr
        195                 200                 205

Tyr Ser Leu Leu Asp Ala Gln Leu Asp Ala Thr His Tyr Ala Met Glu
210                 215                 220

Ala Leu Gly Phe Gly Asn Val Glu Ala Val Leu Gly Glu Thr Gly Cys
225                 230                 235                 240

Pro Asn Lys Gly Lys Ile Gly Lys His Arg Pro Pro Arg Arg Gly Val
                245                 250                 255

Gly Ser Ser Arg Arg Arg Leu Leu Asp Asp Gly Gly Ser Glu Pro Glu
            260                 265                 270

Ala Ser Val Ala Asn Ala Arg Ala Tyr Asn Asn Tyr Val Ile Asn Arg
        275                 280                 285

Val Leu Ser Gly Asn Thr Gly Thr Pro His Arg Pro Arg Ala Asp Met
290                 295                 300

His Val Tyr Ile Phe Ala Leu Phe Asn Glu Asn Asn Lys Ser Ala Asp
```

```
                    305                 310                 315                 320
Pro Asp Asp Val Glu Asn Asn Phe Gly Leu Phe Tyr Pro Asn Met Gln
                325                 330                 335

Lys Ile Tyr Asp Phe Asn Phe
            340

<210> SEQ ID NO 50
<211> LENGTH: 319
<212> TYPE: PRT
<213> ORGANISM: Zea mays

<400> SEQUENCE: 50

Ile Gly Val Cys Tyr Gly Arg Asn Ala Asp Asp Leu Pro Ala Pro Asp
1               5                   10                  15

Lys Val Ala Gln Leu Ile Gln Gln Ser Ile Lys Tyr Val Arg Ile
            20                  25                  30

Tyr Asp Thr Asn Ile Asp Val Ile Lys Ala Phe Ala Asn Thr Gly Val
            35                  40                  45

Glu Leu Met Val Gly Val Pro Asn Ser Asp Leu Leu Ala Phe Ala Gln
        50                  55                  60

Tyr Gln Ser Asn Val Asp Thr Trp Leu Lys Asn Ser Ile Leu Pro Tyr
65                  70                  75                  80

Tyr Pro Asp Thr Met Ile Thr Tyr Ile Thr Val Gly Ala Glu Val Thr
                85                  90                  95

Glu Ser Pro Thr Asn Val Ser Ala Leu Val Val Pro Ala Met Arg Asn
            100                 105                 110

Val His Thr Ala Leu Lys Lys Ala Gly Leu His Lys Lys Ile Thr Ile
        115                 120                 125

Ser Ser Thr His Ser Leu Gly Ile Leu Ser Arg Ser Phe Pro Pro Ser
130                 135                 140

Ala Gly Ala Phe Asn Ser Ser Tyr Ala Tyr Phe Leu Lys Pro Met Leu
145                 150                 155                 160

Gln Phe Leu Val Glu Asn Gln Ala Pro Phe Met Val Asp Leu Tyr Pro
                165                 170                 175

Tyr Tyr Ala Tyr Gln Asn Ser Arg Ser Asn Val Ser Leu Asn Tyr Ala
            180                 185                 190

Leu Phe Ser Pro Glu Ser Gln Asp Val Ile Asp Pro Asn Thr Gly Leu
        195                 200                 205

Val Tyr Thr Asn Met Phe Asp Ala Gln Val Asp Ser Ile Phe Phe Ala
210                 215                 220

Leu Met Ala Leu Asn Phe Lys Thr Leu Lys Ile Met Ile Thr Glu Ser
225                 230                 235                 240

Gly Trp Pro Asn Lys Gly Ala Val Lys Glu Thr Gly Ala Thr Pro Asp
                245                 250                 255

Asn Ala Gln Thr Tyr Asn Thr Asn Leu Ile Arg His Val Val Asn Asp
            260                 265                 270

Ser Gly Thr Pro Ala Lys Pro Gly Glu Glu Ile Asp Val Tyr Ile Phe
        275                 280                 285

Ser Leu Phe Asn Glu Asn Arg Lys Pro Gly Ile Glu Ser Glu Arg Asn
290                 295                 300

Trp Gly Leu Phe Phe Pro Asp Lys Ser Ser Ile Tyr Ser Leu Asp
305                 310                 315

<210> SEQ ID NO 51
<211> LENGTH: 319
```

<212> TYPE: PRT
<213> ORGANISM: Zea mays

<400> SEQUENCE: 51

```
Ile Gly Val Cys Tyr Gly Arg Asn Ala Asp Asp Leu Pro Ala Pro Asp
1               5                   10                  15

Lys Val Ala Gln Leu Ile Gln Gln Ser Ile Lys Tyr Val Arg Ile
            20                  25                  30

Tyr Asp Thr Asn Ile Asp Val Ile Lys Ala Phe Ala Asn Thr Gly Val
            35                  40                  45

Glu Leu Met Val Gly Val Pro Asn Ser Asp Leu Leu Ala Phe Ala Gln
        50                  55                  60

Tyr Gln Ser Asn Val Asp Thr Trp Leu Lys Asn Ser Ile Leu Pro Tyr
65                  70                  75                  80

Tyr Pro Asp Thr Met Ile Thr Tyr Ile Thr Val Gly Ala Glu Val Thr
                85                  90                  95

Glu Ser Pro Thr Asn Val Ser Ala Leu Val Val Pro Ala Met Arg Asn
            100                 105                 110

Val His Thr Ala Leu Lys Lys Ala Gly Leu His Lys Lys Ile Thr Ile
        115                 120                 125

Ser Ser Thr His Ser Leu Gly Ile Leu Ser Arg Ser Phe Pro Pro Ser
130                 135                 140

Ala Gly Ala Phe Asn Ser Ser Tyr Ala Tyr Phe Leu Lys Pro Met Leu
145                 150                 155                 160

Gln Phe Leu Val Glu Asn Gln Ala Pro Phe Met Val Asp Leu Tyr Pro
                165                 170                 175

Tyr Tyr Ala Tyr Gln Asn Ser Arg Ser Asn Val Ser Leu Asn Tyr Ala
            180                 185                 190

Leu Phe Ser Pro Glu Ser Gln Asp Val Ile Asp Pro Asn Thr Gly Leu
        195                 200                 205

Val Tyr Thr Asn Met Phe Asp Ala Gln Val Asp Ser Ile Phe Phe Ala
210                 215                 220

Leu Met Ala Leu Asn Phe Lys Thr Leu Lys Ile Met Ile Thr Glu Ser
225                 230                 235                 240

Gly Trp Pro Asn Lys Gly Ala Val Lys Glu Thr Gly Ala Thr Pro Asp
                245                 250                 255

Asn Ala Gln Thr Tyr Asn Thr Asn Leu Ile Arg His Val Val Asn Asp
            260                 265                 270

Ser Gly Thr Pro Ala Lys Pro Gly Glu Glu Ile Asp Val Tyr Ile Phe
        275                 280                 285

Ser Leu Phe Asn Glu Asn Arg Lys Pro Gly Ile Glu Ser Glu Arg Asn
290                 295                 300

Trp Gly Leu Phe Phe Pro Asp Lys Ser Ser Ile Tyr Ser Leu Asp
305                 310                 315
```

<210> SEQ ID NO 52
<211> LENGTH: 314
<212> TYPE: PRT
<213> ORGANISM: Zea mays

<400> SEQUENCE: 52

```
Met Ala Gly Ile Asn Tyr Gly Arg Ile Ala Asp Asn Leu Pro Pro Pro
1               5                   10                  15

Glu Val Val Val Arg Leu Leu Lys Leu Ala Arg Ile Arg Asn Val Lys
            20                  25                  30
```

Ile Tyr Asp Ala Glu His Lys Val Leu Asp Ala Phe Arg Gly Thr Gly
            35                  40                  45

Leu Asn Leu Val Val Ala Ile Pro Asn Glu Phe Leu Lys Asp Met Ala
 50                  55                  60

Ala Asn Pro Ala Lys Ala Met Asp Trp Leu Thr Glu Asn Val Gln Pro
65                  70                  75                  80

Tyr Tyr Pro Ser Thr Arg Ile Val Gly Ile Thr Val Gly Asn Glu Val
                85                  90                  95

Leu Gly Gly Gln Asp Ala Gly Leu Gln Ala Leu Val Gly Ala Val
            100                 105                 110

Leu Asn Val His Asp Ala Leu Lys Met Leu Arg Leu Asp Ala Lys Ile
            115                 120                 125

Glu Leu Ser Thr Pro His Ser Glu Ala Val Phe Ala Asn Ser Tyr Pro
130                 135                 140

Pro Ser Ala Cys Val Phe Arg Asn Asp Leu Met Val Tyr Leu Arg Pro
145                 150                 155                 160

Leu Leu Asp Phe Phe Ser Lys Thr Gly Ala Pro Phe Tyr Val Asn Ala
                165                 170                 175

Tyr Pro Phe Leu Ala Tyr Met Ser Asp Pro Ser His Ile Asp Ile Asn
            180                 185                 190

Tyr Ala Leu Phe Lys Pro Asn Ala Gly Ile Val Asp Pro Lys Thr Gly
            195                 200                 205

Leu His Tyr Asn Asn Met Phe Asp Ala Gln Val Asp Ala Ala Tyr Phe
            210                 215                 220

Ala Leu Glu Ala Ala Gly Tyr Ser Gly Met Glu Val Arg Val Ala Glu
225                 230                 235                 240

Thr Gly Trp Ala Ser Ala Gly Asp Ala Thr Glu Ala Gly Ala Asn Met
                245                 250                 255

Glu Asn Ala Ile Thr Tyr Asp Arg Asn Leu Arg Lys Arg Leu Phe Leu
            260                 265                 270

Arg Lys Gly Thr Pro Tyr Arg Pro Asp Arg Val Ala Lys Ala Tyr Ile
            275                 280                 285

Phe Ala Leu Phe Asn Glu Asp Leu Lys Pro Gly Pro Thr Ser Glu Arg
290                 295                 300

His Tyr Gly Leu Phe Lys Pro Asp Gly Ser
305                 310

<210> SEQ ID NO 53
<211> LENGTH: 312
<212> TYPE: PRT
<213> ORGANISM: Zea mays

<400> SEQUENCE: 53

Gly Ile Asn Tyr Gly Arg Ile Ala Asp Asn Leu Pro Pro Glu Val
 1               5                  10                  15

Val Val Arg Leu Leu Lys Leu Ala Arg Ile Arg Asn Val Lys Ile Tyr
                20                  25                  30

Asp Ala Glu His Lys Val Leu Asp Ala Phe Arg Gly Thr Gly Leu Asn
            35                  40                  45

Leu Val Val Ala Ile Pro Asn Glu Phe Leu Lys Asp Met Ala Ala Asn
 50                  55                  60

Pro Ala Lys Ala Met Asp Trp Leu Thr Glu Asn Val Gln Pro Tyr Tyr
65                  70                  75                  80

Pro Ser Thr Arg Ile Val Gly Ile Thr Val Gly Asn Glu Val Leu Gly
                85                  90                  95

Gly Gln Asp Ala Gly Leu Ala Gln Ala Leu Val Gly Ala Val Leu Asn
            100                 105                 110

Val His Asp Ala Leu Lys Met Leu Arg Leu Asp Ala Lys Ile Glu Leu
            115                 120                 125

Ser Thr Pro His Ser Glu Ala Val Phe Ala Asn Ser Tyr Pro Pro Ser
            130                 135                 140

Ala Cys Val Phe Arg Asn Asp Leu Met Val Tyr Leu Arg Pro Leu Leu
145                 150                 155                 160

Asp Phe Phe Ser Lys Thr Gly Ala Pro Phe Tyr Val Asn Ala Tyr Pro
                    165                 170                 175

Phe Leu Ala Tyr Met Ser Asp Pro Ser His Ile Asp Ile Asn Tyr Ala
            180                 185                 190

Leu Phe Lys Pro Asn Ala Gly Ile Val Asp Pro Lys Thr Gly Leu His
            195                 200                 205

Tyr Asn Asn Met Phe Asp Ala Gln Val Asp Ala Ala Tyr Phe Ala Leu
            210                 215                 220

Glu Ala Ala Gly Tyr Ser Gly Met Glu Val Arg Val Ala Glu Thr Gly
225                 230                 235                 240

Trp Ala Ser Ala Gly Asp Ala Thr Glu Ala Gly Ala Asn Met Glu Asn
                    245                 250                 255

Ala Ile Thr Tyr Asp Arg Asn Leu Arg Lys Arg Leu Phe Leu Arg Lys
            260                 265                 270

Gly Thr Pro Tyr Arg Pro Asp Arg Val Ala Lys Ala Tyr Ile Phe Ala
            275                 280                 285

Leu Phe Asn Glu Asp Leu Lys Pro Gly Pro Thr Ser Glu Arg His Tyr
            290                 295                 300

Gly Leu Phe Lys Pro Asp Gly Ser
305                 310

<210> SEQ ID NO 54
<211> LENGTH: 317
<212> TYPE: PRT
<213> ORGANISM: Zea mays

<400> SEQUENCE: 54

Gly Val Asn Tyr Gly Arg Ile Ala Asn Asn Ile Pro Ser Pro Asp Lys
1               5                   10                  15

Val Val Glu Leu Leu Arg Arg Ala Lys Ile Arg Asn Val Lys Ile Tyr
            20                  25                  30

Asp Ser Asp His Ser Val Leu Asp Ala Phe Lys Gly Ser Gly Ile Asn
            35                  40                  45

Leu Val Ile Ala Ile Pro Asn Glu Leu Val Lys Asp Met Ala Ala Asn
50                  55                  60

Thr Ser Arg Ser Met Asp Trp Leu Asn Gln Asn Val Gln Pro Tyr Leu
65              70                  75                  80

Pro Gln Thr Arg Ile Val Gly Ile Thr Val Gly Asn Glu Val Leu Gly
                    85                  90                  95

Gly Gln Asp Gln Ser Leu Tyr Gln Pro Leu Val Asp Ala Val Lys Asn
            100                 105                 110

Val Tyr Asp Gly Leu Lys Arg Leu His Leu Glu Arg Lys Ile Glu Leu
            115                 120                 125

Phe Thr Pro His Ser Glu Ala Val Phe Ala Thr Ser Tyr Pro Pro Ser
            130                 135                 140

Ala Cys Val Phe Lys Glu Glu Leu Met Pro Tyr Met Lys Pro Leu Leu

```
                145                 150                 155                 160
        Asp Phe Phe Ala Met Ile Gly Ser Pro Phe Tyr Val Asn Ala Tyr Pro
                            165                 170                 175

Phe Leu Ala Tyr Ile Ser Asp Pro Glu His Ile Asp Ile Asn Tyr Ala
                            180                 185                 190

Leu Phe Lys Pro Asn Lys Gly Ile Ile Asp Pro Asn Asn Ser Leu His
                            195                 200                 205

Tyr Asp Asn Met Phe Asp Ala Gln Val Asp Ala Ala Tyr Ala Ala Leu
                            210                 215                 220

His Ala Ala Gly Tyr Asp Asn Met Glu Val Arg Val Ala Glu Thr Gly
        225                 230                 235                 240

Trp Ala Ser Ser Gly Asp Gln Asn Glu Ala Gly Ala Ser Ser Glu Asn
                            245                 250                 255

Ala Arg Thr Tyr Asn Phe Asn Leu Arg Lys Arg Leu Phe Leu Arg Thr
                            260                 265                 270

Gly Thr Pro Leu Lys Pro Lys Arg Pro Val Lys Ala Tyr Ile Phe Ala
                            275                 280                 285

Leu Phe Asn Glu Asn Gln Lys Pro Gly Ala Gly Ser Glu Arg His Tyr
                            290                 295                 300

Gly Leu Phe Leu Pro Asp Gly Arg Ile Ser Tyr Asp Ile
        305                 310                 315

<210> SEQ ID NO 55
<211> LENGTH: 317
<212> TYPE: PRT
<213> ORGANISM: Zea mays

<400> SEQUENCE: 55

Phe Gly Ile Asn Tyr Gly Gln Ile Ala Asn Asn Leu Pro Gln Pro Thr
        1               5                   10                  15

Gln Val Ser Gly Leu Leu Gln Ser Leu Asn Val Asn Arg Val Lys Leu
                        20                  25                  30

Tyr Asp Ala Asp Pro Ile Val Leu Thr Ala Phe Ala Gly Thr Gly Val
                        35                  40                  45

Glu Phe Ile Ile Gly Asn Asp Asp Leu Tyr Asn Leu Thr Asp Ala Arg
                50                  55                  60

Lys Ala Arg Ala Trp Val Ala Gln His Val Gln Pro Phe Leu Pro Ser
        65                  70                  75                  80

Thr Arg Ile Thr Cys Ile Thr Val Gly Asn Glu Val Leu Ser Gly Lys
                        85                  90                  95

Asp Thr Thr Ala Met Gln Ser Leu Leu Pro Ala Met Gln Thr Val Tyr
                        100                 105                 110

Gln Ala Val Val Ala Leu Gly Leu Gly Gly Val Asn Val Ser Thr
                        115                 120                 125

Ala His Ser Val Asn Ile Leu Ala Ser Ser Tyr Pro Pro Ser Ser Gly
                130                 135                 140

Ala Phe Arg Glu Glu Leu Gly Gln Tyr Ile Gln Pro Ile Leu Asn Phe
        145                 150                 155                 160

His Ala Glu Val Gly Ser Pro Phe Leu Ile Asn Ala Tyr Pro Phe Phe
                            165                 170                 175

Ala Tyr Lys Ala Ser Pro Gly Ser Val Ser Leu Pro Tyr Val Leu Phe
                            180                 185                 190

Glu Pro Asn Pro Gly Val Val Asp Pro Asn Thr Asn Leu Thr Tyr Asp
                            195                 200                 205
```

Asn Met Leu Tyr Ala Gln Ile Asp Ala Val Tyr Ala Ala Met Glu Ala
    210                 215                 220

Met Gly His Ser Asp Leu Thr Val Arg Ile Ser Glu Thr Gly Trp Pro
225                 230                 235                 240

Ser Arg Gly Asp Glu Asp Glu Val Gly Ala Thr Val Ala Asn Ala Ala
                245                 250                 255

Ala Tyr Asn Gly Asn Leu Met Lys Arg Ile Ala Met Gly Gln Gly Thr
            260                 265                 270

Pro Leu Lys Pro His Val Pro Val Asp Val Phe Val Phe Ala Leu Phe
                275                 280                 285

Asn Glu Asp Met Lys Pro Gly Ala Thr Ser Glu Arg Asn Tyr Gly Leu
290                 295                 300

Phe Tyr Pro Asn Gly Thr Pro Val Tyr Ser Leu Gly Phe
305                 310                 315

<210> SEQ ID NO 56
<211> LENGTH: 318
<212> TYPE: PRT
<213> ORGANISM: Zea mays

<400> SEQUENCE: 56

Phe Gly Ile Asn Tyr Gly Gln Ile Ala Asn Asn Leu Pro Asp Pro Thr
1               5                   10                  15

Gln Val Thr Leu Leu Arg Ser Met Asn Val Asn Lys Val Lys Leu
            20                  25                  30

Tyr Asp Ala Asp Pro Arg Val Leu Thr Ala Phe Ala Asn Thr Gly Val
            35                  40                  45

Glu Phe Ile Ile Ala Val Gly Asn Glu Asn Leu Gln Thr Met Ala Gly
    50                  55                  60

Ser Pro Ala Ala Ala Arg Gln Trp Val Ala Ala Asn Val Arg Pro Tyr
65              70                  75                  80

Ile Pro Ala Thr Arg Ile Thr Cys Val Thr Val Gly Asn Glu Val Phe
                85                  90                  95

Ser Gly Asn Asp Thr Ala Thr Met Ala Ser Leu Leu Pro Ala Met Lys
            100                 105                 110

Ala Val His Ala Ala Leu Ala Asp Leu Gly Leu Gly Gly Gln Ala Thr
            115                 120                 125

Val Ser Ser Ala His Ser Val Asn Val Leu Ala Ala Ser Phe Pro Pro
130                 135                 140

Ser Ser Gly Ala Phe Arg Glu Asp Leu Ala Glu Tyr Met Lys Pro Ile
145                 150                 155                 160

Leu Asp Phe His Ala Gln Thr Gly Ser Pro Phe Leu Ile Asn Ala Tyr
                165                 170                 175

Pro Phe Phe Ala Tyr Lys Ala Ser Pro Gly Ser Val Ser Leu Pro Tyr
            180                 185                 190

Val Leu Phe Glu Pro Asn Pro Gly Val Arg Asp Pro Ser Thr Gly Leu
            195                 200                 205

Ser Tyr Asp Asn Met Leu Tyr Ala Gln Ile Asp Ala Val Tyr Ala Ala
    210                 215                 220

Met Lys Ala Met Gly His Thr Asp Val Gly Val Arg Ile Ser Glu Thr
225                 230                 235                 240

Gly Trp Pro Ser Arg Gly Asp Glu Asp Glu Thr Gly Ala Thr Val Gln
                245                 250                 255

Asn Ala Ala Ala Tyr Asn Gly Asn Leu Met Gln Arg Val Ala Met Ser
            260                 265                 270

Gln Gly Thr Pro Leu Lys Pro Asn Val Pro Val Asp Val Tyr Val Phe
         275                 280                 285

Ala Leu Phe Asn Glu Asn Met Lys Pro Gly Pro Thr Ser Glu Arg Asn
    290                 295                 300

Tyr Gly Leu Phe Tyr Pro Asn Gly Ser Pro Val Tyr Ala Leu
305                 310                 315

<210> SEQ ID NO 57
<211> LENGTH: 324
<212> TYPE: PRT
<213> ORGANISM: Zea mays

<400> SEQUENCE: 57

Phe Gly Ile Asn Tyr Gly Gln Ile Ala Asn Asp Leu Pro Asp Pro Ala
1               5                   10                  15

Gln Val Ala Thr Leu Leu Gln Ser Met Gly Val Asn Lys Val Lys Leu
            20                  25                  30

Tyr Asp Ala Asp Pro Arg Val Leu Thr Ala Phe Ala Asn Thr Gly Val
        35                  40                  45

Gly Phe Thr Ile Ala Val Gly Asn Glu Asp Leu Gln Ala Met Ala Ala
    50                  55                  60

Ser Pro Asp Ala Ala Arg Arg Trp Val Ala Ala Asn Val Gln Pro Tyr
65                  70                  75                  80

Val Pro Ala Thr Arg Ile Thr Cys Val Thr Val Gly Asn Glu Val Leu
                85                  90                  95

Ser Gly Asn Asp Thr Ala Ala Met Ala Ser Leu Leu Pro Ala Met Arg
            100                 105                 110

Ala Val His Ala Ala Leu Gly Asp Ala Gly Leu Gly Gln Pro Val Ala
        115                 120                 125

Val Ser Ser Ala His Ser Val Asp Val Leu Ala Thr Ser Phe Pro Pro
130                 135                 140

Ser Ser Gly Ala Phe Arg Glu Asp Leu Ala Gly Tyr Val Arg Pro Ile
145                 150                 155                 160

Leu Asp Phe His Ala Gln Thr Gly Ser Pro Phe Leu Val Asn Ala Tyr
                165                 170                 175

Pro Phe Phe Ser Tyr Lys Ala Ser Pro Gly Pro Gly Pro Gly Gly Val
            180                 185                 190

Ser Leu Pro Tyr Ala Leu Phe Gln Pro Asn Pro Gly Val Arg Asp Pro
        195                 200                 205

Gly Thr Gly Leu Thr Tyr Asp Asn Met Leu Tyr Ala Gln Ile Asp Ala
    210                 215                 220

Val Tyr Ala Ala Met Gln Ala Gly Gly Arg Ala Asp Val Gly Val
225                 230                 235                 240

Thr Val Ser Glu Thr Gly Trp Pro Ser Arg Gly Asp Asp Glu Pro
                245                 250                 255

Gly Ala Thr Ala Gln Asn Ala Ala Tyr Asn Gly Asn Leu Met Arg
            260                 265                 270

Arg Val Ala Ala Gly Gln Gly Thr Pro Leu Arg Pro Ala Val Pro Val
        275                 280                 285

Asp Val Tyr Val Phe Ala Leu Phe Asn Glu Asp Leu Lys Pro Gly Pro
    290                 295                 300

Thr Ser Glu Arg Asn Tyr Gly Leu Leu Tyr Pro Asp Gly Ser Pro Val
305                 310                 315                 320

Tyr Ala Leu Asp

<210> SEQ ID NO 58
<211> LENGTH: 300
<212> TYPE: PRT
<213> ORGANISM: Zea mays

<400> SEQUENCE: 58

Met Gly Val Asn Lys Val Lys Leu Tyr Asp Ala Asp Pro Arg Val Leu
1               5                   10                  15

Thr Ala Phe Ala Asn Thr Gly Val Gly Phe Thr Ile Ala Val Gly Asn
            20                  25                  30

Glu Asp Leu Gln Ala Met Ala Ala Ser Pro Asp Ala Ala Arg Arg Trp
        35                  40                  45

Val Ala Ala Asn Val Gln Pro Tyr Val Pro Ala Thr Arg Ile Thr Cys
    50                  55                  60

Val Thr Val Gly Asn Glu Val Leu Ser Gly Asn Asp Thr Ala Ala Met
65                  70                  75                  80

Ala Ser Leu Leu Pro Ala Met Arg Ala Val His Ala Ala Leu Gly Asp
                85                  90                  95

Ala Gly Leu Gly Gln Pro Val Ala Val Ser Ser Ala His Ser Val Asp
            100                 105                 110

Val Leu Ala Thr Ser Phe Pro Pro Ser Ser Gly Ala Phe Arg Glu Asp
        115                 120                 125

Leu Ala Gly Tyr Val Arg Pro Ile Leu Asp Phe His Ala Gln Thr Gly
    130                 135                 140

Ser Pro Phe Leu Val Asn Ala Tyr Pro Phe Phe Ser Tyr Lys Ala Ser
145                 150                 155                 160

Pro Gly Pro Gly Pro Gly Val Ser Leu Pro Tyr Ala Leu Phe Gln
                165                 170                 175

Pro Asn Pro Gly Val Arg Asp Pro Gly Thr Gly Leu Thr Tyr Asp Asn
            180                 185                 190

Met Leu Tyr Ala Gln Ile Asp Ala Val Tyr Ala Ala Met Gln Ala Ala
        195                 200                 205

Gly Gly Arg Ala Asp Val Gly Val Thr Val Ser Glu Thr Gly Trp Pro
    210                 215                 220

Ser Arg Gly Asp Asp Glu Pro Gly Ala Thr Ala Gln Asn Ala Ala
225                 230                 235                 240

Ala Tyr Asn Gly Asn Leu Met Arg Arg Val Ala Ala Gly Gln Gly Thr
                245                 250                 255

Pro Leu Arg Pro Ala Val Pro Val Asp Val Tyr Val Phe Ala Leu Phe
            260                 265                 270

Asn Glu Asp Leu Lys Pro Gly Pro Thr Ser Glu Arg Asn Tyr Gly Leu
        275                 280                 285

Leu Tyr Pro Asp Gly Ser Pro Val Tyr Ala Leu Asp
    290                 295                 300

<210> SEQ ID NO 59
<211> LENGTH: 318
<212> TYPE: PRT
<213> ORGANISM: Zea mays

<400> SEQUENCE: 59

Met Gly Ile Asn Tyr Gly Gln Ile Ala Asp Asn Leu Pro Ser Pro Ala
1               5                   10                  15

Arg Val Ser Tyr Leu Val Arg Ser Met Gln Val Ser Lys Val Lys Leu
            20                  25                  30

Tyr Asp Ala Asp Pro Tyr Val Leu Ser Ala Phe Val Asp Thr Asp Val
            35                  40                  45

Glu Phe Val Val Gly Ile Gly Asn Glu Asn Val Ser Ala Met Val Glu
    50                  55                  60

Pro Ala Ala Ala Arg Ala Trp Val Glu Arg His Val Gln Pro Tyr Leu
65                  70                  75                  80

Pro Gly Thr Arg Ile Thr Cys Ile Thr Val Gly Asn Glu Val Leu Lys
                85                  90                  95

Gly Asn Asp Ser Ala Leu Lys Ala Ser Leu Leu Pro Ala Met Gln Ser
                100                 105                 110

Val Tyr Gln Ala Leu Thr Ala Val Gly Leu Gln Gly Arg Val Asn Val
            115                 120                 125

Thr Thr Ala His Ser Leu Asp Ile Met Gly Ser Thr Tyr Pro Pro Ser
130                 135                 140

Ala Gly Ala Phe Gly Pro Asp Ala Val Pro Tyr Leu Gln Pro Leu Leu
145                 150                 155                 160

Ala Phe Leu Ser Ala Ala Arg Ser Pro Phe Leu Ile Asn Cys Tyr Pro
                165                 170                 175

Tyr Phe Ala Tyr Lys Ala Asp Pro Gly Asn Val Pro Leu Glu Tyr Val
                180                 185                 190

Leu Phe Gln Pro Asp Ala Ala Gly Val Thr Asp Ala Ser Thr Gly Leu
            195                 200                 205

Arg Tyr Asp Asn Met Leu Tyr Ala Gln Val Asp Ser Val Tyr Ala Ala
210                 215                 220

Ile Gln Lys Leu Gly His Thr Asp Val Asp Val Lys Val Ser Glu Thr
225                 230                 235                 240

Gly Trp Pro Ser Arg Gly Asp Pro Asp Glu Ala Gly Ala Thr Pro Glu
                245                 250                 255

Tyr Ala Arg Thr Tyr Ile Gly Asn Leu Leu Gln Arg Ile Glu Met Gly
                260                 265                 270

Gln Gly Thr Pro Met Arg Pro Ser Ala Pro Val Asp Val Tyr Val Phe
            275                 280                 285

Ala Leu Phe Asn Glu Asn Leu Lys Pro Gly Pro Ala Ser Glu Arg Asn
            290                 295                 300

Tyr Gly Leu Leu Tyr Pro Asp Gly Thr Pro Val Tyr Asp Val
305                 310                 315

<210> SEQ ID NO 60
<211> LENGTH: 318
<212> TYPE: PRT
<213> ORGANISM: Zea mays

<400> SEQUENCE: 60

Met Gly Ile Asn Tyr Gly Gln Ile Ala Asp Asn Leu Pro Ser Pro Ala
1               5                   10                  15

Arg Val Ser Tyr Leu Val Arg Ser Met Gln Val Ser Lys Val Lys Leu
            20                  25                  30

Tyr Asp Ala Asp Pro Tyr Val Leu Ser Ala Phe Val Asp Thr Asp Val
            35                  40                  45

Glu Phe Val Val Gly Ile Gly Asn Glu Asn Val Ser Ala Met Val Glu
    50                  55                  60

Pro Ala Ala Ala Arg Ala Trp Val Glu Arg His Val Gln Pro Tyr Leu
65                  70                  75                  80

Pro Gly Thr Arg Ile Thr Cys Ile Thr Val Gly Asn Glu Val Leu Lys

```
                 85                   90                   95
Gly Asn Asp Ser Ala Leu Lys Ala Ser Leu Leu Pro Ala Met Gln Ser
            100                 105                 110

Val Tyr Gln Ala Leu Thr Ala Val Gly Leu Gln Gly Arg Val Asn Val
            115                 120                 125

Thr Thr Ala His Ser Leu Asp Ile Met Gly Ser Thr Tyr Pro Pro Ser
130                 135                 140

Ala Gly Ala Phe Gly Pro Asp Ala Val Pro Tyr Leu Gln Pro Leu Leu
145                 150                 155                 160

Ala Phe Leu Ser Ala Ala Arg Ser Pro Phe Leu Ile Asn Cys Tyr Pro
                165                 170                 175

Tyr Phe Ala Tyr Lys Ala Asp Pro Gly Asn Val Pro Leu Glu Tyr Val
                180                 185                 190

Leu Phe Gln Pro Asp Ala Ala Gly Val Thr Asp Ala Ser Thr Gly Leu
                195                 200                 205

Arg Tyr Asp Asn Met Leu Tyr Ala Gln Val Asp Ser Val Tyr Ala Ala
210                 215                 220

Ile Gln Lys Leu Gly His Thr Asp Val Asp Val Lys Val Ser Glu Thr
225                 230                 235                 240

Gly Trp Pro Ser Arg Gly Asp Pro Asp Glu Ala Gly Ala Thr Pro Glu
                245                 250                 255

Tyr Ala Arg Thr Tyr Ile Gly Asn Leu Leu Gln Arg Ile Glu Met Gly
                260                 265                 270

Gln Gly Thr Pro Met Arg Pro Ser Ala Pro Val Asp Val Tyr Val Phe
                275                 280                 285

Ala Leu Phe Asn Glu Asn Leu Lys Pro Gly Pro Ala Ser Glu Arg Asn
290                 295                 300

Tyr Gly Leu Leu Tyr Pro Asp Gly Thr Pro Val Tyr Asp Val
305                 310                 315

<210> SEQ ID NO 61
<211> LENGTH: 324
<212> TYPE: PRT
<213> ORGANISM: Zea mays

<400> SEQUENCE: 61

Leu Gly Ile Ser Tyr Gly Arg Val Gly Asn Asn Leu Pro Ala Ala Thr
1               5                   10                  15

Ser Val Pro Gln Ile Val Ala Ser Leu Gly Val Gly Arg Val Arg Leu
                20                  25                  30

Tyr Asp Ala Asp Ser Thr Thr Ile Arg Ala Phe Ala Asn Thr Gly Val
                35                  40                  45

Glu Leu Val Val Gly Val Pro Asp Glu Cys Leu Ala Thr Val Ser Thr
            50                  55                  60

Pro Thr Gly Ala Ala Ser Trp Val Arg Ser Asn Ile Ser Pro Ala Leu
65                  70                  75                  80

Pro Ala Thr Lys Ile Ala Phe Leu Thr Val Gly Asn Glu Val Leu Thr
                85                  90                  95

Gly Val Asn Ser Ser Ser Leu Ser Arg Tyr Leu Leu Pro Ala Met Arg
            100                 105                 110

Cys Leu His Asp Ala Leu Ala Gln Ala Gly Leu Asp Lys Gln Val Ala
            115                 120                 125

Val Thr Thr Ala His Asn Leu Gly Val Leu Ala Thr Ser Tyr Pro Pro
130                 135                 140
```

```
Ser Ser Ala Tyr Phe Arg Lys Asp Leu Leu Pro Met Leu Cys Pro Ile
145                 150                 155                 160

Leu Asp Phe His Ala Arg Ala Gly Ser Pro Phe Leu Val Asn Ala Tyr
            165                 170                 175

Pro Tyr Phe Ala Tyr Ala Glu Glu Pro Thr Gly Val Glu Leu Glu Tyr
            180                 185                 190

Ala Leu Leu Glu Pro Gly His Ala Gly Val Ala Asp Pro Gly Thr Gly
            195                 200                 205

Leu His Tyr Thr Asn Met Leu Ala Ala Gln Val Asp Ala Val Tyr His
            210                 215                 220

Ala Ile Ala Ala Ala Asn Ser Ala Ala Arg Ala Val Glu Val Arg
225                 230                 235                 240

Val Ser Glu Thr Gly Trp Pro Ser Ala Gly Asp Ala Asn Glu Thr Gly
            245                 250                 255

Ala Thr Pro Gln Asn Ala Ala Arg Tyr Asn Gly Asn Val Met Arg Leu
            260                 265                 270

Val Ala Gln Gly Lys Gly Thr Pro Leu Arg Pro Ala Ala Pro Leu Arg
            275                 280                 285

Val Tyr Met Phe Ala Leu Phe Asn Glu Asn Met Lys Pro Gly Pro Thr
            290                 295                 300

Ser Glu Arg Asn Tyr Gly Leu Phe Lys Pro Asp Gly Thr Pro Ala Tyr
305                 310                 315                 320

Glu Leu Ser Tyr

<210> SEQ ID NO 62
<211> LENGTH: 324
<212> TYPE: PRT
<213> ORGANISM: Zea mays

<400> SEQUENCE: 62

Leu Gly Ile Ser Tyr Gly Arg Val Gly Asn Asn Leu Pro Ala Ala Thr
1               5                   10                  15

Ser Val Pro Gln Ile Val Ala Ser Leu Gly Val Gly Arg Val Arg Leu
            20                  25                  30

Tyr Asp Ala Asp Ser Thr Thr Ile Arg Ala Phe Ala Asn Thr Gly Val
            35                  40                  45

Glu Leu Val Val Gly Val Pro Asp Glu Cys Leu Ala Thr Val Ser Thr
50                  55                  60

Pro Thr Gly Ala Ala Ser Trp Val Arg Ser Asn Ile Ser Pro Ala Leu
65                  70                  75                  80

Pro Ala Thr Lys Ile Ala Phe Leu Thr Val Gly Asn Glu Val Leu Thr
            85                  90                  95

Gly Val Asn Ser Ser Ser Leu Ser Arg Tyr Leu Leu Pro Ala Met Arg
            100                 105                 110

Cys Leu His Asp Ala Leu Ala Gln Ala Gly Leu Asp Lys Gln Val Ala
            115                 120                 125

Val Thr Thr Ala His Asn Leu Gly Val Leu Ala Thr Ser Tyr Pro Pro
            130                 135                 140

Ser Ser Ala Tyr Phe Arg Lys Asp Leu Leu Pro Met Leu Cys Pro Ile
145                 150                 155                 160

Leu Asp Phe His Ala Arg Ala Gly Ser Pro Phe Leu Val Asn Ala Tyr
            165                 170                 175

Pro Tyr Phe Ala Tyr Ala Glu Glu Pro Thr Gly Val Glu Leu Glu Tyr
            180                 185                 190
```

```
Ala Leu Leu Glu Pro Gly His Ala Gly Val Ala Asp Pro Gly Thr Gly
            195                 200                 205

Leu His Tyr Thr Asn Met Leu Ala Ala Gln Val Asp Ala Val Tyr His
    210                 215                 220

Ala Ile Ala Ala Ala Asn Ser Ala Ala Arg Ala Val Glu Val Arg
225                 230                 235                 240

Val Ser Glu Thr Gly Trp Pro Ser Ala Gly Asp Ala Asn Glu Thr Gly
            245                 250                 255

Ala Thr Pro Gln Asn Ala Ala Arg Tyr Asn Gly Asn Val Met Arg Leu
            260                 265                 270

Val Ala Gln Gly Lys Gly Thr Pro Leu Arg Pro Ala Ala Pro Leu Arg
            275                 280                 285

Val Tyr Met Phe Ala Leu Phe Asn Glu Asn Met Lys Pro Gly Pro Thr
            290                 295                 300

Ser Glu Arg Asn Tyr Gly Leu Phe Lys Pro Asp Gly Thr Pro Ala Tyr
305                 310                 315                 320

Glu Leu Ser Tyr

<210> SEQ ID NO 63
<211> LENGTH: 324
<212> TYPE: PRT
<213> ORGANISM: Zea mays

<400> SEQUENCE: 63

Leu Gly Ile Asn Tyr Gly Arg Val Gly Asn Leu Pro Pro Pro Gln
1               5                   10                  15

Ser Val Met Pro Leu Leu Glu Gly Leu Gly Ile Gly Arg Val Arg Met
                20                  25                  30

Tyr Asp Ala Asp Pro Thr Val Leu Arg Ala Phe Ala Arg Thr Gly Val
            35                  40                  45

Glu Leu Ile Val Gly Val Pro Asp Glu Cys Leu Ala Ala Val Ala Asp
50                  55                  60

Pro Ser Gly Ala Ala Gln Trp Leu Lys Glu Asn Val Ala Pro Phe Leu
65                  70                  75                  80

Pro Asp Thr Lys Ile Ser Val Leu Ala Val Gly Asn Glu Val Leu Thr
                85                  90                  95

Gly Ala Asn Ser Ser Thr Leu Ser Arg Thr Leu Leu Pro Ala Met Gln
            100                 105                 110

Ser Leu His Gly Ala Val Ala Ala Leu Gly Leu Asp Lys Gln Ile Thr
        115                 120                 125

Val Thr Ser Ala His Asn Leu Gly Val Leu Gly Thr Ser Tyr Pro Pro
130                 135                 140

Ser Ala Gly Ala Phe Arg Lys Asp Leu Leu Pro Tyr Leu Cys Pro Ile
145                 150                 155                 160

Leu Asp Tyr His Ala Arg Thr Gly Ser Pro Phe Leu Val Asn Ala Tyr
                165                 170                 175

Pro Tyr Phe Ala Tyr Ser Ser Asp Pro Arg Gly Val Gln Leu Asp Tyr
            180                 185                 190

Ala Leu Leu Asp Pro Gly Phe Ala Gly Val Gln Asp Pro Asn Ser Arg
        195                 200                 205

Leu His Tyr Pro Asn Leu Leu Val Ala Gln Val Asp Ala Val Tyr His
    210                 215                 220

Ala Ile Ala Ala Ala Asn Thr Ala Ala Ser Arg Val Val Glu Val Arg
225                 230                 235                 240
```

```
Val Ser Glu Thr Gly Trp Pro Ser Ala Gly Ala Ala Asn Glu Thr Ala
            245                 250                 255

Ala Thr Pro Gln Asn Ala Ala Arg Tyr Asn Ser Asn Ala Met Arg Leu
        260                 265                 270

Val Ala Glu Gly Lys Gly Thr Pro Leu Lys Pro Gly Ala Pro Leu Arg
            275                 280                 285

Ala Tyr Val Phe Ala Leu Phe Asn Glu Asn Leu Lys Pro Gly Leu Ala
        290                 295                 300

Ser Glu Arg Tyr Tyr Gly Leu Phe Lys Pro Asp Gly Thr Pro Ala Tyr
305                 310                 315                 320

Glu Leu Ser Phe

<210> SEQ ID NO 64
<211> LENGTH: 293
<212> TYPE: PRT
<213> ORGANISM: Zea mays

<400> SEQUENCE: 64

Leu Gly Ile Asn Tyr Gly Gln Val Ala Asp Asn Leu Pro Pro Pro Gln
 1               5                  10                  15

Ala Ala Leu Val Leu Leu Arg Ala Leu Asn Ala Thr Arg Val Lys Leu
            20                  25                  30

Tyr Asp Ala Asp Ala Arg Val Leu Arg Ala Phe Ala Gly Ser Gly Val
        35                  40                  45

Asp Phe Thr Val Gly Val Pro Asp Arg Leu Val Pro Arg Leu Ala Ala
    50                  55                  60

Asp Arg Gly Ala Ala Ala Trp Val Arg Gly Ser Leu Leu Pro His
 65                  70                  75                  80

Leu Pro Ala Thr Ser Ile Thr Ala Val Thr Val Gly Asn Glu Val Leu
                85                  90                  95

Ser Gly Thr Asp Ala Ala Met His Arg Ala Leu Leu Pro Ala Met Glu
            100                 105                 110

Ala Leu His Ala Ala Val Ala Ala Ser Asn Leu Thr Ser Arg Val Ala
        115                 120                 125

Val Thr Thr Ala His Ser Leu Ala Val Leu Ser Ser Ser Phe Pro Pro
    130                 135                 140

Ser Ala Ala Ala Phe Arg Arg Glu Val Val Pro Tyr Met Ala Pro Leu
145                 150                 155                 160

Leu Gly Phe Leu Ala Pro His Gly Arg Ala Val Pro Gly Gly Val Ala
                165                 170                 175

Asp Ala Ala Thr Gly Leu Arg Tyr Asp Asn Met Leu His Ala Gln Val
            180                 185                 190

Asp Ala Val Arg Ala Ala Ile Cys Ala Ala Asn Tyr Gly Arg Ala Leu
        195                 200                 205

Glu Ile Arg Val Ser Glu Thr Gly Trp Pro Ser Gln Gly Asp Asp Asp
    210                 215                 220

Glu Ala Gly Ala Thr Pro Glu Asn Ala Ala Arg Tyr Asn Gly Asn Leu
225                 230                 235                 240

Met Arg Leu Val Ala Gln Gly Lys Gly Thr Pro Ala Ala Pro Asp Glu
                245                 250                 255

Pro Leu Gln Val Tyr Val Phe Ala Leu Phe Asn Glu Asp Gln Lys Pro
            260                 265                 270

Gly Pro Ala Ser Glu Arg His Tyr Gly Leu Phe Lys Pro Asp Gly Thr
        275                 280                 285
```

```
Pro Ala Tyr Asn Val
        290

<210> SEQ ID NO 65
<211> LENGTH: 372
<212> TYPE: PRT
<213> ORGANISM: Zea mays

<400> SEQUENCE: 65

Leu Gly Ile Asn Tyr Gly Gln Val Ala Asn Leu Pro Pro Ala
  1               5                  10                 15

Gln Val Val Gln Leu Leu Ser Ser Leu Arg Ile Gly Lys Val Arg Ile
             20                  25                  30

Tyr Asp Val Asn Pro Gln Val Leu Thr Ala Phe Ala Gly Thr Gly Ile
             35                  40                  45

Glu Leu Val Val Thr Val Pro Asp Asp Leu Val Pro Gly Met Ala Ser
 50                  55                  60

Ser Ala Ser Gln Ala Leu Gln Trp Val Ser Ala Ser Leu Arg Pro Tyr
 65                  70                  75                  80

Phe Pro Ala Thr Arg Val Thr Gly Ile Ala Val Gly Asn Glu Val Phe
                 85                  90                  95

Thr Gly Asp Asp Glu Gln Leu Lys Ala Ser Leu Val Pro Ala Met Arg
            100                 105                 110

Asn Leu His Ala Ala Leu Ala Gln Leu Gly Met Asp Ala Tyr Val Arg
            115                 120                 125

Val Ser Thr Ala Asn Ser Leu Ala Val Leu Ala Thr Ser Tyr Pro Pro
            130                 135                 140

Ser Gln Gly Val Phe Thr Gln Ala Ala Pro Tyr Met Ala Gln Leu
145                 150                 155                 160

Leu Arg Phe Leu Ala Glu Thr Ser Ser Pro Phe Trp Val Asn Ala Tyr
                165                 170                 175

Pro Tyr Phe Ala Tyr Lys Asp Asp Pro Thr Lys Val Ser Leu Asp Tyr
            180                 185                 190

Ala Leu Ser Asn Pro Ser His Val Gly Ala Val Asp Pro Phe Thr Lys
            195                 200                 205

Leu Gln Tyr Thr Ser Met Leu Tyr Ala Gln Val Asp Ala Val Thr Phe
            210                 215                 220

Ala Ala Ala Arg Leu Gly Tyr Gly Gly Val Pro Val His Val Ser Glu
225                 230                 235                 240

Thr Gly Trp Pro Ser Lys Gly Asp Ala Asn Glu Ala Gly Ala Thr Val
                245                 250                 255

Glu Asn Ala Arg Gln Tyr Asn Arg Asn Leu Leu Met Arg Gln Val Ser
            260                 265                 270

Gly Glu Gly Thr Pro Leu Arg Pro Arg Leu Arg Leu Glu Val Tyr Leu
            275                 280                 285

Phe Ala Leu Phe Asn Glu Asp Met Lys Pro Gly Pro Ala Ser Glu Arg
            290                 295                 300

Asn Tyr Gly Leu Tyr Gln Pro Asp Met Ser Met Val Tyr Asn Val Gly
305                 310                 315                 320

Leu Ser Gln Leu Ala Thr Thr Ser Ala Ala Ser Leu Ser Leu Ala Thr
                325                 330                 335

Ser Pro Ala Ala Arg Thr Thr Asp Val Gly Lys Asp Tyr Ala Gly Leu
            340                 345                 350

Cys Leu Val Ala Val Ser Val Ala Ile Leu Leu Ile Thr Gln Gln Gly
            355                 360                 365
```

Ser Leu Leu Leu
    370

<210> SEQ ID NO 66
<211> LENGTH: 289
<212> TYPE: PRT
<213> ORGANISM: Zea mays

<400> SEQUENCE: 66

Ser Thr Ser Ile Ala Lys Leu Arg Leu Tyr Glu Pro Gln Pro Asp Leu
1               5                   10                  15

Val Ala Ala Leu Ala Gly Ser Asn Ile Ser Ile Leu Leu Gly Ile Pro
            20                  25                  30

Asn Gly Ala Val Pro Asn Leu Ala Ser Ser Pro Ala Ala Ala Ala Ser
        35                  40                  45

Trp Ala Ala Ala Asn Ile Pro Thr Thr Leu Pro Val Ser Ser Ile Ser
    50                  55                  60

Val Gly Asn Glu Leu Leu Asn Ser Gly Asp Pro Thr Leu Ala Pro Gln
65                  70                  75                  80

Leu Leu Pro Ala Met Gln Asn Leu Leu Ala Ala Leu Pro Ala Gly Ser
                85                  90                  95

Thr Thr Lys Ile Ser Thr Val His Ser Met Ala Val Leu Ser Ala Ser
            100                 105                 110

Asp Pro Pro Ser Ser Gly Ala Phe His Pro Asp Leu Ala Gly Ser Leu
        115                 120                 125

Asp Pro Val Leu Asp Phe Leu His Gln Asn Gly Ala Pro Phe Met Ile
    130                 135                 140

Asn Pro Tyr Pro Tyr Phe Ala Tyr Ala Ser Asp Thr Arg Pro Glu Thr
145                 150                 155                 160

Leu Ala Phe Cys Leu Phe Gln Pro Asn Ala Gly Arg Val Asp Ala Val
                165                 170                 175

Ser Gly Leu Thr Tyr Thr Asn Met Phe Asp Ala Gln Leu Asp Ala Ile
            180                 185                 190

Arg Ala Ala Leu Asp Ala Lys Gly Tyr Ser Asp Val Glu Ile Val Ile
        195                 200                 205

Ala Glu Thr Gly Trp Pro Tyr Lys Gly Asp Ala Asp Glu Ala Gly Ala
    210                 215                 220

Thr Val Asp Asn Ala Lys Ala Tyr Asn Ser Asn Leu Val Ala His Leu
225                 230                 235                 240

Lys Ser Gln Val Gly Thr Pro Arg Thr Pro Gly Lys Ser Val Asp Thr
                245                 250                 255

Tyr Ile Phe Ala Leu Tyr Asp Glu Asp Leu Lys Gly Pro Glu Ser
            260                 265                 270

Glu Arg Ser Phe Gly Leu Tyr Lys Thr Asp Leu Thr Ala Asn Tyr Asp
        275                 280                 285

Val

<210> SEQ ID NO 67
<211> LENGTH: 311
<212> TYPE: PRT
<213> ORGANISM: Zea mays

<400> SEQUENCE: 67

Ile Gly Ile Asn Tyr Gly Glu Val Ala Asp Asn Leu Pro Pro Pro Ser
1               5                   10                  15

Ser Thr Ala Arg Leu Val Gln Ser Thr Thr Ile Thr Lys Val Arg Leu
                20                  25                  30

Tyr Gly Thr Asp Pro Ala Ile Ile Ser Ala Phe Ser Gly Thr Gly Val
            35                  40                  45

Ser Leu Leu Leu Gly Ala Thr Asn Gly Asp Ile Ala Asn Leu Ala Ser
        50                  55                  60

Ser Pro Ala Ala Ala Ala Trp Val Ala Ala His Leu Pro Ala Ser
65                  70                  75                  80

Ser Pro Ala Val Ser Thr Val Ser Val Gly Asn Glu Val Leu Phe Ala
                85                  90                  95

Asp Ala Ser Leu Ala Ser Gln Leu Val Pro Ala Met Gln Asn Leu His
            100                 105                 110

Asp Ala Leu Pro Pro Asn Ser Ser Val Lys Val Ser Thr Val Asn Ala
        115                 120                 125

Met Asp Val Leu Ala Ser Ser Asp Pro Pro Ser Ser Gly Ala Phe Lys
130                 135                 140

Pro Glu Leu Ala Ala Ala Leu Asp Pro Leu Leu Ala Phe Leu Ser Lys
145                 150                 155                 160

Thr Gly Ser Pro Phe Leu Ile Asn Pro Tyr Pro Tyr Phe Ala Tyr Leu
                165                 170                 175

Ser Asp Pro Arg Pro Glu Thr Leu Ala Phe Cys Leu Phe Gln Pro Asn
            180                 185                 190

Ala Gly Arg Pro Asp Ala Gly Ser Leu Thr Tyr Thr Asn Met Phe
        195                 200                 205

Asp Ala Gln Val Asp Ala Val Arg Ala Ala Leu Asp Ala Lys Gly Tyr
210                 215                 220

Lys Asp Val Asp Ile Val Val Ala Glu Thr Gly Trp Pro His Lys Gly
225                 230                 235                 240

Asp Pro Asp Glu Ala Gly Ala Thr Val Glu Asn Ala Arg Ala Phe Val
                245                 250                 255

Ser Gly Leu Val Ser His Leu Arg Ser Leu Ser Gly Thr Pro Arg Ala
            260                 265                 270

Pro Gly Lys Ser Val Glu Thr Tyr Ile Phe Ala Met Tyr Asp Glu Asp
        275                 280                 285

Leu Lys Pro Gly Lys Ala Ser Glu Arg Tyr Phe Gly Leu Phe Gln Thr
290                 295                 300

Ser Leu Ala Glu Thr Tyr Pro
305                 310

<210> SEQ ID NO 68
<211> LENGTH: 311
<212> TYPE: PRT
<213> ORGANISM: Zea mays

<400> SEQUENCE: 68

Ile Gly Ile Asn Tyr Gly Glu Val Ala Asp Asn Leu Pro Pro Ser
1               5                   10                  15

Ser Thr Ala Arg Leu Val Gln Ser Thr Thr Ile Thr Lys Val Arg Leu
                20                  25                  30

Tyr Gly Thr Asp Pro Ala Ile Ile Ser Ala Phe Ser Gly Thr Gly Val
            35                  40                  45

Ser Leu Leu Leu Gly Ala Thr Asn Gly Asp Ile Ala Asn Leu Ala Ser
        50                  55                  60

Ser Pro Ala Ala Ala Ala Trp Val Ala Ala His Leu Pro Ala Ser
65                  70                  75                  80

```
Ser Pro Ala Val Ser Thr Val Ser Val Gly Asn Glu Val Leu Phe Ala
                85                  90                  95

Asp Ala Ser Leu Ala Ser Gln Leu Val Pro Ala Met Gln Asn Leu His
            100                 105                 110

Asp Ala Leu Pro Pro Asn Ser Ser Val Lys Val Ser Thr Val Asn Ala
        115                 120                 125

Met Asp Val Leu Ala Ser Ser Asp Pro Ser Ser Gly Ala Phe Lys
130                 135                 140

Pro Glu Leu Ala Ala Ala Leu Asp Pro Leu Leu Ala Phe Leu Ser Lys
145                 150                 155                 160

Thr Gly Ser Pro Phe Leu Ile Asn Pro Tyr Pro Tyr Phe Ala Tyr Leu
                165                 170                 175

Ser Asp Pro Arg Pro Glu Thr Leu Ala Phe Cys Leu Phe Gln Pro Asn
            180                 185                 190

Ala Gly Arg Pro Asp Ala Gly Ser Ser Leu Thr Tyr Thr Asn Met Phe
        195                 200                 205

Asp Ala Gln Val Asp Ala Val Arg Ala Ala Leu Asp Ala Lys Gly Tyr
210                 215                 220

Lys Asp Val Asp Ile Val Val Ala Glu Thr Gly Trp Pro His Lys Gly
225                 230                 235                 240

Asp Pro Asp Glu Ala Gly Ala Thr Val Glu Asn Ala Arg Ala Phe Val
                245                 250                 255

Ser Gly Leu Val Ser His Leu Arg Ser Leu Ser Gly Thr Pro Arg Ala
            260                 265                 270

Pro Gly Lys Ser Val Glu Thr Tyr Ile Phe Ala Met Tyr Asp Glu Asp
        275                 280                 285

Leu Lys Pro Gly Lys Ala Ser Glu Arg Tyr Phe Gly Leu Phe Gln Thr
290                 295                 300

Ser Leu Ala Glu Thr Tyr Pro
305                 310

<210> SEQ ID NO 69
<211> LENGTH: 318
<212> TYPE: PRT
<213> ORGANISM: Zea mays

<400> SEQUENCE: 69

Ile Gly Val Asn Tyr Gly Glu Val Ala Asp Asn Leu Pro Ser Pro Asp
 1               5                  10                  15

Lys Thr Ala Arg Leu Leu Lys Ser Thr Ser Ile Ser Lys Val Arg Leu
            20                  25                  30

Tyr Gly Val Asp Ala Gly Leu Ile Arg Ala Leu Ala Gly Ser Gly Ile
        35                  40                  45

Ser Val Val Val Gly Val Ala Asn Gly Glu Ile Pro Thr Leu Ala Ala
    50                  55                  60

Asp Pro Ala Ala Ala Ser Arg Trp Leu Ala Ala Asn Val Leu Pro Phe
65                  70                  75                  80

Val Pro Ala Thr Thr Ile Ser Ala Val Ala Val Gly Asn Glu Val Leu
                85                  90                  95

Glu Ser Gly Asp Ala Ala Leu Ala Ala Leu Leu Pro Ala Met Gln
            100                 105                 110

Asn Leu Arg Ala Ala Ala Ala Ala Gly Asp Gly Ala Ala Gly Ile
        115                 120                 125

Arg Phe Ser Thr Val Asn Thr Met Gly Val Met Ala Gln Ser Glu Pro
```

```
            130                 135                 140
Pro Ser Ala Gly Ala Phe His Pro Asp Val Ala Pro Gln Leu Gln Gln
145                 150                 155                 160

Ile Leu Gly Phe Leu Ser Lys Thr Gly Ala Pro Phe Met Val Asn Pro
                165                 170                 175

Tyr Pro Trp Phe Ala Tyr Gln Ser Asp Pro Arg Pro Glu Thr Leu Ala
                180                 185                 190

Phe Cys Leu Phe Gln Pro Asn Ala Gly Arg Val Asp Gly Gly Ser Lys
                195                 200                 205

Val Arg Tyr Ala Asn Met Phe Asp Ala Gln Leu Asp Ala Val Lys Ser
210                 215                 220

Ala Leu Val Arg Ala Gly Tyr Gly Gly Val Asp Ile Val Val Ala Glu
225                 230                 235                 240

Thr Gly Trp Pro Thr Arg Gly Asp Ala Gly Glu Pro Gly Ala Thr Val
                245                 250                 255

Glu Asn Ala Arg Ala Tyr Val Ser Asn Leu Val Ala His Leu Arg Ser
                260                 265                 270

Gly Ala Gly Thr Pro Leu Met Pro Gly Arg Ser Val Asp Thr Tyr Leu
                275                 280                 285

Phe Ala Leu Tyr Asp Glu Asp Leu Lys Pro Gly Pro Thr Ser Glu Arg
                290                 295                 300

Ser Phe Gly Leu Tyr His Thr Asp Leu Thr Met Ala Tyr Asp
305                 310                 315

<210> SEQ ID NO 70
<211> LENGTH: 316
<212> TYPE: PRT
<213> ORGANISM: Zea mays

<400> SEQUENCE: 70

Ile Gly Val Asn Tyr Gly Thr Arg Gly Thr Thr Leu Pro Ala Pro Ala
1               5                   10                  15

Asp Val Ala Arg Phe Leu Ala Arg Asp Thr Ile Phe Asp Arg Val Arg
                20                  25                  30

Leu Leu Asp Ala Asp Pro Val Leu Leu Arg Ala Phe Ala Gly Thr Gly
                35                  40                  45

Leu Ala Val Asp Val Thr Val Pro Asn Gly Val Pro His Leu Leu
50                  55                  60

Asn Leu Thr Phe Ala Arg Arg Trp Val Arg Asp Asn Val Thr Pro Tyr
65                  70                  75                  80

Ala Gly Ala Thr Asn Ile Ser Arg Leu Leu Val Gly Asp Glu Val Thr
                85                  90                  95

Thr Glu Ala Asn Arg Thr Leu Leu Leu Ala Leu Val Pro Ala Met Gln
                100                 105                 110

Asn Leu His Thr Ala Leu Val Ala Ser Leu His Gly Arg Val Lys
                115                 120                 125

Val Ser Thr Thr His Ser Leu Gly Val Leu Thr Thr Thr Glu Gln Pro
130                 135                 140

Ser Ala Ala Arg Phe Arg Asp Gly Tyr Asp Ala Ala Ile Val Arg Pro
145                 150                 155                 160

Leu Leu Arg Phe Leu Arg Ala Thr Gly Ala Pro Phe Met Val Asn Ala
                165                 170                 175

Tyr Pro Phe Tyr Ala Leu Ala Asn Asp Ser Ser Leu Asp Phe Ala Leu
                180                 185                 190
```

```
Phe Arg Val Asn Asp Gly Val Met Asp Gln Gly Thr Gly Leu Val Tyr
        195                 200                 205

Gly Asn Met Leu Asp Ala Gln Leu Asp Ala Val His Ser Ala Val Arg
    210                 215                 220

Arg Met Gly Phe Gly Asp Val Asp Ile Ala Val Ser Glu Thr Gly Trp
225                 230                 235                 240

Pro Ser Ala Gly Glu Asp Trp Glu Val Gly Val Gly Ala Asp Leu Ala
                245                 250                 255

Arg Asp Tyr Asn Ser Asn Ala Ile Arg His Leu Gly Ser Gly Val Gly
            260                 265                 270

Thr Pro Leu Met Pro Asn Arg Thr Phe Glu Val Ser Ile Phe Ser Leu
        275                 280                 285

Phe Asp Glu Asn Leu Lys Pro Gly Pro Val Ser Glu Arg Asn Phe Gly
    290                 295                 300

Leu Phe Arg Gly Asp Met Thr Pro Val Tyr Asp Val
305                 310                 315

<210> SEQ ID NO 71
<211> LENGTH: 323
<212> TYPE: PRT
<213> ORGANISM: Zea mays

<400> SEQUENCE: 71

Ile Gly Val Asn Tyr Gly Ala Asn Ala Asp Asn Leu Pro Ser Pro Ala
1               5                   10                  15

Ala Val Ala Ala Phe Leu Thr Lys Ser Thr Thr Ile Asp Arg Val Lys
            20                  25                  30

Leu Phe Asp Ala Asn Pro Ala Phe Leu Asp Ala Phe Ala Ala Asn Ala
        35                  40                  45

Pro Ser Ile Ala Leu Ala Val Ser Ile Pro Asn Ser Ala Leu Pro Ser
    50                  55                  60

Phe Ala Asp Arg Ser Thr Gly Leu Asp Ala Ala Arg Gly Trp Val Arg
65                  70                  75                  80

Asp Asn Leu Ser Pro His Val Ser Ala Gly Ala Asn Ile Thr Leu Leu
                85                  90                  95

Met Ala Gly Asn Glu Val Leu Gly Pro Thr Val Val Pro Asp Leu Val
            100                 105                 110

Val Ala Leu Leu Pro Ala Met Arg Arg Leu Tyr Gln Ala Leu Gln Leu
        115                 120                 125

Glu Gly Leu Pro Lys Val Arg Val Thr Thr Pro His Tyr Leu Gly Ile
    130                 135                 140

Leu Ala Pro Ser Asp Gly Ile Pro Ser Asn Ala Ser Phe Arg Pro Gly
145                 150                 155                 160

Leu Asp Ala Lys Val Leu Ala Pro Met Leu Arg Phe His Asn Asp Thr
                165                 170                 175

Gly Ser Pro Phe Met Val Asn Ala Tyr Pro Tyr Phe Ser Tyr Asn Ala
            180                 185                 190

Ala Thr Leu Asp Tyr Ala Val Phe Arg Pro Asn Ala Gly Val Tyr Asp
        195                 200                 205

Pro Ala Thr Arg Leu Asn Tyr Thr Ser Met Phe Asp Ala Gln Met Asp
    210                 215                 220

Ala Ile His Thr Ala Met Lys Lys Leu Gly Tyr Gly Gly Val Gln Ile
225                 230                 235                 240

Ala Val Gly Glu Ala Gly Trp Pro Thr Lys Ala Glu Ala Gly Gln Val
                245                 250                 255
```

```
Gly Val Gly Pro Glu Glu Ala Arg Asp Phe Asn Ala Gly Met Ile Arg
            260                 265                 270

Val Cys Ser Gly Gly Lys Gly Thr Pro Leu Met Pro Gly Arg Thr Phe
        275                 280                 285

Glu Thr Tyr Val Phe Ser Leu Phe Asp Glu Asn Gln Lys Pro Gly Pro
    290                 295                 300

Val Ala Glu Arg Asn Phe Gly Ile Phe Asn Thr Asp Leu Thr Pro Lys
305                 310                 315                 320

Tyr Asp Leu

<210> SEQ ID NO 72
<211> LENGTH: 323
<212> TYPE: PRT
<213> ORGANISM: Zea mays

<400> SEQUENCE: 72

Ile Gly Val Asn Tyr Gly Ala Asn Ala Asp Asn Leu Pro Ser Pro Ala
1               5                   10                  15

Ala Val Ala Ala Phe Leu Thr Lys Ser Thr Thr Ile Asp Arg Val Lys
            20                  25                  30

Leu Phe Asp Ala Asn Pro Ala Phe Leu Asp Ala Phe Ala Ala Asn Ala
        35                  40                  45

Pro Ser Ile Ala Leu Ala Val Ser Ile Pro Asn Ser Ala Leu Pro Ser
    50                  55                  60

Phe Ala Asp Arg Ser Thr Gly Leu Asp Ala Ala Arg Gly Trp Val Arg
65                  70                  75                  80

Asp Asn Leu Ser Pro His Val Ser Ala Gly Ala Asn Ile Thr Leu Leu
                85                  90                  95

Met Ala Gly Asn Glu Val Leu Gly Pro Thr Val Val Pro Asp Leu Val
            100                 105                 110

Val Ala Leu Leu Pro Ala Met Arg Arg Leu Tyr Gln Ala Leu Gln Leu
        115                 120                 125

Glu Gly Leu Pro Lys Val Arg Val Thr Thr Pro His Tyr Leu Gly Ile
    130                 135                 140

Leu Ala Pro Ser Asp Gly Ile Pro Ser Asn Ala Ser Phe Arg Pro Gly
145                 150                 155                 160

Leu Asp Ala Lys Val Leu Ala Pro Met Leu Arg Phe His Asn Asp Thr
                165                 170                 175

Gly Ser Pro Phe Met Val Asn Ala Tyr Pro Tyr Phe Ser Tyr Asn Ala
            180                 185                 190

Ala Thr Leu Asp Tyr Ala Val Phe Arg Pro Asn Ala Gly Val Tyr Asp
        195                 200                 205

Pro Ala Thr Arg Leu Asn Tyr Thr Ser Met Phe Asp Ala Gln Met Asp
    210                 215                 220

Ala Ile His Thr Ala Met Lys Lys Leu Gly Tyr Gly Val Gln Ile
225                 230                 235                 240

Ala Val Gly Glu Ala Gly Trp Pro Thr Lys Ala Glu Ala Gly Gln Val
                245                 250                 255

Gly Val Gly Pro Glu Glu Ala Arg Asp Phe Asn Ala Gly Met Ile Arg
            260                 265                 270

Val Cys Ser Gly Gly Lys Gly Thr Pro Leu Met Pro Gly Arg Thr Phe
        275                 280                 285

Glu Thr Tyr Val Phe Ser Leu Phe Asp Glu Asn Gln Lys Pro Gly Pro
    290                 295                 300
```

```
Val Ala Glu Arg Asn Phe Gly Ile Phe Asn Thr Asp Leu Thr Pro Lys
305                 310                 315                 320

Tyr Asp Leu

<210> SEQ ID NO 73
<211> LENGTH: 323
<212> TYPE: PRT
<213> ORGANISM: Zea mays

<400> SEQUENCE: 73

Ile Gly Val Asn Tyr Gly Ala Asn Ala Asp Asn Leu Pro Ser Pro Ala
  1               5                  10                  15

Ala Val Ala Ala Phe Leu Thr Lys Ser Thr Thr Ile Asp Arg Val Lys
                 20                  25                  30

Leu Phe Asp Ala Asn Pro Ala Phe Leu Asp Ala Phe Ala Ala Asn Ala
             35                  40                  45

Pro Ser Ile Ala Leu Ala Val Ser Ile Pro Asn Ser Ala Leu Pro Ser
 50                  55                  60

Phe Ala Asp Arg Ser Thr Gly Leu Asp Ala Ala Arg Gly Trp Val Arg
 65                  70                  75                  80

Asp Asn Leu Ser Pro His Val Ser Ala Gly Ala Asn Ile Thr Leu Leu
                 85                  90                  95

Met Ala Gly Asn Glu Val Leu Gly Pro Thr Val Val Pro Asp Leu Val
                100                 105                 110

Val Ala Leu Leu Pro Ala Met Arg Arg Leu Tyr Gln Ala Leu Gln Leu
            115                 120                 125

Glu Gly Leu Pro Lys Val Arg Val Thr Thr Pro His Tyr Leu Gly Ile
130                 135                 140

Leu Ala Pro Ser Asp Gly Ile Pro Ser Asn Ala Ser Phe Arg Pro Gly
145                 150                 155                 160

Leu Asp Ala Lys Val Leu Ala Pro Met Leu Arg Phe His Asn Asp Thr
                165                 170                 175

Gly Ser Pro Phe Met Val Asn Ala Tyr Pro Tyr Phe Ser Tyr Asn Ala
            180                 185                 190

Ala Thr Leu Asp Tyr Ala Val Phe Arg Pro Asn Ala Gly Val Tyr Asp
        195                 200                 205

Pro Ala Thr Arg Leu Asn Tyr Thr Ser Met Phe Asp Ala Gln Met Asp
210                 215                 220

Ala Ile His Thr Ala Met Lys Lys Leu Gly Tyr Gly Gly Val Gln Ile
225                 230                 235                 240

Ala Val Gly Glu Ala Gly Trp Pro Thr Lys Ala Glu Ala Gly Gln Val
                245                 250                 255

Gly Val Gly Pro Glu Glu Ala Arg Asp Phe Asn Ala Gly Met Ile Arg
            260                 265                 270

Val Cys Ser Gly Gly Lys Gly Thr Pro Leu Met Pro Gly Arg Thr Phe
        275                 280                 285

Glu Thr Tyr Val Phe Ser Leu Phe Asp Glu Asn Gln Lys Pro Gly Pro
    290                 295                 300

Val Ala Glu Arg Asn Phe Gly Ile Phe Asn Thr Asp Leu Thr Pro Lys
305                 310                 315                 320

Tyr Asp Leu

<210> SEQ ID NO 74
<211> LENGTH: 321
```

```
<212> TYPE: PRT
<213> ORGANISM: Zea mays

<400> SEQUENCE: 74

Ile Gly Val Asn Ile Gly Thr Ala Met Ser Ser Val Pro Ala Pro Thr
1               5                   10                  15

Gln Ile Thr Thr Leu Leu Arg Ser Gln Asn Ile Arg His Val Arg Leu
            20                  25                  30

Tyr Asp Ala Asp Pro Ala Met Leu Ala Ala Leu Ser Asn Thr Gly Ile
        35                  40                  45

Arg Val Ile Val Ser Val Pro Asn Glu Gln Leu Leu Ala Ile Gly Asn
    50                  55                  60

Ser Asn Ala Thr Ala Ala Asn Trp Val Ala Arg Asn Val Ala Ala His
65                  70                  75                  80

Phe Pro Ala Val Asn Ile Thr Ala Ile Ala Val Gly Ser Glu Val Leu
                85                  90                  95

Ser Ala Gln Pro Ser Ala Ala Pro Leu Leu Met Pro Ala Met Arg Tyr
            100                 105                 110

Leu Gln Asn Ala Leu Val Ala Ala Leu Asp Arg Tyr Ile Lys Val
        115                 120                 125

Ser Thr Pro His Ser Ser Ser Ile Ile Leu Asp Ser Phe Pro Pro Ser
    130                 135                 140

Gln Ala Phe Phe Asn Arg Ser Leu Asp Gly Val Leu Val Pro Met Leu
145                 150                 155                 160

Arg Phe Leu Gln Ser Thr Gly Ser Pro Leu Met Leu Asn Val Tyr Pro
                165                 170                 175

Tyr Tyr Asp Tyr Met Arg Ser Asn Gly Val Ile Pro Leu Asp Tyr Ala
            180                 185                 190

Leu Phe Arg Pro Leu Pro Pro Asn Lys Glu Ala Val Asp Ala Asn Thr
        195                 200                 205

Leu Leu His Tyr Thr Asn Val Phe Asp Ala Val Asp Ala Ala Tyr
    210                 215                 220

Phe Ala Met Ala Tyr Leu Asn Val Thr Asn Val Pro Val Met Val Thr
225                 230                 235                 240

Glu Thr Gly Trp Pro His Lys Gly Asp Ser Ser Glu Pro Asp Ala
                245                 250                 255

Thr Ser Asp Asn Ala Asp Thr Tyr Asn Ser Asn Leu Ile Arg His Val
            260                 265                 270

Met Asn Ser Thr Gly Thr Pro Lys His Pro Gly Val Ala Val Pro Thr
        275                 280                 285

Tyr Val Tyr Glu Leu Tyr Asp Glu Asp Thr Arg Pro Gly Ser Thr Ser
    290                 295                 300

Glu Lys Tyr Trp Gly Leu Phe Asp Met Asn Gly Val Pro Ala Tyr Thr
305                 310                 315                 320

Leu

<210> SEQ ID NO 75
<211> LENGTH: 309
<212> TYPE: PRT
<213> ORGANISM: Zea mays

<400> SEQUENCE: 75

Pro Ala Pro Thr Gln Ile Thr Thr Leu Leu Arg Ser Gln Asn Ile Arg
1               5                   10                  15

His Val Arg Leu Tyr Asp Ala Asp Pro Ala Met Leu Ala Ala Leu Ser
```

```
                20                  25                  30
Asn Thr Gly Ile Arg Val Ile Val Ser Val Pro Asn Glu Gln Leu Leu
            35                  40                  45
Ala Ile Gly Asn Ser Asn Ala Thr Ala Ala Asn Trp Val Ala Arg Asn
 50                  55                  60
Val Ala Ala His Phe Pro Ala Val Asn Ile Thr Ala Ile Ala Val Gly
 65                  70                  75                  80
Ser Glu Val Leu Ser Ala Gln Pro Ser Ala Ala Pro Leu Leu Met Pro
                85                  90                  95
Ala Met Arg Tyr Leu Gln Asn Ala Leu Val Ala Ala Leu Asp Arg
               100                 105                 110
Tyr Ile Lys Val Ser Thr Pro His Ser Ser Ser Ile Ile Leu Asp Ser
           115                 120                 125
Phe Pro Pro Ser Gln Ala Phe Phe Asn Arg Ser Leu Asp Gly Val Leu
           130                 135                 140
Val Pro Met Leu Arg Phe Leu Gln Ser Thr Gly Ser Pro Leu Met Leu
145                 150                 155                 160
Asn Val Tyr Pro Tyr Tyr Asp Tyr Met Arg Ser Asn Gly Val Ile Pro
               165                 170                 175
Leu Asp Tyr Ala Leu Phe Arg Pro Leu Pro Pro Asn Lys Glu Ala Val
           180                 185                 190
Asp Ala Asn Thr Leu Leu His Tyr Thr Asn Val Phe Asp Ala Val Val
           195                 200                 205
Asp Ala Ala Tyr Phe Ala Met Ala Tyr Leu Asn Val Thr Asn Val Pro
           210                 215                 220
Val Met Val Thr Glu Thr Gly Trp Pro His Lys Gly Asp Ser Ser Ser
225                 230                 235                 240
Glu Pro Asp Ala Thr Ser Asp Asn Ala Asp Thr Tyr Asn Ser Asn Leu
               245                 250                 255
Ile Arg His Val Met Asn Ser Thr Gly Thr Pro Lys His Pro Gly Val
           260                 265                 270
Ala Val Pro Thr Tyr Val Tyr Glu Leu Tyr Asp Glu Asp Thr Arg Pro
           275                 280                 285
Gly Ser Thr Ser Glu Lys Tyr Trp Gly Leu Phe Asp Met Asn Gly Val
           290                 295                 300
Pro Ala Tyr Thr Leu
305

<210> SEQ ID NO 76
<211> LENGTH: 321
<212> TYPE: PRT
<213> ORGANISM: Zea mays

<400> SEQUENCE: 76

Ile Gly Val Asn Ile Gly Thr Ala Met Ser Ser Val Pro Ala Pro Thr
 1               5                  10                  15
Gln Ile Thr Thr Leu Leu Arg Ser Gln Asn Ile Arg His Val Arg Leu
                20                  25                  30
Tyr Asp Ala Asp Pro Ala Met Leu Ala Ala Leu Ser Asn Thr Gly Ile
            35                  40                  45
Arg Val Ile Val Ser Val Pro Asn Glu Gln Leu Leu Ala Ile Gly Asn
        50                  55                  60
Ser Asn Ala Thr Ala Ala Asn Trp Val Ala Arg Asn Val Ala Ala His
 65                  70                  75                  80
```

```
Phe Pro Ala Val Asn Ile Thr Ala Ile Ala Val Gly Ser Glu Val Leu
                 85                  90                  95

Ser Ala Gln Pro Asn Ala Ala Pro Leu Leu Met Pro Ala Met Arg Tyr
            100                 105                 110

Leu Gln Asn Ala Leu Val Ala Ala Leu Asp Arg Tyr Ile Lys Ile
            115                 120                 125

Ser Thr Pro His Ser Ser Ile Ile Leu Asp Ser Phe Pro Pro Ser
            130                 135                 140

Gln Ala Phe Phe Asn Arg Ser Leu Asp Ser Val Leu Val Pro Met Leu
145                 150                 155                 160

Lys Phe Leu Gln Ser Thr Gly Ser Pro Leu Met Leu Asn Val Tyr Pro
                165                 170                 175

Tyr Tyr Asp Tyr Met Arg Ser Asn Gly Val Ile Pro Leu Asp Tyr Ala
                180                 185                 190

Leu Phe Arg Pro Leu Pro Ala Asn Lys Glu Ala Val Asp Ala Asn Thr
            195                 200                 205

Leu Leu His Tyr Thr Asn Val Phe Asp Ala Val Asp Ala Ala Tyr
            210                 215                 220

Phe Ala Met Ala Tyr Leu Asn Val Thr Asn Val Pro Val Met Val Thr
225                 230                 235                 240

Glu Thr Gly Trp Pro His Lys Gly Asp Pro Ser Ser Glu Pro Asp Ala
                245                 250                 255

Thr Ser Asp Asn Ala Asp Thr Tyr Asn Ser Asn Leu Ile Arg His Val
                260                 265                 270

Met Asn Ser Thr Gly Thr Pro Lys His Pro Arg Val Ala Val Pro Thr
            275                 280                 285

Tyr Ile Tyr Glu Leu Tyr Asp Glu Asp Thr Arg Pro Gly Ser Thr Ser
290                 295                 300

Glu Lys Tyr Trp Gly Leu Phe Asp Met Asn Gly Val Pro Ala Tyr Thr
305                 310                 315                 320

Leu
```

<210> SEQ ID NO 77
<211> LENGTH: 330
<212> TYPE: PRT
<213> ORGANISM: Zea mays

<400> SEQUENCE: 77

```
Val Gly Val Thr Ile Gly Thr Gln Val Thr Asn Leu Leu Ser Pro Ser
 1               5                  10                  15

Asp Leu Ala Ser Phe Leu Arg Ala Gln Arg Ile Thr Arg Val Arg Leu
                20                  25                  30

Tyr Asp Ala Asp Pro Arg Leu Leu Ser Ala Leu Ala Ala Ser Gly Val
            35                  40                  45

Arg Ala Ile Val Gly Val Pro Asn Asp Glu Leu Leu Ala Leu Gly Ser
 50                  55                  60

Ser Pro Ala Thr Ala Ala Ser Trp Val Ser Arg Val Val Pro Phe
65                  70                  75                  80

Ala Gly Val Asn Ser Ser Thr Pro Asn Val Val Ser Ala Ile Ala Val
                85                  90                  95

Gly Asp Glu Val Pro Thr Ala Leu Pro Ser Ala Leu Pro Val Leu Leu
            100                 105                 110

Pro Ala Ile Arg Ser Leu Ala Ala Ala Leu Ala Ala Asn Leu Ser
            115                 120                 125
```

```
Ser Ile Pro Val Ser Thr Pro Leu Pro Phe Ser Val Val Asp Pro
    130                 135                 140

Phe Pro Pro Ser Gln Ala Phe Asn Gln Ser Leu Asp Lys Ser Phe
145                 150                 155                 160

Val Ala Pro Leu Leu Ala His Leu Ala Asn Thr Ser Ala Pro Leu Met
                165                 170                 175

Leu Asn Leu Tyr Pro Tyr Tyr Ser Leu Met Gln Ser Lys Gly Val Ile
                180                 185                 190

Pro Leu Asp Asn Ala Leu Phe Arg Pro Leu Pro Pro Ser Met Glu Met
            195                 200                 205

Val Asp Pro Asn Thr Leu Leu Arg Tyr Thr Asn Val Phe Asp Ala Met
    210                 215                 220

Leu Asp Ala Val Arg Val Ala Val Arg Asn Leu Asn Ala Thr Gly Gly
225                 230                 235                 240

Ala Gly Val Pro Ile Leu Val Thr Glu Thr Gly Trp Pro Ser Tyr Gly
                245                 250                 255

Asp Arg Arg Ala Glu Pro Tyr Ala Gly Arg Asp Asn Ala Asp Ala Tyr
            260                 265                 270

Asn Ser Asn Leu Ile Lys His Val Leu Glu Glu Lys Ala Gly Thr Pro
    275                 280                 285

Met Ala Pro Gly Ala Gly Ala Gln Ser Ser Ala Tyr Ile Tyr Glu Leu
290                 295                 300

Phe Asn Glu Asp Leu Arg Ala Gly Pro Val Ser Glu Ala Asn Trp Gly
305                 310                 315                 320

Leu Phe Tyr Gly Asn Gly Thr Pro Val Tyr
                325                 330

<210> SEQ ID NO 78
<211> LENGTH: 330
<212> TYPE: PRT
<213> ORGANISM: Zea mays

<400> SEQUENCE: 78

Val Gly Val Thr Ile Gly Thr Gln Val Thr Asn Leu Leu Ser Pro Ser
1               5                   10                  15

Asp Leu Ala Ser Phe Leu Arg Ala Gln Arg Ile Thr Arg Val Arg Leu
                20                  25                  30

Tyr Asp Ala Asp Pro Arg Leu Leu Ser Ala Leu Ala Ala Ser Gly Val
            35                  40                  45

Arg Ala Ile Val Gly Val Pro Asn Asp Glu Leu Leu Ala Leu Gly Ser
    50                  55                  60

Ser Pro Ala Thr Ala Ala Ser Trp Val Ser Arg Arg Val Val Pro Phe
65                  70                  75                  80

Ala Gly Val Asn Ser Ser Thr Pro Asn Val Val Ser Ala Ile Ala Val
                85                  90                  95

Gly Asp Glu Val Pro Thr Ala Leu Pro Ser Ala Leu Pro Val Leu Leu
            100                 105                 110

Pro Ala Ile Arg Ser Leu Ala Ala Ala Leu Ala Ala Ala Asn Leu Ser
        115                 120                 125

Ser Ile Pro Val Ser Thr Pro Leu Pro Phe Ser Val Val Asp Pro
    130                 135                 140

Phe Pro Pro Ser Gln Ala Phe Asn Gln Ser Leu Asp Lys Ser Phe
145                 150                 155                 160

Val Ala Pro Leu Leu Ala His Leu Ala Asn Thr Ser Ala Pro Leu Met
                165                 170                 175
```

```
Leu Asn Leu Tyr Pro Tyr Tyr Ser Leu Met Gln Ser Lys Gly Val Ile
                180                 185                 190

Pro Leu Asp Asn Ala Leu Phe Arg Pro Leu Pro Ser Met Glu Met
            195                 200                 205

Val Asp Pro Asn Thr Leu Leu Arg Tyr Thr Asn Val Phe Asp Ala Met
210                 215                 220

Leu Asp Ala Val Arg Val Ala Val Arg Asn Leu Asn Ala Thr Gly Gly
225                 230                 235                 240

Ala Gly Val Pro Ile Leu Val Thr Glu Thr Gly Trp Pro Ser Tyr Gly
                245                 250                 255

Asp Arg Arg Ala Glu Pro Tyr Ala Gly Arg Asp Asn Ala Asp Ala Tyr
                260                 265                 270

Asn Ser Asn Leu Ile Lys His Val Leu Glu Glu Lys Ala Gly Thr Pro
            275                 280                 285

Met Ala Pro Gly Ala Gly Ala Gln Ser Ser Ala Tyr Ile Tyr Glu Leu
        290                 295                 300

Phe Asn Glu Asp Leu Arg Ala Gly Pro Val Ser Glu Ala Asn Trp Gly
305                 310                 315                 320

Leu Phe Tyr Gly Asn Gly Thr Pro Val Tyr
                325                 330

<210> SEQ ID NO 79
<211> LENGTH: 330
<212> TYPE: PRT
<213> ORGANISM: Zea mays

<400> SEQUENCE: 79

Val Gly Val Thr Ile Gly Thr Gln Val Thr Asn Leu Leu Ser Pro Ser
1               5                   10                  15

Asp Leu Ala Ser Phe Leu Arg Ala Gln Arg Ile Thr Arg Val Arg Leu
            20                  25                  30

Tyr Asp Ala Asp Pro Arg Leu Leu Ser Ala Leu Ala Ala Ser Gly Val
        35                  40                  45

Arg Ala Ile Val Gly Val Pro Asn Asp Glu Leu Leu Ala Leu Gly Ser
    50                  55                  60

Ser Pro Ala Thr Ala Ala Ser Trp Val Ser Arg Arg Val Val Pro Phe
65                  70                  75                  80

Ala Gly Val Asn Ser Ser Thr Pro Asn Val Val Ser Ala Ile Ala Val
                85                  90                  95

Gly Asp Glu Val Pro Thr Ala Leu Pro Ser Ala Leu Pro Val Leu Leu
            100                 105                 110

Pro Ala Ile Arg Ser Leu Ala Ala Ala Leu Ala Ala Ala Asn Leu Ser
        115                 120                 125

Ser Ile Pro Val Ser Thr Pro Leu Pro Phe Ser Val Val Asp Pro
    130                 135                 140

Phe Pro Pro Ser Gln Ala Phe Phe Asn Gln Ser Leu Asp Lys Ser Phe
145                 150                 155                 160

Val Ala Pro Leu Leu Ala His Leu Ala Asn Thr Ser Ala Pro Leu Met
                165                 170                 175

Leu Asn Leu Tyr Pro Tyr Tyr Ser Leu Met Gln Ser Lys Gly Val Ile
                180                 185                 190

Pro Leu Asp Asn Ala Leu Phe Arg Pro Leu Pro Ser Met Glu Met
            195                 200                 205

Val Asp Pro Asn Thr Leu Leu Arg Tyr Thr Asn Val Phe Asp Ala Met
```

Leu Asp Ala Val Arg Val Ala Val Arg Asn Leu Asn Ala Thr Gly Gly
225                 230                 235                 240

Ala Gly Val Pro Ile Leu Val Thr Glu Thr Gly Trp Pro Ser Tyr Gly
            245                 250                 255

Asp Arg Arg Ala Glu Pro Tyr Ala Gly Arg Asp Asn Ala Asp Ala Tyr
                260                 265                 270

Asn Ser Asn Leu Ile Lys His Val Leu Glu Glu Lys Ala Gly Thr Pro
            275                 280                 285

Met Ala Pro Gly Ala Gly Ala Gln Ser Ser Ala Tyr Ile Tyr Glu Leu
        290                 295                 300

Phe Asn Glu Asp Leu Arg Ala Gly Pro Val Ser Glu Ala Asn Trp Gly
305                 310                 315                 320

Leu Phe Tyr Gly Asn Gly Thr Pro Val Tyr
                325                 330

<210> SEQ ID NO 80
<211> LENGTH: 447
<212> TYPE: PRT
<213> ORGANISM: Zea mays

<400> SEQUENCE: 80

Val Gly Val Thr Ile Gly Thr Gln Val Thr Asn Leu Leu Ser Pro Ser
1               5                   10                  15

Asp Leu Ala Ser Phe Leu Arg Ala Gln Arg Ile Thr Arg Val Arg Leu
            20                  25                  30

Tyr Asp Ala Asp Pro Arg Leu Leu Ser Ala Leu Ala Ala Ser Gly Val
        35                  40                  45

Arg Ala Ile Val Gly Val Pro Asn Asp Glu Leu Leu Ala Leu Gly Ser
    50                  55                  60

Ser Pro Ala Thr Ala Ala Ser Trp Val Ser Arg Arg Val Val Pro Phe
65                  70                  75                  80

Ala Gly Val Asn Ser Ser Thr Pro Asn Val Val Ser Ala Ile Ala Val
                85                  90                  95

Gly Asp Glu Val Pro Thr Ala Leu Pro Ser Ala Leu Pro Val Leu Leu
            100                 105                 110

Pro Ala Ile Arg Ser Leu Ala Ala Ala Leu Ala Ala Asn Leu Ser
        115                 120                 125

Ser Ile Pro Val Ser Thr Pro Leu Pro Phe Ser Val Val Asp Pro
130                 135                 140

Phe Pro Pro Ser Gln Ala Phe Phe Asn Gln Ser Leu Asp Lys Ser Phe
145                 150                 155                 160

Val Ala Pro Leu Leu Ala His Leu Ala Asn Thr Ser Ala Pro Leu Met
                165                 170                 175

Leu Asn Leu Tyr Pro Tyr Tyr Ser Leu Met Gln Ser Lys Gly Val Ile
            180                 185                 190

Pro Leu Asp Asn Ala Leu Phe Arg Pro Leu Pro Ser Met Glu Met
        195                 200                 205

Val Asp Pro Asn Thr Leu Leu Arg Tyr Thr Asn Val Phe Asp Ala Met
    210                 215                 220

Leu Asp Ala Val Arg Val Ala Val Arg Asn Leu Asn Ala Thr Gly Gly
225                 230                 235                 240

Ala Gly Val Pro Ile Leu Val Thr Glu Thr Gly Trp Pro Ser Tyr Gly
                245                 250                 255

-continued

Asp Arg Arg Ala Glu Pro Tyr Ala Gly Arg Asp Asn Ala Asp Ala Tyr
            260                 265                 270

Asn Ser Asn Leu Ile Lys His Val Leu Glu Glu Lys Ala Gly Thr Pro
        275                 280                 285

Met Ala Pro Gly Ala Gly Ala Gln Ser Ser Ala Tyr Ile Tyr Glu Leu
    290                 295                 300

Phe Asn Glu Asp Leu Arg Ala Gly Pro Val Ser Glu Ala Asn Trp Gly
305                 310                 315                 320

Leu Phe Tyr Gly Asn Gly Thr Pro Val Tyr Leu Leu His Val Ser Gly
                325                 330                 335

Ala Asp Gly Phe Leu Gly Asn Asp Thr Thr Asp Arg Thr Phe Cys Val
            340                 345                 350

Ala Ala Asp Asp Ala Asp Gln Lys Ala Val Gln Ala Ala Met Asp Trp
        355                 360                 365

Ala Cys Gly Pro Gly Arg Ala Asp Cys Thr Ala Ile Gln Pro Gly Gln
    370                 375                 380

Ala Cys Tyr Gln Pro Asp Asp Val Arg Ser His Ala Ser Phe Ala Phe
385                 390                 395                 400

Asp Ala Tyr Tyr Gln Ser Gln Gly Arg Ala Ala Gly Ser Cys Tyr Phe
                405                 410                 415

Gln Gly Ala Gly Met Val Thr Thr Val Asp Pro Ser Glu Cys His Leu
            420                 425                 430

Ala Phe Phe Ser Ala Cys Ser Ile Val Thr Ile Arg Val Tyr Tyr
        435                 440                 445

<210> SEQ ID NO 81
<211> LENGTH: 330
<212> TYPE: PRT
<213> ORGANISM: Zea mays

<400> SEQUENCE: 81

Val Gly Val Thr Ile Gly Thr Gln Val Thr Asn Leu Leu Ser Pro Ser
1               5                   10                  15

Asp Leu Ala Ser Phe Leu Arg Ala Gln Arg Ile Thr Arg Val Arg Leu
            20                  25                  30

Tyr Asp Ala Asp Pro Arg Leu Leu Ser Ala Leu Ala Ala Ser Gly Val
        35                  40                  45

Arg Ala Ile Val Gly Val Pro Asn Asp Glu Leu Leu Ala Leu Gly Ser
    50                  55                  60

Ser Pro Ala Thr Ala Ala Ser Trp Val Ser Arg Arg Val Val Pro Phe
65                  70                  75                  80

Ala Gly Val Asn Ser Ser Thr Pro Asn Val Val Ser Ala Ile Ala Val
                85                  90                  95

Gly Asp Glu Val Pro Thr Ala Leu Pro Ser Ala Leu Pro Val Leu Leu
            100                 105                 110

Pro Ala Ile Arg Ser Leu Ala Ala Ala Leu Ala Ala Ala Asn Leu Ser
        115                 120                 125

Ser Ile Pro Val Ser Thr Pro Leu Pro Phe Ser Val Val Asp Pro
    130                 135                 140

Phe Pro Pro Ser Gln Ala Phe Phe Asn Gln Ser Leu Asp Lys Ser Phe
145                 150                 155                 160

Val Ala Pro Leu Leu Ala His Leu Ala Asn Thr Ser Ala Pro Leu Met
                165                 170                 175

Leu Asn Leu Tyr Pro Tyr Tyr Ser Leu Met Gln Ser Lys Gly Val Ile
            180                 185                 190

```
Pro Leu Asp Asn Ala Leu Phe Arg Pro Leu Pro Pro Ser Met Glu Met
        195                 200                 205

Val Asp Pro Asn Thr Leu Leu Arg Tyr Thr Asn Val Phe Asp Ala Met
210                 215                 220

Leu Asp Ala Val Arg Val Ala Val Arg Asn Leu Asn Ala Thr Gly Gly
225                 230                 235                 240

Ala Gly Val Pro Ile Leu Val Thr Glu Thr Gly Trp Pro Ser Tyr Gly
                245                 250                 255

Asp Arg Arg Ala Glu Pro Tyr Ala Gly Arg Asp Asn Ala Asp Ala Tyr
                260                 265                 270

Asn Ser Asn Leu Ile Lys His Val Leu Glu Glu Lys Ala Gly Thr Pro
            275                 280                 285

Met Ala Pro Gly Ala Gly Ala Gln Ser Ser Ala Tyr Ile Tyr Glu Leu
        290                 295                 300

Phe Asn Glu Asp Leu Arg Ala Gly Pro Val Ser Glu Ala Asn Trp Gly
305                 310                 315                 320

Leu Phe Tyr Gly Asn Gly Thr Pro Val Tyr
                325                 330

<210> SEQ ID NO 82
<211> LENGTH: 210
<212> TYPE: PRT
<213> ORGANISM: Artificial Sequence
<220> FEATURE:
<223> OTHER INFORMATION: Consensus Sequence

<400> SEQUENCE: 82

Ile Gly Val Asn Tyr Gly Val Ala Asn Leu Pro Pro Val Val Leu Leu
1               5                   10                  15

Arg Ser Ile Lys Val Arg Leu Tyr Asp Ala Asp Val Leu Ala Leu Ala
            20                  25                  30

Gly Thr Gly Ile Val Val Gly Val Pro Asn Leu Ala Ala Ser Ala
        35                  40                  45

Trp Val Asn Val Pro Tyr Pro Ala Ile Val Ala Val Gly Asn Glu Val
50                  55                  60

Leu Leu Pro Ala Met Arg Asn Leu His Ala Leu Ala Gly Leu Val Lys
65                  70                  75                  80

Val Ser Thr Val Ser Val Leu Ala Ser Pro Ser Ala Gly Phe Arg
                85                  90                  95

Leu Met Pro Leu Leu Phe Leu Ala Thr Gly Ala Pro Leu Leu Val Asn
                100                 105                 110

Ile Tyr Pro Tyr Phe Ala Tyr Ile Leu Asp Tyr Ala Leu Phe Pro Val
            115                 120                 125

Val Asp Thr Gly Leu Tyr Thr Asn Met Phe Asp Ala Gln Val Asp Ala
130                 135                 140

Val Tyr Ala Ala Leu Leu Gly Val Val Val Ser Glu Thr Gly Trp
145                 150                 155                 160

Pro Ser Gly Glu Gly Ala Thr Glu Asn Ala Tyr Asn Asn Leu Ile Arg
                165                 170                 175

Val Gly Gly Thr Pro Arg Pro Gly Tyr Ile Phe Ala Leu Phe Asn Glu
                180                 185                 190

Asp Lys Gly Ser Glu Arg Trp Gly Leu Phe Pro Asp Gly Thr Pro Val
            195                 200                 205

Tyr Leu
    210
```

<210> SEQ ID NO 83
<211> LENGTH: 306
<212> TYPE: PRT
<213> ORGANISM: Brachypodium distachyon

<400> SEQUENCE: 83

| Ile | Gly | Val | Cys | Tyr | Gly | Met | Ser | Ala | Asn | Asn | Leu | Pro | Ala | Ala | Asn |
|---|---|---|---|---|---|---|---|---|---|---|---|---|---|---|---|
| 1 | | | | 5 | | | | | 10 | | | | | 15 | |

| Thr | Val | Val | Gly | Met | Phe | Lys | Ser | Asn | Gly | Ile | Asn | Ala | Met | Arg | Leu |
| | | | 20 | | | | | 25 | | | | | 30 | | |

| Tyr | Ala | Pro | Asp | Gln | Ala | Ala | Leu | Gln | Ala | Val | Gly | Gly | Thr | Gly | Val |
| | | 35 | | | | 40 | | | | | 45 | | | | |

| Ser | Val | Ala | Val | Gly | Ala | Pro | Asn | Asp | Val | Leu | Ser | Asn | Ile | Ala | Ser |
| | 50 | | | | | 55 | | | | | 60 | | | | |

| Ser | Pro | Ala | Ala | Ala | Ser | Trp | Val | Arg | Asn | Asn | Ile | Gln | Ala | Tyr |
| 65 | | | | 70 | | | | | 75 | | | | | 80 |

| Pro | Ser | Val | Ser | Phe | Arg | Tyr | Val | Val | Gly | Asn | Glu | Val | Ala | Gly |
| | | | | 85 | | | | | 90 | | | | | 95 |

| Gly | Ala | Thr | Gln | Asn | Leu | Val | Pro | Ala | Met | Lys | Asn | Val | His | Ser | Ala |
| | | | 100 | | | | | 105 | | | | | 110 | | |

| Leu | Ala | Ser | Ala | Gly | Leu | Gly | His | Ile | Lys | Val | Thr | Thr | Ser | Val | Ser |
| | | 115 | | | | 120 | | | | | 125 | | | | |

| Gln | Ala | Ile | Leu | Gly | Val | Tyr | Ser | Pro | Pro | Ser | Ala | Gly | Ser | Phe | Thr |
| | 130 | | | | | 135 | | | | | 140 | | | | |

| Gly | Glu | Ala | Asp | Ala | Phe | Met | Gly | Pro | Val | Val | Gln | Phe | Leu | Ala | Ser |
| 145 | | | | 150 | | | | | 155 | | | | | 160 |

| Ala | Gly | Ser | Pro | Leu | Met | Ala | Asn | Ile | Tyr | Pro | Tyr | Leu | Ala | Trp | Ala |
| | | | | 165 | | | | | 170 | | | | | 175 |

| Tyr | Asn | Pro | Ser | Ala | Met | Asp | Met | Ser | Tyr | Ala | Leu | Phe | Thr | Ala | Ser |
| | | | 180 | | | | | 185 | | | | | 190 | | |

| Gly | Thr | Val | Val | Gln | Asp | Gly | Ala | Tyr | Gly | Tyr | Gln | Asn | Leu | Phe | Asp |
| | | 195 | | | | 200 | | | | | 205 | | | | |

| Thr | Thr | Val | Asp | Ala | Phe | Tyr | Asn | Ala | Met | Ala | Lys | His | Gly | Gly | Asn |
| | 210 | | | | | 215 | | | | | 220 | | | | |

| Gly | Val | Lys | Leu | Val | Val | Ser | Glu | Ser | Gly | Trp | Pro | Ser | Ala | Gly | Gly |
| 225 | | | | 230 | | | | | 235 | | | | | 240 |

| Thr | Ala | Ala | Thr | Pro | Ala | Asn | Ala | Arg | Val | Tyr | Asn | Gln | Tyr | Leu | Ile |
| | | | | 245 | | | | | 250 | | | | | 255 |

| Asn | His | Val | Gly | Arg | Gly | Thr | Pro | Arg | His | Pro | Gly | Ala | Ile | Glu | Thr |
| | | | 260 | | | | | 265 | | | | | 270 | | |

| Tyr | Val | Phe | Ser | Met | Phe | Asn | Glu | Asn | Gln | Lys | Asp | Ser | Gly | Val | Glu |
| | | 275 | | | | 280 | | | | | 285 | | | | |

| Gln | Asn | Trp | Gly | Leu | Phe | Tyr | Pro | Asn | Met | Gln | His | Val | Tyr | Pro | Ile |
| | 290 | | | | | 295 | | | | | 300 | | | | |

| Ser | Phe |
| 305 | |

<210> SEQ ID NO 84
<211> LENGTH: 307
<212> TYPE: PRT
<213> ORGANISM: Zea mays

<400> SEQUENCE: 84

| Ile | Gly | Val | Cys | Tyr | Gly | Met | Ser | Ala | Asn | Asp | Leu | Pro | Ala | Ala | Ser |
|---|---|---|---|---|---|---|---|---|---|---|---|---|---|---|---|
| 1 | | | | 5 | | | | | 10 | | | | | 15 | |

Thr Val Val Ser Met Tyr Lys Ala Asn Gly Ile Ser Ala Met Arg Leu
            20                  25                  30

Tyr Ala Pro Asp Gln Gly Val Leu Gln Ala Val Gly Gly Thr Asp Ile
            35                  40                  45

Ser Val Thr Val Gly Thr Pro Asn Asp Ala Leu Ser Asn Ile Ala Ala
50                      55                  60

Ser Pro Ala Ala Ala Ala Ser Trp Val Arg Asn Asn Ile Gln Ala Tyr
65                  70                  75                  80

Pro Ser Val Ser Phe Arg His Val Cys Val Gly Asn Glu Val Ala Gly
                85                  90                  95

Gly Ala Ala Arg Asn Leu Ala Pro Ala Met Glu Asn Val His Ala Ala
            100                 105                 110

Leu Ala Ala Ala Gly Leu Gly His Ile Lys Val Thr Thr Ser Val Ser
            115                 120                 125

Gln Ala Ile Leu Gly Val Tyr Ser Pro Pro Ser Ala Ala Gln Phe Thr
130                 135                 140

Val Glu Ala Gln Gly Tyr Met Gly Pro Val Leu Lys Phe Leu Ala Arg
145                 150                 155                 160

Thr Gly Ser Pro Leu Met Ala Asn Ile Tyr Pro Tyr Leu Ala Trp Ala
            165                 170                 175

Tyr Asn Pro Ser Ala Met Asp Met Ser Tyr Ala Ile Phe Thr Ser Ser
            180                 185                 190

Gly Thr Val Val Gln Asp Gly Ala Tyr Gly Tyr Gln Asn Leu Phe Asp
            195                 200                 205

Thr Thr Val Asp Ala Phe Tyr Leu Ala Met Ala Ser Asn Gly Gly Gly
            210                 215                 220

Ser Gly Val Pro Leu Val Val Ser Glu Thr Gly Trp Pro Ser Gly Gly
225                 230                 235                 240

Gly Val Gln Ala Thr Pro Ala Asn Ala Arg Val Tyr Asn Gln Tyr Leu
            245                 250                 255

Ile Asn His Val Gly Arg Gly Thr Pro Arg His Pro Gly Gly Ile Glu
            260                 265                 270

Thr Tyr Leu Phe Ser Met Phe Asn Glu Asn Gln Lys Glu Ser Gly Val
            275                 280                 285

Glu Gln Asn Trp Gly Leu Phe Tyr Pro Asn Met His His Val Tyr Pro
290                 295                 300

Ile Ser Phe
305

<210> SEQ ID NO 85
<211> LENGTH: 306
<212> TYPE: PRT
<213> ORGANISM: Brachypodium distachyon

<400> SEQUENCE: 85

Ile Gly Val Cys Tyr Gly Met Ser Ala Asn Asn Leu Pro Ala Ala Asn
 1               5                  10                  15

Thr Val Val Gly Met Phe Lys Ser Asn Gly Ile Asn Ala Met Arg Leu
            20                  25                  30

Tyr Ala Pro Asp Gln Ala Ala Leu Gln Ala Val Gly Gly Thr Gly Val
            35                  40                  45

Ser Val Ala Val Gly Ala Pro Asn Asp Val Leu Ser Asn Ile Ala Ser
50                  55                      60

Ser Pro Ala Ala Ala Ala Ser Trp Val Arg Asn Asn Ile Gln Ala Tyr

```
                65                  70                  75                  80
        Pro Ser Val Ser Phe Arg Tyr Val Val Gly Asn Glu Val Ala Gly
                        85                  90                  95
        Gly Ala Thr Gln Asn Leu Val Pro Ala Met Lys Asn Val His Ser Ala
                        100                 105                 110
        Leu Ala Ser Ala Gly Leu Gly His Ile Lys Val Thr Thr Ser Val Ser
                        115                 120                 125
        Gln Ala Ile Leu Gly Val Tyr Ser Pro Pro Ser Ala Gly Ser Phe Thr
                130                 135                 140
        Gly Glu Ala Asp Ala Phe Met Gly Pro Val Val Gln Phe Leu Ala Ser
        145                 150                 155                 160
        Ala Gly Ser Pro Leu Met Ala Asn Ile Tyr Pro Tyr Leu Ala Trp Ala
                        165                 170                 175
        Tyr Asn Pro Ser Ala Met Asp Met Ser Tyr Ala Leu Phe Thr Ala Ser
                        180                 185                 190
        Gly Thr Val Val Gln Asp Gly Ala Tyr Gly Tyr Gln Asn Leu Phe Asp
                        195                 200                 205
        Thr Thr Val Asp Ala Phe Tyr Asn Ala Met Ala Lys His Gly Gly Asn
                210                 215                 220
        Gly Val Lys Leu Val Val Ser Glu Ser Gly Trp Pro Ser Ala Gly Gly
        225                 230                 235                 240
        Thr Ala Ala Thr Pro Ala Asn Ala Arg Val Tyr Asn Gln Tyr Leu Ile
                        245                 250                 255
        Asn His Val Gly Arg Gly Thr Pro Arg His Pro Gly Ala Ile Glu Thr
                        260                 265                 270
        Tyr Val Phe Ser Met Phe Asn Glu Asn Gln Lys Asp Ser Gly Val Glu
                        275                 280                 285
        Gln Asn Trp Gly Leu Phe Tyr Pro Asn Met Gln His Val Tyr Pro Ile
                        290                 295                 300
        Ser Phe
        305

<210> SEQ ID NO 86
<211> LENGTH: 306
<212> TYPE: PRT
<213> ORGANISM: Sorghum bicolor

<400> SEQUENCE: 86

Ile Gly Val Cys Tyr Gly Met Ser Ala Asn Asn Leu Pro Pro Ala Ser
        1               5                   10                  15
        Thr Val Val Ser Met Tyr Lys Ser Asn Gly Ile Thr Ala Met Arg Leu
                        20                  25                  30
        Tyr Ala Pro Asp Gln Gly Ala Leu Gln Ala Val Gly Gly Ser Gly Ile
                        35                  40                  45
        Ser Val Thr Val Gly Ala Pro Asn Asp Val Leu Ser Ser Ile Ala Gly
                        50                  55                  60
        Ser Pro Ala Ala Ala Ser Trp Val Arg Asn Asn Ile Gln Ala Tyr
        65                  70                  75                  80
        Pro Ser Val Ser Phe Arg Tyr Val Cys Val Gly Asn Glu Val Ala Gly
                        85                  90                  95
        Gly Ala Ala Gln Asn Leu Ala Pro Ala Met Glu Asn Val His Ala Ala
                        100                 105                 110
        Leu Ala Ala Ala Gly Leu Gly His Ile Lys Val Thr Thr Ser Val Ser
                        115                 120                 125
```

```
Gln Ala Ile Leu Gly Val Tyr Ser Pro Pro Ser Ala Gln Phe Thr
130                 135                 140

Ala Glu Ala Gln Gly Phe Met Gly Pro Val Leu Gln Phe Leu Ser Arg
145                 150                 155                 160

Thr Gly Ser Pro Leu Met Ala Asn Ile Tyr Pro Tyr Leu Ala Trp Ala
                165                 170                 175

Tyr Asn Pro Ser Ala Met Asp Met Ser Tyr Ala Leu Phe Thr Ala Ser
                180                 185                 190

Gly Thr Val Val Gln Asp Gly Ala Tyr Gly Tyr Gln Asn Leu Phe Asp
                195                 200                 205

Thr Thr Val Asp Ala Phe Tyr Val Ala Met Gly Arg Asn Gly Gly Ser
210                 215                 220

Gly Val Pro Leu Val Val Ser Glu Ser Gly Trp Pro Ser Gly Gly Gly
225                 230                 235                 240

Val Gln Ala Thr Pro Ala Asn Ala Arg Val Tyr Asn Gln Tyr Leu Val
                245                 250                 255

Asn His Val Arg Arg Gly Thr Pro Arg His Pro Gly Ala Ile Glu Thr
                260                 265                 270

Tyr Leu Phe Ser Met Phe Asn Glu Asn Gln Lys Glu Ser Gly Val Glu
                275                 280                 285

Gln Asn Trp Gly Leu Phe Tyr Pro Asn Met Gln Arg Val Tyr Pro Ile
290                 295                 300

Ser Phe
305

<210> SEQ ID NO 87
<211> LENGTH: 300
<212> TYPE: PRT
<213> ORGANISM: Sorghum bicolor

<400> SEQUENCE: 87

Met Ser Ala Asn Asn Leu Pro Pro Ala Ser Thr Val Val Ser Met Tyr
1               5                   10                  15

Lys Ser Asn Gly Ile Thr Ala Met Arg Leu Tyr Ala Pro Asp Gln Gly
                20                  25                  30

Ala Leu Gln Ala Val Gly Gly Ser Gly Ile Ser Val Thr Val Gly Ala
                35                  40                  45

Pro Asn Asp Val Leu Ser Ser Ile Ala Gly Ser Pro Ala Ala Ala Ala
                50                  55                  60

Ser Trp Val Arg Asn Asn Ile Gln Ala Tyr Pro Ser Val Ser Phe Arg
65                  70                  75                  80

Tyr Val Cys Val Gly Asn Glu Val Ala Gly Ala Ala Gln Asn Leu
                85                  90                  95

Ala Pro Ala Met Glu Asn Val His Ala Leu Ala Ala Ala Gly Leu
                100                 105                 110

Gly His Ile Lys Val Thr Thr Ser Val Ser Gln Ala Ile Leu Gly Val
                115                 120                 125

Tyr Ser Pro Pro Ser Ala Ala Gln Phe Thr Ala Glu Ala Gln Gly Phe
                130                 135                 140

Met Gly Pro Val Leu Gln Phe Leu Ser Arg Thr Gly Ser Pro Leu Met
145                 150                 155                 160

Ala Asn Ile Tyr Pro Tyr Leu Ala Trp Ala Tyr Asn Pro Ser Ala Met
                165                 170                 175

Asp Met Ser Tyr Ala Leu Phe Thr Ala Ser Gly Thr Val Val Gln Asp
                180                 185                 190
```

Gly Ala Tyr Gly Tyr Gln Asn Leu Phe Asp Thr Thr Val Asp Ala Phe
            195                 200                 205

Tyr Val Ala Met Gly Arg Asn Gly Gly Ser Gly Val Pro Leu Val Val
            210                 215                 220

Ser Glu Ser Gly Trp Pro Ser Gly Gly Gly Val Gln Ala Thr Pro Ala
225                 230                 235                 240

Asn Ala Arg Val Tyr Asn Gln Tyr Leu Val Asn His Val Arg Arg Gly
            245                 250                 255

Thr Pro Arg His Pro Gly Ala Ile Glu Thr Tyr Leu Phe Ser Met Phe
            260                 265                 270

Asn Glu Asn Gln Lys Glu Ser Gly Val Glu Gln Asn Trp Gly Leu Phe
            275                 280                 285

Tyr Pro Asn Met Gln Arg Val Tyr Pro Ile Ser Phe
            290                 295                 300

<210> SEQ ID NO 88
<211> LENGTH: 300
<212> TYPE: PRT
<213> ORGANISM: Sorghum bicolor

<400> SEQUENCE: 88

Met Ser Ala Asn Asn Leu Pro Pro Ala Ser Thr Val Val Ser Met Tyr
1               5                   10                  15

Lys Ser Asn Gly Ile Thr Ala Met Arg Leu Tyr Ala Pro Asp Gln Gly
            20                  25                  30

Ala Leu Gln Ala Val Gly Gly Ser Gly Ile Ser Val Thr Val Gly Ala
            35                  40                  45

Pro Asn Asp Val Leu Ser Ser Ile Ala Gly Ser Pro Ala Ala Ala Ala
        50                  55                  60

Ser Trp Val Arg Asn Asn Ile Gln Ala Tyr Pro Ser Val Ser Phe Arg
65                  70                  75                  80

Tyr Val Cys Val Gly Asn Glu Val Ala Gly Gly Ala Gln Asn Leu
            85                  90                  95

Ala Pro Ala Met Glu Asn Val His Ala Ala Leu Ala Ala Ala Gly Leu
            100                 105                 110

Gly His Ile Lys Val Thr Thr Ser Val Ser Gln Ala Ile Leu Gly Val
            115                 120                 125

Tyr Ser Pro Pro Ser Ala Ala Gln Phe Thr Ala Glu Ala Gln Gly Phe
            130                 135                 140

Met Gly Pro Val Leu Gln Phe Leu Ser Arg Thr Gly Ser Pro Leu Met
145                 150                 155                 160

Ala Asn Ile Tyr Pro Tyr Leu Ala Trp Ala Tyr Asn Pro Ser Ala Met
            165                 170                 175

Asp Met Ser Tyr Ala Leu Phe Thr Ala Ser Gly Thr Val Val Gln Asp
            180                 185                 190

Gly Ala Tyr Gly Tyr Gln Asn Leu Phe Asp Thr Thr Val Asp Ala Phe
            195                 200                 205

Tyr Val Ala Met Gly Arg Asn Gly Gly Ser Gly Val Pro Leu Val Val
            210                 215                 220

Ser Glu Ser Gly Trp Pro Ser Gly Gly Gly Val Gln Ala Thr Pro Ala
225                 230                 235                 240

Asn Ala Arg Val Tyr Asn Gln Tyr Leu Val Asn His Val Arg Arg Gly
            245                 250                 255

Thr Pro Arg His Pro Gly Ala Ile Glu Thr Tyr Leu Phe Ser Met Phe

```
                    260                 265                 270
Asn Glu Asn Gln Lys Glu Ser Gly Val Glu Gln Asn Trp Gly Leu Phe
                275                 280                 285
Tyr Pro Asn Met Gln Arg Val Tyr Pro Ile Ser Phe
            290                 295                 300
```

<210> SEQ ID NO 89
<211> LENGTH: 306
<212> TYPE: PRT
<213> ORGANISM: Sorghum bicolor

<400> SEQUENCE: 89

```
Ile Gly Val Cys Tyr Gly Met Ser Ala Asn Asn Leu Pro Pro Ala Ser
  1               5                  10                  15
Thr Val Val Ser Met Tyr Lys Ser Asn Gly Ile Thr Ala Met Arg Leu
                 20                  25                  30
Tyr Ala Pro Asp Gln Gly Ala Leu Gln Ala Val Gly Gly Ser Gly Ile
             35                  40                  45
Ser Val Thr Val Gly Ala Pro Asn Asp Val Leu Ser Ser Ile Ala Gly
         50                  55                  60
Ser Pro Ala Ala Ala Ser Trp Val Arg Asn Asn Ile Gln Ala Tyr
 65                  70                  75                  80
Pro Ser Val Ser Phe Arg Tyr Val Cys Val Gly Asn Glu Val Ala Gly
                 85                  90                  95
Gly Ala Ala Gln Asn Leu Ala Pro Ala Met Glu Asn Val His Ala Ala
            100                 105                 110
Leu Ala Ala Gly Leu Gly His Ile Lys Val Thr Thr Ser Val Ser
        115                 120                 125
Gln Ala Ile Leu Gly Val Tyr Ser Pro Pro Ser Ala Ala Gln Phe Thr
    130                 135                 140
Ala Glu Ala Gln Gly Phe Met Gly Pro Val Leu Gln Phe Leu Ser Arg
145                 150                 155                 160
Thr Gly Ser Pro Leu Met Ala Asn Ile Tyr Pro Tyr Leu Ala Trp Ala
                165                 170                 175
Tyr Asn Pro Ser Ala Met Asp Met Ser Tyr Ala Leu Phe Thr Ala Ser
            180                 185                 190
Gly Thr Val Val Gln Asp Gly Ala Tyr Gly Tyr Gln Asn Leu Phe Asp
        195                 200                 205
Thr Thr Val Asp Ala Phe Tyr Val Ala Met Gly Arg Asn Gly Gly Ser
    210                 215                 220
Gly Val Pro Leu Val Val Ser Glu Ser Gly Trp Pro Ser Gly Gly Gly
225                 230                 235                 240
Val Gln Ala Thr Pro Ala Asn Ala Arg Val Tyr Asn Gln Tyr Leu Val
                245                 250                 255
Asn His Val Arg Arg Gly Thr Pro Arg His Pro Gly Ala Ile Glu Thr
            260                 265                 270
Tyr Leu Phe Ser Met Phe Asn Glu Asn Gln Lys Glu Ser Gly Val Glu
        275                 280                 285
Gln Asn Trp Gly Leu Phe Tyr Pro Asn Met Gln Arg Val Tyr Pro Ile
    290                 295                 300
Ser Phe
305
```

<210> SEQ ID NO 90
<211> LENGTH: 306

<212> TYPE: PRT
<213> ORGANISM: Setaria italica

<400> SEQUENCE: 90

Ile Gly Val Cys Tyr Gly Met Ser Ala Asn Asn Leu Pro Pro Ala Ser
1               5                   10                  15

Thr Val Ile Asp Met Tyr Lys Ala Asn Gly Ile Ser Ala Met Arg Leu
            20                  25                  30

Tyr Ala Pro Asp Gln Gly Ala Leu Gln Ala Val Gly Gly Ser Gly Ile
        35                  40                  45

Ser Val Thr Val Gly Ala Pro Asn Asp Val Leu Ser Asn Ile Ala Ala
    50                  55                  60

Ser Pro Ala Ala Ala Ser Trp Val Arg Asn Asn Ile Gln Ala Tyr
65                  70                  75                  80

Pro Ser Val Ser Phe Arg Tyr Ile Cys Val Gly Asn Glu Val Ala Gly
                85                  90                  95

Gly Ala Ala Gln Asn Leu Ala Pro Ala Met Glu Asn Val His Ala Ala
            100                 105                 110

Leu Ala Ala Ala Gly Leu Gly His Ile Lys Val Thr Thr Ser Val Ser
        115                 120                 125

Gln Ala Ile Leu Gly Val Tyr Ser Pro Pro Ser Ala Ala Glu Phe Thr
    130                 135                 140

Gly Glu Ala Lys Gly Tyr Met Gly Pro Val Leu Ser Phe Leu Ala Arg
145                 150                 155                 160

Thr Gly Ser Pro Leu Met Ala Asn Ile Tyr Pro Tyr Leu Ala Trp Ala
                165                 170                 175

Tyr Asn Pro Ser Ala Met Asp Met Ser Tyr Ala Leu Phe Thr Ser Lys
            180                 185                 190

Gly Thr Val Val Gln Asp Gly Ala Tyr Gly Tyr Gln Asn Leu Phe Asp
        195                 200                 205

Thr Thr Val Asp Ala Phe Tyr Phe Ala Met Gly Arg His Gly Gly Ser
    210                 215                 220

Gly Val Pro Leu Val Val Ser Glu Ser Gly Trp Pro Ser Gly Gly Gly
225                 230                 235                 240

Glu Gln Ala Asn Ala Ala Asn Ala Arg Ile Tyr Asn Gln Tyr Leu Ile
                245                 250                 255

Asn His Val Gly Arg Gly Thr Pro Arg His Pro Gly Gly Ile Glu Thr
            260                 265                 270

Tyr Leu Phe Ser Met Phe Asn Glu Asn Gln Lys Asp Ser Gly Val Glu
        275                 280                 285

Gln Asn Trp Gly Leu Phe Tyr Pro Asn Met Gln His Val Tyr Pro Ile
    290                 295                 300

Ser Phe
305

<210> SEQ ID NO 91
<211> LENGTH: 300
<212> TYPE: PRT
<213> ORGANISM: Setaria italica

<400> SEQUENCE: 91

Met Ser Ala Asn Asn Leu Pro Pro Ala Ser Thr Val Ile Asp Met Tyr
1               5                   10                  15

Lys Ala Asn Gly Ile Ser Ala Met Arg Leu Tyr Ala Pro Asp Gln Gly
            20                  25                  30

Ala Leu Gln Ala Val Gly Gly Ser Gly Ile Ser Val Thr Val Gly Ala
         35                  40                  45

Pro Asn Asp Val Leu Ser Asn Ile Ala Ala Ser Pro Ala Ala Ala Ala
 50                  55                  60

Ser Trp Val Arg Asn Asn Ile Gln Ala Tyr Pro Ser Val Ser Phe Arg
 65                  70                  75                  80

Tyr Ile Cys Val Gly Asn Glu Val Ala Gly Ala Ala Gln Asn Leu
                 85                  90                  95

Ala Pro Ala Met Glu Asn Val His Ala Leu Ala Ala Ala Gly Leu
             100                 105                 110

Gly His Ile Lys Val Thr Thr Ser Val Ser Gln Ala Ile Leu Gly Val
             115                 120                 125

Tyr Ser Pro Pro Ser Ala Ala Glu Phe Thr Gly Glu Ala Lys Gly Tyr
         130                 135                 140

Met Gly Pro Val Leu Ser Phe Leu Ala Arg Thr Gly Ser Pro Leu Met
145                 150                 155                 160

Ala Asn Ile Tyr Pro Tyr Leu Ala Trp Ala Tyr Asn Pro Ser Ala Met
                 165                 170                 175

Asp Met Ser Tyr Ala Leu Phe Thr Ser Lys Gly Thr Val Val Gln Asp
             180                 185                 190

Gly Ala Tyr Gly Tyr Gln Asn Leu Phe Asp Thr Thr Val Asp Ala Phe
         195                 200                 205

Tyr Phe Ala Met Gly Arg His Gly Gly Ser Gly Val Pro Leu Val Val
     210                 215                 220

Ser Glu Ser Gly Trp Pro Ser Gly Gly Gly Glu Gln Ala Asn Ala Ala
225                 230                 235                 240

Asn Ala Arg Ile Tyr Asn Gln Tyr Leu Ile Asn His Val Gly Arg Gly
                 245                 250                 255

Thr Pro Arg His Pro Gly Gly Ile Glu Thr Tyr Leu Phe Ser Met Phe
             260                 265                 270

Asn Glu Asn Gln Lys Asp Ser Gly Val Glu Gln Asn Trp Gly Leu Phe
         275                 280                 285

Tyr Pro Asn Met Gln His Val Tyr Pro Ile Ser Phe
     290                 295                 300

<210> SEQ ID NO 92
<211> LENGTH: 300
<212> TYPE: PRT
<213> ORGANISM: Setaria italica

<400> SEQUENCE: 92

Met Ser Ala Asn Asn Leu Pro Pro Ala Ser Thr Val Ile Asp Met Tyr
 1               5                  10                  15

Lys Ala Asn Gly Ile Ser Ala Met Arg Leu Tyr Ala Pro Asp Gln Gly
                 20                  25                  30

Ala Leu Gln Ala Val Gly Gly Ser Gly Ile Ser Val Thr Val Gly Ala
         35                  40                  45

Pro Asn Asp Val Leu Ser Asn Ile Ala Ala Ser Pro Ala Ala Ala Ala
 50                  55                  60

Ser Trp Val Arg Asn Asn Ile Gln Ala Tyr Pro Ser Val Ser Phe Arg
 65                  70                  75                  80

Tyr Ile Cys Val Gly Asn Glu Val Ala Gly Ala Ala Gln Asn Leu
                 85                  90                  95

Ala Pro Ala Met Glu Asn Val His Ala Leu Ala Ala Ala Gly Leu
             100                 105                 110

```
Gly His Ile Lys Val Thr Thr Ser Val Ser Gln Ala Ile Leu Gly Val
            115                 120                 125

Tyr Ser Pro Pro Ser Ala Ala Glu Phe Thr Gly Glu Ala Lys Gly Tyr
    130                 135                 140

Met Gly Pro Val Leu Ser Phe Leu Ala Arg Thr Gly Ser Pro Leu Met
145                 150                 155                 160

Ala Asn Ile Tyr Pro Tyr Leu Ala Trp Ala Tyr Asn Pro Ser Ala Met
                165                 170                 175

Asp Met Ser Tyr Ala Leu Phe Thr Ser Lys Gly Thr Val Val Gln Asp
            180                 185                 190

Gly Ala Tyr Gly Tyr Gln Asn Leu Phe Asp Thr Thr Val Asp Ala Phe
        195                 200                 205

Tyr Phe Ala Met Gly Arg His Gly Gly Ser Gly Val Pro Leu Val Val
    210                 215                 220

Ser Glu Ser Gly Trp Pro Ser Gly Gly Gly Glu Gln Ala Asn Ala Ala
225                 230                 235                 240

Asn Ala Arg Ile Tyr Asn Gln Tyr Leu Ile Asn His Val Gly Arg Gly
                245                 250                 255

Thr Pro Arg His Pro Gly Gly Ile Glu Thr Tyr Leu Phe Ser Met Phe
            260                 265                 270

Asn Glu Asn Gln Lys Asp Ser Gly Val Glu Gln Asn Trp Gly Leu Phe
        275                 280                 285

Tyr Pro Asn Met Gln His Val Tyr Pro Ile Ser Phe
    290                 295                 300

<210> SEQ ID NO 93
<211> LENGTH: 306
<212> TYPE: PRT
<213> ORGANISM: Setaria italica

<400> SEQUENCE: 93

Ile Gly Val Cys Tyr Gly Met Ser Ala Asn Asn Leu Pro Pro Ala Ser
  1               5                  10                  15

Thr Val Ile Asp Met Tyr Lys Ala Asn Gly Ile Ser Ala Met Arg Leu
             20                  25                  30

Tyr Ala Pro Asp Gln Gly Ala Leu Gln Ala Val Gly Gly Ser Gly Ile
         35                  40                  45

Ser Val Thr Val Gly Ala Pro Asn Asp Val Leu Ser Asn Ile Ala Ala
     50                  55                  60

Ser Pro Ala Ala Ala Ser Trp Val Arg Asn Asn Ile Gln Ala Tyr
 65                  70                  75                  80

Pro Ser Val Ser Phe Arg Tyr Ile Cys Val Gly Asn Glu Val Ala Gly
                 85                  90                  95

Gly Ala Ala Gln Asn Leu Ala Pro Ala Met Glu Asn Val His Ala Ala
            100                 105                 110

Leu Ala Ala Ala Gly Leu Gly His Ile Lys Val Thr Thr Ser Val Ser
        115                 120                 125

Gln Ala Ile Leu Gly Val Tyr Ser Pro Pro Ser Ala Ala Glu Phe Thr
    130                 135                 140

Gly Glu Ala Lys Gly Tyr Met Gly Pro Val Leu Ser Phe Leu Ala Arg
145                 150                 155                 160

Thr Gly Ser Pro Leu Met Ala Asn Ile Tyr Pro Tyr Leu Ala Trp Ala
                165                 170                 175

Tyr Asn Pro Ser Ala Met Asp Met Ser Tyr Ala Leu Phe Thr Ser Lys
```

```
            180                 185                 190
Gly Thr Val Val Gln Asp Gly Ala Tyr Gly Tyr Gln Asn Leu Phe Asp
        195                 200                 205

Thr Thr Val Asp Ala Phe Tyr Phe Ala Met Gly Arg His Gly Gly Ser
210                 215                 220

Gly Val Pro Leu Val Val Ser Glu Ser Gly Trp Pro Ser Gly Gly Gly
225                 230                 235                 240

Glu Gln Ala Asn Ala Ala Asn Ala Arg Ile Tyr Asn Gln Tyr Leu Ile
                245                 250                 255

Asn His Val Gly Arg Gly Thr Pro Arg His Pro Gly Gly Ile Glu Thr
            260                 265                 270

Tyr Leu Phe Ser Met Phe Asn Glu Asn Gln Lys Asp Ser Gly Val Glu
        275                 280                 285

Gln Asn Trp Gly Leu Phe Tyr Pro Asn Met Gln His Val Tyr Pro Ile
    290                 295                 300

Ser Phe
305

<210> SEQ ID NO 94
<211> LENGTH: 306
<212> TYPE: PRT
<213> ORGANISM: Oryza sativa

<400> SEQUENCE: 94

Ile Gly Val Cys Tyr Gly Met Ser Ala Asn Asn Leu Pro Pro Ala Ser
1               5                   10                  15

Ser Val Val Gly Met Tyr Arg Ser Asn Gly Ile Thr Ser Met Arg Leu
            20                  25                  30

Tyr Ala Pro Asp Gln Ala Ala Leu Gln Ser Val Gly Gly Thr Gly Ile
        35                  40                  45

Ser Val Val Val Gly Ala Pro Asn Asp Val Leu Ser Asn Leu Ala Ala
    50                  55                  60

Ser Pro Ala Ala Ala Ser Trp Val Arg Asn Asn Ile Gln Ala Tyr
65                  70                  75                  80

Pro Ser Val Ser Phe Arg Tyr Val Ala Val Gly Asn Glu Val Ala Gly
                85                  90                  95

Gly Ala Thr Ser Ser Leu Val Pro Ala Met Glu Asn Val Arg Gly Ala
            100                 105                 110

Leu Val Ser Ala Gly Leu Gly His Ile Lys Val Thr Thr Ser Val Ser
        115                 120                 125

Gln Ala Leu Leu Ala Val Tyr Ser Pro Pro Ser Ala Ala Glu Phe Thr
    130                 135                 140

Gly Glu Ser Gln Ala Phe Met Ala Pro Val Leu Ser Phe Leu Ala Arg
145                 150                 155                 160

Thr Gly Ala Pro Leu Leu Ala Asn Ile Tyr Pro Tyr Phe Ser Tyr Thr
                165                 170                 175

Tyr Ser Gln Gly Ser Val Asp Val Ser Tyr Ala Leu Phe Thr Ala Ala
            180                 185                 190

Gly Thr Val Val Gln Asp Gly Ala Tyr Gly Tyr Gln Asn Leu Phe Asp
        195                 200                 205

Thr Thr Val Asp Ala Phe Tyr Ala Ala Met Ala Lys His Gly Gly Ser
210                 215                 220

Gly Val Ser Leu Val Val Ser Glu Thr Gly Trp Pro Ser Ala Gly Gly
225                 230                 235                 240
```

```
Met Ser Ala Ser Pro Ala Asn Ala Arg Ile Tyr Asn Gln Asn Leu Ile
                245                 250                 255

Asn His Val Gly Arg Gly Thr Pro Arg His Pro Gly Ala Ile Glu Thr
            260                 265                 270

Tyr Val Phe Ser Met Phe Asn Glu Asn Gln Lys Asp Ala Gly Val Glu
        275                 280                 285

Gln Asn Trp Gly Leu Phe Tyr Pro Asn Met Gln His Val Tyr Pro Ile
    290                 295                 300

Ser Phe
305

<210> SEQ ID NO 95
<211> LENGTH: 300
<212> TYPE: PRT
<213> ORGANISM: Oryza sativa

<400> SEQUENCE: 95

Met Ser Ala Asn Asn Leu Pro Pro Ala Ser Ser Val Val Gly Met Tyr
1               5                   10                  15

Arg Ser Asn Gly Ile Thr Ser Met Arg Leu Tyr Ala Pro Asp Gln Ala
            20                  25                  30

Ala Leu Gln Ser Val Gly Gly Thr Gly Ile Ser Val Val Gly Ala
        35                  40                  45

Pro Asn Asp Val Leu Ser Asn Leu Ala Ala Ser Pro Ala Ala Ala
    50                  55                  60

Ser Trp Val Arg Asn Asn Ile Gln Ala Tyr Pro Ser Val Ser Phe Arg
65                  70                  75                  80

Tyr Val Ala Val Gly Asn Glu Val Ala Gly Gly Ala Thr Ser Ser Leu
                85                  90                  95

Val Pro Ala Met Glu Asn Val Arg Gly Ala Leu Val Ser Ala Gly Leu
            100                 105                 110

Gly His Ile Lys Val Thr Thr Ser Val Ser Gln Ala Leu Leu Ala Val
        115                 120                 125

Tyr Ser Pro Pro Ser Ala Ala Glu Phe Thr Gly Glu Ser Gln Ala Phe
    130                 135                 140

Met Ala Pro Val Leu Ser Phe Leu Ala Arg Thr Gly Ala Pro Leu Leu
145                 150                 155                 160

Ala Asn Ile Tyr Pro Tyr Phe Ser Tyr Thr Tyr Ser Gln Gly Ser Val
                165                 170                 175

Asp Val Ser Tyr Ala Leu Phe Thr Ala Ala Gly Thr Val Val Gln Asp
            180                 185                 190

Gly Ala Tyr Gly Tyr Gln Asn Leu Phe Asp Thr Thr Val Asp Ala Phe
        195                 200                 205

Tyr Ala Ala Met Ala Lys His Gly Gly Ser Gly Val Ser Leu Val Val
    210                 215                 220

Ser Glu Thr Gly Trp Pro Ser Ala Gly Gly Met Ser Ala Ser Pro Ala
225                 230                 235                 240

Asn Ala Arg Ile Tyr Asn Gln Asn Leu Ile Asn His Val Gly Arg Gly
                245                 250                 255

Thr Pro Arg His Pro Gly Ala Ile Glu Thr Tyr Val Phe Ser Met Phe
            260                 265                 270

Asn Glu Asn Gln Lys Asp Ala Gly Val Glu Gln Asn Trp Gly Leu Phe
        275                 280                 285

Tyr Pro Asn Met Gln His Val Tyr Pro Ile Ser Phe
    290                 295                 300
```

<210> SEQ ID NO 96
<211> LENGTH: 300
<212> TYPE: PRT
<213> ORGANISM: Oryza sativa

<400> SEQUENCE: 96

```
Met Ser Ala Asn Asn Leu Pro Pro Ala Ser Val Val Gly Met Tyr
 1               5                  10                  15

Arg Ser Asn Gly Ile Thr Ser Met Arg Leu Tyr Ala Pro Asp Gln Ala
                 20                  25                  30

Ala Leu Gln Ser Val Gly Gly Thr Gly Ile Ser Val Val Gly Ala
             35                  40                  45

Pro Asn Asp Val Leu Ser Asn Leu Ala Ala Ser Pro Ala Ala Ala
 50                  55                  60

Ser Trp Val Arg Asn Asn Ile Gln Ala Tyr Pro Ser Val Ser Phe Arg
 65                  70                  75                  80

Tyr Val Ala Val Gly Asn Glu Val Ala Gly Gly Ala Thr Ser Ser Leu
                 85                  90                  95

Val Pro Ala Met Glu Asn Val Arg Gly Ala Leu Val Ser Ala Gly Leu
                100                 105                 110

Gly His Ile Lys Val Thr Thr Ser Val Ser Gln Ala Leu Leu Ala Val
            115                 120                 125

Tyr Ser Pro Pro Ser Ala Ala Glu Phe Thr Gly Glu Ser Gln Ala Phe
            130                 135                 140

Met Ala Pro Val Leu Ser Phe Leu Ala Arg Thr Gly Ala Pro Leu Leu
145                 150                 155                 160

Ala Asn Ile Tyr Pro Tyr Phe Ser Tyr Thr Tyr Ser Gln Gly Ser Val
                165                 170                 175

Asp Val Ser Tyr Ala Leu Phe Thr Ala Ala Gly Thr Val Val Gln Asp
            180                 185                 190

Gly Ala Tyr Gly Tyr Gln Asn Leu Phe Asp Thr Thr Val Asp Ala Phe
            195                 200                 205

Tyr Ala Ala Met Ala Lys His Gly Gly Ser Gly Val Ser Leu Val Val
210                 215                 220

Ser Glu Thr Gly Trp Pro Ser Ala Gly Gly Met Ser Ala Ser Pro Ala
225                 230                 235                 240

Asn Ala Arg Ile Tyr Asn Gln Asn Leu Ile Asn His Val Gly Arg Gly
                245                 250                 255

Thr Pro Arg His Pro Gly Ala Ile Glu Thr Tyr Val Phe Ser Met Phe
            260                 265                 270

Asn Glu Asn Gln Lys Asp Ala Gly Val Glu Gln Asn Trp Gly Leu Phe
            275                 280                 285

Tyr Pro Asn Met Gln His Val Tyr Pro Ile Ser Phe
            290                 295                 300
```

<210> SEQ ID NO 97
<211> LENGTH: 306
<212> TYPE: PRT
<213> ORGANISM: Zea mays

<400> SEQUENCE: 97

```
Ile Gly Val Ser Tyr Gly Met Ser Gly Asp Asn Leu Pro Pro Ala Ser
 1               5                  10                  15

Thr Val Ile Gly Met Tyr Lys Asp Asn Gly Ile Pro Leu Met Arg Ile
                 20                  25                  30
```

```
Tyr Ala Pro Asp Gln Ala Ala Leu Gln Ala Val Gly Gly Thr Gly Ile
            35                  40                  45

Arg Val Val Ala Gly Ala Pro Asn Asp Val Leu Ser Ser Leu Ala Ala
 50                  55                  60

Ser Pro Ala Ala Ala Ser Trp Val Arg Asn Asn Ile Gln Ala Tyr
 65                  70                  75                  80

Pro Lys Val Ala Phe Arg Cys Val Cys Val Gly Asn Glu Val Glu Gly
                85                  90                  95

Gly Ala Ala Gln Ser Leu Val Pro Ala Met Glu Asn Val Arg Ala Ala
                100                 105                 110

Leu Val Ala Ala Gly Leu Asp Gly Ile Lys Val Thr Thr Ser Val Ser
                115                 120                 125

Gln Ala Ile Leu Gly Gly Tyr Lys Pro Pro Ser Ala Ala Glu Phe Thr
            130                 135                 140

Asp Glu Ala Gln Gly Phe Met Gly Pro Val Leu Arg Phe Leu Ala Arg
145                 150                 155                 160

Thr Gly Ala Pro Leu Met Ala Ser Val Tyr Pro Tyr Phe Thr Tyr Ala
                165                 170                 175

Thr Asn Pro Ala Ala Met Asp Leu Ser Tyr Ala Leu Phe Thr Ala Pro
                180                 185                 190

Gly Thr Val Leu Gln Asp Gly Ala Tyr Glu Tyr Gln Asn Leu Phe Asp
            195                 200                 205

Ala Thr Val Asp Ser Phe Tyr Val Ala Met Ala Asn His Gly Gly Ser
            210                 215                 220

Gly Val Thr Leu Val Val Ser Glu Ser Gly Trp Pro Ser Ala Gly Gly
225                 230                 235                 240

Val Ala Ala Ser Pro Glu Asn Ala Ala Ile Tyr Asn Gln Asn Leu Ile
                245                 250                 255

Asn His Val Gly Arg Gly Thr Pro Arg His Pro Gly Ala Ile Glu Thr
            260                 265                 270

Ile Leu Phe Ser Met Phe Asn Glu Asn Leu Lys Gln Ser Gly Val Glu
        275                 280                 285

Gln Asn Trp Gly Leu Phe Tyr Pro Asn Met Gln Arg Val Tyr Pro Ile
        290                 295                 300

Lys Phe
305

<210> SEQ ID NO 98
<211> LENGTH: 306
<212> TYPE: PRT
<213> ORGANISM: Sorghum bicolor

<400> SEQUENCE: 98

Ile Gly Val Ser Tyr Gly Met Ser Gly Asp Asn Leu Pro Pro Ala Ser
 1               5                  10                  15

Ser Val Ile Gly Met Tyr Lys Asp Asn Gly Ile Ser Leu Met Arg Ile
            20                  25                  30

Tyr Ala Pro Asp Gln Ala Ala Leu Arg Ala Val Gly Gly Thr Gly Ile
            35                  40                  45

Arg Val Val Val Gly Ala Pro Asn Asp Val Leu Ser Ser Leu Ala Ala
 50                  55                  60

Ser Pro Ala Ala Ala Ser Trp Val Arg Asn Asn Ile Gln Ala Tyr
 65                  70                  75                  80

Pro Lys Val Ser Phe Arg Cys Val Cys Val Gly Asn Glu Val Ala Gly
```

```
                85                  90                  95
Gly Ala Ala Gln Asn Leu Val Pro Ala Met Glu Asn Val Arg Ala Ala
            100                 105                 110
Leu Ala Ala Ala Gly Leu Asp Gly Ile Lys Val Thr Thr Ser Val Ser
        115                 120                 125
Gln Ala Ile Leu Gly Gly Tyr Lys Pro Pro Ser Ala Ala Glu Phe Thr
    130                 135                 140
Asp Glu Ala Gln Gly Phe Met Gly Pro Val Leu Asp Phe Leu Ala Arg
145                 150                 155                 160
Thr Gly Ala Pro Leu Met Ala Ser Val Tyr Pro Tyr Phe Thr Tyr Ala
                165                 170                 175
Thr Asn Pro Ser Ala Met Asp Val Ser Tyr Ala Leu Phe Thr Ala Pro
            180                 185                 190
Gly Thr Val Leu Lys Asp Gly Asp Tyr Glu Tyr Gln Asn Leu Phe Asp
        195                 200                 205
Ala Thr Val Asp Ser Phe Tyr Val Ala Met Gly Asn His Gly Gly Ser
    210                 215                 220
Gly Val Thr Leu Val Val Ser Glu Ser Gly Trp Pro Ser Ala Gly Gly
225                 230                 235                 240
Val Ala Ala Ser Pro Glu Asn Ala Ala Ile Tyr Asn Gln Asn Leu Ile
                245                 250                 255
Asn His Val Gly Arg Gly Thr Pro Arg His Pro Gly Ala Ile Glu Thr
            260                 265                 270
Ile Leu Phe Ser Met Phe Asn Glu Asn Leu Lys Glu Asn Gly Val Glu
        275                 280                 285
Gln Asn Trp Gly Leu Phe Tyr Pro Asn Met Gln Arg Val Tyr Pro Ile
    290                 295                 300
Ser Phe
305

<210> SEQ ID NO 99
<211> LENGTH: 306
<212> TYPE: PRT
<213> ORGANISM: Setaria italica

<400> SEQUENCE: 99

Ile Gly Val Ser Tyr Gly Met Ser Gly Asp Asn Leu Pro Pro Ala Ser
1               5                   10                  15
Thr Val Val Gly Met Tyr Lys Ala Asn Gly Ile Pro Leu Met Arg Ile
            20                  25                  30
Tyr Ala Pro Asp Gln Ala Ala Leu Glu Ala Val Gly Gly Thr Gly Ile
        35                  40                  45
Arg Val Val Val Gly Ala Pro Asn Asp Val Leu Ser Ser Leu Ala Ala
    50                  55                  60
Ser Pro Ala Ala Ala Ala Trp Val Arg Asn Asn Ile Ala Ala Tyr
65                  70                  75                  80
Pro Asp Val Thr Phe Arg Cys Val Cys Val Gly Asn Glu Val Glu Gly
                85                  90                  95
Gly Ala Ala Gln Asn Leu Val Pro Ala Met Glu Asn Ile Arg Ala Ala
            100                 105                 110
Leu Ala Ala Ala Gly Leu Asp Gly Ile Lys Val Thr Thr Ser Val Ser
        115                 120                 125
Gln Ala Ile Leu Gly Gly Tyr Lys Pro Pro Ser Ala Ala Glu Phe Thr
    130                 135                 140
```

```
Asp Glu Ala Gln Gly Phe Met Gly Pro Val Leu Glu Phe Leu Ala Arg
145                 150                 155                 160

Thr Gly Ala Pro Leu Met Ala Ser Ile Tyr Pro Tyr Phe Thr Tyr Ala
            165                 170                 175

Thr Asn Pro Ser Ala Met Asp Leu Ser Tyr Ala Leu Phe Thr Ala Pro
        180                 185                 190

Gly Thr Val Leu Gln Asp Gly Thr Tyr Gly Tyr Gln Asn Leu Phe Asp
    195                 200                 205

Ala Thr Val Asp Ser Phe Tyr Val Ala Met Ala Asn His Gly Gly Ala
210                 215                 220

Gly Val Thr Leu Val Val Ser Glu Ser Gly Trp Pro Ser Ala Gly Gly
225                 230                 235                 240

Val Ala Ala Ser Pro Glu Asn Ala Ala Leu Tyr Asn Gln Asn Leu Ile
                245                 250                 255

Asn His Val Gly Arg Gly Thr Pro Arg His Pro Gly Ala Ile Glu Thr
            260                 265                 270

Ile Leu Phe Ser Met Phe Asn Glu Asn Leu Lys Glu Ser Gly Val Glu
        275                 280                 285

Gln Asn Trp Gly Leu Phe Tyr Pro Asn Lys Gln Arg Val Tyr Pro Ile
290                 295                 300

Ser Phe
305

<210> SEQ ID NO 100
<211> LENGTH: 300
<212> TYPE: PRT
<213> ORGANISM: Setaria italica

<400> SEQUENCE: 100

Ile Gly Val Cys Tyr Gly Met Ser Gly Ser Asp Leu Pro Pro Ala Ser
1               5                   10                  15

Thr Val Ile Ser Met Tyr Lys Ser Asn Gly Ile Lys Ala Ile Arg Ile
            20                  25                  30

Tyr Ala Pro Asp Lys Ala Ala Leu Gln Ala Leu Ala Gly Thr Asn Ile
        35                  40                  45

Arg Val Leu Val Gly Ala Pro Asn Asp Val Leu Ser Asn Leu Thr Asp
50                  55                  60

Ala Lys Ala Ala Ala Trp Val Arg Asp Asn Ile Glu Ala Tyr Pro
65                  70                  75                  80

Ser Val Ser Phe Gly Tyr Ile Ala Val Gly Asn Glu Val Ala Gly Lys
                85                  90                  95

Ala Ala Asp Leu Leu Ala Pro Ala Met Glu Asn Val His Ser Ala Leu
            100                 105                 110

Asp Ala Gly Leu Gly His Ile Lys Val Thr Thr Ser Val Ser Gln
        115                 120                 125

Ala Ile Val Val Phe Asn Lys Pro Ser Gly Gly Asn Phe Thr Lys Glu
130                 135                 140

Ala Gln Gly Phe Met Gly Pro Val Leu Lys Phe Leu Ala Arg Thr Gly
145                 150                 155                 160

Ala Pro Leu Met Ala Asn Ile Tyr Pro Tyr Phe Thr Tyr Ala Tyr Asn
                165                 170                 175

Thr Ala Gly Met Asp Val Asp Tyr Ala Leu Phe Thr Ala Pro Gly Thr
            180                 185                 190

Val Val Lys Asp Gly Lys Tyr Asn Tyr Gln Asn Leu Phe Asp Ala Thr
        195                 200                 205
```

```
Val Asp Ala Phe Tyr Glu Ala Met Ala Lys Leu Gly Val Ser Asp Val
    210                 215                 220

Pro Val Leu Val Ser Glu Thr Gly Trp Pro Ser Gly Gly Gly Lys Ala
225                 230                 235                 240

Ala Thr Pro Glu Asn Ala Lys Ile Tyr Asn Gln Asn Leu Ile Glu His
                245                 250                 255

Ile Arg Lys Gly Thr Pro Arg His Pro Glu Pro Ile Lys Thr Tyr Val
                260                 265                 270

Phe Ser Met Phe Asn Glu Asn Gln Lys Asp Lys Gly Val Glu Gln Asn
            275                 280                 285

Trp Gly Leu Phe Tyr Pro Asn Met Lys Pro Val Tyr
290                 295                 300

<210> SEQ ID NO 101
<211> LENGTH: 314
<212> TYPE: PRT
<213> ORGANISM: Brachypodium distachyon

<400> SEQUENCE: 101

Val Gly Val Cys Tyr Gly Met Ser Gly Asn Asn Leu Pro Pro Ala Ser
1               5                   10                  15

Thr Val Val Gly Met Leu Arg Asp Asn Gly Phe Thr Ser Val Arg Leu
                20                  25                  30

Tyr Ala Pro Asp Ala Ala Ala Leu Ala Ala Leu Ala Gly Thr Gly Ile
                35                  40                  45

Gly Val Val Val Gly Ala Pro Asn Asp Val Val Pro Ser Leu Ser Thr
 50                 55                  60

Asn Pro Ser Phe Ala Ala Ser Trp Val Arg Asp Asn Ile Ala Ala His
65                  70                  75                  80

Pro Tyr Val Ser Phe Lys Tyr Leu Ser Val Gly Asn Glu Ile Ser Gly
                85                  90                  95

Glu Asn Thr Gln His Leu Val Pro Ala Met Glu Asn Val Leu Ala Ala
                100                 105                 110

Leu Asn Ala Ala Gly Leu Gly Met Gly Val Gln Val Thr Thr Ala Ile
                115                 120                 125

Ser Gln Ala Thr Ile Ala Val His Thr Pro Ser Ala Gly Ala Phe
130                 135                 140

Ala Glu Asp Cys Lys Pro Phe Leu Leu Pro Val Leu Gln Phe Leu Ala
145                 150                 155                 160

Arg Thr Gly Ala Pro Leu Leu Ala Asn Leu Tyr Pro Tyr Phe Ala Tyr
                165                 170                 175

Thr Tyr Arg Ala Ala Gly Asp Ile Asp Val Ser Phe Ala Leu Phe Thr
                180                 185                 190

Ala Glu Tyr Gln Gly Gly Pro Val Val Gln Asp Gly Glu Tyr Ala Tyr
                195                 200                 205

His Asn Met Phe Asp Ala Thr Val Asp Ala Val His Ala Ala Met Glu
                210                 215                 220

Lys Leu Leu Gly Gly Glu Ser Gly Gly Val Asn Leu Val Ser Glu
225                 230                 235                 240

Thr Gly Trp Pro Ser Ala Gly Gly Glu Ala Ala Ser Val Glu Asn Ala
                245                 250                 255

Arg Thr Tyr Asn Gln Asn Leu Val Asp His Val Arg Lys Gly Thr Pro
                260                 265                 270

Arg Arg Pro Trp Lys Val Glu Thr Tyr Leu Phe Ala Met Phe Asn Glu
```

```
            275                 280                 285
Asn Leu Lys Glu Gly Val Glu Gln Asn Trp Gly Leu Phe Tyr Pro
    290                 295                 300

Ser Thr Asp Arg Val Tyr Pro Ile Asp Phe
305                 310

<210> SEQ ID NO 102
<211> LENGTH: 309
<212> TYPE: PRT
<213> ORGANISM: Zea mays

<400> SEQUENCE: 102

Val Gly Val Cys Tyr Gly Thr Ser Gly Asp Asn Leu Pro Pro Ala Ser
  1               5                  10                  15

Ala Val Val Gly Met Leu Arg Asp Asn Gly Phe Thr Val Arg Leu
                 20                  25                  30

Tyr Trp Pro Asp Gly Asp Ala Leu Ala Ala Leu Gly Gly Ser Gly Ile
                 35                  40                  45

Arg Val Val Val Gly Ala Pro Asn Glu Ala Leu Pro Ala Leu Ala Ser
                 50                  55                  60

Gly Ala Ala Ala Ala Ala Trp Val Arg Asp Asn Val Gln Ala His
 65                  70                  75                  80

Pro Ala Val Ala Phe Arg Tyr Val Val Gly Asn Glu Val Pro Leu
                 85                  90                  95

Glu Gln Ala Pro Leu Leu Val Pro Ala Met Glu Asn Val His Ala Ala
                100                 105                 110

Leu Ala Ala Gly Leu Gly His Val Lys Val Thr Thr Ala Val Ser
                115                 120                 125

Gln Gly Ala Ile Ala Val His Leu Pro Pro Ser Ala Gly Glu Phe Thr
                130                 135                 140

Glu Glu Ala Arg Ser Phe Met Gly Tyr Val Val Ala Phe Leu Ala Arg
145                 150                 155                 160

Thr Arg Ala Pro Leu Leu Ala Asn Leu Tyr Pro Tyr Phe Val Tyr Thr
                165                 170                 175

Leu Gly Leu Gly His Leu Gly Met Asp Phe Ala Leu Phe Thr Ala Pro
                180                 185                 190

Gly Thr Val Val Gln Asp Gly Glu Tyr Gly Tyr Gln Asn Leu Phe Asp
                195                 200                 205

Ala Thr Val Asp Ala Leu Tyr Ala Ala Val Gly Arg Leu Gly Val Ala
                210                 215                 220

Gly Gly Asp Gly Val Arg Val Val Ser Glu Thr Gly Trp Pro Thr
225                 230                 235                 240

Ala Gly Gly Ala Ala Ser Leu Glu Asn Ala Arg Thr Tyr Asn Gln
                245                 250                 255

Asn Leu Val Arg His Val Trp Lys Gly Thr Pro Arg Pro Arg Arg
                260                 265                 270

Val Glu Ala Tyr Val Phe Ala Met Phe Asn Glu Asp Lys Lys Asp Ala
                275                 280                 285

Gly Val Glu Gln Asn Trp Gly Leu Phe Tyr Pro Asn Met Glu Arg Val
                290                 295                 300

Tyr Pro Ile Thr Phe
305

<210> SEQ ID NO 103
<211> LENGTH: 309
```

<212> TYPE: PRT
<213> ORGANISM: Zea mays

<400> SEQUENCE: 103

```
Val Gly Val Cys Tyr Gly Thr Ser Gly Asp Asn Leu Pro Pro Ala Ser
 1               5                  10                  15
Ala Val Val Gly Met Leu Arg Asp Asn Gly Phe Thr Val Val Arg Leu
                20                  25                  30
Tyr Trp Pro Asp Gly Asp Ala Leu Ala Leu Gly Gly Ser Gly Ile
                35                  40                  45
Arg Val Val Val Gly Ala Pro Asn Glu Ala Leu Pro Ala Leu Ala Ser
            50                  55                  60
Gly Ala Ala Ala Ala Ala Trp Val Arg Asp Asn Val Gln Ala His
 65                 70                  75                  80
Pro Ala Val Ala Phe Arg Tyr Val Val Gly Asn Glu Val Pro Leu
                85                  90                  95
Glu Gln Ala Pro Leu Leu Val Pro Ala Met Glu Asn Val His Ala Ala
                100                 105                 110
Leu Ala Ala Gly Leu Gly His Val Lys Val Thr Thr Ala Val Ser
            115                 120                 125
Gln Gly Ala Ile Ala Val His Leu Pro Pro Ser Ala Gly Glu Phe Thr
130                 135                 140
Glu Glu Ala Arg Ser Phe Met Gly Tyr Val Val Ala Phe Leu Ala Arg
145                 150                 155                 160
Thr Arg Ala Pro Leu Leu Ala Asn Leu Tyr Pro Tyr Phe Val Tyr Thr
                165                 170                 175
Leu Gly Leu Gly His Leu Gly Met Asp Phe Ala Leu Phe Thr Ala Pro
            180                 185                 190
Gly Thr Val Val Gln Asp Gly Glu Tyr Gly Tyr Gln Asn Leu Phe Asp
                195                 200                 205
Ala Thr Val Asp Ala Leu Tyr Ala Ala Val Gly Arg Leu Gly Val Ala
            210                 215                 220
Gly Gly Asp Gly Val Arg Val Val Ser Glu Thr Gly Trp Pro Thr
225                 230                 235                 240
Ala Gly Gly Ala Ala Ala Ser Leu Glu Asn Ala Arg Thr Tyr Asn Gln
                245                 250                 255
Asn Leu Val Arg His Val Trp Lys Gly Thr Pro Arg Pro Arg Arg
                260                 265                 270
Val Glu Ala Tyr Val Phe Ala Met Phe Asn Glu Asp Lys Lys Asp Ala
                275                 280                 285
Gly Val Glu Gln Asn Trp Gly Leu Phe Tyr Pro Asn Met Glu Arg Val
            290                 295                 300
Tyr Pro Ile Thr Phe
305
```

<210> SEQ ID NO 104
<211> LENGTH: 309
<212> TYPE: PRT
<213> ORGANISM: Sorghum bicolor

<400> SEQUENCE: 104

```
Val Gly Val Cys Tyr Gly Thr Ser Gly Asp Asn Leu Pro Pro Ala Ser
 1               5                  10                  15
Ala Val Val Gly Met Leu Arg Glu Asn Gly Phe Thr Val Val Arg Leu
                20                  25                  30
```

```
Tyr Trp Pro Asp Gly Glu Ala Leu Ala Ala Leu Gly Gly Ser Gly Ile
         35                  40                  45

Lys Val Val Gly Ala Pro Asn Glu Val Leu Thr Thr Leu Ala Ser
 50                  55                  60

Ser Ala Ser Ala Ala Ala Trp Val Arg Asp Asn Ile Gln Ala His
65                  70                  75                  80

Pro Thr Val Ser Phe Arg Tyr Val Val Gly Asn Glu Val Pro Val
                 85                  90                  95

Gly Gln Thr Gln Phe Leu Val Pro Ala Met Glu Asn Val His Ala Ala
             100                 105                 110

Leu Ala Ala Gly Leu Gly His Val Lys Val Thr Thr Ala Ile Ser
        115                 120                 125

Gln Gly Thr Ile Ala Val His Leu Pro Pro Ser Ala Gly Val Phe Thr
        130                 135                 140

Glu Glu Ala Leu Ser Phe Met Ser Tyr Val Val Ala Phe Leu Ala Arg
145                 150                 155                 160

Thr Arg Ala Pro Leu Leu Ala Asn Leu Tyr Pro Tyr Phe Val Tyr Thr
                165                 170                 175

Leu Ala Leu Gly His Met Ser Met Asp Phe Pro Leu Phe Thr Ala Pro
            180                 185                 190

Glu Thr Val Val Gln Asp Gly Glu Tyr Gly Tyr Gln Asn Leu Phe Asp
        195                 200                 205

Ala Thr Val Asp Ala Leu Tyr Ala Ala Val Gly Arg Leu Gly Val Pro
    210                 215                 220

Gly Gly Glu Arg Val Arg Val Val Val Ser Glu Thr Gly Trp Pro Thr
225                 230                 235                 240

Ala Gly Gly Ala Ala Ala Ser Val Glu Asn Ala Arg Thr Tyr Asn Gln
                245                 250                 255

Asn Leu Val Thr His Val Trp Lys Gly Thr Pro Arg Arg Pro Arg Arg
            260                 265                 270

Val Glu Ala Tyr Val Phe Ala Met Phe Asn Glu Asp Gln Lys Glu Ala
        275                 280                 285

Gly Val Glu Gln Asn Trp Gly Leu Phe Tyr Pro Asn Met Glu Arg Val
    290                 295                 300

Tyr Pro Ile Thr Phe
305

<210> SEQ ID NO 105
<211> LENGTH: 307
<212> TYPE: PRT
<213> ORGANISM: Setaria italica

<400> SEQUENCE: 105

Val Gly Val Cys Tyr Gly Thr Ser Gly Asp Asn Leu Pro Pro Ala Ser
 1               5                  10                  15

Thr Val Val Gly Met Leu Arg Glu Asn Gly Phe Thr Val Arg Leu
             20                  25                  30

Tyr Trp Pro Asp Pro Ala Ala Leu Ala Ala Leu Ala Gly Thr Gly Ile
         35                  40                  45

Lys Val Val Gly Ala Pro Asn Asp Val Leu Pro Ser Leu Ala Ser
 50                  55                  60

Ser Glu Ser Ala Ala Ala Trp Val Arg Gln Asn Ile Gln Ala His
65                  70                  75                  80

Pro Leu Val Thr Phe Arg Tyr Val Val Gly Asn Glu Val Pro Ala
                 85                  90                  95
```

```
Gly Glu Thr Glu His Leu Val Pro Ala Met Glu Asn Val His Ala Ala
            100                 105                 110

Leu Ala Ala Val Gly Leu Gly His Val Lys Val Thr Thr Ala Ile Ser
        115                 120                 125

Gln Gly Thr Ile Ala Val His Leu Pro Pro Ser Ala Gly Ala Phe Thr
    130                 135                 140

Glu Glu Ala Leu Ser Phe Met Gly Tyr Val Val Ala Phe Leu Glu Arg
145                 150                 155                 160

Thr Arg Ala Pro Leu Leu Ala Asn Leu Tyr Pro Tyr Phe Val Tyr Thr
                165                 170                 175

Leu Gly Leu Gly His Met Asp Met Ser Phe Ala Leu Phe Thr Ser Pro
            180                 185                 190

Gly Thr Val Val Gln Asp Gly Glu Tyr Gly Tyr Gln Asn Leu Leu Glu
        195                 200                 205

Ala Ser Val Asp Ala Leu Tyr Thr Ala Val Gly Lys Leu Gly Gly Ser
    210                 215                 220

Arg Val Arg Val Val Ser Glu Thr Gly Trp Pro Thr Ala Gly Gly
225                 230                 235                 240

Ala Ala Ala Ser Val Glu Asn Ala Met Thr Tyr Asn Gln Asn Leu Val
                245                 250                 255

Arg His Val Trp Lys Gly Thr Pro Arg Arg Pro Arg Arg Val Glu
            260                 265                 270

Ala Tyr Val Phe Ala Leu Phe Asn Glu Asn Leu Lys Glu Glu Gly Val
        275                 280                 285

Glu Gln Asn Trp Gly Leu Phe Tyr Pro Asn Met Glu Arg Val Tyr Pro
    290                 295                 300

Ile Thr Phe
305

<210> SEQ ID NO 106
<211> LENGTH: 308
<212> TYPE: PRT
<213> ORGANISM: Oryza sativa

<400> SEQUENCE: 106

Val Gly Val Cys Trp Gly Met Ser Gly Asp Asn Leu Pro Pro Ala Ser
1               5                   10                  15

Lys Val Thr Glu Met Leu Arg Glu Asn Gly Phe Thr Val Val Arg Leu
            20                  25                  30

Tyr Ala Pro Asp Ser Ala Ala Leu Ala Ala Leu Gly Gly Thr Gly Ile
        35                  40                  45

Arg Val Val Val Gly Ala Pro Asn Tyr Asp Leu Pro Ala Leu Ala His
    50                  55                  60

Gly Gly Thr Ala Ala Ala Ala Trp Ile Arg Glu Asn Ile Gln Ala
65                  70                  75                  80

Tyr Pro Thr Val Leu Phe Arg Phe Val Val Gly Asn Glu Val Ala
                85                  90                  95

Gly Ala Asp Thr Gln Leu Leu Val Pro Ala Met Glu Asn Val His Ala
            100                 105                 110

Ala Leu Ala Ala Ala Gly Leu Gly His Ile Lys Val Thr Thr Ser Ile
        115                 120                 125

Ser Gln Ala Thr Ile Gly Val His Ile Pro Pro Ser Ala Gly Glu Phe
    130                 135                 140

Thr Asp Glu Ala Lys Pro Phe Met Ser Tyr Val Ile Pro Phe Leu Glu
```

```
            145                 150                 155                 160
    Arg Thr His Ala Pro Leu Leu Ala Asn Leu Tyr Pro Tyr Phe Ile Tyr
                    165                 170                 175

Ser Tyr Asn Pro Gly Gly Met Asp Ile Ser Phe Ala Leu Phe Thr Ala
                    180                 185                 190

Ser Gly Ala Val Val Gln Asp Gly Glu Tyr Gly Tyr Gln Asn Gln Phe
                    195                 200                 205

Asp Ala Thr Val Asp Ala Leu Tyr Thr Ala Val Ala Lys Leu Gly Gly
                    210                 215                 220

Glu Asn Val Arg Val Val Ser Glu Thr Gly Trp Pro Thr Ala Gly
    225                 230                 235                 240

Gly Val Gly Ala Ser Val Glu Asn Ala Met Thr Phe Asn Gln Asn Leu
                    245                 250                 255

Val Arg His Val Arg Asn Gly Thr Pro Arg His Pro Gly Lys Lys Thr
                    260                 265                 270

Glu Thr Tyr Val Phe Ala Met Phe Asn Glu Asn Leu Lys Glu Ala Gly
                    275                 280                 285

Val Glu Gln Asn Trp Gly Leu Phe Tyr Pro Ser Thr Asp Arg Val Tyr
                    290                 295                 300

Pro Ile Ser Phe
    305

<210> SEQ ID NO 107
<211> LENGTH: 324
<212> TYPE: PRT
<213> ORGANISM: Brachypodium distachyon

<400> SEQUENCE: 107

Val Gly Val Asn Trp Gly Arg Val Ala Asn Asp Leu Pro Ser Pro Ala
    1               5                   10                  15

Ser Val Val Ser Leu Leu Lys Gln His Gly Ile Thr Gln Val Lys Leu
                    20                  25                  30

Tyr Asp Thr Glu Pro Ala Val Leu Arg Ala Leu Ala Asn Thr Gly Val
                    35                  40                  45

Lys Val Ile Val Ala Leu Pro Asn Glu Gln Val Ala Ala Ala Arg
                    50                  55                  60

Arg Pro Ser Tyr Ala Leu Ala Trp Val Arg Arg Asn Val Ala Ala Tyr
    65                  70                  75                  80

Tyr Pro Ala Thr Gln Ile Gln Gly Val Ala Val Gly Asn Glu Val Phe
                    85                  90                  95

Ala Thr Ala Gly Asn Val Thr Ala Gln Leu Val Pro Ala Met Ala Asn
                    100                 105                 110

Ile His Ala Ala Leu Gln Arg Leu Asn Leu Asp Lys Ala Val Lys Val
                    115                 120                 125

Ser Ser Pro Ile Ala Leu Thr Ala Leu Ala Ser Ser Tyr Pro Pro Ser
                    130                 135                 140

Ala Gly Val Phe Arg Glu Glu Leu Ala Gln Ala Val Met Lys Pro Met
    145                 150                 155                 160

Leu Asp Phe Leu Ser Gln Thr Gly Ser Tyr Leu Met Val Asn Ala Tyr
                    165                 170                 175

Pro Phe Phe Ala Tyr Ala Glu Asn Ala Gly Val Ile Ser Leu Asp Tyr
                    180                 185                 190

Ala Leu Phe Arg Pro Asn Ala Gly Glu Leu Asp Ala Gly Ser Gly Leu
                    195                 200                 205
```

```
Lys Tyr Tyr Ser Leu Leu Asp Ala Gln Leu Asp Ala Val Phe Ala Ala
210                 215                 220

Val Gly Lys Leu Gly Gly Asn Ala Tyr Asn Gly Val Arg Leu Val Val
225                 230                 235                 240

Ser Glu Thr Gly Trp Pro Ser Lys Gly Asp Ala Lys Glu Thr Gly Ala
            245                 250                 255

Ala Ala Ser Asn Ala Glu Ala Tyr Asn Gly Asn Leu Val Arg Arg Val
                260                 265                 270

Leu Ser Gly Asn Ala Gly Thr Pro Arg Arg Gly Asp Ala Asp Ile Asp
            275                 280                 285

Val Tyr Leu Phe Ala Leu Phe Asn Glu Asn Gln Lys Pro Gly Pro Thr
290                 295                 300

Ser Glu Arg Asn Tyr Gly Val Phe Tyr Pro Asn Gln Gln Lys Val Tyr
305                 310                 315                 320

Asp Val Glu Phe

<210> SEQ ID NO 108
<211> LENGTH: 322
<212> TYPE: PRT
<213> ORGANISM: Oryza sativa

<400> SEQUENCE: 108

Val Gly Ile Asn Tyr Gly Arg Val Ala Asn Asp Leu Pro Asn Pro Ala
1               5                   10                  15

Ala Val Val Gln Leu Met Lys Gln Gln Gly Ile Ala Gln Val Lys Leu
                20                  25                  30

Tyr Asp Thr Glu Pro Thr Val Leu Arg Ala Leu Ala Asn Thr Gly Ile
            35                  40                  45

Lys Val Val Val Ala Leu Pro Asn Glu Gln Leu Leu Ala Ala Ala Ser
50                  55                  60

Arg Pro Ser Tyr Ala Leu Ala Trp Val Arg Arg Asn Val Ala Ala Tyr
65                  70                  75                  80

Tyr Pro Ala Thr Gln Ile Gln Gly Ile Ala Val Gly Asn Glu Val Phe
                85                  90                  95

Ala Ser Ala Lys Asn Leu Thr Ala Gln Leu Val Pro Ala Met Thr Asn
            100                 105                 110

Val His Ala Ala Leu Ala Arg Leu Ser Leu Asp Lys Pro Val Lys Val
        115                 120                 125

Ser Ser Pro Ile Ala Leu Thr Ala Leu Ala Gly Ser Tyr Pro Pro Ser
130                 135                 140

Ala Gly Val Phe Arg Glu Asp Leu Ala Gln Ala Val Met Lys Pro Met
145                 150                 155                 160

Leu Asp Phe Leu Ala Gln Thr Gly Ser Tyr Leu Met Val Asn Ala Tyr
                165                 170                 175

Pro Phe Phe Ala Tyr Ser Gly Asn Ala Asp Val Ile Ser Leu Asp Tyr
            180                 185                 190

Ala Leu Phe Arg Pro Asn Ala Gly Val Leu Asp Ser Gly Ser Gly Leu
        195                 200                 205

Lys Tyr Tyr Ser Leu Leu Asp Ala Gln Leu Asp Ala Val Phe Thr Ala
210                 215                 220

Val Ser Lys Leu Gly Asn Tyr Asn Ala Val Arg Val Val Ser Glu
225                 230                 235                 240

Thr Gly Trp Pro Ser Lys Gly Asp Ala Lys Glu Thr Gly Ala Ala Ala
            245                 250                 255
```

```
Ala Asn Ala Ala Ala Tyr Asn Gly Asn Leu Val Arg Arg Val Leu Ser
            260                 265                 270

Gly Asn Ala Gly Thr Pro Arg Arg Pro Asp Ala Asp Met Asp Val Tyr
            275                 280                 285

Leu Phe Ala Leu Phe Asn Glu Asn Gln Lys Pro Gly Pro Thr Ser Glu
290                 295                 300

Arg Asn Tyr Gly Val Phe Tyr Pro Asn Gln Gln Lys Val Tyr Asp Val
305                 310                 315                 320

Glu Phe

<210> SEQ ID NO 109
<211> LENGTH: 322
<212> TYPE: PRT
<213> ORGANISM: Oryza sativa

<400> SEQUENCE: 109

Val Gly Ile Asn Tyr Gly Arg Val Ala Asn Asp Leu Pro Asn Pro Ala
1               5                   10                  15

Ala Val Val Gln Leu Met Lys Gln Gln Gly Ile Ala Gln Val Lys Leu
            20                  25                  30

Tyr Asp Thr Glu Pro Thr Val Leu Arg Ala Leu Ala Asn Thr Gly Ile
        35                  40                  45

Lys Val Val Ala Leu Pro Asn Glu Gln Leu Leu Ala Ala Ala Ser
50                  55                  60

Arg Pro Ser Tyr Ala Leu Ala Trp Val Arg Arg Asn Val Ala Ala Tyr
65                  70                  75                  80

Tyr Pro Ala Thr Gln Ile Gln Gly Ile Ala Val Gly Asn Glu Val Phe
                85                  90                  95

Ala Ser Ala Lys Asn Leu Thr Ala Gln Leu Val Pro Ala Met Thr Asn
            100                 105                 110

Val His Ala Ala Leu Ala Arg Leu Ser Leu Asp Lys Pro Val Lys Val
            115                 120                 125

Ser Ser Pro Ile Ala Leu Thr Ala Leu Ala Gly Ser Tyr Pro Pro Ser
130                 135                 140

Ala Gly Val Phe Arg Glu Asp Leu Ala Gln Ala Val Met Lys Pro Met
145                 150                 155                 160

Leu Asp Phe Leu Ala Gln Thr Gly Ser Tyr Leu Met Val Asn Ala Tyr
                165                 170                 175

Pro Phe Phe Ala Tyr Ser Gly Asn Ala Asp Val Ile Ser Leu Asp Tyr
            180                 185                 190

Ala Leu Phe Arg Pro Asn Ala Gly Val Leu Asp Ser Gly Ser Gly Leu
        195                 200                 205

Lys Tyr Tyr Ser Leu Leu Asp Ala Gln Leu Asp Ala Val Phe Thr Ala
210                 215                 220

Val Ser Lys Leu Gly Asn Tyr Asn Ala Val Arg Val Val Ser Glu
225                 230                 235                 240

Thr Gly Trp Pro Ser Lys Gly Asp Ala Lys Glu Thr Gly Ala Ala Ala
                245                 250                 255

Ala Asn Ala Ala Ala Tyr Asn Gly Asn Leu Val Arg Arg Val Leu Ser
            260                 265                 270

Gly Asn Ala Gly Thr Pro Arg Arg Pro Asp Ala Asp Met Asp Val Tyr
        275                 280                 285

Leu Phe Ala Leu Phe Asn Glu Asn Gln Lys Pro Gly Pro Thr Ser Glu
290                 295                 300
```

Arg Asn Tyr Gly Val Phe Tyr Pro Asn Gln Gln Lys Val Tyr Asp Val
305                 310                 315                 320

Glu Phe

<210> SEQ ID NO 110
<211> LENGTH: 322
<212> TYPE: PRT
<213> ORGANISM: Setaria italica

<400> SEQUENCE: 110

Val Gly Val Asn Tyr Gly Arg Val Ala Asn Leu Pro Asn Pro Ser
1               5                   10                  15

Ala Val Val Gln Leu Leu Lys Gln Gln Gly Ile Thr Gln Val Lys Leu
                20                  25                  30

Tyr Asp Thr Asp Pro Thr Val Leu Arg Ala Leu Ala Asn Thr Gly Val
            35                  40                  45

Lys Val Val Ala Leu Pro Asn Glu Gln Val Ala Ala Ala Ser
50                  55                  60

Arg Ala Ser Tyr Ala Leu Leu Trp Val Arg Arg Asn Val Ala Ala Tyr
65                  70                  75                  80

Tyr Pro Ala Thr Gln Ile Gln Gly Ile Ala Val Gly Asn Glu Val Phe
                85                  90                  95

Ala Thr Ala Lys Asn Val Thr Ala Gln Leu Val Pro Ala Met Val Asn
                100                 105                 110

Val His Ala Ala Leu Ala Arg Leu Gly Leu Asp Lys Ala Val Lys Val
            115                 120                 125

Ser Ser Pro Val Ala Leu Thr Ala Leu Ala Asn Ser Tyr Pro Ser Ser
130                 135                 140

Ala Gly Val Phe Arg Glu Asp Leu Ala Gln Pro Val Met Lys Pro Met
145                 150                 155                 160

Leu Asp Phe Leu Ala Gln Thr Gly Ser Tyr Leu Met Val Asn Ala Tyr
                165                 170                 175

Pro Phe Phe Ala Tyr Ser Ala Asn Ala Gly Asp Ile Ser Leu Asp Tyr
                180                 185                 190

Ala Leu Phe Arg Pro Asn Ala Gly Val Gln Asp Ala Gly Asn Gly Leu
            195                 200                 205

Lys Tyr Tyr Ser Leu Leu Asp Ala Gln Leu Asp Ala Val Phe Ala Ala
210                 215                 220

Val Asn Arg Leu Gly Asn Tyr Asn Gly Val Arg Val Val Ser Glu
225                 230                 235                 240

Thr Gly Trp Pro Ser Lys Gly Asp Ala Ser Glu Val Gly Ala Ser Pro
                245                 250                 255

Ala Asn Ala Ala Ala Tyr Asn Gly Asn Leu Ala Arg Arg Val Leu Ser
                260                 265                 270

Gly Asn Ala Gly Thr Pro Leu Arg Pro Asn Ala Asp Met Asp Val Tyr
            275                 280                 285

Leu Phe Ala Leu Phe Asn Glu Asn Gln Lys Pro Gly Pro Thr Ser Glu
290                 295                 300

Arg Asn Tyr Gly Val Phe Tyr Pro Asn Gln Gln Lys Val Tyr Asp Val
305                 310                 315                 320

Glu Phe

<210> SEQ ID NO 111
<211> LENGTH: 356
<212> TYPE: PRT

<213> ORGANISM: Zea mays

<400> SEQUENCE: 111

| | | | | | | | | | | | | | | | |
|---|---|---|---|---|---|---|---|---|---|---|---|---|---|---|---|
|Val|Gly|Val|Ser|Tyr|Gly|Arg|Leu|Gly|Asn|Asp|Leu|Pro|Gly|Thr|Ala|
|1| | | |5| | | |10| | | |15| | | |
|Ser|Val|Val|Lys|Leu|Leu|Lys|Lys|Ser|Gly|Ile|Thr|Ser|Val|Arg|Leu|
| | | |20| | | |25| | | |30| | | | |
|Tyr|Asp|Ala|Asn|Ser|Lys|Val|Leu|Lys|Ala|Leu|Ala|Asn|Thr|Gly|Ile|
| | |35| | | |40| | | |45| | | | | |
|Thr|Val|Met|Val|Met|Leu|Pro|Asn|Asp|Lys|Leu|Ala|Ala|Ala|Ala|Ala|
| |50| | | |55| | | |60| | | | | | |
|Asp|Pro|Ser|Ser|Ala|Arg|Arg|Trp|Val|Arg|Arg|Asn|Val|Ala|Ala|Tyr|
|65| | | |70| | | |75| | | |80| | | |
|Tyr|Pro|Ala|Thr|Gln|Ile|His|Ala|Val|Ala|Val|Gly|Asn|Glu|Val|Phe|
| | | |85| | | |90| | | |95| | | | |
|Glu|Glu|Ala|Lys|Asn|Leu|Thr|Gly|Gln|Leu|Val|Pro|Ala|Met|Ser|Asn|
| | |100| | | |105| | | |110| | | | | |
|Val|His|Asp|Ala|Leu|Val|Lys|Leu|Gly|Leu|Asp|Gly|Ala|Val|Lys|Val|
| |115| | | |120| | | |125| | | | | | |
|Ser|Thr|Pro|Ile|Ala|Phe|Thr|Ala|Leu|Gln|Glu|Ser|Trp|Pro|Pro|Ser|
|130| | | |135| | | |140| | | | | | | |
|Ala|Gly|Arg|Phe|Arg|Asp|Asp|Ile|Ala|Arg|Ser|Val|Met|Lys|Pro|Met|
|145| | | |150| | | |155| | | |160| | | |
|Ile|Asp|Phe|Leu|Glu|Arg|Thr|Gly|Ser|Tyr|Leu|Thr|Val|Asn|Ala|Tyr|
| | | |165| | | |170| | | |175| | | | |
|Pro|Phe|Phe|Ala|Tyr|Ala|Glu|Glu|Pro|Asp|Lys|Ile|Ser|Leu|Asp|Tyr|
| | |180| | | |185| | | |190| | | | | |
|Ala|Leu|Gly|Asn|Ser|Asn|Ala|Thr|Gly|Val|Arg|Asp|Pro|Val|Thr|Gly|
| |195| | | |200| | | |205| | | | | | |
|Leu|Val|Tyr|His|Ser|Leu|Leu|Asp|Ala|Gln|Leu|Asp|Ala|Thr|Tyr|Phe|
|210| | | |215| | | |220| | | | | | | |
|Ala|Met|Glu|Lys|Leu|Gly|Thr|Ser|Arg|Ser|Ser|Ala|Arg|Gly|Pro|Lys|
|225| | | |230| | | |235| | | |240| | | |
|Ser|Val|Ala|Pro|Ala|His|Val|Ser|Glu|Ser|Gly|Trp|Pro|Ser|Gly|
| | | |245| | | |250| | | |255| | | | |
|Gly|Lys|Pro|Lys|Arg|Gly|Gly|Arg|Pro|Arg|Pro|Arg|Pro|Arg|Gly|Gly|
| | |260| | | |265| | | |270| | | | | |
|Gly|Arg|Arg|Leu|Glu|Leu|Glu|Gln|Ala|Gly|Gly|Glu|Ala|Ala|Ser|Val|
| |275| | | |280| | | |285| | | | | | |
|Ala|Asn|Ala|Gln|Ala|Tyr|Asn|Asn|Tyr|Leu|Ile|Lys|Arg|Val|Leu|Ser|
|290| | | |295| | | |300| | | | | | | |
|Gly|Asp|Thr|Gly|Thr|Pro|Tyr|His|Pro|Asp|Ala|Asp|Met|Asp|Val|Tyr|
|305| | | |310| | | |315| | | |320| | | |
|Ile|Phe|Ser|Leu|Phe|Asn|Glu|Asn|Gln|Lys|Gly|Asp|Gly|Ala|Asp|Asp|
| | | |325| | | |330| | | |335| | | | |
|Val|Glu|Gln|His|Phe|Gly|Leu|Phe|Tyr|Pro|Asn|Arg|Thr|Lys|Val|Tyr|
| | |340| | | |345| | | |350| | | | | |
|Glu|Phe|Asp|Phe| | | | | | | | | | | | |
| | |355| | | | | | | | | | | | | |

<210> SEQ ID NO 112
<211> LENGTH: 316
<212> TYPE: PRT
<213> ORGANISM: Zea mays

<400> SEQUENCE: 112

```
Ile Gly Ile Cys His Gly Arg Val Gly Ser Asn Leu Pro Pro Ser
  1               5                  10                  15

Ala Ala Ala Ala Leu Leu Lys Arg Asn Gly Ile Thr Lys Ala Arg Leu
             20                  25                  30

Phe Leu Pro Asp Pro Ala Val Leu Pro Ala Phe Ala Ala Ala Gly Ile
         35                  40                  45

Asp Leu Met Val Gly Val Pro Asn Glu Asn Leu Thr Phe Leu Ala Ala
     50                  55                  60

Ala Gly Pro Glu Gly Ala Ala Gln Trp Leu Arg Ser Ala Val Leu Ala
 65                  70                  75                  80

His Ala Pro Ala Glu Arg Val Arg Cys Leu Ala Val Gly Asn Glu Val
                 85                  90                  95

Leu Tyr Asn Asn Gln Phe Tyr Ala Pro His Leu Val Pro Ala Met Arg
            100                 105                 110

Asn Leu His Ala Ala Leu Ala Thr Leu Gly Leu Asp Gly Arg Val Lys
        115                 120                 125

Val Ser Ser Ala His Ala Ser Ser Val Leu Ala Ser Tyr Pro Pro
130                 135                 140

Ser Ala Gly Ala Phe Asp Ala Ala Ser Leu Pro Val Leu Arg Pro Met
145                 150                 155                 160

Leu Arg Phe Leu Ala Asp Thr Gly Ala Pro Phe Met Val Asn Ala Tyr
                165                 170                 175

Pro Phe Ile Ser His Val Asn Asp Pro Ala Asn Val Gln Leu Ala Tyr
            180                 185                 190

Ala Leu Phe Gly Ala Gly Ala Pro Val Gln Asp Gly Ala Leu Val
        195                 200                 205

Tyr Thr Asn Leu Phe Asp Ala Thr Val Asp Ala Leu Val Ala Ala Leu
    210                 215                 220

Glu Lys Glu Gly Phe Asp Gly Val Pro Val Ala Val Thr Glu Thr Gly
225                 230                 235                 240

Trp Pro Thr Ala Gly His Pro Ala Ala Thr Pro Gln Asn Ala Ala Ala
                245                 250                 255

Tyr Asn Ala Lys Ile Val Glu Arg Ala Ala Arg Gly Val Gly Thr Pro
            260                 265                 270

Lys Arg Pro Gly Val Pro Val Glu Val Phe Leu Phe Asp Leu Tyr Asp
        275                 280                 285

Glu Asp Gly Lys Pro Gly Pro Glu Phe Glu Arg His Phe Gly Ile Phe
    290                 295                 300

Arg Ala Asp Gly Ser Lys Ala Tyr Asp Ile Asn Phe
305                 310                 315
```

<210> SEQ ID NO 113
<211> LENGTH: 316
<212> TYPE: PRT
<213> ORGANISM: Sorghum bicolor

<400> SEQUENCE: 113

```
Ile Gly Ile Cys His Gly Arg Val Gly Ser Asn Leu Pro Pro Ser
  1               5                  10                  15

Ala Ala Ala Ala Leu Leu Lys Gln Asn Gly Ile Thr Lys Ala Arg Leu
             20                  25                  30

Phe Leu Pro Asp Pro Ala Val Leu Pro Ala Phe Ala Ala Ala Gly Ile
         35                  40                  45
```

Asp Leu Met Val Gly Val Pro Asn Glu Asn Leu Thr Phe Leu Ala Ala
50                      55                      60

Ser Gly Pro Glu Gly Ala Ala Gln Trp Leu Arg Ser Ala Val Leu Ala
65                      70                      75                      80

His Ala Pro Ala Asp Arg Val Arg Tyr Leu Ala Val Gly Asn Glu Val
                    85                      90                      95

Leu Tyr Asn Asn Gln Phe Tyr Ala Pro His Leu Val Pro Ala Met Arg
                100                     105                     110

Asn Leu His Ala Ala Leu Ala Ala Leu Gly Leu Gly Arg Val Lys
                115                     120                     125

Val Ser Ser Ala His Ala Ser Ser Val Leu Ala Ala Ser Tyr Pro Pro
130                     135                     140

Ser Ala Gly Ala Phe Asp Ala Ala Ser Leu Pro Val Leu Arg Pro Met
145                     150                     155                     160

Leu Gln Phe Leu Ala Asp Thr Gly Ala Pro Phe Met Val Asn Thr Tyr
                165                     170                     175

Pro Phe Ile Ser Tyr Val Asn Asp Pro Ala Asn Val Gln Leu Ala Tyr
                180                     185                     190

Ala Leu Phe Gly Ala Gly Ala Pro Val Gln Asp Gly Ala Leu Val
                195                     200                     205

Tyr Thr Asn Leu Phe Asp Ala Thr Val Asp Ala Leu Val Ala Ala Leu
                210                     215                     220

Glu Lys Glu Gly Phe Gly Ala Val Pro Val Ala Val Thr Glu Thr Gly
225                     230                     235                     240

Trp Pro Thr Ala Gly His Pro Ala Ala Thr Pro Gln Asn Ala Ala Ala
                245                     250                     255

Tyr Asn Ala Lys Ile Val Glu Arg Ala Val Arg Gly Val Gly Thr Pro
                260                     265                     270

Lys Arg Pro Gly Val Pro Val Glu Val Phe Leu Phe Asp Leu Tyr Asp
                275                     280                     285

Glu Asp Gly Lys Pro Gly Pro Glu Phe Glu Arg His Phe Gly Ile Phe
                290                     295                     300

Arg Ala Asp Gly Gly Lys Ala Tyr Asp Ile Asn Phe
305                     310                     315

<210> SEQ ID NO 114
<211> LENGTH: 316
<212> TYPE: PRT
<213> ORGANISM: Oryza sativa

<400> SEQUENCE: 114

Ile Gly Ile Cys His Gly Arg Val Gly Ser Asn Leu Pro Pro Pro Ala
1               5                       10                      15

Ala Ala Ala Ala Leu Leu Arg Gln Asn Gly Ile Thr Lys Ala Arg Leu
                20                      25                      30

Phe Leu Pro Asp Pro Ala Val Leu Pro Ala Phe Ala Ala Ala Gly Ile
                35                      40                      45

Asp Leu Met Val Gly Val Pro Asn Glu Asn Leu Thr Phe Leu Ser Ala
50                      55                      60

Ala Gly Pro Asp Gly Ala Leu Arg Trp Leu Gln Ser Ala Val Leu Ala
65                      70                      75                      80

His Ala Pro Ala Asp Arg Val Arg Tyr Leu Ala Val Gly Asn Glu Val
                    85                      90                      95

Leu Tyr Asn Asn Gln Phe Tyr Ala Pro His Leu Val Pro Ala Met His
                100                     105                     110

```
Asn Leu His Ala Ala Leu Val Ser Leu Gly Leu Gly Asp Lys Val Lys
            115                 120                 125

Val Ser Ser Ala His Ala Ser Ser Val Leu Ala Ser Ser Tyr Pro Pro
        130                 135                 140

Ser Ala Gly Ala Phe Asp Ala Ala Ser Leu Asp Val Leu Arg Pro Met
145                 150                 155                 160

Leu Arg Phe Leu Ala Asp Thr Gly Ala Pro Phe Met Val Asn Thr Tyr
                165                 170                 175

Pro Phe Ile Ser Tyr Val Asn Asp Pro Val Asn Val Gln Leu Gly Tyr
            180                 185                 190

Ala Leu Phe Gly Ala Gly Ala Pro Ala Val Ser Asp Gly Ala Leu Val
        195                 200                 205

Tyr Thr Asn Met Phe Asp Ala Thr Val Asp Ala Leu Ala Ala Ala Leu
    210                 215                 220

Asp Arg Glu Gly Phe Gly Ala Val Pro Ile Ala Val Thr Glu Thr Gly
225                 230                 235                 240

Trp Pro Thr Ala Gly His Pro Ala Ala Thr Pro Gln Asn Ala Ala Ala
                245                 250                 255

Tyr Asn Ala Lys Ile Val Glu Arg Val Ala Arg Gly Ala Gly Thr Pro
            260                 265                 270

Arg Arg Pro Gly Val Pro Val Glu Val Phe Leu Phe Asp Leu Tyr Asp
        275                 280                 285

Glu Asp Gly Lys Pro Gly Ala Glu Phe Glu Arg His Phe Gly Ile Phe
    290                 295                 300

Arg Ala Asp Gly Ser Lys Ala Tyr Asn Ile Asn Phe
305                 310                 315

<210> SEQ ID NO 115
<211> LENGTH: 312
<212> TYPE: PRT
<213> ORGANISM: Zea mays

<400> SEQUENCE: 115

Ile Gly Val Asn Tyr Gly Met Val Ala Asn Asn Leu Pro Ala Pro Glu
1               5                   10                  15

Gln Val Val Ser Met Tyr Lys Ala Lys Asn Ile Ser Tyr Val Arg Leu
            20                  25                  30

Phe His Pro Asp Thr Asp Ala Leu Asn Ala Leu Arg Gly Ser Gly Val
        35                  40                  45

Gly Val Val Leu Gly Thr Leu Asn Glu Asp Leu Pro Arg Leu Ala Ser
    50                  55                  60

Asp Pro Ser Phe Ala Ala Ser Trp Val Ala Thr Asn Val Gln Pro Phe
65                  70                  75                  80

Ala Gly Ala Val Gln Phe Arg Tyr Ile Asn Ala Gly Asn Glu Val Ile
                85                  90                  95

Pro Gly Asp Ala Ala Ala Arg Val Leu Pro Ala Met Gln Asn Leu Glu
            100                 105                 110

Ser Ala Leu Arg Ser Ala Gly Val Thr Gly Val Pro Val Thr Thr Ala
        115                 120                 125

Val Ala Thr Ser Val Leu Gly Ala Ser Tyr Pro Ser Gln Gly Ala
    130                 135                 140

Phe Ser Glu Ala Ala Ala Ser Val Met Ala Pro Ile Val Ser Tyr Leu
145                 150                 155                 160

Ser Ser Lys Gly Ala Pro Leu Leu Val Asn Val Tyr Pro Tyr Phe Ala
```

```
            165                 170                 175
Tyr Ser Ser Ser Gly Gly Gln Val Ala Leu Gly Tyr Ala Leu Leu Ser
            180                 185                 190

Ala Asp Ala Gly Ala Ala Ser Ser Val Thr Asp Ala Gly Val Val Tyr
            195                 200                 205

Thr Asn Met Phe Asp Ala Ile Val Asp Ala Thr His Ala Ala Val Glu
210                 215                 220

Lys Ala Gly Val Gln Gly Leu Glu Leu Val Val Ser Glu Thr Gly Trp
225                 230                 235                 240

Pro Ser Ala Gly Gly Glu Gly Ala Thr Val Glu Asn Ala Ala Ala Tyr
                245                 250                 255

Asn Asn Asn Val Val Arg His Val Gly Gly Thr Pro Arg Arg Pro
                260                 265                 270

Gly Lys Ala Val Glu Thr Tyr Leu Phe Ala Met Phe Asn Glu Asn Gly
                275                 280                 285

Lys Ala Glu Gly Val Gln His Phe Gly Leu Phe Gln Pro Asp Met
            290                 295                 300

Ser Glu Val Tyr His Val Asp Phe
305                 310

<210> SEQ ID NO 116
<211> LENGTH: 315
<212> TYPE: PRT
<213> ORGANISM: Sorghum bicolor

<400> SEQUENCE: 116

Ile Gly Val Asn Tyr Gly Met Val Ala Asn Asn Leu Pro Ala Pro Glu
1               5                   10                  15

Gln Val Ile Ser Met Tyr Lys Ala Lys Asn Ile Asn Tyr Val Arg Leu
            20                  25                  30

Phe His Pro Asp Thr Ser Val Leu Asn Ala Leu Arg Gly Ser Gly Ile
            35                  40                  45

Gly Val Val Leu Gly Thr Leu Asn Glu Asp Leu Gln Arg Leu Ala Ser
    50                  55                  60

Asp Pro Ser Tyr Ala Ala Ser Trp Val Ala Thr Asn Val Gln Pro Phe
65                  70                  75                  80

Ala Gly Ala Val Gln Phe Arg Tyr Ile Asn Ala Gly Asn Glu Val Ile
                85                  90                  95

Pro Gly Asp Ala Ala Ala Gln Val Leu Pro Ala Met Gln Asn Leu Glu
            100                 105                 110

Ser Ala Leu Arg Ser Ala Gly Val Thr Gly Val Pro Val Thr Thr Ala
            115                 120                 125

Val Ala Thr Ser Val Leu Gly Thr Ser Tyr Pro Pro Ser Gln Gly Ala
    130                 135                 140

Phe Ser Glu Ala Ala Ala Pro Val Met Ala Pro Ile Val Ser Tyr Leu
145                 150                 155                 160

Ser Ser Lys Gly Ala Pro Leu Leu Val Asn Val Tyr Pro Tyr Phe Ala
                165                 170                 175

Tyr Ser Gly Ser Gly Gly Gln Val Ala Leu Gly Tyr Ala Leu Leu Ser
            180                 185                 190

Ser Asp Ala Ser Ala Ala Ser Ser Ser Val Thr Asp Gly Gly Val
        195                 200                 205

Val Tyr Thr Asn Met Phe Asp Ala Ile Val Asp Ala Thr His Ala Ala
    210                 215                 220
```

```
Val Glu Lys Ala Gly Val Gln Gly Leu Glu Leu Val Val Ser Glu Thr
225                 230                 235                 240

Gly Trp Pro Ser Gly Gly Gly Asp Gly Ala Thr Val Glu Asn Ala
            245                 250                 255

Ala Ala Tyr Asn Asn Asn Val Val Arg His Val Gly Gly Thr Pro
        260                 265                 270

Arg Arg Pro Gly Lys Ala Val Glu Thr Tyr Leu Phe Ala Met Phe Asn
            275                 280                 285

Glu Asn Gly Lys Ala Glu Gly Val Glu Gln His Phe Gly Leu Phe Gln
            290                 295                 300

Pro Asp Met Ser Glu Val Tyr His Val Asp Phe
305                 310                 315

<210> SEQ ID NO 117
<211> LENGTH: 315
<212> TYPE: PRT
<213> ORGANISM: Setaria italica

<400> SEQUENCE: 117

Ile Gly Val Asn Tyr Gly Met Val Ala Asn Asn Leu Pro Ala Pro Glu
1               5                   10                  15

Gln Val Ile Ser Met Tyr Val Ala Lys Asn Ile Ser Tyr Val Arg Leu
            20                  25                  30

Phe His Pro Asp Thr Ser Val Leu Thr Ala Leu Arg Gly Ser Gly Ile
        35                  40                  45

Gly Val Val Leu Gly Thr Leu Asn Glu Asp Leu Gln Arg Leu Ala Ser
    50                  55                  60

Asp Gln Ser Phe Ala Ala Ser Trp Val Ala Thr Asn Val Gln Pro Phe
65                  70                  75                  80

Ala Gly Ala Val Gln Phe Arg Tyr Ile Asn Ala Gly Asn Glu Val Ile
                85                  90                  95

Pro Gly Glu Ser Ala Ala His Val Leu Pro Ala Met Gln Asn Leu Glu
            100                 105                 110

Ser Ala Leu Arg Ser Ala Gly Val Ser Gly Val Ala Val Thr Thr Ala
        115                 120                 125

Val Ala Thr Ala Val Leu Gly Ala Ser Tyr Pro Pro Ser Gln Gly Ala
130                 135                 140

Phe Ser Glu Ala Ala Ala Pro Val Met Ala Pro Ile Val Ser Tyr Leu
145                 150                 155                 160

Ser Ser Lys Asn Ala Pro Leu Leu Val Asn Val Tyr Pro Tyr Phe Ala
                165                 170                 175

Tyr Ser Asn Ser Gly Gly Gln Val Ala Leu Gly Tyr Ala Leu Leu Ser
            180                 185                 190

Ala Ala Gly Ser Gly Ala Ala Ser Ser Ser Val Ala Asp Gly Gly
        195                 200                 205

Val Val Tyr Thr Asn Met Phe Asp Ala Ile Val Asp Ala Thr His Ala
210                 215                 220

Ala Val Glu Lys Ala Gly Val Gln Gly Leu Glu Leu Val Val Ser Glu
225                 230                 235                 240

Thr Gly Trp Pro Ser Gly Gly Gly Glu Gly Ala Ser Val Glu Asn Ala
                245                 250                 255

Ala Ala Tyr Asn Asn Asn Val Val Arg His Val Gly Gly Thr Pro
        260                 265                 270

Arg Arg Pro Gly Lys Pro Val Glu Thr Tyr Leu Phe Ala Met Phe Asn
            275                 280                 285
```

-continued

Glu Asn Gln Lys Thr Glu Gly Val Glu Gln His Phe Gly Leu Phe Gln
    290             295                 300

Pro Asp Met Ser Glu Val Tyr His Val Asp Phe
305                 310             315

<210> SEQ ID NO 118
<211> LENGTH: 313
<212> TYPE: PRT
<213> ORGANISM: Zea mays

<400> SEQUENCE: 118

Ile Gly Val Asn Tyr Gly Met Ile Ala Asn Asn Leu Pro Ala Pro Glu
1               5                   10                  15

Gln Val Val Ser Met Tyr Lys Ala Lys Asn Ile Ser Tyr Val Arg Leu
            20                  25                  30

Phe His Pro Asp Thr Thr Val Leu Asn Ala Leu Arg Gly Ser Gly Ile
        35                  40                  45

Gly Val Ile Leu Gly Thr Leu Asn Glu Asp Leu Pro Arg Leu Ala Ser
    50                  55                  60

Asp Pro Ser Phe Ala Ala Ser Trp Val Ala Thr Asn Val Gln Pro Phe
65                  70                  75                  80

Ala Gly Ala Val Gln Phe Arg Tyr Ile Asn Ala Gly Asn Glu Val Ile
                85                  90                  95

Pro Gly Asp Pro Ala Ala Gln Val Leu Pro Ala Met Lys Asn Leu Glu
            100                 105                 110

Ser Ala Leu Arg Ser Ala Gly Val Ala Gly Val Pro Val Thr Thr Ala
        115                 120                 125

Val Ala Thr Ser Val Leu Gly Ala Ser Tyr Pro Pro Ser Gln Gly Ala
    130                 135                 140

Phe Ser Glu Ala Ala Thr Thr Val Met Ala Pro Leu Val Ser Tyr Leu
145                 150                 155                 160

Ser Ser Arg Gly Ala Pro Leu Leu Val Asn Val Tyr Pro Tyr Phe Ala
                165                 170                 175

Tyr Ser Gly Ser Gly Gln Val Ala Leu Gly Tyr Ala Leu Leu Ser
            180                 185                 190

Gly Ala Gly Ala Gly Ala Ser Thr Val Thr Asp Gly Gly Ala Val
        195                 200                 205

Tyr Thr Asn Met Phe Asp Ala Ile Val Asp Ala Thr His Ala Ala Val
    210                 215                 220

Glu Lys Ala Gly Val Gln Gly Leu Glu Leu Val Val Ser Glu Thr Gly
225                 230                 235                 240

Trp Pro Ser Ala Gly Gly Glu Gly Ala Ser Val Glu Asn Ala Ala Ala
                245                 250                 255

Tyr Asn Asn Asn Val Val Arg His Val Asp Gly Gly Thr Pro Arg Arg
            260                 265                 270

Pro Gly Lys Ala Leu Glu Thr Tyr Leu Phe Ala Met Phe Asn Glu Asn
        275                 280                 285

Gly Lys Ala Glu Gly Val Glu Gln His Phe Gly Leu Phe Gln Pro Asp
    290                 295                 300

Met Ser Glu Val Tyr His Val Asp Phe
305                 310

<210> SEQ ID NO 119
<211> LENGTH: 314
<212> TYPE: PRT

<213> ORGANISM: Oryza sativa

<400> SEQUENCE: 119

Ile Gly Val Asn Tyr Gly Met Leu Gly Asn Asn Leu Pro Ser Pro Ala
1               5                   10                  15

Gln Val Ile Ser Met Tyr Lys Ala Lys Asn Ile Asn Tyr Val Arg Leu
            20                  25                  30

Phe His Pro Asp Thr Ala Val Leu Ala Ala Leu Arg Asn Ser Gly Ile
        35                  40                  45

Gly Val Val Leu Gly Thr Tyr Asn Glu Asp Leu Ala Arg Leu Ala Ser
    50                  55                  60

Asp Pro Ser Phe Ala Ala Ser Trp Val Ser Ser Tyr Val Gln Pro Phe
65                  70                  75                  80

Ala Gly Ala Val Ser Phe Arg Tyr Ile Asn Ala Gly Asn Glu Val Ile
                85                  90                  95

Pro Gly Asp Pro Ala Ala Asn Val Leu Pro Ala Met Arg Asn Leu Asp
            100                 105                 110

Ala Ala Leu Lys Ala Ala Gly Ile Ser Gly Ile Pro Val Thr Thr Ala
        115                 120                 125

Val Ala Thr Ser Val Leu Gly Val Ser Tyr Pro Ser Gln Gly Ala
    130                 135                 140

Phe Ser Glu Ala Ala Ser Pro Tyr Met Ala Pro Ile Val Ala Tyr Leu
145                 150                 155                 160

Ala Ser Arg Gly Ala Pro Leu Leu Val Asn Val Tyr Pro Tyr Phe Ala
                165                 170                 175

Tyr Ala Ala Asp Ala Glu Arg Val Gln Leu Gly Tyr Ala Leu Leu Ser
            180                 185                 190

Ala Ser Gln Ser Ala Ser Val Thr Asp Gly Gly Val Thr Tyr Thr Asn
        195                 200                 205

Met Phe Asp Ala Ile Val Asp Ala Ala His Ala Ala Val Glu Lys Ala
    210                 215                 220

Thr Gly Gly Gln Ala Val Glu Leu Val Val Ser Glu Thr Gly Trp Pro
225                 230                 235                 240

Ser Gly Gly Gly Val Gly Ala Thr Val Glu Asn Ala Ala Ala Tyr
                245                 250                 255

Asn Asn Asn Leu Ile Arg His Val Ser Gly Gly Ala Gly Thr Pro Arg
            260                 265                 270

Arg Pro Gly Lys Pro Val Glu Thr Tyr Leu Phe Ala Met Phe Asn Glu
        275                 280                 285

Asn Gln Lys Pro Glu Gly Val Glu Gln His Phe Gly Leu Phe Gln Pro
    290                 295                 300

Asp Met Thr Glu Val Tyr His Val Asp Phe
305                 310

<210> SEQ ID NO 120
<211> LENGTH: 316
<212> TYPE: PRT
<213> ORGANISM: Zea mays

<400> SEQUENCE: 120

Ile Gly Val Asn Tyr Gly Thr Ile Ala Ser Asn Leu Pro Ser Pro Asp
1               5                   10                  15

Lys Val Ile Ala Leu Cys Lys Ala Lys Gly Ile Thr Asp Val Arg Leu
            20                  25                  30

Phe His Pro Asp Thr Ala Val Leu Ala Ala Leu Arg Gly Ser Gly Leu

```
            35                  40                  45
Gly Val Val Leu Gly Thr Leu Asn Glu Asp Leu Ala Arg Leu Ala Ser
 50                  55                  60

Asp Pro Ser Phe Ala Ala Ser Trp Val Gln Tyr Val Arg Pro Phe
 65                  70                  75                  80

Ala Gly Ala Val Arg Phe Arg Tyr Val Ala Gly Asn Glu Val Val
                     85                  90                  95

Pro Gly Asp Leu Ala Ser His Val Leu Pro Ala Met Gln Asn Leu Glu
                    100                 105                 110

Ser Ala Leu Arg Ala Ala Gly Leu Gly Gly Val Arg Val Thr Thr Ala
                    115                 120                 125

Val Ser Thr Ser Val Leu Gly Thr Ser Tyr Pro Pro Ser Gln Gly Ala
                    130                 135                 140

Phe Ser Asp Ala Ala Leu Pro Ser Met Gly Pro Ile Ala Ser Phe Leu
145                 150                 155                 160

Ala Pro Arg Ser Thr Pro Leu Leu Val Asn Val Tyr Pro Tyr Phe Ala
                    165                 170                 175

Tyr Ser Ala Asp Pro Ala Ser Val Ser Leu Asp Tyr Ala Leu Leu Arg
                    180                 185                 190

Ser Asp Ser Gly Gly Gly Ala Val Val Ala Asp Gly Gly Ala Ser
                    195                 200                 205

Tyr Gly Asn Met Phe Asp Ala Ile Val Asp Ala Val Tyr Ala Ala Leu
                    210                 215                 220

Glu Arg Ala Gly Ala Arg Gly Leu Glu Leu Val Val Ser Glu Thr Gly
225                 230                 235                 240

Trp Pro Ser Gly Gly Gly Ala Gly Ala Ser Val Gly Asn Ala Ser
                    245                 250                 255

Ala Tyr Val Asn Asn Val Val Arg His Val Gly Ser Gly Arg Gly Thr
                    260                 265                 270

Pro Arg Arg Pro Gly Lys Pro Val Glu Ala Phe Ile Phe Ala Met Phe
                    275                 280                 285

Asn Glu Asn Gln Lys Pro Glu Gly Val Glu Gln His Phe Gly Met Phe
                    290                 295                 300

Gln Pro Asp Met Thr Glu Val Tyr His Val Asp Phe
305                 310                 315

<210> SEQ ID NO 121
<211> LENGTH: 316
<212> TYPE: PRT
<213> ORGANISM: Sorghum bicolor

<400> SEQUENCE: 121

Ile Gly Val Asn Tyr Gly Met Ile Ala Asn Asn Leu Pro Ser Pro Asp
 1                   5                  10                  15

Lys Val Ile Ala Leu Cys Lys Ala Arg Gly Ile Thr Asp Val Arg Leu
                     20                  25                  30

Phe His Pro Asp Thr Ala Val Leu Ala Leu Gln Gly Ser Gly Leu
                     35                  40                  45

Gly Val Val Leu Gly Thr Leu Asn Glu Asp Leu Ala Arg Leu Ala Ser
 50                  55                  60

Asp Pro Ser Phe Ala Ala Ser Trp Val Gln Thr Tyr Val Gln Pro Phe
 65                  70                  75                  80

Ala Gly Ala Val Arg Phe Arg Tyr Val Ala Ala Gly Asn Glu Val Ile
                     85                  90                  95
```

Pro Gly Asp Leu Ala Ser His Val Leu Pro Ala Met Gln Asn Leu Glu
            100                 105                 110

Ser Ala Leu Arg Ala Ala Gly Leu Gly Asp Gly Asp Gly Val Arg Val
            115                 120                 125

Thr Thr Ala Val Ser Thr Ser Val Leu Gly Ser Ser Tyr Pro Pro Ser
        130                 135                 140

Gln Gly Ala Phe Ser Glu Ala Ala Leu Pro Ser Met Ala Pro Ile Ala
145                 150                 155                 160

Ser Phe Leu Ala Ser Arg Ser Thr Pro Leu Ala Asn Val Tyr Pro
            165                 170                 175

Tyr Phe Ala Tyr Ser Ala Asp Pro Ser Ser Val Pro Leu Asp Tyr Ala
            180                 185                 190

Leu Leu Gln Ser Ala Ser Ala Ala Val Thr Asp Gly Ala Ser Tyr
            195                 200                 205

Gly Asn Met Phe Asp Ala Ile Val Asp Ala Val Tyr Ala Ala Leu Glu
            210                 215                 220

Arg Ala Gly Ala Pro Pro Gly Leu Glu Val Val Ser Glu Thr Gly
225                 230                 235                 240

Trp Pro Ser Gly Gly Gly Ala Gly Ala Ser Val Gly Asn Ala Ala
            245                 250                 255

Ala Tyr Val Asn Asn Val Val Arg His Val Ala Ser Gly Arg Gly Thr
            260                 265                 270

Pro Arg Arg Pro Gly Lys Ala Val Glu Ala Phe Val Phe Ala Met Phe
            275                 280                 285

Asn Glu Asn Gln Lys Pro Glu Gly Val Glu Gln His Phe Gly Leu Phe
            290                 295                 300

Gln Pro Asp Met Thr Glu Val Tyr His Val Asp Phe
305                 310                 315

<210> SEQ ID NO 122
<211> LENGTH: 317
<212> TYPE: PRT
<213> ORGANISM: Setaria italica

<400> SEQUENCE: 122

Ile Gly Val Asn Tyr Gly Met Ile Ala Asn Asn Leu Pro Ser Pro Asp
1               5                   10                  15

Lys Val Ile Ala Leu Tyr Arg Ser Arg Asn Ile Thr Asp Val Arg Leu
            20                  25                  30

Phe His Pro Asn Thr Thr Val Leu Ala Ala Leu Gln Gly Ser Gly Leu
        35                  40                  45

Gly Val Val Leu Gly Thr Leu Asn Glu Asp Leu Ala Arg Leu Ala Ser
    50                  55                  60

Asp Ala Ser Phe Ala Ala Ser Trp Val Gln Ser Tyr Val Gln Pro Phe
65                  70                  75                  80

Ala Gly Ala Val Arg Phe Arg Tyr Val Ala Gly Asn Glu Val Ile
            85                  90                  95

Pro Gly Asp Leu Ala Ala Tyr Val Leu Pro Ala Met Arg Asn Leu Glu
            100                 105                 110

Ser Ala Leu His Ala Ala Gly Ile Ala Gly Val Pro Val Thr Thr Ala
            115                 120                 125

Val Ser Thr Ser Val Leu Gly Ser Ser Tyr Pro Pro Ser Gln Gly Ala
        130                 135                 140

Phe Ser Glu Ala Ala Leu Pro Thr Val Gly Pro Ile Ala Ser Phe Leu
145                 150                 155                 160

```
Ala Ser Arg Ser Thr Pro Leu Leu Val Asn Val Tyr Pro Tyr Phe Ala
                165                 170                 175

Tyr Ala Ala Asp Pro Ser Ser Val Gln Leu Asp Tyr Ala Leu Leu Glu
            180                 185                 190

Pro Ala Ser Ala Ala Val Thr Asp Gly Gly Val Ala Tyr Thr Asn
        195                 200                 205

Met Phe Asp Ala Ile Val Asp Ala Val His Ala Leu Asp Arg Val
210                 215                 220

Ala Gly Ala Gln Gly Gln Glu Gly Val Glu Val Val Ser Glu Thr
225                 230                 235                 240

Gly Trp Pro Ser Gly Gly Gly Ala Gly Ala Ser Val Gly Asn Ala
                245                 250                 255

Ala Ala Tyr Val Asn Asn Val Val Arg His Val Gly Ser Gly Arg Gly
            260                 265                 270

Thr Pro Arg Arg Pro Gly Lys Ala Leu Glu Ala Phe Ile Phe Ala Met
        275                 280                 285

Phe Asn Glu Asn Glu Lys Pro Glu Gly Val Glu Gln His Phe Gly Leu
290                 295                 300

Phe Gln Pro Asp Met Thr Glu Val Tyr His Val Asp Phe
305                 310                 315
```

<210> SEQ ID NO 123
<211> LENGTH: 310
<212> TYPE: PRT
<213> ORGANISM: Oryza sativa

<400> SEQUENCE: 123

```
Ile Gly Val Asn Tyr Gly Met Ile Gly Asn Asn Leu Pro Ser Pro Asp
1               5                   10                  15

Lys Val Ile Ala Leu Tyr Arg Ala Ser Asn Ile Thr Asp Ile Arg Leu
            20                  25                  30

Phe His Pro Asp Thr Thr Val Leu Ala Ala Leu Arg Gly Ser Gly Leu
        35                  40                  45

Gly Val Val Leu Gly Thr Leu Asn Glu Asp Leu Ala Arg Leu Ala Thr
    50                  55                  60

Asp Ala Ser Phe Ala Ala Ser Trp Val Gln Ser Tyr Val Gln Pro Phe
65                  70                  75                  80

Ala Gly Ala Val Arg Phe Arg Tyr Ile Asn Ala Gly Asn Glu Val Ile
                85                  90                  95

Pro Gly Asp Glu Ala Ala Ser Val Leu Pro Ala Met Arg Asn Leu Gln
            100                 105                 110

Ser Ala Leu Arg Ala Ala Gly Leu Gly Val Pro Val Thr Thr Val Val
        115                 120                 125

Ala Thr Ser Val Leu Gly Ser Ser Tyr Pro Pro Ser Gln Gly Ala Phe
    130                 135                 140

Ser Glu Ala Ala Leu Pro Thr Ala Pro Ile Val Ser Phe Leu Ala
145                 150                 155                 160

Ser Ser Gly Thr Pro Leu Leu Val Asn Val Tyr Pro Tyr Phe Ala Tyr
                165                 170                 175

Ser Ala Asp Pro Ser Ser Val Arg Leu Asp Tyr Ala Leu Leu Ser Pro
            180                 185                 190

Ser Thr Ser Ala Ala Val Thr Asp Gly Gly Val Thr Tyr Thr Asn Met
        195                 200                 205

Phe Asp Ala Ile Leu Asp Ala Val Tyr Ala Ala Leu Glu Lys Ala Gly
```

```
                210                 215                 220
Gly Gln Gly Leu Glu Val Val Ser Glu Thr Gly Trp Pro Ser Gly
225                 230                 235                 240

Gly Gly Gly Ala Gly Ala Ser Val Glu Asn Ala Ala Ala Tyr Ser Asn
                245                 250                 255

Asn Leu Val Arg His Val Gly Arg Gly Thr Pro Arg Pro Gly Lys
                260                 265                 270

Ala Val Glu Thr Tyr Ile Phe Ala Met Phe Asn Glu Asn Gln Lys Pro
                275                 280                 285

Glu Gly Val Glu Gln Asn Phe Gly Leu Phe His Pro Asp Met Ser Ala
                290                 295                 300

Val Tyr His Val Asp Phe
305                 310

<210> SEQ ID NO 124
<211> LENGTH: 309
<212> TYPE: PRT
<213> ORGANISM: Zea mays

<400> SEQUENCE: 124

Ile Gly Val Cys Tyr Gly Met Asn Gly Asp Asp Leu Pro Ser Ala Ser
 1               5                  10                  15

Asp Val Val Gln Leu Tyr Lys Asp Asn Gly Ile Asp Ser Met Arg Ile
                20                  25                  30

Tyr Ser Pro Asp Thr Asp Val Leu Gln Ala Leu Ser Gly Ser Gly Ile
                35                  40                  45

Ala Val Thr Val Gly Val Pro Asn Ala Asp Val Gly Gly Leu Ala Ser
                50                  55                  60

Arg Pro Ser Ala Ala Ala Trp Val Gln Ser Tyr Val Leu Ala Phe
65                  70                  75                  80

Pro Ala Val Gln Phe Arg Tyr Ile Ala Val Gly Asn Glu Val Val Ala
                85                  90                  95

Gly Gly Arg Val Leu Leu Pro Ala Met Arg Asn Leu Asp Arg Ala Leu
                100                 105                 110

Ser Ala Ala Gly Leu Ala Asp Asp Ile Lys Val Ser Thr Ala Val Ala
                115                 120                 125

Ile Asp Val Val Gly Ser Ser Phe Pro Pro Ser Ala Gly Thr Phe Ala
130                 135                 140

Pro Ser Ala Gly Tyr Met Ala Arg Val Ala Arg Tyr Leu Gln Ser Thr
145                 150                 155                 160

Gly Ala Pro Leu Leu Ala Asn Leu Tyr Pro Tyr Tyr Ser Tyr Ile Ser
                165                 170                 175

Asp Pro Gly Ala Val Asp Ile Asn Tyr Ala Leu Leu Ala Met Pro Ala
                180                 185                 190

Gly Thr Val Val Val Gln Asp Gly Gly Tyr Ser Tyr Asp Ser Leu Phe
                195                 200                 205

Asp Ala Met Val Asp Cys Phe Tyr Ser Ala Leu Glu Asn Ala Gly Ala
                210                 215                 220

Gly Asn Val Thr Val Val Val Ser Glu Ser Gly Trp Pro Ser Ala Gly
225                 230                 235                 240

Ser Asp Ala Ala Asn Thr Thr Asn Ser Gln Ala Tyr Ser Gln Asn Leu
                245                 250                 255

Ile Asn His Val Gly Gln Gly Thr Pro Lys Arg Pro Gly Pro Ile Glu
                260                 265                 270
```

```
Ala Tyr Ile Phe Ala Thr Phe Asn Glu Asp Gln Lys Leu Gly Asp Asp
            275                 280                 285

Glu Thr Arg Arg His Phe Gly Leu Phe Asn Lys Asp Arg Ser Leu Ala
    290                 295                 300

Tyr Pro Ile Asp Phe
305

<210> SEQ ID NO 125
<211> LENGTH: 304
<212> TYPE: PRT
<213> ORGANISM: Zea mays

<400> SEQUENCE: 125

Ile Gly Val Cys Tyr Gly Val Asn Gly Asp Asn Leu Pro Pro Ala Ser
1               5                   10                  15

Asp Val Val Gln Leu Tyr Gln Ser Asn Gly Ile Asn Leu Met Arg Ile
            20                  25                  30

Tyr Phe Pro Asp Ala Asn Ala Leu Asn Ala Leu Ser Gly Thr Ser Ile
        35                  40                  45

Gly Leu Ile Met Asp Val Pro Asn Thr Asp Leu Ala Ser Leu Ala Ser
    50                  55                  60

Asp Pro Ser Ala Ala Ala Trp Val Gln Ser Asn Val Gln Ala Phe
65                  70                  75                  80

Pro Ser Val Ser Phe Arg Tyr Ile Ala Val Gly Asn Glu Ala Ser Gly
                85                  90                  95

Gly Asp Thr Gly Ser Ile Leu Pro Ala Met Lys Asn Leu Asn Ala Ala
            100                 105                 110

Leu Ala Asn Ala Gly Leu Gly Gly Ser Ile Lys Val Ser Thr Ala Val
        115                 120                 125

Gln Ser Asp Val Thr Gln Gly Phe Pro Pro Ser Gln Gly Thr Phe Ser
    130                 135                 140

Gln Gly Tyr Met Ala Pro Ile Ala Gln Tyr Leu Gln Ser Thr Gly Ala
145                 150                 155                 160

Pro Leu Leu Cys Asn Val Tyr Pro Tyr Phe Ser Tyr Ile Gly Asn Pro
                165                 170                 175

Ala Gln Ile Asp Leu Ser Tyr Ala Leu Phe Thr Ser Pro Gly Thr Val
            180                 185                 190

Val Gln Asp Gly Ser Asn Ala Tyr Gln Asn Leu Phe Asp Ala Leu Val
        195                 200                 205

Asp Thr Phe Val Ser Ala Leu Gln Asn Ala Gly Ala Gly Asn Val Pro
    210                 215                 220

Val Val Val Ser Glu Ser Gly Trp Pro Ser Ala Gly Gly Asp Ala Ala
225                 230                 235                 240

Thr Ala Ala Asn Ala Gln Thr Tyr Asn Gln Asn Leu Ile Asn His Val
                245                 250                 255

Gly Gln Gly Thr Pro Lys Arg Pro Gly Pro Ile Glu Thr Tyr Ile Phe
            260                 265                 270

Ala Met Phe Asn Glu Asp Gln Lys Thr Gly Ala Glu Ser Glu Arg His
        275                 280                 285

Phe Gly Leu Phe Asn Pro Asp Lys Ser Pro Ala Tyr Pro Ile Asn Phe
    290                 295                 300

<210> SEQ ID NO 126
<211> LENGTH: 304
<212> TYPE: PRT
<213> ORGANISM: Sorghum bicolor
```

<400> SEQUENCE: 126

| | | | | | | | | | | | | | | |
|---|---|---|---|---|---|---|---|---|---|---|---|---|---|---|
|Ile|Gly|Val|Cys|Tyr|Gly|Val|Asn|Gly|Asp|Asn|Leu|Pro|Pro|Ala|Ser|
|1| | | |5| | | | |10| | | | |15| |
|Asp|Val|Val|Gln|Leu|Tyr|Gln|Ser|Asn|Gly|Ile|Asn|Leu|Met|Arg|Ile|
| | | |20| | | | |25| | | | |30| | |
|Tyr|Phe|Pro|Asp|Thr|Asn|Ala|Leu|Asn|Ala|Leu|Ser|Gly|Ser|Asn|Ile|
| | |35| | | | |40| | | | |45| | | |
|Gly|Val|Ile|Met|Asp|Val|Pro|Asn|Ser|Asp|Leu|Ser|Ser|Leu|Ala|Ser|
| |50| | | | |55| | | | |60| | | | |
|Asp|Pro|Ser|Ala|Ala|Thr|Trp|Val|Gln|Arg|Asn|Leu|Gln|Ala|Phe|
|65| | | |70| | | |75| | | | |80| | |
|Pro|Gly|Val|Asn|Phe|Lys|Tyr|Ile|Ala|Val|Gly|Asn|Glu|Val|Ser|Gly|
| | | | |85| | | |90| | | | |95| | |
|Gly|Asp|Thr|Asn|Ser|Ile|Leu|Pro|Ala|Met|Gln|Asn|Val|Asn|Ser|Ala|
| | | |100| | | | |105| | | | |110| | |
|Leu|Ala|Asn|Ala|Gly|Leu|Gly|Gly|Ile|Lys|Val|Ser|Thr|Ala|Val|Glu|
| | | |115| | | | |120| | | | |125| | |
|Ser|Gly|Val|Thr|Gln|Gly|Phe|Pro|Ser|Gln|Gly|Ser|Phe|Ser|Gln|
| |130| | | | |135| | | | |140| | | | |
|Gly|Tyr|Met|Gly|Pro|Ile|Ala|Gln|Tyr|Leu|Gln|Ser|Thr|Gly|Ala|Pro|
|145| | | | |150| | | | |155| | | | |160|
|Leu|Leu|Cys|Asn|Val|Tyr|Pro|Tyr|Phe|Ser|Tyr|Thr|Gly|Asn|Glu|Ala|
| | | | |165| | | | |170| | | | |175| |
|Gln|Ile|Ala|Leu|Ser|Tyr|Ala|Leu|Phe|Thr|Ser|Pro|Gly|Thr|Val|Val|
| | | |180| | | | |185| | | | |190| | |
|Gln|Asp|Asp|Asp|Gly|Asn|Ala|Tyr|Gln|Asn|Leu|Phe|Asp|Ala|Leu|Val|
| | | |195| | | | |200| | | | |205| | |
|Asp|Thr|Phe|Val|Ser|Ala|Leu|Glu|Asn|Ala|Gly|Ala|Gly|Asn|Val|Gly|
| | |210| | | | |215| | | | |220| | | |
|Val|Val|Val|Ser|Glu|Ser|Gly|Trp|Pro|Ser|Asp|Gly|Gly|Asp|Ala|Ala|
|225| | | | |230| | | | |235| | | | |240|
|Thr|Pro|Gly|Asn|Ala|Gln|Thr|Tyr|Asn|Gln|Asn|Leu|Ile|Asn|His|Val|
| | | | |245| | | | |250| | | | |255| |
|Gly|Gln|Gly|Thr|Pro|Lys|Arg|Pro|Gly|Ala|Ile|Glu|Thr|Tyr|Ile|Phe|
| | | |260| | | | |265| | | | |270| | |
|Ala|Met|Phe|Asn|Glu|Asp|Lys|Lys|Thr|Gly|Ala|Glu|Thr|Glu|Arg|His|
| | |275| | | | |280| | | | |285| | | |
|Phe|Gly|Leu|Phe|Asn|Pro|Asp|Lys|Ser|Pro|Ala|Tyr|Pro|Ile|Asn|Phe|
| |290| | | | |295| | | | |300| | | | |

<210> SEQ ID NO 127
<211> LENGTH: 303
<212> TYPE: PRT
<213> ORGANISM: Sorghum bicolor

<400> SEQUENCE: 127

| | | | | | | | | | | | | | | |
|---|---|---|---|---|---|---|---|---|---|---|---|---|---|---|
|Ile|Gly|Val|Cys|Tyr|Gly|Val|Asn|Gly|Asp|Asn|Leu|Pro|Ser|Ala|Ser|
|1| | | |5| | | | |10| | | | |15| |
|Asp|Val|Val|Lys|Leu|Tyr|Gln|Ser|Asn|Gly|Ile|Asn|Leu|Met|Arg|Ile|
| | | |20| | | | |25| | | | |30| | |
|Tyr|Phe|Ala|Asp|Thr|Asn|Ala|Leu|Asn|Ala|Leu|Ser|Gly|Ser|Asn|Ile|
| | |35| | | | |40| | | | |45| | | |
|Gly|Val|Ile|Met|Asp|Val|Pro|Asn|Thr|Asp|Leu|Ser|Ser|Leu|Ala|Ser|
| |50| | | | |55| | | | |60| | | | |

```
Asp Pro Ser Ala Ala Ala Thr Trp Val Lys Ser Asn Val Gln Ala Phe
 65                  70                  75                  80

Pro Gly Val Asn Phe Lys Tyr Ile Ala Val Gly Asn Glu Val Ser Gly
                 85                  90                  95

Gly Asp Thr Asn Asn Ile Leu Pro Ala Met Lys Asn Val Asn Ser Ala
            100                 105                 110

Leu Ser Asn Ala Gly Leu Gly Lys Ile Lys Val Ser Thr Ala Val Gln
            115                 120                 125

Ser Gly Val Thr Gln Gly Tyr Pro Ser Gln Gly Ser Phe Ser Gln
130                 135                 140

Ser Tyr Met Ala Pro Ile Ala Gln Tyr Leu Gln Ser Thr Gly Ala Pro
145                 150                 155                 160

Leu Leu Cys Asn Val Tyr Pro Tyr Phe Ser Tyr Thr Gly Asn Glu Ala
                165                 170                 175

Gln Ile Ala Leu Ser Tyr Ala Leu Phe Thr Ser Pro Gly Thr Val Val
            180                 185                 190

Gln Asp Gly Ser Asn Ala Tyr Gln Asn Leu Phe Asp Ala Leu Val Asp
            195                 200                 205

Thr Phe Val Ser Ala Leu Glu Asn Ala Gly Ala Gly Asn Val Gly Val
210                 215                 220

Val Val Ser Glu Ser Gly Trp Pro Ser Ala Gly Gly Asp Ala Ala Thr
225                 230                 235                 240

Pro Gly Asn Ala Gln Thr Tyr Asn Gln Asn Leu Ile Asn His Val Gly
                245                 250                 255

Lys Gly Thr Pro Lys Arg Pro Gly Ala Ile Glu Thr Tyr Ile Phe Ala
            260                 265                 270

Met Phe Asn Glu Asp Lys Lys Thr Gly Ala Glu Thr Glu Arg His Phe
            275                 280                 285

Gly Leu Phe Asn Pro Asp Lys Ser Pro Ala Tyr Ser Ile Asn Phe
            290                 295                 300

<210> SEQ ID NO 128
<211> LENGTH: 303
<212> TYPE: PRT
<213> ORGANISM: Setaria italica

<400> SEQUENCE: 128

Ile Gly Val Cys Tyr Gly Val Asn Gly Asn Gly Leu Pro Ser Ala Gly
  1               5                  10                  15

Asp Val Val Gln Leu Tyr Gln Ser Lys Gly Ile Asn Leu Met Arg Ile
             20                  25                  30

Tyr Phe Pro Asp Ser Asn Ala Leu Gln Ala Leu Ser Gly Ser Asn Ile
             35                  40                  45

Gly Val Ile Met Asp Val Pro Asn Asp Lys Leu Gly Ser Ile Ala Ser
 50                  55                  60

Asp Pro Asn Ala Ala Ala Gly Trp Val Arg Asp Asn Val Gln Ala Phe
 65                  70                  75                  80

Ser Gly Val Ser Phe Arg Tyr Ile Ala Val Gly Asn Glu Val Ala Gly
                 85                  90                  95

Gly Asp Thr Ala Asn Ile Leu Pro Ala Met Arg Asn Ile Asn Asp Ala
            100                 105                 110

Leu Asn Asn Ala Gly Leu Gly Ser Ile Lys Val Ser Thr Ala Val Gln
            115                 120                 125

Ser Gly Val Thr Gln Gly Phe Pro Pro Ser Gln Gly Ser Phe Ser Ala
```

```
                    130                 135                 140
Gly His Met Gly Pro Ile Ala Gln Phe Leu Gln Ser Thr Gly Ala Pro
145                 150                 155                 160

Leu Leu Ala Asn Val Tyr Pro Tyr Phe Ser Tyr Val Gly Asn Gln Ala
                165                 170                 175

Gln Ile Asp Ile Asn Tyr Ala Leu Phe Thr Ser Pro Gly Thr Val Val
                180                 185                 190

Gln Asp Gly Gly Asn Ala Tyr Gln Asn Leu Phe Asp Ala Leu Val Asp
                195                 200                 205

Thr Phe Tyr Ser Ala Leu Glu Asn Ala Gly Ala Gly Ser Val Gly Ile
                210                 215                 220

Val Val Ser Glu Ser Gly Trp Pro Ser Ala Gly Gly Asp Ala Ala Ser
225                 230                 235                 240

Thr Asp Asn Ala Arg Thr Tyr Asn Gln Asn Leu Ile Asn His Val Gly
                245                 250                 255

Gln Gly Thr Pro Lys Arg Pro Gly Ala Ile Glu Thr Tyr Ile Phe Ala
                260                 265                 270

Met Phe Asn Glu Asp Gln Lys Pro Gly Ala Glu Thr Glu Lys His Phe
                275                 280                 285

Gly Leu Phe Asn Pro Asp Lys Ser Pro Val Tyr Asp Ile Asn Phe
                290                 295                 300

<210> SEQ ID NO 129
<211> LENGTH: 303
<212> TYPE: PRT
<213> ORGANISM: Oryza sativa

<400> SEQUENCE: 129

Ile Gly Val Cys Tyr Gly Val Ile Gly Asn Asn Leu Pro Ser Pro Ser
1               5                   10                  15

Asp Val Val Gln Leu Tyr Lys Ser Asn Gly Ile Asp Ser Met Arg Ile
                20                  25                  30

Tyr Phe Pro Arg Ser Asp Ile Leu Gln Ala Leu Ser Gly Ser Ser Ile
                35                  40                  45

Ala Leu Thr Met Asp Val Gly Asn Asp Gln Leu Gly Ser Leu Ala Ser
            50                  55                  60

Asp Pro Ser Ala Ala Ala Phe Val Gln Asn Asn Ile Gln Ala Phe
65                  70                  75                  80

Pro Gly Val Asn Phe Arg Tyr Ile Thr Val Gly Asn Glu Val Ser Gly
                85                  90                  95

Gly Asp Thr Gln Asn Ile Leu Pro Ala Met Gln Asn Met Asn Ser Ala
                100                 105                 110

Leu Ser Ala Ala Gly Leu Gly Asn Ile Lys Val Ser Thr Ser Val Ser
                115                 120                 125

Gln Gly Val Thr Ala Gly Phe Pro Pro Ser Ala Gly Thr Phe Ser Ala
130                 135                 140

Ser His Met Gly Pro Ile Ala Gln Tyr Leu Ala Ser Thr Gly Ala Pro
145                 150                 155                 160

Leu Leu Ala Asn Val Tyr Pro Tyr Phe Ala Tyr Val Gly Asn Gln Ala
                165                 170                 175

Gln Ile Asp Ile Asn Tyr Ala Leu Phe Thr Ser Pro Gly Thr Val Val
                180                 185                 190

Gln Asp Gly Gly Asn Ala Tyr Gln Asn Leu Phe Asp Ala Ile Val Asp
                195                 200                 205
```

```
Thr Phe Tyr Ser Ala Leu Glu Ser Ala Gly Ala Gly Ser Val Pro Ile
    210                 215                 220

Val Val Ser Glu Ser Gly Trp Pro Ser Ala Gly Gly Thr Ala Ala Ser
225                 230                 235                 240

Ala Gly Asn Ala Gln Thr Tyr Asn Gln Asn Leu Ile Asn His Val Gly
                245                 250                 255

Gln Gly Thr Pro Lys Arg Pro Gly Ser Ile Glu Thr Tyr Ile Phe Ala
                260                 265                 270

Met Phe Asn Glu Asn Gln Lys Gly Gly Asp Glu Thr Glu Arg His Phe
                275                 280                 285

Gly Leu Phe Asn Pro Asp Gln Ser Pro Ala Tyr Ser Ile Asn Phe
            290                 295                 300
```

<210> SEQ ID NO 130
<211> LENGTH: 309
<212> TYPE: PRT
<213> ORGANISM: Oryza sativa

<400> SEQUENCE: 130

```
Ile Gly Val Cys Tyr Gly Val Asn Gly Asn Asn Leu Pro Ser Pro Ser
1               5                   10                  15

Asp Val Val Lys Leu Tyr Gln Ser Lys Gly Ile Asp Ser Met Arg Ile
                20                  25                  30

Tyr Phe Pro Arg Ser Asp Ile Leu Gln Ala Leu Thr Gly Ser Asn Ile
            35                  40                  45

Ala Leu Thr Met Gly Val Ala Asn Glu Asn Leu Ser Ala Phe Ala Ser
        50                  55                  60

Asp Pro Ser Ala Val Ala Asn Trp Val Lys Gln Asn Val Gln Val Tyr
65                  70                  75                  80

Pro Gly Val Asn Phe Arg Tyr Ile Ala Val Gly Asn Glu Val Glu Ser
                85                  90                  95

Gly Asn Thr Gln Asn Val Leu Pro Ala Met Gln Asn Met Asn Ser Ala
            100                 105                 110

Leu Ser Ala Ala Gly Leu Ser Asn Ile Lys Val Ser Val Ser Val Ser
        115                 120                 125

Gln Lys Gly Val Leu Ala Gly Tyr Pro Pro Ser Asn Gly Met Phe Ser
    130                 135                 140

Pro Glu Ala Thr Ser Tyr Met Thr Pro Ile Ala Lys Tyr Leu Ala Ser
145                 150                 155                 160

Thr Gly Ala Pro Leu Met Ala Asn Val Tyr Pro Tyr Phe Ala Tyr Val
                165                 170                 175

Gly Asn Leu Arg Ala Gln Ile Asp Asp Ile Asn Tyr Ala Leu Phe Thr
            180                 185                 190

Ser Pro Gly Thr Val Val Pro Asp Gly Ser Lys Ala Tyr Gln Asn Gln
        195                 200                 205

Phe Asp Ala Ile Val Asp Thr Phe Tyr Ser Ala Leu Glu Ser Ala Gly
    210                 215                 220

Ala Gly Ser Val Pro Ile Val Val Ser Glu Ser Gly Trp Pro Ser Ala
225                 230                 235                 240

Gly Gly Thr Ala Ala Ser Ala Ser Asn Ala Gln Thr Tyr Asn Gln Asn
                245                 250                 255

Leu Ile Lys His Val Gly Gln Gly Thr Pro Lys Arg Ala Gly Arg Ile
            260                 265                 270

Glu Thr Tyr Ile Phe Ala Met Phe Asn Glu Asn Asp Lys Arg Gly Asp
        275                 280                 285
```

Glu Thr Glu Arg His Phe Gly Leu Phe Asn Pro Asp Gln Ser Pro Ala
            290                 295                 300

Tyr Thr Ile Asn Phe
305

<210> SEQ ID NO 131
<211> LENGTH: 226
<212> TYPE: PRT
<213> ORGANISM: Oryza sativa

<400> SEQUENCE: 131

Met Gly Val Ala Asn Glu Asn Leu Ser Ala Phe Ala Ser Asp Pro Ser
  1               5                  10                  15

Ala Val Ala Asn Trp Val Lys Gln Asn Val Gln Val Tyr Pro Gly Val
                 20                  25                  30

Asn Phe Arg Tyr Ile Ala Val Gly Asn Glu Val Glu Ser Gly Asn Thr
             35                  40                  45

Gln Asn Val Leu Pro Ala Met Gln Asn Met Asn Ser Ala Leu Ser Ala
     50                  55                  60

Ala Gly Leu Ser Asn Ile Lys Val Ser Val Ser Val Ser Gln Lys Gly
 65                  70                  75                  80

Val Leu Ala Gly Tyr Pro Pro Ser Asn Gly Met Phe Ser Pro Glu Ala
                 85                  90                  95

Thr Ser Tyr Met Thr Pro Ile Ala Lys Tyr Leu Ala Ser Thr Gly Ala
                100                 105                 110

Pro Leu Met Ala Asn Val Tyr Pro Tyr Phe Ala Tyr Val Gly Asn Leu
            115                 120                 125

Arg Ala Gln Ile Asp Asp Ile Asn Tyr Ala Leu Phe Thr Ser Pro Gly
    130                 135                 140

Thr Val Val Pro Asp Gly Ser Lys Ala Tyr Gln Asn Gln Phe Asp Ala
145                 150                 155                 160

Ile Val Asp Thr Phe Tyr Ser Ala Leu Glu Ser Ala Gly Ala Gly Ser
                165                 170                 175

Val Pro Ile Val Val Ser Glu Ser Gly Trp Pro Ser Ala Gly Gly Thr
            180                 185                 190

Ala Ala Ser Ala Ser Asn Ala Gln Thr Tyr Asn Gln Asn Leu Ile Lys
        195                 200                 205

His Val Gly Gln Gly Thr Pro Lys Arg Ala Gly Arg Ile Glu Ile Tyr
    210                 215                 220

Ile Phe
225

<210> SEQ ID NO 132
<211> LENGTH: 308
<212> TYPE: PRT
<213> ORGANISM: Oryza sativa

<400> SEQUENCE: 132

Ile Gly Val Cys Tyr Gly Val Lys Gly Asn Asn Leu Pro Pro Trp His
  1               5                  10                  15

Glu Val Val Gln Leu Tyr Ala Ser Asn Asn Ile Pro Ala Met Arg Ile
                 20                  25                  30

Phe Tyr Pro His His Asp Val Leu Glu Ala Leu Arg Gly Thr Gly Ile
             35                  40                  45

Gly Ile Ser Leu Asp Val Glu Gly Gln Phe Leu Pro Ser Phe Ala Ser
     50                  55                  60

```
Glu Pro Ser Val Ala Ala Ala Trp Val Lys Thr Asn Val Gln Ala Phe
 65                  70                  75                  80

Tyr Pro Ala Val Ser Phe Lys Phe Ile Thr Val Gly Asn Gln Val Ala
                 85                  90                  95

Leu Arg Glu Met Arg Tyr Ile Leu Pro Ala Met Gln Asn Ile Tyr Ala
            100                 105                 110

Ala Leu Ser Ala Val Gly Leu Asp His Ile Lys Val Ser Thr Ser Val
        115                 120                 125

Arg Arg Asp Val Leu Gly Leu Ser Tyr Pro Ser Ala Gly Ala Phe
    130                 135                 140

Ser Ser Ala Met Glu Gln Tyr Met Ala Pro Ile Val Gln Phe Leu Ala
145                 150                 155                 160

Lys Ile Gly Ala Pro Leu Leu Ala Ser Val Phe Pro Tyr Phe Thr Tyr
                165                 170                 175

Val His Asn Gln Glu Gly Ile Asp Ile Asp Tyr Ala Leu Phe Thr Ser
            180                 185                 190

Pro Gly Thr Val Val Gln Asp Gly Glu His Ser Tyr Gln Asn Leu Phe
        195                 200                 205

Asp Ala Ile Val Asp Ala Leu Tyr Ser Ala Met Glu Lys Val Gly Gly
    210                 215                 220

Ser Thr Val Arg Ile Val Val Ser Asp Ser Gly Trp Pro Ser Ala Gly
225                 230                 235                 240

Ala Pro Ala Ala Thr Lys Asp Asn Ala Arg Ala Tyr Val Gln Asn Leu
                245                 250                 255

Ile Asn His Val Ser Lys Gly Thr Pro Lys Arg Pro Val Pro Ile Glu
            260                 265                 270

Thr Tyr Ile Phe Ala Met Phe Asn Glu Asn Glu Lys Thr Gly Asp Glu
        275                 280                 285

Ile Glu Arg Asn Phe Gly Leu Phe Glu Pro Asp Lys Ser Pro Val Tyr
    290                 295                 300

Pro Ile Thr Phe
305

<210> SEQ ID NO 133
<211> LENGTH: 277
<212> TYPE: PRT
<213> ORGANISM: Zea mays

<400> SEQUENCE: 133

Met Arg Ile Tyr Ser Pro Asp Ala Thr Ile Leu Gln Ala Leu Arg Gly
 1               5                  10                  15

Ser Gly Ile Asp Leu Ile Val Asp Glu Thr Asn Leu Asp Ser Leu Ile
            20                  25                  30

Ser Asp Ala Pro Gly Trp Val Gln Ala Asn Leu Gln Pro Tyr Lys Asp
        35                  40                  45

Asp Val Ser Phe Lys Tyr Ile Ala Val Gly Asn Glu Val Glu Gly Gly
    50                  55                  60

Asp Thr Gln Lys Ile Leu Pro Ala Met Gln Ser Leu Ser Asp Ala Leu
 65                  70                  75                  80

Ser Ala Ala Gly Leu Gly Asn Ile Lys Val Ser Thr Ala Val Lys Met
                 85                  90                  95

Ser Val Leu Ala Thr Pro Ser Ser Pro Pro Ser Thr Gly Ala Phe Ala
            100                 105                 110

Asp Pro Ser Val Met Gly Pro Ile Val Arg Phe Leu Ala Gly Val Gly
```

```
            115                 120                 125
Ser Pro Leu Leu Ala Asn Ile Tyr Pro Tyr Phe Ala Tyr Arg Asp Ala
    130                 135                 140

Ala Gly Thr Ile Asp Leu Asn Tyr Ala Leu Phe Gln Pro Ser Thr Thr
145                 150                 155                 160

Val Val Thr Asp Asp Gly Gly Leu Asp Tyr Thr Asn Leu Phe Asp Ala
                165                 170                 175

Met Ala Asp Ala Met Tyr Ser Ala Met Glu Lys Glu Gly Gly Ser Gly
            180                 185                 190

Val Pro Ile Val Val Ser Glu Ser Gly Trp Pro Ser Gly Gly Gly Gly
                195                 200                 205

Thr Gly Ala Glu Thr Val Asp Asn Ala Arg Thr Tyr Asn Gln Asn Leu
            210                 215                 220

Ile Asn His Val Gly Asn Gly Thr Pro Lys Arg Ser Gly Pro Leu Glu
225                 230                 235                 240

Thr Tyr Ile Phe Ala Met Phe Asn Glu Asp Lys Lys Gln Gly Asp Glu
                245                 250                 255

Thr Glu Lys His Phe Gly Leu Phe Asn Gly Pro Asp Gln Ser Pro Val
            260                 265                 270

Tyr Gln Ile Ser Phe
            275

<210> SEQ ID NO 134
<211> LENGTH: 303
<212> TYPE: PRT
<213> ORGANISM: Sorghum bicolor

<400> SEQUENCE: 134

Ile Gly Val Cys Tyr Gly Thr Gln Gly Asp Gly Leu Pro Ser Ala Ala
1               5                   10                  15

Asp Val Val Gln Leu Tyr Gln Ser Lys Gly Ile Gly Ala Met Arg Ile
                20                  25                  30

Tyr Ser Pro Asp Ala Thr Ile Leu Gln Ala Leu Arg Gly Ser Gly Ile
            35                  40                  45

Asp Val Ile Val Asp Glu Thr Asn Leu Asp Ala Leu Ile Ser Asp Ala
        50                  55                  60

Gly Ser Trp Val Gln Ala Asn Val Gln Pro Tyr Ile Gly Asp Val Lys
65                  70                  75                  80

Phe Lys Tyr Ile Ala Val Gly Asn Glu Val Glu Gly Ser Asp Thr Gln
                85                  90                  95

Lys Ile Leu Pro Ala Met Gln Ser Leu Ala Gly Ala Leu Ser Ala Ala
            100                 105                 110

Gly Phe Gly Asp Ile Lys Val Ser Thr Ala Val Lys Met Ser Val Leu
        115                 120                 125

Ala Thr Ser Ser Pro Pro Ser Ser Gly Ala Phe Lys Asp Ser Ser Val
    130                 135                 140

Met Gly Pro Val Val Arg Phe Leu Ala Gly Ser Gly Ala Pro Leu Leu
145                 150                 155                 160

Ala Asn Val Tyr Pro Tyr Phe Ala Tyr Arg Asp Ala Gly Gly Ser Ile
                165                 170                 175

Asp Leu Gly Phe Ser Leu Phe Glu Gln Ser Ser Thr Thr Val Asn Asp
            180                 185                 190

Asp Gly His Val Tyr Thr Asn Leu Phe Asp Ala Met Ala Asp Ala Ile
        195                 200                 205
```

```
Tyr Ser Ala Met Glu Lys Glu Gly Glu Ser Gly Val Pro Ile Val Val
    210                 215                 220

Ser Glu Ser Gly Trp Pro Ser Asp Gly Gly Leu Gly Ala Ser Val
225                 230                 235                 240

Asp Asn Ala Gln Thr Tyr Asn Gln Asn Leu Ile Asn His Val Gly Asn
                245                 250                 255

Gly Thr Pro Lys Arg Ser Gly Pro Leu Glu Thr Tyr Ile Phe Ala Met
                260                 265                 270

Phe Asn Glu Asn Lys Lys Gln Gly Asp Glu Thr Glu Lys His Phe Gly
                275                 280                 285

Leu Phe Asn Gly Gln Asp Lys Ser Pro Val Tyr Pro Ile Ser Phe
    290                 295                 300

<210> SEQ ID NO 135
<211> LENGTH: 301
<212> TYPE: PRT
<213> ORGANISM: Setaria italica

<400> SEQUENCE: 135

Ile Gly Val Cys Tyr Gly Thr His Gly Asp Gly Leu Pro Ser Ala Ala
1               5                   10                  15

Asp Val Val Gln Leu Tyr Arg Ser Asn Gly Ile Asn Arg Met Arg Ile
                20                  25                  30

Tyr Ser Pro Asp Ala Thr Ile Leu Lys Ala Leu Arg Gly Ser Gly Ile
            35                  40                  45

Asp Val Ile Val Asp Glu Thr Asp Leu Asn Ala Leu Leu Ser Asp Ala
        50                  55                  60

Ser Val Trp Val Gln Ala Asn Val Leu Pro Tyr Lys Asp Asp Val Lys
65                  70                  75                  80

Phe Lys Tyr Ile Ala Val Gly Asn Glu Val Glu Gly Ser Asp Thr Gln
                85                  90                  95

Lys Ile Leu Pro Ala Met Gln Lys Leu Asn Ala Ala Leu Ser Ala Ala
            100                 105                 110

Gly Leu Ser Asn Ile Lys Val Ser Thr Ala Val Lys Met Ser Val Leu
        115                 120                 125

Asp Thr Pro Ser Ser Pro Pro Ser Asn Gly Val Phe Ala Asp Pro Ser
130                 135                 140

Ile Met Gly Pro Ile Val Gln Phe Leu Ala Ser Thr Gly Ser Pro Leu
145                 150                 155                 160

Leu Ala Asn Ile Tyr Pro Tyr Phe Ala Tyr Lys Gly Ala Asp Gly Asn
                165                 170                 175

Ile Asp Leu Asn Tyr Ala Leu Phe Lys Pro Ser Pro Thr Ser Asn
            180                 185                 190

Gly Pro Glu Tyr Thr Asn Leu Phe Asp Ala Met Thr Asp Ala Met Tyr
        195                 200                 205

Thr Ala Met Glu Lys Val Gly Gly Ser Asn Val Pro Ile Val Val Ser
    210                 215                 220

Glu Ser Gly Trp Pro Ser Asp Gly Gly Phe Gly Ala Ser Val Gln Asn
225                 230                 235                 240

Ala Gln Thr Tyr Asn Gln Asn Leu Ile His His Val Gly Lys Gly Thr
                245                 250                 255

Pro Lys Arg Pro Gly Ala Leu Glu Thr Tyr Ile Phe Ala Met Phe Asn
            260                 265                 270

Glu Asn Lys Lys Thr Gly Asp Glu Thr Glu Lys His Phe Gly Leu Phe
        275                 280                 285
```

```
Asn Gly Gln Asn Lys Ser Pro Val Tyr Thr Ile Arg Phe
        290                 295                 300
```

<210> SEQ ID NO 136
<211> LENGTH: 300
<212> TYPE: PRT
<213> ORGANISM: Oryza sativa

<400> SEQUENCE: 136

```
Ile Gly Val Cys Asn Gly Ile Leu Gly Asn Asn Leu Pro Ser Pro Ala
  1               5                  10                  15

Asp Val Val Lys Leu Tyr Gln Ser Asn Gly Ile Ala Ala Met Arg Ile
             20                  25                  30

Tyr Ser Pro His Ala Ala Thr Leu Arg Ala Leu Ala Gly Thr Asp Ile
         35                  40                  45

Ala Val Ile Val Asp Glu Pro Ala Ile Asp Gln Phe Leu Thr Leu Ser
     50                  55                  60

Ala Ala Ser Asp Trp Val Gln Ser Asn Ile Lys Pro Tyr Gln Gly Val
 65                  70                  75                  80

Asn Ile Arg Tyr Ile Ala Val Gly Asn Glu Val Ser Gly Asp Ala Thr
                 85                  90                  95

Arg Ser Ile Leu Pro Ala Met Glu Asn Leu Thr Lys Ala Leu Ser Ala
            100                 105                 110

Ala Gly Phe Gly Lys Ile Lys Val Ser Thr Ala Val Lys Met Asp Val
        115                 120                 125

Leu Gly Thr Ser Ser Pro Pro Ser Gly Gly Glu Phe Ser Asp Ala Ala
    130                 135                 140

Val Met Ala Pro Ile Ala Lys Phe Leu Ala Ser Asn Gly Ser Pro Leu
145                 150                 155                 160

Leu Ala Asn Val Tyr Pro Tyr Phe Ala Tyr Lys Gly Gly Asp Val Asp
                165                 170                 175

Leu Asn Phe Ala Leu Phe Gln Pro Thr Thr Ala Thr Val Ala Asp Asp
            180                 185                 190

Gly Arg Thr Tyr Ser Asn Met Phe Ala Ala Met Val Asp Ala Met Tyr
        195                 200                 205

Ser Ala Leu Glu Lys Ala Gly Ala Pro Gly Val Ala Val Val Val Ser
    210                 215                 220

Glu Ser Gly Trp Pro Ser Ala Gly Gly Ser Gly Ala Ser Ala Asp Asn
225                 230                 235                 240

Ala Arg Arg Tyr Asn Gln Gly Leu Ile Asp His Val Gly Met Gly Thr
                245                 250                 255

Pro Lys Arg Ala Gly Ala Met Glu Ala Tyr Ile Phe Ala Met Phe Asn
            260                 265                 270

Glu Asn Gln Lys Asp Gly Asp Glu Thr Glu Arg His Tyr Gly Leu Phe
        275                 280                 285

Asn Pro Asp Lys Ser Pro Ala Tyr Pro Ile Lys Phe
    290                 295                 300
```

<210> SEQ ID NO 137
<211> LENGTH: 310
<212> TYPE: PRT
<213> ORGANISM: Oryza sativa

<400> SEQUENCE: 137

```
Ile Gly Val Cys Tyr Gly Val Val Ala Asn Asn Leu Pro Gly Pro Ser
  1               5                  10                  15
```

Glu Val Val Gln Leu Tyr Arg Ser Lys Gly Ile Asp Ser Met Arg Ile
            20                  25                  30

Tyr Phe Ala Asp Ala Ala Ala Leu Asn Ala Leu Ser Gly Ser Asn Ile
        35                  40                  45

Gly Leu Ile Met Asp Val Gly Asn Gly Asn Leu Ser Ser Leu Ala Ser
    50                  55                  60

Ser Pro Ser Ala Ala Ala Gly Trp Val Arg Asp Asn Ile Gln Ala Tyr
65                  70                  75                  80

Pro Gly Val Ser Phe Arg Tyr Ile Ala Val Gly Asn Glu Val Gln Gly
                85                  90                  95

Ser Asp Thr Ala Asn Ile Leu Pro Ala Met Arg Asn Val Asn Ser Ala
            100                 105                 110

Leu Val Ala Ala Gly Leu Gly Asn Ile Lys Val Ser Thr Ser Val Arg
        115                 120                 125

Phe Asp Ala Phe Ala Asp Thr Phe Pro Pro Ser Ser Gly Arg Phe Arg
130                 135                 140

Asp Asp Tyr Met Thr Pro Ile Ala Arg Phe Leu Ala Thr Gly Ala
145                 150                 155                 160

Pro Leu Leu Ala Asn Val Tyr Pro Tyr Phe Ala Tyr Lys Asp Asp Gln
                165                 170                 175

Glu Ser Gly Gln Lys Asn Ile Met Leu Asn Tyr Ala Thr Phe Gln Pro
            180                 185                 190

Gly Thr Thr Val Val Asp Asn Gly Asn Arg Leu Thr Tyr Thr Cys Leu
        195                 200                 205

Phe Asp Ala Met Val Asp Ser Ile Tyr Ala Ala Leu Glu Lys Ala Gly
210                 215                 220

Thr Pro Ser Val Ser Val Val Ser Glu Ser Gly Trp Pro Ser Ala
225                 230                 235                 240

Gly Gly Lys Val Gly Ala Ser Val Asn Asn Ala Gln Thr Tyr Asn Gln
                245                 250                 255

Gly Leu Ile Asn His Val Arg Gly Gly Thr Pro Lys Lys Arg Arg Ala
            260                 265                 270

Leu Glu Thr Tyr Ile Phe Ala Met Phe Asp Glu Asn Gly Lys Pro Gly
        275                 280                 285

Asp Glu Ile Glu Lys His Phe Gly Leu Phe Asn Pro Asn Lys Ser Pro
290                 295                 300

Ser Tyr Ser Ile Ser Phe
305             310

<210> SEQ ID NO 138
<211> LENGTH: 306
<212> TYPE: PRT
<213> ORGANISM: Oryza sativa

<400> SEQUENCE: 138

Ile Gly Val Cys Tyr Gly Val Ile Gly Asn Asn Leu Pro Ala Ala Ser
1               5                   10                  15

Asp Val Val Lys Leu Tyr Lys Ser Lys Gly Ile Asp Ser Met Arg Ile
            20                  25                  30

Tyr Phe Pro Arg Ser Asp Ile Leu Gln Ala Leu Thr Gly Ser Asn Ile
        35                  40                  45

Ala Leu Thr Met Asp Val Ala Asn Glu Asn Leu Ala Ala Phe Ala Ala
    50                  55                  60

Asp Ala Thr Ala Ala Ala Ala Trp Val Lys Gln Asn Val Gln Ala Tyr

```
                65                  70                  75                  80
        Pro Gly Val Ser Phe Arg Tyr Ile Ala Val Gly Asn Glu Val Thr Gly
                         85                  90                  95

Asp Asp Thr Gly Asn Ile Leu Pro Ala Met Lys Asn Leu Asn Ala Ala
                        100                 105                 110

Leu Ala Ala Gly Leu Gly Val Gly Val Ser Thr Ser Val Ser
                    115                 120                 125

Gln Gly Val Ile Ala Asn Ser Tyr Pro Pro Ser Asn Gly Val Phe Asn
                130                 135                 140

Asp Asp Tyr Met Phe Asp Ile Val Glu Tyr Leu Ala Ser Thr Gly Ala
        145                 150                 155                 160

Pro Leu Leu Val Asn Val Tyr Pro Tyr Phe Ala Tyr Val Gly Asp Thr
                        165                 170                 175

Lys Asp Ile Ser Leu Asn Tyr Ala Thr Phe Gln Pro Gly Thr Thr Val
                        180                 185                 190

Thr Asp Asp Gly Ser Gly Leu Ile Tyr Thr Ser Leu Phe Asp Ala Met
                    195                 200                 205

Val Asp Ser Val Tyr Ala Ala Leu Glu Asp Ala Gly Ala Pro Asp Val
                    210                 215                 220

Gly Val Val Ser Glu Thr Gly Trp Pro Ser Ala Gly Gly Phe Gly
        225                 230                 235                 240

Ala Ser Val Ser Asn Ala Gln Thr Tyr Asn Gln Lys Leu Ile Ser His
                        245                 250                 255

Val Gln Gly Gly Thr Pro Lys Arg Pro Gly Val Ala Leu Glu Thr Tyr
                    260                 265                 270

Val Phe Ala Met Phe Asn Glu Asn Gln Lys Thr Gly Ala Glu Thr Glu
                    275                 280                 285

Arg His Phe Gly Leu Phe Asn Pro Asn Lys Ser Pro Ser Tyr Lys Ile
                    290                 295                 300

Arg Phe
        305

<210> SEQ ID NO 139
<211> LENGTH: 307
<212> TYPE: PRT
<213> ORGANISM: Brachypodium distachyon

<400> SEQUENCE: 139

Ile Gly Val Cys Tyr Gly Val Ile Gly Asn Asn Leu Pro Ser Arg Gly
        1               5                   10                  15

Asp Val Val Asn Leu Tyr Arg Ser Lys Gly Ile Asn Ser Met Arg Ile
                        20                  25                  30

Tyr Phe Ala Asp Ala Gln Ala Leu Ser Ala Leu Arg Asn Ser Gly Ile
                    35                  40                  45

Ala Leu Ile Leu Asp Ile Gly Asn Asp Asn Leu Ala Gly Ile Ala Ser
        50                  55                  60

Ser Ala Ser Asn Ala Ala Thr Trp Val Asn Asn Val Lys Pro Tyr
        65                  70                  75                  80

Tyr Pro Ala Val Asn Ile Lys Tyr Ile Ala Ala Gly Asn Glu Ile Leu
                        85                  90                  95

Gly Gly Ala Thr Gly Ser Ile Val Pro Ala Met Arg Asn Leu Asn Ala
                    100                 105                 110

Ala Leu Ala Ser Ala Gly Leu Gly Asp Arg Ile Lys Val Ser Thr Ser
                115                 120                 125
```

```
Ile Arg Phe Asp Ala Val Ala Asp Ser Phe Pro Pro Ser Lys Gly Val
130                 135                 140

Phe Lys Asp Ala Tyr Met Ser Asp Val Ala Arg Leu Leu Ala Ser Thr
145                 150                 155                 160

Gly Ala Pro Leu Leu Ala Asn Val Tyr Pro Tyr Phe Ala Tyr Arg Asp
                165                 170                 175

Ser Pro Ser Ala Ile Gln Leu Asn Tyr Ala Thr Phe Gln Pro Gly Thr
            180                 185                 190

Gln Val Arg Asp Asp Gly Asn Gly Leu Val Tyr Thr Asn Leu Phe Asp
                195                 200                 205

Ala Met Val Asp Ala Val His Ala Ala Met Glu Lys Ala Gly Ala Gly
210                 215                 220

Gly Val Lys Val Val Val Ser Glu Ser Gly Trp Pro Ser Asp Gly Gly
225                 230                 235                 240

Phe Ala Ala Asn Ala Asp Asn Ala Arg Ala Tyr Asn Gln Gly Leu Ile
                245                 250                 255

Asp His Val Gly Lys Gly Thr Pro Lys Lys Pro Gly Pro Leu Glu Ala
            260                 265                 270

Tyr Ile Phe Ala Met Phe Asn Glu Asn Gln Lys Asp Gly Asn Ala Val
            275                 280                 285

Glu Arg Asn Phe Gly Leu Phe Lys Pro Asp Lys Ser Pro Ala Tyr Asp
290                 295                 300

Ile Arg Phe
305

<210> SEQ ID NO 140
<211> LENGTH: 308
<212> TYPE: PRT
<213> ORGANISM: Zea mays

<400> SEQUENCE: 140

Ile Gly Val Cys Tyr Gly Thr Leu Gly Asn Asn Leu Pro Ser Ser Ser
1               5                   10                  15

Asp Val Val Gln Leu Tyr Arg Ser Lys Gly Ile Lys Gly Met Arg Ile
                20                  25                  30

Tyr Ser Pro Asp Ala Lys Ala Leu Ala Ala Leu Arg Asn Ser Gly Ile
            35                  40                  45

Ala Leu Ile Leu Asp Thr Gly Asn Gly Gly Val Leu Gly Gln Leu
50                  55                  60

Ala Arg Ser Ala Ser Phe Ala Asp Ser Trp Val Gln Ser Asn Val Arg
65                  70                  75                  80

Pro Tyr Tyr Pro Ala Val Gly Ile Lys Tyr Val Ala Val Gly Asn Glu
                85                  90                  95

Val Gln Gly Asp Asp Thr Arg Ser Leu Leu Pro Ala Met Arg Asn Leu
                100                 105                 110

Asp Ala Ala Leu Ala Arg Ala Gly Phe Pro Gly Ile Lys Cys Ser Thr
            115                 120                 125

Ser Val Arg Phe Asp Val Val Ala Asn Ser Phe Pro Pro Ser Ser Gly
130                 135                 140

Ser Phe Ala Gln Gly Tyr Met Ala Asp Val Ala Arg Tyr Leu Ala Gly
145                 150                 155                 160

Thr Gly Ala Pro Leu Leu Ala Asn Val Tyr Pro Tyr Phe Ala Tyr Arg
                165                 170                 175

Asp Asn Pro Arg Asp Ile Ser Leu Gly Tyr Ala Thr Phe Gln Pro Gly
            180                 185                 190
```

```
Thr Thr Val Arg Asp Asn Gly Asn Gly Leu Asn Tyr Asn Asn Leu Phe
        195                 200                 205

Asp Ala Met Val Asp Ala Val Val Ala Ala Leu Glu Lys Ala Gly Ala
        210                 215                 220

Pro Asn Val Arg Val Val Val Ser Glu Ser Gly Trp Pro Ser Ala Gly
225                 230                 235                 240

Gly Phe Gly Ala Ser Val Asp Asn Ala Arg Lys Tyr Asn Gln Gly Leu
                245                 250                 255

Ile Asp His Val Gly Arg Gly Thr Pro Lys Arg Thr Gly Pro Leu Glu
                    260                 265                 270

Thr Phe Val Phe Ala Met Phe Asn Glu Asn Gln Lys Gly Gly Asp Pro
            275                 280                 285

Thr Glu Lys Asn Phe Gly Leu Phe Tyr Gly Asn Lys Gln Pro Val Tyr
        290                 295                 300

Pro Ile Arg Phe
305

<210> SEQ ID NO 141
<211> LENGTH: 307
<212> TYPE: PRT
<213> ORGANISM: Sorghum bicolor

<400> SEQUENCE: 141

Ile Gly Val Cys Tyr Gly Met Leu Gly Asn Asn Leu Pro Ser Ser Ser
1               5                   10                  15

Asp Val Val Gln Leu Tyr Lys Ser Lys Gly Ile Lys Gly Met Arg Ile
            20                  25                  30

Tyr Ser Pro Ser Gln Ser Ala Leu Asn Ala Leu Arg Asn Ser Gly Leu
        35                  40                  45

Ala Val Ile Val Asp Thr Gly Asn Gly Asn Glu Leu Ser Gln Leu Ala
    50                  55                  60

Arg Ser Ala Ser Tyr Ala Ala Ser Trp Val Gln Ser Asn Val Lys Pro
65                  70                  75                  80

Tyr Tyr Pro Ala Val Asn Ile Lys Tyr Ile Ala Val Gly Asn Glu Val
                85                  90                  95

Gln Gly Gly Ala Thr Gln Ser Ile Leu Pro Ala Ile Arg Asn Leu Asp
            100                 105                 110

Ala Ala Leu Ala Arg Ala Gly Leu Ser Ala Ile Lys Cys Ser Thr Ser
        115                 120                 125

Val Arg Phe Asp Val Ile Ala Asn Ser Tyr Pro Pro Ser Ser Gly Ser
    130                 135                 140

Phe Ala Gln Gly Tyr Met Ala Asp Val Ala Arg Tyr Leu Ala Gly Thr
145                 150                 155                 160

Gly Ala Pro Leu Leu Val Asn Val Tyr Pro Tyr Phe Ser Tyr Arg Asp
                165                 170                 175

Asn Pro Arg Asp Ile Ser Leu Gly Tyr Ala Thr Phe Gln Pro Gly Thr
            180                 185                 190

Thr Val Arg Asp Asn Gly Asn Gly Leu Thr Tyr Thr Asn Leu Phe Asp
        195                 200                 205

Ala Met Val Asp Ala Val Val Ala Ala Leu Glu Lys Ala Gly Ala Gly
    210                 215                 220

Gly Val Arg Ile Val Val Ser Glu Ser Gly Trp Pro Ser Ala Gly Gly
225                 230                 235                 240

Ser Gly Ala Ser Val Asp Asn Ala Arg Lys Tyr Asn Gln Gly Leu Ile
```

```
                        245                 250                 255
Asn His Val Gly Arg Gly Thr Pro Lys Arg Gly Thr Leu Glu Thr
            260                 265                 270

Phe Ile Phe Ala Met Phe Asn Glu Asn Gln Lys Thr Gly Asp Pro Thr
            275                 280                 285

Glu Lys Asn Phe Gly Leu Phe Tyr Gly Asn Lys Gln Pro Val Tyr Pro
            290                 295                 300

Ile Ser Phe
305

<210> SEQ ID NO 142
<211> LENGTH: 306
<212> TYPE: PRT
<213> ORGANISM: Setaria italica

<400> SEQUENCE: 142

Ile Gly Val Cys Tyr Gly Val Leu Gly Asn Asn Leu Pro Ser Arg Ser
 1               5                  10                  15

Asp Val Val Gln Leu Tyr Arg Ser Arg Gly Ile Asn Gly Met Arg Ile
            20                  25                  30

Tyr Phe Pro Asp Arg Gln Ala Leu Asp Ala Leu Arg Gly Ser Gly Met
        35                  40                  45

Ala Leu Ile Leu Asp Thr Gly Asn Asp Val Leu Gly Gln Leu Ala Ser
    50                  55                  60

Ser Pro Ser Ser Ala Ala Ser Trp Val Gln Ser Asn Val Arg Pro Tyr
65                  70                  75                  80

Tyr Pro Ala Val Asn Ile Lys Tyr Ile Ala Val Gly Asn Glu Val Ala
                85                  90                  95

Gly Ser Ala Thr Gln Ser Ile Leu Pro Ala Met Arg Asn Leu Asn Ala
            100                 105                 110

Ala Leu Ala Ala Ala Gly Leu Gly Ser Ile Lys Val Ser Thr Ser Val
        115                 120                 125

Gln Ser Asn Val Ile Ala Asn Ser Phe Pro Pro Ser Ser Gly Val Phe
    130                 135                 140

Ala Gln Gly Tyr Met Val Glu Ile Ala Arg Tyr Leu Ala Ser Thr Gly
145                 150                 155                 160

Ala Pro Leu Leu Ala Asn Val Tyr Pro Tyr Phe Ala Tyr Arg Gly Asn
                165                 170                 175

Pro Arg Asp Ile Ser Leu Gly Tyr Ala Thr Phe Gln Pro Gly Thr Thr
            180                 185                 190

Val Arg Asp Gly Gly Asn Gly Leu Thr Tyr Thr Asn Leu Phe Asp Ala
        195                 200                 205

Met Val Asp Ala Thr Val Ala Ala Leu Glu Lys Ala Gly Ala Pro Asn
    210                 215                 220

Val Arg Ile Val Ile Ser Glu Ser Gly Trp Pro Ser Ala Gly Gly Phe
225                 230                 235                 240

Gly Ala Ser Val Glu Asn Ala Arg Asn Tyr Asn Gln Gly Leu Ile Asp
                245                 250                 255

His Val Gly Arg Gly Thr Pro Lys Arg Ser Gly Ala Leu Asp Thr Phe
            260                 265                 270

Ile Phe Ala Met Phe Asn Glu Asn Gln Lys Ser Gly Asp Pro Thr Glu
        275                 280                 285

Arg Asn Phe Gly Leu Phe Tyr Pro Asn Lys Gln Pro Val Tyr Ser Ile
    290                 295                 300
```

Arg Phe
305

<210> SEQ ID NO 143
<211> LENGTH: 307
<212> TYPE: PRT
<213> ORGANISM: Oryza sativa

<400> SEQUENCE: 143

Ile Gly Val Cys Tyr Gly Val Lys Gly Asn Asn Leu Pro Pro Arg Ser
1               5                   10                  15

Glu Val Val Gln Leu Tyr Lys Ser Lys Gly Ile Asn Gly Met Arg Ile
            20                  25                  30

Tyr Tyr Pro Asp Lys Glu Ala Leu Asn Ala Leu Arg Asn Ser Gly Ile
        35                  40                  45

Ala Leu Ile Leu Asp Val Gly Phe Asp Thr Val Ser Tyr Leu Ala
    50                  55                  60

Ala Ser Ser Asn Ala Ala Trp Val Arg Asp Asn Val Arg Pro
65                  70                  75                  80

Tyr Tyr Pro Ala Val Asn Ile Arg Tyr Ile Ala Val Gly Asn Glu Val
                85                  90                  95

Glu Gly Gly Ala Thr Asn Ser Ile Leu Pro Ala Ile Arg Asn Val Asn
            100                 105                 110

Ser Ala Leu Ala Ser Ser Gly Leu Gly Ala Ile Lys Ala Ser Thr Ala
        115                 120                 125

Val Lys Phe Asp Val Ile Ser Asn Ser Tyr Pro Pro Ser Ala Gly Val
    130                 135                 140

Phe Arg Asp Ala Tyr Met Lys Asp Ile Ala Arg Tyr Leu Ala Ser Thr
145                 150                 155                 160

Gly Ala Pro Leu Leu Ala Asn Val Tyr Pro Tyr Phe Ala Tyr Arg Gly
                165                 170                 175

Asn Pro Arg Asp Ile Ser Leu Asn Tyr Ala Thr Phe Arg Pro Gly Thr
            180                 185                 190

Thr Val Arg Asp Pro Asn Asn Gly Leu Thr Tyr Thr Asn Leu Phe Asp
        195                 200                 205

Ala Met Val Asp Ala Val Tyr Ala Ala Leu Glu Lys Ala Gly Ala Gly
    210                 215                 220

Asn Val Lys Val Val Ser Glu Ser Gly Trp Pro Ser Ala Gly Gly
225                 230                 235                 240

Phe Gly Ala Ser Val Asp Asn Ala Arg Ala Tyr Asn Gln Gly Leu Ile
                245                 250                 255

Asp His Val Gly Arg Gly Thr Pro Lys Arg Pro Gly Pro Leu Glu Ala
            260                 265                 270

Tyr Ile Phe Ala Met Phe Asn Glu Asn Gln Lys Asn Gly Asp Pro Thr
        275                 280                 285

Glu Lys Asn Phe Gly Leu Ser Tyr Pro Asn Lys Ser Pro Val Tyr Pro
    290                 295                 300

Ile Arg Phe
305

<210> SEQ ID NO 144
<211> LENGTH: 305
<212> TYPE: PRT
<213> ORGANISM: Oryza sativa

<400> SEQUENCE: 144

Ile Gly Val Cys Tyr Gly Val Leu Gly Asn Leu Pro Ser Arg Ser
1               5                   10                  15

Glu Val Val Gln Leu Tyr Lys Ser Lys Gly Ile Asn Gly Met Arg Ile
            20                  25                  30

Tyr Tyr Pro Asp Lys Glu Ala Leu Asn Ala Leu Arg Asn Ser Gly Ile
            35                  40                  45

Ala Leu Ile Leu Asp Val Gly Asp Gln Leu Ser Asn Leu Ala Ala Ser
50                  55                  60

Ser Ser Asn Ala Ala Ala Trp Val Arg Asp Asn Val Arg Pro Tyr Tyr
65                  70                  75                  80

Pro Ala Val Asn Ile Lys Tyr Ile Ala Val Gly Asn Glu Val Glu Gly
                85                  90                  95

Gly Ala Thr Ser Ser Ile Leu Pro Ala Ile Arg Asn Val Asn Ser Ala
            100                 105                 110

Leu Ala Ser Ser Gly Leu Gly Ala Ile Lys Ala Ser Thr Ala Val Lys
            115                 120                 125

Phe Asp Val Ile Ser Asn Ser Tyr Pro Pro Ser Ala Gly Val Phe Arg
            130                 135                 140

Asp Ala Tyr Met Lys Asp Ile Ala Arg Tyr Leu Ala Ser Thr Gly Ala
145                 150                 155                 160

Pro Leu Leu Ala Asn Val Tyr Pro Tyr Phe Ala Tyr Arg Gly Asn Pro
                165                 170                 175

Arg Asp Ile Ser Leu Asn Tyr Ala Thr Phe Arg Pro Gly Thr Thr Val
            180                 185                 190

Arg Asp Pro Asn Asn Gly Leu Thr Tyr Thr Asn Leu Phe Asp Ala Met
            195                 200                 205

Met Asp Ala Val Tyr Ala Ala Leu Glu Lys Ala Gly Ala Gly Asn Val
210                 215                 220

Arg Val Val Val Ser Glu Ser Gly Trp Pro Ser Ala Gly Gly Phe Gly
225                 230                 235                 240

Ala Ser Val Asp Asn Ala Arg Ala Tyr Asn Gln Gly Leu Ile Asp His
            245                 250                 255

Val Gly Arg Gly Thr Pro Lys Arg Pro Gly Ala Leu Glu Ala Tyr Ile
            260                 265                 270

Phe Ala Met Phe Asn Glu Asn Gln Lys Asn Gly Asp Pro Thr Glu Arg
            275                 280                 285

Asn Phe Gly Leu Phe Tyr Pro Asn Lys Ser Pro Val Tyr Pro Ile Arg
            290                 295                 300

Phe
305

<210> SEQ ID NO 145
<211> LENGTH: 308
<212> TYPE: PRT
<213> ORGANISM: Zea mays

<400> SEQUENCE: 145

His Gly Val Cys Tyr Gly Met Thr Ala Asp Leu Pro Pro Pro Ser
1               5                   10                  15

Glu Val Val Gln Leu Tyr Lys Ser Asn Gly Ile Ala Asn Met Arg Val
            20                  25                  30

Tyr Ser Pro Val Gly Glu Val Met Glu Ala Leu Arg Gly Ser Gly Ile
            35                  40                  45

Gly Leu Val Leu Gly Val Ala Asn Glu Asp Val Ala Ser Leu Ala Thr
50                  55                  60

```
Cys Ala Pro Cys Ala Ala Ser Trp Val Glu Ala Asn Val Arg Pro Tyr
 65                  70                  75                  80

His Gln Asp Val Asn Ile Leu Tyr Ile Ala Val Gly Asn Glu Val Asp
                 85                  90                  95

Ala Ala Ala Ala Ala Gln Thr Ile Leu Pro Ala Met Arg Ser Leu Gln
            100                 105                 110

Ala Ala Leu Ala Ala Ala Gly Leu Ala Gly Ser Ile Lys Val Ser Thr
            115                 120                 125

Cys Val Arg Leu Asp Val Val Thr Asp Thr Phe Pro Pro Ser Ser Gly
130                 135                 140

Ala Phe Ala Gln Pro Tyr Met Val Asp Val Ala Arg Phe Leu Ala Ala
145                 150                 155                 160

Ala Gly Ala Pro Leu Leu Ala Asn Val Tyr Pro Tyr Phe Ala Tyr Arg
                165                 170                 175

Gly Ser Pro Gly Asp Val Gly Leu Gly Tyr Ala Leu Phe Gln Pro Gly
            180                 185                 190

Ala Ala Val Arg Asp Gly Gly Ser Gly Leu Val Tyr Thr Asn Leu Phe
            195                 200                 205

Asp Ala Met Val Asp Ser Val His Ala Ala Leu Glu Lys Ala Gly Ala
210                 215                 220

Pro Asp Val Arg Val Val Ser Glu Ser Gly Trp Pro Ser Ala Gly
225                 230                 235                 240

Gly Ala Ala Ser Val Gln Asn Ala Gln Ala Tyr Val Gln Asn Leu
                245                 250                 255

Val Asp His Val Ala Gln Gly Thr Pro Lys Arg Pro Gly Pro Leu Glu
            260                 265                 270

Thr Tyr Val Phe Ala Met Phe Asn Glu Asn Gln Lys Pro Gly Glu Pro
            275                 280                 285

Thr Glu Lys Asn Phe Gly Leu Phe Tyr Pro Ser Lys Ala Pro Val Tyr
            290                 295                 300

Pro Ile Val Phe
305

<210> SEQ ID NO 146
<211> LENGTH: 308
<212> TYPE: PRT
<213> ORGANISM: Sorghum bicolor

<400> SEQUENCE: 146

Gly Val Cys Tyr Gly Thr Val Ala Asp Asp Leu Pro Pro Ser Glu
 1               5                  10                  15

Val Val Gln Leu Tyr Lys Ser Asn Gly Ile Ser Thr Met Arg Val Tyr
                 20                  25                  30

Phe Pro Asp Ser Lys Val Met Glu Ala Leu Arg Gly Ser Gly Ile Gly
            35                  40                  45

Leu Val Leu Gly Val Ala Asn Glu Asp Ile Ala Asn Leu Ala Ala Cys
            50                  55                  60

Ala Pro Cys Ala Ala Ser Trp Val Gln Thr Asn Val Arg Thr Tyr His
 65                  70                  75                  80

Pro Asp Val Ser Val Leu Tyr Ile Ala Val Gly Asn Glu Val Asp Ala
                 85                  90                  95

Pro Ala Ala Ala Gln Ser Ile Leu Pro Ala Met Arg Asn Leu Gln Ala
            100                 105                 110

Ala Leu Ala Ala Ala Gly Leu Asp Gly Asp Ile Lys Val Ser Thr Cys
```

```
                115                 120                 125
Val Lys Leu Asp Val Val Thr Asn Thr Phe Pro Pro Ser Ser Gly Val
            130                 135                 140

Phe Ala Gln Ala Tyr Met Thr Asp Ile Ala Arg Phe Leu Ala Ala Thr
145                 150                 155                 160

Gly Ala Pro Leu Leu Ala Asn Val Tyr Pro Tyr Phe Ala Tyr Arg Gly
                165                 170                 175

Ser Asn Pro Gly Asp Ile Ser Leu Ser Tyr Ala Leu Phe Gln Pro Gly
            180                 185                 190

Thr Thr Val Arg Asp Gly Gly Ser Gly Leu Val Tyr Thr Asn Leu Leu
            195                 200                 205

Asp Ala Met Val Asp Ser Val His Ala Ala Leu Glu Lys Ala Gly Ala
            210                 215                 220

Pro Thr Val Arg Val Val Val Ser Glu Thr Gly Trp Pro Ser Ala Gly
225                 230                 235                 240

Gly Ala Ala Ala Thr Val Gln Asn Ala Gln Thr Tyr Val Gln Asn Met
                245                 250                 255

Ile Asp His Ala Gly Gln Gly Thr Pro Lys Lys Pro Gly Pro Leu Glu
            260                 265                 270

Thr Tyr Val Phe Ala Met Phe Asn Glu Asp Gln Lys Pro Gly Glu Leu
            275                 280                 285

Thr Glu Arg Asn Phe Gly Leu Phe Tyr Pro Asn Lys Ala Pro Val Tyr
290                 295                 300

Pro Val Val Phe
305

<210> SEQ ID NO 147
<211> LENGTH: 305
<212> TYPE: PRT
<213> ORGANISM: Setaria italica

<400> SEQUENCE: 147

Gly Val Cys Tyr Gly Met Ile Ala Asn Asn Leu Pro Pro Pro Gly Glu
1               5                   10                  15

Val Val Gln Leu Tyr Lys Ser Ser Gly Ile Arg Asn Met Arg Ile Tyr
            20                  25                  30

Phe Pro Asp Ser His Val Met Glu Ala Leu Ser Gly Ser Gly Ile Gly
        35                  40                  45

Leu Ile Leu Gly Val Val Asn Gln Asp Ile Val Gly Leu Ala Gly Cys
50                  55                  60

Gln Ser Cys Ala Ala Ser Trp Val Gln Thr Asn Val Arg Pro Tyr Tyr
65                  70                  75                  80

Pro Ala Val Asn Ile Leu Tyr Ile Ala Val Gly Asn Glu Val Ser Asp
                85                  90                  95

Gly Ala Ala Gln Ser Ile Leu Pro Ala Met Arg Asn Leu Gln Ala Ala
            100                 105                 110

Leu Ala Ala Ala Gly Leu Ala Ala Ile Lys Val Ser Thr Cys Val Arg
            115                 120                 125

Leu Asp Val Val Thr Asn Thr Phe Pro Pro Ser Ala Gly Val Phe Ala
130                 135                 140

Gln Pro Tyr Met Val Asp Ile Ala Gln Phe Leu Ala Gly Ala Gly Ala
145                 150                 155                 160

Ser Leu Leu Ala Asn Val Tyr Pro Tyr Phe Ala Tyr Arg Gly Ser Pro
                165                 170                 175
```

```
Gly Asp Ile Ser Leu Asn Tyr Ala Leu Phe Leu Pro Gly Thr Thr Val
                180                 185                 190

Arg Asp Gly Gly Asn Gly Leu Val Tyr Thr Asn Leu Phe Asp Ala Met
            195                 200                 205

Val Asp Ala Val Val Ala Leu Glu Lys Ala Gly Ala Ala Ser Val
    210                 215                 220

Arg Val Val Ser Glu Ser Gly Trp Pro Ser Ala Gly Gly Thr Ala
225                 230                 235                 240

Ala Ser Val Glu Asn Ala Arg Thr Tyr Val Gln Asn Leu Ile Asp His
                245                 250                 255

Ala Ala Gln Gly Thr Pro Lys Arg Pro Gly Ala Leu Gly Thr Phe Val
            260                 265                 270

Phe Ala Met Phe Asn Glu Asn Gln Lys Pro Gly Glu Leu Thr Glu Gln
        275                 280                 285

Asn Phe Gly Leu Phe Tyr Pro Asn Lys Ser Pro Val Tyr Pro Ile Ile
        290                 295                 300

Phe
305

<210> SEQ ID NO 148
<211> LENGTH: 293
<212> TYPE: PRT
<213> ORGANISM: Setaria italica

<400> SEQUENCE: 148

Ala Ala Gln Val Val Gln Leu Tyr Lys Ser Leu Gly Ile Asn Asn Met
1               5                   10                  15

Arg Ile Tyr Ala Pro Asp Ala His Ala Leu His Ala Leu Arg Glu Ser
            20                  25                  30

Gly Ile Glu Leu Ile Leu Gly Val Ala Asn Glu Asp Leu Ala Gly Leu
        35                  40                  45

Ala Ala Ser Glu Pro Thr Ala Ala Ser Trp Val Gln Ala Asn Val Lys
    50                  55                  60

Pro Tyr Tyr Pro Ala Val Asn Ile Arg Tyr Ile Ala Ile Gly Asn Lys
65                  70                  75                  80

Val Gly Gly Glu Ala Ala His Ser Ile Leu Pro Ala Met Arg Asn Leu
                85                  90                  95

Glu Arg Ala Leu Ala Ala Gly Leu Ala Ala Val Lys Val Ser Thr
            100                 105                 110

Cys Val Arg Leu Asp Val Ile Thr Asn Ser Phe Pro Pro Ser Ala Gly
        115                 120                 125

Val Phe Ala Gln Pro Tyr Met Ala Asp Ile Ala Arg Phe Leu Ala Thr
    130                 135                 140

Thr Gly Ala Pro Leu Leu Ala Asn Val Phe Pro Tyr Phe Ala Tyr Lys
145                 150                 155                 160

Asp Asp Pro Arg Ala Ile Ser Leu Glu Tyr Ala Thr Phe Arg Pro Gly
                165                 170                 175

Thr Thr Val Ser Asp Arg Gly Asn Gly Leu Ser Tyr Thr Asn Leu Phe
            180                 185                 190

Asp Ala Met Val Asp Ala Met Tyr Ala Ala Leu Glu Lys Ala Gly Ala
        195                 200                 205

Ala Gly Val Arg Val Val Ala Glu Thr Gly Trp Pro Ser Ala Ala
    210                 215                 220

Gly Phe Ala Ala Ser Val Asp Asn Ala Arg Ala Tyr Asn Gln Gly Val
225                 230                 235                 240
```

```
Ile Asp His Val Gly Asn Gly Thr Pro Arg Lys Pro Gly Ala Ala Leu
            245                 250                 255

Glu Thr Leu Val Phe Ala Met Phe Asn Glu Asn Gln Lys Pro Gly Glu
            260                 265                 270

Pro Thr Glu Lys Asn Phe Gly Leu Phe Tyr Pro Lys Lys Ser Pro Val
            275                 280                 285

Tyr Pro Ile Ala Phe
            290

<210> SEQ ID NO 149
<211> LENGTH: 306
<212> TYPE: PRT
<213> ORGANISM: Oryza sativa

<400> SEQUENCE: 149

Val Gly Val Cys Tyr Gly Met Ile Gly Asn Asp Leu Pro Ser Lys Ser
  1               5                  10                  15

Asp Val Val Gln Leu Tyr Lys Ser Asn Gly Ile Thr Asp Met Arg Ile
                 20                  25                  30

Tyr Leu Pro Asp Val Glu Ala Met Asn Ala Leu Arg Gly Thr Gly Ile
             35                  40                  45

Gly Leu Ile Val Gly Val Ala Asn Asp Ile Leu Ile Asp Leu Ala Ala
         50                  55                  60

Asn Pro Ala Ser Ala Ala Ser Trp Val Asp Ala Asn Val Lys Pro Phe
 65                  70                  75                  80

Val Pro Ala Val Asn Ile Lys Tyr Ile Ala Val Gly Asn Glu Ile Ser
                 85                  90                  95

Gly Glu Pro Thr Gln Asn Ile Leu Pro Val Met Gln Asn Ile Asn Ala
            100                 105                 110

Ala Leu Ala Ala Ala Ser Ile Thr Gly Val Lys Ala Ser Thr Ala Val
        115                 120                 125

Lys Leu Asp Val Val Thr Asn Thr Phe Pro Pro Ser Ala Gly Val Phe
130                 135                 140

Ala Ala Pro Tyr Met Thr Ala Val Ala Lys Leu Leu Ala Ser Thr Gly
145                 150                 155                 160

Ala Pro Leu Leu Ala Asn Ile Tyr Pro Tyr Phe Ala Tyr Ile Gly Asn
                165                 170                 175

Lys Lys Asp Ile Ser Leu Asn Tyr Ala Thr Phe Gln Ala Gly Thr Thr
            180                 185                 190

Val Pro Asp Pro Asn Thr Gly Leu Val Tyr Thr Asn Leu Phe Asp Ala
        195                 200                 205

Met Val Asp Ser Val Tyr Ala Ala Leu Asp Lys Ala Gly Ala Ala Gly
210                 215                 220

Val Ser Ile Val Val Ser Glu Ser Gly Trp Pro Ser Ala Gly Gly Asp
225                 230                 235                 240

Ser Ala Thr Ile Asp Ile Ala Arg Thr Tyr Val Gln Asn Leu Ile Lys
                245                 250                 255

His Ala Lys Lys Gly Thr Pro Lys Arg Pro Gly Val Ile Glu Thr Tyr
            260                 265                 270

Val Phe Ala Met Phe Asn Glu Asn Gln Lys Pro Gly Glu Ala Thr Glu
        275                 280                 285

Gln Asn Phe Gly Ala Phe Tyr Pro Asn Lys Thr Ala Val Tyr Pro Ile
    290                 295                 300

Asn Phe
```

<210> SEQ ID NO 150
<211> LENGTH: 315
<212> TYPE: PRT
<213> ORGANISM: Brachypodium distachyon

<400> SEQUENCE: 150

Ile Gly Ala Cys Asn Gly Val Ile Gly Ser Asp Leu Pro Ala His
1               5                   10                  15

Asp Val Val Gln Leu Tyr Lys Ser Asn Gly Ile Thr Ala Met Arg Phe
            20                  25                  30

Tyr Asn Pro Gln Pro Glu Leu Leu Asp Ala Leu Arg Gly Ser Gly Ile
        35                  40                  45

Ala Val Ile Leu Gly Thr Ala Asn Ala Asp Val Pro Leu Leu Ala Ser
    50                  55                  60

Lys Pro Gly Tyr Ala Ala Ser Trp Val Ala Thr Asn Val Gln Pro Tyr
65                  70                  75                  80

Tyr Pro Ser Val Asn Ile Ser Tyr Ile Thr Val Gly Asn Glu Ile Thr
                85                  90                  95

Gly Asp Pro Ala Phe Lys Ser Ser Ile Leu Pro Ala Met Lys Ser Leu
            100                 105                 110

His Phe Ala Leu Ala Gly Ala Leu Gly Ala Arg Ala Ala Gly Gly Ile
        115                 120                 125

Lys Val Ser Thr Ala Leu Arg Phe Asp Ala Leu Val Asp Thr Phe Pro
130                 135                 140

Pro Ser Lys Gly Ala Phe Lys Asp Ala Glu Thr Met Val Pro Leu Ala
145                 150                 155                 160

Gly Phe Leu Ala Ser Thr Gly Ala Pro Leu Leu Ala Asp Val Tyr Pro
                165                 170                 175

Tyr Phe Ala Tyr Arg Asp Asn Pro Lys Asp Ile Ala Leu Ser Tyr Ala
            180                 185                 190

Thr Phe Gln Pro Gly Ser Thr Pro Val Arg Asp Asp Gly Ser Gly Leu
        195                 200                 205

Val Tyr Thr Thr Leu Phe Asp Ala Met Val Asp Ala Leu Tyr Ser Ala
    210                 215                 220

Leu Glu Lys Ala Gly Glu Pro Ala Val Arg Val Val Ser Glu Ser
225                 230                 235                 240

Gly Trp Pro Ser Ala Gly Gly Phe Gly Ala Thr Val Glu Asn Ala Arg
                245                 250                 255

Ala Tyr Asn Gln Gly Leu Ile Asp His Val Gly Lys Gly Thr Pro Lys
            260                 265                 270

Arg Pro Gly Ala Pro Val Glu Ala Tyr Ile Phe Ser Met Phe Asn Glu
        275                 280                 285

Asn Leu Lys Pro Gly Asp Glu Thr Glu Arg His Phe Gly Leu Phe Tyr
    290                 295                 300

Pro Ser Lys Ala Pro Val Cys Pro Ile Ser Phe
305                 310                 315

<210> SEQ ID NO 151
<211> LENGTH: 308
<212> TYPE: PRT
<213> ORGANISM: Zea mays

<400> SEQUENCE: 151

Ile Gly Val Cys Tyr Gly Val Leu Gly Ser Gly Leu Pro Ser Lys Ser

```
                1               5                  10                 15
            Asp Val Val Gln Leu Tyr Lys Ser Asn Gly Ile Ala Ser Met Arg Phe
                            20                  25                  30

Tyr Phe Ala Asp Gln Asp Leu Leu Thr Ala Leu Arg Gly Ser Gly Val
                            35                  40                  45

Ala Leu Ala Leu Asp Val Gly Asn Gly Lys Val Gly Glu Leu Ala Ala
                            50                  55                  60

Asp Pro Ala Ser Ala Ser Trp Val Arg Asp Asn Val Gln Ala Tyr
             65                 70                  75                  80

Tyr Pro Asp Val Asp Ile Arg Tyr Val Val Gly Asn Glu Val Val
                                85                  90                  95

Pro Gly Ala Ala Ser Val Leu Gln Ala Met Arg Asn Val His Ala Ala
                            100                 105                 110

Leu Ala Ser Ala Gly Leu Ala Gly Ser Val Lys Val Ser Thr Ala Val
                            115                 120                 125

Lys Met Asp Ala Val Asp Ser Ser Pro Ser Arg Gly Val Phe
                            130                 135                 140

Arg Asp Pro Ala Ala Met Ser Pro Ile Ala Gln Phe Leu Ala Ala Asn
            145                 150                 155                 160

Gly Ala Pro Leu Leu Ala Asn Val Tyr Pro Tyr Phe Ala Tyr Gln Tyr
                                165                 170                 175

Ser Asp Gly Gly Ile Asp Leu Asp Tyr Ala Leu Phe Gln Pro Ser Ser
                            180                 185                 190

Thr Thr Val Thr Asp Pro Ala Asn Gly Leu Val Tyr Thr Asn Leu Phe
                            195                 200                 205

Asp Ala Met Val Asp Ala Val Arg Ala Ala Leu Asp Lys Ala Gly Ala
                            210                 215                 220

Gly Gly Val Asp Val Val Ser Glu Thr Gly Trp Pro Ser Ala Asp
            225                 230                 235                 240

Gly Asn Gly Ala Thr Leu Asp Asn Ala Arg Thr Tyr Asn Gln Asn Leu
                            245                 250                 255

Ile Asp His Ala Ser Lys Gly Thr Pro Arg Lys Pro Gly Pro Met Glu
                            260                 265                 270

Val Tyr Val Phe Ala Met Phe Asn Glu Asp Gln Lys Asp Gly Asp Pro
                            275                 280                 285

Thr Glu Lys Lys Phe Gly Leu Phe Asn Pro Asp Lys Thr Pro Val Tyr
                            290                 295                 300

Pro Ile Asn Phe
            305

<210> SEQ ID NO 152
            <211> LENGTH: 307
            <212> TYPE: PRT
            <213> ORGANISM: Sorghum bicolor

<400> SEQUENCE: 152

Ile Gly Val Cys Tyr Gly Val Ile Gly Ser Gly Leu Pro Ser Lys Ser
              1               5                  10                  15

Asp Val Val Gln Leu Tyr Lys Ser Asn Gly Ile Thr Ser Met Arg Phe
                            20                  25                  30

Tyr Phe Ala Asp Lys Asp Leu Leu Thr Ala Leu Arg Gly Ser Gly Ile
                            35                  40                  45

Ser Leu Ala Leu Asp Val Gly Asn Asp Lys Val Gly Glu Leu Ala Ser
                            50                  55                  60
```

Asp Ser Ala Ala Ala Ala Ser Trp Val Arg Asp Asn Val Gln Ala Tyr
65                  70                  75                  80

Tyr Pro Asp Val Asp Ile Arg Tyr Val Val Gly Asn Glu Val Pro
                85                  90                  95

Gly Ala Ala Ser Val Leu Gln Ala Met Gln Asn Val His Ala Ala Leu
            100                 105                 110

Ala Ser Ala Gly Leu Ala Gly Asn Val Arg Val Ser Thr Ala Val Lys
            115                 120                 125

Met Asp Ala Ile Glu Asn Ser Pro Pro Ser Ser Gly Val Phe Lys
130                 135                 140

Asp Pro Ala Ala Met Ser Pro Ile Val Gln Phe Leu Ala Gly Asn Gly
145                 150                 155                 160

Ala Pro Leu Leu Ala Asn Val Tyr Pro Tyr Phe Ala Tyr Glu Tyr Ser
                165                 170                 175

Asp Gly Ile Asp Leu Asn Tyr Ala Leu Phe Gln Pro Ser Ser Thr Thr
            180                 185                 190

Val Thr Asp Pro Ala Asn Gly Leu Val Tyr Thr Asn Leu Phe Asp Ala
        195                 200                 205

Met Val Asp Ala Val Arg Ala Ala Leu Asp Lys Ala Gly Gly Gly Gly
210                 215                 220

Gly Val Asp Val Val Ser Glu Ser Gly Trp Pro Ser Ala Asp Gly
225                 230                 235                 240

Lys Gly Ala Thr Val Asp Asn Ala Arg Thr Tyr Asn Gln Asn Leu Ile
                245                 250                 255

Asn His Ala Gly Lys Gly Thr Pro Arg Lys Pro Gly Ser Met Glu Val
            260                 265                 270

Tyr Val Phe Ala Met Phe Asn Glu Asp Gln Lys Asp Gly Asp Pro Thr
        275                 280                 285

Glu Lys Lys Phe Gly Leu Phe Asn Pro Asp Lys Thr Pro Val Tyr Pro
    290                 295                 300

Ile Asn Phe
305

<210> SEQ ID NO 153
<211> LENGTH: 305
<212> TYPE: PRT
<213> ORGANISM: Setaria italica

<400> SEQUENCE: 153

Ile Gly Val Cys Tyr Gly Val Ile Gly Ser Gly Leu Pro Ser Lys Ser
1               5                   10                  15

Asp Val Val Gln Leu Tyr Lys Ser Asn Gly Ile Ala Asn Met Arg Phe
                20                  25                  30

Tyr Phe Ala Asp Gln Glu Val Leu Asn Ala Leu Arg Gly Ser Gly Ile
            35                  40                  45

Ser Leu Ala Leu Asp Val Gly Asn Asp Lys Val Gly Asp Leu Ala Asn
        50                  55                  60

Asp Pro Ala Ala Ala Ser Trp Val Lys Asp Asn Val Gln Ala Tyr
65                  70                  75                  80

Tyr Pro Asp Val Ser Ile Arg Tyr Val Val Gly Asn Glu Val Asp
                85                  90                  95

Gly Ala Ala Ser Val Leu Gln Ala Met Lys Asn Val His Asp Ala Leu
            100                 105                 110

Thr Ser Ala Asn Leu Ala Gly Ser Ile Lys Val Ser Thr Ala Val Lys
            115                 120                 125

```
Met Asp Ala Ile Ile Asn Ser Ser Pro Pro Ser Asn Gly Ala Phe Lys
        130                 135                 140

Asp Pro Ser Val Met Ser Pro Ile Val Gln Phe Leu Ala Gly Asn Gly
145                 150                 155                 160

Ala Pro Leu Leu Ala Asn Val Tyr Pro Tyr Phe Ala Tyr Lys Asp Asn
                165                 170                 175

Gln Asn Ile Asp Leu Asn Tyr Ala Leu Phe Glu Pro Ser Ser Thr Thr
            180                 185                 190

Val Gly Asp Pro Asn Gly Leu Thr Tyr Thr Asn Leu Phe Asp Ala Met
        195                 200                 205

Val Asp Ala Val His Ala Ala Leu Asp Lys Val Gly Gly Gly Gly Val
    210                 215                 220

Asp Val Val Ser Glu Ser Gly Trp Pro Ser Ala Asp Gly Arg Gly
225                 230                 235                 240

Ala Thr Val Asp Asn Ala Arg Thr Tyr Asn Gln Asn Leu Ile Asn His
                245                 250                 255

Ala Gly Lys Gly Thr Pro Arg Lys Pro Gly Pro Met Glu Val Tyr Val
            260                 265                 270

Phe Ala Met Phe Asn Glu Asp Asn Lys Asp Gly Asp Pro Thr Glu Lys
        275                 280                 285

Lys Phe Gly Leu Phe Asn Pro Asp Lys Thr Pro Val Tyr Pro Ile Asn
290                 295                 300

Phe
305

<210> SEQ ID NO 154
<211> LENGTH: 301
<212> TYPE: PRT
<213> ORGANISM: Oryza sativa

<400> SEQUENCE: 154

Ile Gly Val Cys Tyr Gly Met Asn Gly Asp Gly Leu Pro Ser Arg Ser
1               5                   10                  15

Asn Val Val Gln Leu Tyr Lys Ser Asn Gly Ile Gly Ala Met Arg Ile
                20                  25                  30

Tyr Ser Ala Asp Arg Glu Ala Leu Asp Ala Leu Arg Gly Ser Gly Ile
            35                  40                  45

Asp Leu Ala Leu Asp Val Gly Glu Arg Asn Asp Val Gly Gln Leu Ala
        50                  55                  60

Ala Asn Ala Asp Ser Trp Val Gln Asp Asn Val Lys Ala Tyr Tyr Pro
65                  70                  75                  80

Asp Val Lys Ile Lys Tyr Ile Val Val Gly Asn Glu Leu Thr Gly Thr
                85                  90                  95

Gly Asp Ala Ala Ser Ile Leu Pro Ala Met Gln Asn Val Gln Ala Ala
            100                 105                 110

Leu Ala Ser Ala Gly Leu Ala Asp Ser Ile Lys Val Thr Thr Ala Ile
        115                 120                 125

Lys Met Asp Thr Leu Ala Ala Ser Ser Pro Ser Ala Gly Val Phe
130                 135                 140

Thr Asn Pro Ser Val Met Glu Pro Ile Val Arg Phe Leu Thr Gly Asn
145                 150                 155                 160

Gly Ala Pro Leu Leu Ala Asn Val Tyr Pro Tyr Phe Ala Tyr Arg Asp
                165                 170                 175

Ser Gln Asp Ile Asp Leu Ser Tyr Ala Leu Phe Gln Pro Ser Ser Thr
```

```
            180             185             190
Thr Val Ser Asp Pro Asn Gly Gly Leu Ser Tyr Thr Asn Leu Phe
        195             200             205
Asp Ala Met Val Asp Ala Val Arg Ala Val Glu Lys Val Ser Gly
        210             215             220
Gly Gly Ser Ser Val Val Asp Val Val Ser Glu Ser Gly Trp Pro
225             230             235             240
Ser Asp Gly Gly Lys Gly Ala Thr Val Glu Asn Ala Arg Ala Tyr Asn
            245             250             255
Gln Asn Leu Ile Asp His Val Ala Gln Gly Thr Pro Lys Lys Pro Gly
            260             265             270
Gln Met Glu Val Tyr Val Phe Ala Leu Phe Asn Glu Asn Arg Lys Glu
            275             280             285
Gly Asp Ala Thr Glu Lys Lys Phe Gly Leu Phe Asn Pro
            290             295             300
```

<210> SEQ ID NO 155
<211> LENGTH: 301
<212> TYPE: PRT
<213> ORGANISM: Oryza sativa

<400> SEQUENCE: 155

```
Ile Gly Val Cys Tyr Gly Met Asn Gly Asp Gly Leu Pro Ser Arg Ser
1               5               10              15
Asn Val Val Gln Leu Tyr Lys Ser Asn Gly Ile Gly Ala Met Arg Ile
                20              25              30
Tyr Ser Ala Asp Arg Glu Ala Leu Asp Ala Leu Arg Gly Ser Gly Ile
            35              40              45
Asp Leu Ala Leu Asp Val Gly Glu Arg Asn Asp Val Gly Gln Leu Ala
        50              55              60
Ala Asn Ala Asp Ser Trp Val Gln Asp Asn Val Lys Ala Tyr Tyr Pro
65              70              75              80
Asp Val Lys Ile Lys Tyr Ile Val Gly Asn Glu Leu Thr Gly Thr
                85              90              95
Gly Asp Ala Ala Ser Ile Leu Pro Ala Met Gln Asn Val Gln Ala Ala
            100             105             110
Leu Ala Ser Ala Gly Leu Ala Asp Ser Ile Lys Val Thr Thr Ala Ile
            115             120             125
Lys Met Asp Thr Leu Ala Ala Ser Pro Pro Ser Ala Gly Val Phe
130             135             140
Thr Asn Pro Ser Val Met Glu Pro Ile Val Arg Phe Leu Thr Gly Asn
145             150             155             160
Gly Ala Pro Leu Leu Ala Asn Val Tyr Pro Tyr Phe Ala Tyr Arg Asp
                165             170             175
Ser Gln Asp Ile Asp Leu Ser Tyr Ala Leu Phe Gln Pro Ser Ser Thr
            180             185             190
Thr Val Ser Asp Pro Asn Gly Gly Leu Ser Tyr Thr Asn Leu Phe
        195             200             205
Asp Ala Met Val Asp Ala Val Arg Ala Val Glu Lys Val Ser Gly
        210             215             220
Gly Gly Ser Ser Val Val Asp Val Val Ser Glu Ser Gly Trp Pro
225             230             235             240
Ser Asp Gly Gly Lys Gly Ala Thr Val Glu Asn Ala Arg Ala Tyr Asn
            245             250             255
```

```
Gln Asn Leu Ile Asp His Val Ala Gln Gly Thr Pro Lys Lys Pro Gly
            260                 265                 270

Gln Met Glu Val Tyr Val Phe Ala Leu Phe Asn Glu Asn Arg Lys Glu
        275                 280                 285

Gly Asp Ala Thr Glu Lys Lys Phe Gly Leu Phe Asn Pro
    290                 295                 300

<210> SEQ ID NO 156
<211> LENGTH: 311
<212> TYPE: PRT
<213> ORGANISM: Oryza sativa

<400> SEQUENCE: 156

His Gly Val Cys Tyr Gly Met Asn Gly Asp Asn Leu Pro Ser Gln Ser
 1               5                  10                  15

Glu Val Val Gln Leu Tyr Lys Ser Asn Gly Ile Gly Ala Met Arg Ile
            20                  25                  30

Tyr Ser Pro Asp Gln Gln Ala Leu Asp Ala Leu Arg Gly Ser Gly Val
        35                  40                  45

Ala Val Ile Ile Asp Val Gly Gly Ser Ser Ala Val Ala Asn Leu Ala
    50                  55                  60

Asn Asn Pro Ser Ala Ala Ala Asp Trp Val Arg Asp Asn Val Gln Ala
65                  70                  75                  80

Tyr Trp Pro Asn Val Ile Ile Arg Tyr Ile Ala Val Gly Asn Glu Leu
                85                  90                  95

Gly Pro Gly Asp Met Gly Thr Ile Leu Pro Ala Met Gln Asn Val Tyr
            100                 105                 110

Asp Ala Leu Val Ser Ala Gly Leu Ser Asn Ser Ile Lys Val Ser Thr
        115                 120                 125

Ala Val Arg Met Asp Val Ile Thr Ala Ser Ser Pro Ser His Gly
    130                 135                 140

Val Phe Arg Pro Asp Leu Gln Gln Phe Met Val Pro Ile Ala Gln Phe
145                 150                 155                 160

Leu Ala Asn Thr Met Ser Pro Leu Leu Ala Asn Val Tyr Pro Tyr Phe
                165                 170                 175

Ala Tyr Arg Asp Asn Pro Arg Asp Ile Pro Leu Asn Tyr Ala Thr Phe
            180                 185                 190

Gln Pro Gly Thr Thr Val Arg Asp Asn Asp Ser Gly Leu Thr Tyr Thr
        195                 200                 205

Asn Leu Phe Asn Ala Met Val Asp Ala Val Tyr Ala Ala Leu Glu Lys
    210                 215                 220

Ala Gly Ala Pro Gly Val Arg Val Val Ser Glu Ser Gly Trp Pro
225                 230                 235                 240

Ser Ala Gly Gly Phe Ala Ala Asn Val Glu Asn Ala Arg Asn His Asn
                245                 250                 255

Gln Gly Val Ile Asp Asn Val Lys Asn Gly Thr Pro Lys Arg Pro Gly
            260                 265                 270

Gln Leu Glu Thr Tyr Val Phe Ala Met Phe Asn Glu Asn Gln Lys Pro
        275                 280                 285

Gly Asp Glu Thr Glu Arg His Phe Gly Leu Phe Tyr Pro Asp Lys Thr
    290                 295                 300

Pro Val Tyr Pro Ile Thr Phe
305                 310

<210> SEQ ID NO 157
```

<211> LENGTH: 311
<212> TYPE: PRT
<213> ORGANISM: Oryza sativa

<400> SEQUENCE: 157

His Gly Val Cys Tyr Gly Met Asn Gly Asp Asn Leu Pro Ser Gln Ser
1               5                   10                  15

Glu Val Val Gln Leu Tyr Lys Ser Asn Gly Ile Gly Ala Met Arg Ile
            20                  25                  30

Tyr Ser Pro Asp Gln Lys Ala Leu Asp Ala Leu Arg Gly Ser Gly Ile
        35                  40                  45

Ala Val Ile Ile Asp Val Gly Ile Gly Ala Val Ala Asn Leu Ala
    50                  55                  60

Asn Asn Pro Ser Ala Ala Ala Asp Trp Val Arg Asp Asn Val Gln Ala
65                  70                  75                  80

Tyr Trp Pro Asn Val Ile Ile Arg Tyr Ile Ala Val Gly Asn Glu Leu
                85                  90                  95

Gly Pro Gly Asp Met Gly Thr Ile Leu Pro Ala Met Gln Asn Val Tyr
            100                 105                 110

Asp Ala Leu Val Ser Ala Gly Leu Ser Asn Ser Ile Lys Val Ser Thr
        115                 120                 125

Ala Val Arg Met Asp Ala Ile Thr Asp Ser Phe Pro Pro Ser His Gly
    130                 135                 140

Val Phe Arg Pro Asp Leu Gln Gln Phe Met Val Pro Ile Ala Gln Phe
145                 150                 155                 160

Leu Ala Asn Thr Met Ser Pro Leu Leu Ala Asn Val Tyr Pro Tyr Phe
                165                 170                 175

Ala Tyr Arg Asp Asn Pro Arg Asp Ile Pro Leu Asn Tyr Ala Thr Phe
            180                 185                 190

Gln Pro Gly Thr Thr Val Arg Asp Asn Asp Ser Gly Leu Thr Tyr Thr
        195                 200                 205

Asn Leu Phe Ser Ala Met Val Asp Ala Val Tyr Ala Ala Leu Glu Lys
    210                 215                 220

Ala Gly Glu Pro Gly Val Arg Val Val Val Ser Glu Ser Gly Trp Pro
225                 230                 235                 240

Ser Ala Gly Gly Phe Ala Ala Asn Val Glu Asn Ala Arg Asn His Asn
                245                 250                 255

Gln Gly Val Ile Asp Asn Val Lys Asn Gly Thr Pro Lys Arg Pro Gly
            260                 265                 270

Gln Leu Glu Thr Tyr Val Phe Ala Met Phe Asn Glu Asn Gln Lys Pro
        275                 280                 285

Gly Asp Glu Thr Glu Arg His Phe Gly Leu Phe Tyr Pro Asp Lys Thr
    290                 295                 300

Pro Val Tyr Pro Ile Thr Phe
305                 310

<210> SEQ ID NO 158
<211> LENGTH: 310
<212> TYPE: PRT
<213> ORGANISM: Oryza sativa

<400> SEQUENCE: 158

His Gly Val Cys Tyr Gly Val Val Gly Asn Asn Leu Pro Ser Arg Ser
1               5                   10                  15

Glu Val Val Gln Leu Tyr Lys Ser Lys Gly Ile Ser Ala Met Arg Ile
            20                  25                  30

```
Tyr Tyr Pro Asp Gln Glu Ala Leu Ala Ala Leu Arg Gly Ser Gly Ile
        35                  40                  45

Ala Val Ile Val Asp Val Gly Asp Lys Gly Ala Val Ala Asn Leu Ala
 50                  55                  60

Asn Asn Pro Ser Ala Ala Ala Asp Trp Val Arg Asn Asn Val Gln Ala
 65                  70                  75                  80

Tyr Trp Pro Ser Val Phe Ile Arg Tyr Ile Ala Val Gly Asn Glu Leu
                 85                  90                  95

Gly Pro Gly Asp Met Gly Thr Ile Leu Pro Ala Met Gln Asn Leu Tyr
            100                 105                 110

Asn Ala Leu Val Ser Ala Gly Leu Ser Asn Ser Ile Lys Val Ser Thr
        115                 120                 125

Ala Val Lys Met Asp Val Ile Thr Asn Ser Phe Pro Pro Ser His Gly
130                 135                 140

Val Phe Arg Pro Asp Leu Gln Arg Phe Ile Val Pro Ile Ala Gln Phe
145                 150                 155                 160

Leu Ala Asn Thr Met Ser Pro Leu Leu Val Asn Val Tyr Pro Tyr Phe
                165                 170                 175

Ala Tyr Arg Asp Asn Pro Arg Asp Ile Pro Leu Asn Tyr Ala Thr Phe
            180                 185                 190

Gln Pro Gly Thr Thr Val Arg Asp Asn Asp Ser Gly Leu Thr Tyr Thr
        195                 200                 205

Asn Leu Phe Ser Ala Met Val Asp Ala Val Tyr Ala Ala Leu Glu Lys
210                 215                 220

Ala Gly Ala Pro Gly Val Arg Val Val Val Ser Glu Ser Gly Trp Pro
225                 230                 235                 240

Ser Ala Gly Gly Phe Ala Ala Asn Val Glu Asn Ala Arg Asn His Asn
                245                 250                 255

Gln Gly Val Ile Asp Asn Val Lys Asn Gly Thr Pro Lys Arg Pro Gly
            260                 265                 270

Gln Leu Glu Thr Tyr Val Phe Ala Met Phe Asn Glu Asn Gln Lys Pro
        275                 280                 285

Gly Asp Glu Thr Glu Arg His Phe Gly Leu Phe Asn Pro Asp Lys Thr
        290                 295                 300

Pro Val Tyr Pro Ile Thr
305                 310

<210> SEQ ID NO 159
<211> LENGTH: 309
<212> TYPE: PRT
<213> ORGANISM: Oryza sativa

<400> SEQUENCE: 159

Gly Val Cys Tyr Gly Val Val Gly Asn Asn Leu Pro Ser Arg Ser Glu
 1               5                  10                  15

Val Val Gln Leu Tyr Lys Ser Lys Gly Ile Ser Ala Met Arg Ile Tyr
                20                  25                  30

Tyr Pro Asp Gln Glu Ala Leu Ala Ala Leu Arg Gly Ser Gly Ile Ala
            35                  40                  45

Val Ile Val Asp Val Gly Asp Lys Gly Ala Val Ala Asn Leu Ala Asn
        50                  55                  60

Asn Pro Ser Ala Ala Ala Asp Trp Val Arg Asn Asn Val Gln Ala Tyr
 65                  70                  75                  80

Trp Pro Ser Val Phe Ile Arg Tyr Ile Ala Val Gly Asn Glu Leu Gly
```

```
                        85                  90                  95
Pro Gly Asp Met Gly Thr Ile Leu Pro Ala Met Gln Asn Leu Tyr Asn
                100                 105                 110

Ala Leu Val Ser Ala Gly Leu Ser Asn Ser Ile Lys Val Ser Thr Ala
                115                 120                 125

Val Lys Met Asp Val Ile Thr Asn Ser Phe Pro Ser His Gly Val
    130                 135                 140

Phe Arg Pro Asp Leu Gln Arg Phe Ile Val Pro Ile Ala Gln Phe Leu
145                 150                 155                 160

Ala Asn Thr Met Ser Pro Leu Leu Val Asn Val Tyr Pro Tyr Phe Ala
                165                 170                 175

Tyr Arg Asp Asn Pro Arg Asp Ile Pro Leu Asn Tyr Ala Thr Phe Gln
                180                 185                 190

Pro Gly Thr Thr Val Arg Asp Asn Asp Ser Gly Leu Thr Tyr Thr Asn
                195                 200                 205

Leu Phe Ser Ala Met Val Asp Ala Val Tyr Ala Ala Leu Glu Lys Ala
    210                 215                 220

Gly Ala Pro Gly Val Arg Val Val Ser Glu Ser Gly Trp Pro Ser
225                 230                 235                 240

Ala Gly Gly Phe Ala Ala Asn Val Glu Asn Ala Arg Asn His Asn Gln
                245                 250                 255

Gly Val Ile Asp Asn Val Lys Asn Gly Thr Pro Lys Arg Pro Gly Gln
                260                 265                 270

Leu Glu Thr Tyr Val Phe Ala Met Phe Asn Glu Asn Gln Lys Pro Gly
                275                 280                 285

Asp Glu Thr Glu Arg His Phe Gly Leu Phe Asn Pro Asp Lys Thr Pro
    290                 295                 300

Val Tyr Pro Ile Thr
305

<210> SEQ ID NO 160
<211> LENGTH: 302
<212> TYPE: PRT
<213> ORGANISM: Sorghum bicolor

<400> SEQUENCE: 160

Asp Asn Leu Pro Ser Arg Ala Asp Val Val Gln Leu Cys Lys Ser Asn
1               5                   10                  15

Asn Ile Gln Ser Met Arg Ile Tyr Phe Pro Asp Gln Ala Ala Leu Ala
                20                  25                  30

Ala Leu Arg Gly Ser Gly Ile Ala Val Ile Leu Asp Val Gly Gly Val
    35                  40                  45

Asp Ala Val Arg Ala Leu Ala Gly Ser Ala Ser Val Ala Ala Asp Trp
50                  55                  60

Val Gln Ala Asn Val Gln Ala Tyr Gln Arg Asp Val Leu Ile Arg Tyr
65                  70                  75                  80

Ile Ala Val Gly Asn Glu Val Gly Pro Gly Asp Gly Ala Ala Ala Leu
                85                  90                  95

Leu Leu Pro Ala Met Arg Asn Val His Ala Ala Leu Val Ser Ala Gly
                100                 105                 110

Leu Asp Gly Ser Ile Lys Val Ser Thr Ala Val Lys Met Asp Ala Phe
    115                 120                 125

Ala Asp Thr Phe Pro Pro Ser Arg Gly Ala Phe Ala Gln Gly Tyr Met
    130                 135                 140
```

```
Ala Asp Val Ala Arg Phe Leu Ala Asp Thr Gly Ala Pro Leu Leu Ala
145                 150                 155                 160

Asn Val Tyr Pro Tyr Phe Ala Tyr Arg Asp Pro Arg Asn Ile Ser
            165                 170                 175

Leu Glu Phe Ala Ser Phe Arg Pro Gly Ala Ala Thr Val Thr Asp Gly
            180                 185                 190

Gly Asn Gly Leu Ala Tyr Thr Asn Leu Leu Asp Ala Met Val Asp Ala
        195                 200                 205

Ile Tyr Ala Ala Leu Glu Lys Ala Gly Ala Pro Gly Val Gln Val Val
        210                 215                 220

Val Ser Glu Ser Gly Trp Pro Ser Ala Gly Gly Phe Ala Ala Ser Val
225                 230                 235                 240

Asp Asn Ala Arg Gln Tyr Asn Gln Gly Val Ile Asp His Val Arg Gln
                245                 250                 255

Gly Thr Pro Arg Arg Pro Gly Leu Leu Glu Thr Tyr Val Phe Ala Met
            260                 265                 270

Phe Asn Glu Asn Gln Lys Thr Gly Asp Glu Ile Glu Arg His Phe Gly
            275                 280                 285

Leu Phe Asn Pro Asp Lys Thr Pro Val Tyr Pro Ile Asn Phe
        290                 295                 300

<210> SEQ ID NO 161
<211> LENGTH: 309
<212> TYPE: PRT
<213> ORGANISM: Setaria italica

<400> SEQUENCE: 161

His Gly Val Cys Tyr Gly Met Leu Gly Ser Asn Leu Pro Ser Arg Ala
1               5                   10                  15

Asp Val Val Glu Leu Tyr Lys Ser Asn Asn Ile Lys Ala Met Arg Ile
            20                  25                  30

Tyr Gly Pro Asp His Gly Ala Leu Asp Ala Leu Arg Gly Ser Gly Ile
        35                  40                  45

Ala Leu Ile Leu Asp Val Gly Gly Ile Gly Asp Val Arg Arg Leu Ala
    50                  55                  60

Gly Ser Ala Ser Glu Ala Ala Trp Val Gln Ala His Val Gln Pro
65                  70                  75                  80

Tyr Ser Arg Asp Val Ile Arg Tyr Ile Ala Val Gly Asn Glu Val
                85                  90                  95

Pro Pro Gly Asp Ala Ala Gly Ile Leu Leu Pro Ala Met Arg Asn Val
            100                 105                 110

Arg Gly Ala Leu Val Ser Ala Gly Leu Asp Gly Ile Lys Val Ser Thr
        115                 120                 125

Ala Val Lys Met Asp Val Phe Thr Asp Thr Phe Pro Pro Ser Arg Gly
    130                 135                 140

Val Phe Arg Asp Pro Ser Val Met Ser Pro Ile Val Gln Phe Leu Ala
145                 150                 155                 160

Gly Thr Gly Ala Pro Leu Leu Ala Asn Val Tyr Pro Tyr Phe Ala Tyr
                165                 170                 175

Lys Asp Asn Pro Arg Asp Ile Asn Leu Asn Phe Ala Thr Phe Arg Pro
            180                 185                 190

Gly Thr Thr Val Arg Asp Gly Asn Gly Leu Val Tyr Thr Asn Leu
        195                 200                 205

Phe Asp Ala Met Val Asp Ala Ile Tyr Ala Ala Leu Glu Lys Ala Gly
210                 215                 220
```

Ala Pro Gly Val Gly Val Val Ser Glu Ser Gly Trp Pro Ser Ala
225                 230                 235                 240

Gly Gly Phe Ala Ala Ser Val Glu Asn Ala Arg Ala His Asn Gln Gly
            245                 250                 255

Val Ile Asp His Val Arg Arg Gly Thr Pro Lys Arg Pro Gly Val Leu
        260                 265                 270

Glu Thr Tyr Val Phe Ala Met Phe Asn Glu Asn Gln Lys Pro Gly Glu
            275                 280                 285

Glu Ile Glu Arg His Phe Gly Leu Phe Asn Pro Asp Lys Ser Pro Val
        290                 295                 300

Tyr Pro Ile Thr Phe
305

<210> SEQ ID NO 162
<211> LENGTH: 312
<212> TYPE: PRT
<213> ORGANISM: Sorghum bicolor

<400> SEQUENCE: 162

His Gly Val Cys Tyr Gly Val Val Gly Asp Asn Leu Pro Ser Arg Ala
1               5                   10                  15

Asp Val Val Gln Leu Tyr Lys Ser Ser Asn Ile His Ala Met Arg Ile
            20                  25                  30

Tyr Tyr Pro Asp Pro Glu Ala Leu Ala Ala Leu Arg Gly Ser Gly Ile
        35                  40                  45

Gly Leu Ile Leu Asp Val Gly Val Asp Val Arg Gly Leu Ala
    50                  55                  60

Ser Ser Ala Ser Ala Ala Ala Trp Val His Ala Asn Val Val Ala
65                  70                  75                  80

His Tyr Pro Asp Val Leu Ile Arg Tyr Ile Ala Val Gly Asn Glu Val
                85                  90                  95

Pro Ala Gly Asp Ala Gly Leu Ile Leu Leu Pro Ala Met Arg Asn Val
            100                 105                 110

Arg Ala Ala Val Ala Ser Ala Gly Leu Ala Gly Ala Ile Lys Val Ser
        115                 120                 125

Thr Ala Val Arg Met Asp Val Val Thr Asp Ser Phe Pro Pro Ser Arg
130                 135                 140

Gly Val Phe Ser Pro Ser Val Gln Arg His Met Val Pro Val Ala Arg
145                 150                 155                 160

Phe Leu Ala Asp Ala Gly Ser Pro Leu Leu Ala Asn Val Tyr Pro Tyr
                165                 170                 175

Phe Ala Tyr Arg Asp Asn Pro Arg Asp Ile Thr Leu Gly Tyr Ala Thr
            180                 185                 190

Phe Gln Pro Gly Thr Ala Val Thr Asp Asp Gly Ser Gly Leu Thr Tyr
        195                 200                 205

Thr Asn Ile Phe Ala Ala Met Val Asp Ala Ile His Ala Ala Leu Glu
    210                 215                 220

Lys Ala Gly Ala Pro Gly Val Arg Ile Val Ser Glu Ser Gly Trp
225                 230                 235                 240

Pro Ser Ala Gly Gly Phe Ala Ala Thr Val Glu Asn Ala Arg Arg Tyr
                245                 250                 255

Asn Gln Gly Leu Ile Asp His Ala Tyr Arg Gly Thr Pro Lys Arg Pro
            260                 265                 270

Gly Ala Leu Glu Thr Tyr Val Phe Ala Met Phe Asn Glu Asn Gln Lys

```
            275                 280                 285
Pro Gly Asp Pro Thr Glu Arg Asn Phe Gly Leu Phe Tyr Pro Asn Lys
    290                 295                 300
Glu Pro Val Tyr Ser Ile Ser Phe
305                 310
```

<210> SEQ ID NO 163
<211> LENGTH: 307
<212> TYPE: PRT
<213> ORGANISM: Setaria italica

<400> SEQUENCE: 163

```
Ile Gly Asp Asn Leu Pro Ser Arg Ala Glu Val Val Gln Leu Tyr Lys
  1               5                  10                  15
Ser Arg Asn Ile Ser Ala Met Arg Ile Tyr His Pro Asp Pro Glu Ala
             20                  25                  30
Leu Ala Ala Leu Arg Gly Ser Gly Ile Ala Leu Val Leu Asp Val Gly
         35                  40                  45
Gly Val Asp Ala Ile Arg Ala Leu Ala Gly Ser Ala Ala Ala Ala Ala
     50                  55                  60
Val Trp Val Glu Ala Asn Val Gln Ala Tyr Tyr Pro Asp Val Leu Ile
 65                  70                  75                  80
Arg Tyr Val Ala Val Gly Asn Glu Val Pro Ala Gly Asp Ala Ala
                 85                  90                  95
Gly Leu Ile Leu Pro Ala Met Arg Asn Val Arg Ala Ala Leu Ala Ala
            100                 105                 110
Ala Gly Leu Ala Gly Ala Val Arg Val Ser Thr Ala Val Arg Met Asp
        115                 120                 125
Val Ile Thr Asp Ser Phe Pro Pro Ser Arg Gly Val Phe Ser Ala Ser
130                 135                 140
Ala Gly Arg His Met Pro Pro Val Ala Arg Phe Leu Ala Asp Thr Gly
145                 150                 155                 160
Ala Pro Leu Leu Ala Asn Val Tyr Pro Tyr Phe Ala Tyr Arg Asp Asn
                165                 170                 175
Pro Arg Asp Ile Ala Leu Ala Tyr Ala Thr Phe Gln Pro Gly Ala Ala
            180                 185                 190
Ala Val Arg Asp Gly Gly Ser Gly Leu Ala Tyr Thr Asn Leu Phe Ala
        195                 200                 205
Ala Met Val Asp Ala Ile His Ala Ala Leu Glu Lys Ala Gly Ala Pro
    210                 215                 220
Gly Val Gly Val Val Ser Glu Ser Gly Trp Pro Ser Ala Gly Gly
225                 230                 235                 240
Phe Ala Ala Thr Val Glu Asn Ala Arg Arg Tyr Asn Gln Gly Leu Ile
                245                 250                 255
Asp Gln Ala Tyr Arg Gly Thr Pro Lys Arg Pro Gly Val Leu Glu Thr
            260                 265                 270
Tyr Val Phe Ala Met Phe Asn Glu Asn Gln Lys Pro Gly Asp Pro Thr
        275                 280                 285
Glu Arg Asn Phe Gly Leu Phe Tyr Pro Asn Lys Gln Pro Val Tyr Pro
    290                 295                 300
Ile Ile Phe
305
```

<210> SEQ ID NO 164
<211> LENGTH: 243

```
<212> TYPE: PRT
<213> ORGANISM: Artificial Sequence
<220> FEATURE:
<223> OTHER INFORMATION: Consensus Sequence

<400> SEQUENCE: 164

Ile Gly Val Cys Tyr Gly Met Gly Asn Asn Leu Pro Ser Ser Val Val
1               5                   10                  15

Leu Tyr Lys Ser Asn Gly Ile Met Arg Leu Tyr Pro Asp Ala Leu Ala
            20                  25                  30

Leu Gly Ser Gly Ile Val Ile Val Gly Asn Asp Leu Ser Leu Ala Ser
            35                  40                  45

Pro Ser Ala Ala Ala Ser Trp Val Arg Asn Val Gln Ala Tyr Pro Ala
    50                  55                  60

Val Phe Arg Tyr Ile Ala Val Gly Asn Glu Val Gly Gly Ala Leu Leu
65                  70                  75                  80

Pro Ala Met Asn Val Ala Ala Leu Ala Ala Ala Gly Leu Gly Ile Lys
                85                  90                  95

Val Ser Thr Ala Val Ser Val Leu Gly Ser Tyr Pro Pro Ser Ala Gly
                100                 105                 110

Phe Thr Ala Tyr Met Gly Pro Ile Leu Phe Leu Ala Thr Gly Ala Pro
            115                 120                 125

Leu Leu Ala Asn Val Tyr Pro Tyr Phe Ala Tyr Asn Ile Leu Tyr Ala
    130                 135                 140

Leu Phe Ala Gly Thr Val Asp Gly Gly Gly Leu Tyr Asn Leu Phe Asp
145                 150                 155                 160

Ala Met Val Asp Ala Val Tyr Ala Ala Leu Glu Lys Gly Gly Val Val
                165                 170                 175

Val Val Ser Glu Ser Gly Trp Pro Ser Ala Gly Gly Ala Ala Ser Val
            180                 185                 190

Glu Asn Ala Arg Tyr Asn Gln Asn Leu Ile His Val Gly Arg Gly Thr
            195                 200                 205

Pro Arg Arg Pro Gly Ile Glu Thr Tyr Val Phe Ala Met Phe Asn Glu
    210                 215                 220

Asn Gln Lys Gly Glu Arg Asn Phe Gly Leu Phe Tyr Pro Asn Val Tyr
225                 230                 235                 240

Pro Ile Phe
```

PLANTS WITH ELEVATED LEVELS OF GLUCAN

CROSS-REFERENCE TO RELATED APPLICATIONS

This is a U.S. National Phase patent application of PCT/US2012/040544, filed Jun. 1, 2012, which claims priority to U.S. Provisional Patent Application No. 61/492,769, filed Jun. 2, 2011, each of which is incorporated herein by reference in its entirety.

STATEMENT AS TO RIGHTS TO INVENTIONS MADE UNDER FEDERALLY SPONSORED RESEARCH OR DEVELOPMENT

This invention was made with government support under awarded Contract No. DE-SC0004822, awarded by the United States Department of Energy to The University of California at Berkeley. The government has certain rights in this invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 416272009700SeqList.txt, date recorded: Feb. 5, 2014, size: 445 KB).

FIELD

The present disclosure relates to mutations in licheninase genes encoding polypeptides with decreased licheninase activity, which when expressed in plants results in elevated levels of glucan in the plants. In particular, the disclosure relates to licheninase nucleic acids and polypeptides related to glucan accumulation in plants, plants with reduced expression of a licheninase nucleic acid, and methods related to the generation of plants with increased glucan content in the cell walls of leaf tissue.

BACKGROUND

Members of the grasses, such as wheat, rice and maize, represent some of the major economically relevant crops. According to the Food and Agriculture Organization, the world production of grasses in 2008 was 2.5 billion metric tons (FAOSTAT: Food and Agriculture Organization of the United Nations, Rome Italy website). In addition to their nutritional importance, grasses have recently attracted attention as potential second generation bioenergy crops due to their potential to produce large quantities of biomass in short times with little agricultural input from growers (Heaton, E A, et al., *Global Change Biology* 14, 2000-14, 2008).

The grasses are noteworthy for their complex cell wall structure that is distinct from that of dicotyledons such as trees. One profound difference is that heteroxylans constitute the major hemicellulose in their primary cell wall. The cell walls of grasses also have less pectic polysaccharides compared to other higher plants. Another major difference in the primary cell wall is the presence of (1,3; 1,4)-β-D-glucans, a polysaccharide that is absent outside the Poales in higher plants. The unique cell wall structure of grasses such as maize has potential to provide large quantities sugars that can be used as feedstocks for the production of biofuels such as ethanol. For example, the glucose containing components of cell walls of maize can be used in the production of ethanol.

There is a need to develop plants, such as grasses, with improved cell wall characteristics such as increased levels of glucose containing polymers.

BRIEF SUMMARY

In order to meet the above needs, the present disclosure provides non-naturally occurring mutant plants having elevated levels of glucan, resulting from a mutation in at least one licheninase gene, and methods of producing and using such plants.

Accordingly, certain aspects of the present disclosure relate to a non-naturally occurring mutant plant containing a mutation in at least one licheninase gene, where the mutant plant has elevated levels of glucan, compared to the levels of glucan in a corresponding plant lacking the mutation in the at least one licheninase gene.

In certain embodiments, the at least one licheninase gene encodes a polypeptide containing consensus sequence SEQ ID NO: 9. In certain embodiments, the at least one licheninase gene contains a nucleic acid sequence selected from: (a) SEQ ID NO: 3 or 7; (b) a homolog of SEQ ID NO: 3 or 7; (c) a paralog of SEQ ID NO: 3 or 7; and (d) an ortholog of SEQ ID NO: 3 or 7. In certain embodiments that may be combined with any of the preceding embodiments, the at least one mutant licheninase gene encodes a polypeptide sequence having a Glu to Ly substitution at position 262 of SEQ ID NO: 4, a Glu to Ly substitution at a position analogous to position 262 of SEQ ID NO: 4, a Glu to Lys substitution at position 242 of SEQ ID NO: 8, or a Glu to Ly substitution at a position analogous to position 242 of SEQ ID NO: 8. In certain embodiments that may be combined with any of the preceding embodiments, the plant has at least a 20% increase in levels of glucan as compared to a corresponding plant lacking the mutation. In certain embodiments that may be combined with any of the preceding embodiments, the plant further contains a mutation in at least one additional licheninase gene. In certain embodiments, the at least one additional licheninase gene encodes a polypeptide containing consensus sequence SEQ ID NO: 9. In certain embodiments that may be combined with any of the preceding embodiments, the at least one licheninase gene or the at least one additional licheninase gene contains a partial deletion or a complete deletion of the gene. In certain embodiments that may be combined with any of the preceding embodiments, the plant further contains a mutation in at least one bm1 gene, a homolog thereof, a paralog thereof, or an ortholog thereof, where the plant exhibits an increased saccharification yield compared to the saccharification yield in a corresponding plant lacking the mutation in the at least one licheninase gene and the mutation in at least one bm1 gene. In certain embodiments that may be combined with any of the preceding embodiments, the plant further contains a mutation in at least one bm3 gene, a homolog thereof, a paralog thereof, or an ortholog thereof, where the plant exhibits an increased saccharification yield compared to the saccharification yield in a corresponding plant lacking the mutation in the at least one licheninase gene and the mutation in at least one bm3 gene. Other aspects of the present disclosure relate to a seed of a plant of any of the preceding embodiments.

Other aspects of the present disclosure relate to a plant containing an RNAi-inducing vector, where the vector generates RNAi against a licheninase gene.

In certain embodiments, the licheninase gene encodes a polypeptide containing consensus sequence SEQ ID NO: 9. In certain embodiments that may be combined with any of the preceding embodiments, the licheninase gene contains a nucleic acid sequence selected from: (a) SEQ ID NO: 3 or 7; (b) a homolog of SEQ ID NO: 3 or 7; (c) a paralog of SEQ ID NO: 3 or 7; and (d) an ortholog of SEQ ID NO: 3 or 7. In certain embodiments that may be combined with any of the preceding embodiments, the plant further contains one or more additional RNAi-inducing vectors, where the vectors generate RNAi against one or more additional licheninase genes. In certain embodiments, the one or more additional licheninase genes encode a polypeptide containing consensus sequence SEQ ID NO: 9. In certain embodiments that may be combined with any of the preceding embodiments, the plant further contains an additional RNAi-inducing vector, where the additional vector generates RNAi against a bm1 gene, a homolog thereof, a paralog thereof, or an ortholog thereof, where the plant exhibits an increased saccharification yield compared to the saccharification yield in a corresponding plant lacking the vectors generating RNAi against a licheninase genes and a bm1 gene. In certain embodiments that may be combined with any of the preceding embodiments, the plant further contains an additional RNAi-inducing vector, where the additional vector generates RNAi against a bm3 gene, a homolog thereof, a paralog thereof, or an ortholog thereof, where the plant exhibits an increased saccharification yield compared to the saccharification yield in a corresponding plant lacking the vectors generating RNAi against a licheninase genes and a bm3 gene. In certain embodiments that may be combined with any of the preceding embodiments, the RNAi-inducing vector or one or more additional RNAi-inducing vectors are stably transformed in the plant. Other aspects of the present disclosure relate to a seed of a plant of any of the preceding embodiments.

Other aspects of the present disclosure relate to a plant having reduced expression of at least one licheninase gene encoding a polypeptide containing consensus sequence SEQ ID NO: 9, where the plant has elevated levels of glucan compared to the levels of glucan in a corresponding plant lacking the reduced expression of the at least one licheninase gene.

In certain embodiments, the polypeptide contains an amino acid sequence selected from: (a) SEQ ID NO 4 or 8; (b) a homolog of SEQ ID NO: 4 or 8; (c) a paralog of SEQ ID NO: 4 or 8; and (d) an ortholog of SEQ ID NO: 4 or 8. In certain embodiments that may be combined with any of the preceding embodiments, the plant further contains reduced expression of at least one additional licheninase gene encoding a polypeptide containing consensus sequence SEQ ID NO: 9. In certain embodiments that may be combined with any of the preceding embodiments, the plant further contains reduced expression of at least one bm1 gene, a homolog thereof, a paralog thereof, or an ortholog thereof, where the plant exhibits an increased saccharification yield compared to the saccharification yield in a corresponding plant having reduced expression of the at least one licheninase gene and reduced expression of the at least one bm1 gene. In certain embodiments that may be combined with any of the preceding embodiments, the plant further contains reduced expression of at least one bm3 gene, a homolog thereof, a paralog thereof, or an ortholog thereof, where the plant exhibits an increased saccharification yield compared to the saccharification yield in a corresponding plant having reduced expression of the at least one licheninase gene and reduced expression of the at least one bm3 gene. In certain embodiments that may be combined with any of the preceding embodiments, the reduced expression of the at least one licheninase gene, the at least one additional licheninase gene, the at least one bm1 gene, and/or the at least one bm3 gene is a result of RNAi, antisense RNA, T-DNA insertion, transposon insertion, or TILLING. Other aspects of the present disclosure relate to a seed of a plant of any of the preceding embodiments.

In certain embodiments that may be combined with any of the preceding embodiments, the plant is selected from corn (*Zea mays*), barley (*Hordeum vulgare*), rice (*Oryza sativa*), sorghum (*Sorghum bicolor*), foxtail millet (*Setaria italica*), sugar cane (*Saccharum* spp.), wheat (*Triticum* spp.), soy (*Glysine* sp.), cotton (*Gossypium* sp.), sugar beet (*Beta vulgaris*), sunflower (*Helianthus* sp.), miscanthus (*Miscanthus* sp.), giant miscanthus (*Miscanthus giganteus*), rape (*Brassica napus*), grass (*Poaceae* sp.), switchgrass (*Panicum virgatum*), giant reed (*Arundo donax*), reed canary grass (*Phalaris arundinacea*), sericea lespedeza (*Lespedeza cuneata*), millet (*Panicum miliaceum*), ryegrass (*Lolium* sp.), timothy-grass (*Phleum* sp.), kochia (*Kochia* sp.), kenaf (*Hibiscus cannabinus*), bahiagrass (*Paspalum* sp.), bermudagrass (*Cynodon dactylon*), pangolagrass (*Digitaria decumbens*), bluestem grass (*Andropogon* sp.), indiangrass (*Sorghastrum* sp.), bromegrass (*Bromus* sp.), elephant grass (*Pennisetum purpureum*), jatropha (*Jatropha* sp.), alfalfa (*Medicago* sp.), clover (*Trifolium*), sunn hemp (*Crotalaria juncea*), fescue (*Festuca* sp.), orchard grass (*Dactylis* sp.), purple false brome (*Brachypodium distachyon*), sesame (*Sesamum indicum*), poplar (*Populus trichocarpa*), spruce (*Picea* sp.), pine (*Pinaceae* spp.), willow (*Salix* sp.), eucalyptus (*Eucalyptus* sp.), castor oil plant (*Ricinus communis*), and palm tree (*Arecaceae* sp.).

Other aspects of the present disclosure relate to a method of increasing levels of glucan in a plant, by reducing the expression in a plant of at least one licheninase gene.

In certain embodiments, the method further includes reducing the expression of at least one additional licheninase gene. In certain embodiments that may be combined with any of the preceding embodiments, the plant has at least a 20% increase in levels of glucan as compared to a corresponding plant lacking the reduced expression.

Other aspects of the present disclosure relate to a method of increasing the amount of glucose generated from biomass in a saccharification procedure, by: (a) obtaining biomass from a plant having reduced expression of at least one licheninase gene; and (b) subjecting the biomass to an enzymatic or chemical saccharification procedure, where an increased amount of glucose is generated from the plant having reduced expression of a licheninase gene, as compared to the amount of glucose generated from a corresponding plant lacking the reduced expression.

In certain embodiments, the plant further contains reduced expression in at least one additional licheninase gene. In certain embodiments that may be combined with any of the preceding embodiments, the amount of glucose generated is increased by at least 20%, as compared to the amount of glucose generated from a corresponding plant lacking the reduced expression. In certain embodiments that may be combined with any of the preceding embodiments, the plant further contains reduced expression of at least one bm1 gene, a homolog thereof, a paralog thereof, or an ortholog thereof. In certain embodiments that may be combined with any of the preceding embodiments, the plant further contains reduced expression of at least one bm3 gene, a homolog thereof, a paralog thereof, or an ortholog thereof. In certain embodiments that may be combined with any of the preceding embodiments, the amount of glucose generated is increased by at least 40%, as compared to the amount of glucose generated from a corresponding plant lacking the reduced expression of at least one licheninase gene and the at least one bm1 gene or the at least one bm3 gene.

Other aspects of the present disclosure relate to a method of increasing the yield of fermentation product from a fermentation reaction, by: (a) obtaining biomass from a plant having reduced expression of at least one licheninase gene; (b) subjecting the biomass to an enzymatic or chemical saccharification procedure; and (c) incubating the degraded biomass with a fermentative organism under conditions suitable to yield a fermentation product, where an increased yield of fermentation product from the fermentation reaction is obtained, as compared to the yield of fermentation product obtained from a fermentation reaction using degraded biomass from a corresponding plant lacking the reduced expression.

In certain embodiments, the plant further contains reduced expression in at least one additional licheninase gene. In certain embodiments that may be combined with any of the preceding embodiments, the plant further contains reduced expression of at least one bm1 gene, a homolog thereof, a paralog thereof, or an ortholog thereof. In certain embodiments that may be combined with any of the preceding embodiments, the plant further contains reduced expression of at least one bm3 gene, a homolog thereof, a paralog thereof, or an ortholog thereof. In certain embodiments that may be combined with any of the preceding embodiments, the at least one licheninase gene encodes a polypeptide containing consensus sequence SEQ ID NO: 9. In certain embodiments that may be combined with any of the preceding embodiments, the at least one licheninase gene contains a nucleic acid sequence is selected from: (a) SEQ ID NO: 3 or 7; (b) a homolog of SEQ ID NO: 3 or 7; (c) a paralog of SEQ ID NO: 3 or 7; and (d) an ortholog of SEQ ID NO: 3 or 7. In certain embodiments that may be combined with any of the preceding embodiments, the reduced expression of the at least one licheninase gene or the at least one additional licheninase gene is a result of mutagenesis of the gene. In certain embodiments that may be combined with any of the preceding embodiments, the reduced expression of the at least one bm1 gene or the at least one bm3 gene is a result of mutagenesis of the gene. In certain embodiments that may be combined with any of the preceding embodiments, the mutagenesis of the gene is by TILLING, T-DNA insertion, or transposon insertion. In certain embodiments that may be combined with any of the preceding embodiments, the mutagenesis of the gene results in a partial deletion or a complete deletion of the gene. In certain embodiments that may be combined with any of the preceding embodiments, the reduced expression of the at least one licheninase gene or the at least one additional licheninase gene is a result of RNAi or antisense RNA. In certain embodiments that may be combined with any of the preceding embodiments, the reduced expression of the at least one bm1 gene or the at least one bm3 gene is a result of RNAi or antisense RNA.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2 depicts the nucleic acid sequence and amino acid sequence of Cal-1 T01 licheninase from the Cal-1 maize mutant and wild-type A619 maize. FIG. 2A shows the nucleic acid sequence of Cal-1 T01 from the Cal-1 maize mutant (SEQ ID NO: 1); FIG. 2B shows the amino acid sequence of Cal-1 T01 from the Cal-1 maize mutant (SEQ ID NO: 2); FIG. 2C shows the nucleic acid sequence of Cal-1 T01 from A619 maize (SEQ ID NO: 3); and FIG. 2D shows the amino acid sequence of Cal-1 T01 from A619 maize (SEQ ID NO: 4). The underlined portion of FIG. 2D shows the GH17 domain of Cal-1 T01. The highlighted regions show the location of the point mutation and corresponding amino acid substitution.

FIG. 3 depicts the nucleic acid sequence and amino acid sequence of Cal-1 T02 licheninase from the Cal-1 maize mutant and wild-type A619 maize. FIG. 3A shows the nucleic acid sequence of Cal-1 T02 from the Cal-1 maize mutant (SEQ ID NO: 5); FIG. 3B shows the amino acid sequence of Cal-1 T02 from the Cal-1 maize mutant (SEQ ID NO: 6); FIG. 3C shows the nucleic acid sequence of Cal-1 T02 from A619 maize (SEQ ID NO: 7); and FIG. 3D shows the amino acid sequence of Cal-1 T02 from A619 maize (SEQ ID NO: 8). The underlined portion of FIG. 3D shows the GH17 domain of Cal-1 T01. The highlighted regions show the location of the point mutation and corresponding amino acid substitution.

FIG. 4 depicts an alignment of the amino acid sequence of the mutant Cal-1 T01 licheninase (SEQ ID NO: 2) with the amino acid sequences of GRMZM2G137535 P01 licheninase from the maize database (SEQ ID NO: 13), the wild-type Cal-1 T01 licheninase (SEQ ID NO: 4); a barley licheninase (SEQ ID NO: 15); and a consensus sequence (SEQ ID NO: 16). Boxed regions depict catalytic amino acid residues.

FIG. 5 depicts an alignment of the amino acid sequence of the mutant Cal-1 T02 licheninase (SEQ ID NO: 6) with the amino acid sequences of GRMZM2G137535 P02 licheninase from the maize database (SEQ ID NO: 14), the wild-type Cal-1 T02 licheninase (SEQ ID NO: 8); a barley licheninase (SEQ ID NO: 15); and a consensus sequence (SEQ ID NO: 17). Boxed regions depict catalytic amino acid residues.

FIG. 8A diagrammatically depicts the monosaccharide composition, by weight, of a hemicellulose extract (extraction by 4 molar potassium hydroxide) derived maize seedlings from wild-type (Mo17) and Cal-1/Mo17 inbred lines, indicating that the high glucan content is present in the hemicellulosic fraction. FIG. 8B diagrammatically depicts the glycosidic linkage composition, by mol %, of that 4M potassium hydroxide fraction, indicating that the high glucan content is due to an increase of mixed linked β-1,3-1,4-glucan compared to wild-type maize.

FIG. 9A diagrammatically depicts the monosaccharide composition of the total hydrolysate of the residue after 4M potassium hydroxide extraction. The main component is glucose representing cellulose. Hence, no difference in cellulose-content is observed. FIG. 9B diagrammatically depicts the lignin content of the Cal-1 maize mutant and wild-type maize (in mass %).

FIG. 11 depicts the kernel yield and biomass of the Cal-1 maize mutant. FIG. 11A diagrammatically depicts the total grain weight (kg). FIG. 11B diagrammatically depicts the total dry biomass weight (kg). FIG. 11C diagrammatically depicts the percent grain moisture. FIG. 11D diagrammatically depicts the percent biomass moisture.

FIG. 12 diagrammatically depicts the activity of the purified Cal-1 licheninase protein.

FIG. 13A diagrammatically depicts the hemicellulosic glucan content of the Cal-1 maize mutant crossed with the bm1 maize mutant and crossed with the bm3 maize mutant. FIG. 13B diagrammatically depicts the saccharification yield of the Cal-1 maize mutant crossed with the bm1 maize mutant and crossed with the bm3 maize mutant.

Figure 14:
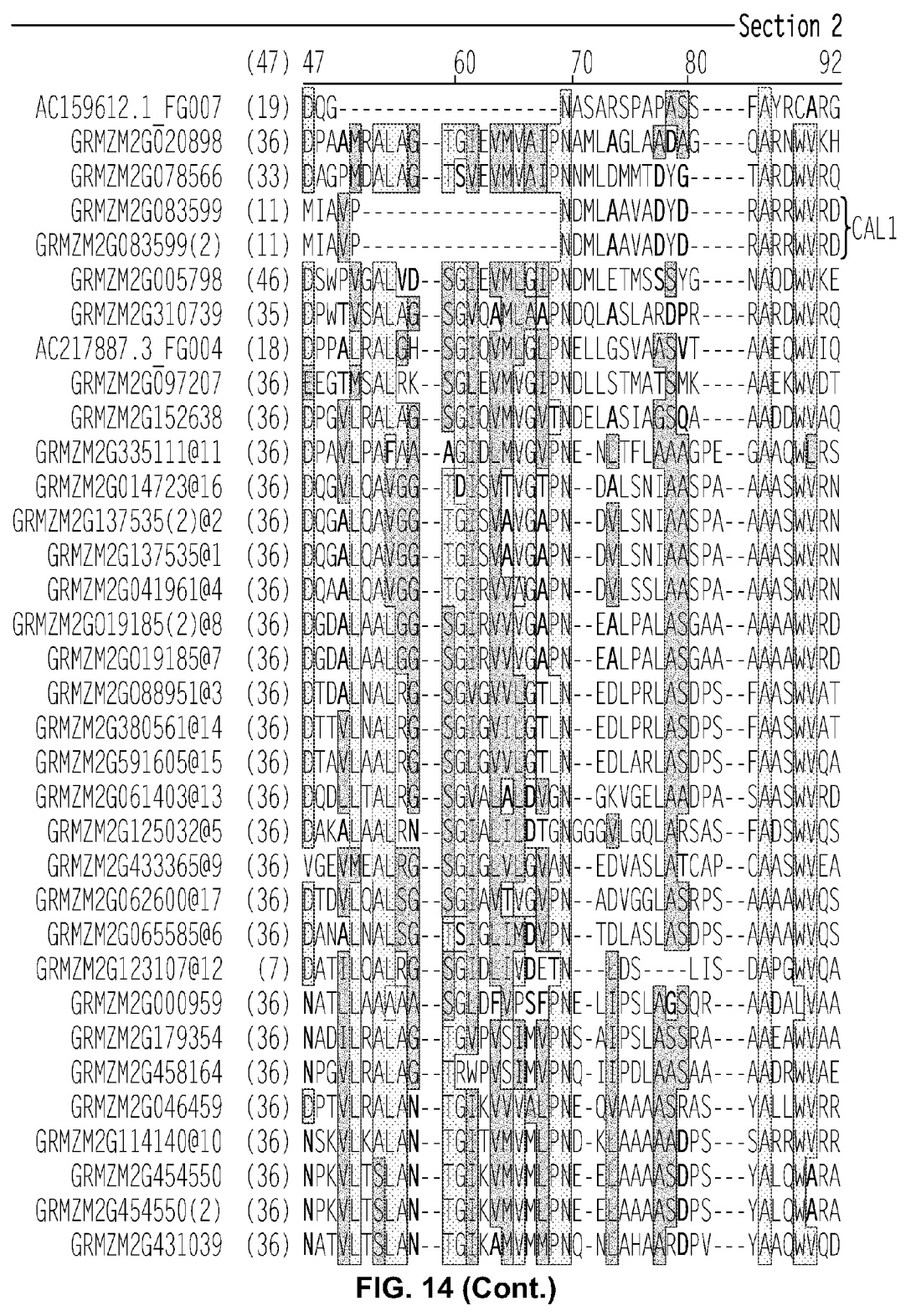
Figure 14:
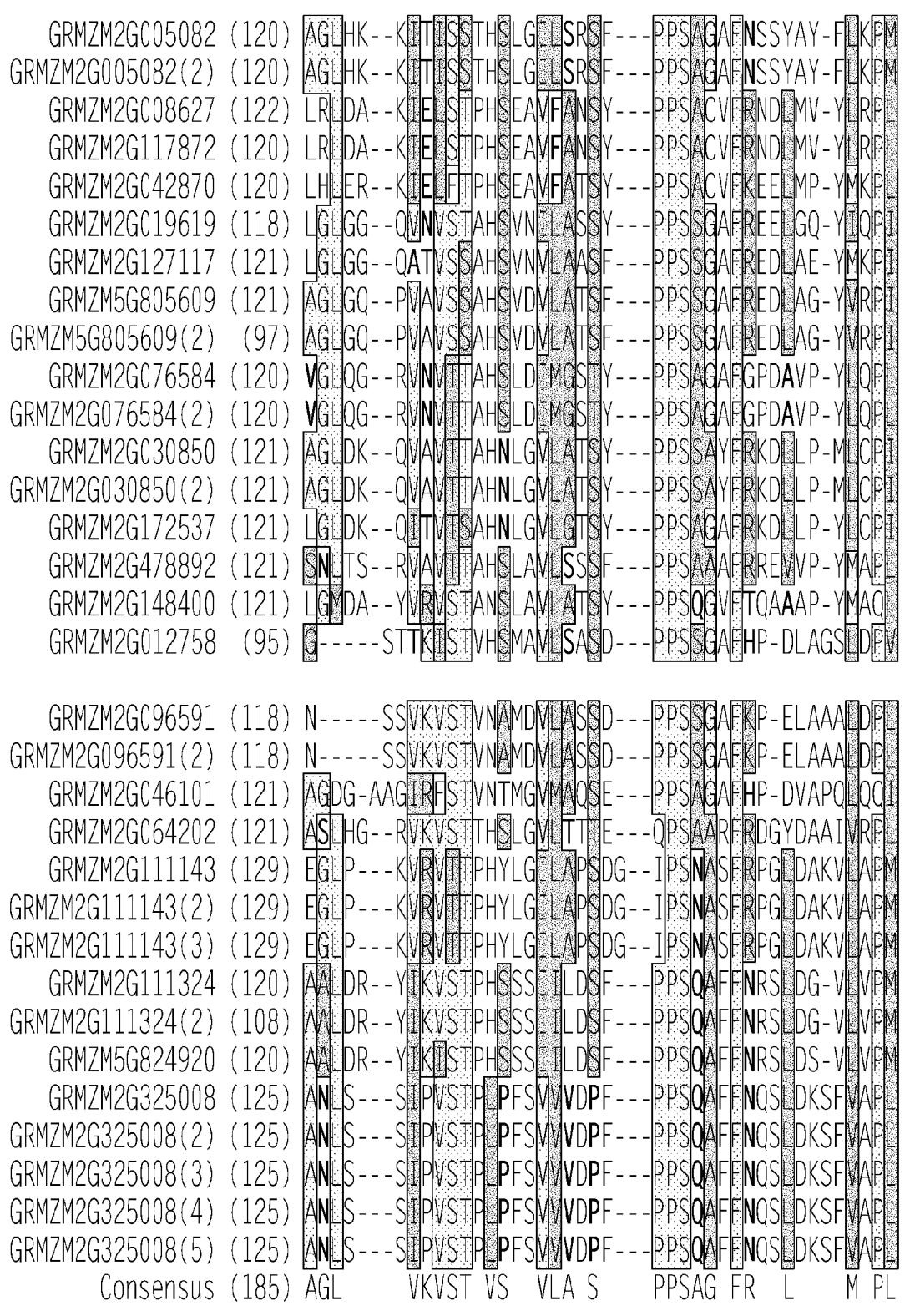

FIG. 14 depicts an amino acid sequence alignment of the GH117 domains of 66 maize proteins having at least 40% amino acid sequence identity with the Cal-1 T01 licheninase (the sequences correspond to SEQ ID NOS: 18-82, in the order as listed except for the amino acid sequences of GRMZM2G137535, which are SEQ ID NOS: 4 and 8).

FIG. 16 depicts an amino acid sequence alignment of the GH117 domains of 77 proteins from grass species *Zea mays, Oryza sativa, Sorghum bicolor, Brachypodium distachyon* and *Setaria italica* having at least 40% amino acid sequence identity with the Cal-1 T01 licheninase (the sequences correspond to SEQ ID NOS: 83-164, in the order as listed except for the amino acid sequences of GRMZM2G137535, which are SEQ ID NOS: 4 and 8).

DETAILED DESCRIPTION

Figure 1:
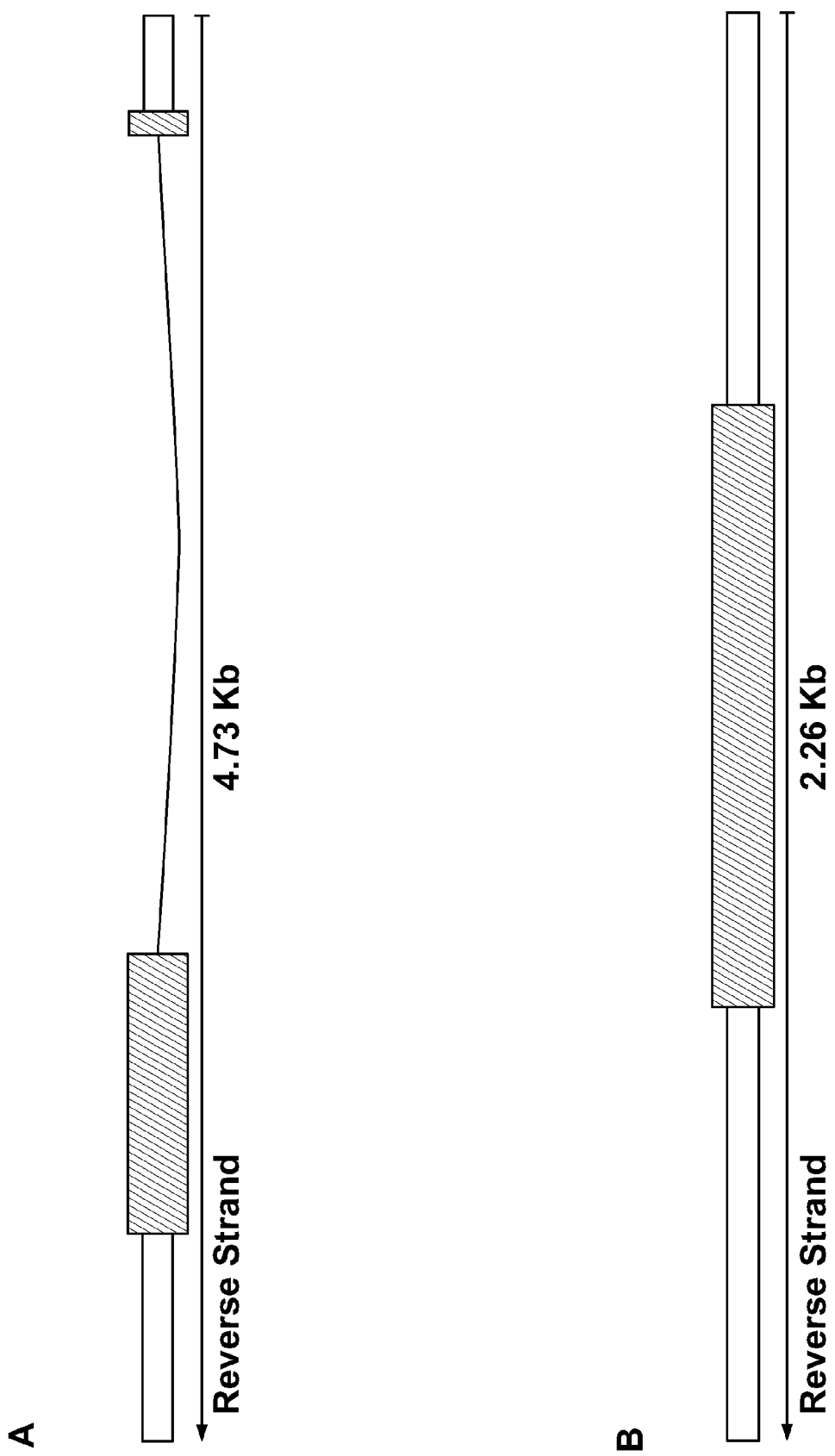
FIG. 1A depicts a protein model of Cal-1 T01.
FIG. 1B depicts a protein model of Cal-1 T02.

The present disclosure relates to non-naturally occurring mutant plants having elevated levels of glucan, and is based, in part, on the discovery that non-transgenic and non-naturally occurring mutant maize plants containing a mutation in the candy leaf-1 (Cal-1) licheninase gene have elevated levels of glucan, as compared to the levels of glucan in wild-type maize plants lacking the mutation. The Cal-1 mutation was determined to be a point mutation encoding an amino substitution of an active site glutamic acid of the licheninase polypeptide, which resulted in a decrease in licheninase activity. This decrease in licheninase activity resulted in elevated levels of β-glucan in the leaf and stem tissues of the mutant plants. Advantageously, mutant plants having elevated levels of glucan provide greater amounts of fermentable glucose, resulting in higher yields of biofuels.

As used herein, "glucan" refers to a polysaccharide of D-glucose monomers linked by glycosidic bonds. Examples of glucans include, without limitation, α-glucans, such as dextran (α-1,6-glucan with α-1,3-branches) and glycogen (α-1,4- and α-1,6-glucan); and β-glucans, such as lichenin (β-1,3- and β-1,4-glucan) and cellulose (β-1,4-glucan). In certain embodiments, the present disclosure relates to maize having elevated levels of glucans, such as lichenin. In general, the primary cell walls of grasses, such as maize, contain glucans.

Certain aspects of the present disclosure relate to using the genetic information (i.e., the nucleotide sequence and structure and sequence of the encoded polypeptide) of genes involved in the production of glucan, the regulation of glucan, and/or the regulation of genes involved in the production of glucan to produce plants having elevated levels of glucan. For example, the genetic information of such glucan-related genes may be used to identify regions of the genes that may be modified (e.g., mutated) to produce elevated levels of glucan in plants, and to identify homologous, paralogous, and orthologous glucan-related genes suitable for use in producing plants with elevated levels of glucan. Plants having elevated levels of glucan may be produced by mutating a glucan-related gene in the plant, by reducing or inhibiting expression of a glucan-related gene in the plant, or by reducing or inhibiting the expression or activity of the polypeptide encoded by a glucan-related gene. Either known glucan-related genes or novel glucan-related genes may be used. In the case of novel glucan-related genes, the genes may be identified, for example, by mutagenizing plants and screening for mutants having elevated levels of glucan. Methods of mutagenizing plants are well known in the art and described herein. Mutants having elevated levels of glucan can then be analyzed to identify the gene mutation resulting in the glucan phenotype. Methods of identifying gene mutations are well known in the art and described herein.

In one particular example, licheninase genes may be used to produce plants having elevated levels of glucan. Licheninase genes encode polypeptides involved in the degradation of the β-glucan lichenin. As used herein, "licheninase" or "polypeptides with licheninase activity", refers to a polypeptide having E.C. 3.2.1.73 activity, which catalyzes the hydrolysis of 1,4-β-D-glucosidic linkages in β-D-glucans containing 1,3- and 1,4-bonds. As used here, a "licheninase" includes, without limitation, licheninases, lichenases, endo-β-1,3-1,4 glucanases, 1,3-1,4-β-D-glucan 4-glucanohydrolases, and mixed linkage β-glucanases.

Accordingly, certain aspects of the present disclosure re relate to a non-naturally occurring mutant plant having elevated levels of glucan compared to the levels of glucan in a corresponding plant lacking the mutation, where the mutant plant contains a mutation in at least one licheninase gene. Other embodiments of the present disclosure relate to a plant having reduced expression of at least one licheninase gene, where the plant has elevated levels of glucan compared to a corresponding plant lacking the reduced expression of the at least one may be reduced to elevate the levels of glucan in plants. In other embodiments, the plants having reduced expression in at least one licheninase gene produce more glucan-released glucose than plants lacking the reduced expression of the at least one licheninase gene. In still other embodiments, biomass derived from plants having reduced expression of at least one licheninase gene provide an increased yield of a fermentation product in a fermentation reaction compared to biomass derived from plants lacking the reduced expression of the at least one licheninase gene.

Other embodiments of the present disclosure relate to methods of producing plants with elevated levels of glucan by reducing expression of at least one licheninase gene in the plant, as well as methods of using such plants, e.g., to increase biofuel yield from plant material. In certain embodiments, the yield of a fermentation product from a fermentation reaction is generally increased with increased levels of glucan in the plant. To obtain sugars, such as glucose, for the fermentation reaction, one or both of enzymatic or chemical degradation of glucan from plant material can be used. The degradation and fermentation of glucan from the plant can be performed in one reaction mixture or using separate reaction mixtures. Plant material from a plant having reduced expression of at least one licheninase gene, e.g., cell wall material from leaves, shoots, stems, etc., can be degraded either enzymatically or chemically in one reaction and the degradation products then fermented in a separate reaction mixture. In other aspects, the degradation reaction and the fermentation reaction are conducted in the same reaction mixture such that the degradation products generated from enzymatic or chemical degradation of the plant biomass is fermented in the same mixture in which the biomass is degraded.

An "increased yield" from a fermentation reaction can thus arise from an increase in the overall amount of product obtained from a reaction.

Plants with Elevated Levels of Glucan

Certain aspects of the present disclosure relate to plants having elevated levels of glucan. In certain embodiments, the elevated levels of glucan are the result of a non-naturally occurring mutation in at least one licheninase gene. In other embodiments, the elevated levels of glucan are the result of reduced expression of at least one licheninase gene. In still other embodiments, the elevated levels of glucan are the result of reduced expression of at least one licheninase polypeptide. In further embodiments, the elevated levels of glucan are the result of reduced licheninase activity in at least one licheninase polypeptide.

As used herein, "elevated" level of glucan refers to increased levels of glucan in a modified plant as compared to the level of glucan in a corresponding non-modified plant. As used herein, a "non-modified" plant refers to a plant that has not been modified in regards to the trait at issue (e.g., in this case, expression levels of at least one licheninase gene).

As used herein, "non naturally-occurring mutation" refers to plants that have been subjected to mutagenesis. Mutagenesis may be accomplished by any method of mutagenesis disclosed herein or any method known in the art. Examples include, without limitation, chemical mutagenesis and radiation mutagenesis.

As used herein, "reduced expression" of a licheninase gene or polypeptide refers to a modified plant having levels of expression that are reduced as compared to the levels of expression in a corresponding non-modified plant. As used herein, "reduced licheninase activity" in a licheninase polypeptide refers to a modified plant having levels of licheninase activity in a licheninase polypeptide that are reduced as compared to the levels of licheninase activity in the licheninase polypeptide in a corresponding non-modified plant.

In some embodiments, plants having an elevated levels of glucan contain levels of glucan that are elevated by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 100%, at least 200%, at least 300%, at least 400%, at least 500%, at least 600%, at least 700%, at least 800%, at least 900%, at least 1,000%, or more compared to the levels of glucan in a corresponding non-modified plant.

In other embodiments, plants having elevated levels of glucan contain reduced expression of at least one licheninase gene, where the level of expression is about 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 125% less, 150% less, 175% less, 200% less, 300% less, 400% less, 500% less, 600% less, 700% less, 800% less, 900% less, 1000% less, or a greater percentage less than the level of expression of the at least one licheninase gene in a corresponding non-modified plant.

In still other embodiments, plants having elevated levels of glucan contain reduced expression of at least one licheninase polypeptide, where the level of expression is about 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 125% less, 150% less, 175% less, 200% less, 300% less, 400% less, 500% less, 600% less, 700% less, 800% less, 900% less, 1000% less, or a greater percentage less than the level of expression of the at least one licheninase polypeptide in a corresponding non-modified plant.

In further embodiments, plants having elevated levels of glucan contain reduced licheninase activity in at least one licheninase polypeptide, where the level of licheninase activity is about 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 125% less, 150% less, 175% less, 200% less, 300% less, 400% less, 500% less, 600% less, 700% less, 800% less, 900% less, 1000% less, or a greater percentage less than the level of licheninase activity in the at least one licheninase polypeptide in a corresponding non-modified plant.

In other embodiments, plants having elevated levels of glucan have been modified to alter the level of one or more polypeptides that affect the levels of glucan in the plant. In yet other embodiments, plants having elevated levels of glucan have been modified to alter the expression of one or more genes encoding one or more polypeptides that affect the levels of glucan.

The present disclosure also includes offspring of plants that have been modified to have elevated levels of glucan. The present disclosure further includes seeds, cuttings, rhizomes, runners, plant cells, and tissues of plants that have been modified to have elevated levels of glucan.

Plant Types

As disclosed herein, various types of plants may be modified to produce plants having elevated levels of glucan. Suitable plants that may be modified include both monocotyledonous plants and dicotyledonous plants. Examples of suitable plants that may be modified to produce plants having elevated levels of glucan include, without limitation, maize (*Zea mays*), barley (*Hordeum vulgare*), rice (*Oryza sativa*), sorghum (*Sorghum bicolor*), foxtail millet (*Setaria italica*), sugar cane (*Saccharum* spp.), wheat (*Triticum* spp.), soy (*Glysine* sp.), cotton (*Gossypium* sp.), sugar beet (*Beta vulgaris*), sunflower (*Helianthus* sp.), miscanthus (*Miscanthus* sp.), giant miscanthus (*Miscanthus giganteus*), switchgrass (*Panicum virgatum*), grass (*Poaceae* sp.), rape (*Brassica napus*), giant reed (*Arundo donax*), reed canary grass (*Phalaris arundinacea*), sericea lespedeza (*Lespedeza cuneata*), millet (*Panicum miliaceum*), ryegrass (*Lolium* sp.), timothy-grass (*Phleum* sp.), kochia (*Kochia* sp.), kenaf (*Hibiscus cannabinus*), bahiagrass (*Paspalum* sp.), bermudagrass (*Cynodon dactylon*), pangolagrass (*Digitaria decumbens*), bluestem grass (*Andropogon* sp.), indiangrass (*Sorghastrum* sp.), bromegrass (*Bromus* sp.), elephant grass (*Pennisetum purpureum*), jatropha (*Jatropha* sp.), alfalfa (*Medicago* sp.), clover (*Trifolium*), sunn hemp (*Crotalaria juncea*), fescue (*Festuca* sp.), orchard grass (*Dactylis* sp.), purple false brome (*Brachypodium distachyon*), sesame (*Sesamum indicum*), poplar (*Populus trichocarpa*), spruce (*Picea* sp.), pine (*Pinaceae* spp.), willow (*Salix* sp.), eucalyptus (*Eucalyptus* sp.), castor oil plant (*Ricinus communis*), and palm tree (*Arecaceae* sp.).

In certain preferred embodiments, plants that may be modified to produce plants having elevated levels of glucan are grasses, such as maize, wheat, rice, *sorghum*, and switchgrass. In some embodiments, the plants of the present disclosure are used as feedstocks for biofuel production and/or the production of commodity chemicals. In other embodiments, plants of the disclosure are used for, without limitation, food, cosmetic, or pharmaceutical production.

Suitable Licheninase Polypeptides

Other aspects of the present disclosure relate to plants having elevated levels of glucan, where the elevated glucan levels are the result of at least one modified licheninase polypeptide having reduced licheninase activity.

As used herein, a "polypeptide" is an amino acid sequence including a plurality of consecutive polymerized amino acid residues (e.g., at least about 15 consecutive polymerized amino acid residues). As used herein, "polypeptide" refers to an amino acid sequence, oligopeptide, peptide, protein, or portions thereof.

Suitable polypeptides of the present disclosure that may be used to produce plant with elevated levels of glucan include, without limitation, licheninase polypeptides that have been modified or inhibited to reduce their licheninase activity compared to the licheninase activity of a corresponding licheninase polypeptide that lacks such a modification. Examples of modified polypeptides include, without limitation, polypeptides containing one or more insertions, duplications, amplifications, truncations, deletions, or amino acid substitutions that reduce the licheninase activity of the polypeptide as compared to the licheninase activity in a corresponding licheninase polypeptide that lacks such a modification, or that inhibit the licheninase activity. Methods of generating and identifying polypeptides with one or more modifications are well known in the art.

As used herein, gene expression, polypeptide expression, or polypeptide activity that has been "inhibited", refers to expression or activity that is below the detection level of any known method of detecting gene or polypeptide expression, or of detecting polypeptide activity.

As disclosed herein, licheninase polypeptides modulate the levels of glucan in plants by hydrolyzing 1,4-β-D-glucosidic linkages in (1,3; 1,4)-β-glucans. Licheninase polypeptides of the present disclosure are members of glycosylhydrolase family 17 (GH17) family of glycosylhydrolases. GH17 polypeptides contain a conserved GH17 domain that is unique to members of the GH17 family of polypeptides. A consensus sequence of the GH17 domain is set forth below (SEQ ID NO: 9):

X-X-XX-X-X-X-X-X-X-[I/L/V/H/A/F]-G-[V/I/A]-
[N/T/S/C]-[Y/N/I/W/H]-G-X-[V/Q/M/S/I/L/T/N/R/A]-
[A/S/G/M/V]-X-[N/H/D/T/S]-[L/P/Q/R/I]-[P/L/I/A]-
X-[P/L//H/A/K/S/T]-X-X-[V/A/M/S/P/L/K/I]-
[V/A/I/M/S/P/L/T]-X-[L/Q/R/K/E/D/M/I/F]-
[L/V/M/G/Y/C/A/I]-[R/L/K/Q/A/E/S/V/L/T]-X-
[S/D/G/A/R/K/L/Q]-X-X-[I/V/F/A]-X-
[K/R/A/L/V/Y/D/S/G/N/M/H]-[V/A/M/L]-[R/K/T]-
[L/S/M/I/T]-[Y/F/I/L]-[D/E/N/L/A/W/H/F/S/G]-
[A/T/P/S/V]-[D/M/E/V/N/Q]-X-X-[V/A/P/T/I/L/F/M]-
[L/M/P/V/I]-X-[A/S]-[L/F/V/A]-[A/V/G/R/S]-
[G/D/H/K/N/R/A]-X-X-[T/S/A/P]-[G/S/D/R/N]-
[I/V/L/W]-X-[V/A/L/F]-[V/M/T/A/I/D]-[V/L/A/P/I]-
[G/A/D/S/M/T]-[V/I/A/L/T/E/F]-[P/T/L/G/A]-[N/D]-
X-X-X-[L/R/A/D/E/G/S/K/I]-X-X-X-
[A/P/DS/R/T/G/I/L/M]-[A/D/Y/S/G/R/Q/T/V/N]-
[S/A/G/D/Y/P/V/M/Q/R/T/N]-X-X-X-X-X-[A/V/S]-
X-X-[W/C/L]-[V/A/L]-X-X-[N/L/A/Y/T/S/H/R]-
[V/I/L|-X-[P/A/R/K/T/S]-[Y/V/N/H/A/F/T/S]-X-
[P/L/F/N/S/G/Q/D]-[A/D/K/R/S/Q/V]-X-X-X-X-X-X-
[I/C/L/F/V/S/T]-X-X-[V/I/L/M]-[A/C/N/V/T/S]-
[V/L/A/G]-[G/D/N]-[N/P/A/E/S/D]-[E/S/V]-
[V/A/F/I/L/T]-X-X-X-X-X-X-X-X-X-X-X-X-X-X-X-
X-X-X-X-X-X-X-X-X-X-X-X-X-X-X-X-X-X-X-X-X-
X-X-X-X-X-X-X-X-X-X-X-[L/T/I/V]-[L/F/V/I/A/M]-
[P/Q/G/D]-A-[M/L/V/I]-[R/Q/K/T/E/A/S/L]-
[N/S/T/A/C/R/Y]-[L/I/V/M/A]-
[H/Q/R/E/D/N/S/A/Y/L]-X-[A/S/G]-[L/I/V/A]-X-X-
[A/L/H/R/V/S/G/N/E]-[G/N/S/R/H/A]-
[L/I/F/H/V/F/M/D]-X-X-X-X-X-[V/I/A/T]-
[K/H/P/R/T/E/N/A]-[V/A/L/C/I/F]-[S/T/V/G/F]-
[T/V/C/S]-X-[V/L/C/H/I/N]-[S/N/A/K/R/Q/T/Y/P]-X-
X-[V/I/A/D]-[L/Y/I/V/T/F/M]-
[A/M/N/D/S/E/Q/G/T/R/L/V]-X-[S/P/Q/T/A]-X-X-X-X-
[P/V/Q/I]-[P/S]-[S/A/Q]-[A/Q/G/R/D/S/T/N]-
[G/Q/E/A/S/C]-X-[F/W/T/S]-
[R/C/D/V/G/E/A/S/N/T/H]-X-X-
[L/P/I/V/L/S/Y/A/D/E]-X-X-X-X-[M/L/V/I]-X-
[P/D/E/S/T/Q/Y/R]-[L/M/I/V]-[L/V/A/I]-X-
[F/Y/L/H]-[L/F/H]-[A/N/H/L/S/Q/E/D/V/R]-X-
[T/N/S/H/K/R/I/V/A]-[G/D/R/N/Q/S]-[A/G/S/T/R]-

-continued

[P/V/A/C/Y/F]-[L/F/Y/V]-[L/T/V/M/F/Y/P/W/L]-

[V/I/A/C/L/I]-[N/S/D]-[I/H/A/V/L/C/P]-[Y/L]-

[P/T]-[Y/R/F/C/W]-[F/S/L/Y]-[A/S/T/V/D]-

[Y/P/H/W/Q/L]-X-X-X-X-X-X-X-X-X-

[I/S/F/V/M/L/E/S/A]-X-[L/V/F/Q/M/I]-

[D/E/N/A/S/G/P]-[Y/F/N]-[A/S/V/C]-

[L/F/Y/I/T/V]-[F/L/G/S]-X-[P/G/S/A/M/V]-X-X-X-X-

X-X-X-X-X-X-X-X-X-[V/G/A/S/N/K/H/T/Y/R/M]-

[V/W/P/I/S/T/R/L/A/Q/M/Y]-[D/V/Q/I/L/T]-X-X-

[T/S/H/N/G/A]-[G/R/N/S/P/A/E/K]-

[L/V/I/A/M/F/N/Y]-X-Y-[T/S/Y/Q/N/G/D/H/A/P]-

[N/D/S]-[M/V/A/L]-[F/L]-[D/Y/H/A/V]-[A/G/T/Q/E]-

[Q/N/T/I/M/L/V]-[V/F/Y/H/A/M/L]-D-[A/T/S/C]-

[V/L/F/T/I/A]-[Y/V/I/H/R/F/T/K]-

[A/S/H/W/L/V/I/F/Y/T]-[A/S]-[L/M/V/I/A]-X-X-

[L/V/A/H/N/I/E/M/K]-[G/N]-X-X-X-X-X-X-X-X-X-X-

X-X-[V/M/L/I/P]-X-[V/I/L/A]-[V/M/I/A/H/R/T/K/L]-

[V/I/L]-[S/G/T/A]-E-[T/V/A/I/S]-G-[W/H/C]-[P/A]-

[S/T/N/Y/H]-X-[G/D/C/A]-X-X-X-X-X-X-X-X-X-X-X-

X-X-X-X-X-X-X-X-X-X-X-X-X-[E/D/N/A/H/Q/Y]-X-

[G/H/Y/N/S/A/Q/V/E/D]-[A/E/G/V]-[T/K/N/S/G]-X-

[E/A/S/K/Q/T/G/D/R/H]-[N/Y/F/L/M/A/E]-[A/S]-X-X-

[Y/F]-[N/Y/Y/S/D/I]-X-[N/G/K/Y]-[L/F/I/V/A/M]-

[I/L/F/M/V/A/R]-[R/Q/D/T/N/E/L/A/K/M/S]-X-

[V/L/M/I/A/Q/C]-X-X-[G/N/S/R/D/Q/L/E]-X-X-X-G-T-

P-X-[R/H/K/A/T/M]-[P/K/T/S]-[G/N/Q/R/D/K/H/A/S]-

X-X-X-X-X-X-X-[Y/F/I/M/S]-[I/L/V/M]-[F/Y]-

[A/G/S/D/E]-[L/M/T]-[F/L/V/I/Y]-[N/D]-E-[D/E/N]-

X-[K/R]-X-X-X-[G/P/D/E/A]-X-X-[S/F/Q/E/T/V/I/A]-

[E/N/H/K/R]-[R/Q/N/K/A]-X-[W/F/Y]-G-[L/I/V/M]-

[F/L/M/Y]-X-[P/Y/F/A/G/K/T/M]-X-[D/N/S]-

[G/M/K/R/Q/E/L]-[T/Q/R/K/S/L/H/E/A/V]-

[P/A/K/H/R/E/L/M/S/I]-[V/K/A/I/S/N/T]-[Y/F]-X-

[L/M/I/V/F]-X-X

In the above domain and all other domains provided herein, the accepted IUPAC single letter amino acid abbreviation is employed.

Accordingly, in certain embodiments, suitable polypeptides that may be modified to produce a plat with elevated levels of glucan contain the consensus sequence set forth in SEQ ID NO: 9.

Additionally, suitable polypeptides that may be modified to produce plants with elevated levels of glucan include the polypeptides encoded by the Cal-1 T01 and Cal-1 T02 licheninase genes. The amino acid sequence of the polypeptide encoded by Cal-1 T01 is set forth in SEQ ID NO: 4 and the amino acid sequence of the polypeptide encoded by Cal-1 T02 is set forth in SEQ ID NO: 8. In certain embodiments, suitable polypeptides contain an amino acid sequence having at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 96%, at least 97%, at least 98%, at least 99%, or higher percent identity to the sequence of SEQ ID NO: 4. In other embodiments, suitable polypeptides contain an amino acid sequence having at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 98%, at least 99%, or higher percent identity to the sequence of SEQ ID NO: 8. In further embodiments, suitable polypeptides contain at least 10, at least 12, at least 14, at least 16, at least 18, at least 20, at least 21, at least 22, at least 23, at least 24, at least 25, at least 30, at least 40, at least 50, at least 60, at least 70, at least 80, at least 90, at least 100, at least 125, at least 150, at least 175, at least 200, at least 225, at least 250, at least 275, at least 300, or more consecutive amino acids of SEQ ID NOs: 4 or 8.

Other suitable polypeptides that may be modified to produce plants with elevated levels of glucan include homologs, paralogs, and/or orthologs of the polypeptides encoded by the Cal-1 T01 and Cal-1 T02 licheninase genes. Methods for identifying polypeptides that are homologs, paralogs, and/or orthologs of a polypeptide of interest are well known to one of skill in the art, as described herein. Examples of suitable polypeptides that are homologous, paralogous, and/or orthologous to the polypeptides encoded by Cal-1 POT and Cal-1 T02 include, without limitation, homologous, paralogous, and/or orthologous licheninase polypeptides from maize (*Zea mays*), barley (*Hordeum vulgare*), rice (*Oryza sativa*), sorghum (*Sorghum bicolor*), foxtail millet (*Setaria italica*), sugar cane (*Saccharum* spp.), wheat (*Triticum* spp.), soy (*Glysine* sp.), cotton (*Gossypium* sp.), sugar beet (*Beta vulgaris*), sunflower (*Helianthus* sp.), miscanthus (*Miscanthus* sp.), giant miscanthus (*Miscanthus giganteus*), switchgrass (*Panicum virgatum*), grass (*Poaceae* sp.), rape (*Brassica napus*), giant reed (*Arundo donax*), reed canary grass (*Phalaris arundinacea*), sericea lespedeza (*Lespedeza cuneata*), millet (*Panicum miliaceum*), ryegrass (*Lolium* sp.), timothy-grass (*Phleum* sp.), kochia (*Kochia* sp.), kenaf (*Hibiscus cannabinus*), bahiagrass (*Paspalum* sp.), bermudagrass (*Cynodon dactylon*), pangolagrass (*Digitaria decumbens*), bluestem grass (*Andropogon* sp.), indiangrass (*Sorghastrum* sp.), bromegrass (*Bromus* sp.), elephant grass (*Pennisetum purpureum*), jatropha (*Jatropha* sp.), alfalfa (*Medicago* sp.), clover (*Trifolium*), sunn hemp (*Crotalaria juncea*), fescue (*Festuca* sp.), orchard grass (*Dactylis* sp.), purple false brome (*Brachypodium distachyon*), sesame (*Sesamum indicum*), poplar (*Populus trichocarpa*), spruce (*Picea* sp.), pine (*Pinaceae* spp.), willow (*Salix* sp.), eucalyptus (*Eucalyptus* sp.), castor oil plant (*Ricinus communis*), and palm tree (*Arecaceae* sp.).

Suitable polypeptides that may also be modified to produce plants with elevated levels of glucan include maize polypeptides that are homologous to the licheninase polypeptides encoded by Cal-1 T01 and Cal-1 T02. For example, suitable polypeptides include, without limitation, the polypeptides encoded by the genes listed in Table 1.

TABLE 1

| Gene ID | Organism of Origin |
|---|---|
| AC159612.1_FG007 | Zea mays |
| GRMZM2G020898 | Zea mays |
| GRMZM2G078566 | Zea mays |
| GRMZM2G083599 | Zea mays |
| GRMZM2G005798 | Zea mays |
| GRMZM2G310739 | Zea mays |
| AC217887.3_FG004 | Zea mays |
| GRMZM2G097207 | Zea mays |
| GRMZM2G152638 | Zea mays |
| GRMZM2G335111 | Zea mays |
| GRMZM2G014723 | Zea mays |
| GRMZM2G137535 | Zea mays |
| GRMZM2G041961 | Zea mays |
| GRMZM2G019185 | Zea mays |
| GRMZM2G088951 | Zea mays |
| GRMZM2G380561 | Zea mays |
| GRMZM2G591605 | Zea mays |
| GRMZM2G061403 | Zea mays |
| GRMZM2G125032 | Zea mays |
| GRMZM2G433365 | Zea mays |
| GRMZM2G062600 | Zea mays |
| GRMZM2G065585 | Zea mays |
| GRMZM2G123107 | Zea mays |
| GRMZM2G000959 | Zea mays |
| GRMZM2G179354 | Zea mays |
| GRMZM2G458164 | Zea mays |
| GRMZM2G046459 | Zea mays |
| GRMZM2G114140 | Zea mays |
| GRMZM2G454550 | Zea mays |
| GRMZM2G431039 | Zea mays |
| GRMZM2G005082 | Zea mays |
| GRMZM2G008627 | Zea mays |
| GRMZM2G117872 | Zea mays |
| GRMZM2G042870 | Zea mays |
| GRMZM2G019619 | Zea mays |
| GRMZM2G127117 | Zea mays |
| GRMZM5G805609 | Zea mays |
| GRMZM2G076584 | Zea mays |
| GRMZM2G030850 | Zea mays |
| GRMZM2G172537 | Zea mays |
| GRMZM2G478892 | Zea mays |
| GRMZM2G148400 | Zea mays |
| GRMZM2G012758 | Zea mays |
| GRMZM2G096591 | Zea mays |
| GRMZM2G046101 | Zea mays |
| GRMZM2G064202 | Zea mays |
| GRMZM2G111143 | Zea mays |
| GRMZM2G111324 | Zea mays |
| GRMZM5G824920 | Zea mays |
| GRMZM2G325008 | Zea mays |

Other suitable polypeptides that may be modified to produce plants with elevated levels of glucan, include *Oryza sativa, Sorghum bicolor, Brachypodium distachyon* and *Setaria italica* polypeptides that are homologous to the licheninase polypeptides encoded by Cal-1 T01 and Cal-1 T02. For example, suitable polypeptides include, without limitation, the polypeptides encoded by the genes listed in Table 2

TABLE 2

| Gene ID | Organism of Origin |
|---|---|
| Bradi2q27140.1 | Brachypodium distachyon |
| Bradi2q27140.2 | Brachypodium distachyon |
| Sb09g018730.1 | Sorghum bicolor |
| Sb09g018730.3 | Sorghum bicolor |
| Sb09g018730.4 | Sorghum bicolor |
| Sb09g018730.2 | Sorghum bicolor |
| Si022614m | Setaria italica |
| Si022791m | Setaria italica |
| Si022794m | Setaria italica |
| Si022731m | Setaria italica |
| LOC_Os05g31140.1 | Oryza sativa |
| LOC_Os05g31140.2 | Oryza sativa |
| LOC_Os05g31140.3 | Oryza sativa |
| Sb09g018750.1 | Sorghum bicolor |
| Si022606m | Setaria italica |
| Si028122m | Setaria italica |
| Bradi2g60500.1 | Brachypodium distachyon |
| Sb03q045480.1 | Sorghum bicolor |
| Si002273m | Setaria italica |
| LOC_Os02g53200.1 | Oryza sativa |
| LOC_Os02g53200.2 | Oryza sativa |
| Si017035m | Setaria italica |
| Sb02g030930.1 | Sorghum bicolor |
| LOC_Os09g36280.1 | Oryza sativa |
| Sb09g024320.1 | Sorghum bicolor |
| Si022492m | Setaria italica |
| LOC_Os05g41610.1 | Oryza sativa |
| Sb03g037270.1 | Sorghum bicolor |
| Si002065m | Setaria italica |
| LOC_Os01g58730.1 | Oryza sativa |
| Sb03g045450.1 | Sorghum bicolor |
| Sb03g045460.1 | Sorghum bicolor |
| Si002182m | Setaria italica |
| LOC_Os01g71340.1 | Oryza sativa |
| LOC_Os01g71400.1 | Oryza sativa |
| LOC_Os01g71650.1 | Oryza sativa |
| LOC_Os01g71930.1 | Oryza sativa |
| Sb08g019670.1 | Sorghum bicolor |
| Si022625m | Setaria italica |
| LOC_Os01q71410.1 | Oryza sativa |
| LOC_OsOlg51570.1 | Oryza sativa |
| LOC_Os01g71350.1 | Oryza sativa |
| Bradi2g60490.1 | Brachypodium distachyon |
| Sb03g045490.1 | Sorghum bicolor |
| Si004560m | Setaria italica |
| LOC_Os01g71380.1 | Oryza sativa |
| LOC_Os01q71670.1 | Oryza sativa |
| Sb03g045510.1 | Sorghum bicolor |
| Si003802m | Setaria italica |
| Si005124m | Setaria italica |
| LOC_Os01g71680.1 | Oryza sativa |
| Bradi2g60560.1 | Brachypodium distachyon |
| Sb03g045520.1 | Sorghum bicolor |
| Si000491m | Setaria italica |
| LOC_Os01g71690.2 | Oryza sativa |
| LOC_Os01g71690.3 | Oryza sativa |
| LOC_Os01g71810.1 | Oryza sativa |
| LOC_Os01g71820.1 | Oryza sativa |
| LOC_Os01g71830.1 | Oryza sativa |
| LOC_Os01g71860.1 | Oryza sativa |
| Sb03g045630.1 | Sorghum bicolor |
| Si002306m | Setaria italica |
| Sb09g025890.1 | Sorghum bicolor |
| Si024558m | Setaria italica |

Modified Polypeptides

In certain embodiments, licheninase polypeptides of the present disclosure are modified to reduce or inhibit the licheninase activity of the polypeptide, which when expressed in plant results in a plant with elevated levels of glucan. Licheninase polypeptide of the present disclosure may be modified to contain one or more amino acid substitutions at active site residues. For example, the polypeptide encoded by Cal-1 T01 may contain an amino acid substitution at one or both of its active site residues (e.g., Glu 262 and Glu 318). In some embodiments, a licheninase polypeptide of the present disclosure contains an amino acid substitution at a position that is analogous to position 262 of SEQ ID NO: 4, the amino acid sequence of the polypeptide encoded by Cal-1 T01 (i.e., at a position corresponding to position 262 in a homolog, ortholog, or paralog of Cal-1 T01). In other embodiments, the amino acid sequence of the polypeptide encoded by Cal-1 T01 contains an amino acid substitution at position 262. In still other embodiments, a licheninase polypeptide of the present disclosure contains an amino acid substitution at a position that is analogous to position 318 of SEQ ID NO: 4 (i.e., at a position corresponding to position 318 in a homolog, ortholog, or paralog of Cal-1 T01). In yet other embodiments, the amino acid sequence of the polypeptide encoded by Cal-1 T01 contains an amino acid substitution at position 318. In yet other embodiments, a licheninase polypeptide of the present disclosure contains an amino acid substitution at a position that is analogous to position 242 of SEQ ID NO: 8, the amino acid sequence of the polypeptide encoded by Cal-1 T02 (i.e., at a position corresponding to position 242 in a homolog, ortholog, or paralog of Cal-1 T02). In still other embodiments, the amino acid sequence of the polypeptide encoded by Cal-1 T02 contains an amino acid substitution at position 242. In further embodiments, a licheninase polypeptide of the present disclosure contains an amino acid substitution at a position that is analogous to position 298 of SEQ ID NO: 8 (i.e., at a position corresponding to position 298 in a homolog, ortholog, or paralog of Cal-1 T02). In other embodiments, the amino acid sequence of the polypeptide encoded by Cal-1 T02 contains an amino acid substitution at position 298. The amino acid substitution may be any substitution that reduces or inhibits the licheninase activity of the polypeptide. In certain preferred embodiments, the amino acid substitution is a glutamic acid (Glu) to lysine (Lys) substitution.

In other embodiments, licheninase polypeptides of the present disclosure contain one or more amino acid substitutions in regions other than the active site that reduce or inhibit the licheninase activity of the polypeptide.

In further embodiments, licheninase polypeptides of the present disclosure are modified to contain an insertion, duplication, amplification, truncation, or deletion that results in reduced or inhibited licheninase activity.

Suitable Licheninase Polynucleotides

Further aspects of the present disclosure relate to plants having elevated levels of glucan, where the elevated glucan levels are the result of at least one modified licheninase polynucleotide encoding a polypeptide having reduced licheninase activity.

Polynucleotides that encode a polypeptide are also referred to herein as "genes". Methods for determining the relationship between a polypeptide and a polynucleotide that encodes the polypeptide are well known in the art. Similarly, methods of determining the polypeptide sequence encoded by a nucleic acid sequence are well known in the art.

As used herein, the terms "polynucleotide", "nucleic acid sequence", "nucleotide sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

Suitable polynucleotides of the present disclosure that may be modified to produce plants with elevated levels of glucan include, without limitation, licheninase genes that have been mutated to have reduced expression compared to the expression of a corresponding licheninase gene that lacks such a modification, or to inhibit expression of the licheninase gene. Examples of suitable mutations include, without limitation, point mutations, nonsense mutations, truncation mutations, missense mutations, substitution mutations, frameshift mutations, loss-of-function mutations, deletion mutations, insertion mutations, duplication mutations, amplification mutations, translocation mutations, or inversion mutations. Methods of generating and identifying polynucleotide with one or more mutations are well known in the art, and include, without limitation, nucleic acid sequencing, polymerase chain reaction, and hybridization.

Other suitable polynucleotides of the present disclosure affect the expression of a licheninase gene. In some embodiments, polynucleotides that affect the expression of a licheninase gene reduce or inhibit gene expression. In other embodiments, polynucleotides that reduce or inhibit gene expression have a sequence that is identical to the sequence of the licheninase gene to be affected. In other embodiments, polynucleotides that reduce or inhibit gene expression have a sequence that is 75% or more, 80% or more, 85% or more, 90% or more, 95% or more, 96% or more, 97% or more, 98% or more, or 99% or more identical to the sequence of the licheninase gene to be affected. In other embodiments, polynucleotides that reduce or inhibit gene expression have a sequence that is identical to a fragment of the sequence of the licheninase gene to be affected. In other embodiments, polynucleotides that reduce or inhibit gene expression have a sequence that is 75% or more, 80% or more, 85% or more, 90% or more, 95% or more, 96% or more, 97% or more, 98% or more, or 99% or more identical to a fragment of the sequence of the licheninase gene to be affected. In other embodiments, polynucleotides that reduce or inhibit gene expression have a sequence that is identical to a complement of the sequence of the licheninase gene to be affected. In other embodiments, polynucleotides that reduce or inhibit gene expression have a sequence that is 75% or more, 80% or more, 85% or more, 90% or more, 95% or more, 96% or more, 97% or more, 98% or more, or 99% or more identical to a complement of the sequence of the licheninase gene to be affected. In other embodiments, polynucleotides that reduce or inhibit gene expression have a sequence that is identical to a fragment of the complement of the sequence of the licheninase gene to be affected. In other embodiments, polynucleotides that reduce or inhibit gene expression have a sequence that is 75% or more, 80% or more, 85% or more, 90% or more, 95% or more, 96% or more, 97% or more, 98% or more, or 99% or more identical to a fragment of the complement of the sequence of the licheninase gene to be affected.

Examples of suitable polynucleotides that may be modified to produce a plant with elevated levels of glucan include, without limitation, polynucleotides encoding a polypeptide containing the consensus sequence set forth in SEQ ID NO: 9.

Additionally, suitable polynucleotides that may be modified to produce plants with elevated levels of glucan include the Cal-1 T01 and Cal-1 T02 licheninase genes. The nucleic acid sequence of Cal-1 T01 is set forth in SEQ ID NO: 3 and the nucleic acid sequence of Cal-1 T02 is set forth in SEQ ID NO: 7. In certain embodiments, suitable polynucleotides contain a nucleic acid sequence that is at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 96%, at least 97%, at least 98%, at least 99%, or higher percent identity to the sequence of SEQ ID NO: 3. In other embodiments, suitable polynucleotides contain a nucleic acid sequence that is at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 98%, at least 99%, or higher percent identity to the sequence of SEQ ID NO: 7.

In further embodiments, suitable polynucleotides encode SEQ ID NO: 4 or SEQ ID NO: 8. In other embodiments, suitable polynucleotides encode polypeptides containing an amino acid sequence having at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 96%, at least 97%, at least 98%, at least 99%, or higher percent identity to the sequence of SEQ ID NO: 4. In still other embodiments, suitable polynucleotides encode polypeptides containing an amino acid sequence having at least 10%, at least 15%, at least 20%, at least 25%, at least 30%, at least 35%, at least 40%, at least 45%, 50%, at least 55%, at least 60%, at least 65%, at least 70%, at least 75%, at least 80%, at least 85%, at least 90%, at least 95%, at least 98%, at least 99%, or higher percent identity to the sequence of SEQ ID NO: 8. In further embodiments, suitable polynucleotides encode polypeptides having at least 10, at least 12, at least 14, at least 16, at least 18, at least 20, at least 21, at least 22, at least 23, at least 24, at least 25, at least 30, at least 40, at least 50, at least 60, at least 70, at least 80, at least 90, at least 100, at least 125, at least 150, at least 175, at least 200, at least 225, at least 250, at least 275, at least 300, or more consecutive amino acids of SEQ ID NOs: 4 or 8.

Other suitable polynucleotides that may be modified to produce plants with elevated levels of glucan include homologs, paralogs, and/or orthologs of the Cal-1 T01 and Cal-1 T02 licheninase genes. Methods for identifying polynucleotides that are homologs, paralogs, and/or orthologs of a polynucleotide of interest are well known to one of skill in the art, as described herein.

Examples of suitable polynucleotides that are homologous, paralogous, or orthologous to Cal-1 T01 and Cal-1 T02 include without limitation, homologous, paralogous, or orthologous polynucleotides from maize (*Zea mays*), barley (*Hordeum vulgare*), rice (*Oryza sativa*), sorghum (*Sorghum bicolor*), foxtail millet (*Setaria italica*), sugar cane (*Saccharum* spp.), wheat (*Triticum* spp.), soy (*Glysine* sp.), cotton (*Gossypium* sp.), sugar beet (*Beta vulgaris*), sunflower (*Helianthus* sp.), miscanthus (*Miscanthus* sp.), giant miscanthus (*Miscanthus giganteus*), switchgrass (*Panicum virgatum*), grass (*Poaceae* sp.), rape (*Brassica napus*), giant reed (*Arundo donax*), reed canary grass (*Phalaris arundinacea*), sericea lespedeza (*Lespedeza cuneata*), millet (*Panicum miliaceum*), ryegrass (*Lolium* sp.), timothy-grass (*Phleum* sp.), kochia (*Kochia* sp.), kenaf (*Hibiscus cannabinus*), bahiagrass (*Paspalum* sp.), bermudagrass (*Cynodon dactylon*), pangolagrass (*Digitaria decumbens*), bluestem grass (*Andropogon* sp.), indiangrass (*Sorghastrum* sp.), bromegrass (*Bromus* sp.), elephant grass (*Pennisetum purpureum*), jatropha (*Jatropha* sp.), alfalfa (*Medicago* sp.), clover (*Trifolium*), sunn hemp (*Crotalaria juncea*), fescue (*Festuca* sp.), orchard grass (*Dactylis* sp.), purple false brome (*Brachypodium distachyon*), sesame (*Sesamum indicum*), poplar (*Populus trichocarpa*), spruce (*Picea* sp.), pine (*Pinaceae* spp.), willow (*Salix* sp.), eucalyptus (*Eucalyptus* sp.), castor oil plant (*Ricinus communis*), and palm tree (*Arecaceae* sp.).

In other embodiments, suitable polynucleotides that may be modified to produce plants with elevated levels of glucan include maize polynucleotides that are homologous to Cal-1 T01 and Cal-1 T02 include. For example, suitable polynucleotides include, without limitation, the genes listed in Table 1. Other suitable polynucleotides include *Oryza sativa*, *Sorghum bicolor*, *Brachypodium distachyon* and *Setaria italica* polynucleotides that are homologous to Cal-1 T01 and Cal-1 T02. For example, suitable polynucleotides include, without limitation, the genes listed in Table 2.

Suitable polynucleotides that may be modified to produce plants with elevated levels of glucan further include fragments of polynucleotides that encode licheninase polypeptides, polynucleotides that are complementary to polynucleotides that encode licheninase polypeptides, and fragments of polynucleotides that are complementary to polynucleotides that encode licheninase polypeptides.

Mutated Polynucleotides

In certain embodiments, licheninase genes of the present disclosure are modified to reduce or inhibit the licheninase activity of the encoded polypeptide. Licheninase genes of the present disclosure may be modified to contain one or more mutations that encode licheninase polypeptides with reduced or inhibited licheninase activity. For example, Cal-1 T01 may be mutated to encode an amino acid substitution at one or both of its active site residues (i.e., Glu 262 and Glu 318). In some embodiments, a mutated polynucleotide encodes a licheninase polypeptide containing an amino acid substitution at a position that is analogous to position 262 of SEQ ID NO: 4, the amino acid sequence of the polypeptide encoded by Cal-1 T01 (i.e., at a position corresponding to position 262 in a homolog, ortholog, or paralog of Cal-1 T01). In other embodiments, a mutated polynucleotide encodes a Cal-1 T01 polypeptide containing an amino acid substitution at position 262. In still other embodiments, a mutated polynucleotide encodes a licheninase polypeptide containing an amino acid substitution at a position that is analogous to position 318 of SEQ ID NO: 4 (i.e., at a position corresponding to position 318 in a homolog, ortholog, or paralog of Cal-1 T01.

In yet other embodiments, a mutated polynucleotide encodes a Cal-1 T01 polypeptide containing an amino acid substitution at position 318. In yet other embodiments, a mutated polynucleotide encodes a licheninase polypeptide containing an amino acid substitution at a position that is analogous to position 242 of SEQ ID NO: 8, the amino acid sequence of the polypeptide encoded by Cal-1 T02 (i.e., at a position corresponding to position 242 in a homolog, ortholog, or paralog of Cal-1 T02). In still other embodiments, a mutated polynucleotide encodes a Cal-1 T02 polypeptide containing an amino acid substitution at position 242. In further embodiments, a mutated polynucleotide encodes a licheninase polypeptide containing an amino acid substitution at a position that is analogous to position 298 of SEQ ID NO: 8 (i.e., at a position corresponding to position 298 in a homolog, ortholog, or paralog of Cal-1 T02). In other embodiments, a mutated polynucleotide encodes a Cal-1 T02 polypeptide containing an amino acid substitution at position 298. The amino acid substitution may be any substitution that reduces or inhibits the licheninase activity of the encoded licheninase polypeptide. In certain preferred embodiments, the amino acid substitution is a glutamate (Glu) to lysine (Lys) substitution.

In further embodiments, the mutated polynucleotide encodes a licheninase polypeptide that contains one or more amino acid substitutions in regions other than the active site that reduce or inhibit the licheninase activity of the polypeptide. In still further embodiments, the mutated polynucleotides encode a truncated licheninase polypeptide having reduced or inhibited licheninase activity. Preferably, the truncated polypeptide lacks licheninase activity.

In yet further embodiments, the mutated polynucleotide contains a duplication, amplification, translocation, or inversion that reduces expression of the encoded polypeptide or that encodes a licheninase polypeptide that has reduced or inhibited licheninase activity. In other embodiments, the mutated polynucleotide contains a loss-of-function mutation and encodes a licheninase polypeptide that has reduced or inhibited licheninase activity.

Brown Midrib (BM) Polynucleotides

Certain embodiments of the present disclosure relate to plants exhibiting an increased saccharification yield, where the increased saccharification yield is the result of the combination of at least one modified licheninase polynucleotide encoding a polypeptide having reduced licheninase activity and at least one modified brown midrib (bm) polynucleotide encoding a polypeptide having reduced activity.

As used herein brown midrib (bm) genes are genes involved in lignin biosynthesis. Examples of bm genes include, without limitation, the maize bm1 gene, the maize bm2 gene, the maize bm3 gene, the maize bm4 gene, homologs thereof, paralogs thereof, and orthologs thereof. Generally, reduced expression of at least one bm gene results in reduced and altered lignin content.

As used herein "saccharification yield" refers to the amount of oligosaccharides and/or monosaccharides produced by the saccharification of biomass derived from a plant of the present disclosure, or part thereof. Saccharification refers to the degradation of complex carbohydrates, such as starch, cellulose, and other plant polysaccharides, into simple sugars, such as oligosaccharides and/or monosaccharides. Any method of biomass saccharification known in the art may be used.

In certain preferred embodiments, plants of the present disclosure having reduced licheninase activity further having reduced expression of at least one bm gene. Preferably, the at least one bm gene is a bm1 gene or a bm3 gene. Without wishing to be bound by theory, it is believed that the bm1 gene encodes cinnamyl alcohol dehydrogenase (CAD) and that the bm3 gene encodes caffeic acid O-methyltransferase (COMT). Advantageously, it has been surprisingly shown that when a plant having reduced expression of a licheninase gene is crossed with a plant having reduced expression of either the bm1 gene or the bm3 gene, the resulting progeny produce a significantly higher saccharification yield than either parental plant alone (FIG. 13).

Accordingly, in certain embodiments, a mutant plant having a mutation in at least one licheninase gene further contains a mutation in at least one bm1 gene or at least one bm3 gene, where the plant having such mutations exhibit an increased saccharification yield compared to the saccharification yield in a corresponding plant lacking the mutation in the at least one licheninase gene and the mutation in at least one bm1 gene or at least one bm3 gene. Methods of generating plants with mutations in at least two genes are well known in the art and include those disclosed herein. Methods for measuring saccharification are also well known in the art.

In other embodiments, a plant containing an RNAi-inducing vector, where the vector generates RNAi against a licheninase gene, further contains an additional RNAi-inducing vector where the additional vector generates RNAi against a bm1 gene or a bm3 gene, and where the plant exhibits an increased saccharification yield compared to the saccharification yield in a corresponding plant lacking the vectors generating RNAi against a licheninase genes and a bm1 gene or bm3 gene.

In other embodiments, a plant having reduced expression of at least one licheninase gene further contains reduced expression of at least one bm1 gene or at least one bm3 gene, where the plant exhibits an increased saccharification yield compared to the saccharification yield in a corresponding plant having reduced expression of the at least one licheninase gene and reduced expression of the at least one bm1 gene or bm3 gene. Any suitable method disclosed herein may be used to reduce expression of the at least one licheninase gene and the at least one bm1 gene or at least one bm3 gene.

Methods of measuring the saccharification yield of a plant are well known in the art and include those disclosed herein. In certain embodiments, the saccharification yield of a plant having reduced expression of a licheninase gene and reduced expression of a bm gene is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, or more, as compared to the saccharification yield of a corresponding plant lacking reduced expression of a licheninase gene and reduced expression of a bm gene. In certain embodiments, an increased saccharification yield results in an increased amounts of glucose.

Methods of Decreasing Gene Expression/Polypeptide Levels in a Plant

Further aspects of the present disclosure relate to producing plants with elevated levels of glucan by decreasing the expression of at least one licheninase gene in the plant. As used herein, "decreasing" the level of expression of a gene includes reducing or inhibiting the expression of a gene. The level of expression of a gene may be assessed by measuring the level of mRNA encoded by the gene, and/or by measuring the level or activity of the polypeptide encoded by the gene.

Gene expression can be decreased using any number of techniques well known in the art. For example, gene expression may by decreased by genetically modifying the genome of a plant through, for example, homologous recombination to replace the wild-type version of a gene of interest with a modified version that has reduced or inhibited expression. Methods of genetically modifying plants are well known in the art.

Another method of decreasing expression is through sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al, *The Plant Cell* 2:279-289, 1990; Flavell, *Proc. Natl. Acad. Sci, USA* 91:3490-3496, 1994; Kooter and Moi, *Current Opin. Biol.* 4:166-171, 1993; and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity can exert a more effective repression of expression of the endogenous sequences. In some embodiments, sequences with substantially greater identity are used, e.g., at least about 80%, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500, or more nucleotides.

RNAi

Endogenous gene expression may also be decreased by means of RNA interference (RNAi) (and indeed co-suppression can be considered a type of RNAi), which uses a double-stranded RNA having a sequence identical or similar to the sequence of the target gene. As used herein RNAi, includes the use of micro RNA, such as artificial miRNA to suppress expression of a gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985, 2000; Waterhouse et al, *Proc. Natl. Acad. Sci. USA* 95:13959-13964, 1998; Tabara et al. *Science* 282:430-431, 1998; Matthew, *Comp Fund Genom* 5: 240-244, 2004; Lu, et al, *Nucleic Acids Res.* 32(21):171, 2004).

Thus, in some embodiments, reduction or inhibition of gene expression is achieved using RNAi techniques. For example, to achieve reduction or inhibition of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the reduced expression of the target gene, e.g., elevated glucan, and/or by monitoring steady-state RNA levels for transcripts encoding the protein. Although the genes used for RNAi need not be completely identical to the target gene, they may be at least 70%, 80%, 90%, 91%, 92%, 93%, 94%, 95%, 96%, 97%, 98%, 99%, or more identical to the target gene sequence. See, e.g., U.S. Patent Application Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Application Publication No. 2003/0221211.

The RNAi polynucleotides may encompass the full-length target RNA or may correspond to a fragment of the target RNA. In some cases, the fragment will have fewer than 100, 200, 300, 400, or 500 nucleotides corresponding to the target sequence. In addition, in some aspects, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will correspond to regions of a target protein that do not occur in other proteins in the organism or that have little similarity to other transcripts in the organism, e.g., selected by comparison to sequences in analyzing publicly-available sequence databases. Similarly, RNAi fragments may be selected for similarity or identity with a conserved sequence of a gene family of interest, such as those described herein, so that the RNAi targets multiple different gene transcripts containing the conserved sequence.

RNAi may be introduced into a cell as part of a larger DNA construct. Often, such constructs allow stable expression of the RNAi in cells after introduction, e.g., by integration of the construct into the host genome. Thus, expression vectors that continually express RNAi in cells transfected with the vectors may be employed for this disclosure. For example, vectors that express small hairpin or stem-loop structure RNAs, or precursors to microRNA, which get processed in vivo into small RNAi molecules capable of carrying out gene-specific silencing (Brummelkamp et al, *Science* 296:550-553, 2002; and Paddison, et al., *Genes & Dev.* 16:948-958, 2002) can be used. Post-transcriptional gene silencing by double-stranded RNA is discussed in further detail by Hammond et al., *Nature Rev Gen* 2: 110-119, 2001; Fire et al., *Nature* 391: 806-811, 1998; and Timmons and Fire, *Nature* 395: 854, 1998.

Methods for selection and design of sequences that generate RNAi are well known in the art (e.g., U.S. Pat. Nos. 6,506,559; 6,511,824; and 6,489,127).

One of skill in the art will recognize that using technology based on specific nucleic acid sequences (e.g., antisense or sense suppression technology), families of homologous genes can be suppressed with a single sense or antisense, discussed below, transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variation between family members.

The term "target gene" or "target sequences", refers to a gene targeted for reduced expression. In one format, one or more different genes can be inhibited using the same interfering RNA. For example, some or all licheninase genes in a plant may be targeted by using an RNAi that is designed to a conserved region of the licheninase gene. In other aspects, an individual licheninase gene may be targeted by using an RNAi that is specific for that gene.

Antisense and Ribozyme Suppression

A reduction or inhibition of gene expression in a plant of a target gene may also be obtained by introducing into plants antisense constructs based on a target gene nucleic acid sequence. For antisense suppression, a target sequence is arranged in reverse orientation relative to the promoter sequence in the expression vector. The introduced sequence need not be a full length cDNA or gene, and need not be identical to the target cDNA or a gene found in the plant variety to be transformed. Generally, however, where the introduced sequence is of shorter length, a higher degree of homology to the native target sequence is used to achieve effective antisense suppression. In some aspects, the introduced antisense sequence in the vector will be at least 30 nucleotides in length, and improved antisense suppression will typically be observed as the length of the antisense sequence increases. In some aspects, the length of the antisense sequence in the vector will be greater than 100 nucleotides. Transcription of an antisense construct as described results in the production of RNA molecules that are the reverse complement of mRNA molecules transcribed from an endogenous target gene. Suppression of a target gene expression can also be achieved using a ribozyme. The production and use of ribozymes are disclosed in U.S. Pat. Nos. 4,987,071 and 5,543,508.

Mutagenesis

In other embodiments, mutagenesis approaches may be used to disrupt or "knockout" the expression of a target gene using either chemical or insertional mutagenesis, or irradiation. In certain embodiments, the mutagenesis results in a partial deletion of the target gene. In other embodiments, the mutagenesis results in a complete deletion of the target gene.

One method of mutagenesis and mutant identification is known as TILLING (for "Targeting Induced Local Lesions in Genomes"). In this method, mutations are induced in the seed of a plant of interest, for example, using ethane methyl sulfonate (EMS) treatment (Hoffman, *Mutation Research* 75(1): 63-129, 1980) or fast neutron bombardment (Li et al., *Plant Journal* 27(3):235-242, 2001). The resulting plants are grown and self-fertilized, and the progeny are assessed. For example, the plants may be assessed using PCR to identify whether a mutated plant has a mutation in a target gene, e.g., that reduces expression of a target gene, or by evaluating whether the plant has increased levels of cell wall glucan content in a part of the plant that expressed the target gene, such as leaf tissue. TILLING can identify mutations that may alter the expression of specific genes or the activity of proteins encoded by these genes (see, Colbert et al. *Plant Physiol* 126:480-484, 2001; McCallum et al. *Nature Biotechnology* 18:455-457, 2000).

Another method for reducing or inhibiting the expression of a target gene is by insertion mutagenesis using the T-DNA of *Agrobacterium tumefaciens*, or transposons (see Winkler et al., *Methods Mol. Biol.* 82:129-136, 1989, and Martienssen *Proc. Natl. Acad. Sci.* 95:2021-2026, 1998). After generating the insertion mutants, the mutants can be screened to identify those containing the insertion in a target gene. Mutants containing a single mutation event at the desired gene may be crossed to generate homozygous plants for the mutation (see, Koncz et al. *Methods in Arabidopsis Research*. World Scientific, 1992).

Another method to disrupt a target gene is by use of the cre-lox system (for example, as described in U.S. Pat. No. 5,658,772).

In some aspects, the disclosure includes mutation of at least one licheninase gene. Examples of genes that may be disrupted by mutagenesis include, without limitation, Cal-1 T01 (SEQ ID NO: 3), Cal-1 T02 (SEQ ID NO: 7), and homologs, paralogs, or orthologs thereof.

Plants Having Multiple Target Genes Inhibited

Expression of at least two target genes may be reduced or inhibited in a plant as described herein. As explained above, such plants can be generated by performing a molecular manipulation that targets multiple related gene targets in a plant, e.g., using an RNAi to a conserved region to inactivate all of the target genes. Such plants can also be obtained by breeding plants each having individual mutations that inactivate different target genes to obtain progeny plants that are inactivated in all of the desired target genes. For example, to obtain a maize plant in which two target genes are inactivated, one of skill can target the genes using RNAi developed to a region that is conserved in both of the maize target genes, or target the genes individually, and breed the resulting mutant plants.

Expression of Target Gene Inhibitors

Expression cassettes containing polynucleotides that encode target gene expression inhibitors, e.g., an antisense or siRNA, can be constructed using methods well known in the art. Constructs include regulatory elements, including promoters and other sequences for expression and selection of cells that express the construct. Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Examples of constitutive plant promoters which may be useful for expressing a target gene sequence include: the cauliflower mosaic virus (CaMV) 35S promoter, which confers constitutive, high-level expression in most plant tissues (see, e.g., Odd et al., *Nature* 313:810, 1985); the nopaline synthase promoter (An et al., *Plant Physiol.* 88:547, 1988); and the octopine synthase promoter (Fromm et al., *Plant Cell* 1:977, 1989).

Additional constitutive regulatory elements including those for efficient expression in monocots also are known in the art, for example, the pEmu promoter and promoters based on the rice Actin-1 5' region (Last et al., *Theor. Appl. Genet.* 81:581, 1991; Mcelroy et al., *Mol. Gen. Genet.* 231:150, 1991; and Mcelroy et al., *Plant Cell* 2:163, 1990). Chimeric regulatory elements, which combine elements from different genes, also can be useful for ectopically expressing a nucleic acid molecule encoding an IND1 polynucleotide (Comai et al., *Plant Mol. Biol.* 15:373, 1990).

Other examples of constitutive promoters include the 1'- or T-promoter derived from T-DNA of *Agrobacterium tumafaciens* (see, e.g., O'Grady, *Plant Mol. Biol.* 29:99-108, 1995); actin promoters, such as the *Arabidopsis* actin gene promoter (see, e.g., Huang, *Plant Mol. Biol.* 33:125-139, 1997); alcohol dehydrogenase (Adh) gene promoters (see, e.g., Millar, *Plant Mol. Biol.* 31:897-904, 1996); ACTI1 from *Arabidopsis* (Huang et al., *Plant Mol. Biol.* 33:125-

139, 1996), CatS from *Arabidopsis* (GenBank No. U43147, Zhong et al., *Mol. Gen. Genet.* 251:196-203, 1996), the gene encoding stearoyl-acyl carrier protein desaturase from *Brassica napus* (Genbank No. X74782, Solocombe et al., *Plant Physiol.* 104:1167-1176, 1994), GPcI from maize (GenBank No. X15596, Martinez et al., *J. Mol. Biol.* 208:551-565, 1989), Gpc2 from maize (GenBank No. U45855, Manjunath et al., *Plant Mol. Biol.* 33:97-112, 1997), and other transcription initiation regions from various plant genes known in the art. See also Holtorf *Plant Mol. Biol.* 29:637-646, 1995.

A variety of plant gene promoters that regulate gene expression in response to various environmental, hormonal, chemical, developmental signals, and in a tissue-active manner are known in the art. Examples of environmental conditions that may affect transcription by inducible promoters include anaerobic conditions, elevated temperature, drought, or the presence of light. Examples of environmental promoters include drought-inducible promoter of maize; the cold, drought, and high salt inducible promoter from potato (Kirch, *Plant Mol. Biol.* 33:897-909, 1997). Plant promoters that are inducible upon exposure to plant hormones, such as auxins, may also be employed. For example, the invention can use the auxin response elements El promoter fragment (AuxREs) in the soybean (*Glycine max* L.) (Liu, *Plant Physiol.* 115:397-407, 1997); the auxin-responsive *Arabidopsis* GST6 promoter (also responsive to salicylic acid and hydrogen peroxide) (Chen, *Plant J.* 10: 955-966, 1996); the auxin-inducible parC promoter from tobacco (Sakai, 37:906-913, 1996); a plant biotin response element (Streit, *Mol. Plant Microbe Interact.* 10:933-937, 1997); and, the promoter responsive to the stress hormone abscisic acid (Sheen, *Science* 274:1900-1902, 1996).

Plant promoters which are inducible upon exposure to chemicals reagents that can be applied to the plant, such as herbicides or antibiotics, may also be used in vectors as described herein. For example, the maize In2 2 promoter, activated by benzenesulfonamide herbicide safeners, can be used; application of different herbicide safeners induces distinct gene expression patterns, including expression in the root, hydathodes, and the shoot apical meristem. Other promoters, e.g., a tetracycline inducible promoter; a salicylic acid responsive element promoter, promoters containing copper-inducible regulatory elements; promoters containing ecdysone inducible regulatory elements; heat shock inducible promoters, a nitrate-inducible promoter, or a light-inducible promoter may also be used.

In some aspects, the plant promoter may direct expression of a polynucleotide of the disclosure in a specific tissue (tissue-specific promoters), such as a leaf or a stem. Tissue specific promoters are transcriptional control elements that are only active in particular cells or tissues at specific times during plant development, such as in vegetative tissues or reproductive tissues. Examples of tissue-specific promoters include promoters that initiate transcription primarily in certain tissues, such as vegetative tissues, e.g., roots or leaves, or reproductive tissues, such as fruit, ovules, seeds, pollen, pistols, flowers, or any embryonic tissue. Other examples are promoters that direct expression specifically to cells and tissues with secondary cell wall deposition, such as xylem and fibers.

Plant expression vectors may also include RNA processing signals that may be positioned within, upstream or downstream of the coding sequence. In addition, the expression vectors may include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g., mannose isomerase).

Once an expression cassette containing a polynucleotide encoding an inhibitor of the expression of a target gene, e.g., an antisense or siRNA, has been constructed, standard techniques may be used to introduce the polynucleotide into a plant in order to modify the target gene activity and accordingly, the levels of glucan in the plant or plant part in which the target gene is expressed. See protocols described in Ammirato et al., *Handbook of Plant Cell Culture-Crop Species.* Macmillan Publ. Co, 1984; Shimamoto et al., *Nature* 338:274-276, 1989; Fromm et al., *Bio/Technology* 8:833-839, 1990; and Vasil et al., *Bio/Technology* 8:429-434, 1990.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleic acid sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369; and 5,610,042.

Following transformation, plants are preferably selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

Sequence Homologs/Orthologs/Paralogs

As used herein, "homologs" are polypeptide or polynucleotide sequences that share a significant degree of sequence identity or similarity. Sequences that are homologs are referred to as being "homologous" to each other. Homologs include sequences that are orthologs or paralogs.

As used herein, "orthologs" are evolutionarily related polypeptide or polynucleotide sequences in different species that have similar sequences and functions, and that develop through a speciation event. Sequences that are orthologs are referred to as being "orthologous" to each other.

As used herein, "paralogs" are evolutionarily related polypeptide or polynucleotide sequences in the same organism that have similar sequences and functions, and that develop through a gene duplication event. Sequences that are paralogs are referred to as being "paralogous" to each other.

Methods of Identification of Homologous Sequences/Sequence Identity and Similarity Several different methods are known to those of skill in the art for identifying homologous sequences, including phylogenetic methods, sequence similarity analysis, and hybridization methods.

Phylogenetic Methods

Phylogenetic trees may be created for a gene family by using a program such as CLUSTAL (Thompson et al. *Nucleic Acids Res.* 22: 4673-4680, 1994; Higgins et al. *Methods Enzymol* 266: 383-402, 1996) or MEGA (Tamura et al. *Mol. Biol. & Evo.* 24:1596-1599, 2007). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou & Nei, *Mol. Biol. & Evo.* 4:406-425, 1987). Homologous sequences may also be identified by a reciprocal BLAST® alignment tool strategy. Evolutionary distances may be computed using the Poisson correction method (Zuckerkandl & Pauling, pp. 97-166 in *Evolving Genes and Proteins*, edited by V. Bryson and H. J. Vogel. Academic Press, New York, 1965).

In addition, evolutionary information may be used to predict gene function. Functional predictions of genes can be greatly improved by focusing on how genes became similar in sequence (i.e., by evolutionary processes) rather than on the sequence similarity itself (Eisen, *Genome Res.* 8: 163-167, 1998). Many specific examples exist in which gene function has been shown to correlate well with gene phylogeny (Eisen, *Genome Res.* 8: 163-167, 1998). By using a phylogenetic analysis, one skilled in the art would recognize that the ability to deduce similar functions conferred by closely-related polypeptides is predictable.

When a group of related sequences are analyzed using a phylogenetic program such as CLUSTAL, closely related sequences typically cluster together or in the same clade (a group of similar genes). Groups of similar genes can also be identified with pair-wise BLAST® alignment tool analysis (Feng and Doolittle, *J. Mol. Evol.* 25: 351-360, 1987). Analysis of groups of similar genes with similar function that fall within one clade can yield sub-sequences that are particular to the clade. These sub-sequences, known as consensus sequences, can be used not only to define the sequences within each clade, but to define the functions of these genes; genes within a clade may contain paralogous sequences, or orthologous sequences that share the same function (see also, for example, *Mount, Bioinformatics: Sequence and Genome Analysis*, p. 543. Cold Spring Harbor Laboratory Press, Cold Spring Harbor, N.Y., 2001).

To find sequences that are homologous to a reference sequence, BLAST® alignment tool nucleotide searches can be performed with the BLASTN® alignment tool program, score=100, wordlength=12, to obtain nucleotide sequences homologous to a nucleotide sequence encoding a protein of the disclosure. BLAST alignment tool protein searches can be performed with the BLASTX® alignment tool program, score=50, wordlength=3, to obtain amino acid sequences homologous to a protein or polypeptide of the disclosure. To obtain gapped alignments for comparison purposes, Gapped BLAST® alignment tool (in BLAST 2.0® alignment tool) can be utilized as described in Altschul et al. (Nucleic Acids Res. 25:3389, 1997). Alternatively, PSI-BLAST® alignment tool (in BLAST 2.0® alignment tool) can be used to perform an iterated search that detects distant relationships between molecules. See Altschul et al. (1997) supra. When utilizing BLAST® alignment tool, Gapped BLAST® alignment tool, or PSI-BLAST® alignment tool, the default parameters of the respective programs (e.g., BLASTN® alignment tool for nucleotide sequences, BLASTX® alignment tool for proteins) can be used.

Sequence Alignment/Sequence Similarity and Identity Analysis

Methods for the alignment of sequences and for the analysis of similarity and identity of polypeptide and polynucleotide sequences are well known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g., charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Non-limiting examples of such mathematical algorithms include the algorithm of Myers and Miller, *CABIOS* 4:11-17 (1988); the local homology algorithm of Smith et al., *Adv. Appl. Math.* 2:482 (1981); the homology alignment algorithm of Needleman and Wunsch, *J. Mol. Biol.* 48:443-453 (1970); the search-for-similarity-method of Pearson and Lipman, *Proc. Natl. Acad. Sci.* 85:2444-2448 (1988); the algorithm of Karlin and Altschul, *Proc. Natl. Acad. Sci. USA* 87:2264-2268 (1990), modified as in Karlin and Altschul, *Proc. Natl. Acad. Sci. USA* 90:5873-5877 (1993).

Computer implementations of these mathematical algorithms can be utilized for comparison of sequences to determine sequence identity and/or similarity. Such implementations include, but are not limited to: CLUSTAL in the PC/Gene program (available from Intelligenetics, Mountain View, Calif.); the AlignX program, version10.3.0 (Invitrogen, Carlsbad, Calif.); and GAP, BESTFIT, BLAST® alignment tool, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. *Gene* 73:237-244 (1988); Higgins et al. *CABIOS* 5:151-153 (1989); Corpet et al. *Nucleic Acids Res.* 16:10881-90 (1988); Huang et al. *CABIOS* 8:155-65 (1992); and Pearson et al. *Meth. Mol. Biol.* 24:307-331 (1994). The BLAST® alignment tool programs of Altschul et al. *J. Mol. Biol.* 215:403-410 (1990) are based on the algorithm of Karlin and Altschul (1990) supra.

Hybridization Methods

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., *Molecular Cloning: A Laboratory Manual*, 2nd Ed., Vol. 1-3, Cold Spring Harbor Laboratory, Cold Spring Harbor, N.Y., 1989 ("Sambrook"); Berger and Kimmel, *Guide to Molecular Cloning Techniques, Methods in Enzymology*, vol. 152 Academic Press, Inc., San Diego, Calif., 1987 ("Berger and Kimmel"); and Anderson and Young, "Quantitative Filter Hybridisation." In: Hames and Higgins, ed., *Nucleic Acid Hybridisation, A Practical Approach*. Oxford, TRL Press, 73-111, 1985).

Encompassed by the disclosure are nucleic acid sequences that are capable of hybridizing to the disclosed nucleic acid sequences, including any polynucleotide within the Sequence Listing, and fragments thereof under various conditions of stringency (see, for example, Wahl and Berger, *Methods Enzymol*. 152: 399-407, 1987; and Kimmel, *Methods Enzymo*. 152: 507-511, 1987). In addition to the nucleotide sequences in the Sequence Listing, full length cDNA, homologs, orthologs, and paralogs of the present nucleotide sequences may be identified and isolated using well-known polynucleotide hybridization methods.

With regard to hybridization, conditions that are highly stringent, and means for achieving them, are well known in the art. See, for example, Sambrook et al. (1989) (supra); Berger and Kimmel (1987) pp. 467-469 (supra); and Anderson and Young (1985)(supra).

Hybridization experiments are generally conducted in a buffer of pH between 6.8 to 7.4, although the rate of hybridization is nearly independent of pH at ionic strengths likely to be used in the hybridization buffer (Anderson and Young (1985) (supra)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency. As a general guideline, high stringency is typically performed at $T_m$-5° C. to $T_m$20° C., moderate stringency at $T_m$-20° C. to $T_m$-35° C. and low stringency at $T_m$-35° C. to $T_m$-50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH.

Hybridization and wash conditions that may be used to bind and remove polynucleotides with less than the desired homology to the nucleic acid sequences or their complements that encode the present transcription factors include, for example: 6×SSC and 1% SDS at 65° C.; 50% formamide, 4×SSC at 42° C.; 0.5×SSC to 2.0×SSC, 0.1% SDS at 50° C. to 65° C.; or 0.1×SSC to 2×SSC, 0.1% SDS at 50° C.-65° C.; with a first wash step of, for example, 10 minutes at about 42° C. with about 20% (v/v) formamide in 0.1× SSC, and with, for example, a subsequent wash step with 0.2×SSC and 0.1% SDS at 65° C. for 10, 20 or 30 minutes.

For identification of less closely related homologs, wash steps may be performed at a lower temperature, e.g., 50° C. An example of a low stringency wash step employs a solution and conditions of at least 25° C. in 30 mM NaCl, 3 mM trisodium citrate, and 0.1% SDS over 30 mM Greater stringency may be obtained at 42° C. in 15 mM NaCl, with 1.5 mM trisodium citrate, and 0.1% SDS over 30 mM Wash procedures will generally employ at least two final wash steps. Additional variations on these conditions will be readily apparent to those skilled in the art (see, for example, U.S. Patent Application Publication No. 2001/0010913).

If desired, one may employ wash steps of even greater stringency, including conditions of 65° C.-68° C. in a solution of 15 mM NaCl, 1.5 mM trisodium citrate, and 0.1% SDS, or about 0.2×SSC, 0.1% SDS at 65° C. and washing twice, each wash step of 10, 20 or 30 mM in duration, or about 0.1×SSC, 0.1% SDS at 65° C. and washing twice for 10, 20 or 30 mM Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C.

Polynucleotide probes may be prepared with any suitable label, including a fluorescent label, a colorimetric label, a radioactive label, or the like. Labeled hybridization probes for detecting related nucleic acid sequences may be produced, for example, by oligolabeling, nick translation, end-labeling, or PCR amplification using a labeled nucleotide.

Methods of Producing Plants with Elevated Levels of Glucan

Methods for producing a plant with elevated levels of glucan are described herein. In some aspects, plants having elevated levels of glucan may be produced by inducing one or more mutations in one or more licheninase genes, or by reducing the gene expression of one or more licheninase genes. Additionally, plants having elevated levels of glucan may be produced by reducing the expression of one or more polypeptides encoded by one or more licheninase genes. In other embodiments, plants having elevated levels of glucan may are produced by reducing the gene expression in a plant of one or more licheninase genes that are homologous, paralogous, or orthologous to the licheninase genes having the nucleic acid sequences of SEQ ID NOs: 3 and 7.

Moreover, plants having elevated levels of glucan may be produced by reducing the expression in a plant of one or more polypeptides encoded by one or more licheninase genes that are homologous, paralogous, or orthologous to the licheninase genes having the nucleic acid sequences of SEQ ID NOs: 3 and 7. Methods for determining sequences homologous, paralogous, or orthologous to a sequence of interest are provided herein. Expression of a target gene or polypeptide may be reduced by any method provided herein for decreasing gene and/or polypeptide expression.

Methods of Evaluating Plants with Elevated Levels of Glucan

After a plant has been altered to potentially elevate the levels of glucan, one or more parts of the plants may be evaluated to determine the level of one or more target gene expression in a part of the plant that expresses the target gene(s), e.g., by evaluating the level of mRNA or protein of the target gene(s), or determining the levels of glucan in the plants. These analyses can be performed using any number of methods known in the art.

Levels of glucan can be measured. For example, cell walls are prepared from plant material. Several methods are known, in the simplest method, the plant material is ground and extracted repeatedly with 96% and 70% ethanol. The resulting 'alcohol insoluble residue' is highly enriched in cell wall material. The sample is dried and resuspended in buffer at neutral pH. An aliquot of the sample is destarched by treatment with 50 µg/1 mL alpha-amylase at 80° C. for 20 min. Following destarching of cell wall material, the matrix polysaccharide composition is determined by acid hydrolysis with 2 M trifluoroacetic acid. The polysaccharide content of acid hydrolysis treated destarched cell wall material can be determined in several different ways, e.g. by gas chromatography or HPLC on an appropriate column, or mass spectrometry.

Plants selected for elevated levels of glucan may further be evaluated to further confirm that the plants provide for improved yield during a saccharification or fermentation process using material from the plant. For example, plant material from a plant with elevated levels of glucan can be compared to plant material from plants that that do not have elevated levels of glucan in a saccharification and/or fermentation process as described below.

Methods of Saccharification Biomass/Making Fermentation Product

Plants that exhibit elevated levels of glucan can be used in a variety of methods. In some embodiments, biomass from plants having elevated levels of glucan is degraded into oligosaccharides and/or monosaccharides. In some embodiments, biomass from plants having elevated levels of glucan is degraded into oligosaccharides and/or monosaccharides, and the oligosaccharides and/or monosaccharides are fermented to produce a biofuel and/or commodity chemical.

Examples of biofuels and/or commodity chemicals include, without limitation, hydrocarbons, such as methane, ethane, ethane, ethyne, propane, propene, propyne, cyclopropane, allene, butane, isobutene, butane, butyne, cyclobutane, methylcyclopropane, butadiene, pentane, isopentane, neopentane, pentene, pentyne, cyclopentane, methylcyclobutane, ethylcyclopropane, pentadiene, isoprene, hexane, hexane, hexyne, cyclohexane, methylcyclopentane, ethylcyclobutane, propylcyclopropane, hexadiene, heptane, heptene, heptyne, cycloheptane, methylcyclohexane. heptadiene, octane, octane, octyne, cyclooctane, octadiene, nonane, nonene, nonyne, cyclononane, nonadiene, decane, decene, decyne, cyclodecane, and decadiene; hydrocarbon derivatives, such as alcohols (e.g., arabinitol, butanol, ethanol, glycerol, methanol, 1,3-propanediol, sorbitol, and xylitol), organic acids (e.g., acetic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid), esters, ketones (e.g., acetone), aldehydes (e.g., furfural), amino acids (e.g., aspartic acid, glutamic acid, glycine, lysine, serine, and threonine), and gases (e.g., carbon dioxide and carbon monoxide); and lipids.

Plant material from a plant having elevated levels of glucan may be subjected to a saccharification procedure. A first step in a saccharification of biomass process is typically a "pretreatment" step. Many different pretreatment procedures may be used and are known in the art, including dilute acid or alkali treatment, steam explosion or ionic liquid treatments. As the beneficial effect of elevated levels of glucan will differ depending on the exact procedure used, several different pretreatment methods can be evaluated. For example, a dilute acid treatment method can be used. The pretreated plant material may then be subjected to enzymatic hydrolysis using a mixture of cell wall degrading enzymes.

Procedures for cell wall pretreatment and enzymatic digestion are well known to those skilled in the art. The yield or efficiency of the procedure can be readily determined by measuring the amount of reducing sugar released, using a standard method for sugar detection, e.g., the dinitrosalicylic acid method well known in the art. Plants engineered in accordance with the disclosure to have elevated levels of glucan provide a higher sugar yield.

Plants having elevated levels of glucan may also be evaluated in comparison to non-modified plants to test for the effect of elevated levels of glucan on subsequent fermentation. For example, degraded biomass may be subjected to fermentation using an organism such as yeast or *E. coli* that can convert the biomass into compounds such as ethanol, butanol, hydrocarbons, lipids, etc. In the simplest test, the yield of ethanol obtained with a given amount of starting plant material and a standard yeast fermentation can be determined. Yield can be determined not only with organisms that can ferment glucose, but also with organisms that have the ability to ferment pentoses and or other sugars derived from the biomass. In addition to determining the yield of product, e.g., ethanol, one can determine the growth rate of the organism. The plants of the disclosure that are engineered to have reduced expression in one or more licheninase genes will exhibit elevated levels of glucan in comparison to corresponding plants that have not been engineered to have reduced expression in one or more licheninase genes. The reduced expression in one or more licheninase genes may result in higher final yields of a fermentation reaction.

Plants having elevated levels of glucan can be used in a variety of reactions, including fermentation reactions. Such reactions are well known in the art. For example, fermentation reactions noted above, e.g., a yeast or bacterial fermentation reaction, may employ plant material derived from a plant having elevated levels of glucan, to obtain ethanol, butanol, hydrocarbons, lipids, and the like. For example the plants with elevated levels of glucan may be used in industrial bioprocessing reactions that include fermentative bacteria, yeast, or filamentous fungi, such as *Corynebacterium* spp., *Brevibacterium* spp., *Rhodococcus* spp., *Azotobacter* spp., *Citrobacter* spp., *Enterobacter* spp., *Clostridium* spp., *Klebsiella* spp., *Salmonella* spp., *Lactobacillus* spp., *Aspergillus* spp., *Saccharomyces* spp.,

*Zygosaccharomyces* spp., *Pichia* spp., *Kluyveromyces* spp., *Candida* spp., *Hansenula* spp., *Dunaliella* spp., *Debaryomyces* spp., *Mucor* spp., *Torulopsis* spp., *Methylobacteria* spp., *Bacillus* spp., *Escherichia* spp., *Pseudomonas* spp., *Serratia* spp., *Rhizobium* spp., and *Streptomyces* spp., *Zymomonas mobilis*, acetic acid bacteria (family Acetobacteraceae), methylotrophic bacteria, *Propionibacterium*, *Acetobacter*, *Arthrobacter*, *Ralstonia*, *Gluconobacter*, *Propionibacterium*, and *Rhodococcus*.

EXAMPLES

The following Examples are merely illustrative and are not meant to limit any aspects of the present disclosure in any way.

Example 1: Generation and Characterization of "Candy-Leaf-1" (Cal-1) Maize Mutant Introduction Lignocellulosic plant materials are considered valuable feedstocks for the biorefinery industry, in particular for the production of biofuels such as ethanol. One way to unlock the energy in lignocellulosic feedstocks is to degrade the material to its monosaccharides, which can then be fermented by microbes to ethanol. The dominant sugar currently preferentially fermented by microbes is glucose. Accordingly, a mutational breeding screen was performed to identify a mutant plant that contains elevated levels of glucan in its lignocellulosic material, and to further identify the gene(s) responsible for the phenotype.

Candy-leaf-1 (Cal-1) is a non-transgenic maize mutant whose stover material contains elevated levels of glucan and which, under standard saccharification conditions, has an elevated glucose yield.

Cal-1 contains a point mutation in a licheninase gene ((1,3; 1,4)-β-glucanase; Glycosylhydrolase family 17; genetic locus in maize: Chr. 6: GRMZM2G137535) that encodes a glutamic acid to a lysine substitution (FIG. 1). Since the glutamic acid is an active site residue, this particular licheninase is inactive. The loss of licheninase activity from this gene results in elevated levels of β-glucanan, which in turn results in higher saccharification yields.

Due to a higher glucan content in its lignocellulosic material (e.g., corn stover), the Cal-1 mutant gives a higher yield in biofuel output, and is thus suitable for use as a feedstock.

EMS Mutagenesis of Maize

Maize, A619 plants were grown in the field in Missouri and pollen was collected. The pollen was sifted to remove any anthers and added to a solution of 0.09% EMS well-dispersed in paraffin oil. The pollen mixed with the EMS for 45 minutes and then was applied to the silks of A619 plants using a paint brush. Resulting kernels were sent to the USDA in Albany and planted in Gill Tract. The plants were selfed. 20 kernels per ear were grown in trays in the greenhouse and tissue was collected from approximately 2 week old seedlings to send to for analysis. The Cal-1 mutant was identified as having high glucose and grown to maturity and crossed with the inbred Mo17 maize line. The resulting crosses were planted and self-pollinations were made. Kernels from those self-pollinations were grown in the greenhouse again, and 2 week seedlings were again harvested for analysis.

Analytical Method for Identifying Cal-1 Mutant from a Chemically Mutagenized Maize Seed Population Selection of mutant lines, including the Cal-1 line, was based on analyzing alterations in matrix polysaccharide monosaccharide composition (Foster C E, et al., Comprehensive Compositional Analysis of Plant Cell Walls (Lignocellulosic biomass) Part II: Carbohydrates. *JoVE*, 37, 2010). The analysis of matrix polysaccharide composition was performed on whole leaf material from 14-day old seedlings, which were freeze-dried after harvest. Analysis of the freeze-dried samples consisted of preparing destarched cell wall material and identifying and quantifying the matrix polysaccharide composition of each mutant maize line.

Mapping of Mutation

The underlying mutation was mapped to a region of maize chromosome 6 that spans an interval of 140.31 to 144.16 Mbp (GRMZM2G137535). Classical mapping procedures were used to identify this region (Neuffer, M G, Mutation induction in maize. In W F Sheridan, ed, *Maize for Biological Research*. Plant Mol. Biol. Assoc., Charlottesville, Va., pp 61-64, 1982; and Neuffer, M G, Mutagenesis. In M Freeling, V Walbot, eds, *The Maize Handbook*. Springer-Verlag, New York, pp 212-219, 1993). Putative proteins encoded in this region were manually annotated by comparison to homologous proteins in rice. From among these putative proteins, the Cal-1 gene was identified as the mutation. The Cal-1 gene encodes a CH17 licheninase. The GRMZM2G137535 region contains two gene models, which were named Cal-1 T01 and Cal-1 T02. The genomic sequences of Cal-1 T01 and Cal-1 T02 are set forth in SEQ ID NOs: 1 and 5, respectively. Additionally, FIG. 1 shows protein models of the polypeptides encoded by Cal-1 T01 and Cal-1 T02.

The GRMZM2G137535 region containing the Cal-1 mutation was amplified and sequenced to identify the Cal-1 mutation. Briefly, the GRMZM2G137535 region containing the Cal-1 mutation was amplified by PCR in multiple segments. The segment carrying the mutation was produced using the forward primer 5'-ACG-TGC-TGT-CCA-ACA-TCG-3' (SEQ ID NO: 10) and the reverse primer 5'-AGG-TGA-TGA-GTC-AGC-CCT-AGC-3' (SEQ ID NO: 11). The PCR was performed using a primer concentration of 40 pmol for each primer in a total volume of 50 µl with Sigma REDTag Ready mix (Sigma-Aldrich). The reaction conditions consisted of an initial 2 min denaturing step at 94° C., followed by 35 cycles of denaturing, annealing and amplification at 94° C. for 30 s, 58° C. for 30 s, and 72° C. for two min respectively. After completion of the last cycle, the reaction was left at 72° C. for an additional 15 min before being cooled to 4° C. The PCR product was then purified using the QIAquick PCR purification kit (Qiagen). The mutation was identified by sequencing the purified PCR product using the primers 5'-ACG-TGC-TGT-CCA-ACA-TCG-3' (SEQ ID NO: 10) and 5'-ACC-AGA-ACC-TCT-TCG-ACA-CCA-3' (SEQ ID NO: 12) in independent sequencing reactions. The results of this analysis are described below.

The nucleotide and amino acid sequences of Cal-1 T01 from the Cal-1 mutant are shown in FIGS. 2A and 2B, respectively. The nucleotide and amino acid sequences of Cal-1 T01 from wild-type A619 maize is shown in FIGS. 2C and 2D, respectively. A comparison of the two sequences shows that the Cal-1 mutant contains a "g" to "a" point mutation in the nucleic acid sequence of Cal-1 T01, corresponding to a Glu to Lys substitution at position 262 of the amino acid sequence.

The nucleotide and amino acid sequences of Cal-1 T02 from the Cal-1 mutant are shown in FIGS. 3A and 3B, respectively. The nucleotide and amino acid sequences of Cal-1 T02 from wild-type A619 maize is shown in FIGS. 3C and 3D, respectively. A comparison of the two sequences shows that the that the Cal-1 mutant contains a "g" to "a" point mutation in the nucleic acid sequence of Cal-1 T02, corresponding to a Glu to Lys substitution at position 242 of the amino acid sequence.

Sequence Alignment

FIG. 4 shows an amino acid sequence alignment of Cal-1 T01 with the GRMZM2G137535 P01 licheninase from the maize database, the Cal-1 T01 licheninase from A619 maize; and a barley licheninase, whose activity and active sites have been determined. The consensus sequence is also included. The sequence alignment showed that the maize Cal-1 T01 licheninase sequence has 78% identity and 99.7% similarity with the barley licheninase.

FIG. 5 shows an amino acid sequence alignment of Cal-1 T02 with the GRMZM2G137535 P02 licheninase from the maize database, the Cal-1 T02 licheninase from A619 maize; and a barley licheninase, whose activity and active sites have been determined. The consensus sequence is also included. The sequence alignment showed that the maize Cal-1 T02 licheninase sequence has 82.3% identity and 99.7% similarity with the barley licheninase.

Example 2: Characterization of Cal-1 Maize Mutant

Materials and Methods

Destarched Cell Wall Material Preparation

The destarched cell wall material preparation was initiated by grinding approximately 60-70 mg of the freeze-dried maize leaf material (Foster C E, et al., Comprehensive Compositional Analysis of Plant Cell Walls (Lignocellulosic biomass) Part II: Carbohydrates. *JoVE*, 37, 2010). The freeze-dried maize leaf material was ground with 5.5 mm stainless steel balls in a 2 ml screw cap centrifugation tube using a retschmill for 1 min at 25 Hz. The steel balls were removed before continuing with the cell wall isolation procedure.

After grinding the plant material, 1.5 ml of 70% aqueous ethanol was added, and the mixture was vortexed thoroughly. Then, the mixture was centrifuged at 10,000 rpm for 10 min to pellet the alcohol-insoluble residue.

The supernatant was then either aspirated or decanted, and the pellet was washed with 1.5 ml of a chloroform/methanol (1:1 v/v) solution. The tube was shaken thoroughly to resuspend the pellet. The resuspended pellet was then centrifuged at 10,000 rpm for 10 min and the supernatant was aspirated or decanted. The pellet was then resuspended in 500 µl of acetone. The acetone solvent was then evaporated with a stream of air at 35° C. until dry. If needed, dried samples were stored at room-temperature until further processing.

Following the acetone wash, samples were treated with alpha-amylase to remove starch (Foster C E, et al., Comprehensive Compositional Analysis of Plant Cell Walls (Lignocellulosic biomass) Part II: Carbohydrates. *JoVE*, 37, 2010). To initiate the starch removal, the pellets were resuspended in 1.5 ml of a 0.1 M sodium acetate buffer at pH 5.0. The centrifugation tubes were then capped and heated for 20 min at 80° C. in a heating block. After heat incubation, the tubes were cooled on ice.

After cooling, the following agents were added to digest the pellets: 35 µl of 0.01% sodium azide ($NaN_3$), 35 µl amylase (50 µg/1 mL $H_2O$; from *Bacillus* species, SIGMA), and 17 µl pullulanase (18.7 units from *Bacillus acidopullu-lyticus*; SIGMA). The tubes were then capped and vortexed thoroughly. The pellet suspensions were then incubated overnight at 37° C. in a shaker. The tubes were oriented horizontally to improve mixing.

After incubation, the pellet suspensions were heated at 100° C. for 10 min in a heating block to terminate digestion. The suspensions were then centrifuged at 10,000 rpm for 10 min, and supernatants containing solubilized starch were discarded.

The remaining pellets were washed three times by adding 1.5 ml water, vortexing, centrifuging, and decanting the water.

After the washes, the pellets were resuspended in 500 µl of acetone. The acetone was evaporated with a stream of air at 35° C. until dry. It was sometimes also necessary to break up the material in the tube with a spatula for better drying.

Dried samples were then stored at room-temperature until further processing.

Cell Wall Polysaccharide Composition

Following preparation of the destarched cell wall material, the cell wall polysaccharide composition of each mutant maize line was determined (Foster C E, et al., Comprehensive Compositional Analysis of Plant Cell Walls (Lignocellulosic biomass) Part II: Carbohydrates. *JoVE*, 37, 2010).

First, 2 mg of cell wall material was weighed into 2 ml centrifugation tubes. Then, 20 µl of an inositol solution (5 mg/ml) was added as an internal standard. Following addition of the inositol solution, the tube walls were rinsed with 250 µl of acetone to collect the cell wall material on the bottom of the tube, and then the acetone was evaporated under very gentle airflow.

Acid hydrolysis of the cell wall polysaccharides was then performed (Foster C E, et al., Comprehensive Compositional Analysis of Plant Cell Walls (Lignocellulosic biomass) Part II: Carbohydrates. *JoVE*, 37, 2010). For the acid hydrolysis, 250 µl of 2 M trifluoroacetic acid (TFA) was added to each sample. The TFA was added carefully to ensure that no material was splashed up onto the tube walls.

The tubes containing the samples with the TFA were capped and incubated for 90 min at 121° C. in a heating block. After incubation, the heating blocks containing the sample tubes were cooled on ice. Then, the tubes were centrifuged at 10,000 rpm for 10 min.

After centrifugation, 100 µl of acidic supernatant containing the cell wall polysaccharide-derived monosaccharide from each tube was transferred to a glass screw cap vial, making sure that the pellet material was not disturbed. The TFA in the glass tube was then evaporated under a gentle stream of air in an evaporation device.

Then, 300 µl of 2-propanol was added to each sample, vortexed, and evaporated at 25° C. This procedure was repeated a total of three times.

Following acid hydrolysis, the released monosaccharides were derivatized into their alditol acetates (Foster C E, et al., Comprehensive Compositional Analysis of Plant Cell Walls (Lignocellulosic biomass) Part II: Carbohydrates. *JoVE*, 37, 2010). First, the monosaccharides were reduced to their corresponding alditols. To accomplish this, 200 µl of a freshly prepared sodium borohydride solution was added to each dried sample. The samples were then incubated in the glass vials at room temperature for 1.5 hours. After the incubation, the solution was neutralized by adding 150 µl of glacial acetic acid, vortexing the tubes, and evaporating the glacial acetic acid at 25° C.

Then, 250 µl of an acetic acid/methanol (1:9, v/v) mixture was added to each sample, vortexed, and evaporated at 25° C. and followed by adding 250 µl of methanol and evaporating it under a stream of air. The methanol wash was repeated a total of three times.

Next, the alditols in each sample were acetylated (Foster C E, et al., Comprehensive Compositional Analysis of Plant Cell Walls (Lignocellulosic biomass) Part II: Carbohydrates. JoVE, 37, 2010). The acetylation was performed by adding 50 µl of acetic anhydride and 50 µl of pyridine. Then the samples were vortexed and incubating for 20 min at 121° C. in a heating block. The samples were then cooled in the block with ice until the temperature decreased to approximately room temperature. The reagents were then evaporated under a gentle stream of air at room temperature. The samples were then washed three times with toluene by adding 200 µl of toluene and evaporating under air.

The final part of the procedure was to extract the alditol acetates (Foster C E, et al., Comprehensive Compositional Analysis of Plant Cell Walls (Lignocellulosic biomass) Part II: Carbohydrates. JoVE, 37, 2010). To accomplish the extraction, 500 µl of ethyl acetate were first added to each sample, and the tubes were swirled lightly. Then, 2 ml of water were added. The tubes were then capped and vortexed. This was followed by centrifuging the tubes at 2,000 rpm for 5 min to obtain clear separate layers, which included ethyl acetate on top and water on bottom.

After centrifugation, 50 µl of the ethyl acetate layer were pipetted into GC/MS (gas chromatography/mass spectrometry) vials with inserts (Foster C E, et al., Comprehensive Compositional Analysis of Plant Cell Walls (Lignocellulosic biomass) Part II: Carbohydrates. JoVE, 37, 2010). The samples were then diluted by adding 100 µl of acetone to the GC/MS vials. The vials were then capped and stored at 4° C. when the GC/MS analysis was not immediately performed.

Gas Chromatography/Mass Spectrometry Analysis

For gas chromatography analysis, the samples were injected into a gas chromatograph (GC) that was equipped with a quadrupole mass spectrometer (MS). A Supelco SP-2380 (30 mm×0.25 mm×0.25 µm film thickness) column was used with a 4 min solvent delay and a flow rate of 1.5 ml/min (Foster C E, et al., Comprehensive Compositional Analysis of Plant Cell Walls (Lignocellulosic biomass) Part II: Carbohydrates. JoVE, 37, 2010).

The injected samples were subjected to the following temperature program: initial hold at 160° C. for 2 min; a 20° C./min ramp to 200° C. and hold for 5 min; a 20° C./min ramp to 245° C. and hold 12 min; spike to 270° C. and hold for 5 min before cooling to the initial temperature of 160° C. (Foster C E, et al., Comprehensive Compositional Analysis of Plant Cell Walls (Lignocellulosic biomass) Part II: Carbohydrates. JoVE, 37, 2010).

Peaks were then identified by mass profiles and/or retention times of standards. Monosaccharides were quantified based on standard curves (Foster C E, et al., Comprehensive Compositional Analysis of Plant Cell Walls (Lignocellulosic biomass) Part II: Carbohydrates. JoVE, 37, 2010).

Results

Cell Wall Polysaccharide Composition

Figure 6:
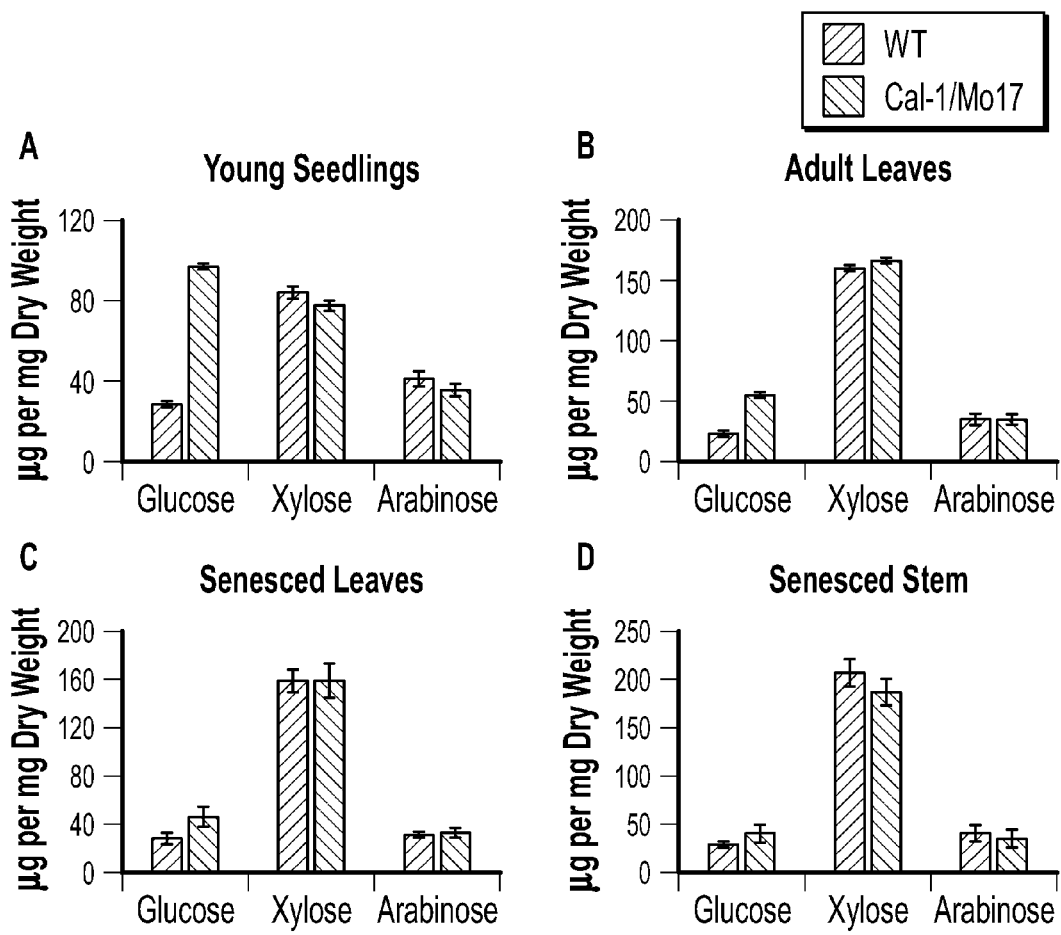
FIG. 6A diagrammatically depicts the amount of monosaccharides by weight of the hemicellulosic fraction, produced by young Cal-1 maize mutant seedlings.
FIG. 6B diagrammatically depicts the amount of monosaccharides by weight of the hemicellulosic fraction, produced by adult Cal-1 maize mutant leaves.
FIG. 6C diagrammatically depicts the amount of monosaccharides by weight of the hemicellulosic fraction, produced by senesced leaf material.
FIG. 6D diagrammatically depicts the amount of monosaccharides by weight of the hemicellulosic fraction, produced by senesced stem material.
Figure 7:
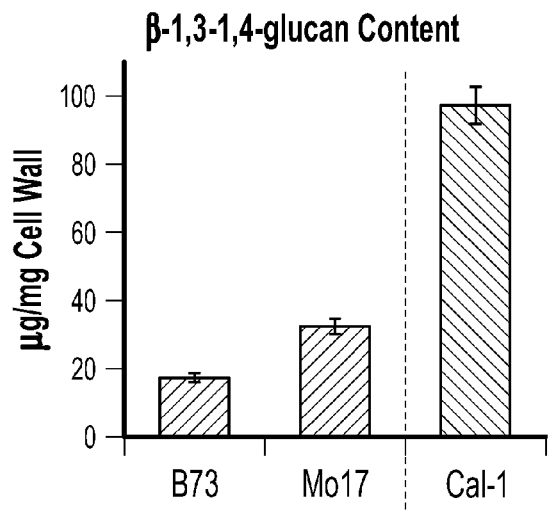
FIG. 7 diagrammatically depicts the cell wall β-1,3-1,4-glucan content of the Cal-1 maize mutant.

The Cal-1 maize mutant was characterized by comparing the hemicellulosic levels of glucan to wildtype maize ('Mo17'). The levels of glucan were determined by measuring the amount of glucose released by the glucan. Analysis was performed on two-week old (young seedling) and eleven-week old leaf material (adult leaves), as well as senesced leaf and stem material (FIG. 6). In all tissues, the Cal-1 mutant showed an increase of glucose released by weak acid hydrolysis (FIG. 6). Additionally, the Cal-1 mutant was shown to have approximately four-fold higher amounts of $\beta$-1,3-1,4-glucan content than the wildtype maize lines 'Mo17' and 'B73' (FIG. 7).

Further analysis of the elevated levels of glucan was also performed. An extraction of cell wall material from mature leaves of the Cal-1 mutant indicated that the elevated levels of glucan, as measured by the amount of released glucose, was found in a 4M potassium hydroxide fraction (FIG. 8A), indicating that the glucan is of hemicellulosic nature rather than cellulosic. Glycosidic linkage analysis of the 4M potassium hydroxide fraction indicated that the increased glucan content included a mixed-linked $\beta$-1,3-1,4-glucan, which is a grass-specific, transient hemicellulosic polymer (FIG. 8B).

The remaining residue, after 4M potassium hydroxide extraction of the leaf material, represented mainly crystalline cellulose. This was confirmed by monosaccharide composition analysis, which showed that glucose was the predominant component (FIG. 9A). Levels of cellulose in adult leaf material from the Cal-1 mutant were also compared with levels in adult leaf material of wild-type maize. The comparison showed no statistically significant difference (FIG. 9A).

The amount of acetylbromide-soluble lignin was also determined for the Cal-1 maize mutant (Foster C E, et al., Comprehensive Compositional Analysis of Plant Cell Walls (Lignocellulosic biomass) Part I: Lignin. JoVE, 37, 2010). Levels of acetylbromide soluble lignin in adult leaf material from the Cal-1 maize mutant were compared with levels in adult leaf material of wild-type maize. This comparison showed no statistically significant difference in acetylbromide soluble lignin content (FIG. 9B).

Figure 10:
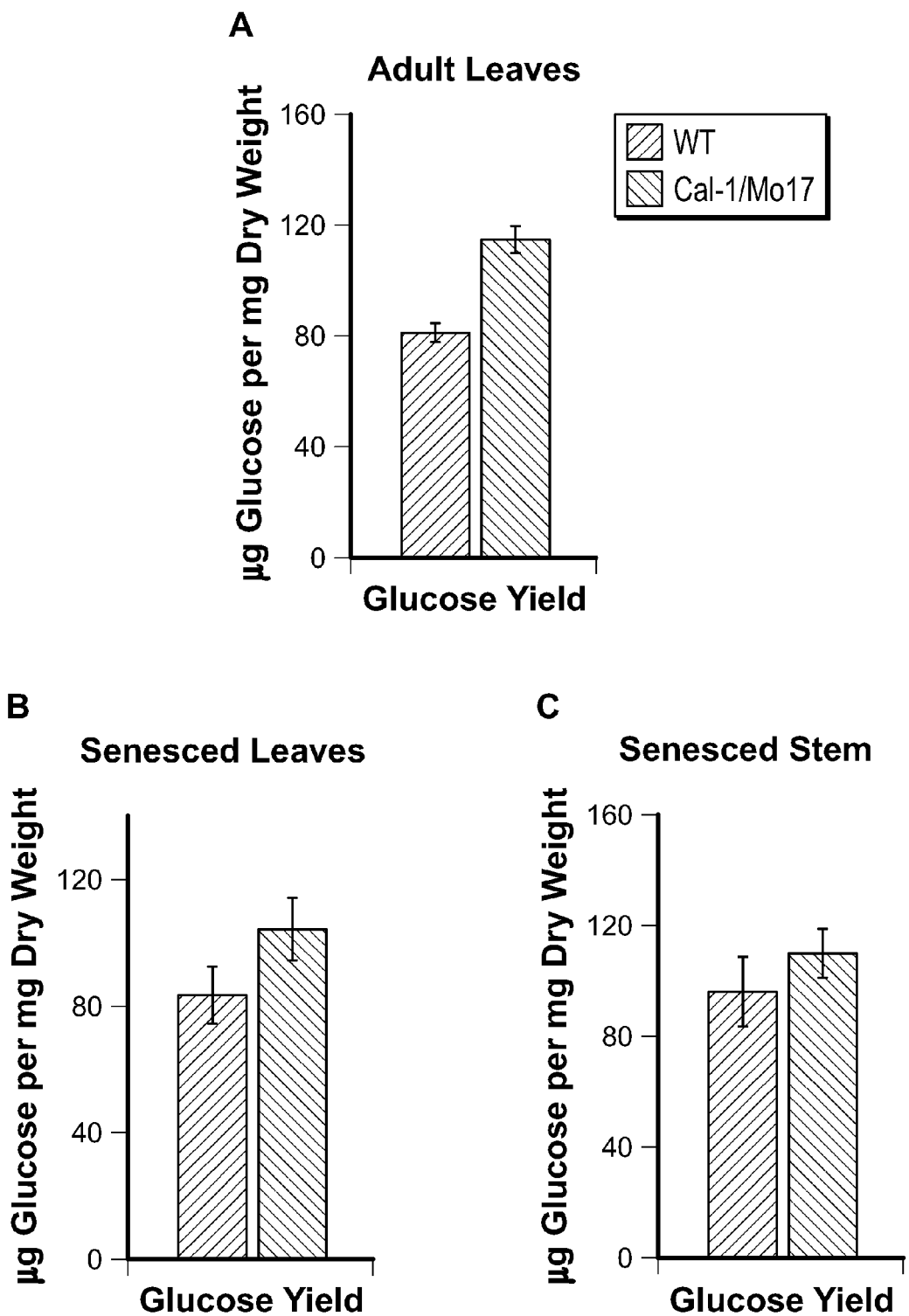
FIG. 10A diagrammatically depicts the amount of glucose, by weight, produced by leaf material from the Cal-1 maize mutant during saccharification of wall material with a mixture of wall degrading enzymes.
FIG. 10B diagrammatically depicts the saccharification yield (glucose) derived from senesced leaves from the Cal-1 maize mutant.
FIG. 10C diagrammatically depicts the saccharification yield (glucose) derived from senesced stem from the Cal-1 maize mutant.

The Cal-1 maize mutant was then evaluated to determine the amount of glucose released by saccharification of cell wall material. Destarched alcohol-insoluble residue from adult leaf material from the Cal-1 maize mutant and from wild-type maize was subjected to a saccharification assay. The assay was performed using a commercial enzyme mix containing multiple enzyme activities, mainly exoglucanase, endoglucanase, hemi-cellulase, and beta-glucosidase. After incubation for 17 hours, the released glucose amount was assayed using a Megazyme GOPOD kit (K-GLUC, Megazyme, Ireland). The Cal-1 maize mutant showed a 40% increase in glucose saccharification yield compared to the wild-type (FIG. 10A). Significant increases in glucose saccharification levels were also observed in senesced leaves (FIG. 10B) and senesced stems (FIG. 10C).

Grain and Biomass Yield

Moreover, field trial with the Cal-1 maize mutant showed that there was no significant difference in kernel (i.e., grain) yield and biomass yield as compared to wildtype maize (FIG. 11).

Cal-1 Protein

Additionally, the Cal-1 protein was isolated, and its licheninase activity was confirmed. The Cal-1 protein was cloned into an expression vector, and the vector was transformed into tobacco plants. The Cal-1 protein was then extracted and purified from the transformed tobacco. The Cal-1 protein was then shown to have licheninase (i.e., mixed-linked glucan endoglucanase) activity (FIG. 12A). Moreover, cellulase activity (endo-$\beta$-1,4-glucanase) and activity against laminarin ($\beta$-1,3-$\beta$-1,6 linked glucan) was not detected with the heterologously expressed protein.

Increased Saccharification Yield

The Cal-1 maize mutant was also crossed to lignin biosynthesis maize mutants bm1 and bm3. The BM1 gene is believed to encode cinnamyl alcohol dehydrogenase (CAD), while the BM3 gene is believed to encode caffeic acid O-methyltransferase (COMT).

As shown in FIG. 13, the crosses of the Cal-1 maize mutant to either the bm1 maize mutant or the bm3 maize mutant surprisingly resulted in a synergistic effect on saccharification yield. In particular, the Cal-1/bm1 cross resulted in a 57% percent increase in saccharification yield as compared to wildtype maize, and the Cal-1/bm3 cross resulted in a 43% increase in saccharification yield as compared to wildtype maize. These results were much higher than the approximate 25% increase over wildtype seen with the Cal-1 mutant, the approximate 10% increase over wildtype seen with the bm1 mutant, or the negligible increase over wildtype seen with the bm3 mutant (FIG. 13B).

Conclusion

These characterizations show that the Ca-1 maize mutant exhibits an increase in cell wall glucan level compared to wild-type maize. In particular, the Cal-1 maize mutant showed increased levels of cell wall-derived mixed-linked hemicellulosic glucan (FIGS. 7 and 8). However, the Cal-1 maize mutant showed no change in crystalline cellulose content or acetylbromide-soluble lignin (FIG. 9). Moreover, when subjected to a saccharification assay, the Cal-1 maize mutant showed a 40% increase in cell wall released glucose compared to wild-type maize. Thus, the Cal-1 maize mutant has improved characteristics for use as a bioenergy crop.

Example 3: Cal-1 Homology Identification

Phylogenetic Tree of *Zea mays* GH17 Domains with at Least 40% Identity to Cal-1 T01

The amino acid sequence of the GH17 domain of Cal-1 T01 was subjected to a BLASTP® alignment tool search and the GH17 domains of 86 proteins were identified that had at least 40% sequence identity with Cal-1 T01. Fifteen proteins with incomplete GH17 domains were eliminated. Five further proteins, the predicted active site was not preserved and were therefore eliminated. The remaining proteins were selected for sequence alignment (FIG. 14).

A consensus sequence of the 66 *Zea mays* GH17 domains was determined and is set forth below (SEQ ID NO: 9):

```
X-X-X-X-X-X-X-X-X-X-[I/L/V/H/A/F]-G-[V/I/A]-
[N/T/S/C]-[Y/N/I/W/H]-G-X-[V/Q/M/S/I/L/T/N/R/A]-
[A/S/G/M/V]-X-[N/H/D/T/S]-[L/P/Q/R/I]-[P/L/I/A]-
X-[P/L//H/A/K/S/T]-X-X-[V/A/M/S/P/L/K/I]-
[V/A/I/M/S/P/L/T]-X-[L/Q/R/K/E/D/M/I/F]-
[L/V/M/G/Y/C/A/I]-[R/L/K/Q/A/E/S/V/L/T]-X-
[S/D/G/A/R/K/L/Q]-X-X-[I/V/F/A]-X-
[K/R/A/L/V/Y/D/S/G/N/M/H]-[V/A/M/L]-[R/K/T]-
[L/S/M/I/T]-[Y/F/I/L]-[D/E/N/L/A/W/H/F/S/G]-
[A/T/P/S/V]-[D/M/E/V/N/Q]-X-X-[V/A/P/T/I/L/F/M]-
[L/M/P/V/I]-X-[A/S]-[L/F/V/A]-[A/V/G/R/S]-
[G/D/H/K/N/R/A]-X-X-[T/S/A/P]-[G/S/D/R/N]-
[I/V/L/W]-X-[V/A/L/F]-[V/M/T/A/I/D]-[V/L/A/P/I]-
[G/A/D/S/M/T]-[V/I/A/L/T/E/F]-[P/T/L/G/A]-[N/D]-
X-X-X-[L/R/A/D/E/G/S/K/I]-X-X-X-
```

-continued

```
[A/P/DS/R/T/G/I/L/M]-[A/D/Y/S/G/R/Q/T/V/N]-
[S/A/G/D/Y/P/V/M/Q/R/T/N]-X-X-X-X-X-X-[A/V/S]-X-
X-[W/C/L]-[V/A/L]-X-X-[N/L/A/Y/T/S/H/R]-[V/I/L]-
X-[P/A/R/K/T/S]-[Y/V/N/H/A/F/T/S]-X-
[P/L/F/N/S/G/Q/D]-[A/D/K/R/S/Q/V]-X-X-X-X-X-X-X-
[I/C/L/F/V/S/T]-X-X-[V/I/L/M]-[A/C/N/V/T/S]-
[V/L/A/G]-[G/D/N]-[N/P/A/E/S/D]-[E/S/V]-
[V/A/F/I/L/T]-X-X-X-X-X-X-X-X-X-X-X-X-X-X-X-X-X-
X-X-X-X-X-X-X-X-X-X-X-X-X-X-X-X-X-X-X-X-X-X-X-X-
X-X-X-X-X-X-X-X-X-X-X-X-[L/T/I/V]-[L/F/V/I/A/M]-
[P/Q/G/D]-A-[M/L/V/I]-[R/Q/K/T/E/A/S/L]-
[N/S/T/A/C/R/Y]-[L/I/V/M/A]-
[H/Q/R/E/D/N/S/A/Y/L]-X-[A/S/G]-[L/I/V/A]-X-X-
[A/L/H/R/V/S/G/N/E]-[G/N/S/R/H/A]-
[L/I/F/H/V/F/M/D]-X-X-X-X-X-[V/I/A/T]-
[K/H/P/R/T/E/N/A]-[V/A/L/C/I/F]-[S/T/V/G/F]-
[T/V/C/S]-X-[V/L/C/H/I/N]-[S/N/A/K/R/Q/T/Y/P]-X-
X-[V/I/A/D]-[L/Y/I/V/T/F/M]-
[A/M/N/D/S/E/Q/G/T/R/L/V]-X-[S/P/Q/T/A]-X-X-X-X-
[P/V/Q/I]-[P/S]-[S/A/Q]-[A/Q/G/R/D/S/T/N]-
[G/Q/E/A/S/C]-X-[F/W/T/S]-
[R/C/D/V/G/E/A/S/N/T/H]-X-X-
[L/P/I/V/L/S/Y/A/D/E]-X-X-X-X-[M/L/V/I]-X-
[P/D/E/S/T/Q/Y/R]-[L/M/I/V]-[L/V/A/I]-X-
[F/Y/L/H]-[L/F/H]-[A/N/H/L/S/Q/E/D/V/R]-X-
[T/N/S/H/K/R/I/V/A]-[G/D/R/N/Q/S]-[A/G/S/T/R]-
[P/V/A/C/Y/F]-[L/F/Y/V]-[L/T/V/M/F/Y/P/W/L]-
[V/I/A/C/L/I]-[N/S/D]-[I/H/A/V/L/C/P]-[Y/L]-
[P/T]-[Y/R/F/C/W]-[F/S/L/Y]-[A/S/T/V/D]-
[Y/P/H/W/Q/L]-X-X-X-X-X-X-X-X-X-X-
[I/S/F/V/M/L/E/S/A]-X-[L/V/F/Q/M/I]-
[D/E/N/A/S/G/P]-[Y/F/N]-[A/S/V/C]-[L/F/Y/I/T/V]-
[F/L/G/S]-X-[P/G/S/A/M/V]-X-X-X-X-X-X-X-X-X-X-X-
X-X-X-[V/G/A/S/N/K/H/T/Y/R/M]-
[V/W/P/I/S/T/R/L/A/Q/M/Y]-[D/V/Q/I/L/T]-X-X-
[T/S/H/N/G/A]-[G/R/N/S/P/A/E/K]-
[L/V/I/A/M/F/N/Y]-X-Y-[T/S/Y/Q/N/G/D/H/A/P]-
[N/D/S]-[M/V/A/L]-[F/L]-[D/Y/H/A/V]-[A/G/T/Q/E]-
[Q/N/T/I/M/L/V]-[V/F/Y/H/A/M/L]-D-[A/T/S/C]-
[V/L/F/T/I/A]-[Y/V/I/H/R/F/T/K]-
```

-continued

[A/S/H/W/L/V/I/F/Y/T]-[A/S]-[L/M/V/I/A]-X-X-

[L/V/A/H/N/I/E/M/K]-[G/N]-X-X-X-X-X-X-X-X-X-X-

X-X-[V/M/L/I/P]-X-[V/I/L/A]-[V/M/I/A/H/R/T/K/L]-

[V/I/L]-[S/G/T/A]-E-[T/V/A/I/S]-G-[W/H/C]-[P/A]-

[S/T/N/Y/H]-X-[G/D/C/A]-X-X-X-X-X-X-X-X-X-X-

X-X-X-X-X-X-X-X-X-X-X-X-X-[E/D/N/A/H/Q/Y]-X-

[G/H/Y/N/S/A/Q/V/E/D]-[A/E/G/V]-[T/K/N/S/G]-X-

[E/A/S/K/Q/T/G/D/R/H]-[N/Y/F/L/M/A/E]-[A/S]-X-X-

[Y/F]-[N/Y/V/S/D/I]-X-[N/G/K/Y]-[L/F/I/V/A/M]-

[I/L/F/M/V/A/R]-[R/Q/D/T/N/E/L/A/K/M/S]-X-

[V/L/M/I/A/Q/C]-X-X-[G/N/S/R/D/Q/L/E]-X-X-X-G-T-

P-X-[R/H/K/A/T/M]-[P/K/T/S]-[G/N/Q/R/D/K/H/A/S]-

X-X-X-X-X-X-X-[Y/F/I/M/S]-[I/L/V/M]-[F/Y]-

[A/G/S/D/E]-[L/M/T]-[F/L/V/I/Y]-[N/D]-E-[D/E/N]-

X-[K/R]-X-X-X-[G/P/D/E/A]-X-X-[S/F/Q/E/T/V/I/A]-

[E/N/H/K/R]-[R/Q/N/K/A]-X-[W/F/Y]-G-[L/I/V/M]-

[F/L/M/Y]-X-[P/Y/F/A/G/K/T/M]-X-[D/N/S]-

[G/M/K/R/Q/E/L]-[T/Q/R/K/S/L/H/E/A/V]-

[P/A/K/H/R/E/L/M/S/I]-[V/K/A/I/S/N/T]-[Y/F]-X-

[L/M/I/V/F]-X-X

Figure 15:
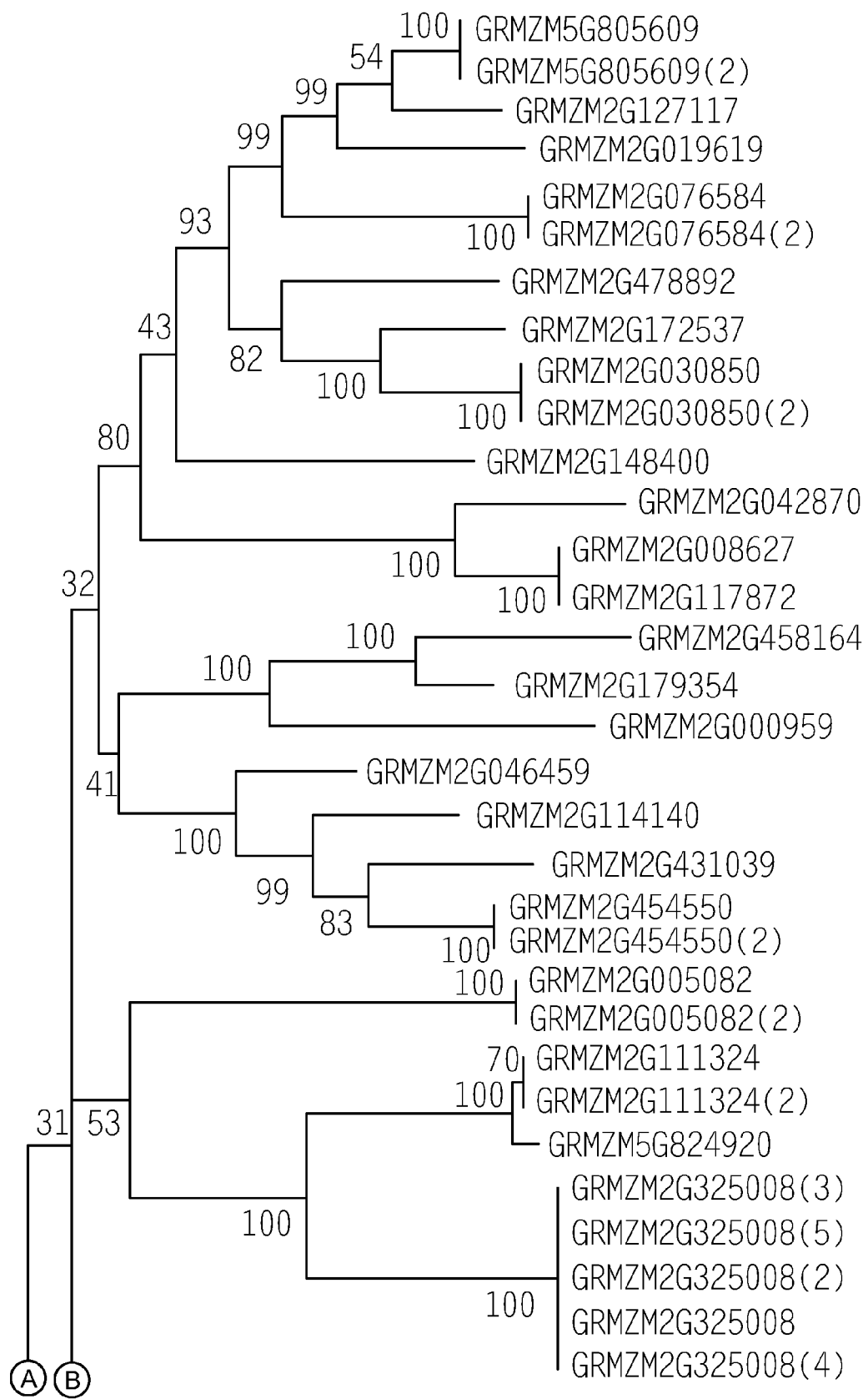
FIG. 15 depicts a phylogenetic tree of the 66 maize proteins having a GH17 domain and at least 40% amino acid sequence identity with the Cal-1 T01 licheninase.
Figure 15:
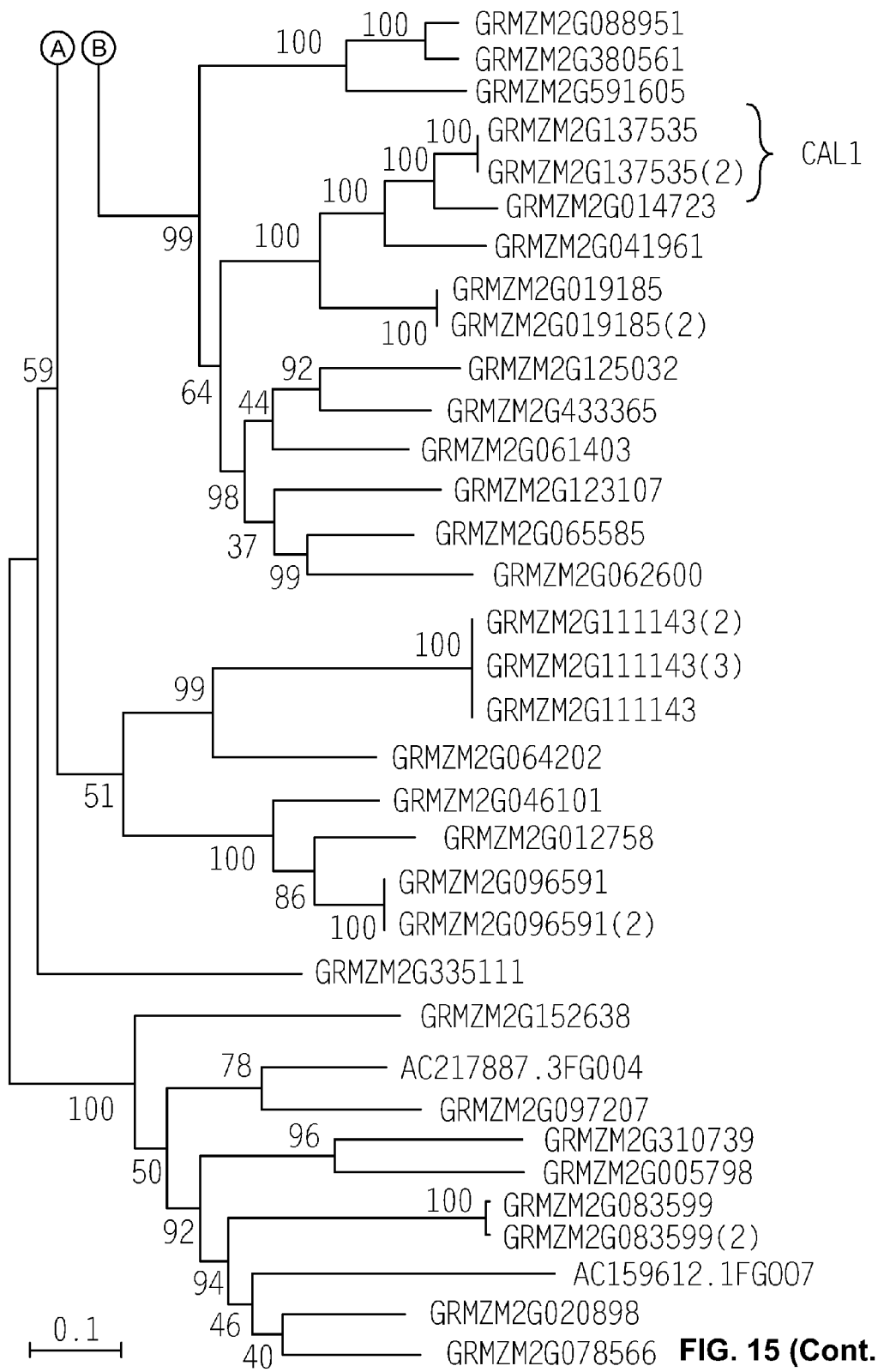

FIG. 15 shows a phylogenetic tree of the aligned proteins that was generated using the Neighbor-Joining method (Saitou N. and Nei M. *Molecular Biology and Evolution* 4:406-425.2, 1987). The bootstrap consensus tree inferred from 500 replicates is taken to represent the evolutionary history of the taxa analyzed (Felsenstein J. *Evolution* 39:783-791, 1985). Branches corresponding to partitions reproduced in less than 50% bootstrap replicates are collapsed. The percentage of replicate trees in which the associated taxa clustered together in the bootstrap test (500 replicates) are shown next to the branches (Felsenstein J. *Evolution* 39:783-791, 1985). The tree is drawn to scale, with branch lengths in the same units as those of the evolutionary distances used to infer the phylogenetic tree. The evolutionary distances were computed using the Poisson correction method and are in the units of the number of amino acid substitutions per site (Zuckerkandl E. and Pauling L. Evolutionary divergence and convergence in proteins. Edited in *Evolving Genes and Proteins* by V. Bryson and H. J. Vogel, pp. 97-166, 1965. Academic Press, New York). The analysis involved the 66 aligned amino acid sequences. All ambiguous positions were removed for each sequence pair. There were a total of 444 positions in the final dataset. Evolutionary analyses were conducted in MEGA5 (Tamura K. et al., *Molecular Biology and Evolution* 24:1596-1599, 2007).

Evolutionary Relationships of *Zea mays, Oryza Sativa, Sorghum Bicolor, Brachypodium Distachyon* and *Setaria italica* to Cal-1 T01

Figure 16:
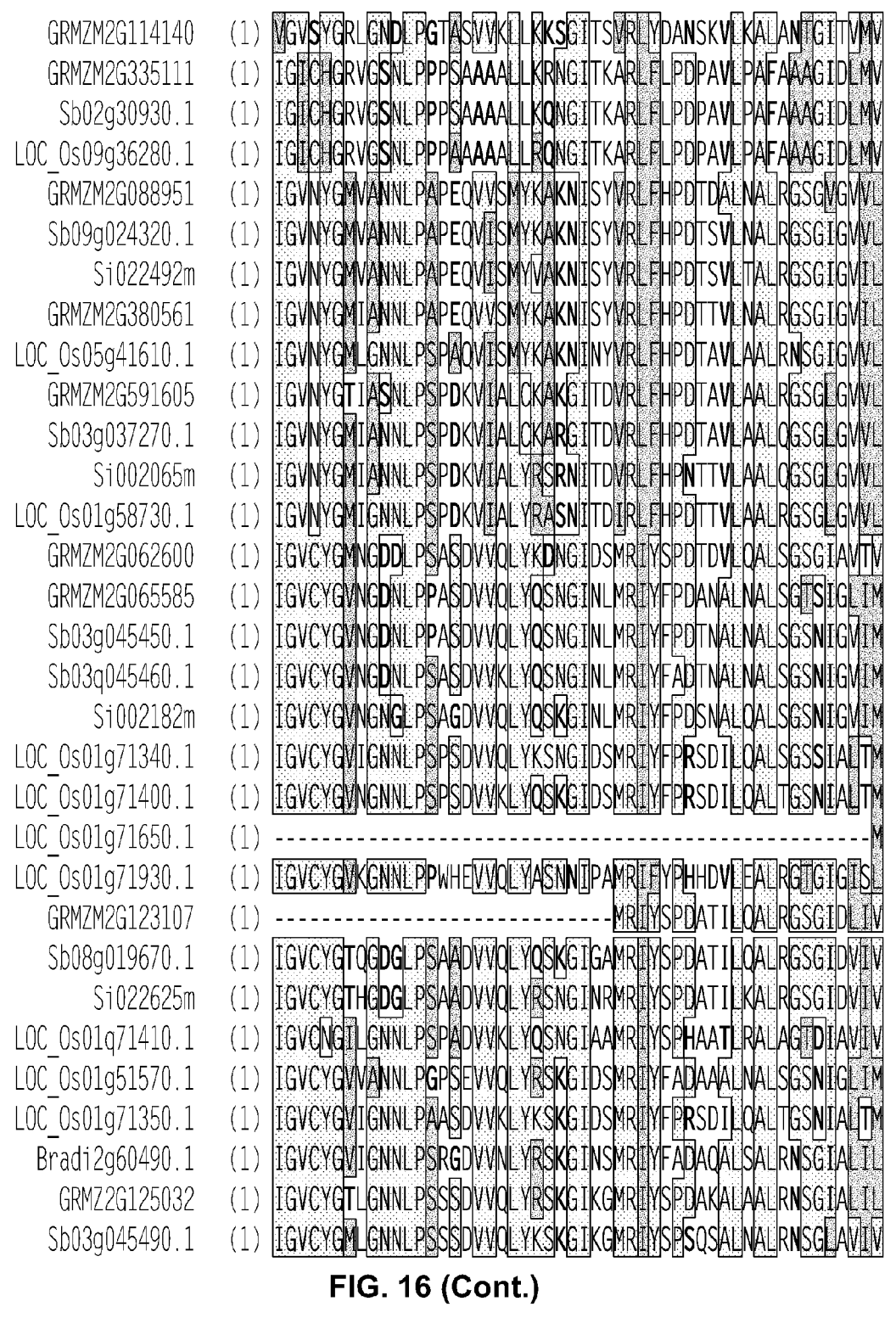
Figure 16:
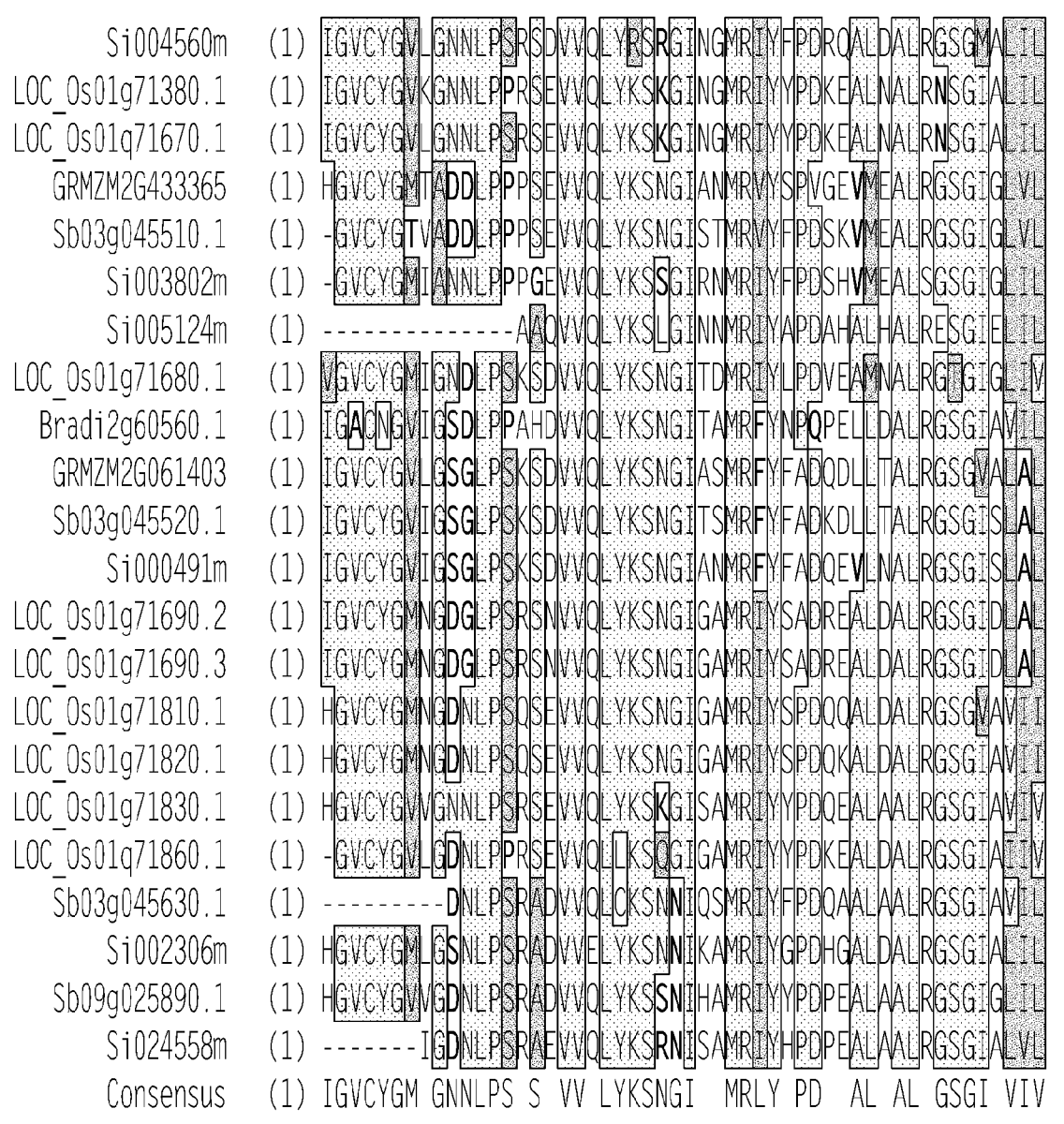
Figure 16:
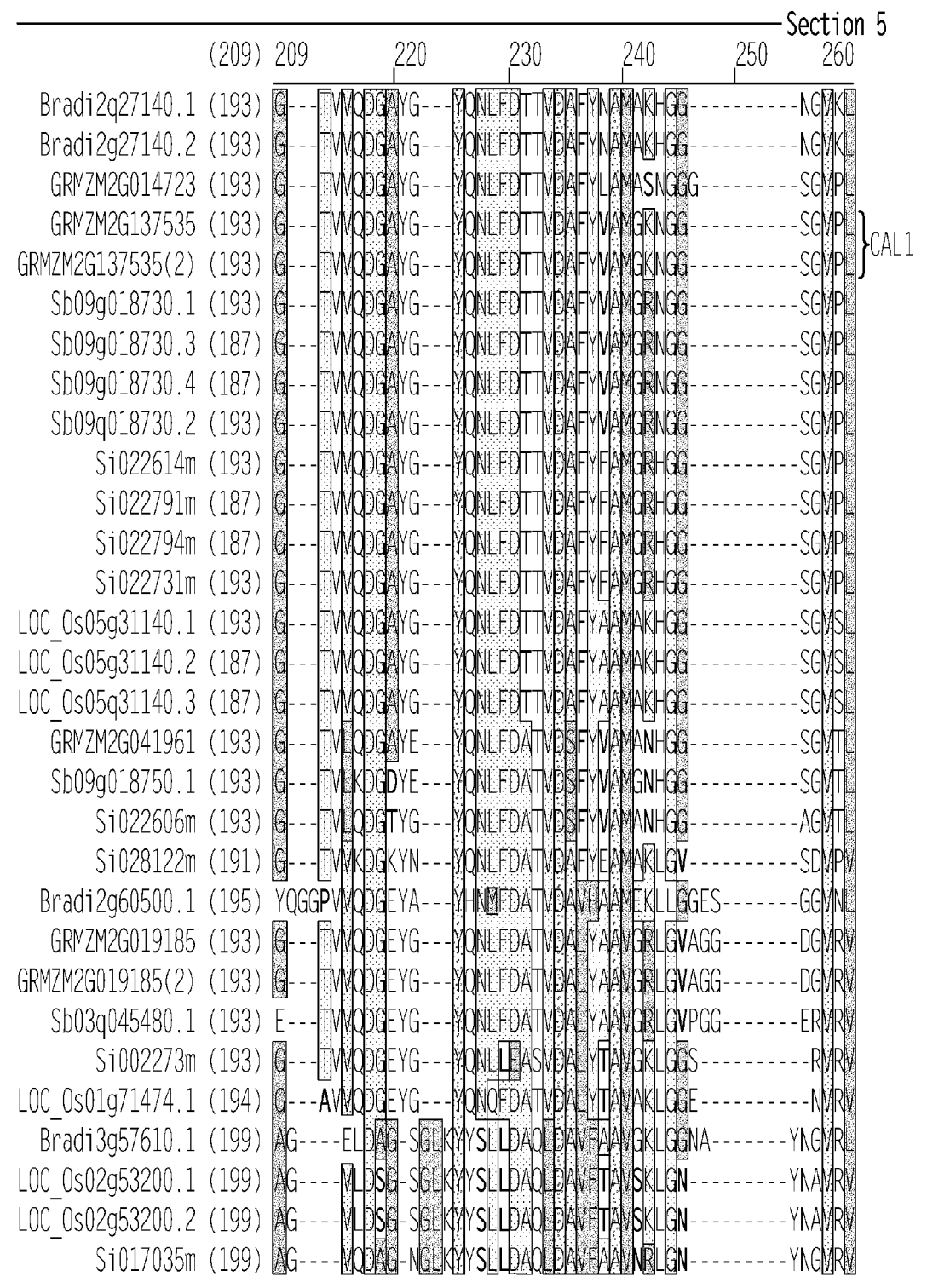

The amino acid sequence of the GH17 domain of Cal-1 T01 was subjected to a BLASTP® alignment tool search and the GH17 domains of 77 *Zea mays, Oryza sativa, Sorghum bicolor, Brachypodium distachyon* and *Setaria italica* proteins were identified that had at least 40% sequence identity with Cal-1 T01. These 77 proteins were selected for sequence alignment (FIG. 16).

Figure 17:
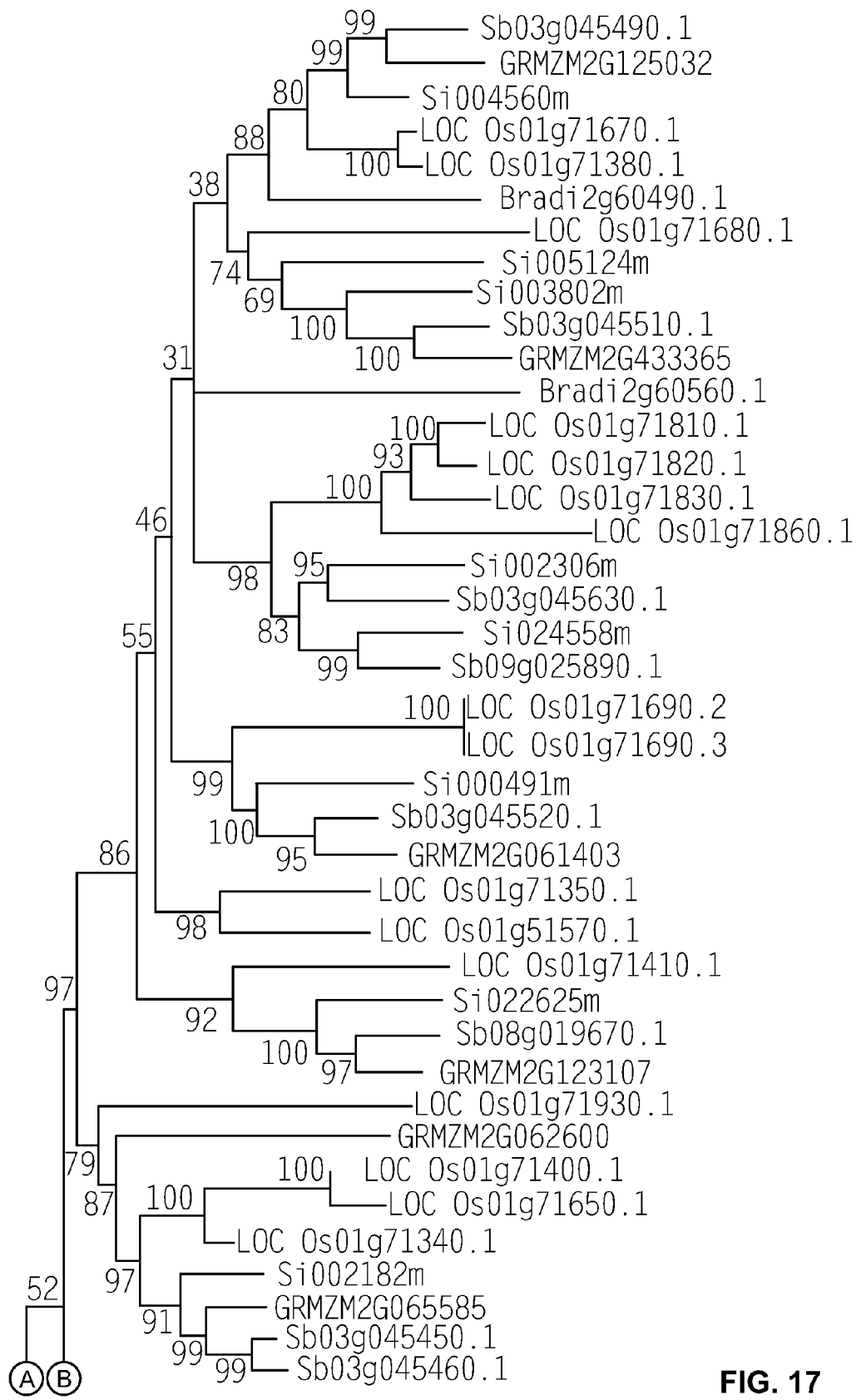
FIG. 17 depicts a phylogenetic tree of the 77 proteins from grass species *Zea mays, Oryza sativa, Sorghum bicolor, Brachypodium distachyon* and *Setaria italica* having a GH17 domain and at least 40% amino acid sequence identity with the Cal-1 T01 licheninase.
Figure 17:
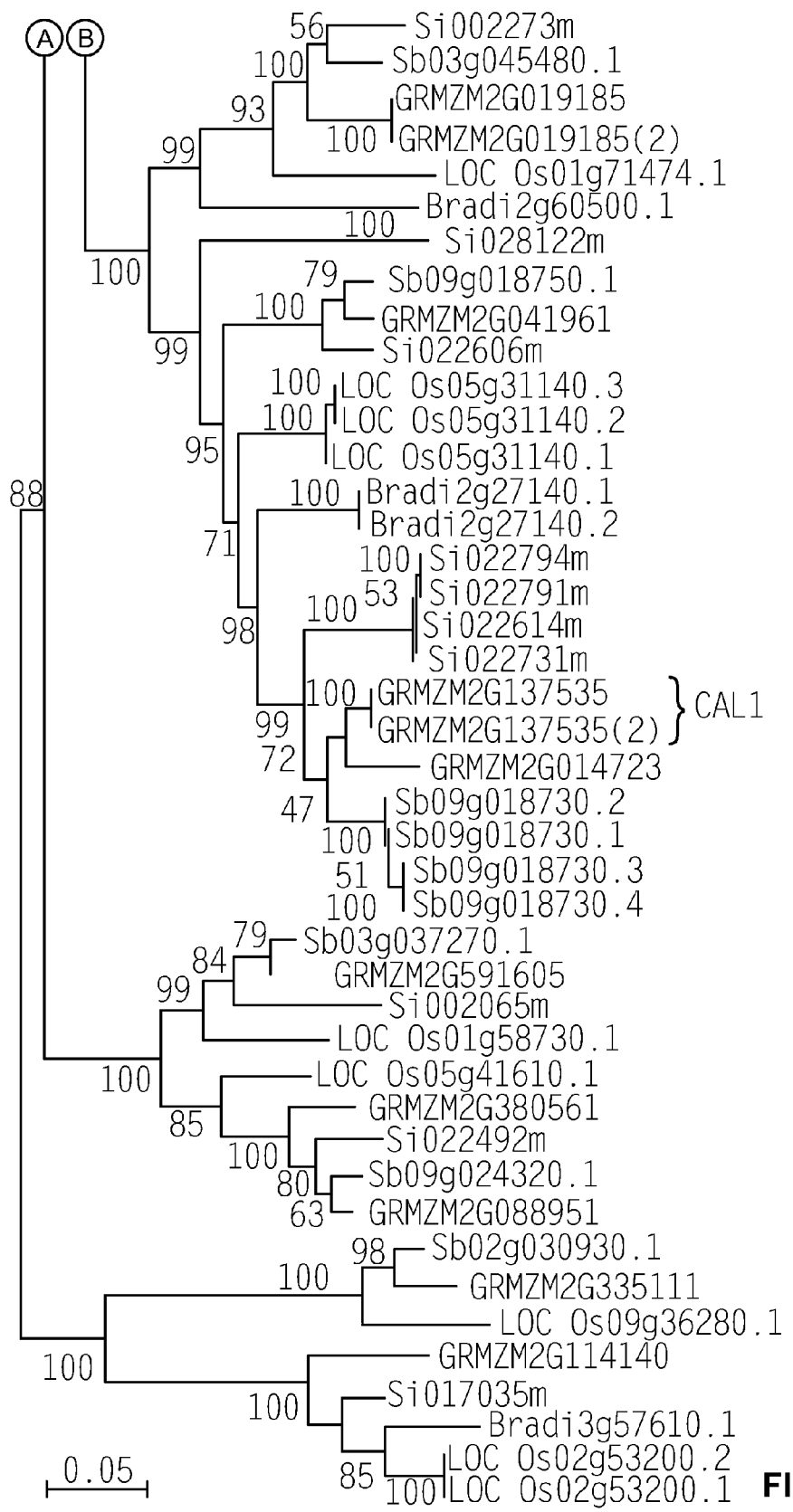

FIG. 17 shows a phylogenetic tree of the aligned proteins that was generated using the Neighbor-Joining method (Saitou N. and Nei M. *Molecular Biology and Evolution* 4:406-425, 1987). The optimal tree with the sum of branch length=8.75872220 is shown. The percentage of replicate trees in which the associated taxa clustered together in the bootstrap test (500 replicates) are shown next to the branches (Felsenstein J. *Evolution* 39:783-791, 1985). The tree is drawn to scale, with branch lengths in the same units as those of the evolutionary distances used to infer the phylogenetic tree. The evolutionary distances were computed using the Poisson correction method and are in the units of the number of amino acid substitutions per site (Zuckerkandl E. and Pauling L. Evolutionary divergence and convergence in proteins. Edited in *Evolving Genes and Proteins* by V. Bryson and H. J. Vogel, pp. 97-166. Academic Press, New York, 1965). The analysis involved the 77 aligned amino acid sequences. All ambiguous positions were removed for each sequence pair. There were a total of 374 positions in the final dataset. Evolutionary analyses were conducted in MEGA5 (Tamura K. et al., *Molecular Biology and Evolution* 24:1596-1599, 2007).

What is claimed:

1. A method of using plant material, the method comprising: subjecting to a saccharification or fermentation process plant material of a maize plant comprising a candy-leaf (Cal-1) licheninase gene mutation encoding an amino acid substitution of an active site glutamic acid, which mutation results in decreased licheninase activity in the plant compared with a corresponding wild-type gene, wherein the plant has elevated levels of glucan compared with a wild-type plant, and the mutation is non-naturally occurring and is derived from non-natural mutagenesis, wherein the licheninase gene encodes SEQ ID NO:4, and the glutamic acid is Glu262 or Glu318, or SEQ ID NO:8, and the glutamic acid is Glu242 or Glu298.

2. The method of claim 1, wherein the gene encodes SEQ ID NO:4, and the glutamic acid is Glu262 or Glu318.

3. The method of claim 1, wherein the gene encodes SEQ ID NO:8, and the glutamic acid is Glu242 or Glu298.

4. The method of claim 1, wherein the gene encodes SEQ ID NO:4, and the mutation is Glu262Lys or Glu318Lys.

5. The method of claim 1, wherein the gene encodes SEQ ID NO:8, and the mutation is Glu242Lys or Glu298Lys.

6. The method of claim 1, wherein the plant further comprises a mutant brown midrib (bm) gene that is selected from maize bm1 and maize bm3.

7. The method of claim 2, wherein the plant further comprises a mutant brown midrib (bm) gene that is selected from maize bm1 and maize bm3.

8. The method of claim 3, wherein the plant further comprises a mutant brown midrib (bm) gene that is selected from maize bm1 and maize bm3.

9. The method of claim 4, wherein the plant further comprises a mutant brown midrib (bm) gene that is selected from maize bm1 and maize bm3.

10. The method of claim 5, wherein the plant further comprises a mutant brown midrib (bm) gene that is selected from maize bm1 and maize bm3.

* * * * *

UNITED STATES PATENT AND TRADEMARK OFFICE
CERTIFICATE OF CORRECTION

PATENT NO. : 9,920,327 B2
APPLICATION NO. : 14/123482
DATED : March 20, 2018
INVENTOR(S) : Markus Pauly, Florian J. Kraemer and Sarah Hake Page 1 of 1

It is certified that error appears in the above-identified patent and that said Letters Patent is hereby corrected as shown below:

On the Title Page

List the second Assignee:
United States Department of Agriculture (Washington DC)

Signed and Sealed this
Seventeenth Day of July, 2018

Andrei Iancu
*Director of the United States Patent and Trademark Office*